United States Patent
Bhattacharya et al.

(10) Patent No.: US 9,394,285 B2
(45) Date of Patent: Jul. 19, 2016

(54) INDOLE AND INDAZOLE COMPOUNDS THAT ACTIVATE AMPK

(71) Applicant: Pfizer Inc., New York, NY (US)

(72) Inventors: Samit Kumar Bhattacharya, Waltham, MA (US); Kimberly O'Keefe Cameron, Cambridge, MA (US); Matthew Scott Dowling, Groton, CT (US); David Christopher Ebner, Somerville, MA (US); David James Edmonds, Arlington, MA (US); Dilinie Prasadhini Fernando, Niantic, CT (US); Kevin James Filipski, Reading, MA (US); Daniel Wei-Shung Kung, Salem, CT (US); Esther Cheng Yin Lee, Brookline, MA (US); Aaron Christopher Smith, North Providence, RI (US); Meihua Mike Tu, Acton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/773,954

(22) PCT Filed: Sep. 24, 2013

(86) PCT No.: PCT/IB2013/058819
§ 371 (c)(1),
(2) Date: Sep. 9, 2015

(87) PCT Pub. No.: WO2014/140704
PCT Pub. Date: Sep. 18, 2014

(65) Prior Publication Data
US 2016/0016940 A1  Jan. 21, 2016

Related U.S. Application Data

(63) Continuation-in-part of application No. 13/831,588, filed on Mar. 15, 2013, now Pat. No. 8,889,730.

(30) Foreign Application Priority Data

Apr. 1, 2013  (WO) .......... PCT/IB2013/052604

(51) Int. Cl.
| | |
|---|---|
| C07D 405/12 | (2006.01) |
| C07D 403/12 | (2006.01) |
| C07D 401/04 | (2006.01) |
| C07D 401/12 | (2006.01) |
| A61K 31/404 | (2006.01) |
| A61K 31/4439 | (2006.01) |
| A61K 31/454 | (2006.01) |
| A61K 31/496 | (2006.01) |
| A61P 13/12 | (2006.01) |
| A61P 3/10 | (2006.01) |

(52) U.S. Cl.
CPC .......... *C07D 405/12* (2013.01); *A61K 31/4439* (2013.01); *C07D 401/04* (2013.01); *C07D 401/12* (2013.01); *C07D 403/12* (2013.01)

(58) Field of Classification Search
CPC .. C07D 209/42; C07D 405/12; C07D 403/12; C07D 401/04; C07D 401/12; A61K 31/404; A61K 31/4439; A61K 31/454; A61K 31/496
USPC .......................................... 514/419; 548/492
See application file for complete search history.

(56) References Cited

U.S. PATENT DOCUMENTS

| | | | |
|---|---|---|---|
| 4,968,680 | A | 11/1990 | Mochida et al. |
| 5,210,092 | A | 5/1993 | Oku et al. |
| 5,215,994 | A | 6/1993 | Oku et al. |
| 5,354,759 | A | 10/1994 | Oku et al. |
| 5,354,763 | A | 10/1994 | Butera et al. |
| 5,629,325 | A | 5/1997 | Lin et al. |
| 5,985,867 | A | 11/1999 | Rodgers et al. |
| 6,387,992 | B1 | 5/2002 | Pastor et al. |
| 7,119,205 | B2 | 10/2006 | Iyengar et al. |
| 7,632,849 | B2 | 12/2009 | Alisi et al. |
| 8,889,730 | B2 | 11/2014 | Bhattacharya et al. |
| 2003/0195244 | A1 | 10/2003 | Hsieh et al. |
| 2004/0059131 | A1 | 3/2004 | Dell et al. |
| 2005/0038068 | A1 | 2/2005 | Iyengar et al. |

(Continued)

FOREIGN PATENT DOCUMENTS

| | | |
|---|---|---|
| CA | 2077919 | 3/1993 |
| CA | 2082023 | 5/1993 |

(Continued)

*Primary Examiner* — Sreeni Padmanabhan
*Assistant Examiner* — Irina Neagu
(74) *Attorney, Agent, or Firm* — James T. Wasicak

(57) ABSTRACT

The present invention relates to indole and indazole compounds of Formula (I) that activate 5' adenosine monophosphate-activated protein kinase (AMPK). The invention also encompasses pharmaceutical compositions containing these compounds and methods for treating or preventing diseases, conditions, or disorders ameliorated by activation of AMPK.

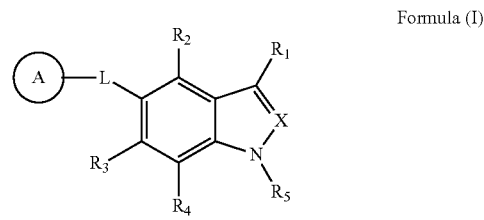

Formula (I)

6 Claims, 1 Drawing Sheet

(56) References Cited

U.S. PATENT DOCUMENTS

| | | | |
|---|---|---|---|
| 2006/0135516 | A1 | 6/2006 | Berdini et al. |
| 2006/0287356 | A1 | 12/2006 | Iyengar et al. |
| 2007/0015771 | A1 | 1/2007 | Matteucci et al. |
| 2007/0078147 | A1 | 4/2007 | Schumacher et al. |
| 2008/0132501 | A1 | 6/2008 | Sun et al. |
| 2008/0171761 | A1 | 7/2008 | Iino et al. |
| 2008/0188521 | A1 | 8/2008 | Grimm et al. |
| 2009/0124680 | A1 | 5/2009 | Yoo et al. |
| 2010/0081658 | A1 | 4/2010 | Chin et al. |
| 2010/0190802 | A1 | 7/2010 | Darwish et al. |
| 2010/0210682 | A1 | 8/2010 | Faltynek et al. |
| 2012/0190677 | A1 | 7/2012 | Feng et al. |
| 2015/0038484 | A1 | 2/2015 | Bhattacharya et al. |

FOREIGN PATENT DOCUMENTS

| | | |
|---|---|---|
| CA | 2083679 | 5/1993 |
| CA | 2083891 | 6/1993 |
| CA | 2129301 | 2/1995 |
| CA | 2156455 | 2/1996 |
| CA | 2164394 | 6/1996 |
| CA | 2260499 | 7/1999 |
| CA | 2317439 | 7/1999 |
| CA | 2282885 | 3/2000 |
| CA | 2357469 | 3/2002 |
| CA | 2454613 | 1/2003 |
| CN | 1296009 | 5/2001 |
| DE | 102004054666 | 5/2006 |
| EP | 1754483 | 2/2007 |
| EP | 1844771 | 10/2007 |
| EP | 1897875 | 3/2008 |
| FR | 2846656 | 5/2004 |
| FR | 2882054 | 8/2006 |
| FR | 2917735 | 12/2008 |
| GB | 2271991 | 5/1995 |
| JP | 2104585 | 4/1990 |
| JP | 2264757 | 10/1990 |
| JP | 5339565 | 12/1993 |
| JP | 8225535 | 9/1996 |
| JP | 2002017387 | 1/2002 |
| JP | 2002017386 | 3/2002 |
| JP | 2003192716 | 7/2003 |
| JP | 2004284997 | 10/2004 |
| JP | 2004284998 | 10/2004 |
| JP | 2005145859 | 6/2005 |
| JP | 2005146091 | 6/2005 |
| JP | 2005298763 | 10/2005 |
| JP | 2006045119 | 2/2006 |
| JP | 2007015952 | 1/2007 |
| JP | 2008106037 | 5/2008 |
| JP | 2008179567 | 8/2008 |
| JP | 2008195642 | 8/2008 |
| JP | 2008208074 | 9/2008 |
| KR | 2009016804 | 2/2009 |
| KR | 20120057716 | 6/2012 |
| WO | 8000661 | 4/1980 |
| WO | 9320065 | 10/1993 |
| WO | 9401415 | 1/1994 |
| WO | 9521836 | 8/1995 |
| WO | 9603377 | 2/1996 |
| WO | 9632379 | 10/1996 |
| WO | 9710214 | 3/1997 |
| WO | 9745425 | 12/1997 |
| WO | 9808821 | 3/1998 |
| WO | 9828292 | 7/1998 |
| WO | 9929660 | 6/1999 |
| WO | 9929661 | 6/1999 |
| WO | 9959973 | 11/1999 |
| WO | 0002550 | 1/2000 |
| WO | 0003997 | 1/2000 |
| WO | 0015622 | 3/2000 |
| WO | 0028993 | 5/2000 |
| WO | 0034263 | 6/2000 |
| WO | 0043394 | 7/2000 |
| WO | 0132621 | 5/2001 |
| WO | 0190074 | 11/2001 |
| WO | 0198266 | 12/2001 |
| WO | 0218363 | 3/2002 |
| WO | 0234744 | 5/2002 |
| WO | 0240481 | 5/2002 |
| WO | 0241910 | 5/2002 |
| WO | 0250031 | 6/2002 |
| WO | 02057216 | 7/2002 |
| WO | 02057237 | 7/2002 |
| WO | 02072549 | 9/2002 |
| WO | 02074768 | 9/2002 |
| WO | 02076926 | 10/2002 |
| WO | 02083624 | 10/2002 |
| WO | 02100833 | 12/2002 |
| WO | 03013511 | 2/2003 |
| WO | 03020719 | 3/2003 |
| WO | 03031440 | 4/2003 |
| WO | 03035005 | 5/2003 |
| WO | 03035065 | 5/2003 |
| WO | 03035644 | 5/2003 |
| WO | 03051277 | 6/2003 |
| WO | 03051366 | 6/2003 |
| WO | 03070686 | 8/2003 |
| WO | 03/082271 | 10/2003 |
| WO | 03082271 | 10/2003 |
| WO | 03097855 | 11/2003 |
| WO | 03099206 | 12/2003 |
| WO | 2004004701 | 1/2004 |
| WO | 2004031158 | 4/2004 |
| WO | 2004048330 | 6/2004 |
| WO | 2004048365 | 6/2004 |
| WO | 2004048374 | 6/2004 |
| WO | 2004063155 | 7/2004 |
| WO | 2004063190 | 7/2004 |
| WO | 2004072033 | 8/2004 |
| WO | 2004074232 | 9/2004 |
| WO | 2004089367 | 10/2004 |
| WO | 2004089380 | 10/2004 |
| WO | 2004089415 | 10/2004 |
| WO | 2004089416 | 10/2004 |
| WO | 2004089470 | 10/2004 |
| WO | 2004089471 | 10/2004 |
| WO | 2004089896 | 10/2004 |
| WO | 2004099192 | 11/2004 |
| WO | 2005005411 | 1/2005 |
| WO | 2005007085 | 1/2005 |
| WO | 2005014554 | 2/2005 |
| WO | 2005016862 | 2/2005 |
| WO | 2005035506 | 4/2005 |
| WO | 2005063767 | 7/2005 |
| WO | 2005092890 | 10/2005 |
| WO | 2005097203 | 10/2005 |
| WO | 2005111038 | 11/2005 |
| WO | 2005121137 | 12/2005 |
| WO | 2005123673 | 12/2005 |
| WO | 2005123675 | 12/2005 |
| WO | 2006010750 | 2/2006 |
| WO | 2006012504 | 2/2006 |
| WO | 2006015775 | 2/2006 |
| WO | 2006034003 | 3/2006 |
| WO | 2006038606 | 4/2006 |
| WO | 2006044509 | 4/2006 |
| WO | 2006049013 | 5/2006 |
| WO | 2006051937 | 5/2006 |
| WO | 2006069097 | 6/2006 |
| WO | 2006071095 | 7/2006 |
| WO | 2006109933 | 10/2006 |
| WO | 2006110516 | 10/2006 |
| WO | 2006115188 | 11/2006 |
| WO | 2006125119 | 11/2006 |
| WO | 2006130437 | 12/2006 |
| WO | 2006130453 | 12/2006 |
| WO | 2006132914 | 12/2006 |
| WO | 2006133559 | 12/2006 |
| WO | 2007000241 | 1/2007 |
| WO | 2007002461 | 1/2007 |
| WO | 2007005785 | 1/2007 |
| WO | 2007022501 | 2/2007 |

(56) References Cited

FOREIGN PATENT DOCUMENTS

| | | |
|---|---|---|
| WO | 2007056184 | 5/2007 |
| WO | 2007056279 | 5/2007 |
| WO | 2007056281 | 5/2007 |
| WO | 2007056582 | 5/2007 |
| WO | 2007058504 | 5/2007 |
| WO | 2007062568 | 6/2007 |
| WO | 2007070818 | 6/2007 |
| WO | 2007070826 | 6/2007 |
| WO | 2007079173 | 7/2007 |
| WO | 2007092751 | 8/2007 |
| WO | 2007093827 | 8/2007 |
| WO | 2007114213 | 10/2007 |
| WO | 2007117465 | 10/2007 |
| WO | 2007121299 | 10/2007 |
| WO | 2007137030 | 11/2007 |
| WO | 2007140183 | 12/2007 |
| WO | 2007142323 | 12/2007 |
| WO | 2008003703 | 1/2008 |
| WO | 2008006432 | 1/2008 |
| WO | 2008016278 | 2/2008 |
| WO | 2008019357 | 2/2008 |
| WO | 2008054748 | 5/2008 |
| WO | 2008071451 | 6/2008 |
| WO | 2008072850 | 6/2008 |
| WO | 2008077079 | 6/2008 |
| WO | 2008079918 | 7/2008 |
| WO | 2008083124 | 7/2008 |
| WO | 2008086854 | 7/2008 |
| WO | 2008089125 | 7/2008 |
| WO | 2008100867 | 8/2008 |
| WO | 2008110863 | 9/2008 |
| WO | 2008111474 | 9/2008 |
| WO | 2008116909 | 10/2008 |
| WO | 2008116910 | 10/2008 |
| WO | 2008116911 | 10/2008 |
| WO | 2008116912 | 10/2008 |
| WO | 2008116914 | 10/2008 |
| WO | 2008118822 | 10/2008 |
| WO | 2008136642 | 11/2008 |
| WO | 2008150899 | 12/2008 |
| WO | 2009012125 | 1/2009 |
| WO | 2009019445 | 2/2009 |
| WO | 2009019446 | 2/2009 |
| WO | 2009026107 | 2/2009 |
| WO | 2009032116 | 3/2009 |
| WO | 2009032124 | 3/2009 |
| WO | 2009037247 | 3/2009 |
| WO | 2009053373 | 4/2009 |
| WO | 2009064852 | 5/2009 |
| WO | 2009065131 | 5/2009 |
| WO | 2009084695 | 7/2009 |
| WO | 2009/100130 | 8/2009 |
| WO | 2009100130 | 8/2009 |
| WO | 2009115427 | 9/2009 |
| WO | 2009115874 | 9/2009 |
| WO | 2009118370 | 10/2009 |
| WO | 2009120783 | 10/2009 |
| WO | 2009124636 | 10/2009 |
| WO | 2009132136 | 10/2009 |
| WO | 2009135580 | 11/2009 |
| WO | 2009136175 | 11/2009 |
| WO | 2009152909 | 12/2009 |
| WO | 2009153307 | 12/2009 |
| WO | 2010000396 | 1/2010 |
| WO | 2010009190 | 1/2010 |
| WO | 2010010186 | 1/2010 |
| WO | 2010036910 | 4/2010 |
| WO | 2010047982 | 4/2010 |
| WO | 2010051176 | 5/2010 |
| WO | 2010051206 | 5/2010 |
| WO | 2010056041 | 5/2010 |
| WO | 2010058858 | 5/2010 |
| WO | 2010/064875 | 6/2010 |
| WO | 2010064875 | 6/2010 |
| WO | 2010068287 | 6/2010 |
| WO | 2010069949 | 6/2010 |
| WO | 2010073011 | 7/2010 |
| WO | 2010075561 | 7/2010 |
| WO | 2010086613 | 8/2010 |
| WO | 2010088392 | 8/2010 |
| WO | 2010110782 | 9/2010 |
| WO | 2010113022 | 10/2010 |
| WO | 2010118009 | 10/2010 |
| WO | 2011004162 | 1/2011 |
| WO | 2011014128 | 2/2011 |
| WO | 2011029855 | 3/2011 |
| WO | 2011032320 | 3/2011 |
| WO | 2011033099 | 3/2011 |
| WO | 2011069298 | 6/2011 |
| WO | 2011078370 | 6/2011 |
| WO | 2011080277 | 7/2011 |
| WO | 2011106273 | 9/2011 |
| WO | 2011123681 | 10/2011 |
| WO | 2011128251 | 10/2011 |
| WO | 2011138307 | 11/2011 |
| WO | 2012026495 | 1/2012 |
| WO | 2012016217 | 2/2012 |
| WO | 2012027548 | 3/2012 |
| WO | 2012033149 | 3/2012 |
| WO | 2012040499 | 3/2012 |
| WO | 2012052372 | 4/2012 |
| WO | 2012001020 | 5/2012 |
| WO | 2012116145 | 8/2012 |
| WO | 2012119978 | 9/2012 |
| WO | 2012119979 | 9/2012 |
| WO | 2013024011 | 2/2013 |
| WO | 2013124158 | 8/2013 |
| ZA | 9810825 | 5/1999 |

US 9,394,285 B2

INDOLE AND INDAZOLE COMPOUNDS THAT ACTIVATE AMPK

FIELD OF THE INVENTION

The present invention relates to indole and indazole compounds that activate 5' adenosine monophosphate-activated protein kinase (AMPK), pharmaceutical compositions containing these compounds, and the use of these compounds for treating or preventing diseases, conditions, or disorders ameliorated by activation of AMPK.

BACKGROUND

Diabetes is a major public health concern because of its increasing prevalence and associated health risks. The disease is characterized by high levels of blood glucose resulting from defects in insulin production, insulin action, or both. Two major forms of diabetes are recognized, type I and type II. Type I diabetes develops when the body's immune system destroys pancreatic beta cells, the only cells in the body that make the hormone insulin that regulates blood glucose. To survive, people with type 1 diabetes must have insulin delivered by injection or a pump. Type II diabetes accounts for about 90 to 95 percent of all diagnosed cases of diabetes. Type II diabetes usually begins as insulin resistance, a disorder in which the cells do not use insulin properly. Key target tissues, including liver, muscle, and adipose tissue, are resistant to the effects of insulin in stimulating glucose and lipid metabolism. As the need for insulin rises, the pancreas gradually loses its ability to produce insulin. Controlling type II diabetes with medication is essential; otherwise it can progress into pancreatic beta-cell failure requiring complete dependence on insulin.

Obesity increases the risk of type II diabetes as well as many other health conditions including coronary heart disease, stroke, and high blood pressure. More than one-third of U.S. adults (over 72 million people) and 17% of U.S. children are obese. During 1980-2008, obesity rates doubled for adults and tripled for children. During the past several decades, obesity rates for all population groups—regardless of age, sex, race, ethnicity, socioeconomic status, education level, or geographic region—have increased markedly.

Research has identified the enzyme 5' adenosine monophosphate-activated protein kinase (AMPK) as a regulator of cellular and whole-body energy homeostasis. AMPK is activated by cellular stress resulting in downstream events that serve to conserve or generate ATP. AMPK is composed of three distinct subunits, each with multiple isoforms: the alpha subunit (alpha 1 or 2); the beta subunit (beta 1 or 2); and the gamma subunit (gamma 1, 2, or 3); for a total of twelve possible heterotrimeric isoforms.

In the liver, activated AMPK phosphorylates a variety of substrates including 3-hydroxy-3-methylglutaryl coenzyme A (HMG-CoA) reductase (Clarke, P. R. & Hardie, D. G., EMBO J 9, 2439-2446 (1990)) and acetyl-CoA carboxylase (Carling, D. et al. FEBS Letters 223, 217-222 (1987)) which inhibits cholesterol biosynthesis and decreases fatty acid synthesis, respectively. Therefore, activation of AMPK should lead to decreases in the levels of triglycerides and cholesterol. AMPK is also thought to regulate plasma glucose levels by decreasing hepatic gluconeogenesis through downregulation of key gene products following phosphorylation of CRTC2 (Koo S. H. et. Al., Nature 437, 1109-1111 (2005)). In muscle and myocardial tissues, AMPK activates the transport activity of glucose transporter 4 (GLUT4) increasing glucose uptake into cells thereby producing an additional avenue for decreasing plasma glucose (Kurth-Kraczek, E. J. et. al., Diabetes 48, 1667-1671 (1999)). AMPK activation has also been shown to enhance mitochondrial biogenesis improving fatty acid oxidation and decreasing circulating lipids (Merrill, G. M. et. al., Am. J. Physiol. 273, E1107-E1112 (1997)). Direct activation of AMPK using AICAR (5-aminoimidazole-4-carboxamide riboside) has been shown to lead to beneficial effects on several metabolic endpoints including improved glucose disposal, decreased hepatic glucose output and decreases in plasma triglycerides and free fatty acids (Song, X. M. et. al., Diabetologia 45, 56-65 (2002); Bergeron, R. et. al., Diabetes 50, 1076-1082 (2001); Buhl, E. S. et. al., Diabetes 50, 12-17 (2001); Iglesias, M. A. et. al., Diabetes 51, 2886-2894 (2002); Fogarty, S. & Hardie, D. G., Biochim et Biophys Acta 1804, 581-591 (2010)). Because of AMPK's pluripotent effects on carbohydrate, lipid, and cholesterol metabolism and biosynthesis, agents that activate AMPK are attractive therapeutic targets for treating metabolic syndrome disorders such as diabetes, obesity, and dyslipidemia.

Decreases in renal AMPK activation have been implicated in the etiology of diseases of the kidney, including diabetic nephropathy, acute kidney injury (AKI), and polycystic kidney disease (PKD); activation of AMPK through hormonal (adiponectin) or pharmacological (AICAR) mechanisms has been shown to be protective in rodent models of these diseases. In diabetic nephropathy decreased AMPK activation in podocytes occurs early in the disease and is associated with increased expression of the NADPH-Oxidase protein Nox4 and increased proteinuria. These effects were reduced following administration of the AMPK activators AICAR, metformin, and Adiponectin (Lee, M J. et. al. American Journal of Physiology—Renal Physiology. 292. F617-F627 (2007); Sharma, K. et. al. Journal of Clinical Investigation. 118. 1645-1656. (2008)). In ischemia/reperfusion models of AKI the AMPK activators metformin and AICAR were shown to dose-dependently reduce subsequent proteinuria, oxidative tissue damage, and kidney macrophage infiltration (Lempiainen, J. et. al. British Journal of Pharmacology 166. 1905-1915 (2012); Seo-Mayer, P. W. et. al. American Journal of Physiology—Renal Physiology, 301, F1346-F1357 (2011)). In two rodent models of PKD the AMPK activator metformin was shown to reduce renal cyst expansion (Takiar, V. et. al. PNAS 108, 2462-2467 (2011)). These studies suggest a broad benefit of AMPK activators in multiple renal diseases.

The compounds of the present invention activate AMPK and are, therefore, useful in treating metabolic disorders such as diabetes, obesity, and dyslipidemia as well as the renal diseases chronic kidney disease, diabetic nephropathy, acute kidney injury and polycystic kidney disease.

SUMMARY OF THE INVENTION

The present invention provides compounds of Formula (I) that activate 5' adenosine monophosphate-activated protein kinase and are useful for treating or preventing disorders ameliorated by activation of AMPK in mammals, particularly humans,

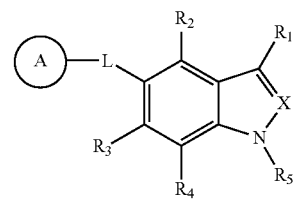

Formula (I)

or a pharmaceutically acceptable salt thereof, wherein

X is N or CH;

$R_1$ is —C(O)O$R_4$, —C(O)N$R_B R_C$, —S(O$_2$)O$R_4$, —S(O$_2$)NHC(O)$R_D$, 5-oxo-4,5-dihydro-1,2,4-oxadiazol-3-yl, or 1H-tetrazol-5-yl;

$R_4$ is H or (C$_1$-C$_6$)alkyl;

$R_B$ and $R_C$ are independently H, (C$_1$-C$_6$)alkyl, or —S(O$_2$)$R_D$;

$R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or N$R_E R_F$;

$R_E$ and $R_F$ are independently H or (C$_1$-C$_6$)alkyl;

$R_2$, $R_3$, and $R_4$ are independently H, (C$_1$-C$_6$)alkoxy, (C$_1$-C$_6$)alkyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_8$)alkyl, mercapto, nitro, —N$R_G R_H$ or (N$R_G R_H$)carbonyl;

$R_G$ and $R_H$ are independently H, (C$_1$-C$_6$)alkyl, or (C$_1$-C$_6$)alkylcarbonyl;

$R_5$ is H or (C$_1$-C$_6$)alkyl;

L is a bond, O, S, N$R_4$, (C$_1$-C$_6$)alkylene, (C$_2$-C$_6$)alkenylene, or (C$_2$-C$_6$)alkynylene;

A is phenyl, 2,3-dihydrobenzo[b][1,4]dioxinyl, 2,3-dihydrobenzofuranyl, 2,3-dihydro-1H-indenyl, imidazolyl, pyrazinyl, pyrazolyl, pyridinyl, pyrimidinyl, or thiazolyl, wherein each is optionally substituted with 1, 2, 3, 4, or 5 substituents that are independently (C$_1$-C$_6$)alkoxy, (C$_1$-C$_6$)alkoxy(C$_1$-C$_6$)alkoxy, (C$_1$-C$_6$)alkoxy(C$_1$-C$_6$)alkyl, (C$_1$-C$_6$)alkoxycarbonyl, (C$_1$-C$_6$)alkyl, (C$_1$-C$_6$)alkylcarbonyl, (C$_1$-C$_6$)alkylthio, aryl, aryl(C$_1$-C$_6$)alkoxy, aryl(C$_1$-C$_6$)alkyl, arylcarbonyl, aryloxy, carboxy, carboxy(C$_1$-C$_6$)alkoxy, carboxy(C$_1$-C$_6$)alkyl, cyano, (C$_3$-C$_8$)cycloalkyl, (C$_3$-C$_8$)cycloalkyl(C$_1$-C$_6$)alkoxy, (C$_3$-C$_8$)cycloalkyl(C$_1$-C$_6$)alkyl, (C$_3$-C$_8$)cycloalkylcarbonyl, (C$_3$-C$_8$)cycloalkyloxy, halogen, halo(C$_1$-C$_6$)alkoxy, halo(C$_1$-C$_6$)alkyl, heteroaryl, heteroaryl(C$_1$-C$_6$)alkoxy, heteroaryl(C$_1$-C$_6$)alkyl, heteroarylcarbonyl, heteroaryloxy, (C$_3$-C$_7$)heterocycle, (C$_3$-C$_7$)heterocycle(C$_1$-C$_6$)alkoxy, (C$_3$-C$_7$)heterocycle(C$_1$-C$_6$)alkyl, (C$_3$-C$_7$)heterocyclecarbonyl, (C$_3$-C$_7$)heterocyclecarbonyl(C$_1$-C$_6$)alkyl, (C$_3$-C$_7$)heterocycleoxy, hydroxy, hydroxy(C$_1$-C$_6$)alkoxy, hydroxy(C$_1$-C$_6$)alkyl, mercapto, nitro, —N$R_J R_K$, (N$R_J R_K$)carbonyl, —N$R_M R_N$, —N$R_M R_N$(C$_1$-C$_6$)alkoxy, (N$R_M R_N$)carbonyl, (N$R_M R_N$)carbonyl(C$_1$-C$_6$)alkyl, or (N$R_M R_N$)carbonyl(C$_1$-C$_6$)alkoxy; wherein the aryl, aryl(C$_1$-C$_6$)alkoxy, aryl(C$_1$-C$_6$)alkyl, arylcarbonyl, and aryloxy are optionally substituted with 1, 2, 3, 4, or 5 substituents that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —N$R_M R_N$, or (N$R_M R_N$)carbonyl; wherein the halo(C$_1$-C$_6$)alkyl is optionally substituted with 1 or 2 hydroxy groups; wherein the (C$_3$-C$_8$)cycloalkyl, (C$_3$-C$_8$)cycloalkyl(C$_1$-C$_6$)alkoxy, (C$_3$-C$_8$)cycloalkyl(C$_1$-C$_6$)alkyl, (C$_3$-C$_8$)cycloalkylcarbonyl, and (C$_3$-C$_8$)cycloalkyloxy are optionally substituted with 1, 2, or 3 substituents that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —N$R_M R_N$, or (N$R_M R_N$)carbonyl; wherein the heteroaryl, heteroaryl(C$_1$-C$_6$)alkoxy, heteroaryl(C$_1$-C$_6$)alkyl, heteroarylcarbonyl, and heteroaryloxy, are optionally substituted with 1, 2, or 3 substituents that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —N$R_M R_N$, or (N$R_M R_N$)carbonyl; and wherein the (C$_3$-C$_7$)heterocycle, (C$_3$-C$_7$)heterocycle(C$_1$-C$_6$)alkoxy, (C$_3$-C$_7$)heterocycle(C$_1$-C$_6$)alkyl, (C$_3$-C$_7$)heterocyclecarbonyl, (C$_3$-C$_7$)heterocyclecarbonyl(C$_1$-C$_6$)alkyl, and (C$_3$-C$_7$)heterocyclooxy, are optionally substituted with 1, 2, or 3 substituents that are independently (C$_1$-C$_6$)alkoxy, (C$_1$-C$_6$)alkoxycarbonyl, (C$_1$-C$_6$)alkoxysulfonyl, (C$_1$-C$_6$)alkyl, (C$_1$-C$_6$)alkylcarbonyl, (C$_1$-C$_6$)alkylsulfonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —N$R_M R_N$, (N$R_M R_N$)carbonyl, or oxo;

$R_J$ and $R_K$ are independently H or (C$_1$-C$_6$)alkyl; and $R_M$ and $R_N$ are independently H, (C$_1$-C$_6$)alkyl, or (C$_1$-C$_6$)alkylcarbonyl; or $R_M$ and $R_N$ together with the nitrogen they are attached to form a 3 to 8 membered ring;

provided that Formula (I) does not encompass
5-(4-bromophenyl)-1H-indole-3-carboxamide;
5-(2',6'-dihydroxy-[1,1'-biphenyl]-4-yl)-1H-indole-3-carboxamide; and
5-(2',6'-dimethoxy-[1,1]biphenyl]-4-yl)-1H-indole-3-carboxamide.

In another embodiment, the present invention provides a pharmaceutical composition comprising a compound of Formula (I) and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (I), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (I), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (I), or a pharmaceutically acceptable salt thereof.

In another aspect, the present invention provides uses for compounds of Formula (I) for preparing, or for the manufacture of, a medicament for treating metabolic disorders in a mammal, particularly a human.

In another aspect, the present invention provides uses for compounds of Formula (I) for preparing, or for the manufacture of, a medicament for treating or preventing type II diabetes in a mammal, particularly a human.

In another aspect, the present invention provides uses for compounds of Formula (I) for preparing, or for the manufacture of, a medicament for treating or preventing obesity in a mammal, particularly a human.

In another aspect, the present invention provides uses for compounds of Formula (I) for preparing, or for the manufacture of, a medicament for treating or preventing dyslipidemia in a mammal, particularly a human.

In another aspect, the present invention provides uses for compounds of Formula (I) for preparing, or for the manufacture of, a medicament for treating renal diseases in a mammal, particularly a human.

In another aspect, the present invention provides uses for compounds of Formula (I) for preparing, or for the manufacture of, a medicament for treating or preventing chronic kidney disease in a mammal, particularly a human.

In another aspect, the present invention provides uses for compounds of Formula (I) for preparing, or for the manufacture of, a medicament for treating or preventing diabetic nephropathy in a mammal, particularly a human.

In another aspect, the present invention provides uses for compounds of Formula (I) for preparing, or for the manufacture of, a medicament for treating or preventing acute kidney injury in a mammal, particularly a human.

In another aspect, the present invention provides uses for compounds of Formula (I) for preparing, or for the manufacture of, a medicament for treating or preventing polycystic kidney disease in a mammal, particularly a human.

DETAILED DESCRIPTION OF THE INVENTION

Figure 1B:
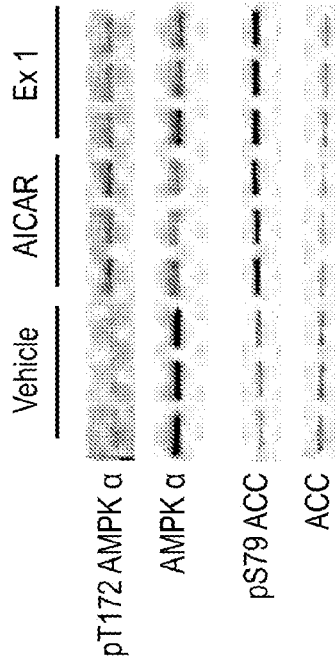
FIG. 1. A. Podocyte apoptosis was measured following 48 hours in media containing no glucose or 30 mM glucose with addition of vehicle, 1 mM AICAR, or Ex 1. Apoptosis was measured by quantifying using commercial cell death ELISA (Roche). B. Western blot analysis of total and phosphorylated AMPK and ACC in podocytes following 48 hour treatment with 30 mM glucose and vehicle, 1 mM AICAR, or Ex 1. C and D. Quantification of triplicate samples from western blots for the phopho/total AMPK and ACC ratio.
Figure 1D:
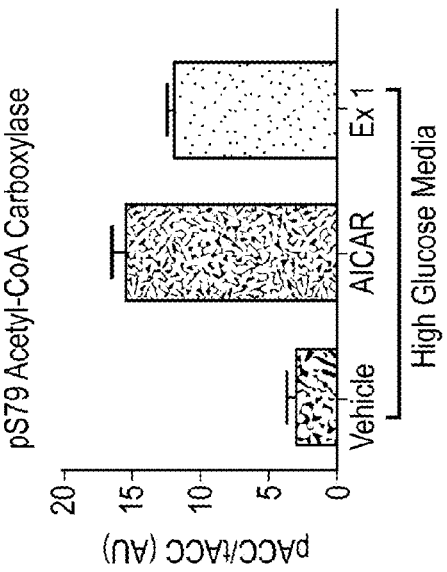
Figure 1A:
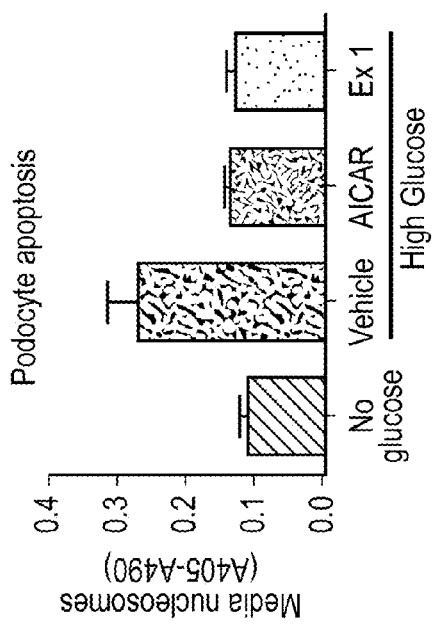
Figure 1C:
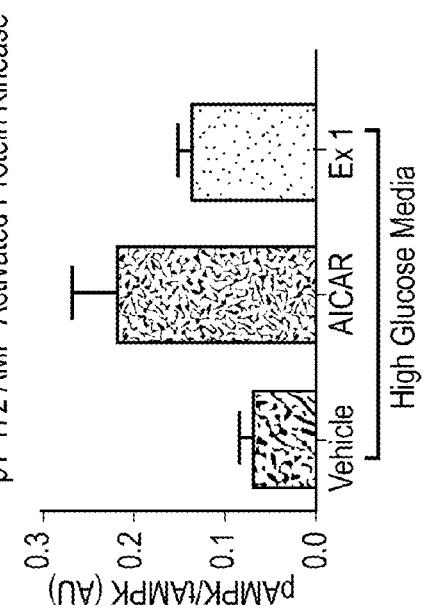

In another embodiment, the present invention provides compounds of Formula (I)

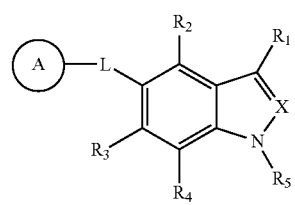

or a pharmaceutically acceptable salt thereof, wherein
X is N or CH;
L is a bond, O, S, $NR_4$, $(C_1-C_6)$alkylene, $(C_2-C_6)$alkenylene, or $(C_2-C_6)$alkynylene;
A is

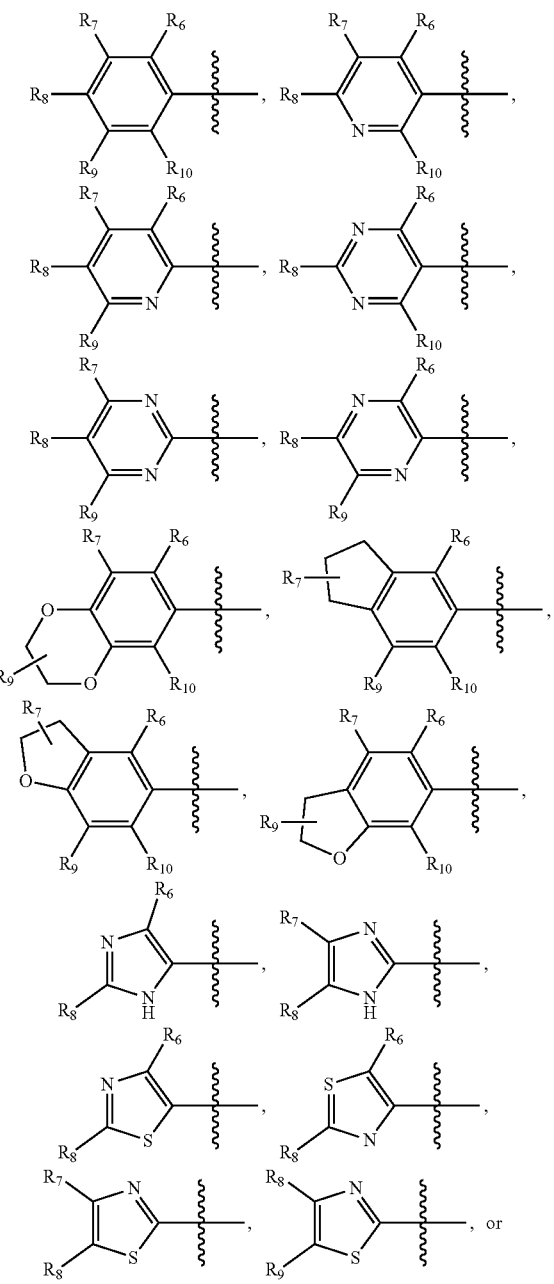

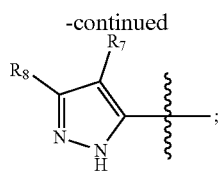

R$_1$ is —C(O)OR$_A$, —C(O)NR$_B$R$_C$, —S(O$_2$)OR$_A$, —S(O$_2$)NHC(O)R$_D$, 5-oxo-4,5-dihydro-1,2,4-oxadiazol-3-yl, or 1H-tetrazol-5-yl;

R$_A$ is H or (C$_1$-C$_6$)alkyl;

R$_B$ and R$_C$ are independently H, (C$_1$-C$_6$)alkyl, or —S(O$_2$)R$_D$;

R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$;

R$_E$ and R$_F$ are independently H or (C$_1$-C$_6$)alkyl;

R$_2$, R$_3$, and R$_4$ are independently H, (C$_1$-C$_6$)alkoxy, (C$_1$-C$_6$)alkyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_8$)alkyl, mercapto, nitro, —NR$_G$R$_H$, or (NR$_G$R$_H$)carbonyl;

R$_G$ and R$_H$ are independently H, (C$_1$-C$_6$)alkyl, or (C$_1$-C$_6$)alkylcarbonyl;

R$_5$ is H or (C$_1$-C$_6$)alkyl;

R$_6$, R$_7$, R$_9$, and R$_{10}$ are independently H, (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —NR$_J$R$_K$, or (NR$_J$R$_K$)carbonyl;

R$_J$ and R$_K$ are independently H or (C$_1$-C$_6$)alkyl;

R$_8$ is H, (C$_1$-C$_6$)alkoxy, (C$_1$-C$_6$)alkoxy(C$_1$-C$_6$)alkoxy, (C$_1$-C$_6$)alkoxy(C$_1$-C$_6$)alkyl, (C$_1$-C$_6$)alkoxycarbonyl, (C$_1$-C$_6$)alkyl, (C$_1$-C$_6$)alkylcarbonyl, (C$_1$-C$_6$)alkylthio, aryl, aryl(C$_1$-C$_6$)alkoxy, aryl(C$_1$-C$_6$)alkyl, arylcarbonyl, aryloxy, carboxy, carboxy(C$_1$-C$_6$)alkoxy, carboxy(C$_1$-C$_6$)alkyl, cyano, (C$_3$-C$_8$)cycloalkyl, (C$_3$-C$_8$)cycloalkyl(C$_1$-C$_6$)alkoxy, (C$_3$-C$_8$)cycloalkyl(C$_1$-C$_6$)alkyl, (C$_3$-C$_8$)cycloalkylcarbonyl, (C$_3$-C$_8$)cycloalkyloxy, halogen, halo(C$_1$-C$_6$)alkoxy, halo(C$_1$-C$_6$)alkyl, heteroaryl, heteroaryl(C$_1$-C$_6$)alkoxy, heteroaryl(C$_1$-C$_6$)alkyl, heteroarylcarbonyl, heteroaryloxy, (C$_3$-C$_7$)heterocycle, (C$_3$-C$_7$)heterocycle(C$_1$-C$_6$)alkoxy, (C$_3$-C$_7$)heterocycle(C$_1$-C$_6$)alkyl, (C$_3$-C$_7$)heterocyclecarbonyl, (C$_3$-C$_7$)heterocyclecarbonyl(C$_1$-C$_6$)alkyl, (C$_3$-C$_7$)heterocycleoxy, hydroxy, hydroxy(C$_1$-C$_6$)alkoxy, hydroxy(C$_1$-C$_6$)alkyl, mercapto, nitro, —NR$_M$R$_N$, —NR$_M$R$_N$(C$_1$-C$_6$)alkoxy, (NR$_M$R$_N$)carbonyl, (NR$_M$R$_N$)carbonyl(C$_1$-C$_6$)alkyl, or (NR$_M$R$_N$)carbonyl(C$_1$-C$_6$)alkoxy; wherein the aryl, aryl(C$_1$-C$_6$)alkoxy, aryl(C$_1$-C$_6$)alkyl, arylcarbonyl, and aryloxy are optionally substituted with 1, 2, 3, 4, or 5 substituents that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —NR$_M$R$_N$, or (NR$_M$R$_N$)carbonyl; wherein the halo(C$_1$-C$_6$)alkyl is optionally substituted with 1 or 2 hydroxy groups; wherein the (C$_3$-C$_8$)cycloalkyl, (C$_3$-C$_8$)cycloalkyl(C$_1$-C$_6$)alkoxy, (C$_3$-C$_8$)cycloalkyl(C$_1$-C$_6$)alkyl, (C$_3$-C$_8$)cycloalkylcarbonyl, and (C$_3$-C$_8$)cycloalkyloxy are optionally substituted with 1, 2, or 3 substituents that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —NR$_M$R$_N$, or (NR$_M$R$_N$)carbonyl; wherein the heteroaryl, heteroaryl(C$_1$-C$_6$)alkoxy, heteroaryl(C$_1$-C$_6$)alkyl, heteroarylcarbonyl, and heteroaryloxy, are optionally substituted with 1, 2, or 3 substituents that are independently (C$_1$-C$_6$)alkoxy, (C$_1$-C$_6$)alkoxycarbonyl, (C$_1$-C$_6$)alkyl, (C$_1$-C$_6$)alkylcarbonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —NR$_M$R$_N$, or (NR$_M$R$_N$)carbonyl; and wherein the (C$_3$-C$_7$)heterocycle, (C$_3$-C$_7$)heterocycle(C$_1$-C$_6$)alkoxy, (C$_3$-C$_7$)heterocycle(C$_1$-C$_6$)alkyl, (C$_3$-C$_7$)heterocyclecarbonyl, (C$_3$-C$_7$)heterocyclecarbonyl(C$_1$-C$_6$)alkyl, and (C$_3$-C$_7$)heterocycleoxy, are optionally substituted with 1, 2, or 3 substituents that are independently (C$_1$-C$_6$)alkoxy, (C$_1$-C$_6$)alkoxycarbonyl, (C$_1$-C$_6$)alkoxysulfonyl, (C$_1$-C$_6$)alkyl, (C$_1$-C$_6$)alkylcarbonyl, (C$_1$-C$_6$)alkylsulfonyl, (C$_1$-C$_6$)alkylthio, carboxy, cyano, halogen, halo(C$_1$-C$_6$)alkoxy, halo(C$_1$-C$_6$)alkyl, hydroxy, hydroxy(C$_1$-C$_6$)alkyl, mercapto, nitro, —NR$_M$R$_N$, (NR$_M$R$_N$)carbonyl, or oxo; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring;

provided that Formula (I) does not encompass
5-(4-bromophenyl)-1H-indole-3-carboxamide;
5-(2',6'-dihydroxy-[1,1'-biphenyl]-4-yl)-1H-indole-3-carboxamide; and
5-(2',6'-dimethoxy-[1,1]biphenyl]-4-yl)-1H-indole-3-carboxamide.

In another embodiment, the present invention provides compounds of Formula (I), or a pharmaceutically acceptable salt thereof, wherein X is N or CH; L is a bond or (C$_2$-C$_6$)alkynylene; A is

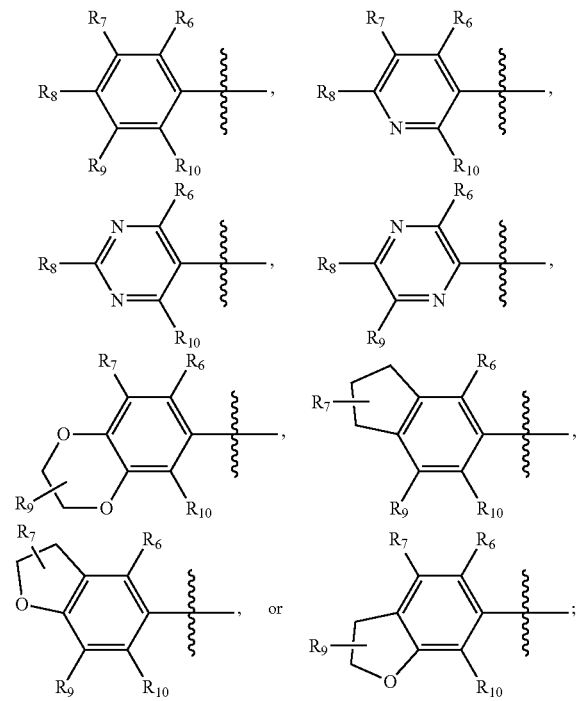

R$_1$ is —C(O)OR$_A$, —C(O)NR$_B$R$_C$, —S(O$_2$)OR$_A$; R$_A$ is H; R$_B$ and R$_C$ are independently H or —S(O$_2$)R$_D$; R$_D$ is (C$_1$-C$_6$)alkyl, —CF$_3$, or phenyl; R$_2$, R$_3$, and R$_4$ are independently H, (C$_1$-C$_6$)alkyl, cyano, or halogen; R$_5$ is H; R$_6$, R$_7$, R$_9$, and R$_{10}$ are independently H, (C$_1$-C$_6$)alkoxy, (C$_1$-C$_6$)alkyl, cyano, halogen, hydroxy, or hydroxy(C$_1$-C$_6$)alkyl; R$_8$ is H, (C$_1$-C$_6$)alkoxy, (C$_1$-C$_6$)alkoxy(C$_1$-C$_6$)alkyl, (C$_1$-C$_6$)alkyl, (C$_1$-C$_6$)alkylcarbonyl, aryl, carboxy(C$_1$-C$_6$)alkoxy, (C$_3$-C$_8$)cycloalkyl, (C₃-C₈)cycloalkyl(C₁-C₆)alkyl, (C₃-C₈)cycloalkyloxy, halo(C₁-C₆)alkyl, heteroaryl(C₁-C₆)alkoxy, (C₃-C₇)heterocycle, (C₃-C₇)heterocycle(C₁-C₆)alkoxy, (C₃-C₇)heterocyclecarbonyl(C₁-C₆)alkyl, (C₃-C₇)heterocycleoxy, hydroxy(C₁-C₆)alkoxy, hydroxy(C₁-C₆)alkyl, —NR$_M$R$_N$, (NR$_M$R$_N$)carbonyl(C₁-C₆)alkyl, or (NR$_M$R$_N$)carbonyl(C₁-C₆)alkoxy; wherein the aryl is optionally substituted with 1 substituent that is (C₁-C₆)alkoxy or hydroxy; wherein the halo(C₁-C₆)alkyl is optionally with 1 hydroxy group; wherein the (C₃-C₈)cycloalkyl, (C₃-C₈)cycloalkyl(C₁-C₆)alkyl, and (C₃-C₈)cycloalkyloxy are optionally substituted with 1 substituent that is carboxy, hydroxy, hydroxy(C₁-C₆)alkyl, or (NR$_M$R$_N$)carbonyl; and wherein the (C₃-C₇)heterocycle and (C₃-C₇)heterocycle(C₁-C₆)alkoxy are optionally substituted with 1 substituent that is (C₁-C₆)alkoxycarbonyl, (C₁-C₆)alkyl, (C₁-C₆)alkylcarbonyl, (C₁-C₆)alkylsulfonyl, hydroxy, hydroxy(C₁-C₆)alkyl, or oxo; and R$_M$ and R$_N$ are independently H, (C₁-C₆)alkyl, or (C₁-C₆)alkylcarbonyl; or R$_M$ and R$_N$ together with the nitrogen they are attached to form a 3 to 8 membered ring.

In another embodiment, the present invention provides compounds of Formula (II)

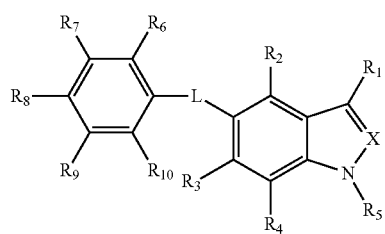

Formula (II)

or a pharmaceutically acceptable salt thereof, wherein X is N or CH; L is a bond, O, S, NR$_4$, (C₁-C₆)alkylene, (C₂-C₆)alkenylene, or (C₂-C₆)alkynylene; R$_1$ is —C(O)OR$_A$, —C(O)NR$_B$R$_C$, —S(O₂)OR$_A$, —S(O₂)NHC(O)R$_D$, 5-oxo-4,5-dihydro-1,2,4-oxadiazol-3-yl, or 1H-tetrazol-5-yl; R$_A$ is H or (C₁-C₆)alkyl; R$_B$ and R$_C$ are independently H, (C₁-C₆)alkyl, or —S(O₂)R$_D$; R$_D$ is (C₁-C₆)alkyl, —CF₃, or phenyl, wherein the phenyl is optionally substituted with 1, 2, 3, 4, or 5 substituents that are independently (C₁-C₆)alkoxy, (C₁-C₆)alkyl, cyano, halogen, halo(C₁-C₆)alkoxy, halo(C₁-C₆)alkyl, hydroxy, mercapto, nitro, or NR$_E$R$_F$; R$_E$ and R$_F$ are independently H or (C₁-C₆)alkyl; R$_2$, R$_3$, and R$_4$ are independently H, (C₁-C₆)alkoxy, (C₁-C₆)alkyl, (C₁-C₆)alkylthio, carboxy, cyano, halogen, halo(C₁-C₆)alkoxy, halo(C₁-C₆)alkyl, hydroxy, hydroxy(C₁-C₈)alkyl, mercapto, nitro, —NR$_G$R$_H$, or (NR$_G$R$_H$)carbonyl; R$_G$ and R$_H$ are independently H, (C₁-C₆)alkyl, or (C₁-C₆)alkylcarbonyl; R$_5$ is H or (C₁-C₆)alkyl; R$_6$, R$_7$, R$_9$, and R$_{10}$ are independently H, (C₁-C₆)alkoxy, (C₁-C₆)alkoxycarbonyl, (C₁-C₆)alkyl, (C₁-C₆)alkylcarbonyl, (C₁-C₆)alkylthio, carboxy, cyano, halogen, halo(C₁-C₆)alkoxy, halo(C₁-C₆)alkyl, hydroxy, hydroxy(C₁-C₆)alkyl, mercapto, nitro, —NR$_J$R$_K$, or (NR$_J$R$_K$)carbonyl; R$_J$ and R$_K$ are independently H or (C₁-C₆)alkyl; R$_8$ is H, (C₁-C₆)alkoxy, (C₁-C₆)alkoxy(C₁-C₆)alkoxy, (C₁-C₆)alkoxy(C₁-C₆)alkyl, (C₁-C₆)alkoxycarbonyl, (C₁-C₆)alkyl, (C₁-C₆)alkylcarbonyl, (C₁-C₆)alkylthio, aryl, aryl(C₁-C₆)alkoxy, aryl(C₁-C₆)alkyl, arylcarbonyl, aryloxy, carboxy, carboxy(C₁-C₆)alkoxy, carboxy(C₁-C₆)alkyl, cyano, (C₃-C₈)cycloalkyl, (C₃-C₈)cycloalkyl(C₁-C₆)alkoxy, (C₃-C₈)cycloalkyl(C₁-C₆)alkyl, (C₃-C₈)cycloalkylcarbonyl, (C₃-C₈)cycloalkyloxy, halogen, halo(C₁-C₆)alkoxy, halo(C₁-C₆)alkyl, heteroaryl, heteroaryl(C₁-C₆)alkoxy, heteroaryl(C₁-C₆)alkyl, heteroarylcarbonyl, heteroaryloxy, (C₃-C₇)heterocycle, (C₃-C₇)heterocycle(C₁-C₆)alkoxy, (C₃-C₇)heterocycle(C₁-C₆)alkyl, (C₃-C₇)heterocyclecarbonyl, (C₃-C₇)heterocyclecarbonyl(C₁-C₆)alkyl, (C₃-C₇)heterocycleoxy, hydroxy, hydroxy(C₁-C₆)alkoxy, hydroxy(C₁-C₆)alkyl, mercapto, nitro, —NR$_M$R$_N$, —NR$_M$R$_N$(C₁-C₆)alkoxy, (NR$_M$R$_N$)carbonyl, (NR$_M$R$_N$)carbonyl(C₁-C₆)alkyl, or (NR$_M$R$_N$)carbonyl(C₁-C₆)alkoxy; wherein the aryl, aryl(C₁-C₆)alkoxy, aryl(C₁-C₆)alkyl, arylcarbonyl, and aryloxy are optionally substituted with 1, 2, 3, 4, or 5 substituents that are independently (C₁-C₆)alkoxy, (C₁-C₆)alkoxycarbonyl, (C₁-C₆)alkyl, (C₁-C₆)alkylcarbonyl, (C₁-C₆)alkylthio, carboxy, cyano, halogen, halo(C₁-C₆) alkoxy, halo(C₁-C₆)alkyl, hydroxy, hydroxy(C₁-C₆)alkyl, mercapto, nitro, —NR$_M$R$_N$, or (NR$_M$R$_N$)carbonyl; wherein the halo(C₁-C₆)alkyl is optionally substituted with 1 or 2 hydroxy groups; wherein the (C₃-C₈)cycloalkyl, (C₃-C₈)cycloalkyl(C₁-C₆)alkoxy, (C₃-C₈)cycloalkyl(C₁-C₆)alkyl, (C₃-C₈)cycloalkylcarbonyl, and (C₃-C₈)cycloalkyloxy are optionally substituted with 1, 2, or 3 substituents that are independently (C₁-C₆)alkoxy, (C₁-C₆)alkoxycarbonyl, (C₁-C₆)alkyl, (C₁-C₆)alkylcarbonyl, (C₁-C₆)alkylthio, carboxy, cyano, halogen, halo(C₁-C₆)alkoxy, halo(C₁-C₆)alkyl, hydroxy, hydroxy(C₁-C₆)alkyl, mercapto, nitro, —NR$_M$R$_N$, or (NR$_M$R$_N$)carbonyl; wherein the heteroaryl, heteroaryl(C₁-C₆)alkoxy, heteroaryl(C₁-C₆)alkyl, heteroarylcarbonyl, and heteroaryloxy, are optionally substituted with 1, 2, or 3 substituents that are independently (C₁-C₆)alkoxy, (C₁-C₆)alkoxycarbonyl, (C₁-C₆)alkyl, (C₁-C₆)alkylcarbonyl, (C₁-C₆)alkylthio, carboxy, cyano, halogen, halo(C₁-C₆)alkoxy, halo(C₁-C₆)alkyl, hydroxy, hydroxy(C₁-C₆)alkyl, mercapto, nitro, —NR$_M$R$_N$, or (NR$_M$R$_N$)carbonyl; and wherein the (C₃-C₇)heterocycle, (C₃-C₇)heterocycle(C₁-C₆)alkoxy, (C₃-C₇)heterocycle(C₁-C₆)alkyl, (C₃-C₇)heterocyclecarbonyl, (C₃-C₇)heterocyclecarbonyl(C₁-C₆)alkyl, and (C₃-C₇)heterocycleoxy, are optionally substituted with 1, 2, or 3 substituents that are independently (C₁-C₆)alkoxy, (C₁-C₆)alkoxycarbonyl, (C₁-C₆)alkoxysulfonyl, (C₁-C₆)alkyl, (C₁-C₆)alkylcarbonyl, (C₁-C₆)alkylsulfonyl, (C₁-C₆)alkylthio, carboxy, cyano, halogen, halo(C₁-C₆)alkoxy, halo(C₁-C₆)alkyl, hydroxy, hydroxy(C₁-C₆)alkyl, mercapto, nitro, —NR$_M$R$_N$, (NR$_M$R$_N$)carbonyl, or oxo; and R$_M$ and R$_N$ are independently H, (C₁-C₆)alkyl, or (C₁-C₆)alkylcarbonyl; and R$_M$ and R$_N$ together with the nitrogen they are attached to form a 3 to 8 membered ring; provided that Formula (II) does not encompass 5-(4-bromophenyl)-1H-indole-3-carboxamide;
5-(2',6'-dihydroxy-[1,1'-biphenyl]-4-yl)-1H-indole-3-carboxamide; and
5-(2',6'-dimethoxy-[1,1]biphenyl]-4-yl)-1H-indole-3-carboxamide.

In another embodiment, the present invention provides compounds of Formula (II), or a pharmaceutically acceptable salt thereof, wherein X is CH or N; L is a bond; R$_1$ is —C(O)OR$_A$, —C(O)NR$_B$R$_C$, —S(O₂)OR$_A$, —S(O₂)NHC(O)R$_D$, 5-oxo-4,5-dihydro-1,2,4-oxadiazol-3-yl, or 1H-tetrazol-5-yl; R$_A$ is H or (C₁-C₆)alkyl; R$_B$ and R$_C$ are independently H, (C₁-C₆)alkyl, or —S(O₂)R$_D$; R$_D$ is (C₁-C₆)alkyl, —CF₃, or phenyl, wherein the phenyl is optionally substituted with 1, 2, 3, 4, or 5 substituents that are independently (C₁-C₆)alkoxy, (C₁-C₆)alkyl, cyano, halogen, halo(C₁-C₆)alkoxy, halo(C₁-C₆)alkyl, hydroxy, mercapto, nitro, or NR$_E$R$_F$; R$_E$ and R$_F$ are independently H or (C₁-C₆)alkyl; R$_2$, R$_3$, and R$_4$ are independently H, (C₁-C₆)alkoxy, (C₁-C₆)alkyl, (C₁-C₆)alkylthio, carboxy, cyano, halogen, halo(C₁-C₆)alkoxy, halo(C₁-C₆)alkyl, hydroxy, hydroxy(C₁-C₈)alkyl, mercapto, nitro, —NR$_G$R$_H$, or (NR$_G$R$_H$)carbonyl; R$_G$ and R$_H$ are independently H, (C₁-C₆)alkyl, or (C₁-C₆)alkylcarbonyl; R$_5$ is H or ($C_1$-$C_6$)alkyl; $R_6$, $R_7$, $R_9$, and $R_{10}$ are independently H, ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_JR_K$ or ($NR_JR_K$)carbonyl; $R_J$ and $R_K$ are independently H or ($C_1$-$C_6$)alkyl; $R_8$ is H, ($C_1$-$C_6$)alkoxy, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, carboxy($C_1$-$C_6$)alkoxy, carboxy($C_1$-$C_6$)alkyl, cyano, halogen, halo($C_1$-$C_6$)alkoxy, halo($C_1$-$C_6$)alkyl, hydroxy, hydroxy($C_1$-$C_6$)alkoxy, hydroxy($C_1$-$C_6$)alkyl, mercapto, nitro, —$NR_MR_N$, —$NR_MR_N$($C_1$-$C_6$)alkoxy, —$NR_MR_N$($C_1$-$C_6$)alkyl, ($NR_MR_N$)carbonyl, ($NR_MR_N$)carbonyl($C_1$-$C_6$)alkyl, or ($NR_MR_N$)carbonyl($C_1$-$C_6$)alkoxy; wherein the halo($C_1$-$C_6$)alkyl is optionally substituted with 1 or 2 hydroxy groups; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_MR_N$($C_1$-$C_6$)alkoxy, ($NR_MR_N$)carbonyl($C_1$-$C_6$)alkyl, or ($NR_MR_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_MR_N$($C_1$-$C_6$)alkoxy, ($NR_MR_N$)carbonyl($C_1$-$C_6$)alkyl, or ($NR_MR_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F or CN; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_MR_N$($C_1$-$C_6$)alkoxy, ($NR_MR_N$)carbonyl($C_1$-$C_6$)alkyl, or ($NR_MR_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$, and $R_{10}$ are H; and $R_8$ is hydroxy($C_1$-$C_6$)alkoxy.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F, or CN; $R_4$ is H; $R_5$ is H; $R_6$, $R_9$, and $R_{10}$ are H; $R_7$ is H or ($C_1$-$C_6$)alkoxy; and $R_8$ is hydroxy($C_1$-$C_6$)alkoxy.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F, or CN; $R_4$ is H; $R_5$ is H; $R_6$, $R_9$, and $R_{10}$ are H; $R_7$ is methoxy; and $R_8$ is hydroxy($C_1$-$C_6$)alkoxy.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$, and $R_{10}$ are H; and $R_8$ is ($C_1$-$C_6$)alkoxy.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F, or CN; $R_4$ is H; $R_5$ is H; $R_6$, $R_7$, $R_9$, and $R_{10}$ are H; and $R_8$ is ($C_1$-$C_6$)alkoxy.

In another embodiment, the present invention provides compounds of Formula (II), or a pharmaceutically acceptable salt thereof, wherein X is CH; L is a bond; $R_1$ is —C(O)O$R_A$; $R_A$ is H; $R_2$ is H or F; $R_3$ is Cl, F, or CN; $R_4$ is H; $R_5$ is H; $R_6$, $R_9$, and $R_{10}$ are H; $R_7$ is methoxy; and $R_8$ is ($C_1$-$C_6$)alkoxy.

In another embodiment, the present invention provides compounds of Formula (II), or a pharmaceutically acceptable salt thereof, wherein X is N; L is a bond; $R_1$ is —C(O)O$R_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_MR_N$($C_1$-$C_6$)alkoxy, ($NR_MR_N$)carbonyl($C_1$-$C_6$)alkyl, or ($NR_MR_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)O$R_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_MR_N$($C_1$-$C_6$)alkoxy, ($NR_MR_N$)carbonyl($C_1$-$C_6$)alkyl, or ($NR_MR_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)O$R_A$; $R_A$ is H; $R_2$ is H or F; $R_3$ is Cl, F, or CN; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)$NR_B R_C$; $R_B$ and $R_C$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)$NR_B R_C$; $R_B$ and $R_C$ are independently H or ($C_1$-$C_6$)alkyl; $R_4$ is H; $R_2$ is H or F; $R_3$ is methyl, cyano, Cl, or F; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)$NR_B R_C$; $R_B$ and $R_C$ are independently H or ($C_1$-$C_6$)alkyl; $R_2$ is H or F; $R_3$ is Cl, F, or CN; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)$NR_B R_C$; $R_B$ and $R_C$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)$NR_B R_C$; $R_B$ and $R_C$ are independently H or ($C_1$-$C_6$)alkyl; $R_4$ is H; $R_2$ is H or F; $R_3$ is methyl, cyano, Cl, or F; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)$NR_B R_C$; $R_B$ and $R_C$ are independently H or ($C_1$-$C_6$)alkyl; $R_2$ is H or F; $R_3$ is Cl, F, or CN; $R_4$ is H; $R_5$ is H; $R_6$, $R_7$, $R_9$, and $R_{10}$ are independently H, ($C_1$-$C_6$)alkoxy, halogen, hydroxy, or hydroxy($C_1$-$C_6$)alkyl; $R_8$ is H, ($C_1$-$C_6$)alkoxy, ($C_1$-$C_6$)alkoxy ($C_1$-$C_6$)alkyl, ($C_1$-$C_6$)alkyl, ($C_1$-$C_6$)alkylcarbonyl, carboxy ($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)$NR_B R_C$; $R_B$ is H; $R_C$ is —S(O$_2$)$R_D$; $R_D$ is ($C_1$-$C_6$)alkyl, —CF$_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_E R_F$; $R_E$ and $R_F$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$, and $R_{10}$ are H; $R_8$ is ($C_1$-$C_6$)alkoxy, ($C_1$-$C_6$)alkoxy($C_1$-$C_6$)alkyl, ($C_1$-$C_6$)alkyl, ($C_1$-$C_6$)alkylcarbonyl, carboxy($C_1$-$C_6$)alkoxy, halo($C_1$-$C_6$)alkyl, hydroxy($C_1$-$C_6$)alkoxy, hydroxy($C_1$-$C_6$)alkyl, —$NR_M R_N$($C_1$-$C_6$)alkoxy, ($NR_M R_N$)carbonyl($C_1$-$C_6$)alkyl, or ($NR_M R_N$)carbonyl($C_1$-$C_6$)alkoxy; wherein the halo($C_1$-$C_6$)alkyl is optionally substituted with 1 hydroxy group; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)$NR_B R_C$; $R_B$ is H; $R_C$ is —S(O$_2$)$R_D$; $R_D$ is ($C_1$-$C_6$)alkyl, —CF$_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_E R_F$; $R_E$ and $R_F$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$, $R_9$, and $R_{10}$ are H; $R_7$ is H or methoxy; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II) or a pharmaceutically acceptable salt thereof, wherein X is CH; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$(C$_1$-C$_6$)alkoxy, (NR$_M$R$_N$)carbonyl(C$_1$-C$_6$)alkyl, or (NR$_M$R$_N$)carbonyl(C$_1$-C$_6$)alkoxy; wherein the halo(C$_1$-C$_6$)alkyl is optionally substituted with 1 hydroxy group; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)NR$_B$R$_C$; $R_B$ is H; $R_C$ is —S(O$_2$)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is Cl, F, or CN; $R_4$ is H; $R_5$ is H; $R_6$, $R_7$, $R_9$, and $R_{10}$ are independently H, (C$_1$-C$_6$)alkoxy, halogen, hydroxy, or hydroxy(C$_1$-C$_6$)alkyl; $R_8$ is (C$_1$-C$_6$)alkoxy, (C$_1$-C$_6$)alkoxy(C$_1$-C$_6$)alkyl, (C$_1$-C$_6$)alkyl, (C$_1$-C$_6$)alkylcarbonyl, carboxy(C$_1$-C$_6$)alkoxy, halo(C$_1$-C$_6$)alkyl, hydroxy(C$_1$-C$_6$)alkoxy, hydroxy(C$_1$-C$_6$)alkyl, —NR$_M$R$_N$(C$_1$-C$_6$)alkoxy, (NR$_M$R$_N$)carbonyl(C$_1$-C$_6$)alkyl, or (NR$_M$R$_N$)carbonyl(C$_1$-C$_6$)alkoxy; wherein the halo(C$_1$-C$_6$)alkyl is optionally substituted with 1 hydroxy group; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is (C$_1$-C$_6$)alkoxy, (C$_1$-C$_6$)alkoxy(C$_1$-C$_6$)alkyl, (C$_1$-C$_6$)alkyl, (C$_1$-C$_6$)alkylcarbonyl, carboxy(C$_1$-C$_6$)alkoxy, halo(C$_1$-C$_6$)alkyl, hydroxy(C$_1$-C$_6$)alkoxy, hydroxy(C$_1$-C$_6$)alkyl, —NR$_M$R$_N$(C$_1$-C$_6$)alkoxy, (NR$_M$R$_N$)carbonyl(C$_1$-C$_6$)alkyl, or (NR$_M$R$_N$)carbonyl(C$_1$-C$_6$)alkoxy; wherein the halo(C$_1$-C$_6$)alkyl is optionally substituted with 1 hydroxy group; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$, $R_9$, and $R_{10}$ are H; $R_7$ is H or methoxy; $R_8$ is (C$_1$-C$_6$)alkoxy, (C$_1$-C$_6$)alkoxy(C$_1$-C$_6$)alkyl, (C$_1$-C$_6$)alkyl, (C$_1$-C$_6$)alkylcarbonyl, carboxy(C$_1$-C$_6$)alkoxy, halo(C$_1$-C$_6$)alkyl, hydroxy(C$_1$-C$_6$)alkoxy, hydroxy(C$_1$-C$_6$)alkyl, —NR$_M$R$_N$(C$_1$-C$_6$)alkoxy, (NR$_M$R$_N$)carbonyl(C$_1$-C$_6$)alkyl, or (NR$_M$R$_N$)carbonyl(C$_1$-C$_6$)alkoxy; wherein the halo(C$_1$-C$_6$)alkyl is optionally substituted with 1 hydroxy group; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$, $R_7$, $R_9$, and $R_{10}$ are independently H, (C$_1$-C$_6$)alkoxy, halogen, hydroxy, or hydroxy(C$_1$-C$_6$)alkyl; $R_8$ is (C$_1$-C$_6$)alkoxy, (C$_1$-C$_6$)alkoxy(C$_1$-C$_6$)alkyl, (C$_1$-C$_6$)alkyl, (C$_1$-C$_6$)alkylcarbonyl, carboxy(C$_1$-C$_6$)alkoxy, halo(C$_1$-C$_6$)alkyl, hydroxy(C$_1$-C$_6$)alkoxy, hydroxy(C$_1$-C$_6$)alkyl, —NR$_M$R$_N$(C$_1$-C$_6$)alkoxy, (NR$_M$R$_N$)carbonyl(C$_1$-C$_6$)alkyl, or (NR$_M$R$_N$)carbonyl(C$_1$-C$_6$)alkoxy; wherein the halo(C$_1$-C$_6$)alkyl is optionally substituted with 1 hydroxy group; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is Cl, F, or CN; $R_4$ is H; $R_5$ is H; $R_6$, $R_7$, $R_9$, and $R_{10}$ are independently H, (C$_1$-C$_6$)alkoxy, halogen, hydroxy, or hydroxy(C$_1$-C$_6$)alkyl; $R_8$ is (C$_1$-C$_6$)alkoxy, (C$_1$-C$_6$)alkoxy(C$_1$-C$_6$)alkyl, (C$_1$-C$_6$)alkyl, (C$_1$-C$_6$)alkylcarbonyl, carboxy(C$_1$-C$_6$)alkoxy, halo(C$_1$-C$_6$)alkyl, hydroxy(C$_1$-C$_6$)alkoxy, hydroxy(C$_1$-C$_6$)alkyl, —NR$_M$R$_N$(C$_1$-C$_6$)alkoxy, (NR$_M$R$_N$)carbonyl(C$_1$-C$_6$)alkyl, or (NR$_M$R$_N$)carbonyl(C$_1$-C$_6$)alkoxy; wherein the halo(C$_1$-C$_6$)alkyl is optionally substituted with 1 hydroxy group; and R$_M$ and R$_N$ are independently H, (C$_1$-C$_6$)alkyl, or (C$_1$-C$_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —S(O$_2$)OR$_A$;

$R_4$ is H; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —S(O$_2$)OR$_A$; $R_A$ is H; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —S(O$_2$)OR$_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is —S(O$_2$)OR$_A$; $R_A$ is H; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —S(O$_2$)NHC(O)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —S(O$_2$)NHC(O)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —NR$_M$R$_N$$(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and R$_M$ and R$_N$ are independently H, $(C_1-C_6)$alkyl, or $(C_1-C_6)$alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —S(O$_2$)NHC(O)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is $-S(O_2)NHC(O)R_D$; $R_D$ is $(C_1-C_6)$alkyl, $-CF_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is $-S(O_2)NHC(O)R_D$; $R_D$ is $(C_1-C_6)$alkyl, $-CF_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is $-S(O_2)NHC(O)R_D$; $R_D$ is $(C_1-C_6)$alkyl, $-CF_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, $-NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 1H-tetrazol-5-yl; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$, $R_7$, $R_9$, and $R_{10}$ are independently H, $(C_1-C_6)$alkoxy, halogen, hydroxy, or hydroxy$(C_1-C_6)$alkyl; $R_8$ is $(C_1-C_6)$alkoxy, $(C_1-C_6)$alkoxy$(C_1-C_6)$alkyl, $(C_1-C_6)$alkyl, $(C_1-C_6)$alkylcarbonyl, carboxy$(C_1-C_6)$alkoxy, halo$(C_1-C_6)$alkyl, hydroxy$(C_1-C_6)$alkoxy, hydroxy$(C_1-C_6)$alkyl, —$NR_MR_N(C_1-C_6)$alkoxy, $(NR_MR_N)$carbonyl$(C_1-C_6)$alkyl, or $(NR_MR_N)$carbonyl$(C_1-C_6)$alkoxy; wherein the halo$(C_1-C_6)$alkyl is optionally substituted with 1 hydroxy group; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH or N; L is a bond; $R_1$ is —C(O)OR$_A$, —C(O)NR$_B$R$_C$, —S(O$_2$)OR$_A$, —S(O$_2$)NHC(O)R$_D$, 5-oxo-4,5-dihydro-1,2,4-oxadiazol-3-yl, or 1H-tetrazol-5-yl; $R_A$ is H or $(C_1-C_6)$alkyl; $R_B$ and $R_C$ are independently H, $(C_1-C_6)$alkyl, or —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$, $R_3$, and $R_4$ are independently H, $(C_1-C_6)$alkoxy, $(C_1-C_6)$alkyl, $(C_1-C_6)$alkylthio, carboxy, cyano, halogen, halo$(C_1-C_6)$alkoxy, halo$(C_1-C_6)$ alkyl, hydroxy, hydroxy($C_1$-$C_8$)alkyl, mercapto, nitro, —$NR_GR_H$, or ($NR_GR_H$)carbonyl; $R_G$ and $R_H$ are independently H, ($C_1$-$C_6$)alkyl, or ($C_1$-$C_6$)alkylcarbonyl; $R_5$ is H or ($C_1$-$C_6$)alkyl; $R_6$, $R_7$, $R_9$, and $R_{10}$ are independently H, ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_JR_K$, or ($NR_JR_K$)carbonyl; $R_J$ and $R_K$ are independently H or ($C_1$-$C_6$)alkyl; $R_8$ is aryl, aryl ($C_1$-$C_6$)alkoxy, aryl($C_1$-$C_6$)alkyl, arylcarbonyl, or aryloxy, wherein each is optionally substituted with 1, 2, 3, 4, or 5 substituents that are independently ($C_1$-$C_6$)alkyl, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_MR_N$, or ($NR_MR_N$)carbonyl; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring; provided that Formula (II) does not encompass 5-(4-bromophenyl)-1H-indole-3-carboxamide;

5-(2',6'-dihydroxy-[1,1'-biphenyl]-4-yl)-1H-indole-3-carboxamide; and 5-(2',6'-dimethoxy-[1,1]biphenyl]-4-yl)-1H-indole-3-carboxamide.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ and $R_5$ are H; $R_6$ and $R_7$ are independently H, F, or methoxy; $R_9$ and $R_{10}$ are H; $R_8$ is aryl wherein the aryl is phenyl substituted with 1 substituent that is hydroxy.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$, $R_5$, $R_6$, $R_7$, $R_9$, and $R_{10}$ are H; $R_8$ is aryl wherein the aryl is phenyl substituted with 1 substituent that is hydroxy.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)$NR_BR_C$; $R_B$ and $R_C$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or (C$_1$-C$_6$)alkyl; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or (C$_1$-C$_6$)alkyl; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or (C$_1$-C$_6$)alkyl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is N; L is a bond; $R_1$ is —C(O)NR$_B$R$_C$; $R_B$ is H; $R_C$ is —S(O$_2$)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; $R_E$ and $R_F$ are independently H or $(C_1-C_6)$alkyl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is $(C_1-C_6)$alkoxy or hydroxy.

In another embodiment, the present invention provides compounds of Formula (II), or a pharmaceutically acceptable salt thereof, wherein X is CH; L is a bond; $R_1$ is —S(O$_2$)OR$_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)OR$_4$; $R_4$ is H; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)OR$_4$; $R_4$ is H; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)OR$_4$; $R_4$ is H; $R_2$ is H or halogen; $R_3$ is (C$_1$-C$_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)OR$_4$; $R_4$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)OR$_4$; $R_4$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)OR$_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)OR$_4$; $R_4$ is H; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$) alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is (C$_1$-C$_6$)alkoxy or hydroxy.

In another embodiment, the present invention provides compounds of Formula (II), or a pharmaceutically acceptable salt thereof, wherein X is N; L is a bond; $R_1$ is —S(O$_2$)NHC (O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$) alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —$S(O_2)NHC$(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$) alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —$S(O_2)NHC$(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —$S(O_2)NHC$(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —$S(O_2)NHC$(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is —$S(O_2)NHC$(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$) alkoxy or hydroxy.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is ($C_1$-$C_6$)alkoxy or hydroxy.

In another embodiment, the present invention provides compounds of Formula (II), or a pharmaceutically acceptable salt thereof, wherein X is N; L is a bond; $R_1$ is 5-oxo-4,5- dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH; L is a bond; $R_1$ is 1H-tetrazol-5-yl; $R_2$ is H or halogen; $R_3$ is $(C_1\text{-}C_6)$alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH; L is a bond; $R_1$ is 1H-tetrazol-5-yl; $R_2$ is H or halogen; $R_3$ is $(C_1\text{-}C_6)$alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 1H-tetrazol-5-yl; $R_2$ is H or halogen; $R_3$ is $(C_1\text{-}C_6)$alkyl, cyano, or halogen; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 1H-tetrazol-5-yl; $R_2$ is H or halogen; $R_3$ is $(C_1\text{-}C_6)$alkyl, cyano, or halogen; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is methyl, cyano, Cl, or F; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is Cl, F, or CN; $R_4$ is H; $R_5$ is H; $R_6$, $R_7$, $R_9$, and $R_{10}$ are H; $R_8$ is aryl wherein the aryl is phenyl substituted with 1 substituent that is $(C_1\text{-}C_6)$alkoxy or hydroxy.

In another embodiment, the present invention provides compounds of Formula (II), or a pharmaceutically acceptable salt thereof, wherein X is CH or N; L is a bond; $R_1$ is —C(O)OR$_A$, —C(O)NR$_B$R$_C$, —S(O$_2$)OR$_A$, —S(O$_2$)NHC(O)R$_D$, 5-oxo-4,5-dihydro-1,2,4-oxadiazol-3-yl, or 1H-tetrazol-5-yl; R$_A$ is H or $(C_1\text{-}C_6)$alkyl; R$_B$ and R$_C$ are independently H, $(C_1\text{-}C_6)$alkyl, or —S(O$_2$)R$_D$; R$_D$ is $(C_1\text{-}C_6)$alkyl, —CF$_3$, or phenyl, wherein the phenyl is optionally substituted with 1, 2, 3, 4, or 5 substituents that are independently $(C_1\text{-}C_6)$alkoxy, $(C_1\text{-}C_6)$alkyl, cyano, halogen, halo$(C_1\text{-}C_6)$alkoxy, halo$(C_1\text{-}C_6)$alkyl, hydroxy, mercapto, nitro, or NR$_E$R$_F$; R$_E$ and R$_F$ are independently H or $(C_1\text{-}C_6)$alkyl; $R_2$, $R_3$, and $R_4$ are independently H, $(C_1\text{-}C_6)$alkoxy, $(C_1\text{-}C_6)$alkyl, $(C_1\text{-}C_6)$alkylthio, carboxy, cyano, halogen, halo$(C_1\text{-}C_6)$alkoxy, halo$(C_1\text{-}C_6)$alkyl, hydroxy, hydroxy$(C_1\text{-}C_8)$alkyl, mercapto, nitro, —NR$_G$R$_H$, or (NR$_G$R$_H$)carbonyl; R$_G$ and R$_H$ are independently H, $(C_1\text{-}C_6)$alkyl, or $(C_1\text{-}C_6)$alkylcarbonyl; $R_5$ is H or $(C_1\text{-}C_6)$alkyl; $R_6$, $R_7$, $R_9$, and $R_{10}$ are independently H, $(C_1\text{-}C_6)$alkoxy, $(C_1\text{-}C_6)$alkoxycarbonyl, $(C_1\text{-}C_6)$alkyl, $(C_1\text{-}C_6)$alkylcarbonyl, $(C_1\text{-}C_6)$alkylthio, carboxy, cyano, halogen, halo$(C_1\text{-}C_6)$alkoxy, halo$(C_1\text{-}C_6)$alkyl, hydroxy, hydroxy$(C_1$-

$C_6$)alkyl, mercapto, nitro, —$NR_JR_K$, or ($NR_JR_K$)carbonyl; $R_J$ and $R_K$ are independently H or ($C_1$-$C_6$)alkyl; $R_8$ is ($C_3$-$C_7$)heterocycle, ($C_3$-$C_7$)heterocycle($C_1$-$C_6$)alkoxy, ($C_3$-$C_7$)heterocycle($C_1$-$C_6$)alkyl, ($C_3$-$C_7$)heterocyclecarbonyl, ($C_3$-$C_7$)heterocyclecarbonyl($C_1$-$C_6$)alkyl, or ($C_3$-$C_7$)heterocycleoxy, wherein each is optionally substituted with 1, 2, or 3 substituents that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylsulfonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_MR_N$, ($NR_MR_N$)carbonyl, or oxo; and $R_M$ and $R_N$ are independently H, ($C_1$-$C_6$)alkyl, or ($C_1$-$C_6$)alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is Cl, F, or CN; $R_4$ is H; $R_5$ is H; $R_6$, $R_7$, $R_9$, and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle or ($C_3$-$C_7$)heterocycle($C_1$-$C_6$)alkoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is Cl, F, or CN; $R_4$ is H; $R_5$ is H; $R_6$, $R_7$, $R_9$, and $R_{10}$ are H; $R_8$ is ($C_3$-$C_7$)heterocycle or ($C_3$-$C_7$)heterocycle($C_1$-$C_6$)alkoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$C(O)OR_4$;

$R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is ($C_3$-$C_7$)heterocycle wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle($C_1$-$C_6$)alkoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is ($C_3$-$C_7$)heterocycle($C_1$-$C_6$)alkoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, $R_9$, and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —C(O)$NR_BR_C$; $R_B$ and $R_C$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —C(O)$NR_BR_C$; $R_B$ and $R_C$ are independently H or ($C_1$-$C_6$)alkyl; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)

heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or $(C_1-C_6)$alkyl; $R_4$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_7)$heterocycle, $(C_3-C_7)$heterocycle$(C_1-C_6)$alkoxy, $(C_3-C_7)$heterocyclecarbonyl$(C_1-C_6)$alkyl, or $(C_3-C_7)$heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is N; L is a bond; $R_1$ is —C(O)NR$_B$R$_C$; R$_B$ is H; R$_C$ is —S(O$_2$)R$_D$; R$_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$NR_BR_C$; $R_B$ is H; $R_C$ is —S(O$_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —C(O)$NR_BR_C$; $R_B$ is H; $R_C$ is —S(O$_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy ($C_1$-$C_6$)alkyl, or oxo.

In another embodiment, the present invention provides compounds of Formula (II), or a pharmaceutically acceptable salt thereof, wherein X is CH; L is a bond; $R_1$ is —S(O$_2$)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —S(O$_2$)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —S(O$_2$)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —S(O$_2$)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —S(O$_2$)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —S(O$_2$)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —S(O$_2$)NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$) alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$S(O_2)NHC(O)R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$) heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is —$S(O_2)NHC(O)R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$) alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —$S(O_2)NHC(O)R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$) alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is —$S(O_2)NHC(O)R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl ($C_1$-$C_6$)alkyl, or ($C_3$-$C_7$)heterocycleoxy, wherein the ($C_3$-$C_7$) heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy ($C_1$-$C_6$)alkyl, or oxo.

In another embodiment, the present invention provides compounds of Formula (II), or a pharmaceutically acceptable salt thereof, wherein X is N; L is a bond; $R_1$ is —$S(O_2)NHC(O)R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$) alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy ($C_1$-$C_6$)alkyl, or oxo.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-

$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is 1H-tetrazol-5-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is 1H-tetrazol-5-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the ($C_3$-$C_7$)heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is ($C_1$-$C_6$)alkoxycarbonyl, ($C_1$-$C_6$)alkyl, ($C_1$-$C_6$)alkylcarbonyl, ($C_1$-$C_6$)alkylsulfonyl, hydroxy, hydroxy($C_1$-$C_6$)alkyl, or oxo.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_7$)heterocycle, ($C_3$-$C_7$)heterocycle($C_1$-$C_6$)alkoxy, ($C_3$-$C_7$)heterocyclecarbonyl($C_1$-$C_6$)alkyl, or ($C_3$-$C_7$)heterocycleoxy, wherein the $(C_3-C_7)$heterocycle is azetidinyl, morpholinyl, oxetanyl, piperazinyl, piperidinyl, pyrrolidinyl, tetrahydrofuran, tetrahydro-2H-pyran, or triazolyl, wherein each is optionally substituted with 1 substituent that is $(C_1-C_6)$alkoxycarbonyl, $(C_1-C_6)$alkyl, $(C_1-C_6)$alkylcarbonyl, $(C_1-C_6)$alkylsulfonyl, hydroxy, hydroxy$(C_1-C_6)$alkyl, or oxo.

In another embodiment, the present invention provides compounds of Formula (II), or a pharmaceutically acceptable salt thereof, wherein X is CH or N; L is a bond; $R_1$ is —C(O)$OR_A$, —C(O)$NR_BR_C$, —S(O$_2$)$OR_A$, —S(O$_2$)NHC(O)$R_D$, 5-oxo-4,5-dihydro-1,2,4-oxadiazol-3-yl, or 1H-tetrazol-5-yl; $R_A$ is H or $(C_1-C_6)$alkyl; $R_B$ and $R_C$ are independently H, $(C_1-C_6)$alkyl, or —S(O$_2$)$R_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$, $R_3$, and $R_4$ are independently H, $(C_1-C_6)$alkoxy, $(C_1-C_6)$alkyl, $(C_1-C_6)$alkylthio, carboxy, cyano, halogen, halo$(C_1-C_6)$alkoxy, halo$(C_1-C_6)$alkyl, hydroxy, hydroxy$(C_1-C_8)$alkyl, mercapto, nitro, —$NR_GR_H$, or $(NR_GR_H)$carbonyl; $R_G$ and $R_H$ are independently H, $(C_1-C_6)$alkyl, or $(C_1-C_6)$alkylcarbonyl; $R_5$ is H or $(C_1-C_6)$alkyl; $R_6$, $R_7$, $R_9$, and $R_{10}$ are independently H, $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_JR_K$, or $(NR_JR_K)$carbonyl; $R_J$ and $R_K$ are independently H or $(C_1-C_6)$alkyl; $R_8$ is heteroaryl, heteroaryl$(C_1-C_6)$alkoxy, heteroaryl$(C_1-C_6)$alkyl, heteroarylcarbonyl, or heteroaryloxy, wherein each is optionally substituted with 1, 2, or 3 substituents that are independently $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_MR_N$, or $(NR_MR_N)$carbonyl; and $R_M$ and $R_N$ are independently H, $(C_1-C_6)$alkyl, or $(C_1-C_6)$alkylcarbonyl; or $R_M$ and $R_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or halogen; $R_3$ is $(C_1-C_6)$alkyl, cyano, or halogen; $R_4$ is H; $R_5$ is H; $R_6$, $R_7$, $R_9$, and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, $R_9$, and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$NR_BR_C$; $R_B$ and $R_C$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)$NR_BR_C$; $R_B$ and $R_C$ are independently H or $(C_1-C_6)$alkyl; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl$(C_1-C_6)$alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)NR$_B$R$_C$; R$_B$ and R$_C$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_4$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)NR$_B$R$_C$; R$_B$ and R$_C$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —C(O)NR$_B$R$_C$; R$_B$ is H; R$_C$ is —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently (C$_1$-C$_6$)alkoxy, (C$_1$-C$_6$)alkyl, cyano, halogen, halo(C$_1$-C$_6$)alkoxy, halo(C$_1$-C$_6$)alkyl, hydroxy, mercapto, nitro, or NR$_E$R$_F$; R$_E$ and R$_F$ are independently H or (C$_1$-C$_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —S(O$_2$)OR$_A$; R$_A$ is H; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —S(O$_2$)OR$_A$; R$_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —S(O$_2$)OR$_A$; R$_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —S(O$_2$)OR$_A$; R$_A$ is H; $R_2$ is H or halogen; $R_3$ is (C$_1$-C$_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl(C$_1$-C$_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —$S(O_2)OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —$S(O_2)OR_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —$S(O_2)$NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —$S(O_2)$NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is —$S(O_2)$NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —$S(O_2)$NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —$S(O_2)$NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is —$S(O_2)$NHC(O)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is 1H-tetrazol-5-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is 1H-tetrazol-5-yl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is heteroaryl($C_1$-$C_6$)alkoxy wherein the heteroaryl is pyridinyl.

In another embodiment, the present invention provides compounds of Formula (II), or a pharmaceutically acceptable salt thereof, wherein X is CH or N; L is a bond; $R_1$ is —C(O)OR$_A$, —C(O)NR$_B$R$_C$, —S(O$_2$)OR$_A$, —S(O$_2$)NHC(O)R$_D$, 5-oxo-4,5-dihydro-1,2,4-oxadiazol-3-yl, or 1H-tetrazol-5-yl; R$_A$ is H or ($C_1$-$C_6$)alkyl; R$_B$ and R$_C$ are independently H, ($C_1$-$C_6$)alkyl, or —S(O$_2$)R$_D$; R$_D$ is ($C_1$-$C_6$)alkyl, —CF$_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or NR$_E$R$_F$; R$_E$ and R$_F$ are independently H or ($C_1$-$C_6$)alkyl; $R_2$, $R_3$, and $R_4$ are independently H, ($C_1$-$C_6$)alkoxy, ($C_1$-$C_6$)alkyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —NR$_G$R$_H$, or (NR$_G$R$_H$)carbonyl; R$_G$ and R$_H$ are independently H, ($C_1$-$C_6$)alkyl, or ($C_1$-$C_6$)alkylcarbonyl; $R_5$ is H or ($C_1$-$C_6$)alkyl; $R_6$, $R_7$, $R_9$, and $R_{10}$ are independently H, ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —NR$_J$R$_K$, or (NR$_J$R$_K$)carbonyl; R$_J$ and R$_K$ are independently H or ($C_1$-$C_6$)alkyl; $R_8$ is ($C_3$-$C_8$)cycloalkyl, ($C_3$-$C_8$)cycloalkyl($C_1$-$C_6$)alkoxy, ($C_3$-$C_8$)cycloalkyl($C_1$-$C_6$)alkyl, ($C_3$-$C_8$)cycloalkylcarbonyl, and ($C_3$-$C_8$)cycloalkyloxy wherein each is optionally substituted with 1, 2, or 3 substituents that are independently ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —NR$_M$R$_N$, or (NR$_M$R$_N$)carbonyl; R$_M$ and R$_N$ are independently H, ($C_1$-$C_6$)alkyl, or ($C_1$-$C_6$)alkylcarbonyl; or R$_M$ and R$_N$ together with the nitrogen they are attached to form a 3 to 8 membered ring.

In another embodiment, the present invention provides compounds of Formula (II), or a pharmaceutically acceptable salt thereof, wherein X is CH; L is a bond; $R_1$ is —C(O)OR$_A$; R$_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (NR$_M$R$_N$)carbonyl; and R$_M$ and R$_N$ are H.

In another embodiment, the present invention provides compounds of Formula (II), or a pharmaceutically acceptable salt thereof, wherein X is CH; L is a bond; $R_1$ is —C(O)OR$_A$; R$_A$ is H; $R_2$ is H or halogen; $R_3$ is ($C_1$-$C_6$)alkyl, cyano, or halogen; $R_4$ is H; $R_5$ is H; $R_6$, $R_9$, and $R_{10}$ are H; $R_7$ is H or methoxy; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy ($C_1$-$C_6$)alkyl, or (NR$_M$R$_N$)carbonyl; and R$_M$ and R$_N$ are H.

In another embodiment, the present invention provides compounds of Formula (II), or a pharmaceutically acceptable salt thereof, wherein X is CH; L is a bond; $R_1$ is —C(O)OR$_A$; R$_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy ($C_1$-$C_6$)alkyl, or (NR$_M$R$_N$)carbonyl; and R$_M$ and R$_N$ are H.

In another embodiment, the present invention provides compounds of Formula (II), or a pharmaceutically acceptable salt thereof, wherein X is CH; L is a bond; $R_1$ is —C(O)OR$_A$; R$_A$ is H; $R_2$ is H or F; $R_3$ is methyl, cyano, Cl, or F; $R_4$ is H; $R_5$ is H; $R_6$, $R_9$, and $R_{10}$ are H; $R_7$ is H or methoxy; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (NR$_M$R$_N$)carbonyl; and R$_M$ and R$_N$ are H.

In another embodiment, the present invention provides compounds of Formula (II), or a pharmaceutically acceptable salt thereof, wherein X is CH; L is a bond; $R_1$ is —C(O)OR$_A$; R$_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (NR$_M$R$_N$)carbonyl; and R$_M$ and R$_N$ are H.

In another embodiment, the present invention provides compounds of Formula (II), or a pharmaceutically acceptable salt thereof, wherein X is CH; L is a bond; $R_1$ is —C(O)OR$_A$; R$_A$ is H; $R_2$ is H or F; $R_3$ is Cl, F, or CN; $R_4$ is H; $R_5$ is H; $R_6$, $R_9$, and $R_{10}$ are H; $R_7$ is H or methoxy; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (NR$_M$R$_N$)carbonyl; and R$_M$ and R$_N$ are H.

In another embodiment, the present invention provides compounds of Formula (II), or a pharmaceutically acceptable salt thereof, wherein X is CH; L is a bond; $R_1$ is —C(O)O$R_4$; $R_4$ is H; $R_2$ is H or methoxy; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl wherein the ($C_3$-$C_8$)cycloalkyl is cyclopropyl or cyclobutyl substituted with hydroxy($C_1$-$C_6$)alkyl.

In another embodiment, the present invention provides compounds of Formula (II), or a pharmaceutically acceptable salt thereof, wherein X is CH; L is a bond; $R_1$ is —C(O)O$R_4$; $R_4$ is H; $R_2$ is H or methoxy; $R_3$ is Cl, F, or CN; $R_4$ is H; $R_5$ is H; $R_6$, $R_9$, and $R_{10}$ are H; $R_7$ is H or methoxy; $R_8$ is ($C_3$-$C_8$)cycloalkyl wherein the ($C_3$-$C_8$)cycloalkyl is cyclopropyl or cyclobutyl substituted with hydroxy($C_1$-$C_6$)alkyl.

In another embodiment, the present invention provides compounds of Formula (II), or a pharmaceutically acceptable salt thereof, wherein X is CH; L is a bond; $R_1$ is —C(O)O$R_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl wherein the ($C_3$-$C_8$)cycloalkyl is cyclobutyl substituted with hydroxy.

In another embodiment, the present invention provides compounds of Formula (II), or a pharmaceutically acceptable salt thereof, wherein X is CH; L is a bond; $R_1$ is —C(O)O$R_4$; $R_4$ is H; $R_2$ is H or F; $R_3$ is Cl, F, or CN; $R_4$ is H; $R_5$ is H; $R_6$, $R_9$, and $R_{10}$ are H; $R_7$ is H or methoxy; $R_8$ is ($C_3$-$C_8$)cycloalkyl wherein the ($C_3$-$C_8$)cycloalkyl is cyclobutyl substituted with hydroxy.

In another embodiment, the present invention provides compounds of Formula (II), or a pharmaceutically acceptable salt thereof, wherein X is N; L is a bond; $R_1$ is —C(O)O$R_4$; $R_4$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)O$R_4$; $R_4$ is H; $R_2$ is H or halogen; $R_3$ is ($C_1$-$C_6$)alkyl, cyano, or halogen; $R_4$ is H; $R_5$ is H; $R_6$, $R_9$, and $R_{10}$ are H; $R_7$ is H or methoxy; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)O$R_4$; $R_4$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)O$R_4$; $R_4$ is H; $R_2$ is H or F; $R_3$ is methyl, cyano, Cl, or F; $R_4$ is H; $R_5$ is H; $R_6$, $R_9$, and $R_{10}$ are H; $R_7$ is H or methoxy; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)O$R_4$; $R_4$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)O$R_4$; $R_4$ is H; $R_2$ is H or F; $R_3$ is Cl, F, or CN; $R_4$ is H; $R_5$ is H; $R_6$, $R_9$, and $R_{10}$ are H; $R_7$ is H or methoxy; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —C(O)N$R_B R_C$; $R_B$ and $R_C$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —C(O)N$R_B R_C$; $R_B$ and $R_C$ are independently H or ($C_1$-$C_6$)alkyl; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy ($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —C(O)N$R_B R_C$; $R_B$ and $R_C$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)N$R_B R_C$; $R_B$ and $R_C$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy ($C_1$-$C_6$)alkyl, or (N$R_M R_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)$NR_BR_C$; $R_B$ and $R_C$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)$NR_BR_C$; $R_B$ and $R_C$ are independently H or ($C_1$-$C_6$)alkyl; $R_2$ is H or F; $R_3$ is Cl, F, or CN; $R_4$ is H; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —C(O)$NR_BR_C$; $R_B$ is H; $R_C$ is —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —C(O)$NR_BR_C$; $R_B$ is H; $R_C$ is —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —C(O)$NR_BR_C$; $R_B$ is H; $R_C$ is —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)$NR_BR_C$; $R_B$ is H; $R_C$ is —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is N; L is a bond; $R_1$ is —C(O)$NR_BR_C$; $R_B$ is H; $R_C$ is —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is N; L is a bond $R_1$ is —C(O)$NR_BR_C$; $R_B$ is H; $R_C$ is —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —S($O_2$)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are independently H, F, or methoxy; $R_9$ and $R_{10}$ are H; $R_8$ is ($C_3$-$C_8$)cycloalkyl or ($C_3$-$C_8$)cycloalkyloxy wherein the ($C_3$-$C_8$)cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or ($NR_MR_N$)carbonyl; and $R_M$ and $R_N$ are H.

In another embodiment, the present invention provides compounds of Formula (II), or a pharmaceutically acceptable salt thereof, wherein X is CH; L is a bond; $R_1$ is —S($O_2$)$OR_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is —S(O$_2$)OR$_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is —S(O$_2$)OR$_A$; $R_A$ is H; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is —S(O$_2$)OR$_A$; $R_A$ is H; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is —S(O$_2$)OR$_A$; $R_A$ is H; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is —S(O$_2$)NHC(O)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is —S(O$_2$)NHC(O)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is —S(O$_2$)NHC(O)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or NR$_E$R$_F$; R$_E$ and R$_F$ are independently H or $(C_1-C_6)$alkyl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is —S(O$_2$)NHC(O)R$_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is 5-oxo-4,5-dihydro-1,2,4-oxadiazol-3-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II) wherein X is N; L is a bond; $R_1$ is 5-oxo-4,5-dihydro-1,2,4-oxadiazol-3-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is 1H-tetrazol-5-yl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is CH; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is 1H-tetrazol-5-yl; $R_2$ is H or halogen; $R_3$ is $(C_1-C_6)$alkyl, cyano, or halogen; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is methyl, cyano, Cl, or F; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy$(C_1-C_6)$alkyl, or $(NR_MR_N)$carbonyl; and $R_M$ and $R_N$ are H.

In another embodiment, the present invention provides compounds of Formula (II), or a pharmaceutically acceptable salt thereof, wherein X is N; L is a bond; $R_1$ is 1H-tetrazol-5-yl; $R_2$ is H or F; $R_3$ is Cl, F, or CN; $R_4$ is H; $R_5$ is H; $R_6$ and $R_7$ are independently H, F, or methoxy; $R_9$ and $R_{10}$ are H; $R_8$ is $(C_3-C_8)$cycloalkyl or $(C_3-C_8)$cycloalkyloxy wherein the $(C_3-C_8)$cycloalkyl is cyclopropyl, cyclobutyl, cyclopentyl, or cyclohexyl, wherein each is optionally substituted with 1 substituent that is carboxy, hydroxy, hydroxy($C_1$-$C_6$)alkyl, or (NR$_M$R$_N$)carbonyl; and R$_M$ and R$_N$ are H.

In another embodiment, the present invention provides a pharmaceutical composition comprising a compound of Formula (II), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (II), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (II), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (II), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (II), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (II), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (II), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (II), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (II), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (II), or a pharmaceutically acceptable salt thereof.

In another aspect, the present invention provides uses for compounds of Formula (II), or a pharmaceutically acceptable salt thereof, for preparing, or for the manufacture of, a medicament for treating metabolic disorders in a mammal, particularly a human.

In another aspect, the present invention provides uses for compounds of Formula (II), or a pharmaceutically acceptable salt thereof, for preparing, or for the manufacture of, a medicament for treating or preventing type II diabetes in a mammal, particularly a human.

In another aspect, the present invention provides uses for compounds of Formula (II), or a pharmaceutically acceptable salt thereof, for preparing, or for the manufacture of, a medicament for treating or preventing obesity in a mammal, particularly a human.

In another aspect, the present invention provides uses for compounds of Formula (II), or a pharmaceutically acceptable salt thereof, for preparing, or for the manufacture of, a medicament for treating or preventing dyslipidemia in a mammal, particularly a human.

In another aspect, the present invention provides uses for compounds of Formula (II) for preparing, or for the manufacture of, a medicament for treating renal diseases in a mammal, particularly a human.

In another aspect, the present invention provides uses for compounds of Formula (II) for preparing, or for the manufacture of, a medicament for treating or preventing chronic kidney disease in a mammal, particularly a human.

In another aspect, the present invention provides uses for compounds of Formula (II) for preparing, or for the manufacture of, a medicament for treating or preventing diabetic nephropathy in a mammal, particularly a human.

In another aspect, the present invention provides uses for compounds of Formula (II) for preparing, or for the manufacture of, a medicament for treating or preventing acute kidney injury in a mammal, particularly a human.

In another aspect, the present invention provides uses for compounds of Formula (II) for preparing, or for the manufacture of, a medicament for treating or preventing polycystic kidney disease in a mammal, particularly a human.

In another embodiment, the present invention provides compounds of Formula (III)

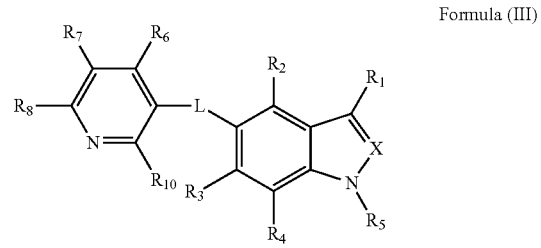

Formula (III)

or a pharmaceutically acceptable salt thereof, wherein X is N or CH; L is a bond, O, S, NR$_4$, ($C_1$-$C_6$)alkylene, ($C_2$-$C_6$)alkenylene, or ($C_2$-$C_6$)alkynylene; $R_1$ is —C(O)OR$_A$, —C(O)NR$_B$R$_C$, —S(O$_2$)OR$_A$, —S(O$_2$)NHC(O)R$_D$, 5-oxo-4,5-dihydro-1,2,4-oxadiazol-3-yl, or 1H-tetrazol-5-yl; R$_A$ is H or ($C_1$-$C_6$)alkyl; R$_B$ and R$_C$ are independently H, ($C_1$-$C_6$)alkyl, or —S(O$_2$)R$_D$; R$_D$ is ($C_1$-$C_6$)alkyl, —CF$_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or NR$_E$R$_F$; R$_E$ and R$_F$ are independently H or ($C_1$-$C_6$)alkyl; $R_2$, $R_3$, and $R_4$ are independently H, ($C_1$-$C_6$)alkoxy, ($C_1$-$C_6$)alkyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_8$)alkyl, mercapto, nitro, —$NR_GR_H$, or ($NR_GR_H$)carbonyl; $R_G$ and $R_H$ are independently H, ($C_1$-$C_6$)alkyl, or ($C_1$-$C_6$)alkylcarbonyl; $R_5$ is H or ($C_1$-$C_6$)alkyl; $R_6$, $R_7$, and $R_{10}$ are independently H, ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_JR_K$, or ($NR_JR_K$)carbonyl; $R_J$ and $R_K$ are independently H or ($C_1$-$C_6$)alkyl; $R_8$ is H, ($C_1$-$C_6$)alkoxy, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkyl, ($C_1$-$C_6$)alkylcarbonyl, ($C_1$-$C_6$)alkylthio, aryl, aryl($C_1$-$C_6$)alkoxy, aryl($C_1$-$C_6$)alkyl, arylcarbonyl, aryloxy, carboxy, carboxy($C_1$-$C_6$)alkoxy, carboxy($C_1$-$C_6$)alkyl, cyano, ($C_3$-$C_8$)cycloalkyl, ($C_3$-$C_8$)cycloalkyl($C_1$-$C_6$)alkoxy, ($C_3$-$C_8$)cycloalkyl($C_1$-$C_6$)alkyl, ($C_3$-$C_8$)cycloalkylcarbonyl, ($C_3$-$C_8$)cycloalkyloxy, halogen, halo($C_1$-$C_6$)alkoxy, halo($C_1$-$C_6$)alkyl, heteroaryl, heteroaryl($C_1$-$C_6$)alkoxy, heteroaryl($C_1$-$C_6$)alkyl, heteroarylcarbonyl, heteroaryloxy, ($C_3$-$C_7$)heterocycle, ($C_3$-$C_7$)heterocycle($C_1$-$C_6$)alkoxy, ($C_3$-$C_7$)heterocycle($C_1$-$C_6$)alkyl, ($C_3$-$C_7$)heterocyclecarbonyl, ($C_3$-$C_7$)heterocyclecarbonyl($C_1$-$C_6$)alkyl, ($C_3$-$C_7$)heterocycleoxy, hydroxy, hydroxy($C_1$-$C_6$)alkoxy, hydroxy($C_1$-$C_6$)alkyl, mercapto, nitro, —$NR_MR_N$, —$NR_MR_N$($C_1$-$C_6$)alkoxy, ($NR_MR_N$)carbonyl, ($NR_MR_N$)carbonyl($C_1$-$C_6$)alkyl, or ($NR_MR_N$)carbonyl($C_1$-$C_6$)alkoxy; wherein the aryl, aryl($C_1$-$C_6$)alkoxy, aryl($C_1$-$C_6$)alkyl, arylcarbonyl, and aryloxy are optionally substituted with 1, 2, 3, 4, or 5 substituents that are independently ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_MR_N$, or ($NR_MR_N$)carbonyl; wherein the halo($C_1$-$C_6$)alkyl is optionally substituted with 1 or 2 hydroxy groups; wherein the ($C_3$-$C_8$)cycloalkyl, ($C_3$-$C_8$)cycloalkyl($C_1$-$C_6$)alkoxy, ($C_3$-$C_8$)cycloalkyl($C_1$-$C_6$)alkyl, ($C_3$-$C_8$)cycloalkylcarbonyl, and ($C_3$-$C_8$)cycloalkyloxy are optionally substituted with 1, 2, or 3 substituents that are independently ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_MR_N$, or ($NR_MR_N$)carbonyl; wherein the heteroaryl, heteroaryl($C_1$-$C_6$)alkoxy, heteroaryl($C_1$-$C_6$)alkyl, heteroarylcarbonyl, and heteroaryloxy, are optionally substituted with 1, 2, or 3 substituents that are independently ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_MR_N$, or ($NR_MR_N$)carbonyl; and wherein the ($C_3$-$C_7$)heterocycle, ($C_3$-$C_7$)heterocycle($C_1$-$C_6$)alkoxy, ($C_3$-$C_7$)heterocycle($C_1$-$C_6$)alkyl, ($C_3$-$C_7$)heterocyclecarbonyl, ($C_3$-$C_7$)heterocyclecarbonyl($C_1$-$C_6$)alkyl, and ($C_3$-$C_7$)heterocycleoxy, are optionally substituted with 1, 2, or 3 substituents that are independently ($C_1$-$C_6$)alkoxy, ($C_1$-$C_6$)alkoxycarbonyl, ($C_1$-$C_6$)alkoxysulfonyl, ($C_1$-$C_6$)alkyl, ($C_1$-$C_6$)alkylcarbonyl, ($C_1$-$C_6$)alkylsulfonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_MR_N$, ($NR_MR_N$)carbonyl, or oxo; and $R_M$ and $R_N$ are independently H, ($C_1$-$C_6$)alkyl, or ($C_1$-$C_6$)alkylcarbonyl; and $R_M$ and $R_N$ together with the nitrogen they are attached to form a 3 to 8 membered ring.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, and $R_{10}$ are H; $R_8$ is ($C_3$-$C_7$)heterocycle.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, and $R_{10}$ are H; $R_8$ is ($C_3$-$C_7$)heterocycle.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, and $R_{10}$ are H; $R_8$ is ($C_3$-$C_7$)heterocycle.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, and $R_{10}$ are H; $R_8$ is ($C_3$-$C_7$)heterocycle wherein the ($C_3$-$C_7$)heterocycle is morpholinyl.

In another embodiment, the present invention provides compounds of Formula (III), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, and $R_{10}$ are H; $R_8$ is ($C_3$-$C_7$)heterocycle.

In another embodiment, the present invention provides compounds of Formula (III), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, and $R_{10}$ are H; $R_8$ is ($C_3$-$C_7$)heterocycle.

In another embodiment, the present invention provides compounds of Formula (III), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, and $R_{10}$ are H; $R_8$ is ($C_3$-$C_7$)heterocycle.

In another embodiment, the present invention provides compounds of Formula (III), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, and $R_{10}$ are H; $R_8$ is ($C_3$-$C_7$)heterocycle wherein the ($C_3$-$C_7$)heterocycle is morpholinyl.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are H; $R_{10}$ is ($C_1$-$C_6$)alkoxy; $R_8$ is ($C_3$-$C_7$)heterocycle.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are H; $R_{10}$ is H or ($C_1$-$C_6$)alkoxy; $R_8$ is ($C_3$-$C_7$)heterocycle wherein the ($C_3$-$C_7$)heterocycle is pyrrolidinyl optionally substituted with ($C_1$-$C_6$)alkoxy or hydroxy.

In another embodiment, the present invention provides compounds of Formula (III), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$ and $R_7$ are H; $R_{10}$ is H or ($C_1$-$C_6$)alkoxy; $R_8$ is ($C_3$-$C_7$)heterocycle wherein the ($C_3$-$C_7$)heterocycle is morpholinyl or pyrrolidinyl where the pyrrolidinyl is optionally substituted with ($C_1$-$C_6$)alkoxy or hydroxy.

In another embodiment, the present invention provides a pharmaceutical composition comprising a compound of Formula (III), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (III), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (III), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (III), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (III), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (III), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (III), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (III), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (III), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (III), or a pharmaceutically acceptable salt thereof.

In another aspect, the present invention provides uses for compounds of Formula (III), or a pharmaceutically acceptable salt thereof, for preparing, or for the manufacture of, a medicament for treating metabolic disorders in a mammal, particularly a human.

In another aspect, the present invention provides uses for compounds of Formula (III), or a pharmaceutically acceptable salt thereof, for preparing, or for the manufacture of, a medicament for treating or preventing type II diabetes in a mammal, particularly a human.

In another aspect, the present invention provides uses for compounds of Formula (III), or a pharmaceutically acceptable salt thereof, for preparing, or for the manufacture of, a medicament for treating or preventing obesity in a mammal, particularly a human.

In another aspect, the present invention provides uses for compounds of Formula (III), or a pharmaceutically acceptable salt thereof, for preparing, or for the manufacture of, a medicament for treating or preventing dyslipidemia in a mammal, particularly a human.

In another aspect, the present invention provides uses for compounds of Formula (III) for preparing, or for the manufacture of, a medicament for treating renal diseases in a mammal, particularly a human.

In another aspect, the present invention provides uses for compounds of Formula (III) for preparing, or for the manufacture of, a medicament for treating or preventing chronic kidney disease in a mammal, particularly a human.

In another aspect, the present invention provides uses for compounds of Formula (III) for preparing, or for the manufacture of, a medicament for treating or preventing diabetic nephropathy in a mammal, particularly a human.

In another aspect, the present invention provides uses for compounds of Formula (III) for preparing, or for the manufacture of, a medicament for treating or preventing acute kidney injury in a mammal, particularly a human.

In another aspect, the present invention provides uses for compounds of Formula (III) for preparing, or for the manufacture of, a medicament for treating or preventing polycystic kidney disease in a mammal, particularly a human.

In another embodiment, the present invention provides compounds of Formula (IV)

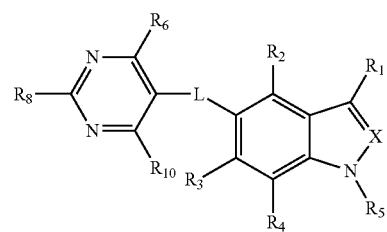

Formula (IV)

or a pharmaceutically acceptable salt thereof, wherein X is N or CH; L is a bond, O, S, $NR_A$, $(C_1-C_6)$alkylene, $(C_2-C_6)$alkenylene, or $(C_2-C_6)$alkynylene; $R_1$ is —C(O)$OR_A$, —C(O)$NR_BR_C$, —S(O$_2$)$OR_A$, —S(O$_2$)NHC(O)$R_D$, 5-oxo-4,5-dihydro-1,2,4-oxadiazol-3-yl, or 1H-tetrazol-5-yl; $R_A$ is H or $(C_1-C_6)$alkyl; $R_B$ and $R_C$ are independently H, $(C_1-C_6)$alkyl, or —S(O$_2$)$R_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$, $R_3$, and $R_4$ are independently H, $(C_1-C_6)$alkoxy, $(C_1-C_6)$alkyl, $(C_1-C_6)$alkylthio, carboxy, cyano, halogen, halo$(C_1-C_6)$alkoxy, halo$(C_1-C_6)$alkyl, hydroxy, hydroxy$(C_1-C_8)$alkyl, mercapto, nitro, —$NR_GR_H$, or $(NR_GR_H)$carbonyl; $R_G$ and $R_H$ are independently H, $(C_1-C_6)$alkyl, or $(C_1-C_6)$alkylcarbonyl; $R_5$ is H or $(C_1-C_6)$alkyl;

$R_6$ and $R_{10}$ are independently H, $(C_1$-$C_6)$alkoxy, $(C_1$-$C_6)$alkoxycarbonyl, $(C_1$-$C_6)$alkyl, $(C_1$-$C_6)$alkylcarbonyl, $(C_1$-$C_6)$alkylthio, carboxy, cyano, halogen, halo$(C_1$-$C_6)$alkoxy, halo$(C_1$-$C_6)$alkyl, hydroxy, hydroxy$(C_1$-$C_6)$alkyl, mercapto, nitro, —$NR_JR_K$, or $(NR_JR_K)$carbonyl; $R_J$ and $R_K$ are independently H or $(C_1$-$C_6)$alkyl; $R_8$ is H, $(C_1$-$C_6)$alkoxy, $(C_1$-$C_6)$alkoxy$(C_1$-$C_6)$alkoxy, $(C_1$-$C_6)$alkoxy$(C_1$-$C_6)$alkyl, $(C_1$-$C_6)$alkoxycarbonyl, $(C_1$-$C_6)$alkyl, $(C_1$-$C_6)$alkylcarbonyl, $(C_1$-$C_6)$alkylthio, aryl, aryl$(C_1$-$C_6)$alkoxy, aryl$(C_1$-$C_6)$alkyl, arylcarbonyl, aryloxy, carboxy, carboxy$(C_1$-$C_6)$alkoxy, carboxy$(C_1$-$C_6)$alkyl, cyano, $(C_3$-$C_8)$cycloalkyl, $(C_3$-$C_8)$cycloalkyl$(C_1$-$C_6)$alkoxy, $(C_3$-$C_8)$cycloalkyl$(C_1$-$C_6)$alkyl, $(C_3$-$C_8)$cycloalkylcarbonyl, $(C_3$-$C_8)$cycloalkyloxy, halogen, halo$(C_1$-$C_6)$alkoxy, halo$(C_1$-$C_6)$alkyl, heteroaryl, heteroaryl$(C_1$-$C_6)$alkoxy, heteroaryl$(C_1$-$C_6)$alkyl, heteroarylcarbonyl, heteroaryloxy, $(C_3$-$C_7)$heterocycle, $(C_3$-$C_7)$heterocycle$(C_1$-$C_6)$alkoxy, $(C_3$-$C_7)$heterocycle$(C_1$-$C_6)$alkyl, $(C_3$-$C_7)$heterocyclecarbonyl, $(C_3$-$C_7)$heterocyclecarbonyl$(C_1$-$C_6)$alkyl, $(C_3$-$C_7)$heterocycleoxy, hydroxy, hydroxy$(C_1$-$C_6)$alkoxy, hydroxy$(C_1$-$C_6)$alkyl, mercapto, nitro, —$NR_MR_N$, —$NR_MR_N(C_1$-$C_6)$alkyl, $(NR_MR_N)$carbonyl, $(NR_MR_N)$carbonyl$(C_1$-$C_6)$alkyl, or $(NR_MR_N)$carbonyl$(C_1$-$C_6)$alkoxy; wherein the aryl, aryl$(C_1$-$C_6)$alkoxy, aryl$(C_1$-$C_6)$alkyl, arylcarbonyl, and aryloxy are optionally substituted with 1, 2, 3, 4, or 5 substituents that are independently $(C_1$-$C_6)$alkoxy, $(C_1$-$C_6)$alkoxycarbonyl, $(C_1$-$C_6)$alkyl, $(C_1$-$C_6)$alkylcarbonyl, $(C_1$-$C_6)$alkylthio, carboxy, cyano, halogen, halo$(C_1$-$C_6)$alkoxy, halo$(C_1$-$C_6)$alkyl, hydroxy, hydroxy$(C_1$-$C_6)$alkyl, mercapto, nitro, —$NR_MR_N$, or $(NR_MR_N)$carbonyl; wherein the halo$(C_1$-$C_6)$alkyl is optionally substituted with 1 or 2 hydroxy groups; wherein the $(C_3$-$C_8)$cycloalkyl, $(C_3$-$C_8)$cycloalkyl$(C_1$-$C_6)$alkoxy, $(C_3$-$C_8)$cycloalkyl$(C_1$-$C_6)$alkyl, $(C_3$-$C_8)$cycloalkylcarbonyl, and $(C_3$-$C_8)$cycloalkyloxy are optionally substituted with 1, 2, or 3 substituents that are independently $(C_1$-$C_6)$alkoxy, $(C_1$-$C_6)$alkoxycarbonyl, $(C_1$-$C_6)$alkyl, $(C_1$-$C_6)$alkylcarbonyl, $(C_1$-$C_6)$alkylthio, carboxy, cyano, halogen, halo$(C_1$-$C_6)$alkoxy, halo$(C_1$-$C_6)$alkyl, hydroxy, hydroxy$(C_1$-$C_6)$alkyl, mercapto, nitro, —$NR_MR_N$, or $(NR_MR_N)$carbonyl; wherein the heteroaryl, heteroaryl$(C_1$-$C_6)$alkoxy, heteroaryl$(C_1$-$C_6)$alkyl, heteroarylcarbonyl, and heteroaryloxy, are optionally substituted with 1, 2, or 3 substituents that are independently $(C_1$-$C_6)$alkoxy, $(C_1$-$C_6)$alkoxycarbonyl, $(C_1$-$C_6)$alkyl, $(C_1$-$C_6)$alkylcarbonyl, $(C_1$-$C_6)$alkylthio, carboxy, cyano, halogen, halo$(C_1$-$C_6)$alkoxy, halo$(C_1$-$C_6)$alkyl, hydroxy, hydroxy$(C_1$-$C_6)$alkyl, mercapto, nitro, —$NR_MR_N$, or $(NR_MR_N)$carbonyl; and wherein the $(C_3$-$C_7)$heterocycle, $(C_3$-$C_7)$heterocycle$(C_1$-$C_6)$alkoxy, $(C_3$-$C_7)$heterocycle$(C_1$-$C_6)$alkyl, $(C_3$-$C_7)$heterocyclecarbonyl, $(C_3$-$C_7)$heterocyclecarbonyl$(C_1$-$C_6)$alkyl, and $(C_3$-$C_7)$heterocycleoxy, are optionally substituted with 1, 2, or 3 substituents that are independently $(C_1$-$C_6)$alkoxy, $(C_1$-$C_6)$alkoxycarbonyl, $(C_1$-$C_6)$alkoxysulfonyl, $(C_1$-$C_6)$alkyl, $(C_1$-$C_6)$alkylcarbonyl, $(C_1$-$C_6)$alkylsulfonyl, $(C_1$-$C_6)$alkylthio, carboxy, cyano, halogen, halo$(C_1$-$C_6)$alkoxy, halo$(C_1$-$C_6)$alkyl, hydroxy, hydroxy$(C_1$-$C_6)$alkyl, mercapto, nitro, —$NR_MR_N$, $(NR_MR_N)$carbonyl, or oxo; and $R_M$ and $R_N$ are independently H, $(C_1$-$C_6)$alkyl, or $(C_1$-$C_6)$alkylcarbonyl; and $R_M$ and $R_N$ together with the nitrogen they are attached to form a 3 to 8 membered ring.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or halogen; $R_3$ is $(C_1$-$C_6)$alkyl, cyano, or halogen; $R_4$ is H; $R_5$ is H; $R_6$ and $R_{10}$ are H; $R_8$ is —$NR_MR_N$; and $R_M$ and $R_N$ are independently H or $(C_1$-$C_6)$alkyl.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or F; $R_3$ is methyl, cyano, Cl, or F; $R_4$ is H; $R_5$ is H; $R_6$ and $R_{10}$ are H; $R_8$ is —$NR_MR_N$; and $R_M$ and $R_N$ are independently H or $(C_1$-$C_6)$alkyl.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or F; $R_3$ is Cl, F, or CN; $R_4$ is H; $R_5$ is H; $R_6$ and $R_{10}$ are H; $R_8$ is —$NR_MR_N$; and $R_M$ and $R_N$ are independently H or $(C_1$-$C_6)$alkyl.

In another embodiment, the present invention provides compounds of Formula (IV), or a pharmaceutically acceptable salt thereof, wherein X is N; L is a bond; $R_1$ is —C(O)OR_A$; $R_A$ is H; $R_2$ is H or halogen; $R_3$ is $(C_1$-$C_6)$alkyl, cyano, or halogen; $R_4$ is H; $R_5$ is H; $R_6$ and $R_{10}$ are H; $R_8$ is —$NR_MR_N$; and $R_M$ and $R_N$ are independently H or $(C_1$-$C_6)$alkyl.

In another embodiment, the present invention provides compounds of Formula (IV), or a pharmaceutically acceptable salt thereof, wherein X is N; L is a bond; $R_1$ is —C(O)OR_A$; $R_A$ is H; $R_2$ is H or F; $R_3$ is methyl, cyano, Cl, or F; $R_4$ is H; $R_5$ is H; $R_6$ and $R_{10}$ are H; $R_8$ is —$NR_MR_N$; and $R_M$ and $R_N$ are independently H or $(C_1$-$C_6)$alkyl.

In another embodiment, the present invention provides compounds of Formula (IV), or a pharmaceutically acceptable salt thereof, wherein X is N; L is a bond; $R_1$ is —C(O)OR_A$; $R_A$ is H; $R_2$ is H or F; $R_3$ is Cl, F, or CN; $R_4$ is H; $R_5$ is H; $R_6$ and $R_{10}$ are H; $R_8$ is —$NR_MR_N$; and $R_M$ and $R_N$ are independently H or $(C_1$-$C_6)$alkyl.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or halogen; $R_3$ is $(C_1$-$C_6)$alkyl, cyano, or halogen; $R_4$ is H; $R_5$ is H; $R_6$ and $R_{10}$ are H; $R_8$ is $(C_3$-$C_7)$heterocycle.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or F; $R_3$ is methyl, cyano, Cl, or F; $R_4$ is H; $R_5$ is H; $R_6$ and $R_{10}$ are H; $R_8$ is $(C_3$-$C_7)$heterocycle.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or F; $R_3$ is Cl, F, or CN; $R_4$ is H; $R_5$ is H; $R_6$ and $R_{10}$ are H; $R_8$ is $(C_3$-$C_7)$heterocycle.

In another embodiment, the present invention provides compounds of Formula (IV), or a pharmaceutically acceptable salt thereof, wherein X is CH; L is a bond; $R_1$ is —C(O)OR_A$; $R_A$ is H; $R_2$ is H or F; $R_3$ is Cl, F, or CN; $R_4$ is H; $R_5$ is H; $R_6$ and $R_{10}$ are H; $R_8$ is $(C_3$-$C_7)$heterocycle wherein the $(C_3$-$C_7)$heterocycle is morpholinyl.

In another embodiment, the present invention provides compounds of Formula (IV), or a pharmaceutically acceptable salt thereof, wherein X is N; L is a bond; $R_1$ is —C(O)OR_A$; $R_A$ is H; $R_2$ is H or halogen; $R_3$ is $(C_1$-$C_6)$alkyl, cyano, or halogen; $R_4$ is H; $R_5$ is H; $R_6$ and $R_{10}$ are H; $R_8$ is $(C_3$-$C_7)$heterocycle.

In another embodiment, the present invention provides compounds of Formula (IV), or a pharmaceutically acceptable salt thereof, wherein X is N; L is a bond; $R_1$ is —C(O)OR_A$; $R_A$ is H; $R_2$ is H or F; $R_3$ is methyl, cyano, Cl, or F; $R_4$ is H; $R_5$ is H; $R_6$ and $R_{10}$ are H; $R_8$ is $(C_3$-$C_7)$heterocycle.

In another embodiment, the present invention provides compounds of Formula (IV), or a pharmaceutically acceptable salt thereof, wherein X is N; L is a bond; $R_1$ is —C(O)

OR$_A$; R$_A$ is H; R$_2$ is H or F; R$_3$ is Cl, F, or CN; R$_4$ is H; R$_5$ is H; R$_6$ and R$_{10}$ are H; R$_8$ is (C$_3$-C$_7$)heterocycle.

In another embodiment, the present invention provides compounds of Formula (IV), or a pharmaceutically acceptable salt thereof, wherein X is N; L is a bond; R$_1$ is —C(O)OR$_A$; R$_A$ is H; R$_2$ is H or F; R$_3$ is Cl, F, or CN; R$_4$ is H; R$_5$ is H; R$_6$ and R$_{10}$ are H; R$_8$ is (C$_3$-C$_7$)heterocycle wherein the (C$_3$-C$_7$)heterocycle is morpholinyl.

In another embodiment, the present invention provides a pharmaceutical composition comprising a compound of Formula (IV), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (IV), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (IV), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (IV), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (IV), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (IV), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (IV), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (IV), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (IV), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (IV), or a pharmaceutically acceptable salt thereof.

In another aspect, the present invention provides uses for compounds of Formula (IV), or a pharmaceutically acceptable salt thereof, for preparing, or for the manufacture of, a medicament for treating metabolic disorders in a mammal, particularly a human.

In another aspect, the present invention provides uses for compounds of Formula (IV), or a pharmaceutically acceptable salt thereof, for preparing, or for the manufacture of, a medicament for treating or preventing type II diabetes in a mammal, particularly a human.

In another aspect, the present invention provides uses for compounds of Formula (IV), or a pharmaceutically acceptable salt thereof, for preparing, or for the manufacture of, a medicament for treating or preventing obesity in a mammal, particularly a human.

In another aspect, the present invention provides uses for compounds of Formula (IV), or a pharmaceutically acceptable salt thereof, for preparing, or for the manufacture of, a medicament for treating or preventing dyslipidemia in a mammal, particularly a human.

In another aspect, the present invention provides uses for compounds of Formula (IV) for preparing, or for the manufacture of, a medicament for treating renal diseases in a mammal, particularly a human.

In another aspect, the present invention provides uses for compounds of Formula (IV) for preparing, or for the manufacture of, a medicament for treating or preventing chronic kidney disease in a mammal, particularly a human.

In another aspect, the present invention provides uses for compounds of Formula (IV) for preparing, or for the manufacture of, a medicament for treating or preventing diabetic nephropathy in a mammal, particularly a human.

In another aspect, the present invention provides uses for compounds of Formula (IV) for preparing, or for the manufacture of, a medicament for treating or preventing acute kidney injury in a mammal, particularly a human.

In another aspect, the present invention provides uses for compounds of Formula (IV) for preparing, or for the manufacture of, a medicament for treating or preventing polycystic kidney disease in a mammal, particularly a human.

In another embodiment, the present invention provides compounds of Formula (V)

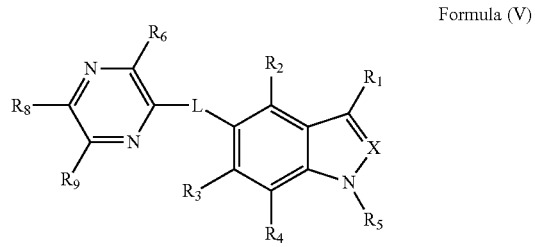

Formula (V)

or a pharmaceutically acceptable salt thereof, wherein X is N or CH; L is a bond, O, S, NR$_4$, (C$_1$-C$_6$)alkylene, (C$_2$-C$_6$)alkenylene, or (C$_2$-C$_6$)alkynylene; R$_1$ is —C(O)OR$_A$, —C(O)NR$_B$R$_C$, —S(O$_2$)OR$_A$, —S(O$_2$)NHC(O)R$_D$, 5-oxo-4,5-dihydro-1,2,4-oxadiazol-3-yl, or 1H-tetrazol-5-yl; R$_A$ is H or (C$_1$-C$_6$)alkyl; R$_B$ and R$_C$ are independently H, (C$_1$-C$_6$)alkyl, or —S(O$_2$)R$_D$; R$_D$ is (C$_1$-C$_6$)alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$, $R_3$, and $R_4$ are independently H, $(C_1-C_6)$alkoxy, $(C_1-C_6)$alkyl, $(C_1-C_6)$alkylthio, carboxy, cyano, halogen, halo$(C_1-C_6)$alkoxy, halo$(C_1-C_6)$alkyl, hydroxy, hydroxy$(C_1-C_8)$alkyl, mercapto, nitro, —$NR_GR_H$, or $(NR_GR_H)$carbonyl; $R_G$ and $R_H$ are independently H, $(C_1-C_6)$alkyl, or $(C_1-C_6)$alkylcarbonyl; $R_5$ is H or $(C_1-C_6)$alkyl; $R_6$ and $R_9$ are independently H, $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_JR_K$, or $(NR_JR_K)$carbonyl; $R_J$ and $R_K$ are independently H or $(C_1-C_6)$alkyl; $R_8$ is H, $(C_1-C_6)$alkoxy, $(C_1-C_6)$alkoxy$(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkylthio, aryl, aryl$(C_1-C_6)$alkoxy, aryl$(C_1-C_6)$alkyl, arylcarbonyl, aryloxy, carboxy, carboxy$(C_1-C_6)$alkoxy, carboxy$(C_1-C_6)$alkyl, cyano, $(C_3-C_8)$cycloalkyl, $(C_3-C_8)$cycloalkyl$(C_1-C_6)$alkoxy, $(C_3-C_8)$cycloalkyl$(C_1-C_6)$alkyl, $(C_3-C_8)$cycloalkylcarbonyl, $(C_3-C_8)$cycloalkyloxy, halogen, halo$(C_1-C_6)$alkoxy, halo$(C_1-C_6)$alkyl, heteroaryl, heteroaryl$(C_1-C_6)$alkoxy, heteroaryl$(C_1-C_6)$alkyl, heteroarylcarbonyl, heteroaryloxy, $(C_3-C_7)$heterocycle, $(C_3-C_7)$heterocycle$(C_1-C_6)$alkoxy, $(C_3-C_7)$heterocycle$(C_1-C_6)$alkyl, $(C_3-C_7)$heterocyclecarbonyl, $(C_3-C_7)$heterocyclecarbonyl$(C_1-C_6)$alkyl, $(C_3-C_7)$heterocycleoxy, hydroxy, hydroxy$(C_1-C_6)$alkoxy, hydroxy$(C_1-C_6)$alkyl, mercapto, nitro, —$NR_MR_N$, —$NR_MR_N(C_1-C_6)$alkoxy, $(NR_MR_N)$carbonyl, $(NR_MR_N)$carbonyl$(C_1-C_6)$alkyl, or $(NR_MR_N)$carbonyl$(C_1-C_6)$alkoxy; wherein the aryl, aryl$(C_1-C_6)$alkoxy, aryl$(C_1-C_6)$alkyl, arylcarbonyl, and aryloxy are optionally substituted with 1, 2, 3, 4, or 5 substituents that are independently $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_MR_N$, or $(NR_MR_N)$carbonyl; wherein the halo$(C_1-C_6)$alkyl is optionally substituted with 1 or 2 hydroxy groups; wherein the $(C_3-C_8)$cycloalkyl, $(C_3-C_8)$cycloalkyl$(C_1-C_6)$alkoxy, $(C_3-C_8)$cycloalkyl$(C_1-C_6)$alkyl, $(C_3-C_8)$cycloalkylcarbonyl, and $(C_3-C_8)$cycloalkyloxy are optionally substituted with 1, 2, or 3 substituents that are independently $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_MR_N$, or $(NR_MR_N)$carbonyl; wherein the heteroaryl, heteroaryl$(C_1-C_6)$alkoxy, heteroaryl$(C_1-C_6)$alkyl, heteroarylcarbonyl, and heteroaryloxy, are optionally substituted with 1, 2, or 3 substituents that are independently $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_MR_N$, or $(NR_MR_N)$carbonyl; and wherein the $(C_3-C_7)$heterocycle, $(C_3-C_7)$heterocycle$(C_1-C_6)$alkoxy, $(C_3-C_7)$heterocycle$(C_1-C_6)$alkyl, $(C_3-C_7)$heterocyclecarbonyl, $(C_3-C_7)$heterocyclecarbonyl$(C_1-C_6)$alkyl, and $(C_3-C_7)$heterocycleoxy, are optionally substituted with 1, 2, or 3 substituents that are independently $(C_1-C_6)$alkoxy, $(C_1-C_6)$alkoxycarbonyl, $(C_1-C_6)$alkoxysulfonyl, $(C_1-C_6)$alkyl, $(C_1-C_6)$alkylcarbonyl, $(C_1-C_6)$alkylsulfonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_MR_N$, $(NR_MR_N)$carbonyl, or oxo; and $R_M$ and $R_N$ are independently H, $(C_1-C_6)$alkyl, or $(C_1-C_6)$alkylcarbonyl; and $R_M$ and $R_N$ together with the nitrogen they are attached to form a 3 to 8 membered ring.

In another embodiment, the present invention provides compounds of Formula (V), or a pharmaceutically acceptable salt thereof, wherein X is CH; L is a bond; $R_1$ is —$C(O)OR_A$; $R_A$ is H; $R_2$ is H or halogen; $R_3$ is $(C_1-C_6)$alkyl, cyano, or halogen; $R_4$ is H; $R_5$ is H; $R_6$ and $R_9$ are H; and $R_8$ is aryl wherein the aryl is phenyl.

In another embodiment, the present invention provides compounds of Formula (V), or a pharmaceutically acceptable salt thereof, wherein X is CH; L is a bond; $R_1$ is —$C(O)OR_A$; $R_A$ is H; $R_2$ is H or F; $R_3$ is methyl, cyano, Cl, or F; $R_4$ is H; $R_5$ is H; $R_6$ and $R_9$ are H; and $R_8$ is aryl wherein the aryl is phenyl.

In another embodiment, the present invention provides compounds of Formula (V), or a pharmaceutically acceptable salt thereof, wherein X is CH; L is a bond; $R_1$ is —$C(O)OR_A$; $R_A$ is H; $R_2$ is H or F; $R_3$ is Cl, F, or CN; $R_4$ is H; $R_5$ is H; $R_6$ and $R_9$ are H; and $R_8$ is aryl wherein the aryl is phenyl.

In another embodiment, the present invention provides compounds of Formula (V), or a pharmaceutically acceptable salt thereof, wherein X is N; L is a bond; $R_1$ is —$C(O)OR_A$; $R_A$ is H; $R_2$ is H or halogen; $R_3$ is $(C_1-C_6)$alkyl, cyano, or halogen; $R_4$ is H; $R_5$ is H; $R_6$ and $R_9$ are H; and $R_8$ is aryl wherein the aryl is phenyl.

In another embodiment, the present invention provides compounds of Formula (V), or a pharmaceutically acceptable salt thereof, wherein X is N; L is a bond; $R_1$ is —$C(O)OR_A$; $R_A$ is H; $R_2$ is H or F; $R_3$ is methyl, cyano, Cl, or F; $R_4$ is H; $R_5$ is H; $R_6$ and $R_9$ are H; and $R_8$ is aryl wherein the aryl is phenyl.

In another embodiment, the present invention provides compounds of Formula (V), or a pharmaceutically acceptable salt thereof, wherein X is N; L is a bond; $R_1$ is —$C(O)OR_A$; $R_A$ is H; $R_2$ is H or F; $R_3$ is Cl, F, or CN; $R_4$ is H; $R_5$ is H; $R_6$ and $R_9$ are H; and $R_8$ is aryl wherein the aryl is phenyl.

In another embodiment, the present invention provides a pharmaceutical composition comprising a compound of Formula (V), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (V), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (V), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (V), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (V), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (V), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (V), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (V), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (V), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (V), or a pharmaceutically acceptable salt thereof.

In another aspect, the present invention provides uses for compounds of Formula (V), or a pharmaceutically acceptable salt thereof, for preparing, or for the manufacture of, a medicament for treating metabolic disorders in a mammal, particularly a human.

In another aspect, the present invention provides uses for compounds of Formula (V), or a pharmaceutically acceptable salt thereof, for preparing, or for the manufacture of, a medicament for treating or preventing type II diabetes in a mammal, particularly a human.

In another aspect, the present invention provides uses for compounds of Formula (V), or a pharmaceutically acceptable salt thereof, for preparing, or for the manufacture of, a medicament for treating or preventing obesity in a mammal, particularly a human.

In another aspect, the present invention provides uses for compounds of Formula (V), or a pharmaceutically acceptable salt thereof, for preparing, or for the manufacture of, a medicament for treating or preventing dyslipidemia in a mammal, particularly a human.

In another aspect, the present invention provides uses for compounds of Formula (V) for preparing, or for the manufacture of, a medicament for treating renal diseases in a mammal, particularly a human.

In another aspect, the present invention provides uses for compounds of Formula (V) for preparing, or for the manufacture of, a medicament for treating or preventing chronic kidney disease in a mammal, particularly a human.

In another aspect, the present invention provides uses for compounds of Formula (V) for preparing, or for the manufacture of, a medicament for treating or preventing diabetic nephropathy in a mammal, particularly a human.

In another aspect, the present invention provides uses for compounds of Formula (V) for preparing, or for the manufacture of, a medicament for treating or preventing acute kidney injury in a mammal, particularly a human.

In another aspect, the present invention provides uses for compounds of Formula (V) for preparing, or for the manufacture of, a medicament for treating or preventing polycystic kidney disease in a mammal, particularly a human.

In another embodiment, the present invention provides compounds of Formula (VI)

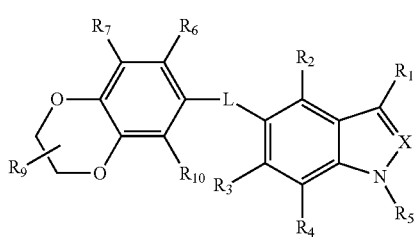

Formula (VI)

or a pharmaceutically acceptable salt thereof, wherein X is N or CH; L is a bond, O, S, $NR_4$, $(C_1-C_6)$alkylene, $(C_2-C_6)$alkenylene, or $(C_2-C_6)$alkynylene; $R_1$ is —C(O)$OR_4$, —C(O)$NR_BR_C$, —S(O$_2$)$OR_4$, —S(O$_2$)NHC(O)$R_D$, 5-oxo-4,5-dihydro-1,2,4-oxadiazol-3-yl, or 1H-tetrazol-5-yl; $R_4$ is H or $(C_1-C_6)$alkyl; $R_B$ and $R_C$ are independently H, $(C_1-C_6)$alkyl, or —S(O$_2$)$R_D$; $R_D$ is $(C_1-C_6)$alkyl, —CF$_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$, $R_3$, and $R_4$ are independently H, $(C_1-C_6)$alkoxy, $(C_1-C_6)$alkyl, $(C_1-C_6)$alkylthio, carboxy, cyano, halogen, halo$(C_1-C_6)$alkoxy, halo$(C_1-C_6)$alkyl, hydroxy, hydroxy$(C_1-C_8)$alkyl, mercapto, nitro, —$NR_GR_H$, or $(NR_GR_H)$carbonyl; $R_G$ and $R_H$ are independently H, $(C_1-C_6)$alkyl, or $(C_1-C_6)$alkylcarbonyl; $R_5$ is H or $(C_1-C_6)$alkyl; $R_6$, $R_7$, $R_9$, and $R_{10}$ are independently H, $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_JR_K$, or $(NR_JR_K)$carbonyl; and $R_J$ and $R_K$ are independently H or $(C_1-C_6)$alkyl.

In another embodiment, the present invention provides compounds of Formula (VI), or a pharmaceutically acceptable salt thereof, wherein X is CH; L is a bond; $R_1$ is —C(O)$OR_4$; $R_4$ is H; $R_2$ is H or halogen; $R_3$ is $(C_1-C_6)$alkyl, cyano, or halogen; $R_4$ is H; $R_5$ is H; $R_6$, $R_7$, and $R_{10}$ are H; and $R_9$ is H or hydroxy$(C_1-C_6)$alkyl.

In another embodiment, the present invention provides compounds of Formula (VI), or a pharmaceutically acceptable salt thereof, wherein X is CH; L is a bond; $R_1$ is —C(O)$OR_4$; $R_4$ is H; $R_2$ is H or F; $R_3$ is methyl, cyano, Cl, or F; $R_4$ is H; $R_5$ is H; $R_6$, $R_7$, and $R_{10}$ are H; and $R_9$ is H or hydroxy$(C_1-C_6)$alkyl.

In another embodiment, the present invention provides compounds of Formula (VI), or a pharmaceutically acceptable salt thereof, wherein X is CH; L is a bond; $R_1$ is —C(O)$OR_4$; $R_4$ is H; $R_2$ is H or F; $R_3$ is Cl, F, or CN; $R_4$ is H; $R_5$ is H; $R_6$, $R_7$, and $R_{10}$ are H; and $R_9$ is hydroxy$(C_1-C_6)$alkyl.

In another embodiment, the present invention provides compounds of Formula (VI), or a pharmaceutically acceptable salt thereof, wherein X is CH; L is a bond; $R_1$ is —C(O)$OR_4$; $R_4$ is H; $R_2$ is H or F; $R_3$ is Cl, F, or CN; $R_4$ is H; $R_5$ is H; $R_6$, $R_7$, $R_9$, and $R_{10}$ are H.

In another embodiment, the present invention provides compounds of Formula (VI), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; $R_6$, $R_7$, and $R_{10}$ are H; and $R_9$ is H or hydroxy($C_1$-$C_6$)alkyl.

In another embodiment, the present invention provides compounds of Formula (VI), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; $R_6$, $R_7$, and $R_{10}$ are H; and $R_9$ is H or hydroxy($C_1$-$C_6$)alkyl.

In another embodiment, the present invention provides compounds of Formula (VI), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, and $R_{10}$ are H; and $R_9$ is hydroxy($C_1$-$C_6$)alkyl.

In another embodiment, the present invention provides compounds of Formula (VI), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; $R_6$, $R_7$, $R_9$, and $R_{10}$ are H.

In another embodiment, the present invention provides a pharmaceutical composition comprising a compound of Formula (VI), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (VI), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (VI), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (VI), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (VI), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (VI), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (VI), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (VI), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (VI), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (VI), or a pharmaceutically acceptable salt thereof.

In another aspect, the present invention provides uses for compounds of Formula (V), or a pharmaceutically acceptable salt thereof, for preparing, or for the manufacture of, a medicament for treating metabolic disorders in a mammal, particularly a human.

In another aspect, the present invention provides uses for compounds of Formula (VI), or a pharmaceutically acceptable salt thereof, for preparing, or for the manufacture of, a medicament for treating or preventing type II diabetes in a mammal, particularly a human.

In another aspect, the present invention provides uses for compounds of Formula (VI), or a pharmaceutically acceptable salt thereof, for preparing, or for the manufacture of, a medicament for treating or preventing obesity in a mammal, particularly a human.

In another aspect, the present invention provides uses for compounds of Formula (VI), or a pharmaceutically acceptable salt thereof, for preparing, or for the manufacture of, a medicament for treating or preventing dyslipidemia in a mammal, particularly a human.

In another aspect, the present invention provides uses for compounds of Formula (VI) for preparing, or for the manufacture of, a medicament for treating renal diseases in a mammal, particularly a human.

In another aspect, the present invention provides uses for compounds of Formula (VI) for preparing, or for the manufacture of, a medicament for treating or preventing chronic kidney disease in a mammal, particularly a human.

In another aspect, the present invention provides uses for compounds of Formula (VI) for preparing, or for the manufacture of, a medicament for treating or preventing diabetic nephropathy in a mammal, particularly a human.

In another aspect, the present invention provides uses for compounds of Formula (VI) for preparing, or for the manufacture of, a medicament for treating or preventing acute kidney injury in a mammal, particularly a human.

In another aspect, the present invention provides uses for compounds of Formula (VI) for preparing, or for the manufacture of, a medicament for treating or preventing polycystic kidney disease in a mammal, particularly a human.

In another embodiment, the present invention provides compounds of Formula (VII)

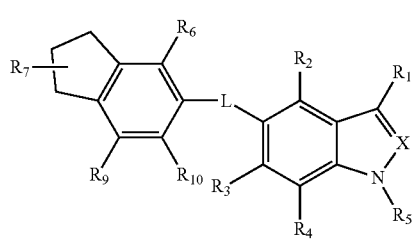

Formula (VII)

or a pharmaceutically acceptable salt thereof, wherein X is N or CH; L is a bond, O, S, $NR_A$, $(C_1-C_6)$alkylene, $(C_2-C_6)$alkenylene, or $(C_2-C_6)$alkynylene; $R_1$ is —C(O)$OR_A$, —C(O)$NR_BR_C$, —S($O_2$)$OR_A$, —S($O_2$)NHC(O)$R_D$, 5-oxo-4,5-dihydro-1,2,4-oxadiazol-3-yl, or 1H-tetrazol-5-yl; $R_A$ is H or ($C_1$-$C_6$)alkyl; $R_B$ and $R_C$ are independently H, ($C_1$-$C_6$)alkyl, or —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$, $R_3$, and $R_4$ are independently H, ($C_1$-$C_6$)alkoxy, ($C_1$-$C_6$)alkyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_8$)alkyl, mercapto, nitro, —$NR_GR_H$, or ($NR_GR_H$)carbonyl; $R_G$ and $R_H$ are independently H, ($C_1$-$C_6$)alkyl, or ($C_1$-$C_6$)alkylcarbonyl; $R_5$ is H or ($C_1$-$C_6$)alkyl; $R_6$, $R_7$, $R_9$, and $R_{10}$ are independently H, ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_JR_K$, or ($NR_JR_K$)carbonyl; and $R_J$ and $R_K$ are independently H or ($C_1$-$C_6$)alkyl.

In another embodiment, the present invention provides compounds of Formula (VII), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; and $R_6$, $R_7$, $R_9$, and $R_{10}$ are H.

In another embodiment, the present invention provides compounds of Formula (VII), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; and $R_6$, $R_7$, $R_9$, and $R_{10}$ are H.

In another embodiment, the present invention provides compounds of Formula (VII), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; and $R_6$, $R_7$, $R_9$, and $R_{10}$ are H.

In another embodiment, the present invention provides compounds of Formula (VII), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; and $R_6$, $R_7$, $R_9$, and $R_{10}$ are H.

In another embodiment, the present invention provides compounds of Formula (VII), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; and $R_6$, $R_7$, $R_9$, and $R_{10}$ are H.

In another embodiment, the present invention provides compounds of Formula (VII), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; and $R_6$, $R_7$, $R_9$, and $R_{10}$ are H.

In another embodiment, the present invention provides a pharmaceutical composition comprising a compound of Formula (VII), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (VII), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (VII), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (VII), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (VII), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (VII), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (VII), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (VII), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (VII), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (VII), or a pharmaceutically acceptable salt thereof.

In another aspect, the present invention provides uses for compounds of Formula (VII), or a pharmaceutically acceptable salt thereof, for preparing, or for the manufacture of, a medicament for treating metabolic disorders in a mammal, particularly a human.

In another aspect, the present invention provides uses for compounds of Formula (VII), or a pharmaceutically acceptable salt thereof, for preparing, or for the manufacture of, a medicament for treating or preventing type II diabetes in a mammal, particularly a human.

In another aspect, the present invention provides uses for compounds of Formula (VII), or a pharmaceutically acceptable salt thereof, for preparing, or for the manufacture of, a medicament for treating or preventing obesity in a mammal, particularly a human.

In another aspect, the present invention provides uses for compounds of Formula (VII), or a pharmaceutically acceptable salt thereof, for preparing, or for the manufacture of, a medicament for treating or preventing dyslipidemia in a mammal, particularly a human.

In another aspect, the present invention provides uses for compounds of Formula (VII) for preparing, or for the manufacture of, a medicament for treating renal diseases in a mammal, particularly a human.

In another aspect, the present invention provides uses for compounds of Formula (VII) for preparing, or for the manufacture of, a medicament for treating or preventing chronic kidney disease in a mammal, particularly a human.

In another aspect, the present invention provides uses for compounds of Formula (VII) for preparing, or for the manufacture of, a medicament for treating or preventing diabetic nephropathy in a mammal, particularly a human.

In another aspect, the present invention provides uses for compounds of Formula (VII) for preparing, or for the manufacture of, a medicament for treating or preventing acute kidney injury in a mammal, particularly a human.

In another aspect, the present invention provides uses for compounds of Formula (VII) for preparing, or for the manufacture of, a medicament for treating or preventing polycystic kidney disease in a mammal, particularly a human.

In another embodiment, the present invention provides compounds of Formula (VIII)

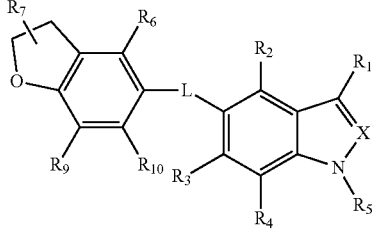

Formula (VIII)

or a pharmaceutically acceptable salt thereof, wherein X is N or CH; L is a bond, O, S, $NR_A$, $(C_1-C_6)$alkylene, $(C_2-C_6)$alkenylene, or $(C_2-C_6)$alkynylene; $R_1$ is —C(O)$OR_A$, —C(O)$NR_BR_C$, —S($O_2$)$OR_A$, —S($O_2$)NHC(O)$R_D$, 5-oxo-4,5-dihydro-1,2,4-oxadiazol-3-yl, or 1H-tetrazol-5-yl; $R_A$ is H or ($C_1$-$C_6$)alkyl; $R_B$ and $R_C$ are independently H, ($C_1$-$C_6$)alkyl, or —S($O_2$)$R_D$; $R_D$ is ($C_1$-$C_6$)alkyl, —$CF_3$, or phenyl, wherein the phenyl is optionally substituted with 1, 2, 3, 4, or 5 substituents that are independently ($C_1$-$C_6$)alkoxy, ($C_1$-$C_6$)alkyl, cyano, halogen, halo($C_1$-$C_6$)alkoxy, halo($C_1$-$C_6$)alkyl, hydroxy, mercapto, nitro, or $NR_ER_F$; $R_E$ and $R_F$ are independently H or ($C_1$-$C_6$)alkyl; $R_2$, $R_3$, and $R_4$ are independently H, ($C_1$-$C_6$)alkoxy, ($C_1$-$C_6$)alkyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_8$)alkyl, mercapto, nitro, —$NR_GR_H$, or ($NR_GR_H$)carbonyl; $R_G$ and $R_H$ are independently H, ($C_1$-$C_6$)alkyl, or ($C_1$-$C_6$)alkylcarbonyl; $R_5$ is H or ($C_1$-$C_6$)alkyl; $R_6$, $R_7$, $R_9$, and $R_{10}$ are independently H, ($C_1$-$C_6$)alkoxy, ($C_1$-$C_6$)alkoxycarbonyl, ($C_1$-$C_6$)alkyl, ($C_1$-$C_6$)alkylcarbonyl, ($C_1$-$C_6$)alkylthio, carboxy, cyano, halogen, halo($C_1$-$C_6$)alkoxy, halo($C_1$-$C_6$)alkyl, hydroxy, hydroxy($C_1$-$C_6$)alkyl, mercapto, nitro, —$NR_JR_K$, or ($NR_JR_K$)carbonyl; and $R_J$ and $R_K$ are independently H or ($C_1$-$C_6$)alkyl.

In another embodiment, the present invention provides compounds of Formula (VIII), or a pharmaceutically acceptable salt thereof, wherein X is CH; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; and $R_6$, $R_7$, $R_9$, and $R_{10}$ are H.

In another embodiment, the present invention provides compounds of Formula (VIII), or a pharmaceutically acceptable salt thereof, wherein X is CH; L is a bond; $R_1$ is —C(O)$OR_A$; $R_A$ is H; $R_2$ is H or F; $R_3$ is methyl, cyano, Cl, or F; $R_4$ is H; $R_5$ is H; and $R_6$, $R_7$, $R_9$, and $R_{10}$ are H.

In another embodiment, the present invention provides compounds of Formula (VIII), or a pharmaceutically acceptable salt thereof, wherein X is CH; L is a bond; $R_1$ is —C(O)$OR_A$; $R_A$ is H; $R_2$ is H or F; $R_3$ is Cl, F, or CN; $R_4$ is H; $R_5$ is H; and $R_6$, $R_7$, $R_9$, and $R_{10}$ are H.

In another embodiment, the present invention provides compounds of Formula (VIII), or a pharmaceutically acceptable salt thereof, wherein X is N; L is a bond; $R_1$ is —C(O)$OR_A$; $R_A$ is H; $R_2$ is H or halogen; $R_3$ is ($C_1$-$C_6$)alkyl, cyano, or halogen; $R_4$ is H; $R_5$ is H; and $R_6$, $R_7$, $R_9$, and $R_{10}$ are H.

In another embodiment, the present invention provides compounds of Formula (VIII), or a pharmaceutically acceptable salt thereof, wherein X is N; L is a bond; $R_1$ is —C(O)$OR_A$; $R_A$ is H; $R_2$ is H or F; $R_3$ is methyl, cyano, Cl, or F; $R_4$ is H; $R_5$ is H; and $R_6$, $R_7$, $R_9$, and $R_{10}$ are H.

In another embodiment, the present invention provides compounds of Formula (VIII), or a pharmaceutically acceptable salt thereof, wherein X is N; L is a bond; $R_1$ is —C(O)$OR_A$; $R_A$ is H; $R_2$ is H or F; $R_3$ is Cl, F, or CN; $R_4$ is H; $R_5$ is H; and $R_6$, $R_7$, $R_9$, and $R_{10}$ are H.

In another embodiment, the present invention provides a pharmaceutical composition comprising a compound of Formula (VIII), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (VIII), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (VIII), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (VIII), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (VIII), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (VIII), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (VIII), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (VIII), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (VIII), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (VIII), or a pharmaceutically acceptable salt thereof.

In another aspect, the present invention provides uses for compounds of Formula (VIII), or a pharmaceutically acceptable salt thereof, for preparing, or for the manufacture of, a medicament for treating metabolic disorders in a mammal, particularly a human.

In another aspect, the present invention provides uses for compounds of Formula (VIII), or a pharmaceutically acceptable salt thereof, for preparing, or for the manufacture of, a medicament for treating or preventing type II diabetes in a mammal, particularly a human.

In another aspect, the present invention provides uses for compounds of Formula (VIII), or a pharmaceutically acceptable salt thereof, for preparing, or for the manufacture of, a medicament for treating or preventing obesity in a mammal, particularly a human.

In another aspect, the present invention provides uses for compounds of Formula (VIII), or a pharmaceutically acceptable salt thereof, for preparing, or for the manufacture of, a medicament for treating or preventing dyslipidemia in a mammal, particularly a human.

In another aspect, the present invention provides uses for compounds of Formula (VIII) for preparing, or for the manufacture of, a medicament for treating renal diseases in a mammal, particularly a human.

In another aspect, the present invention provides uses for compounds of Formula (VIII) for preparing, or for the manufacture of, a medicament for treating or preventing chronic kidney disease in a mammal, particularly a human.

In another aspect, the present invention provides uses for compounds of Formula (VIII) for preparing, or for the manufacture of, a medicament for treating or preventing diabetic nephropathy in a mammal, particularly a human.

In another aspect, the present invention provides uses for compounds of Formula (VIII) for preparing, or for the manufacture of, a medicament for treating or preventing acute kidney injury in a mammal, particularly a human.

In another aspect, the present invention provides uses for compounds of Formula (VIII) for preparing, or for the manufacture of, a medicament for treating or preventing polycystic kidney disease in a mammal, particularly a human.

In another embodiment, the present invention provides compounds of Formula (IX)

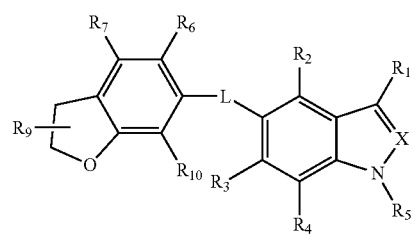

Formula (IX)

or a pharmaceutically acceptable salt thereof, wherein X is N or CH; L is a bond, O, S, $NR_A$, $(C_1-C_6)$alkylene, $(C_2-C_6)$alkenylene, or $(C_2-C_6)$alkynylene; $R_1$ is —$C(O)OR_A$, —$C(O)NR_BR_C$, —$S(O_2)OR_A$, —$S(O_2)NHC(O)R_D$, 5-oxo-4,5-dihydro-1,2,4-oxadiazol-3-yl, or 1H-tetrazol-5-yl; $R_A$ is H or $(C_1-C_6)$alkyl; $R_B$ and $R_C$ are independently H, $(C_1-C_6)$alkyl, or —$S(O_2)R_D$; $R_D$ is $(C_1-C_6)$alkyl, —$CF_3$, or phenyl, wherein the phenyl is optionally substituted with 1, 2, 3, 4, or 5 substituents that are independently $(C_1-C_6)$alkoxy, $(C_1-C_6)$alkyl, cyano, halogen, halo$(C_1-C_6)$alkoxy, halo$(C_1-C_6)$alkyl, hydroxy, mercapto, nitro, or $NR_ER_F$; $R_E$ and $R_F$ are independently H or $(C_1-C_6)$alkyl; $R_2$, $R_3$, and $R_4$ are independently H, $(C_1-C_6)$alkoxy, $(C_1-C_6)$alkyl, $(C_1-C_6)$alkylthio, carboxy, cyano, halogen, halo$(C_1-C_6)$alkoxy, halo$(C_1-C_6)$alkyl, hydroxy, hydroxy$(C_1-C_8)$alkyl, mercapto, nitro, —$NR_GR_H$, or $(NR_GR_H)$carbonyl; $R_G$ and $R_H$ are independently H, $(C_1-C_6)$alkyl, or $(C_1-C_6)$alkylcarbonyl; $R_5$ is H or $(C_1-C_6)$alkyl; $R_6$, $R_7$, $R_9$, and $R_{10}$ are independently H, $(C_1-C_6)$alkoxy, $(C_1-C_6)$alkoxycarbonyl, $(C_1-C_6)$alkyl, $(C_1-C_6)$alkylcarbonyl, $(C_1-C_6)$alkylthio, carboxy, cyano, halogen, halo$(C_1-C_6)$alkoxy, halo$(C_1-C_6)$alkyl, hydroxy, hydroxy$(C_1-C_6)$alkyl, mercapto, nitro, —$NR_JR_K$, or $(NR_JR_K)$carbonyl; and $R_J$ and $R_K$ are independently H or $(C_1-C_6)$alkyl.

In another embodiment, the present invention provides compounds of Formula (IX), or a pharmaceutically acceptable salt thereof, wherein X is CH; L is a bond; $R_1$ is —$C(O)OR_A$; $R_A$ is H; $R_2$ is H or halogen; $R_3$ is $(C_1-C_6)$alkyl, cyano, or halogen; $R_4$ is H; $R_5$ is H; and $R_6$, $R_7$, $R_9$, and $R_{10}$ are H.

In another embodiment, the present invention provides compounds of Formula (IX), or a pharmaceutically acceptable salt thereof, wherein X is CH; L is a bond; $R_1$ is —$C(O)OR_A$; $R_A$ is H; $R_2$ is H or F; $R_3$ is methyl, cyano, Cl, or F; $R_4$ is H; $R_5$ is H; and $R_6$, $R_7$, $R_9$, and $R_{10}$ are H.

In another embodiment, the present invention provides compounds of Formula (IX), or a pharmaceutically acceptable salt thereof, wherein X is CH; L is a bond; $R_1$ is —$C(O)OR_A$; $R_A$ is H; $R_2$ is H or F; $R_3$ is Cl, F, or CN; $R_4$ is H; $R_5$ is H; and $R_6$, $R_7$, $R_9$, and $R_{10}$ are H.

In another embodiment, the present invention provides compounds of Formula (IX), or a pharmaceutically acceptable salt thereof, wherein X is N; L is a bond; $R_1$ is —$C(O)OR_A$; $R_A$ is H; $R_2$ is H or halogen; $R_3$ is $(C_1-C_6)$alkyl, cyano, or halogen; $R_4$ is H; $R_5$ is H; and $R_6$, $R_7$, $R_9$, and $R_{10}$ are H.

In another embodiment, the present invention provides compounds of Formula (IX), or a pharmaceutically acceptable salt thereof, wherein X is N; L is a bond; $R_1$ is —$C(O)OR_A$; $R_A$ is H; $R_2$ is H or F; $R_3$ is methyl, cyano, Cl, or F; $R_4$ is H; $R_5$ is H; and $R_6$, $R_7$, $R_9$, and $R_{10}$ are H.

In another embodiment, the present invention provides compounds of Formula (IX), or a pharmaceutically acceptable salt thereof, wherein X is N; L is a bond; $R_1$ is —$(CH_2)_nC(O)OR_A$; $R_A$ is H; n is 0; $R_2$ is H or F; $R_3$ is Cl, F, or CN; $R_4$ is H; $R_5$ is H; and $R_6$, $R_7$, $R_9$, and $R_{10}$ are H.

In another embodiment, the present invention provides a pharmaceutical composition comprising a compound of Formula (IX), or a pharmaceutically acceptable salt thereof, and at least one pharmaceutically acceptable excipient, diluent, or carrier.

In another embodiment, the present invention provides a method for treating or preventing metabolic disorders in a mammal, particularly a human, where the metabolic disorder is ameliorated by activation of 5' adenosine monophosphate-activated protein kinase comprising administering to the mammal or human, in need of such treatment, a therapeutically effective amount of a compound of Formula (IX), or a pharmaceutically acceptable salt thereof.

In another embodiment, the present invention provides a method for treating or preventing type II diabetes in a mammal, particularly a human, comprising administering to the mammal or human, in need of such treatment, a therapeutically effective amount of a compound of Formula (IX), or a pharmaceutically acceptable salt thereof.

In another embodiment, the present invention provides a method for treating or preventing obesity in a mammal, particularly a human, comprising administering to the mammal or human, in need of such treatment, a therapeutically effective amount of a compound of Formula (IX), or a pharmaceutically acceptable salt thereof.

In another embodiment, the present invention provides a method for treating or preventing dyslipidemia in a mammal, particularly a human, comprising administering to the mammal or human, in need of such treatment, a therapeutically effective amount of a compound of Formula (IX), or a pharmaceutically acceptable salt thereof.

In another embodiment, the present invention provides a method for treating or preventing renal diseases in a mammal, particularly a human, where the renal disease is ameliorated by activation of 5' adenosine monophosphate-activated protein kinase comprising administering to the mammal or human, in need of such treatment, a therapeutically effective amount of a compound of Formula (IX), or a pharmaceutically acceptable salt thereof.

In another embodiment, the present invention provides a method for treating or preventing chronic kidney disease in a mammal, particularly a human, comprising administering to the mammal or human, in need of such treatment, a therapeutically effective amount of a compound of Formula (IX), or a pharmaceutically acceptable salt thereof.

In another embodiment, the present invention provides a method for treating or preventing diabetic nephropathy in a mammal, particularly a human, comprising administering to the mammal or human, in need of such treatment, a therapeutically effective amount of a compound of Formula (IX), or a pharmaceutically acceptable salt thereof.

In another embodiment, the present invention provides a method for treating or preventing acute kidney injury in a mammal, particularly a human, comprising administering to the mammal or human, in need of such treatment, a therapeutically effective amount of a compound of Formula (IX), or a pharmaceutically acceptable salt thereof.

In another embodiment, the present invention provides a method for treating or preventing polycystic kidney disease in a mammal, particularly a human, comprising administering to the mammal or human, in need of such treatment, a therapeutically effective amount of a compound of Formula (IX), or a pharmaceutically acceptable salt thereof.

In another aspect, the present invention provides uses for compounds of Formula (IX), or a pharmaceutically acceptable salt thereof, for preparing, or for the manufacture of, a medicament for treating metabolic disorders in a mammal, particularly a human.

In another aspect, the present invention provides uses for compounds of Formula (IX), or a pharmaceutically acceptable salt thereof, for preparing, or for the manufacture of, a medicament for treating or preventing type II diabetes in a mammal, particularly a human.

In another aspect, the present invention provides uses for compounds of Formula (IX), or a pharmaceutically acceptable salt thereof, for preparing, or for the manufacture of, a medicament for treating or preventing obesity in a mammal, particularly a human.

In another aspect, the present invention provides uses for compounds of Formula (IX), or a pharmaceutically acceptable salt thereof, for preparing, or for the manufacture of, a medicament for treating or preventing dyslipidemia in a mammal, particularly a human.

In another aspect, the present invention provides uses for compounds of Formula (IX) for preparing, or for the manufacture of, a medicament for treating renal diseases in a mammal, particularly a human.

In another aspect, the present invention provides uses for compounds of Formula (IX) for preparing, or for the manufacture of, a medicament for treating or preventing chronic kidney disease in a mammal, particularly a human.

In another aspect, the present invention provides uses for compounds of Formula (IX) for preparing, or for the manufacture of, a medicament for treating or preventing diabetic nephropathy in a mammal, particularly a human.

In another aspect, the present invention provides uses for compounds of Formula (IX) for preparing, or for the manufacture of, a medicament for treating or preventing acute kidney injury in a mammal, particularly a human.

In another aspect, the present invention provides uses for compounds of Formula (IX) for preparing, or for the manufacture of, a medicament for treating or preventing polycystic kidney disease in a mammal, particularly a human.

Definitions

As used throughout this specification and the appended claims, the following terms have the following meanings.

The term "$(C_2-C_8)$alkenylene" means a divalent group derived from a straight or branched chain hydrocarbon of from 2 to 8 carbon atoms containing at least one double bond. Representative examples of alkenylene include, but are not limited to, —CH=CH—, —CH=CH$_2$CH$_2$—, and —CH=C(CH$_3$)CH$_2$—.

The term "$(C_1-C_6)$alkoxy" as used herein, means a $(C_1-C_6)$ alkyl group, as defined herein, appended to the parent molecular moiety through an oxygen atom.

Representative examples of $(C_1-C_6)$alkoxy include, but are not limited to, methoxy, ethoxy, propoxy, 2-propoxy, butoxy, tert-butoxy, pentyloxy, and hexyloxy.

The term "$(C_1-C_6)$alkoxy$(C_1-C_6)$alkoxy" as used herein, means a $(C_1-C_6)$alkoxy group, as defined herein, appended to the parent molecular moiety through another $(C_1-C_6)$alkoxy group, as defined herein. Representative examples of $(C_1-C_6)$ alkoxy$(C_1-C_6)$alkoxy include, but are not limited to, tert-butoxymethoxy, 2-ethoxyethoxy, 2-methoxyethoxy, and methoxymethoxy.

The term "$(C_1-C_6)$alkoxy$(C_1-C_6)$alkyl" as used herein, means a $(C_1-C_6)$alkoxy group, as defined herein, appended to the parent molecular moiety through a $(C_1-C_6)$alkyl group, as defined herein. Representative examples of $(C_1-C_6)$alkoxy $(C_1-C_6)$alkyl include, but are not limited to, tert-butoxymethyl, 2-ethoxyethyl, 2-methoxyethyl, and methoxymethyl.

The term "$(C_1-C_6)$alkoxycarbonyl" as used herein, means a $(C_1-C_6)$alkoxy group, as defined herein, appended to the parent molecular moiety through a carbonyl group, as defined herein. Representative examples of $(C_1-C_6)$alkoxycarbonyl include, but are not limited to, methoxycarbonyl, ethoxycarbonyl, and tert-butoxycarbonyl.

The term "$(C_1-C_6)$alkoxysulfonyl" as used herein, means a $(C_1-C_6)$alkoxy group, as defined herein, appended appended to the parent molecular moiety through a sulfonyl group, as defined herein. Representative examples of $(C_1-C_6)$alkoxysulfonyl include, but are not limited to, methoxysulfonyl, ethoxysulfonyl and propoxysulfonyl.

The term "$(C_1-C_6)$alkyl" as used herein, means a straight or branched chain hydrocarbon containing from 1 to 6 carbon atoms. Representative examples of $(C_1-C_6)$alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "$(C_1-C_6)$alkylcarbonyl" as used herein, means a $(C_1-C_6)$alkyl group, as defined herein, appended to the parent molecular moiety through a carbonyl group, as defined herein. Representative examples of $(C_1-C_6)$alkylcarbonyl include, but are not limited to, acetyl, 1-oxopropyl, 2,2-dimethyl-1-oxopropyl, 1-oxobutyl, and 1-oxopentyl.

The term "$(C_1-C_6)$alkylene" means a divalent group derived from a straight or branched chain hydrocarbon of from 1 to 6 carbon atoms. Representative examples of $(C_1-C_8)$alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, —$CH_2CH(CH_3)CH_2$—, and —$CH_2CH_2CH_2CH_2CH_2$—.

The term "$(C_1-C_6)$alkylsulfonyl" as used herein, means an $(C_1-C_6)$alkyl group, as defined herein, appended to the parent molecular moiety through a sulfonyl group, as defined herein. Representative examples of $(C_1-C_6)$alkylsulfonyl include, but are not limited to, methylsulfonyl and ethylsulfonyl.

The term "$(C_1-C_6)$alkylthio" as used herein, means a $(C_1-C_6)$alkyl group, as defined herein, appended to the parent molecular moiety through a sulfur atom. Representative examples of $(C_1-C_6)$alkylthio include, but are not limited to, methylthio, ethylthio, tert-butylthio, and hexylthio.

The term "aryl" as used herein, means a phenyl or naphthyl group.

The term "aryl$(C_1-C_6)$alkoxy" as used herein, means an aryl group, as defined herein, appended to the parent molecular moiety through an $(C_1-C_6)$alkoxy group, as defined herein.

The term "aryl$(C_1-C_6)$alkyl" as used herein, means an aryl group, as defined herein, appended to the parent molecular moiety through an $(C_1-C_6)$alkyl group, as defined herein. Representative examples of aryl$(C_1-C_6)$alkyl include, but are not limited to, benzyl, 2-phenylethyl, 3-phenylpropyl, and 2-naphth-2-ylethyl.

The term "arylcarbonyl" as used herein, means an aryl group, as defined herein, appended to the parent molecular moiety through a carbonyl group, as defined herein. Examples of arylcarbonyl are benzoyl and naphthoyl.

The term "aryloxy" as used herein, means an aryl group, as defined herein, appended to the parent molecular moiety through an oxygen atom. Examples of aryloxy are phenoxy and naphthalenyloxy.

The term "carbonyl" as used herein, means a —C(O)— group.

The term "carboxy" as used herein, means a —C(O)OH group.

The term "carboxy$(C_1-C_6)$alkoxy" as used herein, means a carboxy group, as defined herein, is attached to the parent molecular moiety through a $(C_1-C_6)$alkoxy group, as defined herein.

The term "carboxy$(C_1-C_6)$alkyl" as used herein, means a carboxy group, as defined herein, is attached to the parent molecular moiety through a $(C_1-C_6)$alkyl group, as defined herein.

The term "cyano" as used herein, means a —CN group.

The term "$(C_3-C_8)$cycloalkyl" as used herein, means a saturated cyclic hydrocarbon group containing from 3 to 8 carbons, examples of $(C_3-C_8)$cycloalkyl include cyclopropyl, cyclobutyl, cyclopentyl, cyclohexyl, cycloheptyl, and cyclooctyl.

The term "$(C_3-C_8)$cycloalkyl$(C_1-C_6)$alkoxy" as used herein, means a $(C_3-C_8)$cycloalkyl group, as defined herein, appended to the parent molecular moiety through a $(C_1-C_6)$alkoxy group, as defined herein.

The term "$(C_3-C_8)$cycloalkyl$(C_1-C_6)$alkyl" as used herein, means a $(C_3-C_6)$cycloalkyl group, as defined herein, appended to the parent molecular moiety through a $(C_1-C_6)$alkyl group, as defined herein. Representative examples of $(C_3-C_8)$cycloalkyl$(C_1-C_6)$alkyl include, but are not limited to, cyclopropylmethyl, 2-cyclobutylethyl, cyclopentylmethyl, cyclohexylmethyl, and 4-cycloheptylbutyl.

The term "$(C_3-C_8)$cycloalkylcarbonyl" as used herein, means $(C_3-C_8)$cycloalkyl group, as defined herein, appended to the parent molecular moiety through a carbonyl group, as defined herein. Representative examples of $(C_3-C_8)$cycloalkylcarbonyl include, but are not limited to, cyclopropylcarbonyl, 2-cyclobutylcarbonyl, and cyclohexylcarbonyl.

The term "$(C_3-C_8)$cycloalkyloxy" as used herein, means $(C_3-C_8)$cycloalkyl group, as defined herein, appended to the parent molecular moiety through an oxygen atom, as defined herein. Representative examples of $(C_3-C_8)$cycloalkyloxy include, but are not limited to, cyclopropyloxy, cyclobutyloxy, cyclopentyloxy, cyclohexyloxy, cycloheptyloxy, and cyclooctyloxy.

The term "Formula (I-IX)" as used herein means compounds of Formula (I), (II), (III), (IV), (V), (VI), (VII), (VIII), and (IX).

The term "halo" or "halogen" as used herein, means —Cl, —Br, —I or —F.

The term "halo$(C_1-C_6)$alkoxy" as used herein, means at least one halogen, as defined herein, appended to the parent molecular moiety through a $(C_1-C_6)$alkoxy group, as defined herein. Representative examples of halo$(C_1-C_6)$alkoxy include, but are not limited to, chloromethoxy, 2-fluoroethoxy, trifluoromethoxy, and pentafluoroethoxy.

The term "halo$(C_1-C_6)$alkyl" as used herein, means at least one halogen, as defined herein, appended to the parent molecular moiety through a $(C_1-C_6)$alkyl group, as defined herein. Representative examples of halo$(C_1-C_6)$alkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and/or optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heteroaryl($C_1$-$C_6$)alkoxy" as used herein, means a heteroaryl group, as defined herein, appended to the parent molecular moiety through an ($C_1$-$C_6$)alkoxy group, as defined herein. Representative examples of heteroaryl($C_1$-$C_6$)alkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, thien-2-ylmethoxy, and thien-3-ylmethoxy.

The term "heteroaryl($C_1$-$C_6$)alkyl" as used herein, means a heteroaryl, as defined herein, appended to the parent molecular moiety through an ($C_1$-$C_6$)alkyl group, as defined herein. Representative examples of heteroaryl($C_1$-$C_6$)alkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "($C_3$-$C_7$)heterocycle" or "($C_3$-$C_7$)heterocyclic" as used herein, means a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The heterocycle is connected to the parent molecular moiety through any carbon atom or any nitrogen atom contained within the heterocycle. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "($C_3$-$C_7$)heterocycle($C_1$-$C_6$)alkoxy" as used herein, means a 3-7 membered heterocycle group, as defined herein, appended to the parent molecular moiety through an ($C_1$-$C_6$)alkoxy group, as defined herein.

The term "($C_3$-$C_7$)heterocycle($C_1$-$C_6$)alkyl" as used herein, means a 3-7 membered heterocycle, as defined herein, appended to the parent molecular moiety through an ($C_1$-$C_6$) alkyl group, as defined herein.

The term "($C_3$-$C_7$)heterocyclecarbonyl" as used herein, means a 3-7 membered heterocycle, as defined herein, appended to the parent molecular moiety through a carbonyl group, as defined herein.

The term "($C_3$-$C_7$)heterocycleoxy" as used herein, means a 3-7 membered heterocycle, as defined herein, appended to the parent molecular moiety through an oxygen atom.

The term "hydroxy" as used herein, means an —OH group.

The term "hydroxy($C_1$-$C_6$)alkoxy" as used herein, means at least one hydroxy group, as defined herein, is appended to the parent molecular moiety through a ($C_1$-$C_6$)alkoxy group, as defined herein. Representative examples of hydroxy($C_1$-$C_6$)alkoxy include, but are not limited to, hydroxymethoxy, 2-hydroxyethoxy, 3-hydroxypropoxy, 2,3-dihydroxypentoxy, and 2-ethyl-4-hydroxyheptoxy.

The term "hydroxy($C_1$-$C_6$)alkyl" as used herein, means at least one hydroxy group, as defined herein, is appended to the parent molecular moiety through a ($C_1$-$C_6$)alkyl group, as defined herein. Representative examples of hydroxy($C_1$-$C_6$) alkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "nitrogen protecting group" as used herein, means those groups intended to protect an amino group against undesirable reactions during synthetic procedures. Representative examples of a nitrogen protecting group include, but are not limited to, acetyl, benzoyl, benzyl, benzyloxycarbonyl (Cbz), formyl, phenylsulfonyl, pivaloyl, tert-butoxycarbonyl (Boc), tert-butylacetyl, ethyloxycarbonyl, trifluoroacetyl, triphenylmethyl (trityl), tert-butyldimethylsilane, and triisopropylsilane.

The term "$NR_ER_F$" as used herein, means two groups, $R_E$ and $R_F$, which are appended to the parent molecular moiety through a nitrogen atom. $R_E$ and $R_F$ are each independently H or ($C_1$-$C_6$)alkyl. Representative examples of $NR_ER_F$ include, but are not limited to, amino, methylamino, dimethylamino, and ethylmethylamino.

The term "($NR_ER_F$)carbonyl" as used herein, means a $NR_ER_F$ group, as defined herein, appended to the parent molecular moiety through a carbonyl group, as defined herein. Representative examples of ($NR_ER_F$)carbonyl include, but are not limited to, aminocarbonyl, (methylamino)carbonyl, (dimethylamino)carbonyl, and (ethylmethylamino)carbonyl.

The term "$NR_G R_H$" as used herein, means two groups, $R_G$ and $R_H$, which are appended to the parent molecular moiety through a nitrogen atom. $R_G$ and $R_H$ are each independently H, $(C_1-C_6)$alkyl, or $(C_1-C_6)$alkylcarbonyl. Representative examples of $NR_G R_H$ include, but are not limited to, amino, methylamino, dimethylamino, ethylmethylamino, acetamido, propionamido, and isobutyramido.

The term "$(NR_G R_H)$carbonyl" as used herein, means a $NR_G R_H$ group, as defined herein, appended to the parent molecular moiety through a carbonyl group, as defined herein. Representative examples of $(NR_G R_H)$carbonyl include, but are not limited to, aminocarbonyl, (methylamino)carbonyl, (dimethylamino)carbonyl, and (ethylmethylamino)carbonyl.

The term "$NR_J R_K$" as used herein, means two groups, $R_J$ and $R_K$, which are appended to the parent molecular moiety through a nitrogen atom. $R_J$ and $R_K$ are each independently H or $(C_1-C_6)$alkyl. Representative examples of $NR_J R_K$ include, but are not limited to, amino, methylamino, dimethylamino, and ethylmethylamino.

The term "$(NR_J R_K)$carbonyl" as used herein, means a $NR_J R_K$ group, as defined herein, appended to the parent molecular moiety through a carbonyl group, as defined herein. Representative examples of $(NR_J R_K)$carbonyl include, but are not limited to, aminocarbonyl, (methylamino)carbonyl, (dimethylamino)carbonyl, and (ethylmethylamino)carbonyl.

The term "$NR_M R_N$" as used herein, means two groups, $R_M$ and $R_N$, which are appended to the parent molecular moiety through a nitrogen atom. $R_M$ and $R_N$ are each independently H, $(C_1-C_6)$alkyl, or $(C_1-C_6)$alkylcarbonyl; or $R_M$ and $R_N$ together with the nitrogen they are attached to form a 3 to 8 membered ring. Representative examples of $NR_M R_N$ include, but are not limited to, amino, methylamino, dimethylamino, ethylmethylamino, aziridinyl, azetidinyl, pyrrolidinyl, piperidinyl, azepanyl, and azocanyl.

The term "$NR_M R_N(C_1-C_6)$alkoxy" as used herein, means a $NR_M R_N$ group, as defined herein, appended to the parent molecular moiety through a $(C_1-C_6)$alkoxy group, as defined herein.

The term "$NR_M R_N(C_1-C_6)$alkyl" as used herein, means a $NR_M R_N$ group, as defined herein, appended to the parent molecular moiety through a $(C_1-C_6)$alkyl group, as defined herein.

The term "$(NR_M R_N)$carbonyl" as used herein, means a $NR_M R_N$ group, as defined herein, appended to the parent molecular moiety through a carbonyl group, as defined herein. Representative examples of $(NR_M R_N)$carbonyl include, but are not limited to, aminocarbonyl, (methylamino)carbonyl, (dimethylamino)carbonyl, and (ethylmethylamino)carbonyl.

The term "$(NR_M R_N)$carbonyl$(C_1-C_6)$alkoxy" as used herein, means a $(NR_M R_N)$carbonyl group, as defined herein, appended to the parent molecular moiety through a $(C_1-C_6)$ alkoxy group, as defined herein.

The term "$(NR_M R_N)$carbonyl$(C_1-C_6)$alkyl" as used herein, means a $(NR_M R_N)$carbonyl group, as defined herein, appended to the parent molecular moiety through a $(C_1-C_6)$ alkyl group, as defined herein.

The term "tautomer," as used herein, means a proton shift from one atom of a molecule to another atom of the same molecule wherein two or more structurally distinct compounds are in equilibrium with each other. Compounds of the present invention may exist as tautomers. The present invention contemplates tautomers due to proton shifts from one atom to another atom of the same molecule generating two or more distinct compounds that are in equilibrium with each other.

The term "therapeutically effective amount" means an amount of a compound of the present invention, or a pharmaceutically acceptable salt thereof, that: (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66:1-19. The salts can be prepared in situ during the final isolation and purification of the compounds of the present invention or separately by reacting a free base (basic nitrogen) with a suitable organic or inorganic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in *IUPAC* 1974 *Recommendations for Section E, Fundamental Stereochemistry, Pure Aool. Chem.*, (1976), 45: 13-30. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution include, but are not limited to (1)

attachment of a chiral auxiliary to a mixture of enantiomers, separation of the resulting mixture of diastereomers by recrystallization or chromatography, and liberation of the optically pure product from the auxiliary or (2) direct separation of the mixture of optical enantiomers on chiral chromatographic columns.

Compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (I) and mixtures thereof.

Tautomers may exist in the compounds of the present invention and are specifically included within the scope of the present invention. The present invention contemplates tautomers due to proton shifts from one atom to another atom of the same molecule generating two or more compounds that are in equilibrium with each other. The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Compounds of the present invention may exist in more than one crystal form. Polymorphs of compounds of Formula I-IX and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula I-IX, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

Compounds of the present invention are useful for treating diseases, conditions and/or disorders ameliorated via activation of AMPK. Another embodiment of the present invention is a pharmaceutical composition comprising a therapeutically effective amount of a compound of the present invention and a pharmaceutically acceptable excipient, diluent or carrier. The compounds of the present invention (including the compositions and processes used herein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" *J. Pharm. Pharmacol.*, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the present invention. The term "solvate" refers to a molecular complex of a compound represented by Formula (I)-(IX), including pharmaceutically acceptable salts thereof, with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention provides a method of treating diseases, conditions and/or disorders activated by the activation of AMPK in an animal, particularly a human, that includes administering to the animal or human in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the activation of AMPK.

One aspect of the present invention is the treatment of obesity, and obesity-related disorders (e.g., overweight, weight gain, or weight maintenance). Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy.

In yet another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the invention is the treatment of nonalcoholic fatty liver disease (NAFLD) and hepatic insulin resistance.

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The compounds of the present invention or pharmaceutical compositions thereof can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be combined with the compounds of the present invention include, for example, those described at page 30, line 20 through page 31, line 30 of WO 2011005611. The lipid lowering agents include bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPARα agonists, FXR receptor modulators, LXR receptor modulators, lipoprotein synthesis inhibitors, rennin angiotensisn system inhibitors, PPAR d partial agonists, bile acid reabsorption inhibitors, PPAR γ agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin bound chromium and other agents that affect lipid composition.

Suitable anti-hypertensive agents that can be combined with the compounds of the present invention include, for example, those described at page 31, line 31 through page 32, line 18 of WO 2011005611. The anti-hypertensive agents include diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, α/β adrenergic blockers, alpha 1 blockers, alpha 2 agonists, aldosterone inhibitors, mineraocorticoid receptor inhibitors, renin inhibitors and angiopoietin-2-binding agents.

Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J.C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine. Preferably, compounds of the present invention and combination therapies are administered in conjunction with exercise and a sensible diet.

All of the recited U.S. patents and publications (including all technical bulletins referenced in the Examples) are incorporated herein by reference in their entireties.

Abbreviations which have been used in the descriptions of the schemes and the examples that follow are: n-BuLi for n-butyllithium; DMAP for 4-dimethylaminopyridine; DME for dimethoxyethane; DMF for N,N-dimethylformamide; EtOAc for ethyl acetate; LAH for lithium aluminum hydride; MeOH for methanol; TFA for trifluoroacetic acid; and THF for tetrahydrofuran.

The present invention encompasses compounds of Formula (I), (II), (III), (IV), (V), (VI), (VII), (VIII), and (IX) when prepared by synthetic processes or by metabolic processes. Preparation of the compounds of the invention by metabolic processes include those occurring in the human or animal body (in vivo) or processes occurring in vitro.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as intermediates for preparing compounds of the present invention. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention protection of remote functionalities such as carboxylic acids, amines, and/or hydroxy groups of intermediates may be necessary. The need for such protection will vary depending on the nature of the remote functionality and the conditions of the preparation methods. Suitable amino-protecting groups (NH-PG) include acetyl, trifluoroacetyl, t-butoxycarbonyl (BOC), benzyloxycarbonyl (Cbz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-PG) include for example, allyl, acetyl, silyl, benzyl, para-methoxybenzyl, trityl, and the like. Carboxylic acid protecting groups include alkyl esters such as methy, ethyl, propyl, and tert-butyl. The need for such protection is readily determined by one skilled in the art. For a general description of protecting groups and their use, see T. W. Greene, Protective Groups in Organic Synthesis, John Wiley & Sons, New York, 1991.

Schemes 1 through 10 outline the general procedures useful for the preparation of compounds of the present invention. It is to be understood, however, that the invention, as fully described herein and as recited in the claims, is not intended to be limited by the details of the following schemes or modes of preparation.

Scheme 1

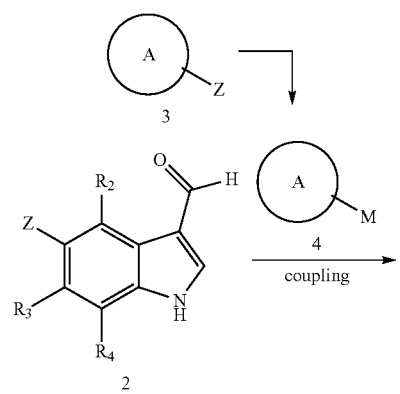

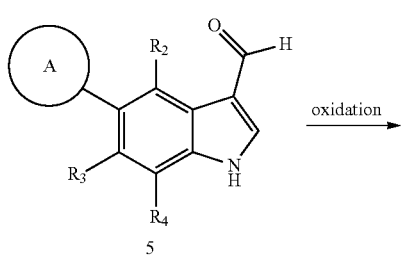

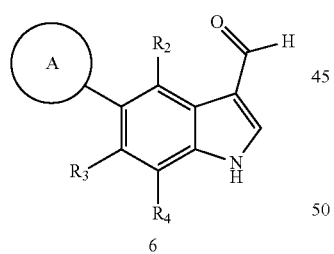

Indole acids of general formula 6, wherein $R_2$, $R_3$, $R_4$, and A are as defined in Formula (I) of the Summary section herein, can be synthesized as shown in Scheme 1. Indoles of general formula 1, wherein Z is Cl, Br, I, triflate, mesylate, or tosylate (purchased or prepared using similar synthetic methodology as found in *Chem. Rev.* 2006, 106, 2875) can be formylated with reagents such as N,N-dimethylformiminium chloride (purchased or prepared in situ with dimethylformamide and an activating agent such as phosphorus oxychloride or oxalyl chloride at temperatures ranging from −78° C. to 120° C.) to provide compounds of general formula 2. Aryl and heteroaryl compounds of general formula 3 (Z is Cl, Br, I, triflate, mesylate, or tosylate), purchased or synthesized using known methods, can be activated to provide compounds of general formula 4, where M is boron, zinc, tin, magnesium, indium, or silicon, by using an appropriate activating reagent including, but not limited to, dialkoxyboranes, bisboron compounds, tributyltin halides, isopropylmagnesium halides, or zinc powder and salts. Compounds of general formula 2 and 4 can be coupled using a variety of palladium and nickel catalysts with a variety of ligands or with no ligands (such as PddppfCl$_2$, tetrakistriphenylphosphine palladium, palladium (II) acetate, Pd$_2$dba$^3$ or the like) at temperatures ranging from 25° C. to 120° C. with conventional heat or with microwave heat for 15 minutes to 24 hours. Oxidation of compounds of general formula 5 to provide compounds of general formula 6 can be effected with sodium chlorite, potassium permanganate, or the like, often with a chloronium ion scavenger such as 2-methyl-2-butene present.

Scheme 2

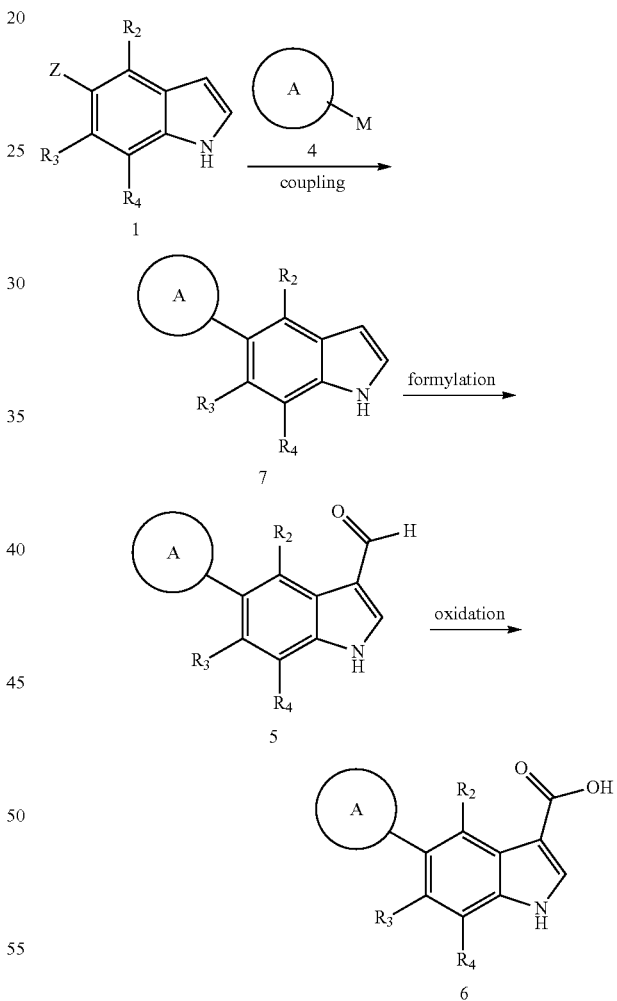

Alternatively in Scheme 2, compounds of general formula 6, wherein $R_2$, $R_3$, $R_4$, and A are as defined in Formula (I) of the Summary section herein, can be prepared by changing the sequence of reactions disclosed in Scheme 1. Indoles of general formula 1 can be coupled to aryl or heteroaryl compounds of general formula 4 to provide indoles of general formula 7 which can be formylated and oxidized as described in Scheme 1 to provide indoles of general formula 6.

Scheme 3

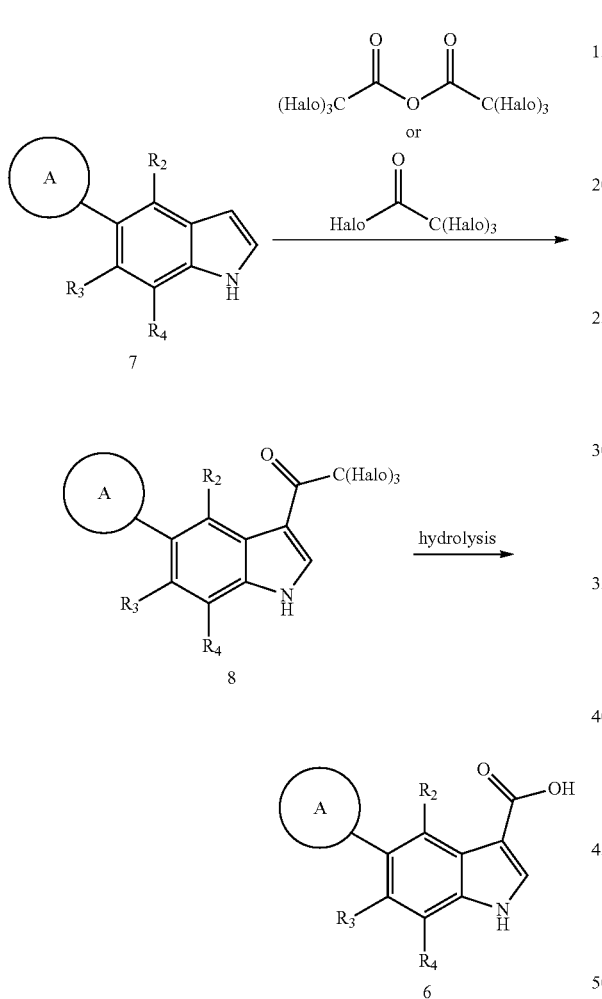

Scheme 4

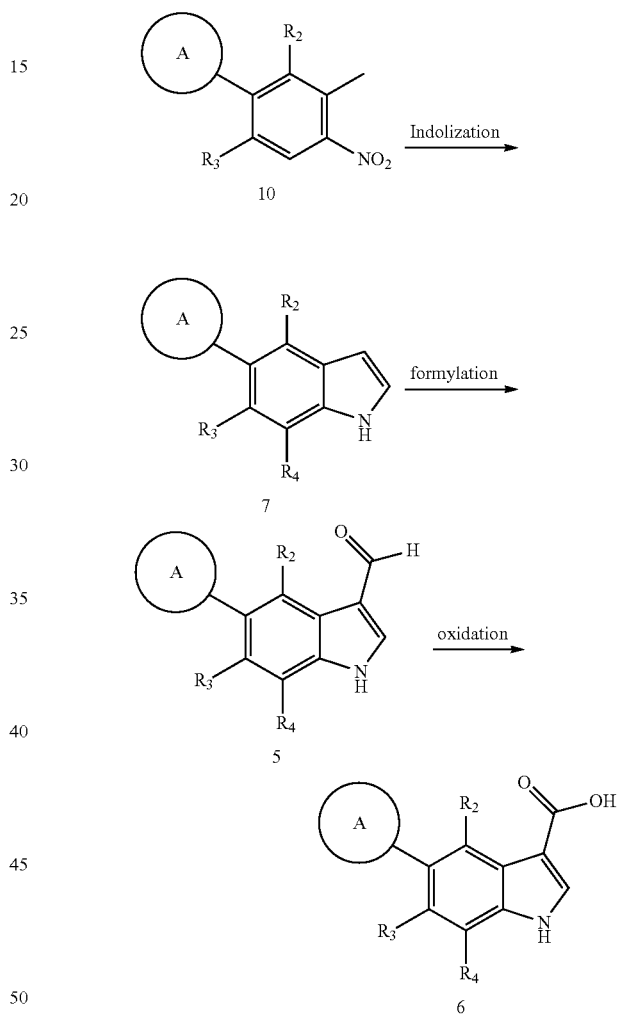

Indole acids of general formula 6, wherein $R_2$, $R_3$, $R_4$, and A are as defined in Formula (I) of the Summary section herein, can be synthesized as shown in Scheme 3. Compounds of general formula 1 and 4 can be coupled in an analogous manner as described in Scheme 1 to provide indoles of general formula 7. Indoles of general formula 7 can be acylated with a variety of reagents including, but not limited to, trichloroacetyl chloride or trifluoroacetic anhydride to provide indoles of general formula 8. Hydrolysis of the trihalomethane group can be effected with an alkaline metal hydroxide (potassium hydroxide, sodium hydroxide, lithium hydroxide) or a carbonate base (potassium carbonate, sodium carbonate, cesium carbonate) in aqueous solution to provide compounds of general formula 6.

Indoles of general formula 6, wherein $R_2$, $R_3$, $R_4$, and A are as defined in Formula (I) of the Summary section herein, can be synthesized as shown in Scheme 4. Nitro compounds of general formula 9, where Z is Cl, Br, I, triflate, mesylate, or tosylate, can be coupled with compounds of general formula 4 using analogous methods as described in Scheme 1 to provide compounds of general formula 10. Nitro compounds of general formula 10 can be treated with dimethylformamide-dimethylacetal followed by treatment with a reducing agent such as palladium and hydrogen, iron in acidic media, tin (II) chloride, or the like to provide indoles of general formula 7. Indoles of general formula 7 can be formulated and oxidized as described in Scheme 1 to provide indoles of general formula 6.

Scheme 5

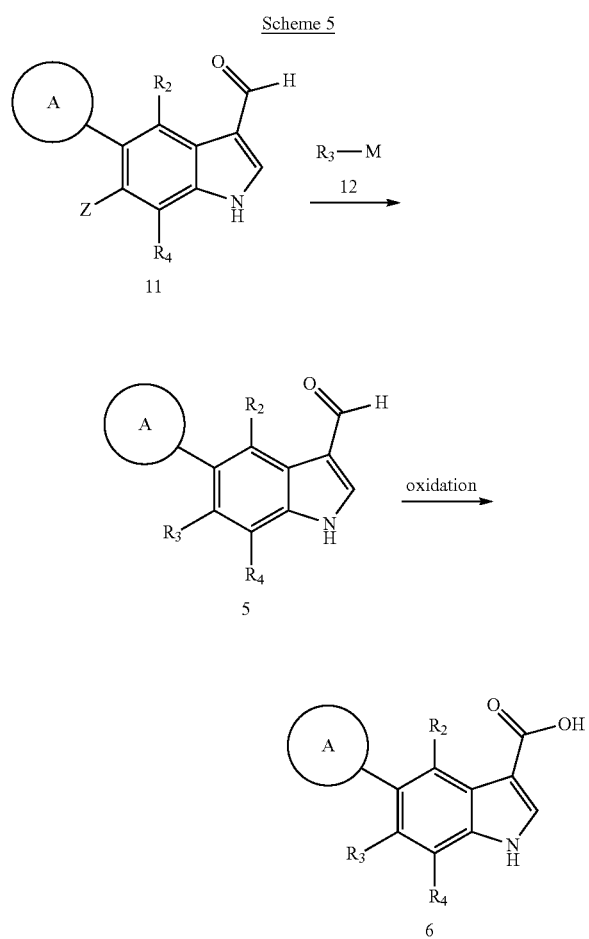

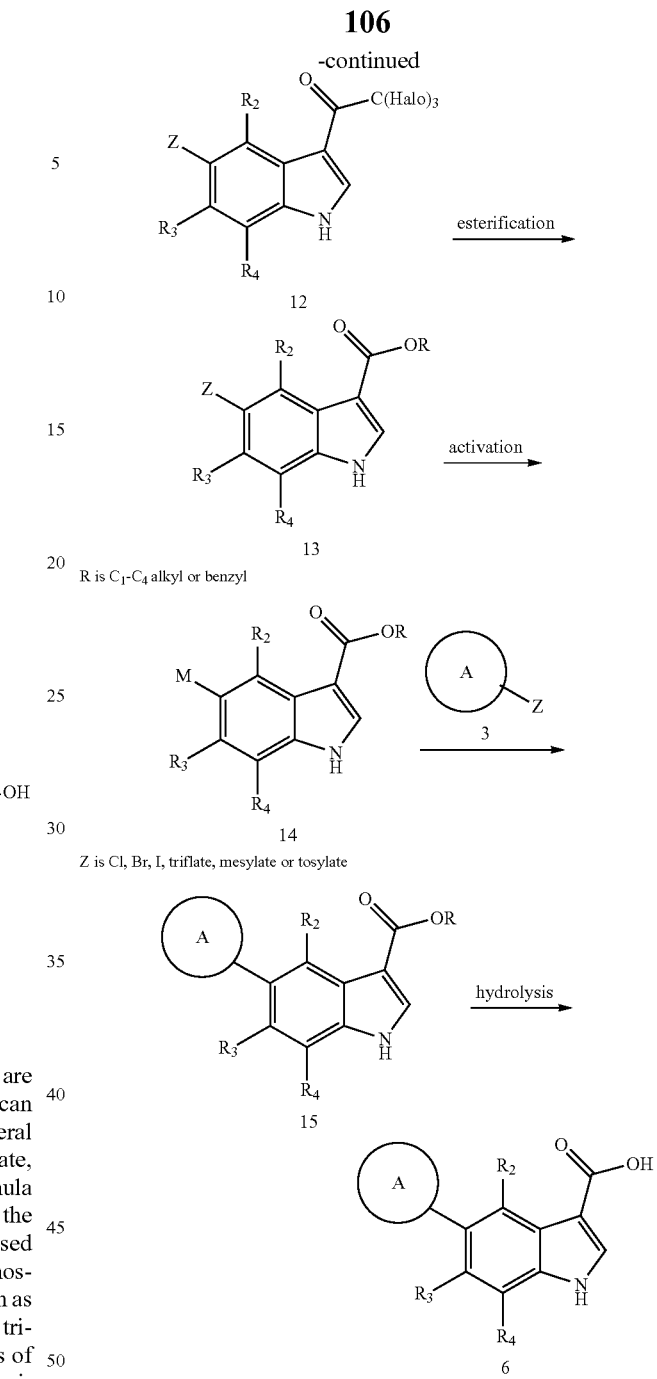

Indoles of general formula 6, wherein $R_2$, $R_3$, $R_4$, and A are as defined in Formula (I) of the Summary section herein, can be synthesized as shown in Scheme 5. Indoles of general formula 11, where Z is Cl, Br, I, triflate, mesylate, or tosylate, can be treated with an alkyl-metal reagent of general formula 12, where M is boron, silicon, tin, zinc, or the like in the presence of a metal catalyst (palladium or nickel based reagents such as PddppfCl$_2$, palladium tetrakistriphenylphosphine, Pd$_2$dba$_3$, or palladium (II) acetate with ligands such as triphenylphosphine, tricyclohexylphosphine, and other trialkylphosphine and triarylphosphines) to provide indoles of general formula 5. Indoles of general formula 5 can be oxidized as described in Scheme 1 to provide compounds of general formula 6.

Scheme 6

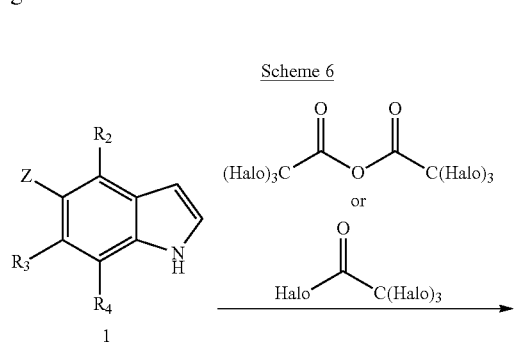

Indoles of general formula 6, wherein $R_2$, $R_3$, $R_4$, and A are as defined in Formula (I) of the Summary section herein, can be synthesized as shown in Scheme 6. Indoles of general formula 1, where Z is Cl, Br, I, triflate, mesylate, or tosylate, can be treated with an acylating reagent such as trichloroacetylchloride or trifluoroacetic anhydride to provide compounds of general formula 12. Compounds of general formula 12 can be treated with an alcohol such as methanol, ethanol, isopropanol, tert-butanol, or benzyl alcohol in the presence of base such as potassium carbonate, sodium carbonate, sodium hydride, sodium metal or the like to provide esters of general formula 13. Esters of general formula 13 can be treated with activating reagents including, but not limited to, dialkoxyboranes, bisboronate compounds, tributyltin halides, isopropylmagnesium halides, or zinc powder and salts, and the like to provide activated indoles of general formula 14, where M is boron, zinc, tin, magnesium, indium, or silicon. Compounds of general formula 3 and 14 can be coupled to provide compounds of general formula 15 using a variety of palladium and nickel catalysts with a variety of ligands or with no ligand (such as PddppfCl$_2$, tetrakistriphenylphosphine palladium, palladium (II) acetate, Pd$_2$dba$_3$, or others) at temperatures typically ranging from 25° C. to 120° C. with conventional heat or with microwave irradiation typically for 15 minutes to 24 hours. Compounds of general formula 15 can be treated with aqueous basic reagents such as lithium hydroxide, sodium hydroxide, or potassium hydroxide, in solvents such as methanol, ethanol, isopropanol, dioxane, or tetrahydrofuran, at temperatures ranging from 25 to 100° C. to provide compounds of general formula 6. When R is tert-butyl, reagents such as hydrochloric acid or trifluoroacetic acid can be used to effect hydrolysis and provide compounds of general formula 6.

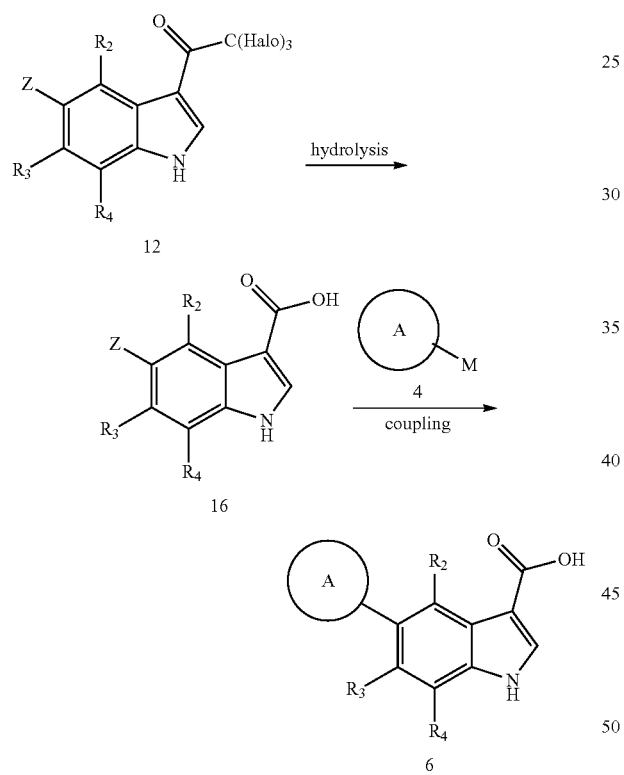

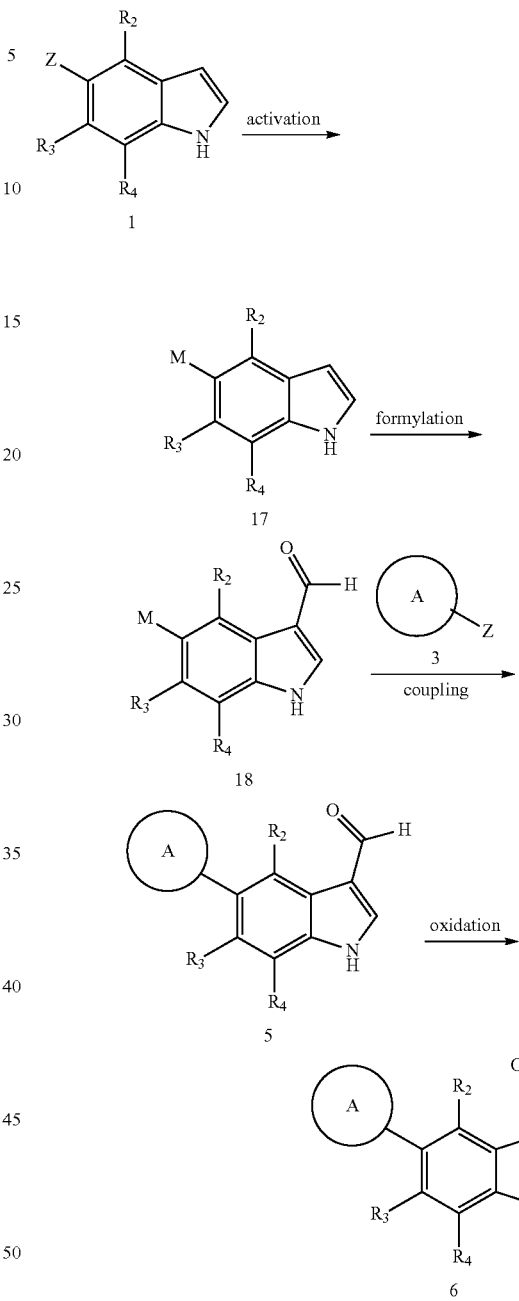

Indoles of general formula 6, wherein R$_2$, R$_3$, R$_4$, and A are as defined in Formula (I) of the Summary section herein, can be synthesized as shown in Scheme 7. Indoles of general formula 12, where Z is Cl, Br, I, triflate, mesylate, or tosylate, can be treated with aqueous base such as lithium hydroxide, sodium hydroxide, or potassium hydroxide in solvents such as dioxane, 1,2-dimethoxyethane, tetrahydrofuran, diethylether, or dichloromethane at temperatures ranging from 0° C. to 100° C. to provide indole acids of general formula 16. Compounds of general formula 16 can be coupled to compounds of general formula 4 to provide compounds of general formula 6 using the conditions/reagents described in Schemes 1-6.

Indoles of general formula 6, wherein R$_2$, R$_3$, R$_4$, and A are as defined in Formula (I) of the Summary section herein, can be synthesized as shown in Scheme 8. Indoles of general formula 1, where Z is Cl, Br, I, triflate, mesylate, or tosylate, can be treated with dialkoxyboranes, bisboronate compounds, tributyltin halides, isopropylmagnesium halides, zinc powder and salts, or the like to provide activated indoles of general formula 17, where M is boron, zinc, tin, magnesium, indium, or silicon. Indoles of general formula 17 can be formylated, coupled to compounds of general formula 3 (Z is Cl, Br, I, triflate, mesylate, or tosylate), and oxidized using conditions/reagents as described in Schemes 1-7 to provide compounds of general formula 6.

Scheme 9

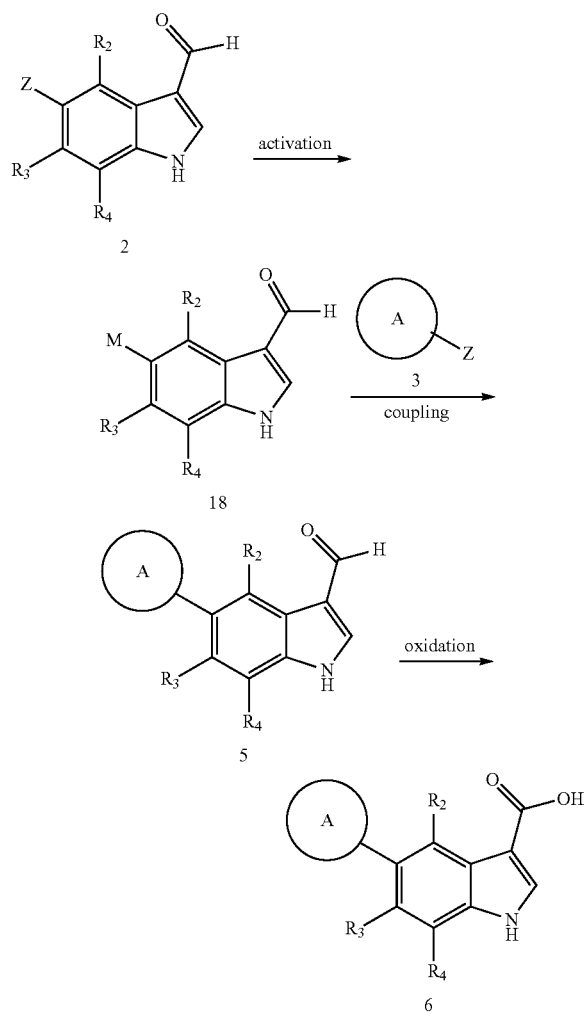

Indoles of general formula 6, wherein $R_2$, $R_3$, $R_4$, and A are as defined in Formula (I) of the Summary section herein, can be synthesized as shown in Scheme 9. Indoles of general formula 2, where Z is Cl, Br, I, triflate, mesylate, or tosylate, can be treated under conditions described in Scheme 6 to provide activated indoles of general formula 18. Compounds of general formula 18 and 3 can be treated to coupling conditions as described in Scheme 1 and then oxidized as described in Scheme 1 to provide indoles of general formula 6.

Scheme 10

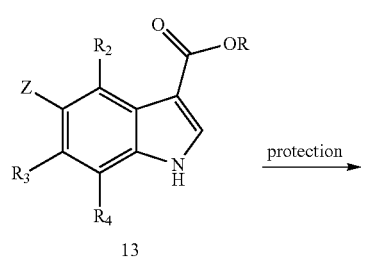

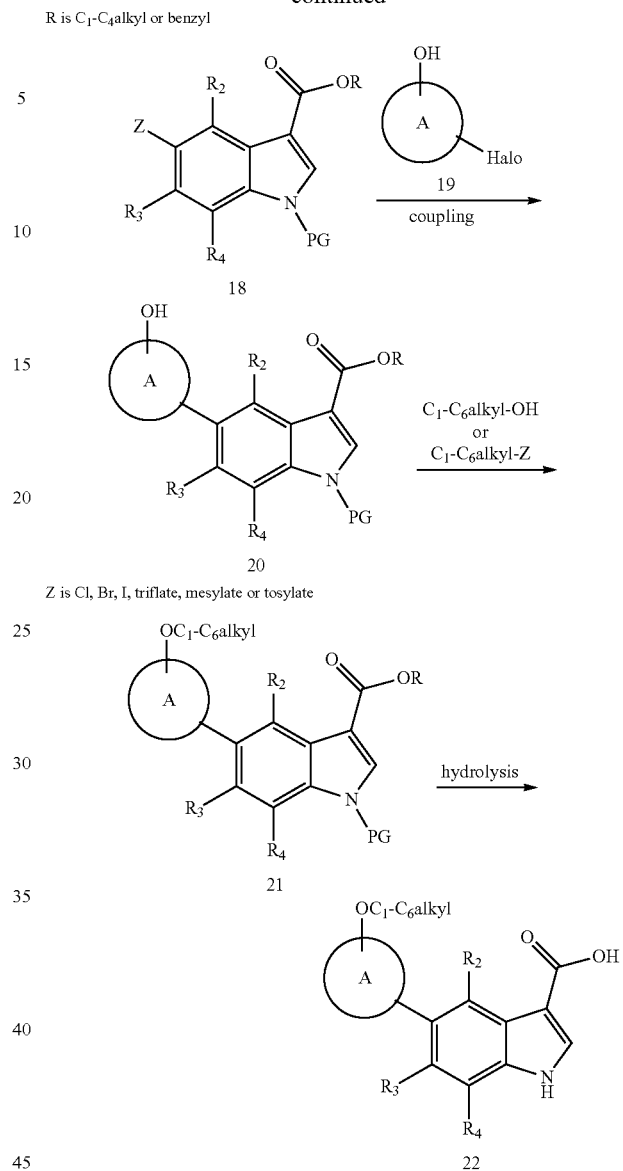

Indoles of general formula 22, wherein $R_2$, $R_3$, $R_4$, and A are as defined in Formula (I) of the Summary section herein, can be synthesized as shown in Scheme 10. Indoles of general formula 13, where Z is Cl, Br, I, triflate, mesylate, or tosylate, can be treated with a nitrogen protecting reagent in the presence of N,N-dimethyl-4-aminopyridine and a base (triethylamine or diisopropylethylamine) to provide indoles of general formula 18, where PG is a nitrogen protecting group that includes, but is not limited to, tert-butyloxycarbonyl, benzyloxycarbonyl, ethyloxycarbonyl, or other carbamate forming protecting groups, acetate, pivaloyl, or other amides, tert-butyldimethylsilane, triisopropylsilane, or other silicon-based protecting groups. Protected indoles of general formula 18 can be coupled with compounds of general formula 19 using conditions/reagents described in Schemes 1-8 to provide indoles of general formula 20. Compounds of general formula 20 can be alkylated under Mitsunobu conditions by treatment with an alcohol, an azodicarboxylate including, but not limited to diethyl azodicarboxylate, diisopropyl azodicarboxylate, di-t-butyl azodicarboxylate, or di-2-methoxyethyl azodicarboxylate, and a trialkyl or triarylphosphine including, but not limited to, tributylphosphine or triphenylphosphine (on polymer-support or in solution) in solvents such as THF, dioxane, or 1,2-di-methoxyethane at temperatures from 25° C. to 100° C. to provide compounds of general formula 21. Alternatively, compounds of general formula 20 can be alkylated by treatment with alkylating reagents in the presence of a base (sodium hydride, potassium hydride, lithium hydroxide, sodium hydroxide, potassium hydroxide, cesium carbonate, triethylamine, or diisopropylethylamine) to provide compounds of general formula 21. Compounds of general formula 21 can be treated under hydrolysis conditions as described in Scheme 7 to provide indoles of general formula 22.

with a halogenating reagent such as such as bromine, N-bromosuccinimide, pyridinium tribromide, iodine, N-iodosuccinimide, chlorine, N-chlorosuccinimide, or the like in a variety of solvents including dimethylformamide to provide halogenated indazoles of general formula 24. A four-step synthetic sequence can be then be conducted, similar to the procedures found in *Synth. Comm.* 2005, 35, 2681-2684, to provide indazoles of general formula 25. These four steps can be executed in one sequence or done step-by-step with isolation after each step at temperatures ranging from 0° C. to ambient temperature. Indazoles of general formula 25 can be coupled to compounds of general formula 4, where M is boron, zinc, tin, magnesium, indium, or silicon, using the procedures described in Scheme 1 to provide indazoles of general formula 26.

Scheme 11

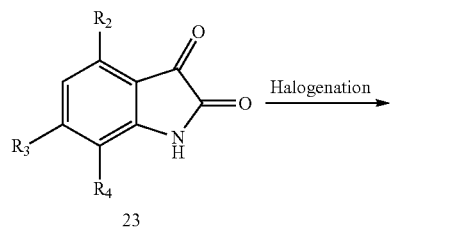

23

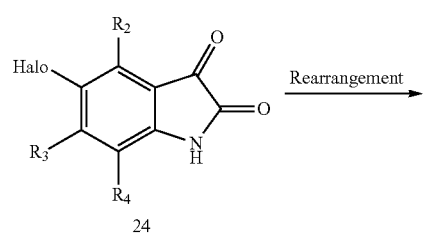

24

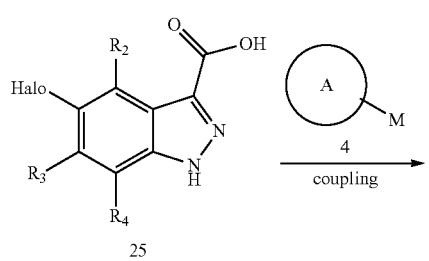

25

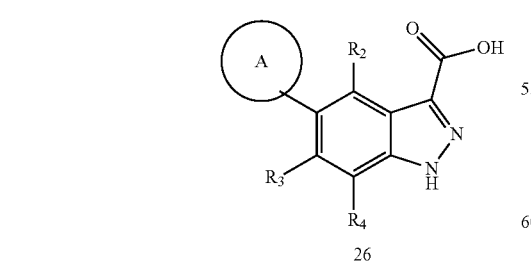

26

Indazoles of general formula 26, wherein $R_2$, $R_3$, $R_4$, and A are as defined in Formula (I) of the Summary section herein, can be synthesized as shown above in Scheme 11. Commercially available isatins of general formula 23 can be treated Scheme 12

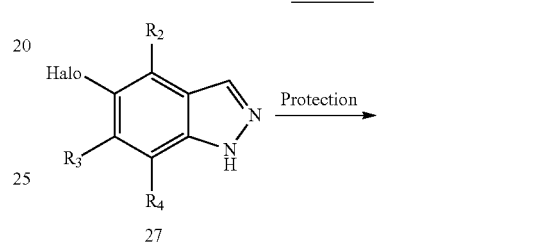

27

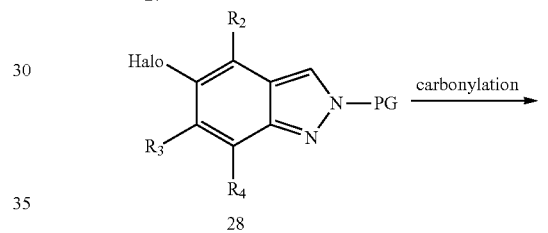

28

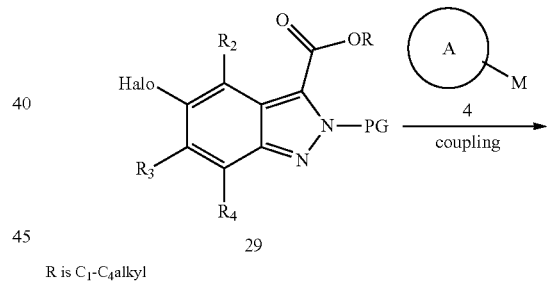

29

R is $C_1$-$C_4$alkyl

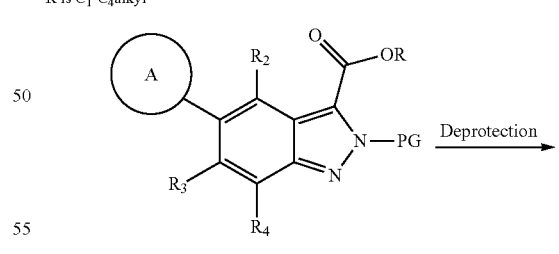

30

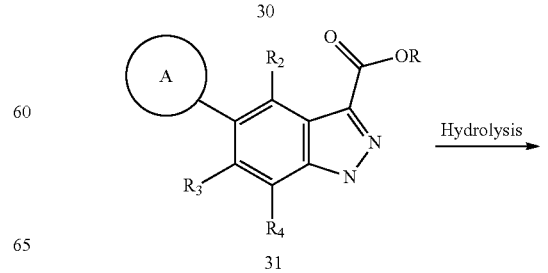

31

113
-continued

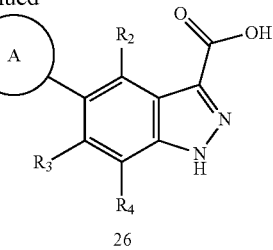

26

Indazoles of general formula 26, wherein $R_2$, $R_3$, $R_4$, and A are as defined in Formula (I) of the Summary section herein, can be synthesized as shown above in Scheme 12. Commercially available Indazoles of general formula 27 can be treated with protecting reagents such as trimethylsilyloxyethoxymethyl chloride (SEM) or the like to provide Indazoles of general formula 28. Introduction of an ester group at the 3-position can be effected by treatment with a metalating reagent such as n-butyl lithium, t-butyl lithium, s-butyl lithium, or the like followed by introduction of reagents such as ethyl chloroformate, carbon dioxide, or other carbon dioxide generating reagents to provide indazoles of general formula 29. Compounds of general formula 29 can be coupled with compounds of general formula 4 using procedures as described in Scheme 1 to provide indazoles of general formula 30. Deprotection of the protecting group can be performed with a variety of both acidic and basic reagents such as hydrogen chloride in methanol, ethanol, or other solvents, tetrabutylammonium fluoride, sodium methoxide, sodium ethoxide, or the like to provide indazoles of general formula 31. Hydrolysis of the ester can be performed in a similar manner as described in Scheme 6 to provide indazoles of general formula 26.

Scheme 13

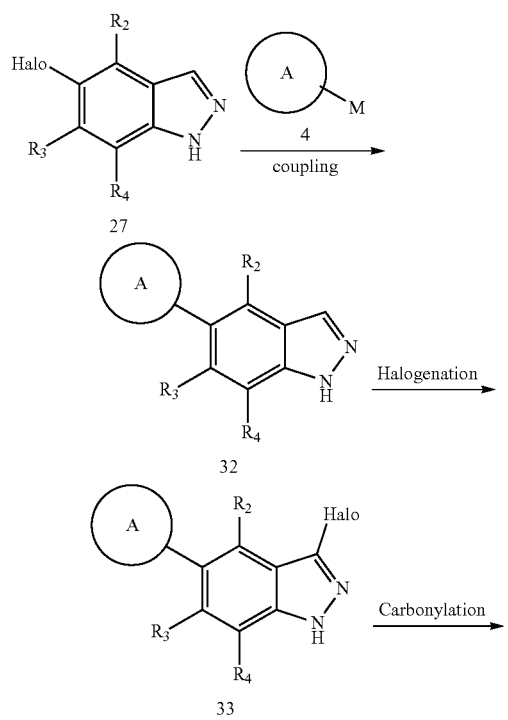

114
-continued

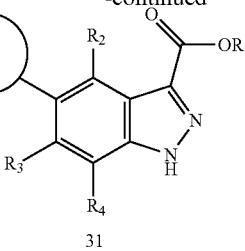

R is $C_1$-$C_4$alkyl or benzyl

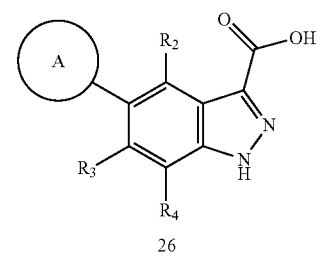

26

Indazoles of general formula 26, wherein $R_2$, $R_3$, $R_4$, and A are as defined in Formula (I) of the Summary section herein, can be synthesized as shown above in Scheme 13. Indazoles of general formula 27 can be coupled with compounds of general formula 4 as described in Scheme 1 to provide indazoles of general formula 32. Halogenation at the 3-position of indazoles can be effected by treatment with a halogen source such as bromine, N-bromosuccinimide, pyridinium tribromide, iodine, N-iodosuccinimide, chlorine, N-chlorosuccinimide, or the like, in the presence of a base such as sodium carbonate, potassium carbonate, cesium carbonate, sodium hydroxide, potassium hydroxide, or sodium hydride in a variety of solvents including dimethylformamide to provide halides of general formula 33. The halides of general formula 33 can be treated with a palladium catalyst such as tetrakistriphenyl phosphine palladium, [1,1'-bis(diphenylphosphino)ferrocene]dichloropalladium(II) (PddppfCl$_2$), tris(dibenzylideneacetone)dipalladium(0) (Pd$_2$dba$_3$), or palladium (II) acetate with a variety of ligands such as triaryl (triphenylphosphine) and trialkylphoshines (dppf) in a solvent or solvent mixture containing alcohol solvents such as methanol, ethanol, isopropanol, or benzyl alcohol, in the presence of an inorganic or organic base such as sodium carbonate, potassium carbonate, cesium carbonate, potassium acetate, sodium acetate, triethylamine, diisopropylethylamine, or the like in an atmosphere of carbon monoxide or a carbon monoxide containing source such as molybdenum hexacarbonyl to provide indazoles of general formula 31. Esters of general formula 31 can be hydrolized as described in Scheme 6 to provide indazoles of general formula 26.

Scheme 14

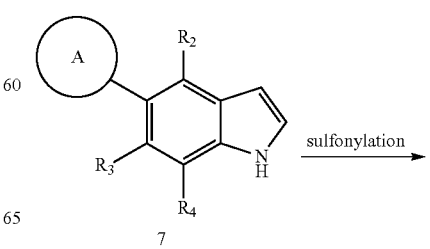

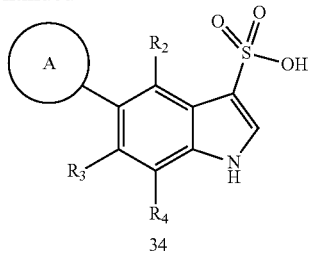

34

Indole-3-sulfonic acids of general formula 34 wherein $R_2$, $R_3$, $R_4$, and A are as defined in Formula (I) of the Summary section herein, can be synthesized as shown in Scheme 14. Indoles of general formula 7 can be treated with a sulfur trioxide source including, but not limited to, sulfur trioxide-pyridine, chlorosulfuric acid, sulfur trioxide (g), or sulfuric acid in the presence of acetic anhydride, or the like, to provide indole-3-sulfonic acids of general formula 34.

EXAMPLES

Example 1

6-Chloro-5-(4-(1-hydroxycyclobutyl)phenyl)-1H-indole-3-carboxylic acid

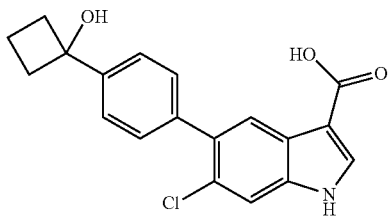 [SMILES: O=C(O)c1c[nH]c2cc(Cl)c(-c3ccc(C4(O)CCC4)cc3)cc12]

Step 1

5-bromo-6-chloro-1H-indole-3-carbaldehyde

A round-bottom flask was charged with DMF (54 mL). Phosphorus oxychloride (6.21 mL, 66.8 mmol) was added dropwise over 5 minutes, and the reaction mixture was stirred at room temperature for an additional 5 minutes. A solution of 5-bromo-6-chloro-1H-indole (7700 mg, 33.41 mmol) in DMF (7 mL) was added dropwise to the reaction mixture, which caused a precipitate to form. The reaction mixture was then heated to 95° C. for 25 minutes. The reaction mixture was treated with 1 N aqueous sodium hydroxide (170 mL) and water (170 mL). The reaction mixture was stirred at 95° C. for 11 minutes. The reaction mixture was cooled to 0° C., and the solids were collected by filtration. The solids were washed with water (50 mL) and diethyl ether (50 mL) and dried in vacuo for 16 hours at 65° C. to afford the title compound (7.77 g, 90%) as a tan solid. MS (AP+) 257.9 (M+H)$^+$. $^1$H NMR (400 MHz, DMSO-$d_6$) δ 9.93 (s, 1H), 8.40 (s, 1H), 8.38 (s, 1H), 7.80 (s, 1H).

Step 2

1-(4-(5,5-Dimethyl-1,3,2-dioxaborinan-2-yl)phenyl) cyclobutanol

A mixture of 5,5,5',5'-tetramethyl-2,2'-bi(1,3,2-dioxaborinane) (16.50 g, 48.33 mmol), oven dried potassium acetate (20.03 g, 204.1 mmol), and 1-(4-bromophenyl)cyclobutanol (10.00 g, 44.03 mmol) in 1,4-dioxane (120 mL) was degassed with $N_2$ for 15 min, then treated with [1,1'-bis(diphenylphosphino)ferrocene]dichloropalladium(II) (2.44 g, 2.99 mmol). The reaction mixture was heated to 110° C. and stirred for 2 hours under $N_2$. The reaction mixture was cooled to room temperature and filtered through celite, eluting with EtOAc. The filtrate was evaporated to give a black oil, which was purified by flash chromatography (0-50% EtOAc/Heptane) three times to afford the title compound (8.68 g, 76%) as a white solid. GC/MS: 259. $^1$H NMR (400 MHz, CD$_3$Cl) δ 7.83 (d, J=8.05 Hz, 2 H), 7.50 (d, J=8.29 Hz, 2 H), 3.78 (s, 4 H), 2.65-2.52 (m, 2 H), 2.38-2.42 (m, 2 H), 1.98-2.03 (m, 1 H), 1.72-1.80 (m, 1 H), 1.03 (s, 6 H).

Step 3

6-Chloro-5-(4-(1-hydroxycyclobutyl)phenyl)-1H-indole-3-carbaldehyde

A mixture of 5-bromo-6-chloro-1H-indole-3-carbaldehyde (6.15 g, 23.8 mmol), 1-[4-(5,5-dimethyl-[1,3,2]dioxaborinan-2-yl)-phenyl]-cyclobutanol (8.35 g, 32.1 mmol), 2 M aqueous potassium carbonate (47.5 mL, 95.0 mmol) in EtOH (33 mL) and toluene (86 mL) was degassed with $N_2$ for 25 minutes, then treated with [1,1'-bis(diphenylphosphino)ferrocene]dichloropalladium(II) (1.93 g, 2.64 mmol). The reaction mixture was heated to 110° C. and stirred for 2 hours. The reaction mixture was cooled to room temperature, poured into a 3:1 mixture of saturated aqueous NH$_4$Cl solution/water (450 mL) and extracted with EtOAc (10×150 mL), followed by 9:1 CH$_2$Cl$_2$/i-PrOH (4×100 mL). The combined organic layers were dried over Na$_2$SO$_4$ and concentrated in vacuo. The crude material was purified by flash chromatography (0-100% EtOAc/heptane, with 0.03% formic acid modifier) to afford the title compound (4.98 g, 64%) as a red solid. MS (ES+) 326.5 (M+H)$^+$. $^1$H NMR (400 MHz, DMSO-$d_6$) δ 12.21 (br. s., 1 H), 9.91 (s, 1 H), 8.35 (s, 1 H), 8.02 (s, 1 H), 7.67 (s, 1 H), 7.54 (d, J=8.00 Hz, 2 H), 7.38 (d, J=8.20 Hz, 2 H), 5.50 (s, 1 H), 2.36-2.45 (m, 2 H), 2.22-2.33 (m, 2 H), 1.92 (m, 1 H), 1.61-1.71 (m, 1 H).

Step 4

6-Chloro-5-(4-(1-hydroxycyclobutyl)phenyl)-1H-indole-3-carboxylic acid

To a solution of 6-chloro-5-[4-(1-hydroxy-cyclobutyl)-phenyl]-1H-indole-3-carbaldehyde (4.88 g, 15.0 mmol) in MeCN (212 mL) and tert-butanol (212 mL) at 0° C. was added 2-methyl-2-butene (120 mL, 1.15 mol), followed by a solution of sodium chlorite (25.5 g, 300 mmol) and sodium phosphate monobasic hydrate (42.5 g, 308 mmol) in water (212 mL) dropwise via addition funnel. The ice bath was removed and the reaction mixture was stirred vigorously at room temperature. After 13 hours, additional 2-methyl-2-butene (50 mL, 480 mmol) was added, followed by sodium chlorite (10.6 g, 125 mmol) and sodium phosphate monobasic hydrate (17.7 g, 125 mmol) as solids. The reaction mixture was stirred at room temperature for an additional 5 hours, and treated with additional 2-methyl-2-butene (25 mL, 240 mmol), solid sodium chlorite (5.3 g, 73 mmol) and solid sodium phosphate monobasic hydrate (8.8 g, 73 mmol). After an additional 4 hours, the reaction mixture was poured into a 4:1 mixture of saturated aqueous NH$_4$Cl solution/water (500 mL), and extracted with EtOAc (3×400 mL). The combined organic layers were dried over Na$_2$SO$_4$ and concentrated in vacuo. The resulting material was loaded onto a silica gel plug and eluted, first with heptane/EtOAc (4:1, 1.5 L), followed by 1:4 heptane/EtOAc (3 L) then EtOAc (1 L). The filtrates from the second and third elutions were combined and concentrated in vacuo. The resulting tan solid was partially dissolved in 4:1 DMF/DCM, loaded onto an Isco silica gel cartridge, and purified by flash chromatography (20-80% EtOAc/heptane, with 0.2% formic acid modifier) to give the title compound (3.65 g, 71%) as a white solid. MS (ES+) 340.2 (M−H)+. $^1$H NMR (500 MHz, DMSO-$d_6$) δ 12.10 (s, 1 H), 11.95 (s, 1 H), 8.08 (s, 1 H), 7.95 (s, 1 H), 7.64 (s, 1 H), 7.57 (d, J=7.1 Hz, 2 H), 7.41 (d, J=7.1 Hz, 2 H), 5.52 (s, 1 H), 2.48-2.40 (m, 2 H), 2.35-2.26 (m, 2 H), 1.97-1.90 (m, 1 H), 1.76-1.62 (m, 1H).

Alternatively, Example 1 may be prepared as follows:

Example 1

Step 1 methyl 5-bromo-6-chloro-1H-indole-3-carboxylate

To a stirred mixture of 5-bromo-6-chloro-1H-indole (60 g, 260 mmol), N,N-dimethylaminopyridine (3.21 g, 26.0 mmol), pyridine (56.5 mL, 703 mmol), and tetrahydrofuran (400 mL) was added in drops at 0° C. neat trichloroacetyl chloride (70.1 mL, 625 mmol). The obtained mixture was warmed to room temperature in 2 h (a precipitate began to form) and was stirred at room temperature for 3 days. Added in drops 110 ml of methanol at 0-10° C. followed by 70 ml of 25% sodium methoxide in methanol (680 mmol) at 0° C. The mixture was then stirred at 45° C. for 3 h. Then 250 ml of water and 200 ml of MTBE were added. The organic extract was separated, washed with brine, dried over magnesium sulfate, and concentrated at 50° C. and 90 mm Hg to ~1/4 of the initial volume. Precipitate was filtered off, washed with MTBE, and dried in vacuum at 45° C. to obtain the title compound (39.9 g, 53% yield). The mother liquor was concentrated to a heavy slurry. Methanol (400 ml) was added and the mixture was stirred at 65° C. for 4 h and slowly cooled to room temperature and stirred overnight. The solid was filtered off, washed with methanol, and dried in vacuo at 45° C. to obtain additional title compound (16.88 g, 22%). Total yield=75%. MS (ES−): 288.0, 290.0 (M+H)+ $^1$H NMR (500 MHz, DMSO-$d_6$) ppm 12.17 (br. s, 1H), 8.26 (s, 1 H), 8.18 (s, 1 H), 7.74 (s, 1 H), 3.82 (s, 3 H).

Step 2 methyl 6-chloro-5-[4-(1-hydroxycyclobutyl)phenyl]-1H-indole-3-carboxylate

A round bottomed flask was charged with [4-(1-hydroxycyclobutyl)phenyl]boronic acid (104.0 g, 541.6 mmol), methyl 5-bromo-6-chloro-1H-indole-3-carboxylate (142.0 g, 492.1 mmol), bis(triphenylphosphine)dichloropalladium (7.0 g, 10 mmol), potassium carbonate solution (183 g, 1.32 mol in 550 mL water), and 2-methyltetrahydrofuran (1.000 L). The mixture was then degassed by bubbling nitrogen gas through the solution for 30 minutes at room temperature with stirring. The mixture was then stirred at 75° C. (internal temperature) for 18 h. The mixture was cooled to room temperature under stirring and 300 ml of heptane was added and the aqueous phase was separated and discarded. Brine (300 ml) was added, stirred at room temperature for 10 min, then the aqueous layer was separated and discarded. The organic phase was stirred at 70° C. and slowly 1400 ml of heptane was added via addition funnel with stirring. A precipitate began to form after first 600 ml was added. Continued stirring at 70° C. for 30 min and cooled to room temperature in 2.5 h. The solid was filtered off, washed with water, and 2-methyltetrahydrofuran/heptane (1:2, 400 ml), dried on the filter during 2 h to obtain crude product. The crude product was stirred in 1300 ml of methanol at 62° C. (internal temperature, gentle reflux) for 8 h and then cooled to room temperature in 3 h and stirred at room temperature overnight. The solid was collected via filtration to obtain the 135 g of material. This material was then dissolved in 900 mL tetrahydrofuran at 60° C. Heptane (300 ml) and silica gel (64 g) were added and the mixture was cooled to room temperature under stirring during 2.5 h. The mixture was filtered through a pad of silica gel and the filter cake was washed with tetrahydrofuran-heptane (3:1) and the filtrate concentrated to dryness. Methanol (500 ml) was added to the residue and the slurry was concentrated again to dryness to obtain the title compound as an off-white solid (131.0 g, 368.0 mmol, 75% yield). MS (ES−): 354.4 (M−H)− $^1$H NMR (400 MHz, DMSO-$d_6$) ppm 12.08 (br. s, 1 H), 8.19 (d, 1 H), 7.94 (s, 1 H), 7.67 (s, 1 H), 7.58 (d, 2 H), 7.40 (s, 2 H), 5.54 (s, 1 H), 3.80 (s, 3 H), 2.39-2.49 (m, 2 H), 2.23-2.37 (m, 2 H), 1.96 (dt, 1 H), 1.63-1.79 (m, 1 H).

Step 3

6-chloro-5-[4-(1-hydroxycyclobutyl)phenyl]-1H-indole-3-carboxylic acid

A round bottomed flask was charged with methyl 6-chloro-5-[4-(1-hydroxycyclobutyl)phenyl]-1H-indole-3-carboxylate (131 g, 368 mmol), methanol (2.20 L), and sodium hydroxide (90.2 g, 2.21 mol in 740 mL water) then stirred at 70° C. for 18 h. The reaction mixture was cooled to room temperature, filtered through celite and the mother liquor was concentrated to ~30% of the initial volume—no precipitate formed. Water (700 ml) was added. The clear tan solution was washed with MTBE (3×250 ml). The organic layers were discarded. To the stirred light-cherry aqueous solution (total volume 1800 ml) at 18~25 C with external cooling was added in drops 38% HCl (200 ml), to pH~2-3 followed by addition of ethyl acetate in one portion (250 ml). After addition of ethyl acetate material began to solidify. To the stirring heterogeneous mixture 250 ml of heptane was slowly added via addition funnel at room temperature, and the mixture was stirred at room temperature for 4 hours. The solid was filtered off, washed with water, washed with ethyl acetate-heptane mixture (1:1), and dried on a filter at room temperature and in vacuum oven at 50° C. to obtain light-yellow solid. To this solid was then added 630 ml of tetrahydrofuran and was stirred at 65° C. (internal temperature) for 4 hours, then slowly 630 ml of ethyl acetate was added from a dropping funnel, and the resulting slurry was slowly cooled under stirring to room temperature overnight. Solid was filtered off, washed with tetrahydrofuran-ethyl acetate (1:1), and dried in vacuum at 50° C. to obtain 107.0 g of solid. The mother liquor was concentrated and the residue was washed with acetone, filtered off, and dried to obtain an additional 12.5 g of solid. This solid was then dissolved in 800 ml of ethanol (containing 0.3 ml of 1 M aqueous NaOH) at 60° C. and 800 ml of water was added slowly via addition funnel under stirring at 55-60° C. In the end of the addition of water a precipitate began to form. The suspension was stirred at 60° C. for 2 h, then at 40° C. for 24 h and at room temperature for 40 hours. The solid was filtered off, washed with ethanol-water (1:1), and dried in vacuum at 50° C. to obtain the title compound as a crystalline off-white solid (72.4 g, 58% yield). The mother liquor was concentrated to ~30% of the initial volume and precipitate formed. It was filtered off and dried in vacuo to obtain additional batch of the title compound (14.5 g, 12% yield). Total yield=70%. MS (ES-): 340.3 (M-H)- 1H NMR (400 MHz, DMSO-d6) ppm 12.12 (s, 1 H) 11.95 (br. s., 1 H) 8.09 (d, 1 H) 7.96 (s, 1 H) 7.65 (s, 1 H) 7.58 (d, 2 H) 7.42 (d, 2 H) 5.53 (s, 1 H) 2.48-2.42 (m, 2 H) 2.32 (m, 2 H) 1.96 (tq, 1 H) 1.62-1.79 (m, 1 H).

Example 2

6-Chloro-5-[4-(hydroxymethyl)phenyl]-1H-indole-3-carboxylic acid

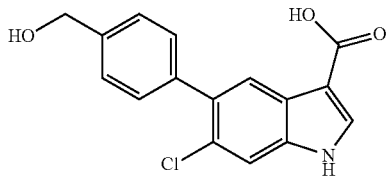 [SMILES: O=C(O)c1c[nH]c2cc(Cl)c(-c3ccc(CO)cc3)cc12]

Step 1

6-Chloro-5-(4-hydroxymethyl-phenyl)-1H-indole-3-carbaldehyde

A mixture of 5-bromo-6-chloro-1H-indole-3-carbaldehyde (783 mg, 3.03 mmol), 4-(hydroxymethyl)benzene boronic acid (460 mg, 3.03 mmol), 2 N aqueous potassium carbonate (6.4 mL, 13 mmol) in toluene (9 mL) and EtOH (13 mL) was degassed with $N_2$ for 5 minutes, then treated with [1,1'-bis(diphenylphosphino)ferrocene]dichloropalladium (II) (247 mg, 0.30 mmol). The mixture was heated in a sealed tube to 120° C. and stirred for 2.5 hours. The reaction mixture was cooled to room temperature, diluted with EtOAc (200 mL), then washed with water (50 mL) and brine (50 mL). The organic layer was dried over $MgSO_4$ and concentrated in vacuo. The resulting brown foam was purified by flash chromatography (20-100% EtOAc/heptane) to afford a pale yellow solid. The solid was dissolved in 5:1 EtOAc/heptane (30 mL), and a colorless precipitate formed. The precipitate was collected by filtration, washed with heptane and dried under vacuum to afford the title compound (173 mg, 20% yield) as a colorless solid. MS (ES+) 286.0 (M+H)+. 1H NMR (500 MHz, CD3OD) δ 9.92 (s, 1 H) 8.07 (s, 1 H) 8.25 (s, 1 H) 7.64 (s, 1 H) 7.44 (m, 4 H) 4.70 (s, 2 H).

Step 2

6-Chloro-5-[4-(hydroxymethyl)phenyl]-1H-indole-3-carboxylic acid

To a solution of 6-chloro-5-(4-hydroxymethyl-phenyl)-1H-indole-3-carbaldehyde (422 mg, 1.48 mmol) in MeCN (18 mL), tert-butanol (18 mL) and 2-methyl-2-butene (12 mL, 110 mmol) at 0° C. was added a solution of sodium chlorite (1.25 g, 14.8 mmol) and sodium phosphate monobasic hydrate (2.04 g, 14.8 mmol) in water (9 mL) dropwise. The ice bath was removed and the solution was stirred at room temperature. After 5 hours, additional 2-methyl-2-butene (3 mL, 27.5 mmol) was added, followed by sodium chlorite (1.25 g, 14.8 mmol) and sodium phosphate monobasic hydrate (2.04 g, 14.8 mmol) in water (9 mL) dropwise. The resulting solution was stirred at room temperature. After 27 hours total reaction time, the solution was concentrated in vacuo to afford a pale yellow solid. Water (5 mL) was added to the solid and the mixture was extracted with EtOAc (2×50 mL). The combined organic layers were concentrated in vacuo and purified by flash chromatography (35-90% EtOAc/heptane, with 0.2% formic acid modifier) to afford a pale yellow solid. The solid was stirred in EtOAc (5 mL) at 55° C. for 6 hours, and the resulting slurry was cooled to room temperature. The precipitate was filtered and washed with EtOAc (1 mL) to afford the title compound (182 mg, 41% yield) as a cream-colored crystalline solid. MS (ES+) 300.0 (M-H)+. 1H NMR (400 MHz, CD3OD) δ 8.00 (s, 1 H) 7.98 (s, 1 H) 7.56 (s, 1 H) 7.40 (m, 4 H) 4.65 (s, 2 H).

Example 3

6-Chloro-5-phenyl-1H-indole-3-carboxylic acid

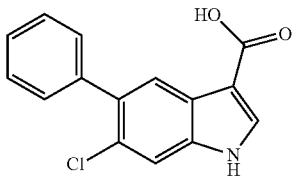 [SMILES: O=C(O)c1c[nH]c2cc(Cl)c(-c3ccccc3)cc12]

Step 1

6-Chloro-5-phenyl-1H-indole-3-carbaldehyde

A mixture of 5-bromo-6-chloro-1H-indole-3-carbaldehyde (200 mg, 0.77 mmol), phenyl boronic acid (114 mg, 0.93 mmol), 2 N aqueous potassium carbonate (1.15 mL, 3.10 mmol) in toluene (3.3 mL) and EtOH (1.1 mL) was degassed with $N_2$, treated with [1,1'-bis(diphenylphosphino)ferrocene]dichloropalladium(II) (56.6 mg, 0.077 mmol), and degassed again with $N_2$. The mixture was subjected to microwave irradiation conditions at 120° C. for 30 minutes. The reaction mixture was cooled to room temperature, diluted with water and extracted with EtOAc (50 mL). The organic layer was washed with brine, dried over $MgSO_4$ and concentrated in vacuo. The crude material was purified by flash chromatography (0-46% EtOAc/petroleum ether) to afford the title compound (190 mg, 98% yield) as a yellow solid.

MS (ES+) 255.9 (M+H)+. 1H NMR (400 MHz, CD3OD) δ 9.91 (s, 1 H), 8.18 (s, 1 H), 8.13 (s, 1 H), 7.63 (s, 1 H), 7.44-7.36 (m, 5 H).

Step 2

6-Chloro-5-phenyl-1H-indole-3-carboxylic acid

To a solution of 6-chloro-5-phenyl-1H-indole-3-carbaldehyde (90 mg, 0.35 mmol) in MeCN (4 mL), tert-butanol (4 mL) and 2-methyl-2-butene (4 mL, 27.5 mmol) at 0° C. was added a solution of sodium chlorite (327 mg, 4.88 mmol) and sodium phosphate monobasic hydrate (761 mg, 4.88 mmol) in water (4 mL) dropwise. The ice bath was removed and the solution was stirred at room temperature. After 6 hours, additional sodium chlorite (327 mg, 4.88 mmol) and sodium phosphate monobasic hydrate (761 mg, 4.88 mmol) were added as solids and the resulting solution was stirred at room temperature for an additional 14 hours. The reaction mixture was concentrated in vacuo and the aqueous residue was extracted with EtOAc (30 mL). The organic layer was washed with brine, dried over $Na_2SO_4$ and concentrated in vacuo. The crude material was purified by reverse phase HPLC to afford the title compound (30.0 mg, 31%) as a white solid. MS (ES+) 271.9 (M+H)+. 1H NMR (400 MHz, DMSO-$d_6$) δ 12.13 (br. s., 1 H), 11.96 (s, 1 H), 8.09 (s, 1 H), 7.93 (s, 1 H), 7.62 (s, 1 H), 7.48-7.38 (m, 5 H).

Example 4

6-Fluoro-5-(4-(1-hydroxycyclobutyl)phenyl)-1H-indole-3-carboxylic acid

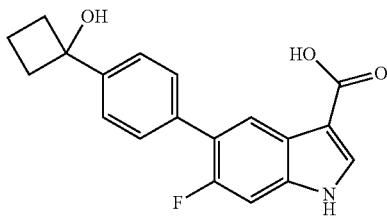 [SMILES: O=C(O)c1c[nH]c2cc(F)c(-c3ccc(C4(O)CCC4)cc3)cc12]

Step 1

1-(4-(4,4,5,5-Tetramethyl-1,3,2-dioxaborolan-2-yl)phenyl)cyclobutanol

To a solution of 1-(4-bromophenyl)cyclobutanol (325 mg, 1.43 mmol) and 5,5,5',5'-tetramethyl-2,2'-bi(1,3,2-dioxaborinane) (437 mg, 1.72 mmol) in anhydrous THF (20 mL) was added potassium acetate (425 mg, 4.33 mmol) and [1,1'-bis(diphenylphosphino)ferrocene]dichloropalladium(II) (40.0 mg, 0.055 mmol). The reaction mixture was degassed with $N_2$ for 3 minutes, and heated to reflux under $N_2$ for 16 hours. The reaction mixture was cooled to room temperature, filtered and washed with petroleum ether (30 mL). The filtrate was concentrated in vacuo, and purified by flash chromatography (9-20% EtOAc/petroleum ether) to afford the title compound (279.0 mg, 71%) as a white solid. 1H NMR (400 MHz, $CDCl_3$) δ 7.76 (d, J=8.00 Hz, 2H), 7.44 (d, J=8.40 Hz, 2H), 2.49 (m, 2H), 2.30 (m, 2H), 1.92 (m, 1H), 1.63 (m, 1H), 1.278 (s, 12H).

Step 2

6-Fluoro-5-(4-(1-hydroxycyclobutyl)phenyl)-1H-indole-3-carbaldehyde

A mixture of 5-bromo-6-fluoro-1H-indole-3-carbaldehyde (90 mg, 0.37 mmol), 1-(4-(4,4,5,5-tetramethyl-1,3,2-dioxaborolan-2-yl)phenyl)cyclobutanol (120 mg, 0.44 mmol), 2 N aqueous potassium carbonate (0.75 mL, 1.49 mmol) in toluene (3.0 mL) and EtOH (1.0 mL) was degassed with $N_2$ for 3 minutes, and treated with [1,1'-bis(diphenylphosphino)ferrocene]dichloropalladium(II) (30.0 mg, 0.041 mmol). The mixture was subjected to microwave irradiation conditions at 110° C. for 2 hours. The reaction mixture was cooled to room temperature, poured into half-saturated aqueous $NH_4Cl$ solution (15 mL) and extracted with EtOAc (6×15 mL). The combined organic layer were washed with brine, dried over $MgSO_4$ and concentrated in vacuo. The crude material was purified by flash chromatography (9-50% EtOAc/petroleum ether) to afford the title compound (58.0 mg, 51% yield) as a yellow solid. 1H NMR (400 MHz, DMSO-$d_6$) δ 10.0 (s, 1H), 8.42 (s, 1H), 8.20 (d, J=8.00 Hz, 1H), 7.66 (d, J=8.40 Hz, 2H), 7.59 (d, J=8.40 Hz, 2H), 7.50 (d, J=10.80 Hz, 1H), 2.48 (m, 2H), 2.41 (m, 2H), 2.02 (m, 1H), 1.76 (m, 1H).

Step 3

6-Fluoro-5-(4-(1-hydroxycyclobutyl)phenyl)-1H-indole-3-carboxylic acid

To a solution of 6-fluoro-5-phenyl-1H-indole-3-carbaldehyde (58.0 mg, 0.19 mmol) in MeCN (3 mL), tert-butanol (3 mL) and 2-methyl-2-butene (2 mL, 13.7 mmol) at 0° C. was added a solution of sodium chlorite (253.0 mg, 3.75 mmol) and sodium phosphate monobasic hydrate (585.0 mg, 3.75 mmol) in water (1.5 mL) dropwise. The ice bath was removed and the solution was stirred at room temperature for 16 hours. The reaction mixture was concentrated in vacuo and the aqueous residue was extracted with EtOAc (3×15 mL). The organic layer was washed with brine, dried over $Na_2SO_4$ and concentrated in vacuo. The crude material was purified by prep-HPLC (Boston Symmetrix ODS-H 150*30 mm*5 μm; 26-46% MeCN in water (0.225% formic acid); flow rate: 30 mL/min) to afford the title compound (9.5 mg, 16%) as a white solid. MS (ES+) 324.1 (M–H)+. 1H NMR (400 MHz, DMSO-$d_6$) δ 12.13 (br.s., 1H), 11.95 (s, 1H), 8.04-8.06 (m, 2H), 7.60 (d, J=8.40 Hz, 2H), 7.53 (d, J=6.80 Hz, 2H), 7.38 (d, J=11.20 Hz, 1H), 5.56 (s, 1H), 2.42-2.49 (m, 2H), 2.29-2.36 (m, 2H), 1.93-1.98 (m, 1H), 1.68-1.73 (m, 1H).

Example 5

6-Chloro-5-(4-(3-hydroxyoxetan-3-yl)phenyl)-1H-indole-3-carboxylic acid

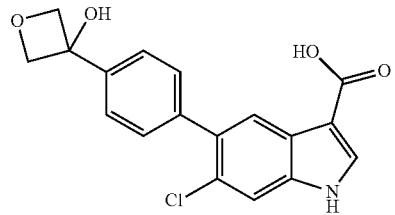 [SMILES: O=C(O)c1c[nH]c2cc(Cl)c(-c3ccc(C4(O)COC4)cc3)cc12]

Step 1

6-chloro-5-(4-(3-hydroxyoxetan-3-yl)phenyl)-1H-indole-3-carbaldehyde

A mixture of 5,5,5',5'-tetramethyl-[2,2']bi[[1,3,2]dioxaborinanyl] (149.0 mg, 0.44 mmol), oven dried potassium acetate (173.0 mg, 1.75 mmol) and 3-(4-bromo-phenyl)-oxetan-3-ol (100.0 mg, 0.44 mmol) in 1,4-dioxane (2 mL) was degassed with $N_2$ for 5 minutes, treated with [1,1'-bis(diphenylphosphino)ferrocene]dichloropalladium(II) (33.0 mg, 0.044 mmol) and subjected to microwave irradiation at 110° C. for 1 hour. The cooled reaction mixture was filtered through celite and concentrated in vacuo to give a black oil. To the dark oil was added 5-bromo-6-chloro-1H-indole-3-carbaldehyde (112.0 mg, 0.43 mmol), 2 N aqueous potassium carbonate (0.4 mL, 0.80 mmol), toluene (1.5 mL) and EtOH (0.5 mL). The reaction mixture was degassed with $N_2$ for 10 minutes, treated with [1,1'-bis(diphenylphosphino)ferrocene]dichloropalladium(II) (25.0 mg, 0.034 mmol), and heated in a pressure tube to 110° C. for 2 hours. The cooled reaction mixture was purified by flash chromatography (33-100% EtOAc/heptanes) to give a solid. The solid was triturated in MeOH and filtered to afford the title compound (50 mg, 35%) as a yellow solid. MS (ES+) 328.0 (M+H)+. $^1$H NMR (400 MHz, DMSO-$d_6$) δ 12.23 (s, 1 H), 9.92 (s, 1 H), 8.35 (s, 1 H), 8.02 (s, 1 H), 7.66 (d, J=9.4 Hz, 2 H), 7.44 (d, J=8.2 Hz, 2 H), 6.36 (s, 1 H), 4.80-4.76 (m, 2 H), 4.75-4.71 (m, 2 H).

Step 2

6-Chloro-5-(4-(3-hydroxyoxetan-3-yl)phenyl)-1H-indole-3-carboxylic acid

To the mixture of 6-chloro-5-[4-(3-hydroxy-oxetan-3-yl)-phenyl]-1H-indole-3-carbaldehyde (50.0 mg, 0.15 mmol) in MeCN (2 mL) was added 2-methyl-2-butene (2.0 mL, 13.7 mmol), followed by sodium chlorite (138 mg, 1.53 mmol) and sodium phosphate monobasic hydrate (211.0 mg, 1.53 mmol) in water (1 mL). The reaction mixture was stirred at room temperature for 20 hours, and concentrated in vacuo. The residue was acidified with 1 N aqueous citric acid (1 mL) and extracted with EtOAc. The organic layer was dried over MgSO$_4$ and concentrated in vacuo. The crude material was purified by flash chromatography (34-80% EtOAc/heptanes, with 0.2% formic acid modifier) to afford the title compound (18 mg, 34%) as a brown solid. MS (ES−) 342.3 (M−H)−. $^1$H NMR (400 MHz, CD$_3$OD) δ 8.02 (s, 1 H), 7.98 (s, 1 H), 7.66 (d, J=8.20 Hz, 2 H), 7.56 (s, 1 H), 7.47 (d, J=8.20 Hz, 2 H), 4.87-4.80 (m, 4 H).

Example 6

4,6-Difluoro-5-(4-(1-hydroxycyclobutyl)phenyl)-1H-indole-3-carboxylic acid

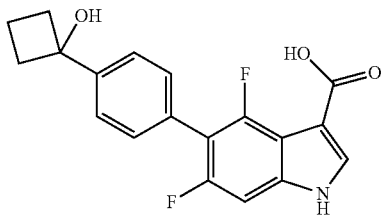 [SMILES: O=C(O)c1c[nH]c2cc(F)c(-c3ccc(C4(O)CCC4)cc3)c(F)c12]

Step 1

4,6-difluoroinoline

To a suspension of 4,6-difluoro-1H-indole (5 g, 32.9 mmol) in dry dichloromethane (100 mL) was added triethylsilane (10 g, 85.5 mmol) at room temperature. The reaction was then cooled to 0° C. and trifluoroacetic acid (50 mL) was added dropwise. The reaction was stirred at room temperature for 4 hours. The mixture was poured into cold saturated aqueous sodium bicarbonate solution and diluted with dichloromethane (200 mL). The layers were separated and the organic phase was dried over sodium sulfate, concentrated in vacuo, and purified by silica chromatography to give the title compound (4.5 g, 90% yield) as colorless oil.

Step 2

5-bromo-4,6-difluoroinoline

To a solution of 4,6-difluoroindoline (4.6 g, 29.8 mmol) in acetonitrile (50 mL) was added a solution of N-bromosuccinimide (3.68 g, 20.6 mmol) acetonitrile (30 mL) at 0° C. dropwise. The reaction was stirred for 30 minutes and quenched with saturated aqueous sodium bicarbonate solution and diluted with ethyl acetate. The layers were separated and the organic phases were dried over sodium sulfate, filtered and concentrated in vacuo. The residue was purified by flash chromatography (0-60% ethyl acetate in petroleum ether) to give the title compound (4.0 g, 58% yield) as colorless oil Step 3

5-bromo-4,6-difluoro-1H-indole

To a solution of 5-bromo-4,6-difluoroindoline (3.6 g, 15.4 mmol) in chloroform (150 mL) was added manganese dioxide (5.3 g, 61 mmol) at room temperature/. The mixture was heated to reflux temperature for 2 hours then cooled to room temperature. The reaction was filtered and the filtrate was concentrated in vacuo. Flash column chromatography was then used to provide the title compound (3.6 g, yield 100%) as brown solid. MS (ES+): 232.0 (M+H). $^1$H NMR (CDCl$_3$, 400 MHz): δ 8.27 (br. s, 1 H), 7.19 (m, 1 H), 7.02 (d, 1 H), 6.61 (m, 1 H).

Step 4

5-Bromo-4,6-difluoro-1H-indole-3-carbaldehyde

To a solution of 5-bromo-4,6-difluoro-1H-indole (1.29 g, 5.56 mmol) in acetonitrile (7.0 mL) was added N,N-dimethylformiminium chloride (1.07 g, 8.34 mmol). The reaction mixture was stirred at room temperature for 45 minutes. To the reaction mixture was added 1N NaOH (15 mL, 15 mmol). The resulting mixture was heated to 100° C. for 60 minutes, cooled to 0° C. and the resulting solid was collected via filtration, washed with water, and air-dried with vacuum to provide 900 mg of the title compound. An additional crop of solids formed in the filtrate, was collected, and dried to provide an additional 371 mg of the title compound for a total of 1.271 g (88% yield). MS (ES+) 260.3 (M+H)+. $^1$H NMR (400 MHz, DMSO-$d_6$) δ 12.58 (br. s, 1 H), 9.93 (d, J=3.90 Hz, 2 H), 8.34 (s, 2 H), 7.39 (dd, J=8.49, 1.07 Hz, 1 H).

Step 5

4,6-Difluoro-5-(4-(1-hydroxycyclobutyl)phenyl)-1H-indole-3-carbaldehyde

A mixture of 5,5,5',5'-tetramethyl-2,2'-bi(1,3,2-dioxaborinane) (188.0 mg, 0.55 mmol), oven dried potassium acetate (230.0 mg, 2.34 mmol), and 1-(4-bromophenyl)cyclobutanol (114.0 mg, 0.50 mmol) in 1,4-dioxane (2 mL) was degassed with N$_2$ for 15 min, then treated with [1,1'-bis(diphenylphosphino)ferrocene]dichloropalladium(II) (20.0 mg, 0.027 mmol). The reaction mixture was subjected to microwave irradiation at 110° C. for 1 hour. The cooled reaction mixture was filtered through celite, rinsed with EtOAc and concentrated to dryness. To the resulting dark solid ((45.0 mg, 0.17 mmol) was added 5-bromo-4,6-difluoro-1H-indole-3-carbaldehyde (45.0 mg, 0.17 mmol), 2 N aqueous potassium carbonate (0.20 mL, 0.40 mmol), toluene (1.5 mL) and EtOH (0.5 mL). The reaction mixture was degassed with $N_2$ for 10 minutes, treated with [1,1'-bis(diphenylphosphino)ferrocene]dichloropalladium(II) (14.0 mg, 0.019 mmol), and heated in a sealed pressure tube at 110° C. for 2 hours. The reaction mixture was cooled to room temperature and purified by flash chromatography (0-67% EtOAc/heptanes) to give the title compound (37 mg, 65%) as a white solid. MS (ES$^+$) 328.0 (M+H)$^+$. $^1$H NMR (500 MHz, $CD_3OD$) δ 10.04 (d, J=2.68 Hz, 1 H), 8.15 (s, 1 H), 7.64 (d, J=8.05 Hz, 2 H), 7.48 (d, J=8.05 Hz, 2 H), 7.21 (d, J=9.51 Hz, 1 H), 2.57-2.66 (m, 2 H), 2.39-2.46 (m, 2 H), 2.03-2.12 (m, 1 H), 1.73-1.83 (m, 1 H).

Step 6

4,6-Difluoro-5-(4-(1-hydroxycyclobutyl)phenyl)-1H-indole-3-carboxylic acid

To a solution of 4,6-difluoro-5-[4-(1-hydroxy-cyclobutyl)-phenyl]-1H-indole-3-carbaldehyde (37.0 mg, 0.11 mmol) in a mixture of MeCN (2 mL), tert-butanol (1 mL) and water (2 mL) was added sodium phosphate monobasic hydrate (214.0 mg, 1.55 mmol), sodium chlorite (114.0 mg, 1.26 mmol) and 2-methyl-2-butene (1.0 mL, 6.85 mmol). The reaction mixture was stirred at room temperature for 24 hours, acidified with 1 N aqueous citric acid solution (1 mL) and extracted with EtOAc. The organic layer was dried over $MgSO_4$ and concentrated in vacuo. The resulting yellow gum was purified by reverse phase HPLC (Column: Waters XBridge C18 19×100, 5 μm; Mobile phase A: 0.03% $NH_4OH$ in water (v/v); Mobile phase B: 0.03% $NH_4OH$ in MeCN (v/v); 95.0% $H_2O$/5.0% MeCN linear to 60% $H_2O$/40% MeCN in 8.5 min, 60% $H_2O$/40% MeCN linear to 0% $H_2O$/100% MeCN in 0.5 min, HOLD at 0% $H_2O$/100% MeCN to 10.0 min. Flow: 25 mL/min) to afford the title compound (9.4 mg, 24%).

MS (ES$^+$) 344.1 (M+H)$^+$. Retention time=2.48 minutes (Waters Atlantis dC18 4.6×50, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 7

6-fluoro-5-[4-(hydroxymethyl)phenyl]-1H-indole-3-carboxylic acid

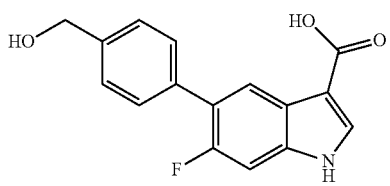 [SMILES: O=C(O)c1c[nH]c2cc(F)c(-c3ccc(CO)cc3)cc12]

Step 1

6-fluoro-5-[4-(hydroxymethyl)phenyl]-1H-indole-3-carbaldehyde

A mixture of 5-bromo-6-fluoro-1H-indole-3-carbaldehyde (100 mg, 0.413 mmol), [4-(hydroxymethyl)phenyl]boronic acid (69 mg, 0.454 mmol), ethanol (1.04 mL), toluene (1.0 mL) and 2 M aqueous potassium carbonate (0.824 mL, 1.65 mmol) were deoxygenated with nitrogen. [1,1'-Bis(diphenylphosphino)ferrocene]dichloropalladium (II) (25 mg, 0.033 mmol) was added and the reaction mixture was deoxygenated with nitrogen for 2 more minutes. The reaction mixture was sealed and heated at 90° C. for 16 hours. After cooling to room temperature, the phases were separated, and the aqueous phase was diluted with water and extracted twice with ethyl acetate. The combined organic layers were concentrated in vacuo and purified using silica gel chromatography (1:3 to 3:1 ethyl acetate/heptanes) to give the title compound (65 mg). MS (ES−) 268.2 (M−H)$^-$.

Step 2

6-fluoro-5-[4-(hydroxymethyl)phenyl]-1H-indole-3-carboxylic acid

A solution of 6-fluoro-5-[4-(hydroxymethyl)phenyl]-1H-indole-3-carbaldehyde (65 mg, 0.24 mmol) in acetonitrile (3 mL) and tert-butanol (3 mL) was treated with 2-methyl-2-butene (2 mL, 18.4 mmol) and cooled to 0° C. A solution of sodium chlorite (410 mg, 4.9 mmol) and sodium dihydrogen phosphate monohydrate (684 mg, 4.96 mmol) in water (3 mL) was added dropwise via an addition funnel. The reaction mixture was warmed to room temperature and stirred for 65 hours. The reaction was partially evaporated in vacuo, and partitioned between water and ethyl acetate. The organic phase was concentrated in vacuo. The crude material was purified using reverse-phase chromatography to give the title compound (20.4 mg).

MS (ES+) 286.0 (M+H)$^+$. Retention time: 2.2 min; Atlantis dC18 5 μm 4.6×50 mm, 95% $H_2O$/5% MeCN linear to 5% $H_2O$/95% MeCN over 4.0 min, HOLD at 5% $H_2O$/95% MeCN to 5.0 min. (0.05% TFA).

Example 8

5-{4-[(1-acetylazetidin-3-yl)oxy]phenyl}-6-chloro-1H-indole-3-carboxylic acid

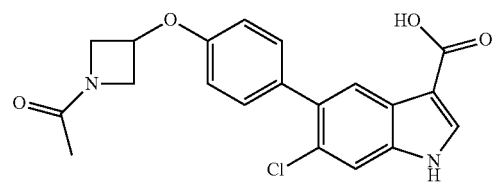 [SMILES: CC(=O)N1CC(Oc2ccc(-c3cc4c(C(=O)O)c[nH]c4cc3Cl)cc2)C1]

Step 1 tert-butyl 3-(4-bromophenoxy)azetidine-1-carboxylate

A mixture of tert-butyl 3-hydroxyazetidine-1-carboxylate (200 mg, 1.15 mmol), 4-bromophenol (240 mg, 1.39 mmol), triphenylphosphine (398 mg, 1.50 mmol) and DIAD (202 mg, 1.39 mmol) in anhydrous THF (5 mL) was heated to 110° C. and stirred under nitrogen for 5 hours. The reaction mixture was concentrated in vacuo to give a brown residue, which was purified by flash chromatography (petroleum ether/ethyl acetate 10:1 to 4:1) to give tert-butyl 3-(4-bromophenoxy)azetidine-1-carboxylate (300 mg, 79.5%) as a white solid.

¹H NMR (400 MHz, CDCl₃) δ 7.39 (d, 2H), 6.72 (d, 2H), 4.84 (m, 1H), 4.28 (m, 2H), 3.99 (m, 2H), 1.44 (s, 9H).

Step 2

3-(4-bromophenoxy)azetidine

To a solution of tert-butyl 3-(4-bromophenoxy)azetidine-1-carboxylate (300 mg, 0.90 mmol) in CH₂Cl₂ (5 mL) was added TFA (5 mL). The mixture was stirred at room temperature overnight. The reaction mixture was concentrated in vacuo to give 3-(4-bromophenoxy)azetidine (207 mg, 100%) as a yellow oil.

Step 3

1-[3-(4-bromophenoxy)azetidin-1-yl]ethanone

To a solution of 3-(4-bromophenoxy)azetidine (207 mg, 0.91 mmol) in CH₂Cl₂ (10 mL) was added triethylamine (276 mg, 2.73 mmol) and acetic anhydride (186 mg, 1.82 mmol). The mixture was stirred at room temperature overnight. The reaction mixture was concentrated in vacuo to give a yellow oil. The crude product was diluted with ethyl acetate (20 mL), washed with 1 N HCl and saturated NaHCO₃, dried over sodium sulfate, and concentrated in vacuo to give 1-[3-(4-bromophenoxy)azetidin-1-yl]ethanone (245 mg, 100%) as a colorless oil. ¹H NMR (400 MHz, CDCl₃) δ 7.40 (d, 2H), 6.61 (d, 2H), 4.89 (m, 1H), 4.49 (m, 1H), 4.37 (m, 1H), 4.17 (m, 1H), 4.03 (m, 1H), 1.90 (s, 3H).

Step 4

1-{3-[4-(5,5-dimethyl-1,3,2-dioxaborinan-2-yl)phenoxy]azetidin-1-yl}ethanone

To a solution of 1-[3-(4-bromophenoxy)azetidin-1-yl]ethanone (200 mg, 0.74 mmol) in 1,4-dioxane (5 mL) was added 5,5,5',5'-tetramethyl-2,2'-bi(1,3,2-dioxaborinane) (184 mg, 0.814 mmol), [1,1'-bis(diphenylphosphino)ferrocene]dichloropalladium(II) (53 mg, 0.074 mmol) and KOAc (363 mg, 3.71 mmol). The mixture was degassed with nitrogen for 3 min and heated to 110° C. by microwave irradiation for 1 hour. The reaction mixture was concentrated in vacuo to give a residue, which was dissolved with ethyl acetate (50 mL) and washed with brine (2×15 mL). The organic layer was dried over sodium sulfate and concentrated in vacuo to give a residue, which was purified by flash chromatography (petroleum ether/ethyl acetate=10:1 to 4:1) to give 1-{3-[4-(5,5-dimethyl-1,3,2-dioxaborinan-2-yl)phenoxy]azetidin-1-yl}ethanone (130 mg, 58%) as a yellow solid.

Step 5

[(1-acetylazetidin-3-yl)oxy]phenyl}-6-chloro-1H-indole-3-carbaldehyde

To a solution of 1-{3-[4-(5,5-dimethyl-1,3,2-dioxaborinan-2-yl)phenoxy]azetidin-1-yl}ethanone (130 mg, 0.43 mmol) in toluene (5 mL) was added 5-bromo-6-chloro-1H-indole-3-carbaldehyde (134 mg, 0.52 mmol), [1,1'-bis(diphenylphosphino)ferrocene]dichloropalladium(II) (32 mg, 0.045 mmol), and 2 M aqueous potassium carbonate (0.86 mL, 1.72 mmol) and ethanol (1.7 mL). The mixture was degassed with nitrogen for 3 min and heated to 110° C. by microwave irradiation for 1 h. The mixture was concentrated in vacuo to give a residue, which was dissolved with ethyl acetate (50 mL) and washed with brine (2×15 mL). The organic layer was dried over sodium sulfate and concentrated in vacuo to give a brown residue, which was purified by flash chromatography (petroleum ether/ethyl acetate=20:1 to 4:1) to give [(1-acetylazetidin-3-yl)oxy]phenyl}-6-chloro-1H-indole-3-carbaldehyde (70 mg, 44%) as a yellow solid.

Step 6

5-{4-[(1-acetylazetidin-3-yl)oxy]phenyl}-6-chloro-1H-indole-3-carboxylic acid

To a solution of [(1-acetylazetidin-3-yl)oxy]phenyl}-6-chloro-1H-indole-3-carbaldehyde (70 mg, 0.19 mmol) in acetonitrile (3 mL) was added tert-butanol (3 mL), water (3 mL), and 2-methyl-2-butene (1.56 mL). The solution was cooled to 0° C., and a solution of sodium chlorite (382 mg, 5.7 mmol) and sodium phosphate monobasic (787 mg, 5.7 mmol) in water (3 mL) was added dropwise. After the addition was complete, the reaction mixture was stirred at room temperature for 96 h. The reaction mixture was quenched with sodium sulfite and concentrated in vacuo to dryness and the resulted solid was washed with DMF. The filtrate was concentrated in vacuo to give a brown residue, which was purified by prep-HPLC to give 5-{4-[(1-acetylazetidin-3-yl)oxy]phenyl}-6-chloro-1H-indole-3-carboxylic acid (10 mg, 14%) as an off-white solid. MS (ES+) 384.8 (M+H)⁺. ¹H NMR (400 MHz, DMSO-d₆) δ 11.95 (s, 1H), 8.05 (s, 1H), 7.94 (s, 1H), 7.62 (s, 1H), 7.37 (d, 2H), 6.93 (d, 2H), 5.09 (m, 1H), 4.65-4.55 (m, 1H), 4.45-4.25 (m, 1H), 4.18-4.15 (m, 1H), 3.88-3.79 (m, 1H), 1.81 (s, 3H).

Example 9

5-{4-[(1-acetylazetidin-3-yl)methoxy]phenyl}-6-chloro-1H-indole-3-carboxylic acid

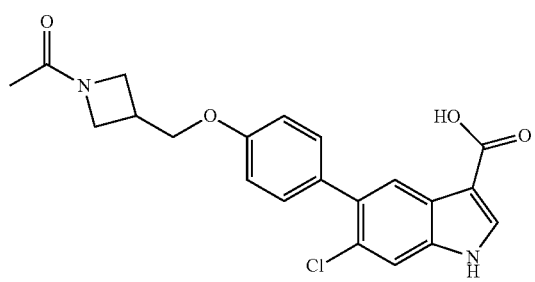 [SMILES: CC(=O)N1CC(COc2ccc(-c3cc4c(C(=O)O)c[nH]c4cc3Cl)cc2)C1]

Step 1 tert-butyl 3-[(4-bromophenoxy)methyl]azetidine-1-carboxylate

A mixture of tert-butyl 3-(hydroxymethyl)azetidine-1-carboxylate (200 mg, 1.07 mmol), 4-bromophenol (222 mg, 1.28 mmol), triphenylphosphine (368 mg, 1.40 mmol) and DIAD (259 mg, 1.28 mmol) in anhydrous THF (5 mL) was heated to 110° C. under nitrogen for 5 hours. The reaction mixture was concentrate in vacuo to give a brown residue, which was purified by flash chromatography (petroleum ether/ethyl acetate 20:1 to 5:1) to give tert-butyl 3-[(4-bromophenoxy)methyl]azetidine-1-carboxylate (310 mg, 84%) as a white solid. $^1$H NMR (400 MHz, CDCl$_3$) δ 7.38 (d, 2H), 6.78 (d, 2H), 4.06 (m, 4H), 3.79 (m, 2H), 2.96 (m, 1H), 1.45 (s, 9H).

Step 2

3-[(4-bromophenoxy)methyl]azetidine

To a solution of tert-butyl 3-[(4-bromophenoxy)methyl]azetidine-1-carboxylate (310 mg, 0.91 mmol) in CH$_2$Cl$_2$ (5 mL) was added TFA (5 mL). The reaction mixture was stirred at room temperature for 16 hours. The reaction mixture was concentrated in vacuo to give 3-[(4-bromophenoxy)methyl]azetidine (220 mg, 100%) as a yellow oil which was used directly in the next step.

Step 3

1-{3-[(4-bromophenoxy)methyl]azetidin-1-yl}ethanone

To a solution of 3-[(4-bromophenoxy)methyl]azetidine (220 mg, 0.91 mmol) in CH$_2$Cl$_2$ (10 mL) was added triethylamine (276 mg, 2.73 mmol) and acetic anhydride (186 mg, 1.82 mmol). The reaction mixture was stirred at room temperature overnight. The reaction mixture was concentrated in vacuo to give a yellow oil. The crude product was diluted with ethyl acetate (20 ml), washed with 1 N HCl followed by saturated aqueous sodium bicarbonate solution, dried over sodium sulfate, and concentrated to give 1-{3-[(4-bromophenoxy)methyl]azetidin-1-yl}ethanone (233 mg, 100%) as a colorless oil. $^1$H NMR (400 MHz, CDCl$_3$) δ 7.38 (d, 2H), 6.78 (d, 2H), 4.28 (m, 1H), 4.24-4.00 (m, 4H), 3.87 (m, 1H), 3.07 (m, 1H), 1.90 (s, 3H)

Step 4

1-(3-{[4-(5,5-dimethyl-1,3,2-dioxaborinan-2-yl)phenoxy]methyl}azetidin-1-yl)ethanone To a mixture of 1-{3-[(4-bromophenoxy)methyl]azetidin-1-yl}ethanone (230 mg, 0.81 mmol), 5,5,5',5'-tetramethyl-2,2'-bi(1,3,2-dioxaborinane) (201 mg, 0.89 mmol) and potassium acetate (397.3 mg, 4.05 mmol) in 1,4-dioxane (5 mL) was added [1,1'-bis(diphenylphosphino)ferrocene]dichloropalladium(II) (59.2 mg, 0.081 mmol). The mixture was degassed with nitrogen for 5 minutes. The mixture was heated to 110° C. and stirred under microwave irradiation for 2 hours. The cooled reaction mixture was filtered and the filtrate was concentrated in vacuo to give a brown residue. The residue was purified by flash column chromatography (petroleum ether/ethyl acetate=20:1 to 3:1) to give 1-(3-{[4-(5,5-dimethyl-1,3,2-dioxaborinan-2-yl)phenoxy]methyl}azetidin-1-yl)ethanone (161 mg, 80%) as a brown solid.

Step 5

5-{4-[(1-acetylazetidin-3-yl)methoxy]phenyl}-6-chloro-1H-indole-3-carbaldehyde

To a mixture of 1-(3-{[4-(5,5-dimethyl-1,3,2-dioxaborinan-2-yl)phenoxy]methyl}azetidin-1-yl)ethanone (160 mg, 0.64 mmol), 5-bromo-6-chloro-1H-indole-3-carbaldehyde (165.4 mg, 0.64 mmol) in 2 M aqueous potassium carbonate (1.3 mL, 2M), toluene (3 mL) and ethanol (1 mL) was added [1,1'-bis(diphenylphosphino)ferrocene]dichloropalladium (II) (46 mg, 0.064 mmol). The mixture was degassed with nitrogen for 5 minutes. The mixture was heated to 110° C. and stirred under microwave irradiation for 2 hours. The cooled reaction mixture was extracted with ethyl acetate (10 mL×3). The combined organic layers was dried over sodium sulfate, filtered, and concentrated in vacuo to give a brown residue. The residue was purified by flash column chromatography (petroleum ether/ethyl acetate=20:1 to 3:1) to give 5-{4-[(1-acetylazetidin-3-yl)methoxy]phenyl}-6-chloro-1H-indole-3-carbaldehyde (127 mg, 52%) as a brown solid. $^1$H NMR (400 MHz, CDCl$_3$) δ 10.01 (s, 1H), 7.60-7.39 (m, 5H), 6.99 (d, 2H), 4.30 (m, 1H), 4.20-4.09 (m, 4H), 3.93 (m, 1H), 3.07 (m, 1H), 1.91 (s, 3H).

Step 6

5-{4-[(1-acetylazetidin-3-yl)methoxy]phenyl}-6-chloro-1H-indole-3-carboxylic acid To a mixture of 5-{4-[(1-acetylazetidin-3-yl)methoxy]phenyl}-6-chloro-1H-indole-3-carbaldehyde (120 mg, 0.31 mmol) in acetonitrile (6 mL) and tert-butanol (6 mL) was added 2-methyl-2-butene (2.17 g, 31 mmol). The mixture was cooled to 0° C., and treated with a solution of sodium chlorite (418 mg, 6.2 mmol) and sodium phosphate monobasic hydrate (856 mg, 6.2 mmol) in water (6 mL). The reaction mixture was stirred at room temperature for 16 hours. A solution of sodium sulfite was added slowly to the reaction mixture, and stirred for 1 hour. The reaction mixture was partially evaporated in vacuo. The aqueous residue was extracted with ethyl acetate (10 mL×3). The combined organic layers were dried over sodium sulfate, filtered, and concentrated in vacuo to give a brown residue. The residue was purified by preparative HPLC to give 5-{4-[(1-acetylazetidin-3-yl)methoxy]phenyl}-6-chloro-1H-indole-3-carboxylic acid (15 mg, 12%) as a white solid. MS (ES+) 399.0 (M+H)$^+$. $^1$H NMR (400 MHz, CD$_3$OD): δ 8.01 (m, 2H), 7.57 (s, 1H), 7.39 (d, 2H), 7.03 (d, 2H), 4.40 (m, 1H), 4.21 (m, 2H), 4.15 (m, 2H), 3.90 (m, 1H), 3.11 (m, 1H), 1.90 (s, 3H).

Example 10

5-{4-[2-(acetylamino)ethoxy]phenyl}-6-chloro-1H-indole-3-carboxylicacid

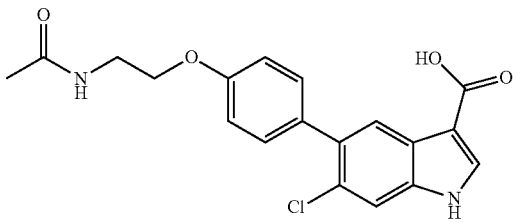 [SMILES: CC(=O)NCCOc1ccc(-c2cc3c(C(=O)O)c[nH]c3cc2Cl)cc1]

Step 1

N-[2-(4-bromophenoxy)ethyl]acetamide

To a solution of 2-(4-bromophenoxy)ethanamine (500 mg, 2.3 mmol) in CH$_2$Cl$_2$ (20 mL) was added triethylamine (700 mg, 6.9 mmol) and acetic anhydride (470 mg, 4.6 mmol). The reaction mixture was stirred at room temperature for 16 hours. The reaction mixture was concentrated in vacuo to give a yellow residue. The crude product was diluted with ethyl acetate (20 mL), washed with 1 N HCl followed by saturated sodium bicarbonate, dried over sodium sulfate and concentrated in vacuo to give N-[2-(4-bromophenoxy)ethyl]acetamide (400 mg, 67%) as a white solid. $^1$H NMR (400 MHz, CDCl$_3$) δ 7.39 (d, 2 H), 6.76 (d, 2 H), δ 5.89 (m, 1 H), 4.00 (m, 2 H), 3.67 (m, 2 H), δ 2.01 (s, 3 H).

Step 2

N-{2-[4-(5,5-dimethyl-1,3,2-dioxaborinan-2-yl)phenoxy]ethyl}acetamide

To a mixture of N-[2-(4-bromophenoxy)ethyl]acetamide (200 mg, 0.78 mmol) in 1,4-dioxane (5 mL) were added 5,5,5',5'-tetramethyl-2,2'-bi(1,3,2-dioxaborinane) (193 mg, 0.85 mmol), [1,1'-bis(diphenylphosphino)ferrocene]dichloropalladium(II) (55 mg, 0.077 mmol) and KOAc (380 mg, 3.88 mmol). The mixture was degassed with nitrogen for 3 min and heated to 110° C. by microwave irradiation for 1 h. The cooled reaction mixture was concentrated in vacuo to give a residue, which was dissolved with ethyl acetate (30 mL) and washed with brine (2×15 mL). The organic layer was dried over sodium sulfate and concentrated in vacuo to give a residue, which was purified by flash chromatography (petroleum ether/ethyl acetate=10:1 to 4:1) to give N-{2-[4-(5,5-dimethyl-1,3,2-dioxaborinan-2-yl)phenoxy]ethyl}acetamide (100 mg, 44%) as a yellow solid.

Step 3

N-{2-[4-(6-chloro-3-formyl-1H-indol-5-yl)phenoxy]ethyl}acetamide

To a solution of N-{2-[4-(5,5-dimethyl-1,3,2-dioxaborinan-2-yl)phenoxy]ethyl}acetamide (100 mg, 0.35 mmol) in ethanol (1.4 mL) were added 5-bromo-6-chloro-1H-indole-3-carbaldehyde (107 mg, 0.42 mmol), [1,1'-bis(diphenylphosphino)ferrocene]dichloropalladium(II) (26 mg, 0.036 mmol), 2 M aqueous potassium carbonate (2 mol/L, 0.7 mL) and toluene (4.2 mL). The mixture was degassed with nitrogen for 3 min and heated to 110° C. by microwave irradiation for 1 h. The mixture was concentrated in vacuo to give a residue, which was dissolved with ethyl acetate (50 mL) and washed with brine (2×15 mL). The organic layer was dried over sodium sulfate and concentrated in vacuo to give a brown residue, which was purified by flash chromatography (petroleum ether/ethyl acetate=10:1 to 2:1) to give N-{2-[4-(6-chloro-3-formyl-1H-indol-5-yl)phenoxy]ethyl}acetamide (80 mg, 65%) as a yellow solid.

Step 4

5-{4-[2-(acetylamino)ethoxy]phenyl}-6-chloro-1H-indole-3-carboxylic acid

To a solution of N-{2-[4-(6-chloro-3-formyl-1H-indol-5-yl)phenoxy]ethyl}acetamide (80 mg, 0.23 mmol) in acetonitrile (3 mL) was added tert-butanol (3 mL) and 2-methyl-2-butene (1.89 mL). The reaction mixture was cooled to 0° C., and treated with a solution of sodium chlorite (452 mg, 6.74 mmol) and sodium phosphate monobasic (930 g, 6.74 mmol) in water (3 mL) dropwise. The reaction mixture was stirred at room temperature for 40 h. The reaction mixture was quenched with sodium sulfite and concentrated in vacuo to give a solid. The crude product was washed with DMF and the filtrate was concentrated in vacuo to give a brown residue, which was purified by prep-HPLC to give 5-{4-[2-(acetylamino)ethoxy]phenyl}-6-chloro-1H-indole-3-carboxylic acid (22 mg, 26%) as an off-white solid. MS (ES+) 373.1 (M+H)$^+$. $^1$H NMR (400 MHz, DMSO-d$_6$) δ 11.93 (s, 1 H), 8.14 (br. s., 1 H), 8.06 (s, 1 H), 7.93 (s, 1 H), 7.62 (s, 1 H), 7.34 (d, 2 H), 7.02 (d, 2 H), 4.03 (t, 2 H), 3.45-3.43 (m, 2 H), 1.84 (s, 3 H).

Example 11

5-{4-[2-(azetidin-1-yl)-2-oxoethyl]phenyl}-6-chloro-1H-indole-3-carboxylic acid

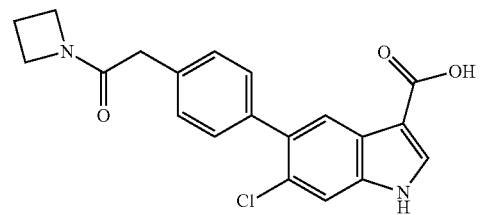 [SMILES: O=C(O)c1c[nH]c2cc(Cl)c(-c3ccc(CC(=O)N4CCC4)cc3)cc12]

Step 1

1-(azetidin-1-yl)-2-(4-bromophenyl)ethanone

A mixture of (4-bromophenyl)acetic acid (1 g, 4.65 mmol), azetidine hydrochloride (481 mg, 5.12 mmol), HATU (1.95 g, 5.12 mmol) and NMM (1.03 g, 10.23 mmol) in DMF (30 mL) was stirred at room temperature for 16 hours. The reaction mixture was diluted with EtOAc and washed with 1 N HCl (15 mL×2) and 1 M aqueous K$_2$CO$_3$ (15 mL×2). The organic phase was washed with brine, dried over sodium sulfate and concentrated in vacuo to give 1-(azetidin-1-yl)-2-(4-bromophenyl)ethanone (1.37 g) as a solid which was used directly in the next step without purification. $^1$H NMR (400 MHz, CD$_3$OD) δ 7.47 (d, 2H), 7.197 (d, 2H), 4.26 (t, 2H), 4.01 (t, 2H), δ 3.45 (s, 2H), δ 2.30 (p, 2H).

Step 2

1-(azetidin-1-yl)-2-[4-(5,5-dimethyl-1,3,2-dioxaborinan-2-yl)phenyl]ethanone

To a degassed mixture of 1-(azetidin-1-yl)-2-(4-bromophenyl)ethanone (1.37 g, 5.4 mmol), 5,5,5',5'-tetramethyl-2,2'-bi(1,3,2-dioxaborinane) (1.83 g, 8.1 mmol) and KOAc (1.59 g, 16.2 mmol) in dry 1,4-dioxane (50 mL) was added [1,1'-bis(diphenylphosphino)ferrocene]dichloropalladium (II) (198 mg, 0.27 mmol). The reaction mixture was heated to reflux for 50 min with stirring. The reaction mixture was acidified with 1 N HCl and extracted with EtOAc (2×50 mL). The combined organic phases were washed with brine, dried over sodium sulfate and concentrated to give crude 1-(azetidin-1-yl)-2-[4-(5,5-dimethyl-1,3,2-dioxaborinan-2-yl)phenyl]ethanone (1.55 g, 100%) which was used directly in the next step.

MS (ES+) 220.0 (M+H)$^+$[M=RB(OH)$_2$].

Step 3

5-{4-[2-(azetidin-1-yl)-2-oxoethyl]phenyl}-6-chloro-1H-indole-3-carbaldehyde

To a degassed mixture of 1-(azetidin-1-yl)-2-[4-(5,5-dimethyl-1,3,2-dioxaborinan-2-yl)phenyl]ethanone (0.78 g, 2.7 mmol), 5-bromo-6-chloro-1H-indole-3-carbaldehyde (700 mg, 2.7 mmol) and 2 M aqueous K$_2$CO$_3$ (5.4 mL, 10.8 mmol) in a solvent mixture of toluene and EtOH (v/v=3/1, 14 mL) was added [1,1'-bis(diphenylphosphino)ferrocene]dichloropalladium(II) (197.6 mg, 0.27 mmol). The reaction mixture was stirred under microwave irradiation at 120° C. for 30 min. After cooling to room temperature, the reaction mixture was partitioned between water and EtOAc (50 mL/50 mL). The organic layer was washed with brine, dried over sodium sulfate and concentrated in vacuo. The residue was purified by flash column (first EtOAc in Petroleum 25%, then MeOH in DCM 10%) to give 5-{4-[2-(azetidin-1-yl)-2-oxoethyl]phenyl}-6-chloro-1H-indole-3-carbaldehyde (0.4 g, 42%) as a brown solid.

MS (ES+) 353.0 (M+H)$^+$.

Step 4

5-{4-[2-(azetidin-1-yl)-2-oxoethyl]phenyl}-6-chloro-1H-indole-3-carboxylic acid

To a solution of 5-{4-[2-(azetidin-1-yl)-2-oxoethyl]phenyl}-6-chloro-1H-indole-3-carbaldehyde (0.16 g, 0.453 mmol) in acetonitrile (8 mL) and tert-butanol (8 mL) was added 2-methyl-2-butene (8 mL). The reaction mixture was cooled to 0° C. and treated with a solution of sodium chlorite (456 mg, 5 mmol) and sodium phosphate monobasic dihydrate (1.06 g, 6.8 mmol) in water (6 mL). The reaction mixture was stirred for 2 hours at room temperature, and treated with additional sodium chlorite (607 mg, 6.67 mmol), sodium phosphate monobasic dihydrate (1.41 g, 9.04 mmol) and 2-methyl-2-butene (1 mL). The resulting mixture was stirred at room temperature overnight. The reaction mixture was partially evaporated in vacuo and extracted with EtOAc (30 mL×3). The combined organic layers were dried over sodium sulfate and concentrated in vacuo. The residue was purified via prep-HPLC to give 5-{4-[2-(azetidin-1-yl)-2-oxoethyl]phenyl}-6-chloro-1H-indole-3-carboxylic acid (25 mg) as a yellow solid.

MS (ES+) 369.0 (M+H)$^+$. $^1$H NMR (400 MHz, DMSO-d$_6$) δ 11.99 (br, 1 H), 8.07 (s, 1 H), 7.94 (s, 1 H), 7.64 (s, 1 H), 7.37-7.32 (m, 4 H), 4.21 (m, 2 H), 3.86 (m, 2 H), 3.16 (s, 2 H), 2.20 (m, 2 H).

Example 12

6-cyano-5-[4-(1-hydroxycyclobutyl)phenyl]-1H-indole-3-carboxylic acid

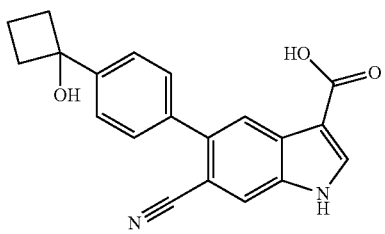 [SMILES: N#Cc1cc2[nH]cc(C(=O)O)c2cc1-c1ccc(C2(O)CCC2)cc1]

Step 1

5-bromo-2,3-dihydro-1H-indole-6-carbonitrile

A solution of 2,3-dihydro-1H-indole-6-carbonitrile (2.5 g, 17.34 mmol) in MeCN (69 mL) was cooled to 0° C. and treated with NBS (3310 mg, 17.7 mmol). The light red reaction mixture was stirred at room temperature for 20 minutes, and was then poured into saturated aqueous sodium bicarbonate (200 mL). The product was extracted with ethyl acetate (2×200 mL), and the combined organic layers were dried over sodium sulfate, filtered and concentrated in vacuo. The crude product was purified using flash chromatography eluting with heptanes/ethyl acetate (95:5 to 60:40) to give the title compound (2.26 g, 58%) as a white solid. MS (ES−): 219.0, 221.0 ($^{79}$Br M+H, $^{81}$Br M+H).

$^1$H NMR (400 MHz, CDCl$_3$) δ 7.32 (s, 1H), 6.78 (s, 1H), 3.65 (t, J=8.6 Hz, 2H), 3.09 (t, J=8.6 Hz, 2H).

Step 2

5-bromo-1H-indole-6-carbonitrile

A solution of 2,3-dihydro-1H-indole-6-carbonitrile (1.38 g, 6.18 mmol) in chloroform (61.9 mL) was treated with activated manganese dioxide (2.39 g, 25 mmol) and heated to 60° C. under reflux. After 2 hours, the cooled reaction mixture was filtered through celite, washing with dichloromethane and evaporated in vacuo to give the title compound (1.22 g, 89%) as an off-white solid. MS (ES−) 219.0 (M−H)$^-$. $^1$H NMR (500 MHz, CDCl$_3$) δ 8.55 (br. s., 1H), 7.92 (s, 1H), 7.78 (s, 1H), 7.45 (s, 1H), 6.60 (s, 1H).

Step 3

5-bromo-3-formyl-1H-indole-6-carbonitrile

Phosphorus oxychloride (1.39 mL, 14.9 mmol) was added dropwise over 5 minutes to DMF (10 mL) with stirring. The clear mixture was stirred at room temperature for 10 minutes. A solution of 5-bromo-1H-indole-6-carbonitrile (1.10 g, 4.97 mmol) in DMF (1.5 with 0.5 mL wash) was added to the clear red solution, and the reaction mixture was stirred at room temperature for 5 min. The resulting grey suspension was heated to 80° C. under nitrogen for 25 min, and then allowed to cool to room temperature. The reaction mixture was treated slowly with water (30 mL) and aqueous 1 N NaOH (30 mL) at room temperature. The resulting thick suspension was then heated to 85° C. for five minutes with vigorous stirring. The reaction mixture was allowed to cool to room temperature over 5 minutes, and the solids were collected by filtration. The solids were dried in vacuo for 16 hours at 55° C. to afford the title compound (1.15 g, 92%) as a cream-colored solid. MS (ES−) 247.1 (M−H)$^-$. $^1$H NMR (500 MHz, DMSO-d$_6$) δ 12.76 (br. s., 1H), 9.99 (s, 1H), 8.60 (s, 1H), 8.43 (s, 1H), 8.18 (s, 1H).

Step 4

3-formyl-5-[4-(1-hydroxycyclobutyl)phenyl]-1H-indole-6-carbonitrile

A suspension of 5-bromo-3-formyl-1H-indole-6-carbonitrile (250 mg, 1.00 mmol), 1-[4-(5,5-dimethyl-1,3,2-dioxaborinan-2-yl)phenyl]cyclobutanol (300 mg, 1.16 mmol) and 2 M aqueous potassium carbonate solution (1.26 mL, 2.51 mmol) in toluene (2.1 mL) and ethanol (1.25 mL) was degassed with nitrogen for 10 minutes, then treated with [1,1'-bis(diphenylphosphino)ferrocene]dichloropalladium (II) (73.2 mg, 0.1 mmol) and heated to 85° C. for 1 hour, at which point the reaction mixture was treated with a solution of 1-[4-(5,5-dimethyl-1,3,2-dioxaborinan-2-yl)phenyl]cyclobutanol (40 mg) and [1,1'-bis(diphenylphosphino)ferrocene]dichloropalladium(II) (30 mg) in DMF (0.6 mL). After 3.5 hours, the clear red reaction mixture was cooled to room temperature and poured into half-diluted ammonium chloride solution (100 mL). The product was extracted with ethyl acetate (6×70 mL). The combined organic layers were dried over sodium sulfate, filtered and evaporated. The crude product was purified using flash chromatograph eluting with heptanes/ethyl acetate (with 0.2% formic acid) (9:1 to 1:9) to give the title compound (223 mg, 70%) as an off-white solid. MS (ES–) 315.2 (M–H)⁻. $^1$H NMR (500 MHz, DMSO-d$_6$) δ 12.62 (br. s., 1 H), 10.02 (s, 1 H), 8.59 (s, 1 H), 8.21 (s, 1 H), 8.13 (s, 1 H), 7.64 (d, J=8.3 Hz, 2 H), 7.56 (d, J=8.3 Hz, 2 H), 5.59 (s, 1 H), 2.48-2.43 (m, 2 H), 2.32-2.25 (m, 2H), 2.01-1.92 (m, 1H), 1.77-1.67 (m, 1H).

Step 5

6-cyano-5-[4-(1-hydroxycyclobutyl)phenyl]-1H-indole-3-carboxylic acid

A solution of 3-formyl-5-[4-(1-hydroxycyclobutyl)phenyl]-1H-indole-6-carbonitrile (223 mg, 0.705 mmol) in tetrahydrofuran (6 mL) and tert-butanol (6 mL) was treated with 2-methyl-2-butene (2.25 mL, 21.2 mmol) and cooled to 0° C. The reaction mixture was then treated with a solution of sodium chlorite (594 mg, 7.0 mmol) and sodium phosphate monobasic hydrate (1.0 g, 7.2 mmol) and warmed to room temperature. The reaction mixture was stirred vigorously at room temperature for 7 hours, and was then poured into saturated aqueous ammonium chloride (40 mL). The product was extracted with ethyl acetate (4×25 mL), and the combined organic layers were dried over sodium sulfate, filtered and concentrated in vacuo. The crude product was purified using flash chromatography eluting with heptanes/ethyl acetate (with 0.2% formic acid) (85:15 to 0:100). The fractions containing product were combined, concentrated in vacuo, diluted with toluene (40 mL) and concentrated in vacuo to give the title compound (157 mg, 67%) as a white solid. This material was dissolved in ethanol (3.5 mL) with heating at 80° C., and treated with water (ca. 3 mL) dropwise with heating at 80° C. The resulting solution was stored at room temperature for two hours, then at 8° C. for 2 hours. The resulting crystals were collected by filtration, washed with water (2 mL) and dried in vacuo at 60° C. for 14 hours to give the title compound (100 mg, 42.7%) as an off-white crystalline solid.

MS (ES–) 331.2 (M–H)⁻. $^1$H NMR (500 MHz, DMSO-d$_6$) δ 12.36 (br. s, 1H), 12.34 (br. s, 1H), 8.30 (s, 1H), 8.12 (s, 1H), 8.07 (s, 1H), 7.63 (d, 2H), 7.54 (d, 2H), 5.58 (d, J=1.2 Hz, 1H), 2.48-2.43 (m, 2H), 2.32-2.30 (m, 2H), 1.99-1.94 (m, 1H), 1.76-1.66 (m, 1H).

Example 13

6-chloro-5-[2-fluoro-4-(1-hydroxycyclobutyl)phenyl]-1H-indole-3-carboxylic acid

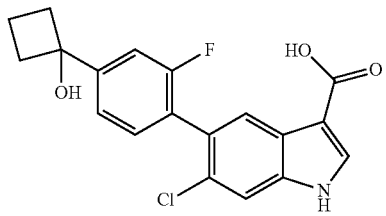 [SMILES: O=C(O)c1c[nH]c2cc(Cl)c(-c3ccc(C4(O)CCC4)cc3F)cc12]

Step 1

1-(4-bromo-3-fluorophenyl)cyclobutanol

To 1-bromo-2-fluoro-4-iodobenzene (2390 mg, 7.90 mmol) in tetrahydrofuran (20 mL) at –40° C. was added isopropyl magnesium chloride.lithium chloride (1.3 M in THF, 6.4 mL, 5.1 mmol) dropwise. The reaction mixture was stirred at –40° C. for 10 minutes, and treated with additional isopropyl magnesium chloride.lithium chloride (1.3 M in THF, 1 mL, 1.3 mmol). The reaction mixture was stirred at –40° C. for an additional 20 minutes and then treated with cyclobutanone (624 mg, 8.72 mmol) dropwise at –40° C. The reaction mixture was warmed to room temperature, and stirred at room temperature for 16 hours. The reaction mixture was quenched with water and extracted with ethyl acetate (3×240 mL). The combined organic layers were dried over sodium sulfate, filtered and concentrated in vacuo to afford the title compound (1.7 g, 91%) as an oil.

Step 2

1-[4-(5,5-dimethyl-1,3,2-dioxaborinan-2-yl)-3-fluorophenyl]cyclobutanol

A suspension of 1-(4-bromo-3-fluorophenyl)cyclobutanol (805 mg, 2.6 mmol), 5,5,5',5'-tetramethyl-2,2'-bi-1,3,2-dioxaborinane (1170 mg, 3.42 mmol), potassium acetate (772 mg, 7.88 mmol) and [1,1'-bis(diphenylphosphino)ferrocene] dichloropalladium(II) (107 mg, 0.13 mmol) in 1,4-dioxane (3 mL) was sealed in a reaction vessel and heated to 130° C. for 1 hour. The reaction mixture was diluted with water (10 mL) and extracted with ethyl acetate (3×10 mL). The combined organic layers were dried over sodium sulfate, filtered and concentrated in vacuo. The crude product was purified using flash chromatography eluting with heptanes/ethyl acetate (0:100 to 50:50) to give the title compound (450 mg, 62%).

Step 3

6-chloro-5-[2-fluoro-4-(1-hydroxycyclobutyl)phenyl]-1H-indole-3-carbaldehyde

A suspension of 5-bromo-6-chloro-1H-indole-3-carbaldehyde (150 mg, 0.44 mmol), 1-[4-(5,5-dimethyl-1,3,2-dioxaborinan-2-yl)-3-fluorophenyl]cyclobutanol (181 mg, 0.652 mmol), 2 M aqueous potassium carbonate (0.87 mL, 1.74 mmol) and [1,1'-bis(diphenylphosphino)ferrocene]dichloropalladium(II) (18 mg, 0.022 mmol) in ethanol (4 mL) was sealed in a reaction vessel and heated thermally to 130° C. for 3 hours. The reaction mixture was diluted with water (10 mL) and extracted with ethyl acetate (3×10 mL). The combined organic layers were washed with brine and dried over sodium sulfate, filtered and concentrated in vacuo. The crude product was purified using flash chromatography eluting with heptanes/ethyl acetate (0:100 to 60:40) to give the title compound (57 mg, 58%). $^1$H NMR (500 MHz, DMSO-d$_6$) δ 12.18-12.38 (m, 1 H), 9.95 (s, 1 H), 8.40 (s, 1H), 8.04 (s, 1H), 7.73 (s, 1H), 7.34-7.50 (m, 3H), 5.68 (s, 1H), 2.40-2.47 (m, 2H), 2.21-2.38 (m, 2H), 1.90-1.99 (m, 1H), 1.68-1.81 (m, 1H).

Step 4

6-chloro-5-[2-fluoro-4-(1-hydroxycyclobutyl)phenyl]-1H-indole-3-carboxylic acid

To a solution of 6-chloro-5-[2-fluoro-4-(1-hydroxycyclobutyl)phenyl]-1H-indole-3-carbaldehyde (57 mg, 0.17 mmol) in acetonitrile (1 mL) and tert-butanol (1 mL) was added a solution of sodium chlorite (112 mg, 1.7 mmol), sodium phosphate monobasic hydrate (199 mg, 1.7 mmol) in water (2 mL) and 2-methyl-2-butene (0.72 mL, 6.8 mmol). The mixture was stirred at room temperature for 24 hours. The mixture was concentrated in vacuo and treated with ethanol. The solids were filtered and the filtrate was concentrated in vacuo to give crude product, which was purified using reverse phase chromatography to give the title compound (12 mg, 20%). MS (ES+) 360.057 (M+H)+. Retention time: 2.60 min. Column: Waters Atlantis dC18 4.6×50 mm, 5 μm. Modifier: TFA 0.05%. Gradient: 95% $H_2O$/5% MeCN linear to 5% $H_2O$/95% MeCN over 4.0 min, HOLD at 5% $H_2O$/95% MeCN to 5.0 min. Flow: 2.0 mL/min.

Example 14

6-chloro-5-{4-[1-(methoxycarbonyl)pyrrolidin-3-yl]phenyl}-1H-indole-3-carboxylic acid

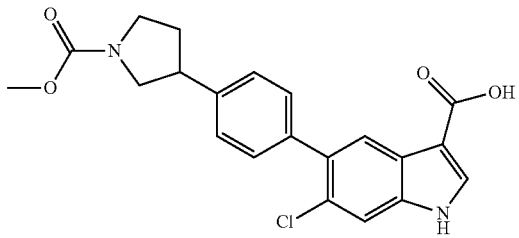 [SMILES: COC(=O)N1CCC(c2ccc(-c3cc4c(C(=O)O)c[nH]c4cc3Cl)cc2)C1]

Step 1 methyl 3-(4-bromophenyl)pyrrolidine-1-carboxylate

Triethylamine (192 mg, 1.9 mmol) was added to a suspension of 3-(4-bromophenyl)pyrrolidine hydrochloride (200 mg, 0.76 mmol) in anhydrous THF (5 mL). The reaction mixture was stirred for 5 minutes and treated with methyl chloroformate (0.1 g, 1.05 mmol). The reaction mixture was stirred for 16 hours at room temperature. The reaction mixture was diluted with water and extracted with EtOAc (2×15 mL). The combined organic layers were washed with brine, dried over $Na_2SO_4$ and concentrated in vacuo to give methyl 3-(4-bromophenyl)pyrrolidine-1-carboxylate (0.24 g, quantitative yield) as an oil which was used for next step directly. MS (ES+) 283.9 (M+H)+.

Step 2 methyl 3-[4-(5,5-dimethyl-1,3,2-dioxaborinan-2-yl)phenyl]pyrrolidine-1-carboxylate To a degassed mixture of methyl 3-(4-bromophenyl)pyrrolidine-1-carboxylate (0.76 mmol), 5,5,5',5'-tetramethyl-2,2'-bi(1,3,2-dioxaborinane) (258 mg, 1.14 mmol) and KOAc (223 mg, 2.28 mmol) in dry 1,4-dioxane (10 mL) was added [1,1'-bis(diphenylphosphino)ferrocene]dichloropalladium (II) (28 mg, 0.038 mmol). The resulting mixture was heated to reflux under nitrogen for 40 min. The reaction mixture was partitioned between water and EtOAc. The organic layer was washed with brine, dried over $Na_2SO_4$ and concentrated in vacuo. The residue was purified by flash column eluting with EtOAc/petroleum ether (0:100 to 30:70) to give methyl 3-[4-(5,5-dimethyl-1,3,2-dioxaborinan-2-yl)phenyl]pyrrolidine-1-carboxylate (158 mg) as a white solid. 1H NMR (CDCl3, 400 MHz) δ 7.69 (d, J=7.6 Hz, 2 H), 7.15 (d, J=7.6 Hz, 2 H), 3.85-3.81 (m, 1 H), 3.69 (s, 4 H), 3.65 (s, 3 H), 3.54-3.50 (m, 1 H), 3.43-3.24 (m, 3 H), 2.22-2.21 (m, 1 H), 1.98-1.89 (m, 1 H), 0.95 (s, 6 H).

Step 3 methyl 3-[4-(6-chloro-3-formyl-1H-indol-5-yl)phenyl]pyrrolidine-1-carboxylate

To a degassed mixture of methyl 3-[4-(5,5-dimethyl-1,3,2-dioxaborinan-2-yl)phenyl]pyrrolidine-1-carboxylate (0.158 g, 0.5 mmol), 5-bromo-6-chloro-1H-indole-3-carbaldehyde (142.5 mg, 0.55 mmol) and 2 N aqueous potassium carbonate (1.0 mL, 2.0 mmol) in toluene (3 mL) and EtOH (1 mL) was added [1,1'-bis(diphenylphosphino)ferrocene]dichloropalladium(II) (36.6 mg, 0.05 mmol). The resulting mixture was heated to 115° C. in a microwave for 30 min. The reaction mixture was partitioned between water and EtOAc. The organic layer was washed with brine, dried over $Na_2SO_4$ and concentrated in vacuo. The residue was purified by flash chromatography on silica gel eluting with EtOAc/petroleum ether (0:100 to 57:43) to give methyl 3-[4-(6-chloro-3-formyl-1H-indol-5-yl)phenyl]pyrrolidine-1-carboxylate (0.13 g, 68%) as a yellow solid, which was used in the next step without further purification.

MS (ES+) 383.1 (M+H)+.

Step 4

6-chloro-5-{4-[1-(methoxycarbonyl)pyrrolidin-3-yl]phenyl}-1H-indole-3-carboxylic acid To a solution of methyl 3-[4-(6-chloro-3-formyl-1H-indol-5-yl)phenyl]pyrrolidine-1-carboxylate (124 mg, 0.325 mmol) in acetonitrile (4 mL) and tert-butanol (4 mL) was added 2-methyl-2-butene (4 mL). The reaction mixture was cooled to 0° C. and treated with a solution of sodium chlorite (327 mg, 3.59 mmol) and sodium phosphate monobasic dihydrate (761 mg, 4.875 mmol) in water (2 mL). After the resulting mixture was stirred for 2 hours at room temperature, additional sodium chlorite (435.5 mg, 4.79 mmol) and sodium phosphate monobasic dihydrate (1.014 g, 6.5 mmol) in water (2 mL) and 2-methyl-2-butene (1 mL) was added. The resulting mixture was stirred at room temperature for 16 h. The reaction mixture was evaporated in vacuo and the aqueous residue was extracted with EtOAc (3×20 mL). The combined organic layers were dried over $Na_2SO_4$ and concentrated in vacuo. The residue was dissolved in DMSO and purified via prep-HPLC to give 6-chloro-5-{4-[1-(methoxycarbonyl)pyrrolidin-3-yl]phenyl}-1H-indole-3-carboxylic acid (60 mg, 46%) as a white solid. The racemic mixture was separated by preparative chiral SFC to give 16 mg of peak 1 or Example 14A (>99% ee, ret time=4.73 minutes), and 17 mg of peak 2 or Example 14B (>93% ee, ret time=5.33 minutes) using ChiralPak AD-H Minigram-1, 60/40 $CO_2$/MeOH 0.2% isopropylamine, 10 mL/min, 120 Bar. MS (ES+) 398.9 (M+H)+. 1H NMR (400 MHz, DMSO-d6) δ 12.14 (br, 1 H), 11.97 (s, 1 H), 8.08 (d, 1 H), 7.94 (s, 1 H), 7.61 (s, 1 H), 7.38 (m, 4 H), 3.81 (m, 1 H), 3.61 (s, 3 H), 3.54 (m, 1 H), 3.40 (m, 2 H), 3.28 (m, 1 H), 2.25 (m, 1 H), 2.00 (m, 1 H).

Example 15

5-[4-(1-acetylpyrrolidin-3-yl)phenyl]-6-chloro-1H-indole-3-carboxylic acid

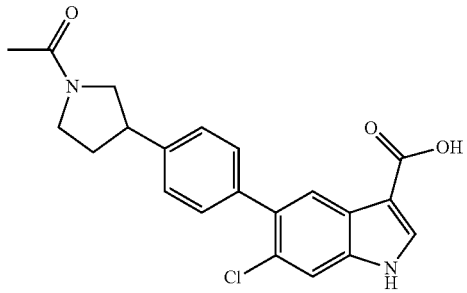 [SMILES: CC(=O)N1CCC(c2ccc(-c3cc4c(C(=O)O)c[nH]c4cc3Cl)cc2)C1]

Step 1

1-[3-(4-bromophenyl)pyrrolidin-1-yl]ethanone

Triethylamine (192 mg, 1.9 mmol) was added to a suspension of 3-(4-bromophenyl)pyrrolidine hydrochloride (200 mg, 0.76 mmol) in anhydrous THF (5 mL). The mixture was stirred at room temperature for 5 minutes and then treated with acetyl chloride (66 mg, 0.84 mmol). The reaction mixture was stirred for 20 hours at room temperature. The reaction mixture was diluted with water and extracted with EtOAc (2×20 mL). The combined organic layers were washed with brine, dried over $Na_2SO_4$ and concentrated in vacuo to give 1-[3-(4-bromophenyl)pyrrolidin-1-yl]ethanone (0.24 g, quantitative yield) as an oil which was used directly in the next step. MS (ES+) 267.9 $(M+H)^+$.

Step 2

1-{3-[4-(5,5-dimethyl-1,3,2-dioxaborinan-2-yl)phenyl]pyrrolidin-1-yl}ethanone

To a degassed mixture of 1-[3-(4-bromophenyl)pyrrolidin-1-yl]ethanone (194 mg, 0.72 mmol), 5,5,5',5'-tetramethyl-2,2'-bi(1,3,2-dioxaborinane) (129 mg, 0.57 mmol) and KOAc (212 mg, 2.16 mmol) in dry 1,4-dioxane (8 mL) was added [1,1'-bis(diphenylphosphino)ferrocene]dichloropalladium (II) (26.4 mg, 0.036 mmol). The reaction mixture was heated to reflux under nitrogen for 30 min. After cooling to room temperature, the reaction mixture was partitioned between water and EtOAc. The organic layer was washed with brine, dried over $Na_2SO_4$ and concentrated in vacuo to give crude 1-{3-[4-(5,5-dimethyl-1,3,2-dioxaborinan-2-yl)phenyl]pyrrolidin-1-yl}ethanone (340 mg) as an oil which was used in the next step without further purification. MS (ES+) 234.2 $(M+H)^+$ $[M=RB(OH)_2]$

Step 3

5-[4-(1-acetylpyrrolidin-3-yl)phenyl]-6-chloro-1H-indole-3-carbaldehyde

To a degassed mixture of crude 1-{3-[4-(5,5-dimethyl-1,3,2-dioxaborinan-2-yl)phenyl]pyrrolidin-1-yl}ethanone (assume 0.38 mmol), 5-bromo-6-chloro-1H-indole-3-carbaldehyde (98.4 mg, 0.38 mmol) and 2 N aqueous potassium carbonate (0.76 mL, 1.52 mmol) in toluene (2.25 mL) and ethanol (0.75 mL) was added [1,1'-bis(diphenylphosphino)ferrocene]dichloropalladium(II) (27.8 mg, 0.038 mmol). The reaction mixture was heated to 110° C. in a microwave for 30 minutes. After cooling to room temperature, the reaction mixture was partitioned between water and EtOAc. The organic phase was washed with brine, dried over $Na_2SO_4$ and concentrated in vacuo. The residue was purified by flash column (first EtOAc in Petroleum ether, then MeOH in $CH_2Cl_2$) to give 5-[4-(1-acetylpyrrolidin-3-yl)phenyl]-6-chloro-1H-indole-3-carbaldehyde (52 mg) as an orange solid. MS (ES+) 389.0 $(M+Na)^+$

Step 4

5-[4-(1-acetylpyrrolidin-3-yl)phenyl]-6-chloro-1H-indole-3-carboxylic acid

To a solution of 5-[4-(1-acetylpyrrolidin-3-yl)phenyl]-6-chloro-1H-indole-3-carbaldehyde (60 mg, 0.163 mmol) in acetonitrile (3 mL) and tert-butanol (3 mL) was added 2-methyl-2-butene (3 mL). The reaction mixture was cooled to 0° C. and treated with a solution of sodium chlorite (164 mg, 1.8 mmol) and sodium phosphate monobasic dihydrate (381 mg, 2.445 mmol) in water (1.5 mL). The reaction mixture was stirred for 2 hours at room temperature and treated with additional sodium chlorite (218 mg, 2.4 mmol) and sodium phosphate monobasic dihydrate (509 g, 3.26 mmol) in water (1.5 mL) and 2-methyl-2-butene (0.5 mL). The resulting mixture was stirred at room temperature for an additional 16 h. The reaction mixture was evaporated in vacuo and the aqueous residue was extracted with EtOAc (3×20 mL). The combined organic layers were dried over $Na_2SO_4$ and concentrated in vacuo. The residue was dissolved in DMSO and purified via prep-HPLC to give 5-[4-(1-acetylpyrrolidin-3-yl)phenyl]-6-chloro-1H-indole-3-carboxylic acid (25 mg) as a white solid. MS (ES+) 383.0 $(M+H)^+$. $^1H$ NMR (400 MHz, DMSO-$d_6$) δ 11.96 (br, 1 H), 8.08 (d, 1 H), 7.93 (s, 1 H), 7.64 (s, 1 H), 7.38 (m, 4 H), 3.1-3.9 (m, 5 H), 2.2-2.5 (m, 1 H), 1.9-2.1 (m, 4 H).

Example 16

6-chloro-5-{4-[1-(methylsulfonyl)pyrrolidin-3-yl]phenyl}-1H-indole-3-carboxylic acid

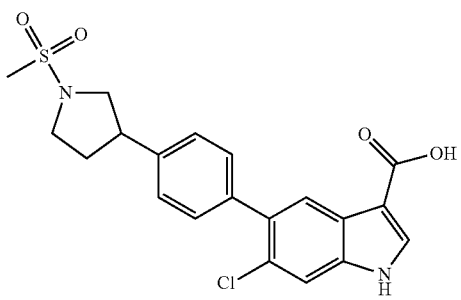 [SMILES: CS(=O)(=O)N1CCC(c2ccc(-c3cc4c(C(=O)O)c[nH]c4cc3Cl)cc2)C1]

Step 1

3-(4-bromophenyl)-1-(methylsulfonyl)pyrrolidine

Triethylamine (192 mg, 1.9 mmol) was added to a suspension of 3-(4-bromophenyl)pyrrolidine hydrochloride (200 mg, 0.76 mmol) in anhydrous THF (5 mL). The reaction mixture was stirred at room temperature for 5 minutes and treated with methanesulfonyl chloride (100 mg, 0.84 mmol). After the reaction mixture was stirred at room temperature for 20 hours, the mixture was diluted with water and extracted with EtOAc (2×20 mL). The combined organic layers were washed with brine, dried over $Na_2SO_4$ and concentrated in vacuo to give 3-(4-bromophenyl)-1-(methylsulfonyl)pyrrolidine (0.25 g, quantitative yield) as a solid which was used for next step directly. MS (ES+) 303.9, 305.9 ($^{79}$Br M+H, $^{81}$Br M+H)$^+$ Step 2

3-[4-(5,5-dimethyl-1,3,2-dioxaborinan-2-yl)phenyl]-1-(methylsulfonyl)pyrrolidine To a degassed mixture of 3-(4-bromophenyl)-1-(methylsulfonyl)pyrrolidine (125 mg, 0.38 mmol), 5,5,5',5'-tetramethyl-2,2'-bi(1,3,2-dioxaborinane) (128.8 mg, 0.57 mmol) and KOAc (112 mg, 1.14 mmol) in dry dioxane (4 mL) was added [1,1'-bis(diphenylphosphino)ferrocene]dichloropalladium(II) (14 mg, 0.019 mmol). The reaction mixture was heated to reflux under nitrogen for 30 min. After cooling to room temperature, the reaction mixture was partitioned between water and EtOAc. The organic layer was washed with brine, dried over $Na_2SO_4$ and concentrated in vacuo to give 3-[4-(5,5-dimethyl-1,3,2-dioxaborinan-2-yl)phenyl]-1-(methylsulfonyl)pyrrolidine (150 mg) as an oil which was used directly in the next step without further purification.
MS (ES+) 269.7 (M+H)$^+$[M=R(OH)$_2$]

Step 3

6-chloro-5-{4-[1-(methylsulfonyl)pyrrolidin-3-yl]phenyl}-1H-indole-3-carbaldehyde To a degassed mixture of crude 3-[4-(5,5-dimethyl-1,3,2-dioxaborinan-2-yl)phenyl]-1-(methylsulfonyl)pyrrolidine (assume 0.38 mmol), 5-bromo-6-chloro-1H-indole-3-carbaldehyde (98.4 mg, 0.38 mmol) and 2 N aqueous potassium carbonate (0.76 mL, 1.52 mmol) in toluene (2.25 mL) and ethanol (0.75 mL) was added [1,1'-bis(diphenylphosphino)ferrocene]dichloropalladium(II) (27.8 mg, 0.038 mmol). The reaction mixture was heated to 110° C. in a microwave for 30 min. After cooling to room temperature, the reaction mixture was partitioned between water and ethyl acetate. The organic layer was washed with brine, dried over $Na_2SO_4$ and concentrated in vacuo. The residue was purified by flash chromatography on silica gel eluting with EtOAc/petroleum ether (0:100 to 100:0) to give 6-chloro-5-{4-[1-(methylsulfonyl)pyrrolidin-3-yl]phenyl}-1H-indole-3-carbaldehyde (100 mg) as a yellow solid. MS (ES+) 402.9 (M+H)$^+$ Step 4

6-chloro-5-{4-[1-(methylsulfonyl)pyrrolidin-3-yl]phenyl}-1H-indole-3-carboxylic acid To a solution of 6-chloro-5-{4-[1-(methylsulfonyl)pyrrolidin-3-yl]phenyl}-1H-indole-3-carbaldehyde (120 mg, 0.298 mmol) in acetonitrile (5 mL) and tert-butanol (5 mL) was added 2-methyl-2-butene (4 mL). The reaction mixture was cooled to 0° C. and treated with a solution of sodium chlorite (299.5 mg, 3.29 mmol) and sodium phosphate monobasic dihydrate (697 mg, 4.47 mmol) in water (2 mL) dropwise. After the reaction mixture was stirred for 2 h at room temperature, additional sodium chlorite (399.3 mg, 4.39 mmol) and sodium phosphate monobasic dihydrate (930 mg, 5.96 mmol) in $H_2O$ (2 mL) and 2-methyl-2-butene (1 mL) was added. The reaction mixture was stirred at room temperature for 16 h. The reaction mixture was evaporated in vacuo and the aqueous residue was extracted with EtOAc (3×40 mL). The combined organic layers were dried over $Na_2SO_4$ and concentrated in vacuo. The residue was dissolved in DMSO and purified via prep-HPLC to give 6-chloro-5-{4-[1-(methylsulfonyl)pyrrolidin-3-yl]phenyl}-1H-indole-3-carboxylic acid (56 mg) as a white solid.
MS (ES+) 441.0 (M+Na)$^+$. $^1$H NMR (400 MHz, DMSO-$d_6$) δ 12.10 (br. s., 1 H), 11.96 (br, 1 H), 8.08 (d, 1 H), 7.94 (s, 1 H), 7.63 (s, 1 H), 7.41 (m, 4 H), 3.77 (m, 1 H), 3.5 (m, 2 H), 3.3 (m, 1 H), 3.2 (m, 1 H), 2.98 (s, 3 H), 2.3 (m, 1 H), 2.1 (m, 1 H).

Example 17

6-chloro-5-[4-(pyrrolidin-3-yl)phenyl]-1H-indole-3-carboxylic acid

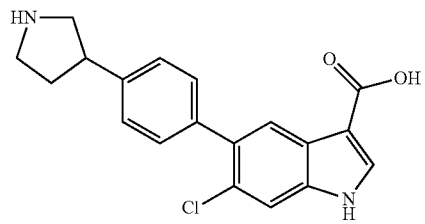 [SMILES: O=C(O)c1c[nH]c2cc(Cl)c(-c3ccc(C4CCNC4)cc3)cc12]

Step 1 tert-butyl 3-(4-bromophenyl)pyrrolidine-1-carboxylate

Triethylamine (192 mg, 1.9 mmol) was added to a suspension of 3-(4-bromophenyl)pyrrolidine hydrochloride (200 mg, 0.76 mmol) in anhydrous THF (5 mL). The reaction mixture was stirred at room temperature for 5 minutes and treated with di-tert-butyl dicarbonate (183 mg, 0.84 mmol). The resulting mixture was stirred for 20 hours at room temperature. The reaction mixture was diluted with water and extracted with EtOAc (2×15 mL). The combined organic layers were washed with brine, dried over $Na_2SO_4$ and concentrated in vacuo to give tert-butyl 3-(4-bromophenyl)pyrrolidine-1-carboxylate (0.29 g, quantitative yield) as an oil which was used directly in the next step. MS (ES+) 269.9 (M−tBu+H)$^+$ Step 2 tert-butyl 3-[4-(5,5-dimethyl-1,3,2-dioxaborinan-2-yl)phenyl]pyrrolidine-1-carboxylate To a degassed mixture of tert-butyl 3-(4-bromophenyl)pyrrolidine-1-carboxylate (124 mg, 0.38 mmol), 5,5,5',5'-tetramethyl-2,2'-bi(1,3,2-dioxaborinane) (129 mg, 0.57 mmol) and KOAc (112 mg, 1.14 mmol) in dry 1,4-dioxane (4 mL) was added [1,1'-bis(diphenylphosphino)ferrocene]dichloropalladium(II) (14 mg, 0.019 mmol). The resulting mixture was heated to reflux under nitrogen for 40 minutes. The reaction mixture was partitioned between water and EtOAc.

The organic layer was washed with brine, dried over Na$_2$SO$_4$ and concentrated in vacuo. The residue was purified by flash chromatography on silica gel eluting with EtOAc/petroleum ether (0:100 to 22:78) to give tert-butyl 3-[4-(5,5-dimethyl-1,3,2-dioxaborinan-2-yl)phenyl]pyrrolidine-1-carboxylate (80 mg) as a white solid.

$^1$H NMR (400 MHz, CDCl$_3$) δ 7.68 (d, 2H), 7.15 (d, 2H), 3.75 (m, 1H), 3.68 (s, 4H), 3.58-3.48 (m, 1H), 3.40-3.18 (m, 3H), 2.22-2.18 (m, 1H), 1.98-1.85 (m, 1H), 1.40 (s, 9H), 0.95 (s, 6H).

Step 3 tert-butyl 3-[4-(6-chloro-3-formyl-1H-indol-5-yl)phenyl]pyrrolidine-1-carboxylate To a degassed mixture of tert-butyl 3-[4-(5,5-dimethyl-1,3,2-dioxaborinan-2-yl)phenyl]pyrrolidine-1-carboxylate (85 mg, 0.237 mmol), 5-bromo-6-chloro-1H-indole-3-carbaldehyde (67.3 mg, 0.26 mmol) and 2 N aqueous potassium carbonate (0.47 mL, 0.94 mmol) in toluene (1.12 mL) and ethanol (0.38 mL) was added [1,1'-bis(diphenylphosphino)ferrocene]dichloropalladium(II) (17.3 mg, 0.0237 mmol). The reaction mixture was heated to 120° C. in a microwave for 30 min. The reaction mixture was partitioned between water and EtOAc. The EtOAc layer was washed with brine, dried over Na$_2$SO$_4$ and concentrated in vacuo. The residue was purified by preparative thin-layer chromatography (EtOAc/petroleum ether=1:2) to give tert-butyl 3-[4-(6-chloro-3-formyl-1H-indol-5-yl)phenyl]pyrrolidine-1-carboxylate (40 mg) as a yellow solid. MS (ES+) 447.0 (M+Na)$^+$.

Step 4

5-{4-[1-(tert-butoxycarbonyl)pyrrolidin-3-yl]phenyl}-6-chloro-1H-indole-3-carboxylic acid To a solution of tert-butyl 3-[4-(6-chloro-3-formyl-1H-indol-5-yl)phenyl]pyrrolidine-1-carboxylate (43 mg, 0.1 mmol) in acetonitrile (1.2 mL) and tert-butanol (1.2 mL) was added 2-methyl-2-butene (1.2 mL). The reaction mixture was cooled to 0° C. and treated with a solution of sodium chlorite (100 mg, 1.1 mmol) and sodium phosphate monobasic dihydrate (234 mg, 1.5 mmol) in water (0.6 mL). After the resulting mixture was stirred for 2 h at room temperature, additional sodium chlorite (134 mg, 1.47 mmol) and sodium phosphate monobasic dihydrate (312 mg, 2.0 mmol) in H$_2$O (0.6 mL) was added to the reaction mixture. The resulting mixture was stirred at room temperature for 16 h. The reaction mixture was concentrated in vacuo and the aqueous residue was extracted with EtOAc (3×20 mL). The combined organic layers were dried over Na$_2$SO$_4$ and concentrated in vacuo. The residue was dissolved in DMSO and purified via pre-HPLC to give 5-{4-[1-(tert-butoxycarbonyl)pyrrolidin-3-yl]phenyl}-6-chloro-1H-indole-3-carboxylic acid (16 mg, 36%) as a white solid. MS (ES+) 463.1 (M+Na)$^+$.

Step 5

6-chloro-5-[4-(pyrrolidin-3-yl)phenyl]-1H-indole-3-carboxylic acid

To a mixture of 5-{4-[1-(tert-butoxycarbonyl)pyrrolidin-3-yl]phenyl}-6-chloro-1H-indole-3-carboxylic acid (15 mg, 0.0341 mmol) in dichloromethane (2 mL) was added TFA (0.213 g, 1.87 mmol) and the resulting mixture was stirred for 45 min at room temperature. The reaction mixture was concentrated in vacuo to give 6-chloro-5-[4-(pyrrolidin-3-yl)phenyl]-1H-indole-3-carboxylic acid (15 mg) as an off-white solid. MS (ES+) 341.0 (M+H)$^+$. $^1$H NMR (400 MHz, DMSO-d$_6$) δ 11.99 (br, 1H), 8.92 (br, 1H), 8.09 (d, 1H), 7.94 (s, 1H), 7.65 (s, 1H), 7.43 (m, 4H), 3.70 (m, 1H), 3.50 (m, 4H), 3.17 (m, 1H), 2.04 (m, 1H).

Example 18

6-chloro-5-[4-(oxetan-3-yloxy)phenyl]-1H-indole-3-carboxylic acid

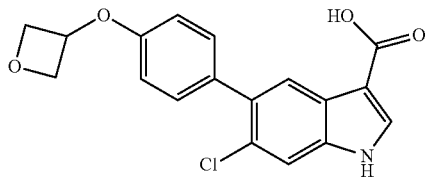 [SMILES: O=C(O)c1c[nH]c2cc(Cl)c(-c3ccc(OC4COC4)cc3)cc12]

Step 1

3-(4-bromophenoxy)oxetane

To oxetan-3-ol (112 mg, 1.5 mmol) in THF (5 mL) was added 4-bromophenol (200 mg, 1.16 mmol), polymeric triphenylphosphine (0.5 g, 1.5 mmol) and DIAD (305 mg, 1.5 mmol). The reaction mixture was degassed with nitrogen for 2 min and stirred at 110° C. for 17 hours. The cooled reaction mixture was filtered and the filtrate was concentrated in vacuo to give a residue, which was dissolved in ethyl acetate (50 mL) and washed with 2 M NaOH (3×15 mL) and brine (2×20 mL). The organic layer was dried over Na$_2$SO$_4$ and concentrated in vacuo to give a residue, which was purified by flash chromatography on silica gel eluting with EtOAc/petroleum ether (1:10) to give 3-(4-bromophenoxy)oxetane (140 mg, 53%) as a colorless solid. $^1$H NMR (400 MHz, CDCl$_3$) δ 7.37 (d, 2H), δ 6.55 (d, 2H), 5.19-5.13 (m, 1H), 4.97-4.94 (m, 2H), 4.76-4.73 (m, 2H).

Step 2

5,5-dimethyl-2-[4-(oxetan-3-yloxy)phenyl]-1,3,2-dioxaborinane

To a solution of 3-(4-bromophenoxy)oxetane (266 mg, 1.16 mmol) in 1,4-dioxane (5 mL) was added 5,5,5',5'-tetramethyl-2,2'-bi(1,3,2-dioxaborinane) (288 mg, 1.27 mmol), [1,1'-bis(diphenylphosphino)ferrocene]dichloropalladium (II) (83 mg, 0.116 mmol) and KOAc (0.57 g, 5.82 mmol). The reaction mixture was degassed with nitrogen for 3 min and heated to 110° C. in a microwave for 1 h. The mixture was concentrated in vacuo to give a residue, which was dissolved with ethyl acetate (30 mL) and washed with brine (2×10 mL). The organic layer was dried over Na$_2$SO$_4$ and concentrated in vacuo to give a residue, which was purified by flash chromatography on silica gel eluting with EtOAc/petroleum ether (1:10 to 1:2) to give 5,5-dimethyl-2-[4-(oxetan-3-yloxy)phenyl]-1,3,2-dioxaborinane (90 mg, 30%) as a colorless oil. $^1$H NMR (400 MHz, CDCl$_3$) δ 7.73 (d, 2H), 6.67 (d, 2H), 5.23 (m, 1H), 4.99-4.96 (m, 2H), 4.78-4.75 (m, 2H), 3.75 (s, 4H), 1.01 (s, 6H).

Step 3

6-chloro-5-[4-(oxetan-3-yloxy)phenyl]-1H-indole-3-carbaldehyde

To a solution of 5,5-dimethyl-2-[4-(oxetan-3-yloxy)phenyl]-1,3,2-dioxaborinane (90 mg, 0.35 mmol) in ethanol (1.4 mL) was added 5-bromo-6-chloro-1H-indole-3-carbaldehyde (110 mg, 0.43 mmol), [1,1'-bis(diphenylphosphino)ferrocene]dichloropalladium(II) (26 mg, 0.036 mmol), 2 M aqueous potassium carbonate (0.7 mL, 1.4 mmol) and toluene (4 mL). The mixture was degassed with $N_2$ for 3 min and heated to 110° C. by microwave irradiation for 1 h. The mixture was concentrated in vacuo to give a residue, which was dissolved with ethyl acetate (30 mL) and washed with brine (2×10 mL). The organic layer was dried over $Na_2SO_4$ and concentrated in vacuo to give a residue, which was purified by flash chromatography on silica gel eluting with EtOAc/petroleum ether (1:10 to 1:1) to give 6-chloro-5-[4-(oxetan-3-yloxy)phenyl]-1H-indole-3-carbaldehyde (100 mg, 87%) as a colorless oil.

Step 4

6-chloro-5-[4-(oxetan-3-yloxy)phenyl]-1H-indole-3-carboxylic acid

To a solution of 6-chloro-5-[4-(oxetan-3-yloxy)phenyl]-1H-indole-3-carbaldehyde (100 mg, 0.34 mmol) in acetonitrile (4 mL) was added tert-butanol (4 mL), water (4 mL) and 2-methyl-2-butene (2.52 mL). The reaction mixture was stirred for 2 minutes and treated with sodium chlorite (620 mg, 9.25 mmol) and sodium phosphate monobasic (1.45 g, 9.29 mmol). The mixture was stirred at room temperature for 17 hours. The reaction was quenched with sodium sulfite and the mixture was concentrated in vacuo to give a residue, which was extracted with ethyl acetate (3×10 mL). The combined organic layers were washed with brine (2×10 mL), dried over $Na_2SO_4$ and concentrated in vacuo to give a residue, which was purified by prep-HPLC to give 6-chloro-5-[4-(oxetan-3-yloxy)phenyl]-1H-indole-3-carboxylic acid (45 mg, 42%) as an off-white solid. MS (ES+) 343.9 $(M+H)^+$. $^1$H NMR (400 MHz, DMSO-$d_6$) δ 11.32 (s, 1H), 8.07 (s, 1H), 7.92 (s, 1H), 7.62 (s, 1H), 7.35 (d, 2H), 6.87 (d, 2H), 5.35-5.32 (m, 1H), 4.97-4.94 (m, 2H), 4.61-4.58 (m, 2H).

Example 19

6-chloro-5-{4-[2-(morpholin-4-yl)ethoxy]phenyl}-1H-indole-3-carboxylic acid

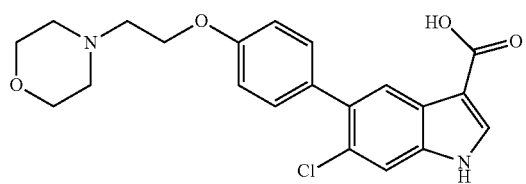 [SMILES: O=C(O)c1c[nH]c2cc(Cl)c(-c3ccc(OCCN4CCOCC4)cc3)cc12]

Step 1

4-[2-(4-bromophenoxy)ethyl]morpholine

To a mixture of 2-(morpholin-4-yl)ethanol (197 mg, 1.5 mmol) in THF (5 mL) was added 4-bromophenol (200 mg, 1.16 mmol), polymeric triphenylphosphine (0.5 g, 1.5 mmol) and DIAD (305 mg, 1.5 mmol). The mixture was degassed with nitrogen for 2 min and stirred at 110° C. for 17 hours. The cooled reaction mixture was filtered and the filtrate was concentrated in vacuo to give a residue, which was dissolved with ethyl acetate (50 mL), washed with 2 M aqueous NaOH (3×15 mL) and brine (2×20 mL). The organic layer was dried over sodium sulfate and concentrated in vacuo to give a residue, which was purified by flash chromatography on silica gel to give 4-[2-(4-bromophenoxy)ethyl]morpholine (480 mg, 100%) as a yellow solid. $^1$H NMR (400 MHz, CDCl$_3$) δ 7.35 (d, 2H), δ 6.70 (d, 2H), 4.07 (t, 2H), 3.74-3.71 (m, 4H), 2.78 (t, 2H), 2.57-2.55 (m, 4H).

Step 2

4-{2-[4-(5,5-dimethyl-1,3,2-dioxaborinan-2-yl)phenoxy]ethyl}morpholine

To a solution of 4-[2-(4-bromophenoxy)ethyl]morpholine (498 mg, 1.74 mmol) in 1,4-dioxane (10 mL) was added 5,5,5',5'-tetramethyl-2,2'-bi(1,3,2-dioxaborinane) (431 mg, 1.91 mmol), [1,1'-bis(diphenylphosphino)ferrocene]dichloropalladium(II) (124 mg, 0.174 mmol) and KOAc (0.853 g, 8.7 mmol). The mixture was degassed with nitrogen for 3 min and heated to 110° C. by microwave irradiation for 1 h. The mixture was concentrated in vacuo to give a residue, which was dissolved with ethyl acetate (50 mL) and washed with brine (2×15 mL). The organic layer was dried over $Na_2SO_4$ and concentrated in vacuo to give a residue, which was purified by flash chromatography to give 4-{2-[4-(5,5-dimethyl-1,3,2-dioxaborinan-2-yl)phenoxy]ethyl}morpholine (190 mg, 34%) as a colorless oil.

Step 3

6-chloro-5-{4-[2-(morpholin-4-yl)ethoxy]phenyl}-1H-indole-3-carbaldehyde

To a solution of 4-{2-[4-(5,5-dimethyl-1,3,2-dioxaborinan-2-yl)phenoxy]ethyl}morpholine (190 mg, 0.6 mmol) in ethanol (2.4 mL) were added 5-bromo-6-chloro-1H-indole-3-carbaldehyde (187 mg, 0.72 mmol), [1,1'-bis(diphenylphosphino)ferrocene]dichloropalladium(II) (45 mg, 0.06 mmol), 2 M aqueous potassium carbonate (1.2 mL, 2.4 mmol) and toluene (7 mL). The mixture was degassed with nitrogen for 3 min and heated to 110° C. by microwave irradiation for 1 h. The mixture was concentrated in vacuo to give a residue, which was dissolved with ethyl acetate (50 mL) and washed with brine (2×15 mL). The organic layer was dried over $Na_2SO_4$ and concentrated in vacuo to give a residue, which was purified by flash chromatography to give 6-chloro-5-{4-[2-(morpholin-4-yl)ethoxy]phenyl}-1H-indole-3-carbaldehyde (130 mg, 57%) as a yellow oil.

Step 4

6-chloro-5-{4-[2-(morpholin-4-yl)ethoxy]phenyl}-1H-indole-3-carboxylic acid

To a solution of 6-chloro-5-{4-[2-(morpholin-4-yl)ethoxy]phenyl}-1H-indole-3-carbaldehyde (130 mg, 0.34 mmol) in acetonitrile (4 mL) was added tert-butanol (4 mL), water (4 mL) and 2-methyl-2-butene (2.76 mL). After stirred for 2 min, sodium chlorite (680 mg, 10.15 mmol) and sodium phosphate monobasic (1.59 mg, 10.19 mmol) were added to the reaction mixture. The mixture was stirred at room temperature for 16 hours. The reaction was quenched with sodium sulfite and the mixture was concentrated in vacuo to give a residue, which was extracted with ethyl acetate (3×10 mL). The combined organic layers were washed with brine (2×15 mL), dried over $Na_2SO_4$ and concentrated in vacuo to give a residue, which was purified by prep-HPLC to give 6-chloro-5-{4-[2-(morpholin-4-yl)ethoxy]phenyl}-1H-indole-3-carboxylic acid (30 mg, 22%) as a yellow solid. MS (ES+) 401.1 (M+H)+. $^1$H NMR (400 MHz, $CD_3OD$) δ 8.28 (s, 1H), 8.02 (s, 1H), 7.98 (s, 1H) 7.57 (s, 1H), 7.39 (d, 2H), 7.04 (d, 2H), 4.31 (m, 2H), 3.83 (m, 4H), 3.17 (m, 2H), 2.96 (m, 4H).

Example 20

4,6-difluoro-5-[4-(3-hydroxyoxetan-3-yl)phenyl]-1H-indole-3-carboxylic acid

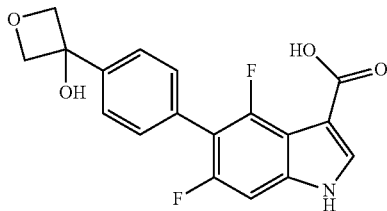 [SMILES: O=C(O)c1c[nH]c2cc(F)c(-c3ccc(C4(O)COC4)cc3)c(F)c12]

Step 1

4-bromo-3,5-difluoro-2-iodoaniline

To a solution of the 4-bromo-3,5-difluoroaniline (5 g, 20 mmol) in acetic acid (60 mL) was added NIS (5.68 g). The reaction mixture was stirred at room temperature for two hours, and poured into water (300 mL). The product was extracted with ethyl acetate (2×200 mL), and the combined organic layers were washed with 1 N aqueous NaOH (200 mL) and saturated aqueous sodium thiosulfate (100 mL). The organic layer was dried over sodium sulfate, filtered and concentrated in vacuo. The oily residue was filtered through a plug of silica gel, eluting with heptane/ethyl acetate (4:1). The filtrate was concentrated in vacuo to give the title compound (7.34 g) as a white solid. $^1$H NMR (500 MHz, $CDCl_3$) δ 6.44 (dd, J=10.00, 1.95 Hz, 1 H) 4.46 (br. s., 2 H).

Step 2

4-bromo-3,5-difluoro-2-[(trimethylsilyl)ethynyl] aniline

A solution of 4-bromo-3,5-difluoro-2-iodoaniline (3.0 g, 9.0 mmol) in triethylamine (50 mL) was degassed with nitrogen for 10 minutes, then treated with copper iodide (209 mg, 1.10 mmol), Dichlorobis(triphenylphosphine)palladium(II), (769 mg 1.10 mmol), and ethynyl(trimethyl)silane (1.42 mL, 10.1 mmol). The reaction mixture was stirred at room temperature for 10 minutes. The reaction mixture turned dark and formed a precipitate. After two hours, the reaction mixture was treated with DMF (8 mL) and stirred for an additional 72 hours at room temperature. The reaction mixture was heated to 50° C. for 16 hours. After cooling to room temperature, the reaction mixture was concentrated in vacuo, azeotroping with heptanes (3×100 mL). The black oil was partitioned between diethyl ether (300 mL) and water (300 mL), and the organic phase was washed with brine, dried over sodium sulfate, filtered and concentrated in vacuo to give a dark solid. The crude product was purified by flash chromatography to give the title compound (1.75 g). MS (ES+) 306.0 ((M+2)+H)+.

Step 3

5-bromo-4,6-difluoro-1H-indole

A solution of 4-bromo-3,5-difluoro-2-[(trimethylsilyl) ethynyl]aniline (1.75 g, 5.77 mmol) in DMF (80 mL) was treated with copper iodide (2.2 g, 11.5 mmol). The reaction mixture was sealed and heated to 110° C. for 3.75 hours. The black reaction mixture was cooled to room temperature, and poured into saturated aqueous ammonium chloride (300 mL). The product was extracted with ethyl acetate/heptane (2:1, 3×200 mL), and the combined organic layers were dried over sodium sulfate, filtered and concentrated in vacuo to give a black oil. The crude product was purified using flash chromatography on silica gel, eluting with heptanes/EtOAc (100:0 to 1:1) to give the title compound (350 mg). MS (ES+) 233.9 ((M+2)+H)+

Step 4

5-bromo-4,6-difluoro-1H-indole-3-carbaldehyde

To a solution of 5-bromo-4,6-difluoro-1H-indole (285 mg, 1.23 mmol) in DMF (2 mL) was added N-(chloromethylidene)-N-methylmethanaminium (236 mg, 1.84 mmol) at room temperature. The reaction mixture was stirred for 30 min, and treated with additional N-(chloromethylidene)-N-methylmethanaminium (100 mg). The mixture was stirred for an additional 30 minutes at room temperature. The reaction mixture was then treated with 1 N aqueous NaOH (2.5 mL) and water (2.5 mL). The mixture was stirred at 100° C. for 30 min. After cooling to room temperature, the solvents were evaporated in vacuo, and the residue was diluted with THF (2 mL) and water (2 mL). The resulting mixture was stirred at room temperature for 2 hours, and the resulting solids were collected by filtration. The solids were washed with water and heptanes and dried in vacuo to give the title compound (157 mg) as a brown solid. MS (ES+) 261.8 ((M+2)+H)+.

Step 5

3-[4-(5,5-dimethyl-1,3,2-dioxaborinan-2-yl)phenyl] oxetan-3-ol

A mixture of 3-(4-bromophenyl)oxetan-3-ol (345 mg, 1.51 mmol), 5,5,5',5'-tetramethyl-2,2'-bi-1,3,2-dioxaborinane (374 mg, 1.66 mmol), KOAc (704 mg, 7.18 mmol) and [1,1'-bis(diphenylphosphino)ferrocene]dichloropalladium(II) (55 mg, 0.075 mmol) was sealed in a reaction vessel and evacuated and back-filled with nitrogen. The reaction mixture was diluted with anhydrous deoxygenated 1,4-dioxane (5 mL) and heated to 110° C. for 15 hours. The cooled reaction mixture was filtered through celite, eluting with ethyl acetate. The filtrate was concentrated in vacuo to give the title compound.

Step 6

4,6-difluoro-5-[4-(3-hydroxyoxetan-3-yl)phenyl]-1H-indole-3-carbaldehyde

A mixture of 5-bromo-4,6-difluoro-1H-indole-3-carbaldehyde (157 mg, 0.64 mmol), 3-[4-(5,5-dimethyl-1,3,2-dioxaborinan-2-yl)phenyl]oxetan-3-ol (190 mg, 0.725 mmol), and 2 M aqueous potassium carbonate (1.2 mL, 2.4 mmol) in toluene (4 mL) and ethanol (2 mL) was degassed with nitrogen for 10 minutes, then treated with [1,1'-bis(diphenylphosphino)ferrocene]dichloropalladium(II) (44 mg, 0.06 mmol). The reaction mixture was sealed and heated to for 110° C. for 16 hours. The cooled reaction mixture was diluted with ethyl acetate and ammonium chloride. The layers were separated and the organic layer was washed with brine, dried over sodium sulfate, and concentrated in vacuo. The crude product was purified by flash column chromatography to give the title compound (38 mg).

Step 7

4,6-difluoro-5-[4-(3-hydroxyoxetan-3-yl)phenyl]-1H-indole-3-carboxylic acid

A solution of 4,6-difluoro-5-[4-(3-hydroxyoxetan-3-yl) phenyl]-1H-indole-3-carbaldehyde (38 mg, 0.12 mmol) was dissolved in acetonitrile (1 mL) and warm tert-butanol (0.3 mL). The reaction mixture was treated with 2-methyl-2-butene (0.3 ml), cooled to 0° C., and treated with a solution of sodium chlorite (199 mg, 2.36 mmol) and sodium phosphate monobasic hydrate (332 mg, 2.41 mmol) in water (1 mL) via addition funnel. The ice bath was removed, and the reaction mixture was warmed to room temperature and stirred for 5 hours. The reaction mixture was diluted with water (2 mL) and NH$_4$Cl (2 mL). The product was extracted with EtOAc (3×20 mL). The organic layer was concentrated in vacuo to give the crude product, which was purified using prep-HPLC to give the title compound (4.3 mg). MS (ES+) 346.0 (M+H)$^+$. Retention time: 2.04 min. Column: Waters Atlantis dC18 4.6×50 mm, 5 μm. Modifier: TFA 0.05%. Gradient: 95% H$_2$O/5% MeCN linear to 5% H$_2$O/95% MeCN over 4.0 min, HOLD at 5% H$_2$O/95% MeCN to 5.0 min. Flow: 2.0 mL/min.

Example 21

2,2-dimethylpropoxy)phenyl]-1H-indole-3-carboxylic acid

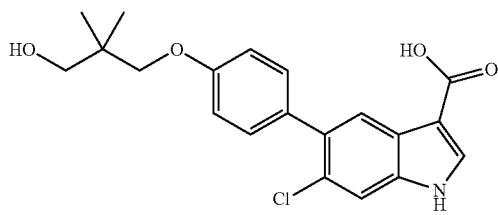 [SMILES: CC(C)(CO)COc1ccc(-c2cc3c(C(=O)O)c[nH]c3cc2Cl)cc1]

Step 1

3-(4-bromophenoxy)-2,2-dimethylpropan-1-ol

To a mixture of 4-bromophenol (300 mg, 1.74 mmol) in DMF (10 mL) was added 3-bromo-2,2-dimethylpropan-1-ol (579 mg, 3.47 mmol) and potassium carbonate (720 mg, 5.22 mmol). The mixture was degassed with nitrogen three times and heated to 90° C. for 48 h. The mixture was cooled to room temperature and then filtered. The filtrate was concentrated in vacuo to give a residue, which was purified by flash chromatography (EtOAc/petroleum ether=1:10 to 1:1) to give 3-(4-bromophenoxy)-2,2-dimethylpropan-1-ol (130 mg, 29%) as a yellow oil. $^1$H NMR (400 MHz, CDCl$_3$) δ 7.37 (d, 2H), 6.79 (d, 2H), 3.73 (s, 2H), 3.54 (s, 2H), 1.02 (s, 6H).

Step 2

3-[4-(5,5-dimethyl-1,3,2-dioxaborinan-2-yl)phenoxy]-2,2-dimethylpropan-1-ol

To a solution of 3-(4-bromophenoxy)-2,2-dimethylpropan-1-ol (130 mg, 0.5 mmol) in 1,4-dioxane (10 mL) was added 5,5,5',5'-tetramethyl-2,2'-bi(1,3,2-dioxaborinane) (125 mg, 0.55 mmol), [1,1'-bis(diphenylphosphino)ferrocene]dichloropalladium(II) (36 mg, 0.05 mmol) and potassium acetate (245 mg, 2.5 mmol). The mixture was degassed with nitrogen for 3 min and heated to 110° C. by microwave irradiation for 1 h. The cooled reaction mixture was concentrated in vacuo to give a residue, which was dissolved with ethyl acetate (30 mL) and washed with brine (3×10 mL). The organic layer was dried over sodium sulfate and concentrated in vacuo to give a residue, which was purified by flash chromatography (EtOAc/petroleum ether=1:10 to 1:2) to give 3-[4-(5,5-dimethyl-1,3,2-dioxaborinan-2-yl)phenoxy]-2,2-dimethylpropan-1-ol (60 mg, 41%) as a white solid. $^1$H NMR (400 MHz, CDCl$_3$) δ 7.73 (d, 2H), 6.89 (d, 2H), 3.79 (s, 2H), 3.75 (s, 4H), 3.55 (s, 2H), 1.03 (s, 6H), 1.01 (s, 6H).

Step 3

6-chloro-5-[4-(3-hydroxy-2,2-dimethylpropoxy)phenyl]-1H-indole-3-carbaldehyde

To a solution of 3-[4-(5,5-dimethyl-1,3,2-dioxaborinan-2-yl)phenoxy]-2,2-dimethylpropan-1-ol (60 mg, 0.21 mmol) in toluene (6 mL) was added 5-bromo-6-chloro-1H-indole-3-carbaldehyde (64 mg, 0.25 mmol), [1,1'-bis(diphenylphosphino)ferrocene]dichloropalladium(II) (15 mg, 0.021 mmol), 2 M aqueous potassium carbonate (0.42 mL, 0.84 mmol) and ethanol (2 mL). The reaction mixture was degassed with nitrogen for 3 min and heated to 110° C. by microwave irradiation for 1 h. The cooled reaction mixture was concentrated in vacuo to give a residue, which was dissolved with ethyl acetate (30 mL) and washed with brine (2×10 mL). The organic layer was dried over sodium sulfate and concentrated in vacuo to give a residue, which was purified by flash chromatography to give 6-chloro-5-[4-(3-hydroxy-2,2-dimethylpropoxy)phenyl]-1H-indole-3-carbaldehyde (60 mg, 82%) as an off-white solid.

Step 4

2,2-dimethylpropoxy)phenyl]-1H-indole-3-carboxylic acid

To a solution of 6-chloro-5-[4-(3-hydroxy-2,2-dimethylpropoxy)phenyl]-1H-indole-3-carbaldehyde (60 mg, 0.17 mmol) in acetonitrile (3 mL) was added tert-butanol (3 mL), water (3 mL) and 2-methyl-2-butene (1.38 mL). The reaction mixture was stirred for 2 min then treated with sodium chlorite (338 mg, 3.76 mmol) and sodium phosphate monobasic (787 mg, 5.04 mmol). The mixture was stirred at room temperature overnight. The reaction was quenched with sodium sulfite and concentrated in vacuo to give a residue, which was dissolved with ethyl acetate (50 mL), washed with brine (3×15 mL), dried over sodium sulfate and concentrated in vacuo. The residue was purified by prep-HPLC to give 2,2-dimethylpropoxy)phenyl]-1H-indole-3-carboxylic acid (20 mg, 32%) as an off-white solid. MS (ES−) 372.1 (M−H)$^-$. $^1$H NMR (400 MHz, CD$_3$OD) δ 8.01 (s, 1H), 7.99 (s, 1H) 7.56 (s, 1H), 7.35 (d, 2H), 6.98 (d, 2H), 3.80 (s, 2H), 3.49 (s, 2H), 1.04 (s, 6H).

Example 22

4,6-difluoro-5-(4-(1-(hydroxymethyl)cyclopropyl)phenyl)-1H-indole-3-carboxylic acid

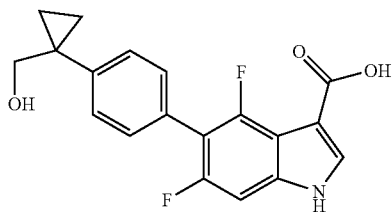 [SMILES: O=C(O)c1c[nH]c2cc(F)c(-c3ccc(C4(CO)CC4)cc3)c(F)c12]

Step 1

{1-[4-(5,5-dimethyl-1,3,2-dioxaborinan-2-yl)phenyl]cyclopropyl}methanol

To a solution of [1-(4-bromophenyl)cyclopropyl]methanol (1200 mg, 5.3 mmol) in THF (40 mL) was added 5,5,5',5'-tetramethyl-2,2'-bi-1,3,2-dioxaborinane (1600 mg, 6.87 mmol), KOAc (2600 mg, 26.5 mmol) and Pd(dppf)Cl$_2$ (197 mg, 0.27 mmol) at room temperature under N$_2$. The reaction mixture was stirred at 70° C. under N$_2$ for 3 hours. The reaction was filtered, the filtrate was concentrated, and purified by column chromatography to give the title compound (1.3 g, 95%) as a white solid. $^1$H NMR (400 MHz, CDCl$_3$) δ 7.74 (d, 2 H), 7.34 (d, 2 H), 3.75 (s, 4 H), 3.68 (s, 2 H), 0.99 (s, 6 H), 0.88 (m, 2 H), 0.85 (m, 2 H).

Step 2

4,6-difluoro-5-{4-[1-(hydroxymethyl)cyclopropyl]phenyl}-1H-indole-3-carbaldehyde A solution of 5-bromo-4,6-difluoro-1H-indole-3-carbaldehyde (200 mg, 0.77 mmol) and {1-[4-(5,5-dimethyl-1,3,2-dioxaborinan-2-yl)phenyl]cyclopropyl}methanol (200 mg, 0.77 mmol) in toluene (6 mL) and EtOH (2 mL) was added a solution of potassium carbonate (318 mg, 2.31 mmol) in water (1.0 mL) and Pd(dppf)Cl$_2$ (31 mg, 0.04 mmol) at room temperature under N$_2$. The reaction was cooled to room temperature, and extracted with ethyl acetate (20 mL×3). The organic layers were washed with brine (20 mL), dried over sodium sulfate, concentrated, and purified by column chromatography to give the title compound (70 mg, 28%) as a yellow solid. $^1$H NMR (400 MHz, CD$_3$OD) δ 10.00 (s, 1 H), 8.12 (s, 1 H), 7.49 (d, 2 H), 7.40 (d, 2 H), 7.19 (d, 1 H), 3.69 (s, 2 H), 0.89 (s, 4 H).

Step 3

4,6-difluoro-5-(4-(1-(hydroxymethyl)cyclopropyl)phenyl)-1H-indole-3-carboxylic acid To a solution of 4,6-difluoro-5-{4-[1-(hydroxymethyl)cyclopropyl]phenyl}-1H-indole-3-carbaldehyde (70 mg, 0.214 mmol) in acetonitrile (4.6 mL), t-Butanol (4.6 mL) and 2-methyl-2-butene (3.0 mL) was added a solution of sodium chlorite (289 mg, 4.28 mmol) and NaH$_2$PO$_4$ (590 mg, 4.28 mmol) in water (4.6 mL) at 0° C. The reaction mixture was stirred at room temperature for 18 h. The reaction was quenched with a solution of sodium sulfate (674 mg, 5.35 mmol) in water (5.0 mL), and extracted with ethyl acetate (20 mL×3). The organic layers were washed with brine (20 mL×1) and dried over sodium sulfate, filtered, concentrated, and purified which was purified by preparative HPLC to give the title compound (17.4 mg, 24%) as a white solid. MS (AP+) 343.9 (M+1)$^+$. $^1$H NMR (400 MHz, CD$_3$OD) δ 8.00 (s, 1 H), 7.48 (d, 2 H), 7.39 (d, 2 H), 7.11 (d, 1 H), 3.71 (s, 2 H), 0.91 (s, 4 H).

Example 23

6-cyano-5-{4-[1-(hydroxymethyl)cyclopropyl]phenyl}-1H-indole-3-carboxylic acid

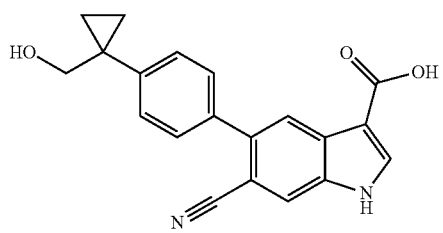 [SMILES: N#Cc1cc2[nH]cc(C(=O)O)c2cc1-c1ccc(C2(CO)CC2)cc1]

Step 1

3-formyl-5-{4-[1-(hydroxymethyl)cyclopropyl]phenyl}-1H-indole-6-carbonitrile

To a suspension of 5-bromo-3-formyl-1H-indole-6-carbonitrile (300 mg, 1.20 mmol) and {1-[4-(5,5-dimethyl-1,3,2-dioxaborinan-2-yl)phenyl]cyclopropyl}methanol (358 mg, 1.10 mmol) in toluene (4 mL) and ethanol (2 mL) was added 2 M aq. potassium carbonate (2 mL, 4 mmol) then was degassed with nitrogen for 10 minutes. The reaction was treated with [1,1'-bis(diphenylphosphino)ferrocene]dichloro palladium and dichloromethane (98 mg, 0.12 mmol). The reaction mixture was heated to 115° C. in a sealed 20 mL microwave vial for 2 hours. The reaction mixture was allowed to cool slowly to room temperature and stirred for 16 hours. The reaction was diluted with ethyl acetate (50 mL) and water (50 mL) and filtered through a pad of celite. The filtrate was extracted and the layers were separated. The aqueous layer was washed an additional time with ethyl acetate. The combined organic layers were washed with brine, dried over magnesium sulfate, filtered and concentrated under reduced pressure. The magnesium sulfate was washed with a 20% methanol/dichloromethane solution and concentrated under reduced pressure yielding 370 mg of crude. Methanol (40 mL) was passed through the above pad of celite and the filtrate was concentrated under reduced pressure yielding 100 mg of a yellow solid. The crude materials were combined and purified using the Biotage SP4 automated chromatography unit (SNAP 50 g silica gel column) and eluting with a gradient of 0-100% ethyl acetate followed by a gradient of 0-20% methanol/dichloromethane to yield 236 mg (62%) of the title compound as a solid. MS (ES+) 315.5 (M−H)$^+$. $^1$H NMR (400 MHz, CD$_3$OD) δ 9.98 (s, 1 H), 8.38 (s, 1 H), 8.30 (d, 1 H), 7.99 (d, 1 H), 7.52 (d, 4 H), 3.71 (s, 2 H), 0.93 (m, 4 H)

Step 2

6-cyano-5-{4-[1-(hydroxymethyl)cyclopropyl]phenyl}-1H-indole-3-carboxylic acid A partial solution/suspension of 3-formyl-5-{4-[1-(hydroxymethyl)cyclopropyl]phenyl}-1H-indole-6-carbonitrile (236 mg, 0.746 mmol) in tetrahydrofuran/t-butanol (6 mL/6 mL) was treated with 2-methyl-2-butene (4 mL, 40 mmol) followed by a solution of sodium chlorite (942 mg, 11 mmol) and sodium phosphate (monobasic and monohydrate, 1585 mg, 11.48 mmol) in water (4 mL) via glass pipet. The reaction was stoppered and allowed to stir overnight at room temperature. After 16 hours, the reaction mixture was poured into half-diluted saturated aqueous ammonium chloride solution (50 mL) and extracted with ethyl acetate (three times). The combined organic layers were washed with brine, dried over sodium sulfate, filtered and concentrated under reduced pressure to yield 346 mg of the crude desired product. The crude material was diluted with methanol (25 mL) and the mixture was heated to reflux. The resulting solution was allowed to cool to room temperature slowly. As the solution was cooling, the sides of the flask were scratched with a glass pipette and stirred at room temperature for 4 hours resulting in a precipitate. The precipitate showed birefringence under the microscope and the mixture was allowed to stir overnight at room temperature (18 hours). After 18 hours, the mixture was filtered and the filter cake was washed with methanol (2 mL) and dried under high vacuum for 40 minutes yielding 127 mg (51%) of desired product as a crystalline solid. The melting point range was determined by a starting temperature of 250° C. and a gradient of 2° C./minute which produced a melting point of 270.9-271.6° C. (determined by the Buchi Melting Point B-545). MS (ES+) 331.4 (M–H)+. $^1$H NMR (400 MHz, DMSO-d$_6$) δppm 12.35 (br. s, 1 H), 12.33 (br. s, 1 H), 8.29 (d, J=2.3 Hz, 1 H), 8.09 (s, 1 H), 8.05 (s, 1 H), 7.48 (d, J=8.4 Hz, 2 H), 7.43 (d, J=8.4 Hz, 2 H), 4.73 (t, J=5.7 Hz, 1 H), 3.60 (d, J=5.7 Hz, 2 H), 0.86-0.93 (m, 2 H), 0.78-0.85 (m, 2 H).

Example 24

4,6-difluoro-5-[4-(2-hydroxyethoxy)phenyl]-1H-indole-3-carboxylic acid

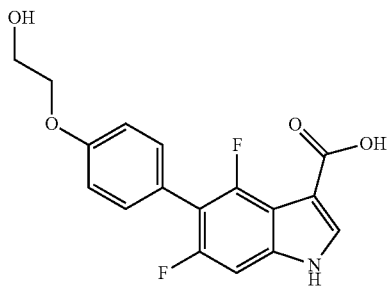 [SMILES: O=C(O)c1c[nH]c2cc(F)c(-c3ccc(OCCO)cc3)c(F)c12]

Step 1

2-[4-(5,5-dimethyl-1,3,2-dioxaborinan-2-yl)phenoxy]ethanol

A mixture bis(neopentyl glycolato)diboron (8.52 g, 24.96 mmol), oven dried potassium acetate (10.4 g, 105.97 mmol), and 2-(4-bromo-phenoxy)-ethanol (4.93 g, 22.71 mmol) in 1,4-dioxane (60 mL) in a 250 mL round bottom flask was degassed with nitrogen for 10 minutes then treated with [1,1'-bis(diphenylphosphino)ferrocene]dichloro palladium, dichloromethane (1.26 g, 1.544 mmol) and heated to 100° C. overnight (16 hours). The following morning, the reaction mixture was diluted with ethyl acetate and filtered through a plug of celite washing with ethyl acetate. The filtrate was concentrated under reduced pressure. The crude material (17.7 g) was divided into two batches and were purified using the Biotage SP4 automated chromatography unit (SNAP 100 g silica gel column for each lot) and eluting with a gradient of 0-100% ethyl acetate/heptane yielding 5.28 g (93%) of the title compound (9.7:1 desired product to boronate bi-products). $^1$H NMR (400 MHz, CDCl$_3$) δppm 7.74 (d, 2 H), 6.90 (d, 2 H), 4.19-4.02 (m, 2 H), 4.01-3.85 (m, 2 H), 3.75 (s, 4 H), 1.02 (s, 6 H).

Step 2

4,6-difluoro-5-[4-(2-hydroxyethoxy)phenyl]-1H-indole-3-carbaldehyde

A solution of 5-bromo-4,6-difluoro-1H-indole-3-carbaldehyde (150 mg, 0.58 mmol) and 2-[4-(5,5-dimethyl-1,3,2-dioxaborinan-2-yl)phenoxy]ethanol (158 mg, 0.64 mmol) in toluene (5 mL) and EtOH (1.6 mL) was added to a solution of potassium carbonate (240 mg, 1.74 mmol) in water (1.2 mL) and Pd(dppf)Cl$_2$ (24 mg, 0.029 mmol) at room temperature under N$_2$. TLC (petroleum ether/EtOAc=1:1) showed the reaction was complete. The reaction was cooled to room temperature, and extracted with ethyl acetate (20 mL×2). The organic layers were washed with brine (10 mL), dried over sodium sulfate, concentrated in vacuo, and purified by column chromatography to give the title compound (70 mg, 38%) as a yellow solid.

$^1$H NMR (400 MHz, CD$_3$OD) δ 10.00 (s, 1 H), 8.13 (s, 1 H), 7.49 (d, 2 H), 7.19 (d, 1 H), 7.05 (d, 2 H), 4.12 (t, 2 H), 3.90 (t, 2 H).

Step 3

4,6-difluoro-5-[4-(2-hydroxyethoxy)phenyl]-1H-indole-3-carboxylic acid

To a solution of 4,6-difluoro-5-[4-(2-hydroxyethoxy)phenyl]-1H-indole-3-carbaldehyde (70 mg, 0.221 mmol) in acetonitrile (4.6 mL), t-butanol (4.6 mL) and 2-methyl-2-butene (3.0 mL) was added a solution of sodium chlorite (298 mg, 4.42 mmol) and sodium dihydrogen phosphate (610 mg, 4.42 mmol) in water (4.6 mL) in an ice-bath. The reaction mixture was stirred at room temperature for 18 h. TLC (petroleum ether/EtOAc=1:1) showed the reaction was complete. The reaction was quenched with a solution of sodium sulfite (612 mg, 4.86 mmol) in water (5.0 mL), and extracted with ethyl acetate (20 mL×3). The organic layers were washed with brine (10 mL) and dried over sodium sulfate, filtered and concentrated to give a crude residue, which was purified by reverse phase HPLC to give the title compound (21.1 mg, 29%) as a white solid. MS (AP+) 333.9 (M+1)+. $^1$H NMR (400 MHz, CD$_3$OD) δ 8.00 (s, 1 H), 7.49 (d, 2 H), 7.12 (d, 1 H), 7.05 (d, 2 H), 4.13 (t, 2 H), 3.92 (t, 2 H)

Example 25

6-fluoro-5-[4-(1-hydroxycyclobutyl)-3-methoxyphenyl]-1H-indole-3-carboxylic acid

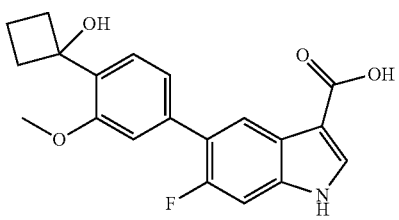 [SMILES: COc1cc(-c2cc3c(C(=O)O)c[nH]c3cc2F)ccc1C1(O)CCC1]

Step 1

1-[4-(5,5-dimethyl-1,3,2-dioxaborinan-2-yl)-2-methoxyphenyl]cyclobutanol

A 250 mL round bottom flask was charged with 1-(4-bromo-2-methoxyphenyl)cyclobutanol (4.756 g, 18.50 mmol), dioxane (90 mL), bis(neopentyl glycolato)diboron (4.60 g, 20.3 mmol), and potassium acetate (oven dried, 9.08 g, 92.5 mmol). Nitrogen was bubbled through the solution for 10 minutes. [1,1'-bis(diphenylphosphino)ferrocene]dichloro palladium, dichloromethane (1.09 g, 1.33 mmol) was then added and the reaction was heated to reflux for 3 hours. The reaction mixture was cooled to room temperature and filtered through celite, washed with ethyl acetate, and concentrated under reduced pressure. The crude material was purified using the Biotage Isolera One (SNAP 100 g silica gel column) and eluted with a gradient of 0-100% ethyl acetate/heptane yielding 4.86 g (90%) of the title compound as an oil that solidified upon standing. GC/MS: 289 (m/z). $^1$H NMR (500 MHz, CDCl$_3$) δ 7.42 (d, J=7.3 Hz, 1 H), 7.34 (s, 1 H), 7.31 (d, J=7.6 Hz, 1 H), 3.92 (s, 3 H), 3.77 (s, 4 H), 2.43-2.58 (m, 2 H), 2.28-2.42 (m, 2 H), 1.94-2.10 (m, 1 H), 1.58-1.69 (m, 1 H), 1.03 (s, 6 H)

Step 2

6-fluoro-5-[4-(3-hydroxyoxetan-3-yl)-3-methoxyphenyl]-1H-indole-3-carbaldehyde

To a solution of 3-[4-(5,5-dimethyl-1,3,2-dioxaborinan-2-yl)-2-methoxyphenyl]oxetan-3-ol (101 mg, 0.348 mmol) and 5-bromo-6-fluoro-1H-indole-3-carbaldehyde (88.5 mg, 0.365 mmol) in toluene/ethanol (8 mL, 3:1) was added 2 N potassium carbonate (145 mg, 1.051 mmol) and Pd(dppf)Cl$_2$ (30 mg, 0.041 mol). The reaction was degassed with N$_2$ for 2 minutes. The reaction was heated to 110° C. for 3 hours. The reaction mixture was concentrated to give a crude residue, which was purified by column chromatography on a silica gel to afford the title compound (86 mg, 73%) as an off-white solid. $^1$H NMR (400 MHz, CDCl3) δ 9.98 (s, 1H), 8.80 (br. s, 1H), 8.32 (d, 1H), 7.79 (d, 1H), 7.32 (d, 1H), 7.15 (m, 2H), 7.07 (s, 1H), 3.88 (s, 3H), 3.62 (s, 1H), 2.50 (m, 2H), 2.34 (m, 2H), 1.98 (m, 1H), 1.64 (m, 1H)

Step 3

6-fluoro-5-[4-(1-hydroxycyclobutyl)-3-methoxyphenyl]-1H-indole-3-carboxylic acid 6-fluoro-5-[4-(3-hydroxyoxetan-3-yl)-3-methoxyphenyl]-1H-indole-3-carbaldehyde (86 mg, 0.2534 mmol) was dissolved in MeCN (6 mL) and warm t-butanol (6 mL). 2-methyl-2-butene (4 mL) was then added and cooled to 0° C. Sodium chlorite (342 mg, 5.07 mmol) and sodium dihydrogen phosphate dihydrate (791 mg, 5.07 mmol) were dissolved in water (3 mL). The aqueous solution was added to the organic solution dropwise via addition funnel and the ice bath was removed and the mixture was allowed to warm to room temperature. The reaction was quenched with saturated aqueous sodium sulfite, concentrated to remove the organics and extracted with EtOAc (20 mL×3). The combined organics were washed with brine (20 mL), dried and concentrated to give a crude residue, which was purified by prep HPLC to afford the title compound (7.3 mg, 8.1%) as an off-white solid.

MS (AP+) 337.8 (M–H$_2$O+H)$^+$. $^1$H NMR (400 MHz, DMSO-d$_6$) δ 12.10 (s, 1H), 11.90 (s, 1H), 8.05 (s, 1 H), 8.02 (s, 1H), 7.35 (d, 2H), 7.08 (s, 1H), 7.04 (d, 1H), 5.00 (s, 1H), 3.82 (s, 3H), 2.60 (m, 2H), 2.20 (m, 2H), 2.00 (m, 1H), 1.61 (m, 1H).

Example 26

4,6-difluoro-5-[4-(1-hydroxy-2-methylpropan-2-yl)phenyl]-1H-indole-3-carboxylic acid

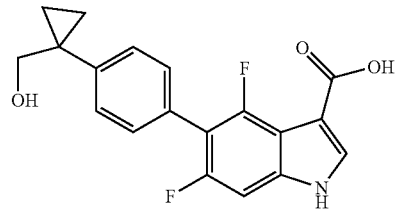 [SMILES: O=C(O)c1c[nH]c2cc(F)c(-c3ccc(C4(CO)CC4)cc3)c(F)c12]

Step 1

2-(4-bromophenyl)-2-methylpropan-1-ol

To a solution of [2-(4-bromophenyl)-2-methylpropoxy](tert-butyl)dimethylsilane (500 mg, 1.46 mmol) in MeOH (5 mL) was added dropwise HCl/MeOH (5 mL) at room temperature. The reaction mixture was stirred at room temperature for 2 hours. The reaction was concentrated to give a crude residue, which was purified by column chromatography to give the title compound (250 mg, 75%) as a colorless oil. $^1$H NMR (400 MHz, CDCl$_3$) δ 7.38 (d, 2 H), 7.19 (d, 2 H), 3.50 (s, 2 H), 1.23 (s, 6 H).

Step 2

2-[4-(5,5-dimethyl-1,3,2-dioxaborinan-2-yl)phenyl]-2-methylpropan-1-ol

To a solution of 2-(4-bromophenyl)-2-methylpropan-1-ol (250 mg, 1.1 mmol) and 5,5,5',5'-tetramethyl-2,2'-bi-1,3,2-dioxaborinane (298 mg, 1.3 mmol) in THF (20 mL) was added KOAc (539 mg, 5.5 mmol) and Pd(dppf)Cl$_2$ (40 mg, 0.055 mmol) at room temperature under N$_2$. The reaction was filtered and the filtrate was concentrated to give a crude, which was purified by column chromatography to give the title compound (120 mg, 42%) as a white solid. $^1$H NMR (400 MHz, CDCl$_3$) δ 7.72 (d, 2 H), 7.32 (d, 2 H), 3.69 (s, 4 H), 3.56 (m, 2 H), 1.27 (s, 6 H), 0.95 (s, 6 H)

Step 3

4,6-difluoro-5-[4-(1-hydroxy-2-methylpropan-2-yl) phenyl]-1H-indole-3-carbaldehyde To a solution of 2-[4-(5,5-dimethyl-1,3,2-dioxaborinan-2-yl)phenyl]-2-methylpropan-1-ol (102 mg, 0.386 mmol) and 5-bromo-4,6-difluoro-1H-indole-3-carbaldehyde (100 mg, 0.386 mmol) in toluene (6 mL) and EtOH (2 mL) was added a solution of potassium carbonate (160 mg, 1.159 mmol) in water (1.0 mL) and Pd(dppf)Cl$_2$ (15.8 mg, 0.019 mmol) at room temperature under N$_2$. The reaction was cooled to room temperature, and extracted with ethyl acetate (10 mL×2). The organic layers were washed with brine (10 mL), and dried over sodium sulfate and concentrated to give a crude residue, which was purified by column chromatography to give the title compound (40 mg, 32%) as a yellow solid. $^1$H NMR (400 MHz, CD$_3$OD) δ 10.0 (s, 1 H), 8.13 (s, 1 H), 7.51 (d, 2 H), 7.40 (d, 2 H), 7.19 (d, 1 H), 3.63 (s, 2 H), 1.36 (s, 6 H).

Step 4

4,6-difluoro-5-[4-(1-hydroxy-2-methylpropan-2-yl) phenyl]-1H-indole-3-carboxylic acid To a solution of 4,6-difluoro-5-[4-(1-hydroxy-2-methylpropan-2-yl)phenyl]-1H-indole-3-carbaldehyde (40 mg, 0.122 mmol) in acetonitrile (2.3 mL), t-butanol (2.3 mL) and 2-methyl-2-butene (1.5 mL) was added a solution of sodium chlorite (164 mg, 2.43 mmol) and sodium dihydrogen phosphate (335 mg, 2.43 mmol) in water (2.3 mL) at 0° C. The reaction mixture was stirred at room temperature for 18 h. The reaction was quenched with a solution of sodium sulfite (337 mg, 2.68 mmol) in water (5.0 mL), and extracted with ethyl acetate (10 mL×3). The organic layers were washed with brine (10 mL) and dried over sodium sulfate, filtered and concentrated to give a crude residue, which was purified by reverse phase HPLC to give the title compound (14.6 mg, 42%) as a white solid.

MS (AP+) 367.8 (M+Na)$^+$. $^1$H NMR (400 MHz, CD$_3$OD) δ 8.00 (s, 1 H), 7.51 (d, 2 H), 7.42 (d, 2 H), 7.13 (d, 1 H), 3.64 (s, 2 H), 1.37 (s, 6 H)

Example 27

5-{4-[1-(hydroxymethyl)cyclopropyl]phenyl}-6-methyl-1H-indole-3-carboxylic acid

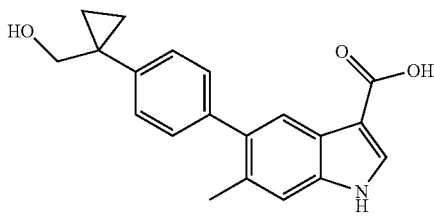 [SMILES: Cc1cc2[nH]cc(C(=O)O)c2cc1-c1ccc(C2(CO)CC2)cc1]

Step 1

5-bromo-6-methyl-1H-indole-3-carbaldehyde

Phosphorus oxychloride (0.73 g, 4.79 mmol) and DMF (5.0 mL) were mixed together and stirred for 5 min. A solution of 5-bromo-6-methyl-1H-indole (500 mg, 2.39 mmol) in DMF (3.0 mL) was added to the solution slowly and complete solid was formed which stopped stirring. The solution was adjusted to pH=10 with 1 N NaOH, then heated to 100° C. for 1 min. The reaction was cooled to room temperature. The precipitated solids were filtered and dried to give the title compound (480 mg, 85%) as a yellow solid. $^1$H NMR (400 MHz, DMSO-d$_6$) δ 12.2 (s, 1 H), 9.88 (s, 1 H), 8.28 (s, 1 H), 8.23 (s, 1 H), 7.49 (s, 1 H), 2.44 (s, 3 H).

Step 2

5-{4-[1-(hydroxymethyl)cyclopropyl]phenyl}-6-methyl-1H-indole-3-carbaldehyde

A solution of 5-bromo-6-methyl-1H-indole-3-carbaldehyde (200 mg, 0.84 mmol) and {1-[4-(5,5-dimethyl-1,3,2-dioxaborinan-2-yl)phenyl]cyclopropyl}methanol (242 mg, 0.93 mmol) in toluene (6 mL) and EtOH (2.0 mL) was added to a solution of potassium carbonate (350 mg, 2.52 mmol) in water (1.0 mL) and Pd(dppf)Cl$_2$ (34 mg, 0.042 mmol) at room temperature under N$_2$. TLC (petroleum ether/EtOAc=1:1) showed the reaction was complete. The reaction was cooled to room temperature, and extracted with ethyl acetate (20 mL×3). The organic layers were washed with brine (20 mL), dried over sodium sulfate and concentrated to give a crude ARRR!!!!, which was purified by column chromatography to give the title compound (190 mg, 74%) as a yellow solid. $^1$H NMR (400 MHz, CD$_3$OD) δ 9.83 (s, 1 H), 8.05 (s, 1 H), 7.93 (s, 1 H), 7.41 (d, 2 H), 7.37 (s, 1 H), 7.27 (d, 2 H), 3.69 (s, 2 H), 2.31 (s, 3 H), 0.89 (d, 4 H).

Step 3

5-{4-[1-(hydroxymethyl)cyclopropyl]phenyl}-6-methyl-1H-indole-3-carboxylic acid

To a solution of 5-{4-[1-(hydroxymethyl)cyclopropyl] phenyl}-6-methyl-1H-indole-3-carbaldehyde (50 mg, 0.164 mmol) in acetonitrile (3.3 mL), t-butanol (3.3 mL) and 2-methyl-2-butene (2.2 mL) was added a solution of sodium chlorite (221 mg, 3.28 mmol) and sodium dihydrogen phosphate (452 mg, 3.28 mol) in water (3.3 mL) at 0° C. The reaction mixture was stirred at room temperature for 18 h. TLC (petroleum ether/EtOAc=1:1) showed most of the starting material was consumed. The reaction was quenched with a solution of sodium sulfite (455 mg, 3.61 mmol) in water (3.0 mL), and extracted with ethyl acetate (20 mL×3). The organic layers were washed with brine (20 mL) and dried over sodium sulfate, filtered and concentrated to give a crude residue, which was purified by reverse phase HPLC to give the title compound (9.3 mg, 18%) as a white solid. MS (AP+) 322.1 (M+1)$^+$. $^1$H NMR (400 MHz, CD$_3$OD) 7.89 (s, 1 H), 7.82 (s, 1 H), 7.40 (d, 2 H), 7.30 (s, 1 H), 7.28 (d, 2 H), 3.69 (s, 2 H), 2.30 (s, 3 H), 0.89 (m, 4 H).

Example 28

4,6-difluoro-5-[4-(3-hydroxypropoxy)phenyl]-1H-indole-3-carboxylic acid

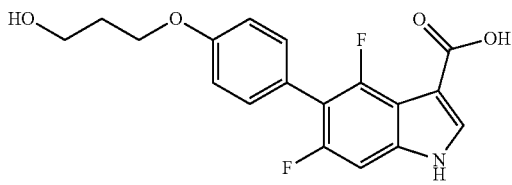 [SMILES: O=C(O)c1c[nH]c2cc(F)c(-c3ccc(OCCCO)cc3)c(F)c12]

Step 1

3-(4-bromophenoxy)propan-1-ol

To a solution of 4-bromophenol (10 g, 58 mmol) in DMF (10 mL) was added 3-bromopropan-1-ol (9.6 g, 69 mmol) and potassium carbonate (13.6 g, 98 mmol). The mixture was stirred at room temperature for 12 h. LCMS showed the reaction was almost complete. The mixture was partitioned between water and ethyl acetate (20 mL×3), The combined organics were dried and concentrated to give the title compound that was used in the next step without further purification (14.7 g, quant). $^1$H NMR (400 MHz, CD$_3$OD) δ 7.36 (d, 2 H), 6.84 (d, 2 H), 4.05 (t, 2 H), 3.72 (t, 2 H), 1.96 (m, 2 H).

Step 2

3-(4-(5,5-dimethyl-1,3,2-dioxaborinan-2-yl)phenoxy)propan-1-ol

To a suspension of oven dried potassium acetate (27.6 g, 281 mmol) and 3-(4-bromophenoxy)propan-1-ol (13.0 g, 56.3 mmol) in dry dioxane (100 mL) was added bis(neopentylglycolato) diboron (14.0 g, 61.9 mmol). The solvent was degassed by passing nitrogen through the system for 10 min. Pd(dppf)Cl$_2$ (1.0 g, 1.3 mmol) was added and the reaction heated to 90° C. The reaction was cooled, diluted with ethyl acetate then filtered through celite and stripped. Residue was then filtered through a plug of silica gel with ethyl acetate then concentrated in vacuo. The residue was then adsorbed onto a 25 g column with dichloroethane and purified by silica gel chromatography (100 g, 20-60% EtOAc/Heptane). The one major peak was isolated to give the title product as a yellow oil (17.78 g, quant.) that was used without any further purification. GCMS: 264

Step 3

4,6-difluoro-5-[4-(3-hydroxypropoxy)phenyl]-1H-indole-3-carbaldehyde

To the slurry of 5-bromo-4,6-difluoro-1H-indole-3-carbaldehyde was added 2 M potassium carbonate (0.7 mL) and the mixture was stirred at room temperature for 5 min. Then 3-(4-(5,5-dimethyl-1,3,2-dioxaborinan-2-yl)phenoxy)propan-1-ol (120 mg, 0.46 mmol) and Pd(dppf)Cl$_2$ (20 mg) was added to the reaction. The reaction was heated to 90° C. for 30 min. Solvent was removed under reduced pressure to give a residue, which was purified by silica gel chromatography (petroleum ether/ethyl acetate=4:1) to give the title compound (30 mg, 20%) as a yellow solid.

Step 4

4,6-difluoro-5-[4-(3-hydroxypropoxy)phenyl]-1H-indole-3-carboxylic acid

To a mixture of 4,6-difluoro-5-[4-(3-hydroxypropoxy)phenyl]-1H-indole-3-carbaldehyde (30 mg, 0.1 mmol) in ACN/t-butanol=1/1 (2 mL) was added 2-methyl-2-butene (0.5 mL) and cooled to 0° C. and added the aqueous solution of sodium chlorite (180 mg, 0.5 mL) and sodium dihydrogen phosphate (270 mg, 2 mmol) in water (0.5 mL) dropwise via additional funnel. The reaction was stirred at room temperature for 10 h. The reaction was quenched with sodium sulfite. The mixture was partioned between dichloromethane and water. The combined organics were concentrated to give a residue, which was purified by reverse phase HPLC to give the title compound (15 mg, 43%) as a white solid. MS (AP+) 348.1 (M+H)$^+$. $^1$H NMR (400 MHz, CD$_3$OD) δ 7.74 (s, 1 H), 7.36 (d, 2 H), 7.03-6.98 (m, 3 H), 4.14 (t, 2 H), 3.77 (t, 2 H), 2.04-2.01 (m, 2 H).

Example 29

6-chloro-5-(3-methoxyphenyl)-1H-indole-3-carboxylic acid

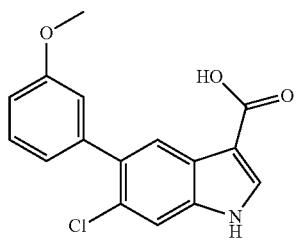 [SMILES: COc1cccc(-c2cc3c(C(=O)O)c[nH]c3cc2Cl)c1]

Step 1

6-chloro-5-(3-methoxyphenyl)-1H-indole-3-carbaldehyde

To a solution of 5-bromo-6-chloro-1H-indole-3-carbaldehyde (300 mg, 2 mmol) in dioxane/DMF=1/1 (4 mL) was added (3-methoxyphenyl)boronic acid (463 mg, 1.8 mmol), potassium carbonate (828 mg, 6 mmol) in water (1 mL), and Pd (dppf)Cl$_2$ (50 mg) in a microwave vial. The sealed vial was irradiated in the microwave on a Biotage Smith Synthesizer at 110° C. for 30 min, TLC (petroleum ether/ethyl acetate=1:1) showed the reaction was complete. The solvent was removed in vacuo and the mixture was partitioned between ethyl acetate and water. The combined organics were dried over sodium sulfate, concentrated in vacuo, and purified by combiflash to give the title compound (270 mg, 47%) as a yellow solid $^1$H NMR (400 MHz, CD$_3$OD) δ 9.90 (s, 1 H), 8.18 (s, 1 H), 8.13 (s, 1 H), 7.62 (s, 1 H), 7.36-7.34 (m, 1 H), 7.01-6.93 (m, 3 H), 3.84 (s, 3 H)

Step 2

6-chloro-5-(3-methoxyphenyl)-1H-indole-3-carboxylic acid

To a solution of 6-chloro-5-(3-methoxyphenyl)-1H-indole-3-carbaldehyde (100 mg, 0.35 mmol) in ACN/t-butanol=1/1 (4 mL) was added 2-methyl-2-butene (1 mL) at 0° C. and stirred 10 min. Then an aqueous solution of sodium chlorite (315 mg, 3.5 mmol) and sodium dihydrogen phosphate (480 mg, 3.5 mmol) in water (1 mL) was added to the system dropwise. The reaction was stirred at room temperature for 10 h. The reaction was quenched with sodium sulfite. The mixture was partitioned between DCM and water. The combined organics were dried and concentrated to give a residue, which was purified by reverse phase HPLC to give the title compound (40 mg, 38%) as a white solid. MS (AP−) 300.1 (M−1)⁻. ¹H NMR (400 MHz, CD₃OD) δ 8.01 (s, 1 H), 8.00 (s, 1 H), 7.58 (s, 1 H), 7.33 (t, 1 H), 7.01-6.97 (m, 2 H), 6.93 (dd, 1 H), 3.84 (m, 1 H).

Example 30

6-chloro-5-[4-(3-hydroxypropoxy)phenyl]-1H-indole-3-carboxylic acid

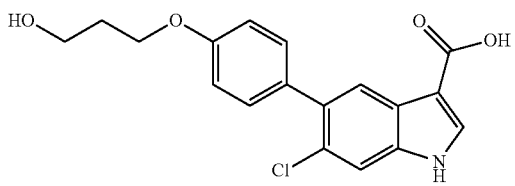 [SMILES: O=C(O)c1c[nH]c2cc(Cl)c(-c3ccc(OCCCO)cc3)cc12]

Step 1

6-chloro-5-[4-(3-hydroxypropoxy)phenyl]-1H-indole-3-carbaldehyde

To a solution of 3-[4-(5,5-dimethyl-1,3,2-dioxaborinan-2-yl)phenoxy]propan-1-ol (4.9 g, 18.6 mmol) in ethanol (25 ml) was added 5-bromo-6-chloro-1H-indole-3-carbaldehyde (4.0 g, 15 mmol) followed by toluene (50 ml) and 2 N aq. potassium carbonate (26.3 ml, 52.6 mmol). Nitrogen was bubbled though the solution for 15 min, then Pd(dppf)Cl₂ (0.46 g, 0.62 mol) was added and reaction heated to 100° C. An additional portion of 3-[4-(5,5-dimethyl-1,3,2-dioxaborinan-2-yl)phenoxy]propan-1-ol (1.0 g) in ethanol (4 ml) was added and heating continued for 30 min. The reaction was allowed to cool to room temperature and stirred for 3 days. The reaction was partitioned between water and EtOAc and stirred. The layers were separated and the organic layers were washed with water which resulted in a thick emulsion. The emulsion was filtered through celite to attempt to break the emulsion which had limited effect. Upon standing, emulsion was reduced. Layers were separated and organic washed with brine, dried over sodium sulfate, filtered and stripped. Residue was mostly dissolved in MeOH, filtered to remove solids then adsorbed onto silica gel then purified by silica gel chromatography (30-100% EtOAc/Heptane). The second peak was isolated to afford the title compound (2.2 g, 43%) as a yellow solid that was taken on to the next reaction without further purification.

MS (AP+) 330.2 (M+1)⁺. ¹H NMR (400 MHz, DMSO-d₆) δ 12.22 (br. s, 1 H), 9.94 (s, 1 H) 8.37 (d, 1 H), 8.02 (s, 1 H), 7.68 (s, 1 H), 7.34 (d, 2 H), 7.01 (d, 2 H), 4.57 (t, 1 H), 4.09 (t, 2 H), 3.59 (q, 2 H), 1.90 (quin, 2 H).

Step 2

6-chloro-5-[4-(3-hydroxypropoxy)phenyl]-1H-indole-3-carboxylic acid

To an ice cooled thin suspension of 6-chloro-5-[4-(3-hydroxypropoxy)phenyl]-1H-indole-3-carbaldehyde (2.2 g, 6.7 mmol) in a mixture of THF (60 ml) and t-BuOH (60 ml) was added 2-methyl-2-butene (22 mL, 210 mmol). Separately, sodium chlorite (5.6 g, 66.7 mmol) and sodium phosphate monohydrate (monobasic, 9.2 g, 66.7 mmol) were dissolved in water (50 mL) and added to the original solution via addition funnel over 30 min. The clear mixture was warmed to room temperature and stirred for 20 hours. The mixture was cooled to 0° C. and more 2-Me-2-butene (10 mL) was added, followed by slow addition of a solution of sodium chlorite (2.8 g) and sodium phosphate (monobasic and monohydrate, 4.6 g) in water (18 mL) then stirred at room temperature for 4 hrs. Methyl t-butyl ether (100 ml) and heptane (100 ml) were added and the organic phase was separated and washed with 0.3 M aqueous sodium hydroxide. The aqueous solution was acidified with 1 M HCl and extracted with a mixture of 150 ml of ethyl acetate and 50 ml of heptane. The extract was washed with brine, dried over sodium sulfate, and concentrated. The crude residue was dissolved in acetone and loaded onto silica gel and solvents were removed. The material absorbed on silica gel was placed on silica gel and flash column chromatography (40% to 70% acetone/heptanes) was used to provide 1.5 g of a tan solid. The solid was dissolved in MeOH at 60° C. Water (10 ml) was added dropwise until solids almost persisted. After 5 min, solids formed and the mixture was allowed to cool slowly and stirred for 2 days at room temperature. Solids were collected by vacuum filtration and rinsed with a 50% MeOH/Water solution then dried over a nitrogen ram for 1 hour then in a drying pistol for 2 hours to afford the title compound (1.23 g, 53%) as a crystalline white solid. Melting point: 209.3-209.6. MS (AP−) 344.1 (M−H)⁻. ¹H NMR (400 MHz, DMSO-d₆) δ 12.10 (s, 1 H), 11.92 (d, 1 H), 8.07 (d, 1 H), 7.93 (s, 1 H), 7.61 (s, 1 H), 7.34 (d, 2 H), 7.00 (d, 2 H), 4.56 (t, 1 H), 4.09 (t, 2 H), 3.59 (q, 2 H), 1.89 (quin, 2 H).

Example 31

6-Chloro-5-(4-ethoxyphenyl)-1H-indole-3-carboxylic acid

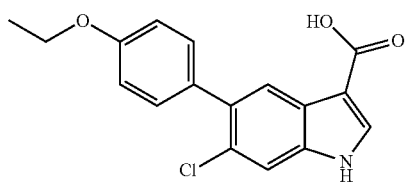 [SMILES: CCOc1ccc(-c2cc3c(C(=O)O)c[nH]c3cc2Cl)cc1]

Step 1

6-Chloro-5-(4-ethoxyphenyl)-1H-indole

A solution of 5-bromo-6-chloro-1H-indole (5.92 g, 25.7 mmol), sodium carbonate (5.45 g, 51.4 mmol) and (4-ethoxyphenyl)boronic acid (5.12 g, 30.8 mmol) in EtOH/water/toluene (30 mL, each) was degassed with N$_2$ for 5 minutes, treated with tetrakis(triphenylphosphine)palladium (1.8 g, 16.57 mmol) and degassed for an additional 5 minutes. The reaction mixture was heated to reflux under N$_2$ for 16 hours. The reaction mixture was cooled to room temperature, poured into dilute NH$_4$Cl solution (200 mL), and extracted with CH$_2$Cl$_2$ (3×100 mL). The combined organic layers were washed with brine (100 mL), dried over Na$_2$SO$_4$ and concentrated in vacuo. The crude material was purified by flash chromatography (9-25% EtOAc/petroleum ether) to afford the title compound (6.03 g, 86%) as a white solid. $^1$H NMR (400 MHz, CDCl$_3$) δ 8.07 (br, 1 H), 7.50 (s, 1 H), 7.43 (s, 1 H), 7.33 (d, 2 H), 7.15 (m, 1 H), 6.89 (d, 2 H), 6.46 (s, 1 H), 4.02 (q, J=7.00 Hz, 2 H), 1.36 (t, J=7.00 Hz, 3 H).

Step 2

2,2,2-Trichloro-1-(6-chloro-5-(4-ethoxyphenyl)-1H-indol-3-yl)ethanone

To a solution of 6-chloro-5-(4-ethoxyphenyl)-1H-indole (500.0 mg, 1.84 mmol) in anhydrous THF (5 mL) was added pyridine (436.0 mg, 5.52 mmol) and trichloroacetyl chloride (10 mL) at 0° C. under N$_2$. The reaction mixture was stirred at room temperature under N$_2$ for 12 hours. The mixture was poured into 0.5 N HCl (200 mL) and extracted with EtOAc (3×100 mL). The combined organic layers were washed with brine (100 mL), dried over Na$_2$SO$_4$ and concentrated in vacuo. The crude material was purified by flash chromatography (9-25% EtOAc/petroleum ether:EtOAc) to give the title compound (70.0 mg, 9%) as a green solid. $^1$H NMR (400 MHz, CDCl$_3$) δ 8.80 (br, 1 H), 8.40 (s, 1 H), 8.36 (d, J=3.2 Hz, 1 H), 7.59 (s, 1 H), 7.42 (d, 2H), 6.97 (d, 2 H), 4.12 (q, J=7.00 Hz, 2 H), 1.45 (t, J=7.00 Hz, 3 H).

Step 3

6-Chloro-5-(4-ethoxyphenyl)-1H-indole-3-carboxylic acid

To a solution of 2,2,2-trichloro-1-(6-chloro-5-(4-ethoxyphenyl)-1H-indol-3-yl)ethanone (70.0 mg, 0.17 mmol) in DME (1 mL) was added 1 N KOH (0.71 mmol, 0.71 mL). The reaction mixture was stirred at room temperature for 12 hours, and concentrated in vacuo. The crude material was diluted with water (5 mL), and acidified to pH 2.5 with 1 N HCl to form a white precipitate. The precipitate was filtered, washed with water (20 mL) and dried under vacuum to provide the title compound (37 mg, 70%) as an off-white solid.

MS (ES+) 315.9 (M+H)$^+$. $^1$H NMR (400 MHz, DMSO-d$_6$) δ 12.21 (br. s., 1H), 12.00 (s, 1H), 8.13 (d, J=2.80 Hz, 1H), 7.99 (s, 1H), 7.40 (d, J=8.80 Hz, 1H), 7.06 (d, J=8.80 Hz, 2H), 4.13 (q, J=6.80 Hz, 2H), 1.43 (t, J=6.80 Hz, 3H).

Example 32

6-Cyano-5-(4-methoxyphenyl)-1H-indole-3-carboxylic acid

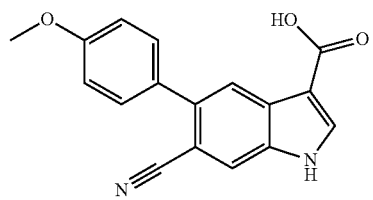 [SMILES: COc1ccc(-c2cc3c(C(=O)O)c[nH]c3cc2C#N)cc1]

Step 1

4'-Methoxy-5-methyl-4-nitro-biphenyl-2-carbonitrile

A mixture of 2-bromo-4-methyl-5-nitro-benzonitrile (522.0 mg, 2.17 mmol), 4-methoxyphenyl boronic acid (329.0 mg, 2.17 mmol) and 2 N aqueous potassium carbonate (6.56 mL, 13.1 mmol) in EtOH (6 mL) and toluene (3 mL) was degassed with N$_2$ for 5 minutes, treated with [1,1'-bis(diphenylphosphino)ferrocene]dichloropalladium(II) (180.0 mg, 0.22 mmol), and degassed with N$_2$ for an additional 5 minutes. The reaction mixture was sealed and heated to 80° C. for 3 hours. The reaction was cooled to room temperature and the layers were separated. The organic layer was filtered and the solids were air dried to give the title compound (145 mg). The filtrate was concentrated in vacuo and the residue was purified by flash chromatography (25-75% EtOAc/heptane) to give the title compound (337 mg). The two lots of the title compound were combined (482 mg, 83% yield). $^1$H NMR (400 MHz, DMSO-d$_6$) δ 8.59 (s, 1 H), 7.78 (s, 1 H), 7.63 (d, J=8.78 Hz, 2 H), 7.14 (d, J=8.59 Hz, 2 H), 3.85 (s, 3 H), 2.64 (s, 3 H).

Step 2

5-(4-Methoxy-phenyl)-1H-indole-6-carbonitrile

A mixture of 4'-methoxy-5-methyl-4-nitro-biphenyl-2-carbonitrile (118.0 mg, 0.44 mmol) and tris(dimethylamino)methane (128.0 mg, 0.88 mmol) in toluene (15 mL) was heated to reflux for 2 hours. The reaction mixture was concentrated in vacuo. The resulting residue was dissolved in EtOH (1 mL) and water (0.10 mL), and treated with iron powder (64.0 mg, 1.15 mmol), followed by concentrated HCl (28.0 mg, 0.29 mmol). The reaction mixture was heated to reflux for an additional 16 hours, and quenched with 1 N aqueous NaOH (0.288 mL). The solution was filtered through celite and rinsed with EtOH (10 mL). The filtrate was concentrated in vacuo to give the title compound (35 mg, 49% yield). MS (ES−) 247.1 (M−1)$^−$. $^1$H NMR (400 MHz, DMSO-d$_6$) δ 7.95 (s, 1 H), 7.68 (d, J=2.73 Hz, 1 H), 7.66 (s, 1 H), 7.48 (d, J=8.59 Hz, 2 H), 7.05 (d, J=8.59 Hz, 2 H), 6.58 (d, J=2.73 Hz, 1 H), 3.82 (s, 3 H).

Step 3

3-Formyl-5-(4-methoxy-phenyl)-1H-indole-6-carbonitrile

Phosphorous oxychloride (84.3 mg, 0.54 mmol) was added to DMF (1 mL) at 0° C. and the reaction mixture was stirred for 15 minutes. To this solution was added 5-(4-methoxyphenyl)-1H-indole-6-carbonitrile (150.0 mg, 0.60 mmol) in DMF (1 mL) and the reaction mixture was stirred at 40° C. for 1 hour. The reaction mixture was cooled to room temperature, treated with additional phosphorous oxychloride (84.3 mg, 0.54 mmol) and stirred at 45° C. for an additional hour. The reaction mixture was cooled to room temperature, and quenched with water (10 mL). The solution was concentrated in vacuo, and the residue was partitioned between water (10 mL) and EtOAc (10 mL). The layers were separated and the organic layer was concentrated in vacuo. The crude material was slurried in $CH_2Cl_2$, and the resulting solid was filtered and air dried to give the title compound (85 mg, 51% yield). MS (ES$^-$) 275.1 (M–1)$^-$. $^1$H NMR (400 MHz, DMSO-$d_6$) δ 12.63 (br. s., 1 H), 10.00 (s, 1 H), 8.58 (d, J=3.12 Hz, 1 H), 8.17 (s, 1 H), 8.10 (s, 1 H), 7.51 (d, J=8.59 Hz, 2 H), 7.09 (d, J=8.80 Hz, 2 H), 3.83 (s, 3 H).

Step 4

6-Cyano-5-(4-methoxyphenyl)-1H-indole-3-carboxylic acid

A solution of sodium chlorite (8.1 mg, 0.072 mmol) in water (2 mL) was added dropwise to a solution of 3-formyl-5-(4-methoxy-phenyl)-1H-indole-6-carbonitrile (50.0 mg, 0.18 mmol), sodium phosphate monohydrate (5.60 mg, 0.04 mmol) and 25% hydrogen peroxide (25.9 mg, 0.19 mmol) in MeCN (2 mL) and water (1 mL) at 0° C.

The reaction mixture was stirred at 0° C. for 30 minutes, and warmed to room temperature. Additional sodium chlorite (16.2 mg, 0.144 mmol) and MeCN (5 mL) were added, and the reaction mixture was stirred at room temperature for another 16 hours. The reaction was quenched with sodium sulfite (46.6 mg, 0.362 mmol) and acidified with concentrated HCl (1 mL) to form precipitates. The solid was filtered, washed with water (5 mL) and air dried to give the title compound (14 mg, 26% yield). MS (ES$^-$) 291.1 (M–1)$^-$. $^1$H NMR (400 MHz, DMSO-$d_6$) δ 12.35 (br. s., 1 H), 12.14 (br. s, 1 H), 8.29 (d, J=2.73 Hz, 1 H), 8.07 (s, 1 H), 8.04 (s, 1 H), 7.50 (d, J=8.20 Hz, 2 H), 7.08 (d, J=8.39 Hz, 2 H), 3.83 (s, 3 H).

Example 33

6-Chloro-5-(4-methoxy-phenyl)-1H-indole-3-carboxylic acid

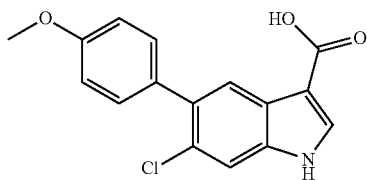

Step 1

6-Chloro-5-(4-methoxy-phenyl)-1H-indole

A mixture of 5-bromo-6-chloro-1H-indole (60.3 g, 261.6 mmol), 4-methoxyphenylboronic acid (54.8 g, 353 mmol), 4 N aqueous potassium carbonate (262 mL, 1.05 mol) in toluene (750 mL) and EtOH (250 mL) was degassed with $N_2$ for 35 minutes and treated with [1,1'-bis(diphenylphosphino)ferrocene]dichloropalladium(II) (6.41 g, 7.85 mmol). The reaction mixture was placed in a pre-heated oil bath at 105° C. and stirred for 1.5 hours. The reaction was removed from the oil bath, quickly cooled to room temperature and poured into EtOAc (2 L) and 0.5 N HCl (500 mL). The organic layer was separated, washed with 0.5 N NaOH (1×500 mL) followed by saturated brine (1×500 mL), dried over $MgSO_4$ and concentrated in vacuo to afford a black oil. The oil was passed through a pad of silica gel, eluting with 15% EtOAc/heptane. Product fractions were concentrated to afford 55.3 g gray solid. The solid was triturated in 1:1 ether/heptane (50 mL) and filtered to afford the title compound (25 g, 37% yield) as a cream-colored solid. MS (ES+) 258.5 (M+H)$^+$. $^1$H NMR (400 MHz, CDCl$_3$) δ 8.15 (br. s., 1 H), 7.58 (s, 1 H), 7.52 (s, 1 H), 7.42 (d, J=8.78 Hz, 2 H), 7.24 (t, J=2.68 Hz, 1 H), 6.98 (d, J=8.78 Hz, 2 H), 6.55 (br. s., 1 H), 3.88 (s, 3 H).

Step 2

6-Chloro-5-(4-methoxy-phenyl)-1H-indole-3-carbaldehyde

6-Chloro-5-(4-methoxy-phenyl)-1H-indole (25.0 g, 97 mmol), (chloromethylene)dimethyliminium chloride (18.8 g, 147 mmol) and MeCN (100 mL) were stirred at room temperature for 20 minutes. To the resulting bright yellow slurry was added 1 N NaOH (400 mL, 400 mmol) and water (400 mL). The reaction mixture was heated to 100° C. for 45 minutes, then cooled to 0° C. The slurry was filtered, and the collected solid was washed with water and air dried to afford the title compound as a yellow solid. MS (ES+) 286.5 (M+H)$^+$. $^1$H NMR (400 MHz, CDCl$_3$) δ 10.06 (s, 1 H), 8.74 (br. s., 1 H), 8.29 (s, 1 H), 7.87 (d, J=2.93 Hz, 1 H), 7.58 (s, 1 H), 7.42 (d, J=8.54 Hz, 2 H), 6.98 (d, J=8.54 Hz, 2 H), 3.88 (s, 3 H)

Step 3

6-Chloro-5-(4-methoxy-phenyl)-1H-indole-3-carboxylic acid

To a solution of 6-chloro-5-(4-methoxy-phenyl)-1H-indole-3-carbaldehyde (27.7 g, 97 mmol) in MeCN (400 mL), tert-butanol (400 mL) and 2-methyl-2-butene (400 mL, 3.76 mol) at 0° C. was added a solution of sodium chlorite (82.0 g, 970 mmol) and sodium phosphate monobasic hydrate (134.0 g, 970 mmol) in water (400 mL) dropwise over 20 minutes. The ice bath was removed and the mixture was stirred at room temperature. At the 16-hour and 20-hour time points, additional 2-methyl-2-butene (200 mL, 1.88 mol) was added, followed by solid sodium chlorite (82.0 g, 970 mmol) and solid sodium phosphate monobasic hydrate (134.0 g, 970 mmol). After a total of 22 hours, the reaction mixture was poured into a solution of saturated $NH_4Cl$ (800 mL) and water (200 mL), then extracted with EtOAc (4×500 mL). The combined organic layers were dried over $MgSO_4$, and concentrated in vacuo to afford 62 g of a mustard-colored semi-solid. This solid was triturated in $CHCl_3$ (70 mL), filtered and dried under high vacuum to afford 18.5 g pale yellow solid. The solid was stirred in EtOAc (50 mL) overnight at 55° C., then filtered hot and washed with room temperature EtOAc to afford the title compound (19.5 g, 63% for 2 steps) as a pale yellow solid. MS (ES+) 302.5 (M+H)$^+$. $^1$H NMR (500 MHz, DMSO-$d_6$) δ 12.10 (br. s., 1 H), 11.93 (br. s., 1 H), 8.07 (d, J=2.68 Hz, 1 H), 7.93 (s, 1 H), 7.62 (s, 1 H), 7.35 (d, J=8.54 Hz, 2 H), 7.01 (d, J=8.78 Hz, 2 H), 3.81 (s, 3 H).

Example 34

6-Fluoro-5-(4-methoxy-phenyl)-1H-indole-3-carboxylic acid

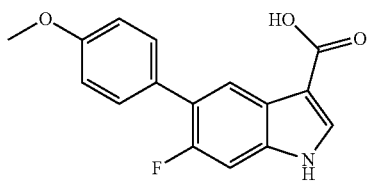

Step 1

6-Fluoro-5-(4-methoxy-phenyl)-1H-indole

A mixture of 5-bromo-6-fluoro-1H-indole (600.0 mg, 2.80 mmol), 4-methoxyphenyl boronic acid (426.0 mg, 2.80 mmol), 2 N aqueous potassium carbonate (8.49 mL, 16.98 mmol) in EtOH (8 mL) and toluene (3 mL) were degassed with $N_2$ for 5 minutes, treated with [1,1'-bis(diphenylphosphino)ferrocene]dichloropalladium(II) (180.0 mg, 0.22 mmol), and degassed for an additional 5 minutes. The reaction mixture was sealed and heated to 80° C. for 16 hours. The reaction was cooled to room temperature and the layers were separated. The organic layer was concentrated in vacuo and the crude material was purified by flash chromatography (25-75% EtOAc/heaptane) to give the title compound (147 mg, 22% yield). MS (ES+) 242.3 (M+1)+.

Step 2

6-Fluoro-5-(4-methoxy-phenyl)-1H-indole-3-carbaldehyde

Phosphorous oxychloride (185.0 mg, 1.20 mmol) was added to DMF (2 mL) at 0° C. and the reaction mixture was stirred for 15 minutes. To this solution was added 6-fluoro-5-(4-methoxy-phenyl)-1H-indole (147.0 mg, 0.61 mmol) in DMF (2 mL) and the reaction mixture was stirred at 95° C. for 20 minutes. The reaction mixture was cooled to room temperature, treated with 1 N aqueous NaOH (3 mL) and heated to 100° C. for 1 minute. The reaction mixture was cooled to room temperature and filtered. The collected solids were air dried to give the title compound (106 mg, 65% yield). MS (ES+) 270.2 (M+1)+.

Step 3

6-Fluoro-5-(4-methoxy-phenyl)-1H-indole-3-carboxylic acid

To a solution of 6-fluoro-5-(4-methoxy-phenyl)-1H-indole-3-carbaldehyde (106.0 mg, 0.39 mmol) in MeCN (5 mL) and water (3 mL) was added sodium phosphate monobasic hydrate (12.3 mg, 0.087 mmol), 25% hydrogen peroxide (56.3 mg, 0.41 mmol) and sodium chlorite (44.5 mg, 0.39 mmol). The reaction mixture was stirred for one hour at room temperature and additional MeCN (5 mL) and sodium chlorite (44.5 mg, 0.39 mmol) were added. The reaction mixture was heated to 50° C. for one hour, cooled to room temperature and stirred for another 16 hours. The reaction was quenched with sodium sulfite (405.0 mg, 3.15 mmol) and acidified with 3 N HCl (1 mL). The reaction solution was partially concentrated in vacuo, and extracted with EtOAc (10 mL). The organic layer was concentrated in vacuo and purified by reverse phase HPLC (Waters Sunfire C18 19×100, 5 µm; Mobile phase A: 0.05% TFA in water (v/v); Mobile phase B: 0.05% TFA in MeCN (v/v); Gradient: 80:20 A:B linear to 40:60 A:B in 8.5 min to 100% B to 9.0 min, hold at 100% B from 9.0 to 10.0 min. Flow: 25 mL/min) to give the title compound (6.8 mg, 6% yield). MS (ES+) 286.2 (M+1)+. Retention time=2.73 minutes (Waters Atlantis dC18 4.6×50, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 35

5-[4-(1-hydroxycyclobutyl)phenyl]-6-methyl-1H-indole-3-carboxylic acid

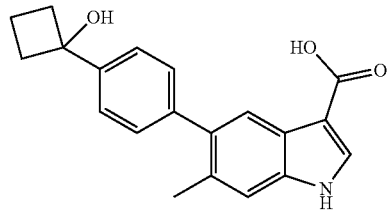 [SMILES: Cc1cc2[nH]cc(C(=O)O)c2cc1-c1ccc(C2(O)CCC2)cc1]

Step 1

5-[4-(1-hydroxycyclobutyl)phenyl]-6-methyl-1H-indole-3-carbaldehyde

A mixture of dicyclohexyl(2',6'-dimethoxybiphenyl-2-yl)phosphane (62.8 mg, 0.153 mmol), palladium acetate (13.7 mg, 0.061 mmol), tribasic potassium phosphate monohydrate (566 mg, 2.46 mmol), and methyl boronic acid (184 mg, 3.07 mmol) was sealed in a microwave tube and evacuated and backfilled with nitrogen three times. Deoxygenated 1,4-dioxane (1.5 mL) was added and the mixture was stirred vigorously at room temperature for one hour. A solution of 6-chloro-5-[4-(1-hydroxy-cyclobutyl)-phenyl]-1H-indole-3-carbaldehyde (400 mg, 1.23 mmol) in 1,4-dioxane (2.5 mL) was degassed with nitrogen for 10 minutes then added to the reaction mixture. The reaction mixture was heated at 120° C. for three hours under microwave irradiation, and then allowed to stir at room temperature for 12 hours. The reaction mixture was poured into saturated ammonium chloride solution (20 mL) and extracted with ethyl acetate (3×20 mL). The combined organic layers were dried over sodium sulfate, filtered and evaporated. Flash silica gel chromatography was performed on the crude product utilizing a solvent system of heptanes/ethyl acetate (9:1 to 1:1) to give the title compound. MS (ES+) 306.5 (M+H)+. 1H NMR (400 MHz, CD3OD) δ 9.86 (s, 1H), 8.06 (s, 1H), 7.95 (s, 1H), 7.55 (d, 2H), 7.38 (s, 1H), 7.36 (d, 2H), 2.61 (m, 2H), 2.39 (m, 2H), 2.34 (s, 3H), 2.05 (m, 1H), 1.75 (m, 1H).

Step 2

5-[4-(1-hydroxycyclobutyl)phenyl]-6-methyl-1H-indole-3-carboxylic acid

A partial suspension of 5-[4-(1-hydroxycyclobutyl)phenyl]-6-methyl-1H-indole-3-carbaldehyde (130 mg, 0.426 mmol) in tetrahydrofuran (3 mL) and tert-butanol (3 mL) was treated with 2-methyl-2-butene (2.27 mL, 21.4 mmol) followed by a solution of sodium chlorite (538 mg, 6.4 mmol) and sodium phosphate monobasic hydrate (904 mg, 6.5 mmol) in water (2 mL) via glass pipet at room temperature. The reaction mixture was stirred vigorously at room temperature for 62 hours, and was poured into half-diluted saturated aqueous ammonium chloride solution (50 mL). The product was extracted with ethyl acetate (3×60 mL), and the combined organic layers were dried over sodium sulfate, filtered and evaporated. The crude product was purified using reverse-phase chromatography to give the title compound. MS (ES−) 320.2 (M−H)⁻. $^1$H NMR (600 MHz, DMSO-$d_6$) δ 7.95 (d, J=3.1 Hz, 1H), 7.79 (s, 1H), 7.54 (d, J=8.0 Hz, 2H), 7.35 (s, 1H), 7.31 (d, J=8.0 Hz, 2H), 5.50 (s, 1H), 2.48-2.41 (m, 2H), 2.35-2.26 (m, 5H), 1.99-1.88 (m, 1H), 1.74-1.62 (m, 1H).

Example 36

6-chloro-5-[4-(1-hydroxy-2-methylpropan-2-yl)phenyl]-1H-indole-3-carboxylic acid

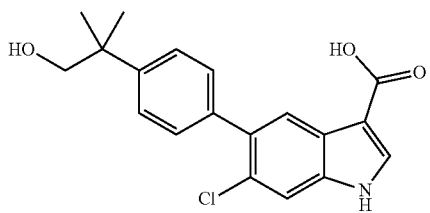 [SMILES: CC(C)(CO)c1ccc(-c2cc3c(C(=O)O)c[nH]c3cc2Cl)cc1]

Step 1

5-[4-(1-{[tert-butyl(dimethyl)silyl]oxy}-2-methylpropan-2-yl)phenyl]-6-chloro-1H-indole-3-carbaldehyde A mixture of 5,5,5',5'-tetramethyl-2,2'-bi-1,3,2-dioxaborinane (549 mg, 1.6 mmol), oven-dried potassium acetate (666 mg, 6.79 mmol), and [2-(4-bromophenyl)-2-methylpropoxy](tert-butyl)dimethylsilane (503 mg, 1.46 mmol) in 1,4-dioxane (4.88 mL) was degassed for 10 minutes, then treated with [1,1'-bis(diphenylphosphino)ferrocene]dichloropalladium (II) (100 mg, 0.137 mmol). The mixture was sealed in a microwave vial and heated to 110° C. in a microwave for 1 hour. The black reaction mixture was then diluted with heptane (50 mL) and filtered through a plug of silica gel, eluting with 4:1 heptane/ethyl acetate. The filtrate was evaporated in vacuo to give a dark semi solid (638 mg). The crude product was dissolved in toluene (4 mL). 2.38 mL of this solution was diluted with ethanol (1 mL) and treated with 2 M aqueous potassium carbonate solution (1.16 mL, 2 mmol), and 5-bromo-6-chloro-1H-indole-3-carbaldehyde (150 mg, 0.58 mmol). The mixture was degassed with nitrogen for 15 minutes, treated with [1,1'-bis(diphenylphosphino)ferrocene]dichloropalladium(II) (33.7 mg, 0.046 mmol) and heated in an oil bath at 100° C. for 3 hours. The reaction mixture was treated with an additional 0.35 mL of the boronate solution prepared above and [1,1'-bis(diphenylphosphino)ferrocene]dichloropalladium(II) (15 mg) and heated at 100° C. for an additional 3 hours. The cooled reaction mixture was poured into saturated aqueous ammonium chloride solution and extracted with ethyl acetate (3×50 mL). The combined organic layers were dried over sodium sulfate, filtered and evaporated to give a dark oil, which was directly purified using silica gel chromatography (100:0 to 6:4 heptane/ethyl acetate) to give the title compound as a white solid (130 mg, 50%). MS (ES−) 440.7 (M−H)⁻. $^1$H NMR (500 MHz, CDCl$_3$) δ 10.07 (s, 1H), 8.30 (s, 1H), 7.87 (d, J=2.7 Hz, 1H), 7.58 (s, 1H), 7.46-7.42 (m, 4 H), 3.59 (s, 2H), 1.37 (s, 6H), 0.88 (s, 9H), −0.02 (s, 6H).

Step 2

5-[4-(1-{[tert-butyl(dimethyl)silyl]oxy}-2-methylpropan-2-yl)phenyl]-6-chloro-1H-indole-3-carboxylic acid A solution of 5-[4-(1-{[tert-butyl(dimethyl)silyl]oxy}-2-methylpropan-2-yl)phenyl]-6-chloro-1H-indole-3-carbaldehyde (130 mg, 0.294 mmol) in tetrahydrofuran (2.5 mL) and tert-butanol (2.5 mL) was treated with 2-methyl-2-butene (2.19 mL, 20.6 mmol) followed by a solution of sodium chlorite (496 mg, 5.9 mmol) and sodium phosphate monobasic hydrate (811 mg, 5.9 mmol) in water (2.5 mL) via glass pipet at room temperature. The reaction mixture was stirred vigorously at room temperature for 15 hours, and was poured into saturated aqueous ammonium chloride solution (35 mL). The product was extracted with ethyl acetate (3×25 mL), and the combined organic layers were dried over sodium sulfate, filtered and evaporated to give the title compound as an amber oil. MS (ES−) 456.6 (M−H)⁻. $^1$H NMR (400 MHz, CD$_3$OD) δ 8.01 (s, 1H), 7.99 (d, J=1.2 Hz, 1H), 7.57 (s, 1H), 7.43 (d, 2H), 7.37 (d, 2H), 3.63 (s, 2H), 1.36 (s, 6H), 0.86 (s, 9H), −0.05 (s, 6H).

Step 3

6-chloro-5-[4-(1-hydroxy-2-methylpropan-2-yl)phenyl]-1H-indole-3-carboxylic acid A solution of 5-[4-(1-{[tert-butyl(dimethyl)silyl]oxy}-2-methylpropan-2-yl)phenyl]-6-chloro-1H-indole-3-carboxylic acid (76 mg, 0.17 mmol) in DMF (0.55 mL) was treated with solid cesium fluoride (507 mg, 3.32 mmol) and stirred at room temperature for one hour. The reaction mixture was then heated at 60° C. for two hours, then at 50° C. for two hours. The cooled reaction mixture was then poured into saturated ammonium chloride solution (20 mL) and extracted with ethyl acetate (3×20 mL). The combined organic layers were dried over sodium sulfate, filtered and evaporated to give the title compound as an orange oil. The crude product was dissolved in DMSO (1.8 mL) and 0.9 mL of this solution was purified using reverse-phase chromatography to give the title Compound. MS (ES−) 342.0 (M−H)⁻. Retention time: 1.61 min; Waters Xbridge dC18 5 µm 4.6×50 mm, 95% H$_2$O/5% MeCN linear to 5% H$_2$O/95% MeCN over 4.0 min, HOLD at 5% H$_2$O/95% MeCN to 5.0 min. (0.03% NH$_4$OH). Flow: 2.0 mL/min.

Example 37

6-chloro-5-(3,4-dimethoxyphenyl)-1H-indole-3-carboxylic acid

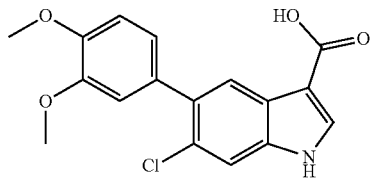 [SMILES: COc1ccc(-c2cc3c(C(=O)O)c[nH]c3cc2Cl)cc1OC]

Step 1 methyl 5-bromo-6-chloro-1H-indole-3-carboxylate

A mixture of 5-bromo-6-chloro-1H-indole (15.1 g, 65.5 mmol), tetrahydrofuran (100 mL), pyridine (18.4 mL, 229 mmol) and DMAP (808 mg, 6.55 mmol) was cooled to 0° C. and treated with trichloroacetyl chloride (22.1 mL, 197 mmol) dropwise over 30 minutes. The reaction mixture was stirred at room temperature for 64 hours then cooled to 10° C. Methanol (100 mL) was added dropwise to the reaction mixture over 10 minutes, producing a dark homogenous solution. Potassium carbonate (54.9 g, 393 mmol) was then added portion-wise and the ice bath was removed. Stirring was kept at a vigorous pace and allowed to continue for 2 hours, during which time the reaction turned dark green and produced an exotherm. The reaction was quenched slowly with 1 M HCl (until acidic pH was maintained) and diluted with ethyl acetate. The organic layer was washed with 1 M HCl. The aqueous layer was back-extracted twice with ethyl acetate. The combined organic layers were then washed carefully with saturated sodium bicarbonate solution followed by brine. The organic layer was dried over magnesium sulfate, filtered and concentrated in vacuo to provide the title compound as a brown solid (18.7 g, 99%).

MS (ES+): 288.0 (M+H)+. 1H NMR (500 MHz, DMSO-$d_6$) δ 8.24 (s, 1H), 8.16 (s, 1H), 7.72 (s, 1 H), 3.81 (s, 3H).

Step 2 methyl 6-chloro-5-(5,5-dimethyl-1,3,2-dioxaborinan-2-yl)-1H-indole-3-carboxylate A mixture of methyl 5-bromo-6-chloro-1H-indole-3-carboxylate (10.5 g, 36.39 mmol), 5,5,5',5'-tetramethyl-2,2'-bi-1,3,2-dioxaborinane (9.04 g, 40.0 mmol), and oven-dried potassium acetate (17.9 g, 182 mmol), in 1,4-dioxane (170 mL) was degassed with nitrogen for 10 minutes, then treated with [1,1'-bis(diphenylphosphino)ferrocene]dichloropalladium(II) (1.6 g, 2.18 mmol). The reaction mixture was heated at 110° C. with stirring for 3 h. The reaction was then cooled to room temperature and filtered through celite, eluting with ethyl acetate. The filtrate was concentrated in vacuo then placed on a pad of silica gel and eluted with ethyl acetate. The filtrate was evaporated in vacuo and loaded onto a silica gel column with a minimal amount of methylene chloride and eluted with ethyl acetate/heptane (1:4 to 1:1) to provide the title compound (5.6 g, 48%) as a tan solid. MS (ES+) 254.1 (M+H)+ (M=RB(OH)$_2$ on LCMS). 1H NMR (500 MHz, DMSO-$d_6$) δ 11.98 (br. s., 1 H), 8.29 (s, 1 H), 8.10 (d, J=2.93 Hz, 1 H), 7.46 (s, 1 H), 3.80 (s, 3 H), 3.79 (s, 4 H), 1.01 (s, 6 H).

Step 3 methyl 6-chloro-5-(3,4-dimethoxyphenyl)-1H-indole-3-carboxylate

A mixture of methyl 6-chloro-5-(5,5-dimethyl-1,3,2-dioxaborinan-2-yl)-1H-indole-3-carboxylate (100 mg, 0.31 mmol), 4-bromoveratrole (83 mg, 0.37 mmol), and aqueous potassium carbonate solution (2 M, 0.62 mL, 1.24 mmol) in toluene (1.8 mL) and ethanol (0.6 mL) was degassed with nitrogen for 5 minutes then treated with [1,1'-bis(diphenylphosphino)ferrocene]dichloropalladium(II) (13.8 mg, 0.016 mmol). The reaction mixture was heated to 110° C. for 2.5 h. The reaction was cooled to room temperature and poured into water and ethyl acetate. The layers were separated and the aqueous layer was back-extracted twice with ethyl acetate. The combined organic layers were dried over sodium sulfate, filtered, and concentrated in vacuo. Flash column chromatography was performed on the crude product using heptanes/ethyl acetate (4:1 to 1:1) to give the title compound (90 mg 84%). MS (ES+) 346.2 (M+H)+. 1H NMR (500 MHz, DMSO-$d_6$) δ 12.05 (br. s., 1 H), 8.17 (s, 1 H), 7.94 (s, 1 H), 7.64 (s, 1 H), 7.04 (d, J=8.29 Hz, 1 H), 6.98 (s, 1 H), 6.93 (d, J=8.29 Hz, 1 H), 3.81 (s, 3 H), 3.79 (s, 3 H), 3.78 (s, 3 H).

Step 4

6-chloro-5-(3,4-dimethoxyphenyl)-1H-indole-3-carboxylic acid

A solution of methyl 6-chloro-5-(3,4-dimethoxyphenyl)-1H-indole-3-carboxylate (75 mg, 0.22 mmol), methanol (2.2 mL), and aqueous sodium hydroxide (1 M, 0.75 mL, 0.75 mmol) was heated at 75° C. for 24 hours. The reaction was acidified with 1 M HCl to pH=2 then diluted with ethyl acetate. The aqueous layer was back-extracted twice with ethyl acetate. The combined organic layers were dried over sodium sulfate, filtered, and concentrated in vacuo to provide a crude solid. The crude product was dissolved in methylene chloride and methanol and silica gel was added. The solvent was removed in vacuo and the crude material adsorbed onto silica was loaded onto a column of silica gel and eluted with ethyl acetate (with 0.2% formic acid)/heptanes (1:1 to 1:0) to provide the title compound (17 mg, 24%) as a tan solid.

MS (ES+) 332.1 (M+H)+. 1H NMR (500 MHz, DMSO-$d_6$) δ 12.10 (br. s., 1H), 11.92 (br. s., 1H), 8.07 (d, J=2.93 Hz, 1H), 7.95 (s, 1H), 7.61 (s, 1H), 7.03 (d, J=8.29 Hz, 1H), 6.99 (d, J=1.71 Hz, 1H), 6.93 (dd, J=8.17, 1.83 Hz, 1H), 3.81 (s, 3H), 3.78 (s, 3H).

Example 38

(±)-6-chloro-5-(4-{[trans-2-hydroxycyclopentyl]oxy}phenyl)-1H-indole-3-carboxylic acid

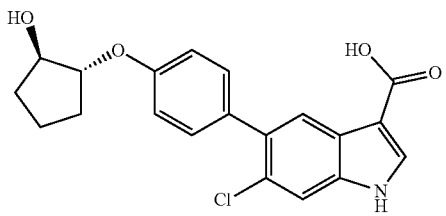 [SMILES: O=C(O)c1c[nH]c2cc(Cl)c(-c3ccc(O[C@@H]4CCC[C@H]4O)cc3)cc12]

Step 1

(±)-methyl 6-chloro-5-(4-{[trans-2-hydroxycyclopentyl]oxy}phenyl)-1H-indole-3-carboxylate A mixture of methyl 6-chloro-5-(5,5-dimethyl-1,3,2-dioxaborinan-2-yl)-1H-indole-3-carboxylate (92.6 mg, 0.288 mmol) and (±)-trans-2-(4-bromophenoxy)-cyclopentanol (37 mg, 0.14 mmol) in ethanol (0.2 mL), toluene (0.3 mL), and 2 M aqueous potassium carbonate (0.288 mL, 0.576 mmol) was sealed in a microwave vial and degassed with nitrogen for 10 minutes. [1,1'-bis(diphenylphosphino)ferrocene]dichloropalladium(II) (10.2 mg, 0.014 mmol) was added, and the reaction mixture was resealed and heated to 90° C. in an oil bath for 1 hour. The reaction mixture was cooled to room temperature and poured into 0.5 N HCl (10 mL). The product was extracted with ethyl acetate (3×10 mL), and the combined organic layers were dried over sodium sulfate, filtered and evaporated. The crude product was purified using silica gel chromatography (4:1 to 1:4 heptane/ethyl acetate) to give the title compound (49 mg, 88%) as a white solid. MS (ES−) 384.2 (M−H)−. $^1$H NMR (500 MHz, CD$_3$OD) δ 8.00 (s, 1H), 7.98 (s, 1H), 7.57 (s, 1H), 7.34 (d, J=8.5 Hz, 2H), 6.99 (d, J=8.5 Hz, 2H), 4.57 (br. s., 1H), 4.26 (br. s., 1H), 3.87 (s, 3H), 2.25-2.15 (m, 1H), 2.10-2.02 (m, 1H), 1.91-1.77 (m, 3H), 1.72-1.62 (m, 1H).

Step 2

(±)-6-chloro-5-(4-{[trans-2-hydroxycyclopentyl]oxy}phenyl)-1H-indole-3-carboxylic acid A solution of (±)-methyl 6-chloro-5-(4-{[trans-2-hydroxycyclopentyl]oxy}phenyl)-1H-indole-3-carboxylate (32 mg, 0.083 mmol) in methanol (0.845 mL) was treated with 1 N aqueous sodium hydroxide (0.291 mL, 0.291 mmol). The solution was heated to 75° C. in a sealed vial for 24 hours. The cooled reaction mixture was poured into 0.3 N HCl (7 mL) and extracted with ethyl acetate (3×5 mL). The combined organic layers were dried over sodium sulfate, filtered and evaporated. The crude product was purified using reverse-phase chromatography to give the title compound. MS (ES−) 370.0 (M−H)−. Retention time: 1.66 min; Waters Xbridge dC18 5 μm 4.6×50 mm, 95% H$_2$O/5% MeCN linear to 5% H$_2$O/95% MeCN over 4.0 min, HOLD at 5% H$_2$O/95% MeCN to 5.0 min. (0.03% NH$_4$OH). Flow: 2.0 ml/min.

Example 39

6-chloro-5-{4-[3-(morpholin-4-yl)propoxy]phenyl}-1H-indole-3-carboxylic acid

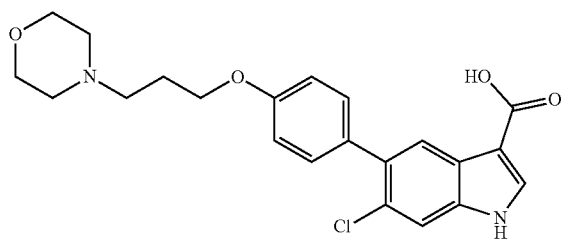 [SMILES: O=C(O)c1c[nH]c2cc(Cl)c(-c3ccc(OCCCN4CCOCC4)cc3)cc12]

Step 1 methyl 6-chloro-5-{4-[3-(morpholin-4-yl)propoxy]phenyl}-1H-indole-3-carboxylate

A mixture of methyl 6-chloro-5-(5,5-dimethyl-1,3,2-dioxaborinan-2-yl)-1H-indole-3-carboxylate (45 mg, 0.14 mmol), 4-[3-(4-bromophenoxy)-propyl]-morpholine (42 mg, 0.14 mmol) prepared using the procedure in Le Sann, C.; Huddleston, J.; Mann, J. Tetrahedron, 2007, 63, 12903-12911, and 2 M potassium carbonate solution (0.28 mL, 0.56 mmol) in toluene (0.9 mL) and ethanol (0.3 mL) was degassed with nitrogen for 5 minutes then treated with [1,1'-bis(diphenylphosphino)ferrocene]dichloropalladium(II) (6.0 mg, 0.007 mmol). The reaction vessel was sealed and heated at 110° C. for 2.5 h. The cooled reaction mixture was poured into water and ethyl acetate. The layers were separated and the aqueous layer was back-extracted twice with ethyl acetate. The combined organic layers were dried over sodium sulfate, filtered, and concentrated in vacuo. The crude product was purified using flash column chromatography eluting with heptanes/ethyl acetate (4:1 to 0:1) and ethyl acetate/methanol (9:1) to give the title compound (24 mg, 40%). MS (ES+) 429.2 (M+H)$^+$. $^1$H NMR (400 MHz, CD$_3$OD) δ 8.37 (br. s., 1H), 7.98 (s, 1H), 7.95 (s, 1H), 7.55 (s, 1H), 7.33 (d, J=8.59 Hz, 2H), 6.97 (d, J=8.78 Hz, 2H), 4.11 (t, J=5.95 Hz, 2H), 3.84 (s, 3H), 3.79 (t, J=4.69 Hz, 4H), 2.89-2.97 (m, 2H), 2.86 (m, 4H), 2.11 (dt, J=15.42, 5.86 Hz, 2H).

Step 2

6-chloro-5-{4-[3-(morpholin-4-yl)propoxy]phenyl}-1H-indole-3-carboxylic acid

A solution of methyl 6-chloro-5-{4-[3-(morpholin-4-yl)propoxy]phenyl}-1H-indole-3-carboxylate (24 mg, 0.056 mmol) in methanol (0.5 mL) and 1 M sodium hydroxide (0.17 mL, 0.17 mmol) was heated at 75° C. for 24 hours. The reaction was acidified with 1 M HCl to pH=2 then diluted with ethyl acetate. The layers were separated and the aqueous layer was back-extracted twice with ethyl acetate. The combined organic layers were dried over sodium sulfate, filtered, and concentrated in vacuo. The crude product was purified using reverse-phase chromatography to give the title compound as the formic acid salt. MS (ES+) 415.129 (M+H)$^+$ Retention time: 2.2 min; Waters Atlantis dC18 5 μm 4.6×50 mm, 95% H$_2$O/5% MeCN linear to 5% H$_2$O/95% MeCN over 4.0 min, HOLD at 5% H$_2$O/95% MeCN to 5.0 min. (0.05% TFA) Flow: 2.0 mL/min.

Example 40

6-chloro-5-[4-(1-hydroxycyclobutyl)-2-methylphenyl]-1H-indole-3-carboxylic acid

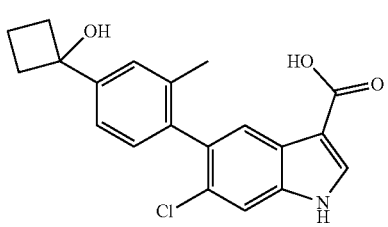 [SMILES: Cc1cc(C2(O)CCC2)ccc1-c1cc2c(C(=O)O)c[nH]c2cc1Cl]

Step 1

1-(4-bromo-3-methylphenyl)cyclobutanol

To a solution of 2-bromo-4-iodo-1-methylbenzene (0.40 mL, 2.8 mmol) in tetrahydrofuran (5 mL) at −78° C. was added n-butyl lithium (2.5 M in hexane, 1.33 mL, 3.33 mmol) dropwise over 15 minutes. The reaction mixture was stirred at −78° C. for 30 minutes, then treated with neat cyclobutanone (0.21 mL, 2.8 mmol) dropwise over 10 minutes. The reaction mixture was stirred at −78° C. for an additional 1.5 hours, then was quenched with saturated aqueous ammonium chloride solution and extracted with ethyl acetate (2×). The combined organic layers were dried over magnesium sulfate, filtered and concentrated in vacuo to afford 800 mg yellow oil, which was purified by flash chromatography (40 g silica, 0-100% ethyl acetate/heptane, 17 column volumes). Product fractions were combined and concentrated in vacuo to afford the title compound as a pale pink oil (536 mg, 80% yield). GCMS: 240/242 (m/z). $^1$H NMR (500 MHz, CDCl$_3$) δ 7.51 (d, J=8.29 Hz, 1 H), 7.37 (d, J=2.44 Hz, 1 H), 7.17 (dd, J=8.29, 2.20 Hz, 1 H), 2.45-2.56 (m, 3 H), 2.43 (s, 3 H), 2.34 (m, 2 H), 1.96-2.06 (m, 1 H), 1.64-1.74 (m, 1 H).

Step 2 methyl 6-chloro-5-[4-(1-hydroxycyclobutyl)-2-methylphenyl]-1H-indole-3-carboxylate A mixture of methyl 6-chloro-5-(5,5-dimethyl-1,3,2-dioxaborinan-2-yl)-1H-indole-3-carboxylate (90 mg, 0.28 mmol), 1-(4-bromo-3-methylphenyl)cyclobutanol (68 mg, 0.28 mmol), 4 M aqueous potassium carbonate (0.28 mL, 1.12 mmol), toluene (3 mL), and ethanol (1 mL) was sparged with nitrogen for 10 minutes, then treated with [1,1'-bis(diphenylphosphino)ferrocene]dichloropalladium(II) dichloromethane adduct (11 mg, 0.013 mmol). The reaction mixture was placed in a pre-heated oil bath at 105° C. and stirred. After 2 hours the reaction was cooled to room temperature, diluted with ethyl acetate, washed with water and saturated brine, dried over magnesium sulfate, filtered and concentrated in vacuo to afford 150 mg brown solid, which was purified by flash chromatography (0:100 to 70:30 ethyl acetate/heptane gradient). Product fractions were combined and concentrated in vacuo to afford the title compound as a colorless solid (65 mg, 63% yield). MS (ES−) 368.2 (M−H)−. $^1$H NMR (400 MHz, CDCl$_3$) δ 8.85 (br s, 1 H) 7.99 (s, 1 H) 7.93 (d, J=2.93 Hz, 1 H) 7.52 (s, 1 H) 7.33-7.43 (m, 2 H) 7.20 (d, J=7.81 Hz, 1 H) 3.87 (s, 3 H) 2.58-2.69 (m, 2 H) 2.34-2.45 (m, 2 H) 2.14 (s, 3 H) 2.04-2.11 (m, 1 H) 1.69-1.81 (m, 1 H).

Step 3

6-chloro-5-[4-(1-hydroxycyclobutyl)-2-methylphenyl]-1H-indole-3-carboxylic acid Methyl 6-chloro-5-[4-(1-hydroxycyclobutyl)-2-methylphenyl]-1H-indole-3-carboxylate (65 mg, 0.18 mmol) was dissolved in MeOH (3 mL) and 1 N aqueous NaOH (1 mL, 1 mmol). The mixture was stirred at 75° C. for 16 hours, was cooled to room temperature and then treated with Aldrich Amberjet 1200H acidic resin (~1 g). The mixture was stirred for 5 minutes until a pH of 3 was obtained. The resin was filtered and washed with methanol and the filtrate was concentrated in vacuo to afford 60 mg colorless solid, which was purified by reversed-phase HPLC (retention time: 1.83 min; Column: Xbridge C18 5 µm 4.6×50 µm; Mobile phase A: 0.03% NH$_4$OH in water (v/v); Mobile phase B: 0.03% NH$_4$OH in acetonitrile (v/v); Gradient: 95.0% H$_2$O/5.0% MeCN linear to 5% H$_2$O/95% MeCN in 5 min, Flow: 25 mL/min.) to afford the title compound (36.6 mg, 58% yield). MS (ES−) 354.265 (M−H)−.

Example 41

6-chloro-5-[4-(1-hydroxycyclobutyl)-3-methylphenyl]-1H-indole-3-carboxylic acid

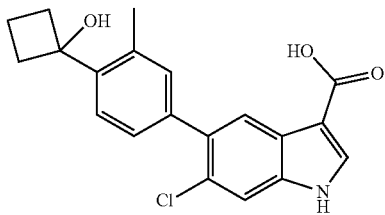 [SMILES: Cc1cc(-c2cc3c(C(=O)O)c[nH]c3cc2Cl)ccc1C1(O)CCC1]

Step 1

1-(4-bromo-2-methylphenyl)cyclobutanol

To a solution of 4-bromo-1-iodo-2-methylbenzene (0.24 mL, 1.6 mmol) in tetrahydrofuran (5 mL) at −78° C. was added n-butyl lithium (2.5 M in hexane, 0.8 mL, 2.0 mmol) dropwise over 15 minutes. The reaction mixture was stirred at −78° C. for 30 minutes, treated with neat cyclobutanone (0.12 mL, 1.6 mmol) dropwise over 10 minutes and stirred at −78° C. for an additional 1.5 hours. The reaction was quenched with saturated aqueous ammonium chloride solution, warmed to room temperature and extracted with ethyl acetate (2×). The combined organic layers were dried over magnesium sulfate, filtered and concentrated in vacuo to afford 500 mg yellow semi-solid, which was purified by flash chromatography (12 g silica, 0-50% ethyl acetate/heptane, 18 column volumes). Product fractions were combined and concentrated in vacuo to afford the title compound as a colorless waxy solid (290 mg, 73% yield). GCMS 240/242 (M)+; $^1$H NMR (400 MHz, CDCl$_3$) δ 7.23-7.31 (m, 2 H), 7.11 (d, J=8.20 Hz, 1 H), 2.55-2.64 (m, 2 H), 2.28-2.38 (m, 5 H), 2.07-2.20 (m, 1 H), 1.93 (s, 1 H), 1.62-1.74 (m, 1 H).

Step 2 methyl 6-chloro-5-[4-(1-hydroxycyclobutyl)-3-methylphenyl]-1H-indole-3-carboxylate A mixture of methyl 6-chloro-5-(5,5-dimethyl-1,3,2-dioxaborinan-2-yl)-1H-indole-3-carboxylate (81 mg, 0.25 mmol), 1-(4-bromo-2-methylphenyl)cyclobutanol (61 mg, 0.25 mmol), 4 M aqueous potassium carbonate (0.51 mL, 1 mmol), toluene (3 mL), and ethanol (1 mL) was sparged with nitrogen for 10 minutes, then treated with [1,1'-bis(diphenylphosphino)ferrocene]dichloropalladium(II) dichloromethane adduct (10 mg, 0.012 mmol). The reaction mixture was placed in a pre-heated oil bath at 105° C. and stirred. After 2 hours the reaction was cooled to room temperature, diluted with ethyl acetate, washed with water and saturated brine, dried over magnesium sulfate, filtered and concentrated in vacuo to afford 113 mg brown foam. The foam was dissolved in chloroform and a precipitate formed, which was collected by filtration to afford the title compound as a beige solid (44 mg, 47% yield).

MS (ES−) 368.2 (M−H)⁻. ¹H NMR (500 MHz, CD₃OD) δ 8.00 (s, 1H), 7.97 (s, 1H), 7.58 (s, 1H), 7.40 (d, J=7.56 Hz, 1H), 7.19-7.27 (m, 2H), 3.87 (s, 3H), 2.69-2.79 (m, 2H), 2.39-2.51 (m, 5H), 2.11-2.23 (m, 1H), 1.69-1.81 (m, 1H).

Step 3

6-chloro-5-[4-(1-hydroxycyclobutyl)-3-methylphenyl]-1H-indole-3-carboxylic acid

Methyl 6-chloro-5-[4-(1-hydroxycyclobutyl)-3-methylphenyl]-1H-indole-3-carboxylate (44 mg, 0.12 mmol) was dissolved in methanol (3 mL) and 1 N aqueous sodium hydroxide (1 mL, 1 mmol), and the mixture was stirred at 75° C. for 41 hours. The mixture was cooled to room temperature and treated with Aldrich Amberjet 1200H acidic resin (~1 g), then stirred for 5 minutes until a pH of 3 was obtained. The resin was filtered and washed with methanol and the filtrate was concentrated in vacuo to afford 39 mg colorless solid, which was purified by reversed-phase HPLC to afford the title compound (36.6 mg, 58% yield). MS (ES−) 354.265 (M−H)⁻. retention time=2.79 min; Column: Waters Atlantis dC18 4.6×50 mm, 5 μm; Modifier: TFA 0.05%; Gradient: 95% H₂O/5% MeCN linear to 5% H₂O/95% MeCN over 4.0 min, HOLD at 5% H₂O/95% MeCN to 5.0 min; Flow: 2.0 mL/min Example 42

6-chloro-5-[3-fluoro-4-(1-hydroxycyclobutyl)phenyl]-1H-indole-3-carboxylic acid

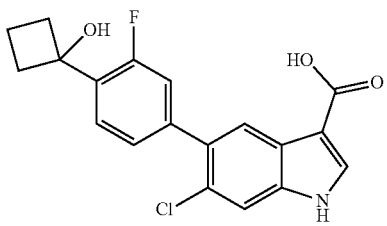 [SMILES: O=C(O)c1c[nH]c2cc(Cl)c(-c3ccc(C4(O)CCC4)c(F)c3)cc12]

Step 1

1-(4-bromo-2-fluorophenyl)cyclobutanol

To a solution of 4-bromo-2-fluoro-1-iodobenzene (500 mg, 1.66 mmol) in tetrahydrofuran (5 mL) at −78° C. was added n-butyl lithium (2.5 M in hexane, 0.8 mL, 0.8 mmol) dropwise over 15 minutes. The reaction mixture was stirred at −78° C. for 30 minutes, treated with neat cyclobutanone (0.12 mL, 1.66 mmol) dropwise over 10 minutes, and stirred at −78° C. for an additional 1.5 hours. The reaction was quenched with saturated aqueous NH₄Cl, warmed to room temperature and extracted with ethyl acetate (2×). The combined organic layers were dried over magnesium sulfate, filtered and concentrated in vacuo to afford 300 mg yellow oil, which was purified by silica gel chromatography (12 g silica, 0-50% ethyl acetate/heptane, 21 column volumes). Product fractions were combined and concentrated in vacuo to afford the title compound as a colorless oil (215 mg, 53% yield).

GCMS 244/246. (m/z)¹H NMR (500 MHz, CDCl₃) δ 7.20-7.31 (m, 3H), 2.56-2.66 (m, 2H), 2.40-2.55 (m, 1H), 2.31-2.40 (m, 2H), 2.14 (m, 1H), 1.75 (m, 1H).

Step 2 methyl 6-chloro-5-[3-fluoro-4-(1-hydroxycyclobutyl)phenyl]-1H-indole-3-carboxylate A mixture of methyl 6-chloro-5-(5,5-dimethyl-1,3,2-dioxaborinan-2-yl)-1H-indole-3-carboxylate (75 mg, 0.23 mmol), 1-(4-bromo-2-fluorophenyl)cyclobutanol (57 mg, 0.23 mmol), 4 M aqueous potassium carbonate (0.47 mL, 0.9 mmol), toluene (3 mL), and ethanol (1 mL) was sparged with nitrogen for 10 minutes, then treated with [1,1'-bis(diphenylphosphino)ferrocene]dichloropalladium(II) dichloromethane adduct (9 mg, 0.011 mmol). The reaction mixture was placed in a pre-heated oil bath at 105° C. and stirred for 2 hours. The reaction was cooled to room temperature, diluted with ethyl acetate, washed with water and saturated brine (1× each), dried over magnesium sulfate, filtered and concentrated in vacuo to afford a brown semi-solid, which was purified by flash chromatography (12 g silica, 10-50% ethyl acetate/heptane, 21 column volumes). The product fractions were combined and concentrated in vacuo to afford the title compound as a colorless solid (49 mg, 56% yield). MS (ES−) 372.2 (M−H)⁻. ¹H NMR (400 MHz, CDCl₃) δ 8.59 (s, 1 H), 8.10 (s, 1 H), 7.94 (d, J=2.93 Hz, 1 H), 7.54 (s, 1 H), 7.38-7.44 (m, 1 H), 7.18-7.28 (m, 2 H), 3.89 (s, 3 H), 2.66-2.77 (m, 2 H), 2.42 (m, 2 H), 2.11-2.22 (m, 1 H), 1.74-1.86 (m, 1 H).

Step 3

6-chloro-5-[3-fluoro-4-(1-hydroxycyclobutyl)phenyl]-1H-indole-3-carboxylic acid

Methyl 6-chloro-5-[3-fluoro-4-(1-hydroxycyclobutyl)phenyl]-1H-indole-3-carboxylate (49 mg, 0.13 mmol) was dissolved in MeOH (3 mL) and 1 N NaOH (1 mL, 1 mmol), and the mixture was stirred at 75° C. for 41 hours. The mixture was cooled to room temperature and treated with Aldrich Amberjet 1200H acidic resin (~1 g), then stirred for 5 minutes until a pH of 3 was obtained. The resin was filtered and washed with methanol and the filtrate was concentrated in vacuo to afford 50 mg colorless solid, which was purified by reversed-phase HPLC to afford the title compound (37 mg, 58% yield). MS (ES−) 358.1 (M−H)⁻; retention time=2.71 min; Column: Waters Atlantis dC18 4.6×50 mm, 5 μm; Modifier: TFA 0.05%; Gradient: 95% H₂O/5% MeCN linear to 5% H₂O/95% MeCN over 4.0 min, HOLD at 5% H₂O/95% MeCN to 5.0 min; Flow: 2.0 mL/min.

Example 43

5-(biphenyl-4-yl)-6-chloro-1H-indole-3-carboxylic acid

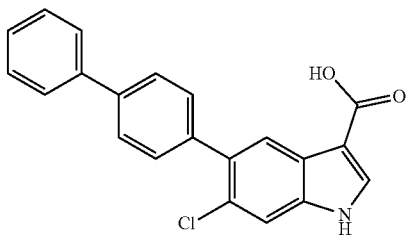 [SMILES: O=C(O)c1c[nH]c2cc(Cl)c(-c3ccc(-c4ccccc4)cc3)cc12]

Step 1 methyl 5-(biphenyl-4-yl)-6-chloro-1H-indole-3-carboxylate

A mixture of methyl 5-bromo-6-chloro-1H-indole-3-carboxylate (150 mg, 0.52 mmol), 4-biphenylboronic acid (113 mg, 0.57 mmol) and 2M aqueous potassium carbonate (2M, 1.04 mL, 2.08 mmol) in toluene (3.0 mL) and ethanol (1.0 mL) was degassed with nitrogen for 10 minutes. The reaction mixture was then treated with [1,1'-bis(diphenylphosphino)ferrocene]dichloropalladium(II) (20.0 mg, 0.026 mmol) and heated at 110° C. for 2 h in a sealed reaction vessel, which caused the reaction to appear burnt orange. The reaction mixture was cooled to room temperature and poured into ethyl acetate and water. The layers were separated and the aqueous layer was back-extracted with ethyl acetate. The combined organic layers were washed with brine, dried over sodium sulfate, filtered and concentrated in vacuo. The material was then dissolved in ethyl acetate and methanol then silica gel was added. The solvent was removed and the crude material adsorbed onto silica gel was added to a column of silica gel and eluted with ethyl acetate/heptanes (1:4 to 1:1) to give the desired product as a tan solid 61 mg (35% yield). MS (ES+) 362.5 (M+H)$^+$. $^1$H NMR (400 MHz, CDCl$_3$) δ 8.53 (br. s., 1 H), 8.17 (s, 1H), 7.94 (d, J=2.15 Hz, 1H), 7.61-7.72 (m, 4H), 7.57 (d, J=6.05 Hz, 2H), 7.45 (t, J=7.61 Hz, 2H), 7.31-7.40 (m, 1H), 3.89 (s, 3H).

Step 2

5-(biphenyl-4-yl)-6-chloro-1H-indole-3-carboxylic acid

A solution of methyl 5-(biphenyl-4-yl)-6-chloro-1H-indole-3-carboxylate (50 mg, 0.14 mmol) in methanol (1.5 mL) and sodium hydroxide (1 M, 0.50 mmol, 0.50 mL) was stirred at 75° C. for 24 hours. The cooled reaction mixture was neutralized to an acidic pH with 1M HCl and extracted twice with ethyl acetate. The combined organic layers were dried over sodium sulfate, filtered, and concentrated in vacuo. Methylene chloride was then added and solid precipitated. The slurry was stirred for 30 minutes then filtered and washed with methylene chloride and a small amount of ethyl acetate. The solids were dried in vacuo to provide the desired product as a tan solid (17 mg, 35% yield). MS (ES+) 348.1 (M+H)$^+$. $^1$H NMR (500 MHz, DMSO-d$_6$) δ 12.14 (br. s., 1H), 11.98 (br. s., 1H), 8.10 (d, J=2.93 Hz, 1H), 8.01 (s, 1H), 7.75 (t, J=8.42 Hz, 4H), 7.67 (s, 1H), 7.54 (d, J=8.05 Hz, 2H), 7.50 (t, J=7.56 Hz, 2H), 7.32-7.45 (m, 1H).

Example 44

6-chloro-5-(2-fluoro-4-methoxyphenyl)-1H-indole-3-carboxylic acid

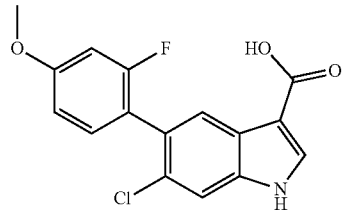 [SMILES: COc1ccc(-c2cc3c(C(=O)O)c[nH]c3cc2Cl)c(F)c1]

Step 1 methyl 6-chloro-5-(2-fluoro-4-methoxyphenyl)-1H-indole-3-carboxylate

A mixture of methyl 5-bromo-6-chloro-1H-indole-3-carboxylate (150 mg, 0.52 mmol), (3-fluoro-4-methoxyphenyl)boronic acid (93 mg, 0.55 mmol) and aqueous 2M potassium carbonate (2M, 1.04 mL, 2.08 mmol) in toluene (3.0 mL) and ethanol (1.0 mL) was degassed with nitrogen for 10 minutes then treated with [1,1'-bis(diphenylphosphino)ferrocene]dichloropalladium(II) (20.0 mg, 0.026 mmol). The reaction mixture was then heated at 110° C. for 2 h in a sealed reaction vessel, which caused the reaction mixture to appear burnt orange. The cooled reaction mixture was poured into ethyl acetate and water. The layers were separated and the aqueous layer was back-extracted with ethyl acetate. The combined organic layers were washed with brine, dried over sodium sulfate, filtered and concentrated in vacuo. The material was then dissolved in ethyl acetate and methanol then silica gel was added. The solvent was removed and the crude material adsorbed onto silica gel was added to a column of silica gel and eluted with ethyl acetate/heptane (1:4 to 1:1) to provide the desired product (55 mg, 32% yield) as a tan solid. MS (ES+) 334.5 (M+H)$^+$. $^1$H NMR (400 MHz, DMSO-d$_6$) δ 12.07 (br. s., 1 H), 8.15 (s, 1 H), 7.86 (s, 1 H), 7.63 (s, 1 H), 7.26 (t, J=8.69 Hz, 1 H), 6.90 (dd, J=11.91, 2.15 Hz, 1 H), 6.85 (dd, J=8.49, 2.24 Hz, 1 H), 3.80 (s, 3 H), 3.76 (s, 3 H).

Step 2

6-chloro-5-(2-fluoro-4-methoxyphenyl)-1H-indole-3-carboxylic acid

A mixture of methyl 6-chloro-5-(2-fluoro-4-methoxyphenyl)-1H-indole-3-carboxylate (50 mg, 0.15 mmol) in methanol (1.5 mL) and aqueous 1M sodium hydroxide (1 M, 0.50 mmol, 0.50 mL) was heated at 75° C. for 24 hours. The reaction was then acidified with 1M HCl to pH=2 and diluted with ethyl acetate. The layers were separated and the aqueous layer was back-extracted twice with ethyl acetate. The combined organic layers were dried over sodium sulfate, filtered, and concentrated in vacuo to provide a crude solid. A small amount of methylene chloride was added and the crude material slurried for 5 minutes. The solid was then filtered and washed with ethyl acetate to provide the title compound (13 mg, 27% yield).

MS (ES+) 320.0 (M+H)$^+$. $^1$H NMR (500 MHz, DMSO-d$_6$) δ 12.12 (br. s., 1 H), 11.98 (br. s., 1 H), 8.09 (d, J=2.68 Hz, 1 H), 7.91 (s, 1 H), 7.64 (s, 1 H), 7.29 (t, J=8.54 Hz, 1 H), 6.93 (dd, J=11.95, 1.95 Hz, 1 H), 6.88 (dd, J=8.42, 2.07 Hz, 1 H), 3.83 (s, 3 H).

Example 45

6-chloro-5-{4-[1-(methylsulfonyl)azetidin-2-yl]phenyl}-1H-indole-3-carboxylic acid

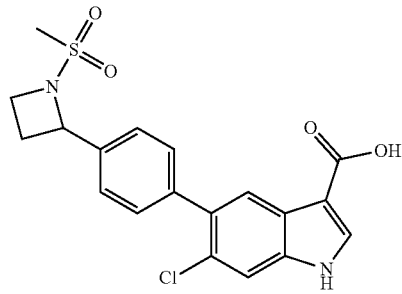 [SMILES: CS(=O)(=O)N1CCC1c1ccc(-c2cc3c(C(=O)O)c[nH]c3cc2Cl)cc1]

181

Step 1

2-(4-bromophenyl)-1-(methylsulfonyl)azetidine

To a mixture of 2-(4-bromophenyl)azetidine (200 mg, 0.808 mmol) and triethylamine (98 mg, 0.97 mmol) in anhydrous dichloromethane (6 mL) was added methanesulfonyl chloride (111 mg, 0.97 mmol). The mixture was stirred at rt for 5 hours. The mixture was poured into ethyl acetate and washed with water. The organic phase was dried over sodium sulfate, filtered, concentrated in vacuo to give the title compound (200 mg, 85% yield) as a yellow oil. $^1$H NMR (400 MHz, CDCl$_3$): δ7.50 (d, 2 H), 7.25 (d, 2 H), 5.30-5.20 (m, 1 H), 420-4.00 (m, 2 H), 3.63 (s, 3 H), 2.70 (m, 1 H), 2.15 (m, 1 H).

Step 2 methyl 6-chloro-5-{4-[1-(methylsulfonyl)azetidin-2-yl]phenyl}-1H-indole-3-carboxylate A mixture of methyl 6-chloro-5-(5,5-dimethyl-1,3,2-dioxaborinan-2-yl)-1H-indole-3-carboxylate (100 mg, 0.311 mmol), 2-(4-bromophenyl)-1-(methylsulfonyl)azetidine (108.2 mg, 0.373 mmol), 2.0 M potassium carbonate solution (0.5 mL, 1.0 mmol), and Pd(dppf)Cl$_2$ (30 mg, 0.03 mmol) in toluene/ethanol (1.44 mL/0.48 mL) was stirred at 110° C. for 2.5 hours. TLC (petroleum ether/ethyl acetate=3:1) showed that the reaction was complete. The mixture was poured into ethyl acetate and washed with water. The organic phase was dried over sodium sulfate, filtered, and concentrated to give a residue, which was purified by prep-TLC to give the title compound (80 mg, 62% yield) as a white solid. $^1$H NMR (400 MHz, DMSO-d$_6$): δ 12.30-12.10 (s, 1 H), 8.2 (s, 1 H), 7.92 (s, 1 H), 7.65 (s, 1 H), 7.55 (d, 2 H), 7.45 (d, 2 H), 5.35 (m, 1 H), 4.32 (m, 1 H), 4.0 (m, 1 H), 3.75 (s, 3 H), 3.15 (m, 2 H), 3.05 (s, 3 H).

Step 3

6-chloro-5-{4-[1-(methylsulfonyl)azetidin-2-yl]phenyl}-1H-indole-3-carboxylic acid To a solution of methyl 6-chloro-5-{4-[1-(methylsulfonyl)azetidin-2-yl]phenyl}-1H-indole-3-carboxylate (80 mg, 0.22 mmol) in methanol (8 mL) was added 1.0 M aq. NaOH (2.0 mL, 2.0 mmol). The mixture was stirred at 70° C. for 24 hours. The mixture was adjusted to pH 7 and purified by prep-HPLC to give the title compound (20 mg, 13% yield) as a white solid. MS (ES+) 445.0 (M+CH$_3$CN)$^+$. $^1$H NMR (400 MHz, DMSO-d$_6$): δ 8.05 (s, 1 H), 7.95 (s, 1 H), 7.65 (s, 1 H), 7.50-7.30 (m, 4 H), 4.70 (m, 1 H), 3.10 (m, 2 H), 2.89 (s, 3 H), 1.90-1.80 (m, 2 H).

182

Example 46

5-[4-(1-acetylazetidin-2-yl)phenyl]-6-chloro-1H-indole-3-carboxylic acid

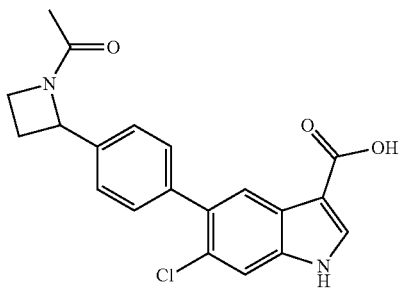 [SMILES: CC(=O)N1CCC1c1ccc(-c2cc3c(C(=O)O)c[nH]c3cc2Cl)cc1]

Step 1

1-[2-(4-bromophenyl)azetidin-1-yl]ethanone

To a mixture of 2-(4-bromophenyl)azetidine (200 mg, 0.808 mmol) and triethylamine (98 mg, 0.97 mmol) in anhydrous dichloromethane (6 mL) was added acetic anhydride (200 mg, 0.97 mmol). The mixture was stirred at rt for 5 hours. The mixture was poured into ethyl acetate and washed with water. The organic phase was dried over sodium sulfate, filtered, and concentrated in vacuo to give the title compound (100 mg, 49% yield) as a yellow oil that was taken on without further purification.

Step 2 methyl 5-[4-(1-acetylazetidin-2-yl)phenyl]-6-chloro-1H-indole-3-carboxylate A mixture of methyl 6-chloro-5-(5,5-dimethyl-1,3,2-dioxaborinan-2-yl)-1H-indole-3-carboxylate (100 mg, 0.311 mmol), 1-[2-(4-bromophenyl)azetidin-1-yl]ethanone (100 mg, 0.373 mmol), 2.0 M aqueous potassium carbonate (0.50 mL, 1.0 mmol), and Pd(dppf)Cl$_2$ (30 mg, 0.03 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue. This was purified by preparative TLC to give the title compound (40 mg, 51% yield) as a white solid.

Step 3

5-[4-(1-acetylazetidin-2-yl)phenyl]-6-chloro-1H-indole-3-carboxylic acid

To a solution of methyl 5-[4-(1-acetylazetidin-2-yl)phenyl]-6-chloro-1H-indole-3-carboxylate (40 mg, 0.11 mmol) in methanol (8 mL) was added 1.0 M aq. NaOH (2.0 mL, 2.0 mmol). The mixture was stirred at 70° C. for 24 hours. The mixture was adjusted to pH 7 and purified by reverse phase HPLC to give the title compound (3 mg, 7% yield) as a white solid.

MS (ES+) 369.1 (M+H)+. 1H NMR (400 MHz, CD3OD): δ 8.05 (s, 1 H), 7.95 (s, 1 H), 7.60 (s, 1 H), 7.40 (m, 4 H), 4.80-4.70 (m, 3 H), 2.00-1.90 (m, 2 H), 1.93 (s, 3H).

Example 47

6-chloro-5-{4[(2S)-pyrrolidin-2-ylmethoxy]phenyl}-1H-indole-3-carboxylic acid

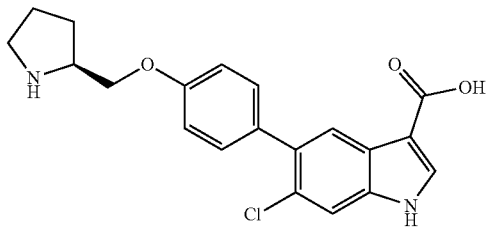 [SMILES: O=C(O)c1c[nH]c2cc(Cl)c(-c3ccc(OC[C@@H]4CCCN4)cc3)cc12]

Step 1 methyl 6-chloro-5-{4[(2S)-pyrrolidin-2-ylmethoxy]phenyl}-1H-indole-3-carboxylate A mixture of methyl 6-chloro-5-(5,5-dimethyl-1,3,2-dioxaborinan-2-yl)-1H-indole-3-carboxylate (80 mg, 0.146 mmol), (S)-2-((4-bromophenoxy)methyl)pyrrolidine (77 mg, 0.3 mmol), 2.0 M aqueous potassium carbonate (0.5 mL, 1.0 mmol), and Pd(dppf)Cl2 (10 mg, 0.01 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue, which was purified by preparative TLC to give the title compound (40 mg, 42% yield) as a white solid. 1H NMR (400 MHz, CDCl3): δ 7.92 (s, 1 H), 7.80 (s, 1 H), 7.55 (s, 1 H), 7.45 (d, 2 H), 6.85 (d, 2 H), 4.10 (m, 1 H), 3.75 (s, 3 H), 3.65 (m, 1 H), 3.52 (m, 1 H), 3.05 (m, 2 H), 2.05 (m, 1 H), 1.90 (m, 2 H), 1.70 (m, 1 H).

Step 2

6-chloro-5-{4[(2S)-pyrrolidin-2-ylmethoxy]phenyl}-1H-indole-3-carboxylic acid

To a solution of methyl 6-chloro-5-{4-[(2S)-pyrrolidin-2-ylmethoxy]phenyl}-1H-indole-3-carboxylate (40 mg, 0.22 mmol) in methanol (8 mL) was added 1.0 M aqueous NaOH (2.0 mL, 2.0 mL). The mixture was stirred at 70° C. for 24 hours. The mixture was adjusted to pH 7 and purified by reverse phase HPLC to give the title compound (10 mg, 11% yield) as a white solid.

MS (ES+) 371.2 (M+H)+. 1H NMR (400 MHz, DMSO-d6): δ12.00 (S, 1 H), 8.35 (s, 1 H), 8.05 (s, 1 H), 7.95 (s, 1 H), 7.60 (s, 1 H), 7.35 (m, 2 H), 7.0 (m, 2 H), 4.05 (m, 2 H), 3.70 (m, 1 H), 3.05 (m, 2 H), 2.01 (m, 1 H), 1.8 (m, 2 H), 1.62 (m, 1 H).

Example 48

6-chloro-5-{4-[2-(piperazin-1-yl)ethoxy]phenyl}-1H-indole-3-carboxylic acid

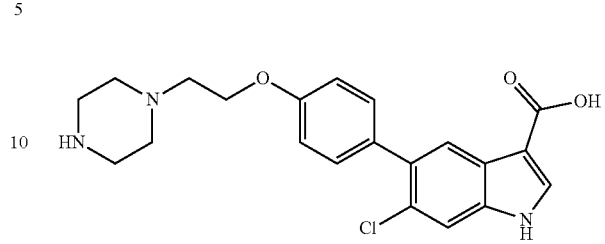

Step 1 methyl 6-chloro-5-{4-[2-(piperazin-1-yl)ethoxy]phenyl}-1H-indole-3-carboxylate

A mixture of methyl 6-chloro-5-(5,5-dimethyl-1,3,2-dioxaborinan-2-yl)-1H-indole-3-carboxylate (80 mg, 0.15 mmol), 1-(2-(4-bromophenoxy)ethyl)piperazine (86 mg, 0.30 mmol), 2.0 M aqueous potassium carbonate (0.50 mL, 1.0 mmol), and Pd(dppf)Cl2 (10 mg, 0.01 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated in vacuo to give a residue, which was purified by preparative TLC to give the title compound (40 mg, 40% yield) as a white solid. 1H NMR (400 MHz, CDCl3): δ8.50 (s, 1 H), 8.10 (s, 1 H), 7.98 (s, 1 H), 7.55 (m, 1 H), 7.45 (m, 2 H), 7.00 (m, 2 H), 4.20 (m, 2 H), 3.90 (s, 3 H), 2.99 (m, 4 H), 2.85 (m, 2 H), 2.60 (m, 4 H).

Step 2

6-chloro-5-{4-[2-(piperazin-1-yl)ethoxy]phenyl}-1H-indole-3-carboxylic acid

To a solution of compound methyl 6-chloro-5-{4-[2-(piperazin-1-yl)ethoxy]phenyl}-1H-indole-3-carboxylate (80 mg, 0.22 mmol) in methanol (8 mL) was added aq. NaOH (2 mL, 1.0 N). The mixture was stirred at 70° C. for 24 hours. The mixture was adjusted to pH 7 and purified by reverse phase HPLC to give the title compound (10 mg, 11% yield) as a white solid. MS (ES+) 400.2 (M+H)+. 1H NMR (400 MHz, DMSO-d6): δ 12.00 (S, 1 H), 8.35 (s, 1 H), 8.05 (s, 1 H), 7.95 (s, 1 H), 7.60 (s, 1 H), 7.35 (d, 2 H), 7.00 (m, 2 H), 4.10 (m, 2 H), 2.90 (m, 4 H), 2.70 (m, 2 H), 2.60 (m, 4 H).

Example 50

6-chloro-5-(4-{[(1S,2S)-2-hydroxycyclohexyl]oxy}phenyl)-1H-indole-3-carboxylic acid

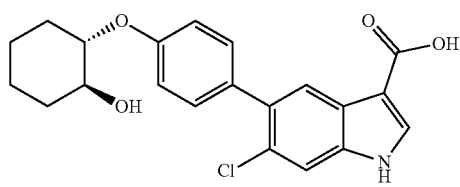 [SMILES: O=C(O)c1c[nH]c2cc(Cl)c(-c3ccc(O[C@H]4CCCC[C@@H]4O)cc3)cc12]

Step 1 methyl 6-chloro-5-(4-{[(1S,2S)-2-hydroxycyclohexyl]oxy}phenyl)-1H-indole-3-carboxylate A mixture of methyl 6-chloro-5-(5,5-dimethyl-1,3,2-dioxaborinan-2-yl)-1H-indole-3-carboxylate (80 mg, 0.15 mmol), (1S,2S)-2-(4-bromophenoxy)cyclohexanol (81 mg, 0.30 mmol), 2.0 M aqueous potassium carbonate (0.50 mL, 1.0 mmol), and Pd(dppf)Cl$_2$ (10 mg, 0.01 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue, which was purified by preparative TLC to give the title compound (80 mg, 90% yield) as a white solid.

Step 2

6-chloro-5-(4-{[(1S,2S)-2-hydroxycyclohexyl]oxy}phenyl)-1H-indole-3-carboxylic acid To a solution of methyl 6-chloro-5-(4-{[(1S,2S)-2-hydroxycyclohexyl]oxy}phenyl)-1H-indole-3-carboxylate (80 mg, 0.22 mmol) in methanol (8 mL) was added aq. 1.0M NaOH (2.0 mL, 2.0 mmol). The mixture was stirred at 70° C. for 24 hours. The mixture was adjusted to pH 7 and purified by reverse phase HPLC to give the title compound (12.6 mg, 16% yield) as a white solid. MS (ES+) 408.2 (M+Na)$^+$. $^1$H NMR (400 MHz, DMSO-d$_6$): δ 12.40-11.90 (br. s, 1 H), 11.85 (s, 1 H), 8.10 (s, 1 H), 7.90 (s, 1 H), 7.61 (m, 1 H), 7.32 (d, 2 H), 7.00 (d, 2 H), 4.93 (m, 1 H), 4.10 (m, 1 H), 3.57 (m, 1 H), 2.05 (m, 1 H), 1.88 (m, 1 H), 1.53 (m, 2 H), 1.40-1.10 (m, 4 H).

Example 51

6-chloro-5-(4-methylphenyl)-1H-indole-3-carboxylic acid

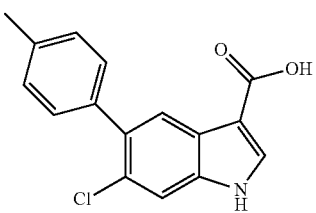 [SMILES: Cc1ccc(-c2cc3c(C(=O)O)c[nH]c3cc2Cl)cc1]

Step 1 methyl 6-chloro-5-(4-methylphenyl)-1H-indole-3-carboxylate

A mixture of methyl 6-chloro-5-(5,5-dimethyl-1,3,2-dioxaborinan-2-yl)-1H-indole-3-carboxylate (80 mg, 0.15 mmol), 4-bromotoluene (56 mg, 0.30 mmol), 2.0 M aqueous potassium carbonate (0.5 mL, 1.0 mmol), and Pd(dppf)Cl$_2$ (10 mg, 0.01 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue, which was purified by preparative TLC to give the title compound (80 mg, 100% yield) as a white solid. $^1$H NMR (400 MHz, CDCl$_3$): δ 8.51 (br. s, 1 H), 8.15 (s, 1 H), 7.98 (s, 1 H), 7.55 (s, 1 H), 7.42 (d, 2 H), 7.25 (d, 2 H), 3.90 (s, 3 H), 2.42 (s, 3 H).

Step 2

6-chloro-5-(4-methylphenyl)-1H-indole-3-carboxylic acid

To a solution of methyl 6-chloro-5-(4-methylphenyl)-1H-indole-3-carboxylate (80 mg, 0.22 mmol) in methanol (8 mL) was added 1.0M aqueous NaOH (2.0 mL, 2.0 mmol). The mixture was stirred at 70° C. for 24 hours. The mixture was adjusted to pH 7 and purified by reverse phase HPLC to give the title compound (10 mg, 13% yield) as a white solid. MS (ES+) 286.1 (M+H)$^+$. $^1$H NMR (400 MHz, DMSO): 612.20-11.95 (br. s, 1H), 11.90 (br. s, H), 8.10 (s, 1H), 7.95 (s, 1H), 7.65 (s, 1H), 7.35-7.20 (m, 4H), 2.35 (s, 3H).

Example 52

6-chloro-5-{4-[3-(piperazin-1-yl)propoxy]phenyl}-1H-indole-3-carboxylic acid

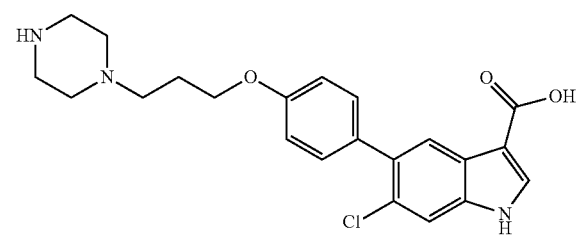 [SMILES: O=C(O)c1c[nH]c2cc(Cl)c(-c3ccc(OCCCN4CCNCC4)cc3)cc12]

Step 1 tert-butyl 4-(3-(4-bromophenoxy)propyl)piperazine-1-carboxylate

To a mixture of 1-bromo-4-(3-bromopropoxy)benzene (300 mg, 1.02 mmol) and tert-butyl piperazine-1-carboxylate (144 mg, 1.02 mmol) in acetonitrile (6.0 mL) was added Cs$_2$CO$_3$ (365 mg, 1.10 mmol). The mixture was stirred at 75° C. for 5 hours. The mixture was poured into ethyl acetate and washed with water. The organic phase was dried over sodium sulfate, filtered, and concentrated to give the title compound (300 mg, 75% yield) as a yellow oil. $^1$H NMR (400 MHz, CDCl$_3$): δ 7.40 (d, 2 H), 6.75 (d, 2 H), 3.95 (m, 2 H), 3.42 (m, 4 H), 2.54 (t, 2 H), 2.40 (m, 4 H), 2.01-1.89 (m, 2 H), 1.50-1.40 (s, 9 H).

Step 2

1-(3-(4-bromophenoxy)propyl)piperazine

To a mixture of tert-butyl 4-(3-(4-bromophenoxy)propyl)piperazine-1-carboxylate (200 mg, 0.50 mmol) in ethyl acetate (10 mL) was added HCl/ethyl acetate (20 mL). The mixture was stirred at rt for 4 hours. The mixture was concentrated to give the title compound (150 mg, 100% yield) as a white solid.

Step 3 methyl 6-chloro-5-{4-[3-(piperazin-1-yl)propoxy]phenyl}-1H-indole-3-carboxylate

A mixture of methyl 6-chloro-5-(5,5-dimethyl-1,3,2-dioxaborinan-2-yl)-1H-indole-3-carboxylate (100 mg, 0.311 mmol), 1-(3-(4-bromophenoxy)propyl)piperazine (149 mg, 0.373 mmol), 2.0 M aqueous potassium carbonate (0.5 mL, 1.0 mmol), and Pd(dppf)Cl$_2$ (30 mg, 0.03 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue, which was purified by preparative TLC to give the title compound (90 mg, 70% yield) as a white solid.

Step 4

6-chloro-5-{4-[3-(piperazin-1-yl)propoxy]phenyl}-1H-indole-3-carboxylic acid

To a solution of methyl 6-chloro-5-{4-[3-(piperazin-1-yl)propoxy]phenyl}-1H-indole-3-carboxylate (90 mg, 0.22 mmol) in methanol (8 mL) was added 1.0 M aqueous NaOH (2.0 mL, 2.0 mmol). The mixture was stirred at 70° C. for 24 hours. The mixture was adjusted to pH 7 and purified by reverse phase HPLC to give the title compound (42 mg, 47% yield) as a white solid.

MS (ES+) 414.0 (M+H)$^+$. $^1$H NMR (400 MHz, DMSO-d$_6$): δ 7.30 (s, 1 H), 7.05 (s, 1 H), 6.70 (s, 1 H), 6.55 (d, 2 H), 6.15 (d, 2 H), 3.80 (m, 2 H), 3.30 (m, 2 H), 2.30 (m, 4 H), 1.85 (m, 4 H), 1.20 (m, 2 H).

Example 53

6-chloro-5-{4-[3-(4-methylpiperazin-1-yl)propoxy]phenyl}-1H-indole-3-carboxylic acid

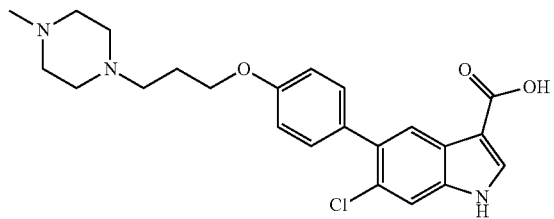 [SMILES: CN1CCN(CCCOc2ccc(-c3cc4c(C(=O)O)c[nH]c4cc3Cl)cc2)CC1]

Step 1

1-(3-(4-bromophenoxy)propyl)-4-methylpiperazine

To a mixture of 1-bromo-4-(3-bromopropoxy)benzene (300 mg, 1.02 mmol) and 1-methylpiperazine (100 mg, 1.02 mmol) in CH$_3$CN (6 mL) was added Cs$_2$CO$_3$ (365 mg, 1.10 mmol). The mixture was stirred at 75° C. for 5 hours. The mixture was poured into ethyl acetate and washed with water. The organic phase was dried over sodium sulfate, filtered, and concentrated to give the title compound (280 mg, 75% yield) as a yellow oil.

$^1$H NMR (400 MHz, DMSO-d$_6$): δ 7.32 (d, 2 H), 6.80 (d, 2 H), 3.88 (m, 2 H), 2.51-2.09 (m, 10 H), 2.05 (s, 3 H), 1.75 (m, 2 H).

Step 2 methyl 6-chloro-5-{4-[3-(4-methylpiperazin-1-yl)propoxy]phenyl}-1H-indole-3-carboxylate A mixture of of methyl 6-chloro-5-(5,5-dimethyl-1,3,2-dioxaborinan-2-yl)-1H-indole-3-carboxylate (100 mg, 0.311 mmol), 1-(3-(4-bromophenoxy)propyl)-4-methylpiperazine (130 mg, 0.373 mmol), 2.0 M aqueous potassium carbonate (0.50 mL, 1.0 mmol), and Pd(dppf)Cl$_2$ (30 mg, 0.03 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue, which was purified by preparative TLC to give the title compound (80 mg, 75% yield) as a white solid.

Step 3

6-chloro-5-{4-[3-(4-methylpiperazin-1-yl)propoxy]phenyl}-1H-indole-3-carboxylic acid To a solution of methyl 6-chloro-5-{4-[3-(4-methylpiperazin-1-yl)propoxy]phenyl}-1H-indole-3-carboxylate (80 mg, 0.22 mmol) in methanol (8 mL) was added 1.0 M aqueous NaOH (2.0 mL, 2.0 mmol). The mixture was stirred at 70° C. for 24 hours. The mixture was adjusted to pH 7 and purified by reverse phase HPLC to give the title compound (25 mg, 28% yield) as a white solid. MS (ES+) 428.1 (M+H)$^+$. $^1$H NMR (400 MHz, CD$_3$OD): δ 8.41 (br. s, 1H), 8.03 (s, 1H), 7.97 (s, 1 H), 7.56 (s, 1 H), 7.34 (d, 2 H), 6.98 (d, 2 H), 4.12 (t, 2 H), 3.20-2.75 (m, 10 H), 2.70 (s, 3 H), 2.10-2.01 (m, 2 H).

Example 54

6-chloro-5-{4-[3-(3-oxomorpholin-4-yl)propoxy]phenyl}-1H-indole-3-carboxylic acid

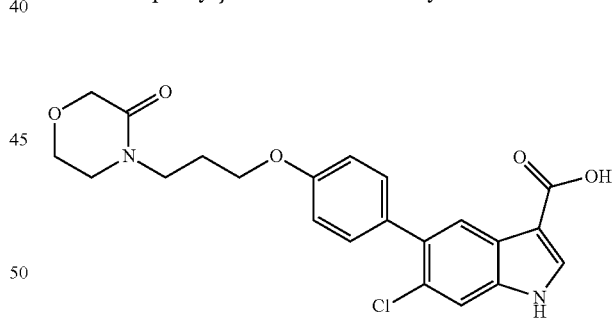

Step 1

4-(3-(4-bromophenoxy)propyl)morpholin-3-one

To a mixture of 1-bromo-4-(3-bromopropoxy)benzene (300 mg, 1.02 mmol) and morpholin-3-one (100 mg, 1.02 mmol) in DMF (6 mL) was added NaH (365 mg, 1.10 mmol). The mixture was stirred at 75° C. for 5 hours. The mixture was poured into ethyl acetate and washed with water. The organic phase was dried over sodium sulfate, filtered, and concentrated to give the title compound (100 mg, 35%) as a yellow oil.

Step 2 methyl 6-chloro-5-{4-[3-(3-oxomorpholin-4-yl)pro-poxy]phenyl}-1H-indole-3-carboxylate A mixture of of methyl 6-chloro-5-(5,5-dimethyl-1,3,2-dioxaborinan-2-yl)-1H-indole-3-carboxylate (100 mg, 0.311 mmol), 4-(3-(4-bromophenoxy)propyl)morpholin-3-one (100 mg, 0.373 mmol), 2 N potassium carbonate (0.5 mL, 2 mmol), and Pd(dppf)Cl$_2$ (30 mg, 0.03 mmol) in toluene/ethanol (1.44 mL/0.48 mL) was stirred at 110° C. for 2.5 hours. The mixture was poured into ethyl acetate and washed with water. The organic phase was dried over sodium sulfate, filtered, and concentrated to give a residue, which was purified by preparative TLC to give the title compound (50 mg, 50% yield) as a white solid.

Step 3

6-chloro-5-{4-[3-(3-oxomorpholin-4-yl)propoxy]phenyl}-1H-indole-3-carboxylic acid To a solution of methyl 6-chloro-5-{4-[3-(3-oxomorpholin-4-yl)propoxy]phenyl}-1H-indole-3-carboxylate (55 mg, 0.22 mmol) in methanol (8 mL) was added 1.0 M aq. NaOH (2.0 mL, 2.0 mmol). The mixture was stirred at 70° C. for 24 hours. The mixture was adjusted to pH 7 and purified by reverse phase HPLC to give the title compound as a white solid (5 mg, 9% yield). MS (ES+) 429.1 (M+H)$^+$. $^1$H NMR (400 MHz, CD$_3$OD): δ 7.90 (m, 2 H), 7.5 (s, 1 H), 7.29 (d, 2 H), 6.92 (d, 2 H), 4.05 (m, 4 H), 3.83 (t, 2 H), 3.58 (t, 2 H), 3.42 (t, 2 H), 2.05 (m, 2 H).

Example 55

(S)-6-Chloro-5-(3-methoxy-4-(pyrrolidin-2-yl-methoxy)phenyl)-1H-indole-3-carboxylic acid

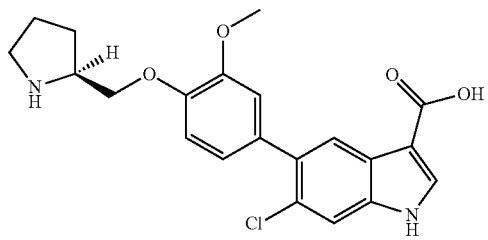 [SMILES: COc1cc(-c2cc3c(C(=O)O)c[nH]c3cc2Cl)ccc1OC[C@@H]1CCCN1]

Step 1

(S)-tert-butyl 2-(((methylsulfonyl)oxy)methyl)pyrro-lidine-1-carboxylate

To a solution of (S)-tert-butyl 2-(hydroxymethyl)pyrrolidine-1-carboxylate (201 mg, 1.00 mmol) and triethylamine (0.21 mL, 1.5 mmol) in tert-butyl methyl ether (4 mL) was added methanesulfonyl chloride (0.095 mL, 1.2 mmol). After 90 min., the mixture was filtered, washing the white solid with tert-butyl methyl ether (3×2 mL). The filtrate was concentrated in vacuo to provide the title compound as a colorless oil. $^1$H NMR (400 MHz, CDCl$_3$,): δ 4.40-3.95 (m, 3H), 3.49-3.32 (m, 2H), 3.02 (s, 3H), 2.11-1.80 (m, 4H), 1.48 (s, 9H).

Step 2

(S)-tert-butyl 2-((4-bromo-2-methoxyphenoxy)me-thyl)pyrrolidine-1-carboxylate

To a solution of (S)-tert-butyl 2-(((methylsulfonyl)oxy)methyl)pyrrolidine-1-carboxylate (279 mg, 1.00 mmol) and 4-bromo-2-methoxyphenol (325 mg, 1.57 mmol) in N,N-dimethylformamide (5.55 mL) was added cesium carbonate (651 mg, 2.00 mmol). The mixture was heated to 100° C. After 22 h, the mixture was allowed to cool to 23° C. and diluted with water (30 mL). The mixture was extracted with ethyl acetate (3×30 mL). The combined organics were dried over sodium sulfate and filtered. The filtrate was concentrated in vacuo. Purification by column chromatography (silica gel, 0-50% ethyl acetate in dichloromethane) afforded the title compound as an amber oil. MS (ES+) 408.2 (M+Na)$^+$. $^1$H NMR (400 MHz, CDCl$_3$): δ 7.07-6.79 (m, 3H), 4.25-4.10 (m, 2H), 4.01-3.73 (m, 1H), 3.84 (s, 3H), 3.48-3.26 (m, 2H), 2.16-1.80 (m, 4H), 1.48 (s, 9H).

Step 3

(S)-methyl 5-(4-((1-(tert-butoxycarbonyl)pyrrolidin-2-yl)methoxy)-3-methoxyphenyl)-6-chloro-1H-indole-3-carboxylate To a solution of (S)-tert-butyl 2-((4-bromo-2-methoxyphenoxy)methyl)pyrrolidine-1-carboxylate (77 mg, 0.20 mmol) in toluene (1.5 mL) was added methyl 6-chloro-5-(5,5-dimethyl-1,3,2-dioxaborinan-2-yl)-1H-indole-3-carboxylate (77 mg, 0.24 mmol), [1,1'-bis(diphenylphosphino)ferrocene]dichloropalladium(II) dichloromethane complex (6.7 mg, 0.0080 mmol), ethanol (absolute, 0.5 mL), and potassium carbonate (2 M solution in water, 0.4 mL, 0.80 mmol). Nitrogen was bubbled through the mixture for 20 min. The mixture was then sealed and heated to 90° C. After 18 h, the mixture was allowed to cool to 23° C., diluted with ethyl acetate (5 mL), and filtered through Celite. The filtrate was dried over sodium sulfate and concentrated in vacuo. Purification by column chromatography (silica gel, 0-50% ethyl acetate in heptane) afforded the title compound contaminated with neopentyl glycol.
MS (ES+) 515.3 (M+H)$^+$. $^1$H NMR (400 MHz, CDCl$_3$): δ 8.60 (br. s, 1H), 8.14 (br. s, 1H), 7.95 (d, 1H), 7.55 (s, 1H), 7.17-6.97 (m, 3H), 4.35-4.20 (m, 2H), 4.10-3.81 (m, 1H), 3.91 (s, 3H), 3.90 (s, 3H), 3.50-3.28 (m, 2H), 2.24-1.83 (m, 4H), 1.51 (br. s, 9H).

Step 4

(S)-methyl 6-chloro-5-(3-methoxy-4-(pyrrolidin-2-ylmethoxy)phenyl)-1H-indole-3-carboxylate To a solution of (S)-methyl 5-(4-((1-(tert-butoxycarbonyl)pyrrolidin-2-yl)methoxy)-3-methoxyphenyl)-6-chloro-1H-indole-3-carboxylate (25.8 mg, 0.050 mmol) in dichloromethane (0.5 mL) was added hydrogen chloride (4 M solution in dioxane, 0.075 mL, 0.30 mmol). After 2 h, the solution was concentrated in vacuo to provide the title compound as the hydrochloride salt contaminated with neopentyl glycol. MS (ES+) 415.2 (M+H)$^+$. $^1$H NMR (400 MHz, DMSO-d$_6$): δ 8.80 (br. s, 1H), 8.17 (d, 1H), 7.94 (s, 1H), 7.65 (s, 1H), 7.11 (d, 1H), 7.06 (d, 1H), 6.96 (dd, 1H), 4.34-4.26 (m, 2H), 4.15 (dd, 1H), 4.01-3.92 (m, 1H), 3.82 (s, 3H), 3.79 (s, 3H), 3.29-3.19 (m, 2H), 2.21-2.10 (m, 1H), 2.08-1.86 (m, 2H), 1.83-1.72 (m, 1H).

Step 5

(S)-6-chloro-5-(3-methoxy-4-(pyrrolidin-2-ylmethoxy)phenyl)-1H-indole-3-carboxylic acid To a solution of (S)-methyl 6-chloro-5-(3-methoxy-4-(pyrrolidin-2-ylmethoxy)phenyl)-1H-indole-3-carboxylate hydrochloride (22.6 mg, 0.050 mmol) in methanol (0.26 mL) was added tetrahydrofuran (0.26 mL) and sodium hydroxide (1 N in water, 0.26 mL, 0.26 mmol). The mixture was then sealed and heated to 65° C. After 41 h, the mixture was allowed to cool to 23° C., concentrated in vacuo, diluted with water (1 mL), then acidified to pH 7.5 with hydrochloric acid (1 N in water). The solid was filtered and purified by reverse phase HPLC to provide the title compound. MS (ES+) 401.2 (M+H)+. HPLC retention time: 1.44 min, Waters XBridge C18, 5 μm, 4.6×50 mm, 0.03% NH$_4$OH, 5-95% acetonitrile in water gradient over 4.0 min, hold at 95% acetonitrile in water to 5.0 min, flow 2.0 mL/min.

Example 56

6-chloro-5-(4-(2-hydroxypropan-2-yl)-3-methoxyphenyl)-1H-indole-3-carboxylic acid

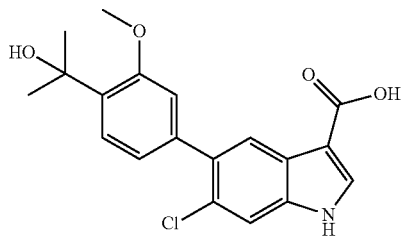 [SMILES: COc1cc(-c2cc3c(C(=O)O)c[nH]c3cc2Cl)ccc1C(C)(C)O]

Step 1

2-(4-bromo-2-methoxyphenyl)propan-2-ol

To a solution of 5-bromo-2-iodoanisole (668 mg, 2.14 mmol) and acetone (0.471 mL, 6.40 mmol) in tetrahydrofuran (7.62 mL) at −78° C. was added n-BuLi (2.5M in hexane, 0.940 mL, 2.35 mmol) in a dropwise manner. The reaction mixture was stirred at −78° C. for 2 hours. The reaction mixture was quenched with saturated aqueous ammonium chloride, warmed to room temperature and extracted with ethyl acetate (2×). The combined organic layers were dried over magnesium sulfate and filtered, and concentrated under reduced pressure yielding 680 mg of crude oil. Purification by column chromatography (0-10% ethyl acetate/heptanes) afforded the title compound (133 mg, 25% yield) as a clear, colorless oil. MS (ES+) 226.9 (M−H$_2$O+H)+. $^1$H NMR (400 MHz, CDCl$_3$) δ: 7.20 (d, 1H), 7.06-7.10 (m, 1H), 7.04 (d, 1H), 3.91 (s, 3H), 1.58 (s, 6H).

Step 2 methyl 6-chloro-5-(4-(2-hydroxypropan-2-yl)-3-methoxyphenyl)-1H-indole-3-carboxylate To a solution of 2-(4-bromo-2-methoxyphenyl)propan-2-ol (50.0 mg, 0.20 mmol) in toluene (0.81 mL) was added methyl 6-chloro-5-(5,5-dimethyl-1,3,2-dioxaborinan-2-yl)-1H-indole-3-carboxylate (72 mg, 0.22 mmol), ethanol (0.43 mL), and tetrahydrofuran (0.43 mL). This was followed by the addition of 2M potassium carbonate aqueous (0.58 mL, 1.2 mmol). The reaction was evacuated and back filled with nitrogen (3×) then Pd(dppf)Cl$_2$ (19.0 mg, 0.023 mmol) was added and the reaction heated to 115° C. for 3 hours. The reaction was then cooled to room temperature and filtered through a pad of celite washing with ethyl acetate. The filtrate was concentrated under reduced pressure and purified via column chromatography (0-40% ethyl acetate/heptanes) to provide the title compound (45 mg, 59% yield) as a solid.

MS (ES+) 356.1 (M−H$_2$O+H)+. $^1$H NMR (400 MHz, CDCl$_3$) δ: 8.52 (s, 1H), 8.14 (s, 1H), 7.95 (d, 1H), 7.56 (s, 1H), 7.37 (d, 1H), 7.04-7.09 (m, 2H), 4.23 (s, 1H), 3.96 (s, 3H), 3.90 (s, 3H), 1.67 (s, 6H).

Step 3

6-chloro-5-(4-(2-hydroxypropan-2-yl)-3-methoxyphenyl)-1H-indole-3-carboxylic acid To a flask containing methyl 6-chloro-5-(4-(2-hydroxypropan-2-yl)-3-methoxyphenyl)-1H-indole-3-carboxylate (24.0 mg, 0.064 mmol) was added methanol (0.64 mL), and 1N NaOH (0.19 mL, 0.19 mmol). The reaction was heated at 70° C. for 18 h. The reaction was then concentrated to remove most of the methanol and then dissolved in water. 0.19 mL of 1 N HCl was then added to the mixture to pH 2. Solid precipitated out. The solid was collected with a Buchner funnel and washed with water to provide crude 6-chloro-5-(4-(2-hydroxypropan-2-yl)-3-methoxyphenyl)-1H-indole-3-carboxylic acid. The crude material was purified by reverse phase chromatography to give the title compound. MS (ES−) 358.1 (M−H)−: Retention time: 1.40 min. Column: Waters XBridge dC18 4.6×50 mm, 5 μm. Modifier: NH$_4$OH 0.03%. Gradient: 95% H$_2$O/5% MeCN linear to 5% H$_2$O/95% MeCN over 4.0 min, HOLD at 5% H$_2$O/95% MeCN to 5.0 min. Flow: 2.0 mL/min.

Example 57

6-chloro-5-(2,3-dihydrobenzofuran-6-yl)-1H-indole-3-carboxylic acid

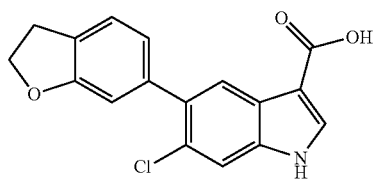 [SMILES: O=C(O)c1c[nH]c2cc(Cl)c(-c3ccc4c(c3)OCC4)cc12]

A 0.25 M solution of 6-bromo-2,3-dihydrobenzofuran was prepared in dioxane. A 0.30 M solution of methyl 6-chloro-5-(5,5-dimethyl-1,3,2-dioxaborinan-2-yl)-1H-indole-3-carboxylate was also prepared in dioxane. Lastly, a 1.00 M solution of K$_3$PO$_4$ was prepared in water. In a vial was added 400 uL of the 0.30 M dioxane solution of 6-bromo-2,3-dihydrobenzofuran (100 umol, 1.00 eq). 400 uL of the 0.25 M dioxane solution of methyl 6-chloro-5-(5,5-dimethyl-1,3,2-dioxaborinan-2-yl)-1H-indole-3-carboxylate (120 umol, 1.20 eq) was then added followed by the addition of 200 uL of the 1.00 M aqueous solution of K$_3$PO$_4$ (200 umol, 2.00 eq). Under nitrogen atmosphere was added (1,1'-bis(di-tert-butylphosphino)ferrocene palladium dichloride (3.9 mg, 6.0 umol, 0.06 eq). The vial was caped and shook for 2 hours at 120° C. The reaction was filtered and concentrated by Speedvac. The residue was washed with saturated aqueous sodium bicarbonate and extracted with ethyl acetate (1 mL, 3×). The organic layer was collected and dried over anhydrous sodium sulfate, filtered, and concentrated to give crude methyl 6-chloro-5-(2,3-dihydrobenzofuran-6-yl)-1H-indole-3-carboxylate. To the crude intermediate was added anhydrous tetrahydrofuran (1.5 mL) followed by Me$_3$SiOK (128 mg, 1000 umol, 10.0 eq). The vial was capped and shaken at 80° C. for 16 hours. The reaction was concentrated by Speedvac and the residue was purified by preparative HPLC to provide the title compound. MS (ES+) 314 (M+H)$^+$. Retention time: 2.56 min. Column: Agella Venusil ASB dC18 150×21.2 mm, 5 μm. Modifier: TFA 0.225%. Gradient: 66% H$_2$O/34% MeCN linear to 36% H$_2$O/64% MeCN over 10.0 min., HOLD at 100% MeCN to 1.0 min. Flow: 30.0 mL/min.

Example 58

6-chloro-5-[3-fluoro-4-(3-hydroxypropoxy)phenyl]-1H-indole-3-carboxylic acid

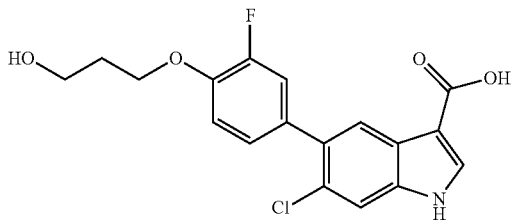 [SMILES: O=C(O)c1c[nH]c2cc(Cl)c(-c3ccc(OCCCO)c(F)c3)cc12]

Step 1 methyl 6-chloro-5-[3-fluoro-4-(3-hydroxypropoxy)phenyl]-1H-indole-3-carboxylate

To a mixture of 3-(4-bromo-2-fluorophenoxy)propan-1-ol (93 mg, 0.37 mmol), methyl 6-chloro-5-(5,5-dimethyl-1,3,2-dioxaborinan-2-yl)-1H-indole-3-carboxylate (100 mg, 0.31 mmol) and potassium carbonate (128 mg, 0.93 mmol) in Toluene/EtOH (5 mL, 3:1) and water (1 ml) was added Pd(dppf)Cl$_2$ (22 mg, 0.031 mmol). The mixture was degassed and purged with nitrogen for 5 minutes, then allowed to heat to 110° C. and stirred for 30 minutes. The reaction mixture was concentrated in vacuo to give a brown residue. The residue was purified by flash chromatography to give the title compound (85 mg, 73% yield) as a pale solid. $^1$H NMR (400 MHz, CD$_3$OD) δ 8.04 (d, 2H), 7.61 (m, 2H), 7.18 (m, 2H), 4.21 (m, 2H), 3.89 (s, 3H), 3.82 (t, 2H), 2.08 (m, 2H).

Step 2

6-chloro-5-[3-fluoro-4-(3-hydroxypropoxy)phenyl]-1H-indole-3-carboxylic acid

To a mixture of methyl 6-chloro-5-[3-fluoro-4-(3-hydroxypropoxy)phenyl]-1H-indole-3-carboxylate (85 mg, 0.23 mmol) in methanol (5 mL) and water (2 mL) was added sodium hydroxide (90 mg, 2.3 mmol). The reaction mixture was heated at 70° C. and stirred for 24 hours. The mixture was acidified by 1N HCl to pH 4 and extracted with ethyl acetate (10 mL×3). The combined organic layers was dried over sodium sulfate, filtered, and concentrated in vacuo to give a brown residue. It was purified by preparative HPLC to give the title compound (31 mg, 52% yield) as a white solid. MS (AP−) 386.1 (M+Na)$^-$. $^1$H NMR (400 MHz, DMSO-d$_6$) δ 12.14 (s, 1H), 11.98 (s, 1H), 8.08 (s, 1H), 7.925 (s, 1H), 7.62 (s, 1H), 7.25-7.15 (m, 3H), 4.59 (t, 1H), 4.16 (t, 2H), 3.58 (q, 2H), 1.90 (m, 2H).

Example 59

6-chloro-5-[4-(3-hydroxypropoxy)-3-methoxyphenyl]-1H-indole-3-carboxylic acid

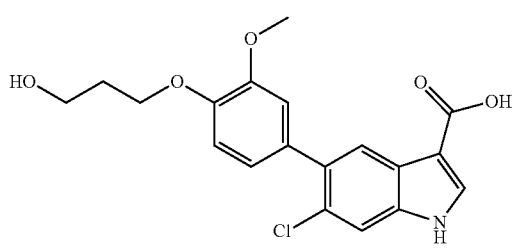 [SMILES: COc1cc(-c2cc3c(C(=O)O)c[nH]c3cc2Cl)ccc1OCCCO]

Step 1 methyl 6-chloro-5-[4-(3-hydroxypropoxy)-3-methoxyphenyl]-1H-indole-3-carboxylate To a mixture of 3-(4-bromo-2-methoxyphenoxy)propan-1-ol (97 mg, 0.37 mmol), methyl 6-chloro-5-(5,5-dimethyl-1,3,2-dioxaborinan-2-yl)-1H-indole-3-carboxylate (100 mg, 0.31 mmol) and potassium carbonate (128 mg, 0.93 mmol) in toluene/EtOH (5 mL, 3:1) and water (1 ml) was added Pd(dppf)Cl$_2$ (22 mg, 0.031 mmol). The mixture was degassed and purged with nitrogen for 5 minutes, then allowed to heat to 110° C. and stirred for 30 minutes. The reaction mixture was concentrated in vacuo to give a brown residue. The residue was purification by flash chromatography to give the title compound (92 mg, 76% yield) as a pale solid. $^1$H NMR (400 MHz, CD$_3$OD) δ 8.01 (s, 1H), 8.00 (s, 1H), 7.58 (s, 1H), 7.03 (m, 2H), 7.00 (m, 1H), 4.18 (m, 2H), 3.87 (s, 3H), 3.80 (m, 2H), 3.37 (s, 3H), 2.05 (m, 2H).

Step 2

6-chloro-5-[4-(3-hydroxypropoxy)-3-methoxyphenyl]-1H-indole-3-carboxylic acid

To a mixture of methyl 6-chloro-5-[4-(3-hydroxypropoxy)-3-methoxyphenyl]-1H-indole-3-carboxylate (92 mg, 0.24 mmol) in MeOH (5 mL) and water (2 mL) was added NaOH (94 mg, 2.4 mmol). The reaction mixture was heated at 70° C. and stirred for 24 hours. TLC (petroleum ether/ethyl acetate=1:1) showed the reaction was complete. The mixture was acidified by 1N HCl to pH 4 and extracted with ethyl acetate (10 mL×3). The combined organic layers was dried over sodium sulfate, filtered, and concentrated in vacuo to give a brown residue. It was purified by preparative HPLC to give the title compound (35 mg, 35% yield) as a white solid. MS (AP−) 398.1 (M+Na)$^-$. $^1$H NMR (400 MHz, DMSO-d$_6$) δ 11.93 (s, 1H), 8.07 (s, 1H), 7.93 (s, 1H), 7.60 (s, 1H), 7.02 (d, 1H), 6.97 (s, 1H) 6.89 (dd, 1H), 4.04 (t, 2H), 3.77 (s, 3H), 3.51 (t, 2H), 1.88 (m, 2H).

Example 60

6-chloro-5-[4-(3-hydroxyoxetan-3-yl)-3-methoxyphenyl]-1H-indole-3-carboxylic acid

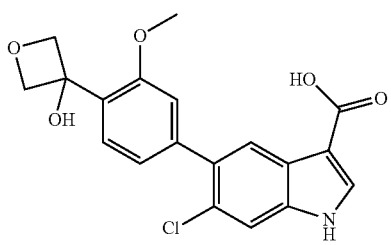 [SMILES: COc1cc(-c2cc3c(C(=O)O)c[nH]c3cc2Cl)ccc1C1(O)COC1]

Step 1

3-(4-bromo-2-methoxyphenyl)oxetan-3-ol

To a solution of 5-bromo-2-iodoanisole (533 mg, 1.30 mmol) and oxetan-3-one (0.12 mL, 2.0 mmol) in tetrahydrofuran (5 mL) at −78° C. followed by the addition of n-butyl lithium (2.5M in hexane, 0.56 mL, 1.4 mmol) dropwise over 5 minutes. The reaction mixture was stirred at −78° C. for 2 hours. The reaction mixture was quenched with saturated aqueous ammonium chloride, warmed to room temperature and extracted two times with ethyl acetate. The combined organic layers were dried over sodium sulfate, filtered, and concentrated under reduced pressure yielding 476 mg of crude material. The crude material was purified using the Biotage Isolera One (SNAP 25 g silica gel column) and eluting with a gradient of 0-70% ethyl acetate/heptane yielding 137 mg (41% yield) of the title compound. $^1$H NMR (500 MHz, CDCl$_3$) δ 7.15 (dd, J=8.1, 1.7 Hz, 1 H), 7.13 (d, J=8.1 Hz, 1 H), 7.07 (d, J=1.5 Hz, 1 H), 4.99 (d, J=7.1 Hz, 2 H), 4.84 (d, J=7.3 Hz, 2 H), 3.87 (s, 3 H)

Step 2 methyl 6-chloro-5-[4-(3-hydroxyoxetan-3-yl)-3-methoxyphenyl]-1H-indole-3-carboxylate To a solution of methyl 6-chloro-5-(5,5-dimethyl-1,3,2-dioxaborinan-2-yl)-1H-indole-3-carboxylate (70 mg, 0.27 mmol) and 3-(4-bromo-2-methoxyphenyl)oxetan-3-ol (96 mg, 0.30 mmol) in toluene (1.2 mL), ethanol (0.6 mL), and tetrahydrofuran (0.6 mL) followed by the addition of 2M potassium carbonate aqueous (0.6 mL, 1 mmol). Nitrogen was bubbled through the reaction for 5 minutes then [1,1'-bis(diphenylphosphino)ferrocene]dichloro palladium, dichloromethane (25 mg, 0.031 mmol) was added and the reaction heated to 115° C. for 16 hours. The reaction was then cooled to room temperature and filtered through a pad of celite washing with ethyl acetate. The filtrate was concentrated under reduced pressure and passed through silica yielding 104 mg of the title compound that was brought forward without further purification. MS (ES+) 386.1 (M−H)$^+$.

Step 3

6-chloro-5-[4-(3-hydroxyoxetan-3-yl)-3-methoxyphenyl]-1H-indole-3-carboxylic acid To a mixture of methyl 6-chloro-5-[4-(3-hydroxyoxetan-3-yl)-3-methoxyphenyl]-1H-indole-3-carboxylate (100 mg, 0.258 mmol) in methanol (3 mL) and sodium hydroxide (1 M, 1.0 mL, 1.0 mmol) was heated to 70° C. for 24 hours. The reaction was concentrated under reduced pressure and the reaction was acidified with 1 M hydrochloric acid aqueous to pH=2 then diluted with ethyl acetate. The layers were separated and the aqueous extracted with ethyl acetate two additional times. The combined organic layers were dried over sodium sulfate, filtered, and concentrated under reduced pressure yielding 83 mg of the crude desired product. A portion of the crude material (60 mg) was purified by prep-HPLC (Phenomenex HILIC (Diol) 250×21.2 mm 5 μm; Mobile phase A: heptane; Mobile Phase B: Ethanol, gradient 95% A/5% B hold for 1.5 minutes, linear gradient to 0% A/100% B in 8.5 minutes, Hold at 0% A/100% B for 1 minutes; flow rate: 28 ml/min) to afford the title compound (16.9 mg, 17.5%) as a solid. MS (ES−) 372.0 (M−H)$^-$. $^1$H NMR (500 MHz, DMSO-d$_6$) δ 12.13 (br. s, 1 H), 11.96 (br. s, 1 H), 8.10 (d, J=2.2 Hz, 1 H), 7.98 (s, 1 H), 7.65 (s, 1 H), 7.29 (d, J=7.8 Hz, 1 H), 7.05 (d, J=1.5 Hz, 1 H), 6.99 (dd, J=7.6, 1.5 Hz, 1 H), 5.89 (s, 1 H), 5.02 (d, J=6.8 Hz, 2 H), 4.67 (d, J=6.8 Hz, 2 H), 3.81 (s, 3 H)

Example 61

6-chloro-5-[4-(1-hydroxycyclobutyl)-3-methoxyphenyl]-1H-indole-3-carboxylic acid

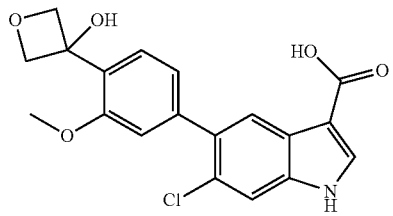 [SMILES: COc1cc(-c2cc3c(C(=O)O)c[nH]c3cc2Cl)ccc1C1(O)COC1]

Step 1

1-(4-bromo-2-methoxyphenyl)cyclobutanol

To a solution of 5-bromo-2-iodoanisole (10.0 g, 31.9 mmol) and cyclobutanone (3.6 mL, 48 mmol) in tetrahydrofuran (107 mL) at −78° C. followed by the addition of n-butyl lithium (2.5 M in hexane, 15.6 mL, 39.0 mmol) dropwise over 20 minutes. The reaction mixture was stirred at −78° C. for 2.5 hours. The reaction mixture was quenched with saturated aqueous ammonium chloride and the reaction mixture was warmed to room temperature and extracted two times with ethyl acetate. The combined organic layers were dried over magnesium sulfate, filtered, and concentrated under reduced pressure yielding 9.73 g of crude material. The crude material was purified using the Biotage Isolera One (SNAP 100 g silica gel column) and eluting with a gradient of 0-70% ethyl acetate/heptane yielding 4.75 g (57.9% yield) of the title compound.

GC/MS: 257. $^1$H NMR (500 MHz, CDCl$_3$) δ 7.19-7.14 (m, 1 H), 7.12-7.01 (m, 1 H), 7.04 (d, J=2.0 Hz, 1 H), 3.88 (s, 3 H), 2.53-2.40 (m, 2 H), 2.39-2.28 (m, 2 H), 2.11-2.00 (m, 1 H), 1.67-1.55 (m, 1 H).

Step 2 methyl 6-chloro-5-[4-(1-hydroxy-cyclobutyl)-3-methoxy-phenyl]-1H-indole-3-carboxylate A mixture of methyl 6-Chloro-5-(5,5-dimethyl-[1,3,2]dioxaborinan-2-yl)-1H-indole-3-carboxylate (50 mg, 0.16 mmol), 1-(4-Bromo-3-methoxy-phenyl)cyclobutanol (52 mg, 0.2 mmol), 2 M aqueous potassium carbonate (0.31 mL, 0.63 mmol), toluene (3 mL), and ethanol (1 mL) was sparged with nitrogen for 10 minutes, then treated with [1,1'-bis(diphenylphosphino)ferrocene]dichloropalladium(II) dichloromethane adduct (6 mg, 0.007 mmol). The reaction mixture was heated to 100° C. and stirred. After 2 hours the reaction was cooled to room temperature, diluted with ethyl acetate, washed with water and saturated brine, dried over magnesium sulfate, filtered and concentrated in vacuo to afford a yellow oil, which was purified by flash chromatography (12 g silica, 0-35% ethyl acetate/heptane, 24 column volumes). Product fractions were combined and concentrated in vacuo to afford the title compound as a colorless solid (19 mg, 32% yield). MS (ES−) 341.2 (M−H)$^-$; $^1$H NMR (500 MHz, CD$_3$OD) δ 8.03 (d, J=1.95 Hz, 2 H), 7.60 (s, 1 H), 7.38 (d, J=7.56 Hz, 1 H), 7.06 (d, J=1.46 Hz, 1 H), 7.01 (dd, J=7.68, 1.59 Hz, 1 H), 3.89 (d, J=7.32 Hz, 6 H), 2.65-2.75 (m, 2 H), 2.34-2.44 (m, 2 H), 2.08-2.19 (m, 1 H), 1.70-1.80 (m, 1 H).

Step 3

6-Chloro-5-[4-(1-hydroxy-cyclobutyl)-3-methoxy-phenyl]-1H-indole-3-carboxylic acid Methyl 6-Chloro-5-[4-(1-hydroxy-cyclobutyl)-3-methoxy-phenyl]-1H-indole-3-carboxylate (19 mg, 0.05 mmol) was dissolved in methanol (3 mL) and 1N aqueous sodium hydroxide (1 mL, 1 mmol), and the mixture was stirred at 70° C. for 22 hours. The mixture was cooled to room temperature and treated with saturated ammonium chloride (0.5 mL) and concentrated in vacuo to afford 18 mg colorless solid, which was purified by reversed-phase HPLC to afford the title compound (8.0 mg, 44% yield). MS (ES−) 370.1626 (M−H)$^-$. retention time=1.67 min; Column: Waters Atlantis dC18 4.6× 50 mm, 5 μm; Modifier: TFA 0.05%; Gradient: 95% H$_2$O/5% MeCN linear to 5% H$_2$O/95% MeCN over 4.0 min, HOLD at 5% H$_2$O/95% MeCN to 5.0 min; Flow: 2.0 mL/min.

Example 62

6-chloro-5-[4-(1-hydroxycyclobutyl)-2-methoxyphenyl]-1H-indole-3-carboxylic acid

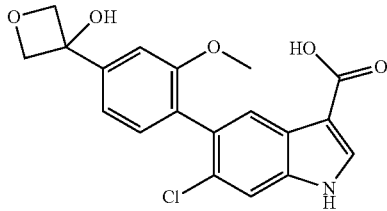 [SMILES: COc1cc(C2(O)COC2)ccc1-c1cc2c(C(=O)O)c[nH]c2cc1Cl]

Step 1

1-(4-Bromo-3-methoxy-phenyl)cyclobutanol

To a solution of 2-bromo-5-iodoanisole (400 mg, 1.28 mmol) in tetrahydrofuran (5 mL) at −78° C. was added n-butyl lithium (2.5 M in hexane, 0.62 mL, 1.55 mmol) dropwise over 15 minutes. The reaction mixture was stirred at −78° C. for 30 minutes, then treated with neat cyclobutanone (0.1 mL, 1.3 mmol) dropwise over 10 minutes and stirred at −78° C. for an additional 1.5 hours. The reaction was quenched with saturated aqueous ammonium chloride solution, warmed to room temperature and extracted with ethyl acetate (2×). The combined organic layers were dried over magnesium sulfate, filtered and concentrated in vacuo to afford a yellow oil, which was purified by flash chromatography (12 g silica, 0-50% ethyl acetate/heptane, 27 column volumes). Product fractions were combined and concentrated in vacuo to afford the title compound as a pale yellow oil (40 mg, 12% yield). GCMS 256/258 (M)$^+$; $^1$H NMR (500 MHz, CDCl$_3$) δ 7.53 (d, J=8.29 Hz, 1 H), 7.09 (d, J=1.95 Hz, 1 H), 6.98 (dd, J=8.17, 1.83 Hz, 1 H), 3.94 (s, 3H), 2.51-2.61 (m, 2H), 2.35-2.46 (m, 2 H), 2.02-2.10 (m, 1 H), 1.66-1.79 (m, 1 H).

Step 2 methyl 6-chloro-5-[4-(1-hydroxy-cyclobutyl)-2-methoxy-phenyl]-1H-indole-3-carboxylate A mixture of methyl 6-Chloro-5-(5,5-dimethyl-[1,3,2]dioxaborinan-2-yl)-1H-indole-3-carboxylate (50 mg, 0.16 mmol), 1-(4-Bromo-3-methoxy-phenyl)cyclobutanol (40 mg, 0.16 mmol), 2M aqueous potassium carbonate (0.31 mL, 0.63 mmol), toluene (3 mL), and ethanol (1 mL) was sparged with nitrogen for 10 minutes, then treated with [1,1'-bis(diphenylphosphino)ferrocene]dichloropalladium(II) dichloromethane adduct (6 mg, 0.007 mmol). The reaction mixture was heated to 100° C. and stirred. After 2 hours the reaction was cooled to room temperature, diluted with ethyl acetate, washed with water and saturated brine, dried over magnesium sulfate, filtered and concentrated in vacuo to afford 60 mg brown foam, which was purified by flash chromatography (12 g silica, 0-95% ethyl acetate/heptane, 35 column volumes). Product fractions were combined and concentrated in vacuo to afford the title compound as a colorless solid (6.0 mg, 10% yield). MS (ES−) 384.2 (M−H)$^-$; $^1$H NMR (500 MHz, CD$_3$OD) δ 8.01 (s, 1 H), 7.91 (s, 1 H), 7.55 (s, 1 H), 7.21 (s, 1 H), 7.17-7.19 (m, 2 H), 3.87 (s, 3 H), 3.79 (s, 3 H), 2.59-2.67 (m, 2 H), 2.38-2.47 (m, 2 H), 2.02-2.12 (m, 1 H), 1.75-1.86 (m, 1 H).

Step 3

6-chloro-5-[4-(1-hydroxy-cyclobutyl)-2-methoxy-phenyl]-1H-indole-3-carboxylic acid Methyl 6-Chloro-5-[4-(1-hydroxy-cyclobutyl)-2-methoxy-phenyl]-1H-indole-3-carboxylate (6 mg, 0.02 mmol) was dissolved in methanol (1 mL) and 1N aqueous sodium hydroxide (0.2 mL, 0.2 mmol), and the mixture was stirred at 75° C. for 22 hours. The mixture was cooled to room temperature and treated with saturated ammonium chloride (0.5 mL) and concentrated in vacuo to afford 6 mg colorless solid, which was purified by reversed-phase HPLC to afford the title compound (2.7 mg, 50% yield). MS (ES−) 370.2 (M−H)$^-$. retention time=1.55 min; Column: Waters Atlantis dC18 4.6× 50 mm, 5 μm; Modifier: TFA 0.05%; Gradient: 95% H$_2$O/5%

MeCN linear to 5% H₂O/95% MeCN over 4.0 min, HOLD at 5% H₂O/95% MeCN to 5.0 min; Flow: 2.0 mL/min.

Example 63

5-(4-azetidin-2-yl-phenyl)-6-chloro-1H-indole-3-carboxylic acid

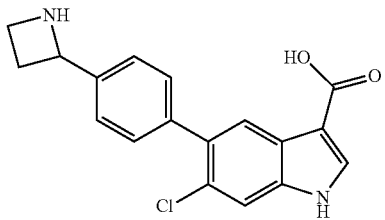 [SMILES: O=C(O)c1c[nH]c2cc(Cl)c(-c3ccc(C4CCN4)cc3)cc12]

Step 1 methyl 5-(4-azetidin-2-yl-phenyl)-6-chloro-1H-indole-3-carboxylate

A mixture of methyl 6-Chloro-5-(5,5-dimethyl-[1,3,2]dioxaborinan-2-yl)-1H-indole-3-carboxylate (50 mg, 0.16 mmol), 2-(4-bromophenyl)azetidine hydrochloride (400 mg, 1.24 mmol), 2M aqueous potassium carbonate (3.11 mL, 6.22 mmol), toluene (9 mL), and ethanol (3 mL) was sparged with nitrogen for 10 minutes, then treated with [1,1'-bis(diphenylphosphino)ferrocene]dichloropalladium(II) dichloromethane adduct (46 mg, 0.056 mmol). The reaction mixture was heated to 100° C. and stirred. After 2 hours the reaction was cooled to room temperature, diluted with ethyl acetate, washed with water and saturated brine, dried over magnesium sulfate, filtered and concentrated in vacuo to afford a yellow oil, which was purified by flash chromatography (40 g silica, 0-40% methanol/ethyl acetate (1% TEA modifier), 24 column volumes). Product fractions were combined and concentrated in vacuo to afford the title compound as a yellow solid (207 mg, 49% yield). MS (ES+) 341.2 (M+H)⁺; ¹H NMR (500 MHz, CD₃OD) δ 7.98 (d, J=3.90 Hz, 2 H), 7.56 (s, 1 H), 7.41 (s, 4 H), 5.02 (t, J=8.17 Hz, 1 H), 3.84 (s, 3 H), 3.68-3.79 (m, 1 H), 3.34-3.45 (m, 1 H), 2.47-2.66 (m, 2 H).

Step 2

5-(4-Azetidin-2-yl-phenyl)-6-chloro-1H-indole-3-carboxylic acid

Methyl 5-(4-Azetidin-2-yl-phenyl)-6-chloro-1H-indole-3-carboxylate (80 mg, 0.24 mmol) was dissolved in methanol (4 mL) and 1N aqueous sodium hydroxide (1 mL, 1 mmol), and the mixture was stirred at 70° C. for 22 hours. The mixture was cooled to room temperature and treated with saturated ammonium chloride (0.5 mL) and concentrated in vacuo to afford 77 mg yellow solid, which was purified by reversed-phase HPLC to afford the title compound (8 mg, 10% yield). MS (ES−) 325. 2 (M−H)⁻. retention time=1.44 min; Column: Waters Atlantis dC18 4.6×50 mm, 5 µm; Modifier: TFA 0.05%; Gradient: 95% H₂O/5% MeCN linear to 5% H₂O/95% MeCN over 4.0 min, HOLD at 5% H₂O/95% MeCN to 5.0 min; Flow: 2.0 mL/min.

Example 64

6-chloro-5-[4-(2-oxopyrrolidin-1-yl)phenyl]-1H-indole-3-carboxylic acid

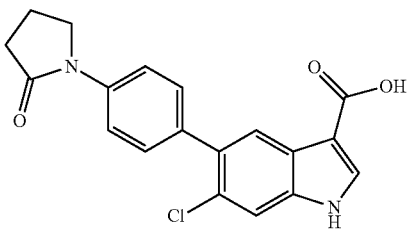 [SMILES: O=C(O)c1c[nH]c2cc(Cl)c(-c3ccc(N4CCCC4=O)cc3)cc12]

Step 1

1-(4-bromophenyl)pyrrolidin-2-one

The mixture of pyrrolidin-2-one (1.3 g, 15 mmol), 1-bromo-4-iodobenzene (2.8 g, 9.8 mmol), copper iodide (0.19 g, 0.98 mmol), cesium fluoride (3.7 g, 25 mmol) and N,N'-dimethylethylenediamine (186 mg, 0.196 mmol) in 1,4-dioxane (100 mL) was evacuated and back-filled with nitrogen three times. The reaction mixture was stirred at room temperature for 48 hours. The mixture was filtered and the filtrate was concentrated to give a white solid. The solid was purified by combi flash silica gel chromatography to give the title compound (1.1 g, 46% yield) as a white solid. ¹H NMR (400 MHz, CDCl₃): δ 7.52 (d, 2H), 7.48 (d, 2H), 3.83 (t, 2H), 2.59 (t, 2H), 2.18 (m, 2H).

Step 2 methyl 6-chloro-5-[4-(2-oxopyrrolidin-1-yl)phenyl]-1H-indole-3-carboxylate

To a mixture of 1-(4-bromophenyl)pyrrolidin-2-one (120 mg, 0.50 mmol), methyl-6-chloro-5-(5,5-dimethyl-1,3,2-dioxaborinan-2-yl)-1H-indole-3-carboxylate (160 mg, 0.50 mmol) and potassium acetate (147 mg, 1.50 mmol) in 1,4-dioxane (3 mL) was added PddppfCl₂ (36.5 mg, 0.050 mmol). The mixture was degassed and purged with nitrogen for 5 minutes, then allowed to heat to 100° C. and stirred under microwave irradiation for 40 minutes. The reaction mixture was concentrated in vacuo to give a brown residue. The residue was purified by combi flash silica gel chromatography to give the title compound (112 mg, 61% yield) as a white solid.

Step 3

6-chloro-5-[4-(2-oxopyrrolidin-1-yl)phenyl]-1H-indole-3-carboxylic acid

To a mixture of methyl 6-chloro-5-[4-(2-oxopyrrolidin-1-yl)phenyl]-1H-indole-3-carboxylate (112 mg, 0.30 mmol) in methanol (3 mL) and water (3 mL) was added sodium hydroxide (36 mg, 0.94 mmol). The reaction mixture was heated at 75° C. and stirred for 48 hours. The mixture was acidified to pH=4 using 1 N hydrochloric acid and concentrated to give a brown solid. It was purified by reverse phase HPLC to give the title compound (40 mg, 37% yield) as a pale solid. MS (ES+) 355.1 (M+H)+. $^1$H NMR (400 MHz, DMSO-d$_6$) δ 12.11 (br. s, 1 H), 11.95 (br. s, 1 H), 8.07 (s, 1 H), 7.95 (s, 1 H), 7.75 (d, 2 H), 7.62 (s, 1 H), 7.43 (d, 2 H), 3.89 (t, 2 H), 2.53 (m, 2 H), 2.09 (m, 2 H).

Example 65

5-[4-(1-acetylpiperidin-4-yl)phenyl]-6-chloro-1H-indole-3-carboxylic acid

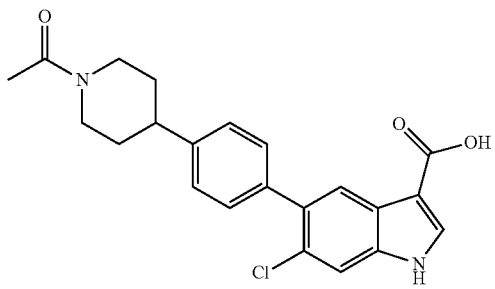 [SMILES: CC(=O)N1CCC(c2ccc(-c3cc4c(C(=O)O)c[nH]c4cc3Cl)cc2)CC1]

Step 1

1-[4-(4-bromophenyl)piperidin-1-yl]ethanone

To a solution of 4-(4-bromophenyl)piperidine (400 mg, 1.70 mmol) in dichloromethane (20 mL) was added triethylamine (340 mg, 3.40 mmol) and acetic anhydride (500 mg, 5.10 mmol). The mixture was stirred at room temperature for 2 hours. The reaction mixture was concentrated under reduced pressure to give a crude residue. The material was partitioned between water (20 mL) and ethyl acetate (20 mL). The layers were separated and the aqueous layer was washed two additional times with ethyl acetate (30 mL). The combined organics layers were dried over anhydrous sodium sulfate, filtered and concentrated under reduced pressure to give the title compound (260 mg, 60% yield) as a yellow oil. $^1$H NMR (400 MHz, CDCl$_3$) δ 7.27 (d, 2 H), 6.91 (d, 2 H), 4.63 (d, 1 H), 3.77 (d, 1 H), 3.00 (t, 1 H), 2.57-2.42 (t, 2 H), 1.97 (s, 3 H), 1.75-1.68 (m, 2 H), 1.47-1.40 (m, 2 H).

Step 2 methyl 5-[4-(1-acetylpiperidin-4-yl)phenyl]-6-chloro-1H-indole-3-carboxylate

To a solution of 1-[4-(4-bromophenyl)piperidin-1-yl]ethanone (200 mg, 0.70 mmol) in 1,4-dioxane/H$_2$O (5 mL/1 mL) was added methyl-6-chloro-5-(5,5-dimethyl-1,3,2-dioxaborinan-2-yl)-1H-indole-3-carboxylate (183 mg, 1.20 mmol), potassium carbonate (270 mg, 2.10 mmol) and PddppfCl$_2$ (50 mg, 0.070 mmol). The reaction mixture was degassed with nitrogen and the mixture was heated to 90° C. for 30 minutes. The reaction was concentrated under reduced pressure to give a crude product. The material was partitioned between water (20 mL) and ethyl acetate (20 mL). The layers were separated and the aqueous layer was washed two additional times with ethyl acetate (30 mL). The combined organics layers were dried over anhydrous sodium sulfate, filtered and concentrated under reduced pressure to to give the title compound (240 mg, 83% yield) which was used in the next step without further purification.

Step 3

5-[4-(1-acetylpiperidin-4-yl)phenyl]-6-chloro-1H-indole-3-carboxylic acid

To a solution of methyl 5-[4-(1-acetylpiperidin-4-yl)phenyl]-6-chloro-1H-indole-3-carboxylate (120 mg, 0.30 mmol) in MeOH (4 mL) was added sodium hydroxide (1 mL, 1 M). The mixture was heated to 70° C. for 24 h. Solvent was removed under reduced pressure. The residue was acidified to pH=5 and dried in vacuum to give an oil, which was purified by preparative HPLC to give the title compound (35 mg, 30% yield) as an off-white solid.

MS (ES+) 396.9 (M+H)+. $^1$H NMR (400 MHz, DMSO-d$_6$) δ 12.12 (s, 1 H), 11.95 (s, 1 H), 8.08 (d, 1 H), 7.94 (s, 1 H), 7.63 (s, 1 H), 7.39-7.32 (m, 4 H), 4.56 (d, 1 H), 3.95 (d, 1 H), 3.35-3.19 (m, 1 H), 3.86-3.83 (m, 1 H), 2.80-2.64 (m, 1 H), 2.03 (s, 3 H), 1.89-1.82 (m, 2 H), 1.70-1.47 (m, 2 H).

Example 66

6-chloro-5-[4-(1-hydroxy-2-methylpropan-2-yl)-3-methoxyphenyl]-1H-indole-3-carboxylic acid

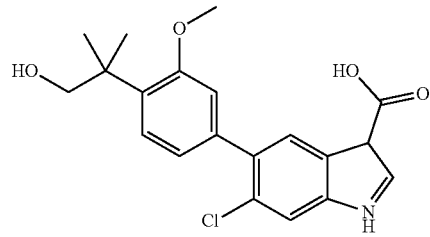 [SMILES: COc1cc(-c2cc3c(cc2Cl)N=CC3C(=O)O)ccc1C(C)(C)CO]

Step 1

Diethyl 2-(4-bromo-2-methoxyphenyl)malonate

A mixture of 4-bromo-1-iodo-2-methoxybenzene (1100 mg, 3.5 mmol), diethylmalonate (1240 mg, 7.70 mmol), cesium carbonate (1830 mg, 5.60 mmol), 2-picolinic acid (62 mg, 0.39 mmol), copper (I) iodide (34 mg, 0.18 mmol), and dioxane (7 ml) was stirred at 55° C. for 2 days. A very heavy slurry formed, LCMS indicates that the starting iodoarene is about 70% consumed. The mixture was cooled to room temperature and diluted with 30 mL of water and extracted with ethyl acetate. The extract was washed with water, brine, dried over magnesium sulfate, and concentrated to obtain the title compound which was about 60% pure by LCMS and was used for the next step without purification. GCMS (ES+) 344 (M+).

Step 2

Ethyl 2-(4-bromo-2-methoxyphenyl)acetate

A mixture of diethyl 2-(4-bromo-2-methoxyphenyl)malonate (1213 mg, 3.500 mmol), lithium chloride (620 mg, 14.6 mmol), and DMSO (6 ml) was stirred at 120° C. for 20 hours, then at 150° C. for 4 hours, and again at 120° C. for 20 hours. The reaction was cooled to room temperature, diluted with 25 mL of water, and extracted with ethyl acetate-heptane mixture (1:1). The extract was washed with brine (2 times), dried over magnesium sulfate, and loaded on silica gel. Chromatography on a silica gel column, eluting with a gradient from 0% to 30% of ethyl acetate in heptane gave the title compound (405 mg, 42% yield over two steps). GCMS (ES+) 272 (M+).

Step 3

Ethyl 2-(4-bromo-2-methoxyphenyl)-2-methylpropanoate

To a stirred solution of ethyl 2-(4-bromo-2-methoxyphenyl)acetate (105 mg, 0.38 mmol) in THF (4 mL) were added successively, in drops, 1 M solution of t-BuOK in THF (1.2 mL, 1.2 mmol) and iodomethane (0.10 mL, 1.6 mmol) at 0° C. The resulting mixture was warmed to room temperature in 30 min and stirred for 2 hours—the starting ester is consumed, the target product formed formed (TLC, GCMS). To the obtained mixture 1 M solution of potassium bisulfate (2 mL) was added followed by addition of water (5 mL). The mixture was extracted with ethyl acetate. The organic extract was washed with brine, dried over anhydrous magnesium sulfate, and concentrated to obtain the title compound (110 mg, 95% yield), which was used for the next step without purification. GCMS (ES+) 300 (M+). $^1$H NMR (500 MHz, CDCl$_3$) δ 7.15 (s, 1H), 7.11 (d, J=1.5 Hz, 1H), 6.98 (d, J=2.0 Hz, 1H), 4.11 (q, J=7.1 Hz, 2H), 3.78 (s, 3H), 1.50 (s, 6H), 1.17 (t, J=7.1 Hz, 3H).

Step 4

2-(4-Bromo-2-methoxyphenyl)-2-methylpropan-1-ol

To a stirred solution of ethyl 2-(4-bromo-2-methoxyphenyl)-2-methylpropanoate (110 mg, 0.36 mmol) in THF (4 mL) was added 1 M solution of lithium aluminum hydride in THF (0.4 mL, 0.4 mmol) at −60° C. and the reaction mixture was warmed up to 0° C. in 40 min (the starting material is still present by TLC) and then allowed to stir at room temperature for 4 hours—now the starting material is consumed (TLC). A solution of sodium hydroxide (105 mg) in water (0.2 mL) was added and the mixture was stirred at room temperature for 30 min. Then 3 mL of methylene chloride (3 mL), silica gel (1 g), and anhydrous magnesium sulfate (1 g) were added and the mixture was stirred for 2 hours. Solids were filtered off and mother liquor was concentrated to give the title compound (85 mg). By GCMS, this is a mixture of the target primary alcohol and de-brominated primary alcohol (40% of the desired product by GCMS). This mixture was used for the next step without purification. GCMS (ES+) 258 (M+).

Step 5

Methyl 6-chloro-5-(4-(1-hydroxy-2-methylpropan-2-yl)-3-methoxyphenyl)-1H-indole-3-carboxylate A mixture of 2-(4-bromo-2-methoxyphenyl)-2-methylpropan-1-ol (crude product from Step 4, containing 40% of the desired material, 75 mg, 0.12 mmol), methyl 6-chloro-5-(5,5-dimethyl-1,3,2-dioxaborinan-2-yl)-1H-indole-3-carboxylate (45 mg, 0.14 mmol), PdCl$_2$(dppf) (11 mg, 0.013 mmol), potassium carbonate (80 mg, 0.58 mmol), toluene (0.6 mL), ethanol (0.3 mL), water (0.3 mL) and THF (0.3 mL) was stirred at 115° C. for 2.5 hours. The reaction mixture was cooled to room temperature and extracted with ethyl acetate (4 mL) of ethyl acetate. The extract was loaded on silica gel. Chromatography on a silica gel column, eluting with a gradient from 10% to 40% of ethyl acetate in heptane gave the title compound (25 mg, 56% yield). MS (ES−) 386.2 (M−H)−. Retention time: 3.38 min. Column: Phenomenex Gemini-NX, 4.6 mm×50 mm, C18, 3 μm, 110A; Column Temperature 60° C. Mobile Phase A: 0.1% formic acid in water (v/v); Mobile Phase B: 0.1% formic acid in acetonitrile (v/v) Gradient Profile: Flow-1.5 mL/min. Initial conditions: A-95%, B-5%; Linear Ramp to A-0%, B-100% over 0.0-4.10 min; hold at A-0%, B-100% from 4.10-4.50 min; return to initial conditions 4.60-5.0 min.

Step 6

6-Chloro-5-[4-(1-hydroxy-2-methylpropan-2-yl)-3-methoxyphenyl]-1H-indole-3-carboxylic acid A mixture of the methyl 6-chloro-5-(4-(1-hydroxy-2-methylpropan-2-yl)-3-methoxyphenyl)-1H-indole-3-carboxylate (25 mg, 0.064 mmol), 2.4 ml of methanol (2.4 mL), and 0.8 mL of 1 M aqueous solution of sodium hydroxide (0.8 mL, 0.8 mmol) was stirred at 70° C. for 24 hours—the starting material is consumed by TLC and LCMS. The reaction mixture was cooled to room temperature, diluted with 1 M solution of potassium bisulfate (1 mL) and the obtained mixture was concentrated. The residue was partitioned between ethyl acetate and water. The organic extract was washed with brine, dried over anhydrous magnesium sulfate and loaded on silica gel. A silica gel column was equilibrated with 30% ethyl acetate in heptane. Chromatography on this column, eluting with a solution of 3% of acetic acid and 30% of ethyl acetate in heptane gave the title compound (18 mg, 73% yield). MS (ES−) 372.1 (M−H)−. Retention time: 3.00 min Column: Phenomenex Gemini-NX, 4.6 mm×50 mm, C18, 3 μm, 110A; Column Temperature 60° C. Mobile Phase A: 0.1% formic acid in water (v/v); Mobile Phase B: 0.1% formic acid in acetonitrile (v/v) Gradient Profile: Flow-1.5 mL/min. Initial conditions: A-95%, B-5%; Linear Ramp to A-0%, B-100% over 0.0-4.10 min; hold at A-0%, B-100% from 4.10-4.50 min; return to initial conditions 4.60-5.0 min.

Example 67

6-chloro-5-(2'-hydroxybiphenyl-4-yl)-1H-indole-3-carboxylic acid

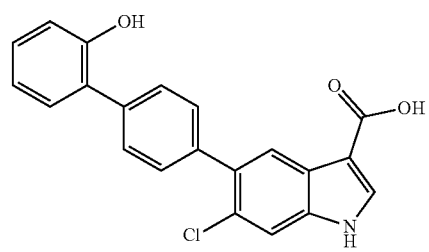 [SMILES: O=C(O)c1c[nH]c2cc(Cl)c(-c3ccc(-c4ccccc4O)cc3)cc12]

Step 1 methyl 6-chloro-5-(2'-hydroxybiphenyl-4-yl)-1H-indole-3-carboxylate

A glass tube was charged with 4'-(4,4,5,5-tetramethyl-1,3,2-dioxaborolan-2-yl)-[1,1'-biphenyl]-2-ol (86.2 mg, 0.29 mmol), methyl 5-bromo-6-chloro-1H-indole-3-carboxylate (84 mg, 0.29 mmol), toluene (1.2 mL), THF (0.6 mL), EtOH (0.6 mL), and 2.0 M potassium carbonate solution (0.6 mL, 1.2 mmol). Nitrogen was then bubbled through the mixture for 5 minutes then [1,1'-bis(diphenylphosphino)ferrocene] dichloropalladium(II) (28 mg, 0.032 mmol) was added. The tube was sealed and heated to 115° C. for 2 hours. The reaction was cooled to room temperature, opened, and neutralized with 1.0 M sodium hydrogensulfate then diluted with ethyl acetate. The layers were separated and the aqueous extracted with ethyl acetate (×2). The combined organic layers were dried over sodium sulfate, filtered, and concentrated in vacuo. Flash column chromatography (20% to 100% ethyl acetate/heptane) was then used to to provide the title compound as a white solid (80 mg, 73% yield). MS (ES−) 376.1 (M−H). $^1$H NMR (500 MHz, DMSO-$d_6$) δ 12.09 (br. s., 1 H), 9.60 (s, 1 H), 8.19 (s, 1 H), 7.98 (s, 1 H), 7.68 (s, 1 H), 7.65 (d, 2 H), 7.47 (d, 2 H), 7.34 (dd, 1 H), 7.19 (dt, 1 H), 6.98 (d, 1 H), 6.91 (dt, 1 H), 3.81 (s, 3 H).

Step 2

6-chloro-5-(2'-hydroxybiphenyl-4-yl)-1H-indole-3-carboxylic acid

A round bottomed flask was charged with methyl 6-chloro-5-(2'-hydroxybiphenyl-4-yl)-1H-indole-3-carboxylate (80 mg, 0.21 mmol), methanol (1.8 mL), and sodium hydroxide solution (1.0 M, 0.60 mL, 0.60 mmol) then heated to 70° C. with stirring for 15 h. The reaction was then cooled to room temperature and quenched with 1.0 M Hydrochloric acid and diluted with ethyl acetate. The layers were separated and the aqueous extracted with ethyl acetate (×3). The combined organic layers were dried over sodium sulfate, filtered, and concentrated in vacuo. Reverse phase HPLC was then used to provide the title compound (13 mg, 16% yield). MS (ES−) 362.0 (M−H)−. Retention time: 1.93 min Waters Xbridge dC18 5 μm 4.6×50 mm, 95% H$_2$O/5% MeCN linear to 5% H$_2$O/95% MeCN over 4.0 min, HOLD at 5% H$_2$O/95% MeCN to 5.0 min. (0.03% NH$_4$OH). Flow: 2.0 mL/min.

Example 68

6-Bromo-5-(2'-hydroxybiphenyl-4-yl)-1H-indole-3-carboxylic acid

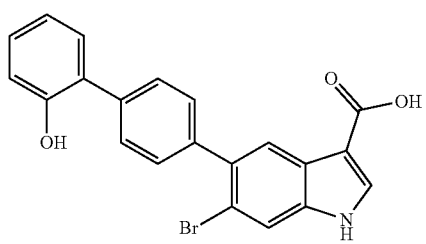 [SMILES: O=C(O)c1c[nH]c2cc(Br)c(-c3ccc(-c4ccccc4O)cc3)cc12]

Step 1

Methyl 6-bromo-5-iodo-1H-indole-3-carboxylate

To a suspension of methyl 5-iodo-1H-indole-3-carboxylate (1.20 g, 3.09 mmol) in acetic acid (30 ml) was added a solution of bromine (0.15 ml, 2.9 mmol) in acetic acid (5 ml). Reaction was heated to reflux and stirred for 3 hours. The reaction was then cooled and poured onto ice water, then partitioned between water and dichloromethane. The aqueous layer was extracted with 10% MeOH/DCM (2×100 mL). The organics were combined, washed with brine, and dried over sodium sulfate, filtered and concentrated to give a dark red semi solid. The residue was taken up in methanol (30 ml). Concentrated sulfuric acid (0.5 ml) was added and mixture was heated to 70° C. for 2 days. The reaction was cooled then concentrated in vacuo and the residue partitioned between ethyl acetate and aqueous sodium bicarbonate solution. The layers were separated and organic washed with brine, dried over sodium sulfate, filtered and concentrated to give a reddish solid. The residue was dissolved in methanol/dichloromethane and adsorbed onto silica gel and purified by silica gel chromatography (50 g, 20-100% ethyl acetate/heptane). The major peak was isolated to afford a mixture of the title compound and methyl 5-iodo-1H-indole-3-carboxylate confirmed as a brown solid (260 mg) that was taken forward without further purification.

Step 2

Methyl 6-bromo-5-(2'-hydroxybiphenyl-4-yl)-1H-indole-3-carboxylate

To a solution of methyl 6-bromo-5-iodo-1H-indole-3-carboxylate (100 mg, 0.26 mmol) in toluene (1 ml) and ethanol (1 ml) was added 4'-(4,4,5,5-tetramethyl-1,3,2-dioxaborolan-2-yl)biphenyl-2-ol (70 mg, 0.24 mmol) followed by aqueous potassium carbonate (2 M, 1 ml, 2.0 mmol). The solvent was degassed by passing nitrogen through the system for 5 min. Pd(dppf)Cl$_2$ (10 mg, 0.0053 mmol) was added then sealed and reaction heated to 110° C. The reaction was cooled then partitioned between water and ethyl acetate, then washed with brine, dried over sodium sulfate, filtered, concentrated in vacuo to afford the title compound mixed with unidentified byproducts as a dark tan solid (120 mg). TLC (50% EtOAc/Heptane) indicates no separation between product and byproducts. Crude was taken on to the next step without purification.

Step 3

6-Bromo-5-(2'-hydroxybiphenyl-4-yl)-1H-indole-3-carboxylic acid

To a semi suspension of crude methyl 6-bromo-5-(2'-hydroxybiphenyl-4-yl)-1H-indole-3-carboxylate (120 mg, 0.284 mmol) in methanol (4 ml) was added 1N NaOH (1 mL, 1 mmol) then heated to 70° C. for 16 hrs. 5N NaOH (1 mL, 5 mmol) was then added and heating continued for 24 hrs. The reaction was cooled and quenched with 4N HCl in dioxane (2 ml, 8 mmol) then concentrated to give a brown solid which was purified by reverse phase preparative HPLC to afford the title compound as a tan solid (9 mg, 8%) MS (AP−) 406.0 (M−H)−. $^1$H NMR (400 MHz, MeOH-$d_4$) δ: 8.10 (s, 1H), 7.99 (s, 1H), 7.80 (s, 1H), 7.63 (d, 2H), 7.46 (d, 2H), 7.35 (dd, 1H), 7.17 (td, 1H), 6.86-6.98 (m, 2H).

Example 69

6-chloro-5-[2-cyano-4-(1-hydroxycyclobutyl)phenyl]-1H-indole-3-carboxylic acid

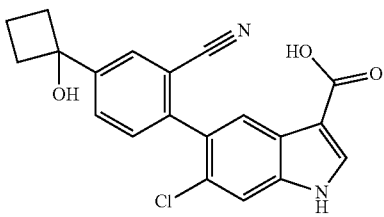 [SMILES: N#Cc1cc(C2(O)CCC2)ccc1-c1cc2c(C(=O)O)c[nH]c2cc1Cl]

Step 1

2-bromo-5-(1-hydroxycyclobutyl)benzonitrile

To 2-bromo-5-iodobenzonitrile (1457 mg, 4.730 mmol) in tetrahydrofuran (10 mL) at −40° C. was added isopropyl magnesium chloride.lithium chloride (1.3 M in THF, 4.4 mL, 5.7 mmol) dropwise. The mixture was stirred at −40° C. for 10 minutes, and was then treated with cyclobutanone (0.4 mL, 5.2 mmol) dropwise at −40° C. The reaction mixture was warmed to room temperature and stirred at that temperature for 16 hours. The reaction mixture was poured into water (10 mL) and extracted with ethyl acetate (3×20 mL). The combined organic layers were dried over sodium sulfate, filtered and concentrated in vacuo to give the title compound which was used directly in the next step without further purification.

Step 2

2-(5,5-dimethyl-1,3,2-dioxaborinan-2-yl)-5-(1-hydroxycyclobutyl)benzonitrile

A suspension of 2-bromo-5-(1-hydroxycyclobutyl)benzonitrile (1193 mg, 3.800 mmol), 5,5,5',5'-tetramethyl-2,2'-bi-1,3,2-dioxaborinane (1680 mg, 4.920 mmol), potassium acetate (1110 mg, 11.40 mmol) and [1,1'-bis(diphenylphosphino)ferrocene]dichloropalladium(II) (154 mg, 0.189 mmol) in 1,4-dioxane (10 mL) was sealed in a microwave tube and thermally heated to 120° C. for 1 hour. The reaction mixture was poured into water (30 mL) and extracted with ethyl acetate (2×30 mL). The combined organic layers were dried over sodium sulfate, filtered and concentrated in vacuo. The crude product was purified by flash chromatography using heptanes/ethyl acetate (0:100 to 50:50) to give the title compound (1.0 g, 94% yield).

Step 3

6-chloro-5-[2-cyano-4-(1-hydroxycyclobutyl)phenyl]-1H-indole-3-carboxylic acid

A suspension of 5-bromo-6-chloro-1H-indole-3-carboxylic acid (100 mg, 0.54 mmol), 2-(5,5-dimethyl-1,3,2-dioxaborinan-2-yl)-5-(1-hydroxycyclobutyl)benzonitrile (124 mg, 0.435 mmol), 0.5 M aqueous potassium phosphate (1.74 mL, 0.87 mmol) and [1,1'-bis(diphenylphosphino)ferrocene]dichloropalladium(II) (11 mg, 0.014 mmol) in ethanol (4 mL) was sealed in a microwave tube and heated to 85° C. for 45 minutes. The reaction was diluted with water and extracted with ethyl acetate (2×10 mL). The reaction mixture was filtered through celite and the phases were separated. The organic phase was dried over sodium sulfate, filtered and concentrated in vacuo and the residue was purified by reverse phase chromatography to give the title compound. MS (ES−) 365.1 (M−H)⁻. Retention time: 1.60 min. Column: Waters Atlantis dC18 4.6×50 mm, 5 μm. Modifier: TFA 0.05%. Gradient: 95% $H_2O$/5% MeCN linear to 5% $H_2O$/95% MeCN over 4.0 min, HOLD at 5% $H_2O$/95% MeCN to 5.0 min. Flow: 2.0 ml/min.

Example 70

5-[4-(2-amino-2-oxoethoxy)phenyl]-6-chloro-1H-indole-3-carboxylic acid

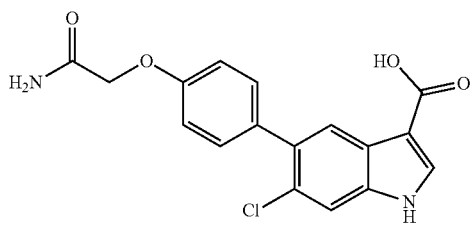 [SMILES: NC(=O)COc1ccc(-c2cc3c(C(=O)O)c[nH]c3cc2Cl)cc1]

Step 1

2-(4-bromophenoxy)acetamide

To a solution of (4-bromophenoxy)acetic acid (500 mg, 2.00 mmol) in dichloromethane (10 mL) and DMF (0.2 mL) was added 2 M oxalyl choride in methylene chloride (5 mL, 10 mmol). The reaction mixture was stirred at room temperature for 2 hours, and the solvent was removed under reduced pressure. Ammonium hydroxide (15 mL) was added dropwise via additional funnel. After addition, the mixture was extracted with EtOAc (3×20 mL). The combined organic layers were dried and concentrated in vacuo to give 2-(4-bromophenoxy)acetamide (350 mg, 70% yield) as a yellow solid. ¹H NMR (400 MHz, $CDCl_3$): δ 7.37-7.35 (m, 2 H), 6.81-6.79 (m, 2 H), 4.59 (s, 2 H).

Step 2

6-chloro-5-(5,5-dimethyl-1,3,2-dioxaborinan-2-yl)-1H-indole

To a solution of 5-bromo-6-chloro-1H-indole (5.0 g, 22 mmol) in DMSO (30 mL) was added 5,5,5',5'-tetramethyl-2,2'-bi-1,3,2-dioxaborinane (6.4 g, 28 mmol) and KOAc (10.3 g, 0.11 mol). The sealed vial was heated to 100° C. for 1 h. The reaction was quenched with water (100 mL) mL) and extracted with ethyl acetate. The combined organics were dried and concentrated in vacuo to give the title compound (2.9 g, 55% yield) as a yellow solid.

¹H NMR (400 MHz, $CDCl_3$) δ 8.11 (br. s., 1 H), 7.99 (s, 1 H), 7.37 (s, 1 H), 7.14 (s, 1 H), 6.51 (s, 1 H), 3.83 (s, 4 H), 1.08 (s, 6 H).

Step 3

2-[4-(6-chloro-3-formyl-1H-indol-5-yl)phenoxy]acetamide

A mixture of 6-chloro-5-(5,5-dimethyl-1,3,2-dioxaborinan-2-yl)-1H-indole (260 mg, 1.00 mmol) and N,N-dimethylformiminium chloride (250 mg, 2.00 mmol) in dry 1,4-dioxane (5 mL) and DMF (1 mL) was sealed in a reaction vessel and stirred at room temperature for 10 minutes to give a white slurry. To the slurry was added 2 M aqueous potassium carbonate (2.5 mL, 5 mmol), 2-(4-bromophenoxy)acetamide (240 mg, 1.00 mmol) and [1,1'-bis(diphenylphosphino)ferrocene]dichloropalladium(II) (50 mg). The sealed vial was degassed with nitrogen and heated to 90° C. for 30 minutes. The reaction was quenched with water (20 mL), and extracted with EtOAc (3×20 mL). The combined organic layers were dried and concentrated in vacuo to give 2-[4-(6-chloro-3-formyl-1H-indol-5-yl)phenoxy]acetamide (250 mg, 55% yield) as a yellow solid.

Step 4

5-[4-(2-amino-2-oxoethoxy)phenyl]-6-chloro-1H-indole-3-carboxylic acid

To a mixture of 2-[4-(6-chloro-3-formyl-1H-indol-5-yl)phenoxy]acetamide (100 mg, 0.30 mmol) in acetonitrile (5 mL) and tert-butanol (5 mL) was added 2-methyl-2-butene (4 mL). The reaction mixture was cooled to 0° C. and treated with a solution of sodium chlorite (540 mg, 6.00 mmol) and sodium phosphate monobasic hydrate (850 mg, 6.00 mmol) in water (5 mL) dropwise via additional funnel. The ice bath was removed and the reaction was stirred at room temperature for 48 h. The solvent was removed in vacuo to give a residue, which was purified by prep-HPLC (Prep-HPLC: Column: Kromasil Eternity-5-C18 150*30 mm*5 μm Mobile phase: from 24% MeCN in water (0.225% FA) to 34% MeCN in water (0.225% FA); Wavelength: 220 nm Flow rate: 30 mL/min) to give 5-[4-(2-amino-2-oxoethoxy)phenyl]-6-chloro-1H-indole-3-carboxylic acid (22 mg, 20% yield) as a white solid. MS (ES+) 344.8 (M+H)+. 1H NMR (400 MHz, CD3OD) δ 8.01-7.99 (m, 2 H), 7.57 (s, 1 H), 7.43-7.39 (m, 2 H), 7.07-7.05 (m, 2 H), 4.56 (s, 2 H).

Example 71

6-chloro-5-[4-(2-hydroxyethyl)phenyl]-1H-indole-3-carboxylic acid

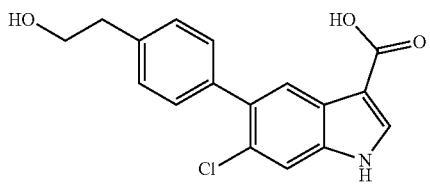 [SMILES: O=C(O)c1c[nH]c2cc(Cl)c(-c3ccc(CCO)cc3)cc12]

Step 1

6-chloro-5-[4-(2-hydroxyethyl)phenyl]-1H-indole-3-carbaldehyde

A mixture of 6-chloro-5-(5,5-dimethyl-1,3,2-dioxaborinan-2-yl)-1H-indole (260 mg, 1.00 mmol) and N,N-dimethylformiminium chloride (250 mg, 2.00 mmol) in dry 1,4-dioxane (5 mL) and DMF (1 mL) was sealed in a reaction vessel and stirred at room temperature for 10 minutes to give a white slurry. To the slurry was added 2 M aqueous potassium carbonate (2.5 mL, 5.0 mmol), 2-(4-bromophenyl)ethanol (200 mg, 1.00 mmol) and [1,1'-bis(diphenylphosphino)ferrocene]dichloropalladium(II) (50 mg). The sealed vial was degassed and heated to 90° C. for 30 min. The cooled reaction mixture was poured into water (20 mL), and extracted with EtOAc (3×20 mL). The combined organic layers were dried and concentrated in vacuo to give 6-chloro-5-[4-(2-hydroxyethyl)phenyl]-1H-indole-3-carbaldehyde (180 mg, 68% yield) which was used in the next step without purification.

Step 2

6-chloro-5-[4-(2-hydroxyethyl)phenyl]-1H-indole-3-carboxylic acid

To a mixture of 6-chloro-5-[4-(2-hydroxyethyl)phenyl]-1H-indole-3-carbaldehyde (150 mg, 0.50 mmol) in acetonitrile (5 mL) and tert-butanol (5 mL) was added 2-methyl-2-butene (5 mL). The reaction mixture was cooled to 0° C. and treated with a solution of sodium chlorite (900 mg, 10.0 mmol) and sodium phosphate monobasic hydrate (1.4 g, 10 mmol) in water (5 mL) dropwise via additional funnel. Then ice bath was removed, and the reaction was stirred at room temperature for 20 hours. The solvent was removed in vacuo to give a residue, which was purified by pre-HPLC (Kromasil Eternity-5-C18 150×30 mm×5 μm Mobile phase: from 26% MeCN in water (0.1% TFA) to 41% MeCN in water (0.1% TFA); Wavelength: 220 nm Flow rate: 30 mL/min) to give 6-chloro-5-[4-(2-hydroxyethyl)phenyl]-1H-indole-3-carboxylic acid (35 mg, 25% yield) as a white solid. MS (ES+) 337.9 (M+Na)+. 1H NMR (400 MHz, CD3OD) δ 8.01-7.99 (m, 2 H), 7.57 (s, 1 H), 7.37 (d, 2 H), 7.30 (d, 2 H), 3.80 (t, 2 H), 2.91 (t, 2 H).

Example 72

6-chloro-5-{4-[1-(hydroxymethyl)cyclobutyl]phenyl}-1H-indole-3-carboxylic acid

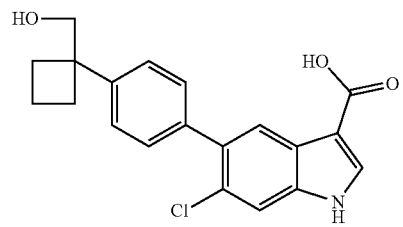 [SMILES: O=C(O)c1c[nH]c2cc(Cl)c(-c3ccc(C4(CO)CCC4)cc3)cc12]

Step 1

1-(4-bromophenyl)cyclobutanecarboxylic acid

To a solution of 1-(4-bromophenyl)cyclobutanecarbonitrile (1.0 g, 4.2 mmol) in EtOH (28 mL) and water (2 mL) was added KOH (2.1 g, 42 mmol). The reaction mixture was heated to reflux for 16 hours. The reaction was then quenched with 1M hydrochloric acid in order to adjust pH to 7. The organic solvents were removed in vacuo to give a residue, which was dissolved in ethyl acetate (40 mL), then washed with brine (3×10 mL). The organic phase was concentrated in vacuo, and the resulting oil was purified by flash chromatography on silica gel (petroleum ether/ethyl acetate=8:1) to give 1-(4-bromophenyl)cyclobutanecarboxylic acid (0.8 g, 79% yield) as a white solid. $^1$H NMR (400 MHz, DMSO-$d_6$) δ 7.47 (d, 2 H), 7.19 (d, 2 H), 2.70-2.63 (m, 2 H), 2.33-2.26 (m, 2 H), 1.89-1.87 (m, 1 H), 1.75-1.71 (m, 1 H).

Step 2

[1-(4-bromophenyl)cyclobutyl]methanol

To a solution of 1-(4-bromophenyl)cyclobutanecarboxylic acid (300 mg, 1.20 mmol) in 1,4-dioxane (5 mL) was added borane dimethylsulfide complex (0.24 mL, 2.4 mmol) dropwise at 0° C. The ice bath was removed, and the reaction mixture was stirred at room temperature for 10 min. The reaction mixture was quenched with methanol (20 mL). The organic solvents were removed under reduced pressure to give a residue, which was dissolved in ethyl acetate, then washed with brine. The organic phase was concentrated to give [1-(4-bromophenyl)cyclobutyl]methanol (170 mg, 62% yield) as a yellow oil which was used directly in the next step.

Step 3

6-chloro-5-{4-[1-(hydroxymethyl)cyclobutyl]phenyl}-1H-indole-3-carbaldehyde

A mixture of 6-chloro-5-(5,5-dimethyl-1,3,2-dioxaborinan-2-yl)-1H-indole (260 mg, 1.00 mmol) and N,N-dimethylformiminium chloride (250 mg, 2.00 mmol) in dry dioxane (5 mL) and DMF (1 mL) was sealed in a reaction vessel and stirred at room temperature for 10 minutes to give a white slurry. To the slurry was added 2M aqueous potassium carbonate (2.5 mL, 5.0 mmol), [1-(4-bromophenyl)cyclobutyl]methanol (240 mg, 1.00 mmol) and [1,1'-bis(diphenylphosphino)ferrocene]dichloropalladium(II) (50 mg). The reaction mixture was degassed with nitrogen and heated to 90° C. for 30 minutes. The reaction was quenched with water (20 mL) and extracted with EtOAc (3×20 mL). The combined organic phases were dried and concentrated in vacuo to give 6-chloro-5-{4-[1-(hydroxymethyl)cyclobutyl]phenyl}-1H-indole-3-carbaldehyde (180 mg, 68% yield), which was used into next step without further purification.

Step 4

6-chloro-5-{4-[1-(hydroxymethyl)cyclobutyl]phenyl}-1H-indole-3-carboxylic acid

To a mixture of 6-chloro-5-{4-[1-(hydroxymethyl)cyclobutyl]phenyl}-1H-indole-3-carbaldehyde (80 mg, 0.24 mmol) in acetonitrile (6 mL) and tert-butanol (6 mL) was added 2-methyl-2-butene (3 mL). The reaction mixture was cooled to 0° C. and treated with a solution of sodium chlorite (420 mg, 4.80 mmol) and sodium phosphate monobasic hydrate (650 mg, 4.80 mmol) in water (3 mL) dropwise via additional funnel. The ice bath was removed, and the reaction mixture was stirred at room temperature for 24 hours. The solvent was removed in vacuo to give a residue, which was purified by prep-HPLC (Kromasil Eternity-5-C18 150*30 mm*5 µm Mobile phase: from 35% MeCN in water (0.1% TFA) to 50% MeCN in water (0.1% TFA); Wavelength: 220 nm Flow rate: 30 mL/min) to give 6-chloro-5-{4-[1-(hydroxymethyl)cyclobutyl]phenyl}-1H-indole-3-carboxylic acid (25 mg, 32% yield) as a white solid. MS (ES+) 377.9 (M+Na)$^+$. $^1$H NMR (400 MHz, CD$_3$OD) δ 8.01 (s, 1H), 7.97 (s, 1H), 7.57 (s, 1 H), 7.39 (d, 2 H), 7.23 (d, 2 H), 3.70 (s, 2H), 2.39-2.30 (m, 4 H), 2.11-2.09 (m, 1 H), 1.92-1.91 (m, 1 H).

Example 73

6-chloro-5-[2-(dimethylamino)pyrimidin-5-yl]-1H-indole-3-carboxylic acid

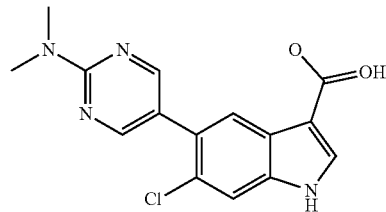 [SMILES: CN(C)c1ncc(-c2cc3c(C(=O)O)c[nH]c3cc2Cl)cn1]

Step 1

6-chloro-5-[2-(dimethylamino)pyrimidin-5-yl]-1H-indole-3-carbaldehyde

To a solution of 6-chloro-5-(5,5-dimethyl-1,3,2-dioxaborinan-2-yl)-1H-indole (150 mg, 0.57 mmol) in anhydrous 1,4-dioxane (5 mL) and DMF (1 mL) was added N,N-dimethylformiminium chloride (145 mg, 1.13 mmol). The reaction mixture was stirred at room temperature for 20 minutes to give a thick solution. The reaction mixture was then treated with 2 N aqueous potassium carbonate (393 mg, 2.85 mmol), 5-bromo-N,N-dimethylpyrimidin-2-amine (115 mg, 0.57 mmol) and [1,1'-bis(diphenylphosphino)ferrocene]dichloropalladium(II) (50 mg, 0.068 mmol) and degassed with nitrogen for 2 minutes. The reaction mixture was heated to 90° C. for 30 minutes. After cooling to room temperature, the solvents were removed in vacuo and the residue was purified by column chromatography on silica gel (EtOAc/petroleum ether=1:5 to 1:1) to afford 6-chloro-5-[2-(dimethylamino) pyrimidin-5-yl]-1H-indole-3-carbaldehyde (100 mg, 58.3% yield) as a yellow solid. $^1$H NMR (400 MHz, DMSO-$d_6$) δ 12.25 (s, 1 H), 9.92 (s, 1 H), 8.40 (s, 2 H), 8.36 (s, 1 H), 8.01 (s, 1 H), 7.69 (s, 1 H), 3.15 (s, 6 H).

Step 2

6-chloro-5-[2-(dimethylamino)pyrimidin-5-yl]-1H-indole-3-carboxylic acid 6-chloro-5-[2-(dimethylamino)pyrimidin-5-yl]-1H-indole-3-carbaldehyde (100 mg, 0.333 mmol) was dissolved in acetonitrile (6 mL) and warm tert-butanol (6 mL) and treated with 2-methyl-2-butene (4 mL). The reaction mixture was cooled to 0° C. and treated with a solution of sodium chlorite (450 mg, 6.65 mmol) and sodium phosphate monobasic dihydrate (1.04 g, 6.65 mmol) in water (3 mL) dropwise via addition funnel. The reaction mixture was warmed to room temperature and stirred for 20 hours. The reaction mixture was concentrated to remove the organics and extracted with EtOAc (3×20 mL). The combined organic layers were washed with brine (20 mL), dried and concentrated in vacuo. The crude product was purified by prep-HPLC (Column: Agella venusil ASB C18 150×21.2 mm×5 µm; Mobile phase: from 20% MeCN in water (0.1% HCl) to 45% MeCN in water (0.1% HCl) Wavelength: 220 nm) to give 6-chloro-5-[2-(dimethylamino)pyrimidin-5-yl]-1H-indole-3-carboxylic acid (43 mg, 41% yield) as a yellow solid. MS (ES+) 316.9 (M+H)+. 1H NMR (400 MHz, DMSO-d6) δ 11.98 (s, 1 H), 8.42 (s, 2 H), 8.08 (d, 1 H), 7.93 (s, 1 H), 7.65 (s, 1 H), 3.17 (s, 6 H).

Example 74

6-chloro-5-[4-(1-methylpyrrolidin-3-yl)phenyl]-1H-indole-3-carboxylic acid

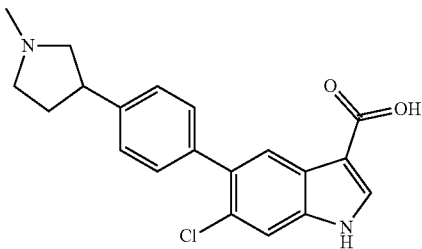

Step 1

3-(4-bromophenyl)-1-methylpyrrolidine

To a mixture of 3-(4-bromophenyl)pyrrolidine hydrochloride (200 mg, 0.76 mmol) in methanol (6 mL) was added triethylamine (77 mg, 0.76 mmol) and several drops of acetic acid. The reaction mixture was stirred at room temperature for 5 min and treated with aqueous formaldehyde (37%, 0.2 mL) and sodium triacetoxyborohydride (322 mg, 1.52 mmol). The reaction mixture was stirred for 18 h at room temperature. The methanol was evaporated in vacuo and the residue was partitioned between water and EtOAc. The phases were separated and the aqueous phase was back-extracted with EtOAc. The combined organic phases were washed with brine, dried over Na2SO4, and concentrated in vacuo to give 3-(4-bromophenyl)-1-methylpyrrolidine (0.247 g) as a solid, which was used in the next step without further purification. MS (ES+) 239.9 (M+H)+.

Step 2

6-chloro-5-[4-(1-methylpyrrolidin-3-yl)phenyl]-1H-indole-3-carbaldehyde

To 6-chloro-5-(5,5-dimethyl-1,3,2-dioxaborinan-2-yl)-1H-indole (118 mg, 0.446 mmol) in anhydrous 1,4-dioxane (3.7 mL) and anhydrous DMF (0.74 mL) was added N,N-dimethylformiminium chloride (114 mg, 0.892 mmol). The reaction mixture was stirred for 10 min at room temperature, yielding a thick suspension. The reaction mixture was treated with 2 N aqueous potassium carbonate (1.1 mL, 2.2 mmol), 3-(4-bromophenyl)-1-methylpyrrolidine (120 mg, 0.446 mmol), and [1,1'-bis(diphenylphosphino)ferrocene]dichloropalladium(II) (26 mg, 0.036 mmol). The resulting mixture was heated at 90° C. for 30 min. The reaction mixture was cooled and partitioned between water and EtOAc. The aqueous phase was extracted twice with EtOAc, and the combined organic phases were dried over sodium sulfate and concentrated in vacuo to give 6-chloro-5-[4-(1-methylpyrrolidin-3-yl)phenyl]-1H-indole-3-carbaldehyde (0.23 g, 16% yield) which was used directly in the next step. MS (ES+) 339.0 (M+H)+.

Step 3

6-chloro-5-[4-(1-methylpyrrolidin-3-yl)phenyl]-1H-indole-3-carboxylic acid

To a solution of 6-chloro-5-[4-(1-methylpyrrolidin-3-yl)phenyl]-1H-indole-3-carbaldehyde (crude, 0.23 g, 0.68 mmol) in acetonitrile (8 mL) and tert-butanol (8 mL) was added 2-methyl-2-butene (8 mL). The reaction mixture was cooled to 0° C. and treated with a solution of sodium chlorite (683 mg, 7.50 mmol) and sodium phosphate monobasic dihydrate (1.59 g, 10.2 mmol) in water (4 mL) dropwise. The reaction mixture was stirred at room temperature for two hours and treated with additional sodium chlorite (911 mg, 10.0 mmol) and sodium phosphate monobasic dihydrate (2.12 g, 13.6 mmol) in H2O (4 mL) and 2-methyl-2-butene (2 mL). The resulting mixture was stirred at room temperature for 16 h. The reaction mixture was evaporated in vacuo and the aqueous residue was extracted with EtOAc (3×30 mL). The combined organic layers were dried over Na2SO4 and concentrated in vacuo. The residue was purified via prep-HPLC to give 6-chloro-5-[4-(1-methylpyrrolidin-3-yl)phenyl]-1H-indole-3-carboxylic acid (10 mg) as a solid. MS (ES+) 354.9 (M+H)+. 1H NMR (400 MHz, CD3OD) δ 8.01 (m, 2 H), 7.59 (s, 1 H), 7.3-7.5 (m, 4 H), 3.40-4.00 (m, 5 H), 3.06 (s, 3 H), 2.1-2.7 (m, 2 H).

Example 75

6-chloro-5-{4-[1-(hydroxymethyl)cyclopropyl]phenyl}-1H-indole-3-carboxylic acid

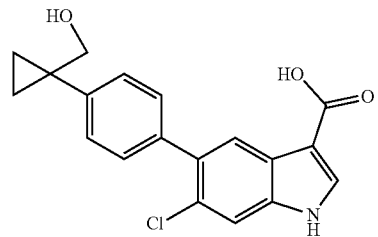 [SMILES: O=C(O)c1c[nH]c2cc(Cl)c(-c3ccc(C4(CO)CC4)cc3)cc12]

Step 1

6-chloro-5-{4-[1-(hydroxymethyl)cyclopropyl]phenyl}-1H-indole-3-carbaldehyde

A mixture of 6-chloro-5-(5,5-dimethyl-1,3,2-dioxaborinan-2-yl)-1H-indole (156 mg, 0.60 mmol) and N,N-dimethylformiminium chloride (150 mg, 1.20 mmol) in dry 1,4-dioxane (4 mL) and DMF (0.7 mL) was sealed in a vial and stirred at room temperature for 10 min to give a white slurry. To the reaction mixture was then added 2 M aqueous potassium carbonate (2.5 mL, 5 mmol), [1-(4-bromophenyl)cyclopropyl]methanol (140 mg, 0.6 mmol) and [1,1'-bis(diphenylphosphino)ferrocene]dichloropalladium(II) (50 mg). The reaction mixture was degassed and heated to 90° C. for 30 min. The cooled reaction mixture was diluted with water (20 mL), and then washed with EtOAc (3×20 mL). The combined organic layers were dried and concentrated in vacuo to give crude 6-chloro-5-{4-[1-(hydroxymethyl)cyclopropyl]phenyl}-1H-indole-3-carbaldehyde (160 mg, 90% yield), which was used in the next step without further purification. $^1$H NMR (400 MHz, DMSO-$d_6$) δ 11.10 (s, 1 H), 8.77 (s, 1 H), 8.56 (s, 1 H), 7.92 (s, 1 H), 7.39-7.34 (m, 4 H), 4.70 (br.s., 1 H), 3.56 (s, 2 H), 0.88-0.86 (m, 2 H), 0.79-0.77 (m, 2 H).

Step 2

6-chloro-5-{4-[1-(hydroxymethyl)cyclopropyl]phenyl}-1H-indole-3-carboxylic acid

To a mixture of 6-chloro-5-{4-[1-(hydroxymethyl)cyclopropyl]phenyl}-1H-indole-3-carbaldehyde (80 mg, 0.24 mmol) in acetonitrile (3 mL) and tert-butanol (3 mL) was added 2-methyl-2-butene (3 mL). The reaction mixture was cooled to 0° C. and treated with a solution of sodium chlorite (420 mg, 4.80 mmol) and sodium phosphate monobasic (650 mg, 4.80 mmol) in water (3 mL) dropwise via addition funnel. The reaction mixture was warmed to room temperature and stirred for 20 hours. The solvent was removed in vacuo to give a residue, which was purified by prep-HPLC (Column: Boston Symmetrix ODS-H 150*30 mm*5 μm Mobile phase: from 36% MeCN in water (0.1% TFA) to 36% MeCN in water (0.1% TFA); Wavelength: 220 nm Flow rate: 30 mL/min) to give 6-chloro-5-{4-[1-(hydroxymethyl)cyclopropyl]phenyl}-1H-indole-3-carboxylic acid (25 mg, 32% yield) as a white solid. MS (ES+) 364.0 (M+Na)$^+$. $^1$H NMR (400 MHz, DMSO-$d_6$) δ 12.13 (s, 1 H), 11.96 (s, 1 H), 8.07 (d, 1 H), 7.92 (s, 1 H), 7.62 (s, 1 H), 7.38-7.32 (m, 4 H), 4.73-4.71 (m, 1 H), 3.58-3.57 (m, 2 H), 0.88-0.77 (m, 4 H).

Example 76

6-chloro-5-[2-(morpholin-4-yl)pyrimidin-5-yl]-1H-indole-3-carboxylic acid

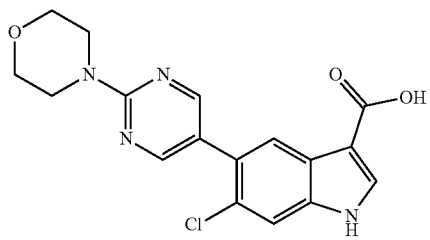 [SMILES: O=C(O)c1c[nH]c2cc(Cl)c(-c3cnc(N4CCOCC4)nc3)cc12]

Step 1

6-chloro-5-[2-(morpholin-4-yl)pyrimidin-5-yl]-1H-indole-3-carbaldehyde

To a solution of 6-chloro-5-(5,5-dimethyl-1,3,2-dioxaborinan-2-yl)-1H-indole (154 mg, 0.584 mmol) in anhydrous 1,4-dioxane (5 mL) and DMF (1 mL) was added N,N-dimethylformiminium chloride (150 mg, 1.17 mmol). The reaction mixture was stirred at room temperature for 20 minutes, then treated with 2 M aqueous potassium carbonate (400 mg, 2.90 mmol), 4-(5-bromopyrimidin-2-yl)morpholine (145 mg, 0.594 mmol) and [1,1'-bis(diphenylphosphino)ferrocene]dichloropalladium(II) (50 mg, 0.068 mmol). The reaction was degassed with nitrogen for 2 minutes and heated to 90° C. for 30 minutes. The cooled reaction mixture was concentrated in vacuo and purified by column chromatography on silica gel (petroleum ether/EtOAc=1:4) to afford 6-chloro-5-[2-(morpholin-4-yl)pyrimidin-5-yl]-1H-indole-3-carbaldehyde (159 mg, 79.4% yield) as an yellow solid. $^1$H NMR (400 MHz, DMSO-$d_6$) δ 12.36 (s, 1 H), 10.01 (s, 1 H), 8.55 (s, 2 H), 8.46 (s, 1 H), 8.12 (s, 1 H), 7.79 (s, 1 H), 3.84 (m, 4 H), 3.77 (m, 4 H).

Step 2

6-chloro-5-[2-(morpholin-4-yl)pyrimidin-5-yl]-1H-indole-3-carboxylic acid 6-chloro-5-[2-(morpholin-4-yl)pyrimidin-5-yl]-1H-indole-3-carbaldehyde (159 mg, 0.464 mmol) was dissolved in acetonitrile (6 mL) and warm tert-butanol (6 mL) and treated with 2-methyl-2-butene. The reaction mixture was cooled to 0° C. and treated with a solution of sodium chlorite (630 mg, 9.27 mmol) and sodium phosphate monobasic dihydrate (1.45 g, 9.30 mmol) in water (5 mL) via addition funnel. The mixture was stirred at room temperature overnight. The reaction mixture was then concentrated in vacuo to remove the organics and extracted with EtOAc (3×20 mL). The combined organics were washed with brine (20 mL), dried and concentrated in vacuo to give a crude, which was purified by prep-HPLC to give 6-chloro-5-[2-(morpholin-4-yl)pyrimidin-5-yl]-1H-indole-3-carboxylic acid (67.6 mg, 40.60% yield) as a white solid. MS (ES+) 359.1 (M+H)$^+$. $^1$H NMR (400 MHz, DMSO-$d_6$) δ 12.22 (s, 1 H), 12.03 (s, 1 H), 8.49 (m, 2 H), 8.12 (m, 1 H), 7.97 (s, 1 H), 7.69 (s, 1 H), 3.78 (m, 4 H), 3.70 (m, 4 H).

Example 77

6-chloro-5-{4-[2-(morpholin-4-yl)-2-oxoethyl]phenyl}-1H-indole-3-carboxylic acid

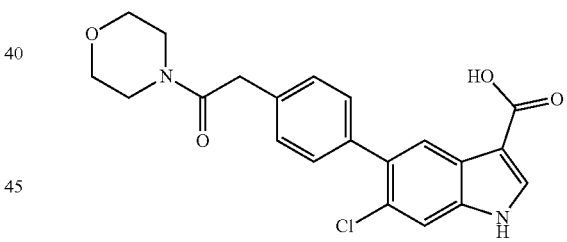

Step 1

6-chloro-5-{4-[2-(morpholin-4-yl)-2-oxoethyl]phenyl}-1H-indole-3-carbaldehyde

To a solution of 6-chloro-5-(5,5-dimethyl-1,3,2-dioxaborinan-2-yl)-1H-indole (153 mg, 0.581 mmol) in anhydrous 1,4-dioxane (5 mL) and DMF (1 mL) was added N,N-dimethylformiminium chloride (160 mg, 1.25 mmol). The reaction mixture was stirred at room temperature for 20 minutes, and then treated with 2 N aqueous potassium carbonate (1.44 mL, 2.90 mmol) and 2-(4-bromophenyl)-1-(morpholin-4-yl)ethanone (165 mg, 0.58 mmol). The reaction was degassed with nitrogen, and treated with [1,1'-bis(diphenylphosphino)ferrocene]dichloropalladium(II) (50 mg, 0.068 mmol). The reaction mixture was stirred at 90° C. for 30 minutes, cooled to room temperature, and poured into water (15 mL). The product was extracted with ethyl acetate (3×20 mL), and the combined organic phases were dried and concentrated in vacuo to give the title compound (249 mg, >100% yield) as a red solid, which was used in the next step without further purification.

Step 2

6-chloro-5-{4-[2-(morpholin-4-yl)-2-oxoethyl]phenyl}-1H-indole-3-carboxylic acid To a solution of 6-chloro-5-{4-[2-(morpholin-4-yl)-2-oxoethyl]phenyl}-1H-indole-3-carbaldehyde (249 mg, 0.650 mmol) in acetonitrile (6 mL) and tert-butanol (6 mL) was added 2-methyl-2-butene (4 mL). The reaction mixture was cooled to 0° C. and treated with a solution of sodium chlorite (880 mg, 13.1 mmol) and sodium phosphate monobasic dihydrate (2030 mg, 13.01 mmol) in water (3 mL) via addition funnel. The icebath was removed and the mixture was allowed to warm to room temperature. The reaction mixture was stirred at room temperature for 18 hours. The reaction was quenched with aqueous sodium sulfite, concentrated in vacuo and extracted with ethyl acetate (4×25 mL). The combined organic phases were washed with brine (20 mL), dried and concentrated in vacuo. The crude product was purified by prep-HPLC (Column: Phenomenex Synergi C18 150*30 mm*4 μm; Mobile phase: from 38% MeCN in water (0.225% FA) to 58% MeCN in water (0.225% FA); Wavelength: 220 nm) to afford the title compound (65 mg, 28% yield) as a white solid. MS (ES+) 399.0 (M+H)+. $^1$H NMR (400 MHz, CD$_3$OD) δ 8.03 (s, 1H), 8.01 (s, 1H), 7.59 (s, 1H), 7.43 (d, 2H), 7.34 (d, 2H), 3.87 (s, 2H), 3.65 (m, 4H), 3.52 (m, 2H), 3.55 (m, 2H).

Example 78

5-[4-(1-carboxycyclobutyl)phenyl]-6-chloro-1H-indole-3-carboxylic acid

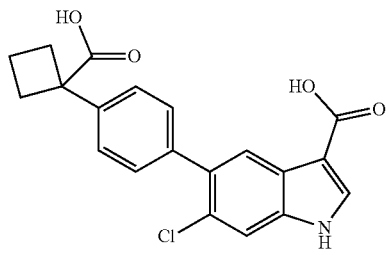 [SMILES: O=C(O)c1c[nH]c2cc(Cl)c(-c3ccc(C4(C(=O)O)CCC4)cc3)cc12]

Step 1

1-[4-(6-chloro-3-formyl-1H-indol-5-yl)phenyl]cyclobutanecarboxylic acid

To a solution of 6-chloro-5-(5,5-dimethyl-1,3,2-dioxaborinan-2-yl)-1H-indole (200 mg, 0.80 mmol) in 1,4-dioxane (5 mL) and DMF (1 mL) was added N,N-dimethylformiminium chloride (250 mg, 2.00 mmol). The reaction mixture was sealed and stirred at room temperature for 10 minutes. To the resulting slurry was added 2 M aqueous potassium carbonate (2 mL, 4 mmol), 1-(4-bromophenyl)cyclobutanecarboxylic acid (255 mg, 1.00 mmol) and [1,1'-bis(diphenylphosphino)ferrocene]dichloropalladium(II) (50 mg). The reaction mixture was degassed with nitrogen, sealed, and heated to 90° C. for 30 minutes. The reaction was quenched with H$_2$O (20 mL), then washed with ethyl acetate (3×20 mL). The combined organic phases were dried and concentrated in vacuo to give the title compound (180 mg, 63% yield) in crude form, which was used in the next step without further purification. $^1$H NMR (400 MHz, CD$_3$OD) δ 9.90 (s, 1 H), 8.17 (s, 1 H), 8.13 (s, 1 H), 7.62-7.61 (m, 1 H), 7.48-7.45 (m, 2 H), 7.41-7.37 (m, 2 H), 2.86-2.79 (m, 2 H), 2.62-2.45 (m, 2 H), 2.05-2.01 (m, 2 H).

Step 2

5-[4-(1-carboxycyclobutyl)phenyl]-6-chloro-1H-indole-3-carboxylic acid

To a mixture of 1-[4-(6-chloro-3-formyl-1H-indol-5-yl)phenyl]cyclobutane carboxylic acid (120 mg, 0.30 mmol) in acetonitrile (3 mL) and tert-butanol (3 mL) was added 2-methyl-2-butene (3 mL). The reaction mixture was cooled to 0° C. and treated with a solution of sodium chlorite (550 mg, 6.00 mmol) and sodium phosphate monobasic (800 mg, 6.00 mmol) in water (3 mL) dropwise via additional funnel. The ice water bath was removed, and the reaction mixture was stirred at room temperature for 18 hours. The reaction mixture was concentrated in vacuo to give a residue, which was purified by prep-HPLC (Column: Boston Symmetrix ODS-H 150*30 mm*5 μm Mobile phase: from 39% MeCN in water (0.1% TFA) to 39% MeCN in water (0.1% TFA); Wavelength: 220 nm Flow rate: 30 mL/min;) to give the title compound (35 mg, 27% yield) as a white solid. MS (ES+) 392.0 (M+Na)+. $^1$H NMR (400 MHz, CD$_3$OD) δ 8.03 (s, 1H), 7.99 (s, 1H), 7.58 (s, 1H), 7.44-7.38 (m, 4 H), 2.90-2.84 (m, 2 H), 2.62-2.54 (m, 2 H), 2.11-1.97 (m, 1 H), 1.95-1.91 (m, 1 H).

Example 79

6-chloro-5-[4-(5-oxomorpholin-2-yl)phenyl]-1H-indole-3-carboxylic acid

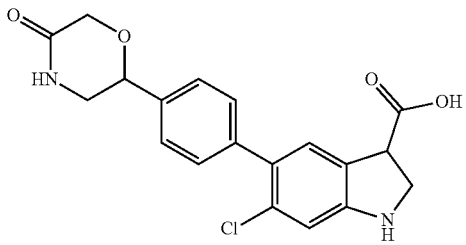 [SMILES: O=C1COC(c2ccc(-c3cc4c(cc3Cl)NCC4C(=O)O)cc2)CN1]

Step 1

N-(2-(4-bromophenyl)-2-hydroxyethyl)-2-chloroacetamide

To a solution of compound 2-amino-1-(4-bromophenyl)ethanol (2.0 g, 10 mmol) in CH$_2$Cl$_2$ (40 mL) and water (40 mL) was added NaOH (0.48 g, 12 mmol) and chloroacetyl chloride (1.7 g, 15 mmol) at 0° C. After addition, the mixture was allowed to warm to room temperature and stirred for 6 hours. The layers were separated. The organic was washed with 3% HCl and saturated NaHCO$_3$, dried over sodium sulfate, and concentrated to afford the title compound (2.0 g, 76% yield) as a yellow solid. $^1$H NMR: (400 MHz, CDCl$_3$):δ

7.45 (d, 2H), 7.19 (d, 2H), 6.98 (br. s, 1H), 4.80 (m, 1H), 4.01 (s, 2H), 3.68 (m, 1H), 3.30 (m, 1H), 2.82 (br. s, 1H):

Step 2

6-(4-bromophenyl)morpholin-3-one

To a solution of N-(2-(4-bromophenyl)-2-hydroxyethyl)-2-chloroacetamide (2.0 g, 6.8 mmol) in THF (20 mL) was added potassium t-butoxide (0.46 g, 8.2 mmol). The mixture was stirred at room temperature overnight. The reaction mixture was quenched with water (20 mL), extracted with ethyl acetate (20 mL×3). The combined organic layers was dried over sodium sulfate, filtered, and concentrated in vacuo to give the title compound (1.6 g, 92% yield) as a yellow solid. $^1$H NMR: (400 MHz, CDCl$_3$): δ7.46 (d, 2H), 7.20 (d, 2H), 6.56 (s, 1H), 4.67 (m, 1H), 4.35 (d, 1H), 4.24 (d, 1H), 3.40 (m, 2H):

Step 3

6-chloro-5-[4-(5-oxomorpholin-2-yl)phenyl]-1H-indole-3-carbaldehyde

The mixture of 6-chloro-5-(5,5-dimethyl-1,3,2-dioxaborinan-2-yl)-1H-indole (150 mg, 0.57 mmol) and N,N-dimethylformiminium chloride (217 mg, 1.70 mmol) in DMF/dioxane (6 mL, 1:5) was stirred at room temperature for 20 minutes. Then 2.0 M potassium carbonate (3 mL), 6-(4-bromophenyl)morpholin-3-one (146 mg, 0.57 mmol) and [1,1'-bis(diphenylphosphino)ferrocene]dichloropalladium(II) (41 mg, 0.057 mmol) was added to the mixture. The reaction mixture was purged with nitrogen for 3 minutes, heated to 90° C. and stirred for 30 minutes. The reaction mixture was extracted with ethyl acetate (10 mL×3). The organic layers were combined, dried over sodium sulfate, and concentrated in vacuo to give the title compound (150 mg, 75% yield) as a brown solid that was brought forward without further purification.

Step 4

6-chloro-5-[4-(5-oxomorpholin-2-yl)phenyl]-1H-indole-3-carboxylic acid

To a solution of 6-chloro-5-[4-(5-oxomorpholin-2-yl)phenyl]-1H-indole-3-carbaldehyde (150 mg, 0.42 mmol) in acetonitrile (5 mL) and t-BuOH (5 mL) was added 2-methyl-2-butene (2.9 g, 42 mmol). The mixture was cooled to 0° C. with ice bath. Sodium chlorite (1.15 g, 12.7 mmol) and sodium phosphate monobasic hydrate (1.75 g, 12.7 mmol) were dissolved in water (5 mL). The aqueous was added to the organic solution and the mixture was allowed to warm to room temperature. The reaction mixture was stirred at room temperature for 48 hours. A solution of sodium sulfite was added slowly to the stirring mixture. The reaction mixture was allowed to stir 1 hour. Then the organics were removed under reduced pressure. The aqueous layer was extracted with ethyl acetate (10 mL×3). The combined organic layers was dried over sodium sulfate, filtered, and concentrated in vacuo to give a brown residue. The residue was purified by reverse phase HPLC to give the title compound (40 mg, 26% yield) as an off-white solid. MS (ES+) 371.0 (M+H)$^+$. $^1$H NMR (400 MHz, DMSO-d6) δ 12.00 (s, 1H), 8.20 (s, 1H), 8.10 (s, 1H), 7.93 (s, 1H), 7.63 (s, 1H), 7.48 (d, 2H), 7.44 (d, 2H), 4.65 (m, 1H), 4.22 (s, 2H), 3.46 (m, 2H).

Example 80

6-chloro-5-[4-(3-hydroxypropyl)phenyl]-1H-indole-3-carboxylic acid

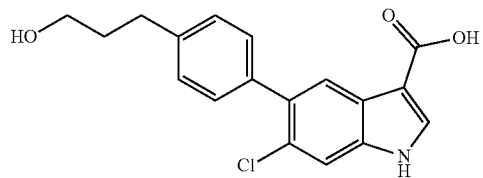 [SMILES: O=C(O)c1c[nH]c2cc(Cl)c(-c3ccc(CCCO)cc3)cc12]

Step 1

6-chloro-5-[4-(3-hydroxypropyl)phenyl]-1H-indole-3-carbaldehyde

To a solution of 6-chloro-5-(5,5-dimethyl-1,3,2-dioxaborinan-2-yl)-1H-indole (100 mg, 0.379 mmol) in dioxane (2 mL) and DMF (0.1 mL) was added N,N-dimethylformiminium chloride (180 mg, 0.36 mmol). The resulting mixture was stirred at room temperature for 20 min. The reaction was quenched with 2.0 N potassium carbonate (1.5 mL, 3.0 mmol), then 3-(4-bromophenyl)propan-1-ol (81.5 mg, 0.379 mmol) and Pd(dppf)Cl$_2$ (28 mg, 0.037 mmol) were added, then heated to 90° C. for 30 min. The reaction mixture was extracted with EtOAc (3 mL×3), combined the organic layers and concentrated in vacuo to afford the title compound (40 mg, 27% yield) after purification via preparative TLC.

Step 2

6-chloro-5-[4-(3-hydroxypropyl)phenyl]-1H-indole-3-carboxylic acid

To 6-chloro-5-[4-(3-hydroxypropyl)phenyl]-1H-indole-3-carbaldehyde (40 mg, 0.13 mmol) in 2-methyl-2-butene/t-butanol/water (v/v/v=1/1/1, 6 mL) was added sodium dihydrogen phosphate (30.5 mg, 0.254 mmol) and sodium chlorite (23 mg, 0.25 mmol) at room temperature. The resulting mixture was stirred at room temperature for 14 hours. The reaction mixture was added sodium sulfite (0.254 mmol), diluted with water, extracted with EtOAc, then concentrated in vacuo and purified via preparative HPLC to give the title compound (6.0 mg, 14% yield).

MS (AP−) 328.0 (M−H)$^−$. $^1$H NMR (400 MHz, CD$_3$OD) δ 6.71 (d, 2 H), 6.28 (s, 1 H), 6.06 (d, 2 H), 5.98 (d, 2 H), 2.33 (t, 2H), 1.46 (m, 2H), 0.61 (m, 2H).

Example 81

6-chloro-5-[3-fluoro-4-(2-hydroxyethoxy)phenyl]-1H-indole-3-carboxylic acid

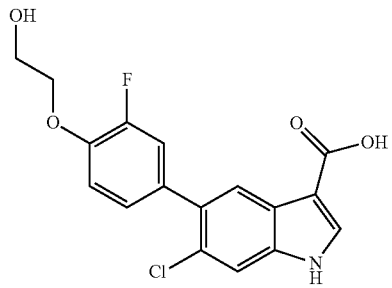 [SMILES: O=C(O)c1c[nH]c2cc(Cl)c(-c3ccc(OCCO)c(F)c3)cc12]

Step 1

6-chloro-5-[3-fluoro-4-(2-hydroxyethoxy)phenyl]-1H-indole-3-carbaldehyde

A mixture of 6-chloro-5-(5,5-dimethyl-1,3,2-dioxaborinan-2-yl)-1H-indole (100 mg, 0.38 mmol) and N,N-dimethylformiminium chloride (97 mg, 0.76 mmol) in DMF (3 mL) and dioxane (0.6 mL) was stirred at room temperature for 30 min. Potassium carbonate (2 mL, 4 mmol, 2 N) was added to the mixture. Then 2-(4-bromo-2-fluorophenoxy)ethanol (89 mg, 0.38 mmol) and Pd(dppf)Cl$_2$ (20 mg, 0.03 mmol) was added to the reaction. The mixture was degassed by passing nitrogen through the solution for 5 min. and stirred at 80° C. for 2 hrs. The reaction was cooled and concentrated. The residue was dissolved with EtOAc (100 mL), washed with water (30 mL), saturated ammonium chloride (30 mL), brine (30 mL), dried over sodium sulfate and concentrated to afford a crude product. The crude was further purified by silica gel chromatography (PE/EtOAc=20% to 50%) to give the title compound (40 mg, 30% yield) as a light yellow oil. $^1$H NMR (400 MHz, CD$_3$OD) δ 9.89 (s, 1H), 8.17 (s, 1H), 8.11 (s, 1H), 7.62 (s, 1H), 7.20 (m, 3H), 4.18 (t, 2H), 3.93 (t, 2H).

Step 2

6-chloro-5-[3-fluoro-4-(2-hydroxyethoxy)phenyl]-1H-indole-3-carboxylic acid

To a solution of 6-chloro-5-[3-fluoro-4-(2-hydroxyethoxy)phenyl]-1H-indole-3-carbaldehyde (40 mg, 0.12 mmol) in water (1 mL) and t-butanol (1 mL) was added sodium chlorite (210 mg, 2.30 mmol), 2-methyl-2-butene (0.5 mL) and sodium dihydrogen phosphate (350 mg, 2.90 mmol). The reaction solution was stirred at room temperature for 10 hrs. The reaction was diluted with water (5 mL) and extracted with dichloromethane (20 mL×3). The combined organic phase was washed with water (20 mL), brine (20 mL), dried over sodium sulfate and concentrated to give a crude product. The crude was purified by preparative HPLC to give the title compound (20 mg, 49% yield) as off-white solid. MS (AP−) 348.0 (M−H)$^−$. $^1$H NMR (400 MHz, CD$_3$OD) δ 8.05 (s, 1H), 8.01 (s, 1H), 7.60 (s, 1H), 7.20 (m, 3H), 4.21 (t, 2H), 3.95 (t, 2H).

Example 82

6-chloro-5-{4-[2-(methylamino)-2-oxoethoxy]phenyl}-1H-indole-3-carboxylic acid

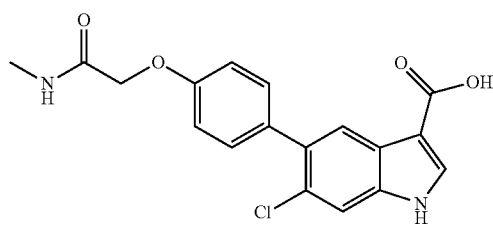 [SMILES: CNC(=O)COc1ccc(-c2cc3c(C(=O)O)c[nH]c3cc2Cl)cc1]

Step 1

2-(4-bromophenoxy)-N-methylacetamide

To a solution of (4-bromophenoxy)acetic acid (500 mg, 2.10 mmol) in N,N-dimethylformamide (15 mL) was added methylamine hydrochloride (320 mg, 5.10 mmol), (1-(3-dimethylaminopropyl)-3-ethylcarbodiimide (570 mg, 3.00 mmol), 1-hydroxybenzotriazole (400 mg, 3.00 mmol) and N-methyl-morpholine (600 mg, 6.00 mmol). The mixture was stirred at room temperature overnight. The reaction was quenched with water (20 mL), and then washed three times with ethyl acetate (20 mL). The combined organics was dried and concentrated to give the title compound (580 mg, 90% yield) that was used without further purification. $^1$H NMR (400 MHz, CDCl$_3$) δ 7.45 (d, 2H), 6.79 (d, 2H), 6.56 (s, 1H), 4.46 (s, 2H), 2.91 (d, 3H).

Step 2

2-[4-(6-chloro-3-formyl-1H-indol-5-yl)phenoxy]-N-methylacetamide

To the slurry of methyl-6-chloro-5-(5,5-dimethyl-1,3,2-dioxaborinan-2-yl)-1H-indole-3-carboxylate (240 mg, 1.0 mmol) was added 2 M potassium carbonate (2.5 mL, 5.0 mmol), 2-(4-bromophenoxy)-N-methylacetamide (240 mg, 1.00 mmol) and PddppfCl$_2$ (50 mg, 0.061 mmol). The sealed vial was heated to 90° C. for 30 min. The reaction was cooled to room temperature and quenched with water (20 mL), and then washed three times with ethyl acetate (20 mL). The combined organics were dried and concentrated to give the title compound (250 mg, 55% yield) as a yellow solid that was used without further purification. $^1$H NMR (400 MHz, DMSO-d$_6$) δ 9.94 (s, 1H), 8.37 (d, 1H), 8.02 (s, 1H), 7.68 (s, 1H), 7.38 (d, 2H), 7.05 (d, 2H), 4.52 (s, 2H), 2.68 (d, 3H).

Step 3

6-chloro-5-{4-[2-(methylamino)-2-oxoethoxy]phenyl}-1H-indole-3-carboxylic acid

To a mixture of 2-[4-(6-chloro-3-formyl-1H-indol-5-yl)phenoxy]-N-methylacetamide (120 mg, 0.35 mmol) in acetonitrile/t-butanol (4 mL/4 mL) was added 2-methyl-2-butene (4 mL). The reaction mixture was cooled to 0° C. followed by the addition of an aqueous solution of sodium chlorite (630 mg, 7.00 mmol) and sodium phosphate (monobasic and monohydrate, 930 mg, 7.00 mmol) in water (5 mL) dropwise via additional funnel. The ice bath was removed and the reaction was stirred at room temperature overnight. The reaction was quenched with sodium sulfite. The reaction mixture was concentrated under reduced pressure and the resulting residue was purified by pre-HPLC to give the title compound (60 mg, 47% yield) as a white solid. MS (ES+) 359.0 (M+H)$^+$. $^1$H NMR (400 MHz, DMSO-d$_6$) δ 12.12 (s, 1H), 11.94-11.93 (m, 1H), 8.07 (d, 2H), 7.92 (s, 1H), 7.62 (s, 1H), 7.37 (d, 2H), 7.04 (d, 2H), 4.52 (s, 2H), 2.68 (d, 3H).

Example 83

6-chloro-5-[4-(pyrrolidin-2-yl)phenyl]-1H-indole-3-carboxylic acid

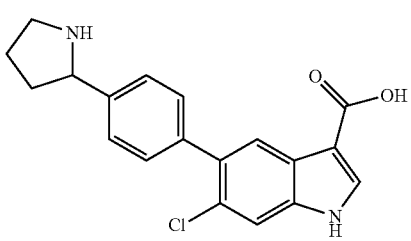 [SMILES: O=C(O)c1c[nH]c2cc(Cl)c(-c3ccc(C4CCCN4)cc3)cc12]

Step 1 tert-butyl 2-[4-(6-chloro-3-formyl-1H-indol-5-yl)phenyl]pyrrolidine-1-carboxylate To a suspension of 6-chloro-5-(5,5-dimethyl-1,3,2-dioxaborinan-2-yl)-1H-indole (150 mg, 0.57 mmol) in mixture solvent of 1,4-dioxane/N,N-dimethylformamide (5:1, 3 mL) was added vilsmeier salt (165 mg, 1.71 mmol) under nitrogen. The mixture was stirred at room temperature for 30 minutes under nitrogen. Potassium carbonate (2.0 M in water, 1.5 mL) was added and stirred for 10 minutes, followed by the addition of tert-butyl 2-(4-bromophenyl)pyrrolidine-1-carboxylate (180 mg, 0.55 mmol), the mixture was degassed with nitrogen for 10 min., then treated with Pd(dppf)Cl$_2$ (62 mg, 0.086 mmol). The reaction mixture was stirred at 90° C. for 30 minutes. The mixture was filtered through a Celite pad and the filtrate was partitioned between ethyl acetate (10 mL) and water (20 mL). The aqueous phase was extracted two times with ethyl acetate (10 mL), the combined organic layers were washed with brine (15 mL), dried over sodium sulfate, filtered, and concentrated to afford crude product which was purified by silica-gel chromatography to give the title compound (170 mg, 72.2% yield).

Step 2

5-{4-[1-(tert-butoxycarbonyl)pyrrolidin-2-yl]phenyl}-6-chloro-1H-indole-3-carboxylic acid The tert-butyl 2-[4-(6-chloro-3-formyl-1H-indol-5-yl)phenyl]pyrrolidine-1-carboxylate (160 mg, 0.377 mmol) was dissolved in acetonitrile (9 mL) and warm t-butanol (9 mL) followed by the addition of 2-methyl-2-butene (6.00 mL, 56.5 mmol) and cooled to 0° C. followed by the addition of an aqueous solution of sodium chlorite (763 mg, 11.3 mmol) and sodium phosphate (monobasic and monohydrate, 1.56 g, 11.3 mmol) in water (5 mL) dropwise via additional funnel. The ice bath was removed and the mixture was allowed to warm to room temperature. The suspension was stirred overnight. To the suspension was added sodium sulfite (1.43 g, 11.3 mmol) in water (3 mL) and the resultant mixture concentrated to remove the organic solvent followed by extraction three times with ethyl acetate (15 mL). The combined organic layers were dried over sodium sulfate, filtered, and concentrated to afford crude product which was purified by reverse phase HPLC to afford the title compound (140 mg, 84.2% yield).

Step 3

6-chloro-5-[4-(pyrrolidin-2-yl)phenyl]-1H-indole-3-carboxylic acid

To a suspension of 5-{4-[1-(tert-butoxycarbonyl)pyrrolidin-2-yl]phenyl}-6-chloro-1H-indole-3-carboxylic acid (140 mg, 0.318 mmol) in ethyl acetate (10 mL) was added hydrogen chloride in ethyl acetate (4 N HCl in EtOAc, 10 mL) under nitrogen. The suspension was stirred for 4.5 hours at room temperature. The mixture was concentrated to afford the desired product (100 mg, 83.5% yield). MS (ES+) 341 (M+H)$^+$. $^1$H NMR (400 MHz, DMSO-d$_6$) δ 12.07 (s, 1H), 8.10 (s, 1H), 7.95 (s, 1H), 7.66 (s, 1H), 7.62 (d, 2H), 7.52 (d, 2H), 4.60 (s, 1H), 3.35 (s, 4H), 2.49 (m, 2 H).

Example 84

6-chloro-5-{4-[1-(methylsulfonyl)pyrrolidin-2-yl]phenyl}-1H-indole-3-carboxylic acid

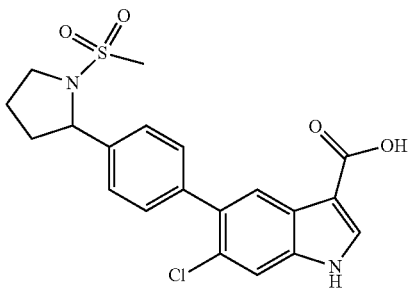 [SMILES: CS(=O)(=O)N1CCCC1c1ccc(-c2cc3c(C(=O)O)c[nH]c3cc2Cl)cc1]

Step 1

2-(4-bromophenyl)pyrrolidine hydrogen chloride

The suspension of tert-butyl 2-(4-bromophenyl)pyrrolidine-1-carboxylate (1.2 g, 3.7 mmol) in anhydrous methanol (10 mL) was added hydrogen chloride in methanol (20 mL, 4.0 M in MeOH) under nitrogen. The reaction was stirred at room temperature for 1.5 hours. The mixture was concentrated to afford the title compound (0.99 g, quantitative yield) which was used without purification in the next step.

Step 2

2-(4-bromophenyl)-1-(methylsulfonyl)pyrrolidine

To a suspension of 2-(4-bromophenyl)pyrrolidine hydrogen chloride (250 mg, 0.952 mmol) in anhydrous methylene chloride (5 mL) was added triethylamine (0.66 mL, 4.76 mmol) under N$_2$. The mixture was stirred at room temperature for 15 min. under N$_2$. After 15 min., methanesulfonyl chloride (0.31 g, 2.72 mmol) was added and the mixture was stirred at room temperature under N$_2$ overnight. Additional methanesulfonyl chloride (0.29 g, 2.54 mmol) and triethylamine (0.35 mL, 2.38 mmol) were added and stirred at room temperature for 4 h. The reaction was concentrated, and to the residue was added water (20 mL) and methylene chloride (18 mL), and the organic phase was washed with water (10 mL×3), brine (15 mL×1), dried over sodium sulfate and concentrated to afford the desired product (240 mg, 85.2% yield) which was used without further purification in the next step.

Step 3

6-chloro-5-{4-[1-(methylsulfonyl)pyrrolidin-2-yl]phenyl}-1H-indole-3-carbaldehyde To a suspension of 6-chloro-5-(5,5-dimethyl-1,3,2-dioxaborinan-2-yl)-1H-indole (210 mg, 0.80 mmol) in a solvent mixture of 1,4-dioxane/N,N-dimethylformamide=5:1 (3 mL) was added Vilsmer-salt (232 mg, 4.80 mmol) under nitrogen and the mixture was stirred at room temperature for 30 minutes. Potassium carbonate (2.0 M in water, 2.0 mL) was added to the above suspension followed by the addition of 2-(4- bromophenyl)-1-(methylsulfonyl)pyrrolidine (240 mg, 0.79 mmol) in a solvent mixture of 1,4-dioxane/N,N-dimethylformamide=5:1 (3 mL) added under nitrogen. The mixture was degassed with nitrogen for 10 minutes. The mixture was treated with Pd(dppf)Cl$_2$ (87 mg, 0.12 mmol) and stirred at 90° C. under nitrogen for 30 minutes. The mixture was filtered through a celite pad and the filtrate was partitioned between ethyl acetate (10 mL) and water (20 mL). The aqueous phase was extracted three additional times with ethyl acetate (10 mL) and the combined the organic phases were washed with brine (15 mL), dried over sodium sulfate, filtered and concentrated to afford crude which was purified by silica-gel chromatography to give the title compound (76.7 mg, 24.0% yield).

Step 4

6-chloro-5-{4-[1-(methylsulfonyl)pyrrolidin-2-yl]phenyl}-1H-indole-3-carboxylic acid To a mixture of 6-chloro-5-{4-[1-(methylsulfonyl)pyrrolidin-2-yl]phenyl}-1H-indole-3-carbaldehyde (75 mg, 0.19 mmol) in acetonitrile/t-butanol (4.5 mL/4.5 mL) was added 2-methyl-2-butene (3.00 mL, 28.2 mmol). The reaction mixture was cooled to 0° C. followed by the addition of an aqueous solution of sodium chlorite (377 mg, 5.58 mmol) and sodium phosphate (monobasic and monohydrate, 770 mg, 5.58 mmol) in water (9 mL) dropwise via additional funnel. The ice bath was removed and the reaction was stirred at room temperature overnight. The following morning, 2-methyl-2-butene (1.50 mL, 14.1 mmol) and an aqueous solution of sodium chlorite (125 mg, 1.86 mmol) and sodium phosphate (monobasic and monohydrate, 257 mg, 1.86 mmol) in water (3 mL) was added in a dropwise manner. The reaction was allowed to stir overnight at room temperature. The reaction was quenched with sodium sulfite (940 mg, 7.44 mmol) in water (3 mL). The reaction mixture was concentrated under reduced pressure to remove the volatile organics. The aqueous layer was extracted three times with ethyl acetate. The combined organic layers were dried over sodium sulfate, filtered, and concentrated under reduced pressure. The resulting residue was purified by reverse phase HPLC to give the desired product (40.1 mg, 51.2% yield). MS (ES+) 441.0 (M+Na)$^+$. $^1$H NMR (400 MHz, DMSO-d$_6$) δ 11.95 (s, 1H), 8.07 (s, 1H), 7.95 (s, 1H), 7.64 (s, 1H), 7.40 (m, 4H), 4.94-4.91 (m, 1H), 3.51-3.49 (s, 2H), 2.95 (s, 3H), 2.40-2.30 (m, 1H), 1.91-1.86 (m, 3H).

Example 85

6-chloro-5-[4-(1-methylpyrrolidin-2-yl)phenyl]-1H-indole-3-carboxylic acid

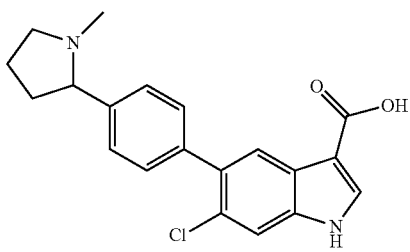 [SMILES: CN1CCCC1c1ccc(-c2cc3c(C(=O)O)c[nH]c3cc2Cl)cc1]

Step 1

2-(4-bromophenyl)-1-methylpyrrolidine

To a suspension of 2-(4-bromophenyl)pyrrolidine hydrogen chloride (200 mg, 0.76 mmol) in anhydrous MeOH (5 mL) was added formaldehyde (114 mg, 3.80 mmol) under N$_2$. The mixture was stirred at room temperature for 2 h under N$_2$. After 2 h, NaBH(OAc)$_3$ (242 mg, 1.14 mmol) was added and the mixture was stirred at room temperature under N$_2$ overnight. Additional formaldehyde (2 mL) and NaBH(OAc)$_3$ (242 mg, 1.14 mmol) were then added and the mixture was stirred at room temperature for 5 hrs. The reaction was concentrated and water was added (20 mL) with dichloromethane (8 mL). The layers were separated and the water was extracted with dichloromethane (8 mL×3). The organic layers were combined, washed with brine, dried over sodium sulfate, and concentrated to afford the title compound (0.203 g, quantitative yield) which was used without further purification. $^1$H NMR (400 MHz, DMSO-d$_6$) δ 7.51 (d, 2H), 7.28 (d, 2H), 3.15-3.10 (t, 1 H), 3.04-3.00 (t, 1 H), 2.22-2.18 (q, 1H), 2.13-2.09 (m, 1H), 2.05 (s, 3H), 1.80-1.65 (m, 2H), 1.53-1.50 (m, 1H).

Step 2

6-chloro-5-[4-(1-methylpyrrolidin-2-yl)phenyl]-1H-indole-3-carbaldehyde

To a suspension of 6-chloro-5-(5,5-dimethyl-1,3,2-dioxaborinan-2-yl)-1H-indole (290 mg, 1.10 mmol) in mixture of 1,4-dioxane/N,N-dimethylformamide=5:1 (3 mL) was added Vilsmer-salt (330 mg, 3.30 mmol) under nitrogen and stirred at room temperature for 30 minutes. Potassium carbonate (2.0 M in water, 2.9 mL) was added to the above suspension followed by the addition of 2-(4-bromophenyl)-1-methylpyrrolidine (200 mg, 0.84 mmol) in a mixture of 1,4-dioxane/N,N-dimethylformamide=5:1 (3 mL). The mixture was degassed with nitrogen for 10 minutes. The mixture was then treated with Pd(dppf)Cl$_2$ (125 mg, 0.165 mmol). The mixture was stirred at 90° C. under nitrogen for 30 minutes. The mixture was filtered through a celite pad and the filtrate was partitioned between ethyl acetate (10 mL) and water (20 mL), the aqueous phase was extracted three additional times with ethyl acetate (10 mL) and the combined organic phases were washed with brine (15 mL), dried over sodium sulfate, filtered and concentrated to afford crude product which was purified by silica-gel chromatography to afford the title compound (150 mg, 53.2% yield).

Step 3

6-chloro-5-[4-(1-methylpyrrolidin-2-yl)phenyl]-1H-indole-3-carboxylic acid

To a mixture of 6-chloro-5-[4-(1-methylpyrrolidin-2-yl)phenyl]-1H-indole-3-carbaldehyde (150 mg, 0.443 mmol) in acetonitrile/t-butanol (9 mL/9 mL) was added 2-methyl-2-butene (7.50 mL, 28.2 mmol). The reaction mixture was cooled to 0° C. followed by the addition of an aqueous solution of sodium chlorite (598 mg, 8.86 mmol) and sodium phosphate (monobasic and monohydrate, 1220 mg, 8.860 mmol) in water (9 mL) dropwise via syringe. The ice bath was removed and the reaction was stirred at room temperature overnight. The reaction was quenched with sodium sulfite (1.12 g, 8.86 mmol) in water (3 mL). The reaction mixture was concentrated under reduced pressure to remove the volatile organics. The aqueous layer was extracted three times with ethyl acetate. The combined organic layers were dried over sodium sulfate, filtered, and concentrated under reduced pressure. The resulting residue was purified by reverse phase HPLC to give the title compound (10 mg, 5.0% yield). MS (ES+) 355.0 (M+H)+. $^1$H NMR (400 MHz, CD$_3$OD) δ 8.11 (s, 1H), 7.97 (s, 1H), 7.59-7.58 (m, 5H), 4.19 (m, 1H), 3.74-3.71 (m, 1H), 3.17-3.14 (m, 1H), 2.70 (s, 3H), 2.55-2.52 (m, 1H), 2.33-2.21 (m, 1H), 2.28-2.21 (m, 3H).

Example 86

6-chloro-5-[2-fluoro-4-(2-hydroxyethoxy)phenyl]-1H-indole-3-carboxylic acid

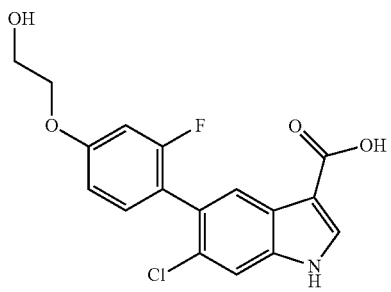 [SMILES: O=C(O)c1c[nH]c2cc(Cl)c(-c3ccc(OCCO)cc3F)cc12]

Step 1

6-chloro-5-[2-fluoro-4-(2-hydroxyethoxy)phenyl]-1H-indole-3-carbaldehyde

A mixture of 6-chloro-5-(5,5-dimethyl-1,3,2-dioxaborinan-2-yl)-1H-indole (100 mg, 0.38 mmol) and N,N-dimethylformiminium chloride (97 mg, 0.76 mmol) in DMF (3 mL) and dioxane (0.6 mL) was stirred at room temperature for 30 min. Potassium carbonate (2 mL, 4 mmol, 2 N) was added to the mixture. Then 2-(4-bromo-3-fluorophenoxy)ethanol (96 mg, 0.38 mmol) and Pd(dppf)Cl$_2$ (20 mg, 0.03 mmol) was added to the reaction. The mixture was degassed by passing nitrogen through the solution for 5 min. and stirred at 80° C. for 2 hrs. The reaction was cooled and concentrated. The residue was dissolved by EtOAc (100 mL), washed with water (30 mL), saturated NH$_4$Cl (30 mL), brine (30 mL), dried over sodium sulfate and concentrated to afford a crude product. The crude was further purified by silica gel chromatography (PE/EtOAc=20% to 50%) to give the title compound (40 mg, 31% yield) as a light yellow oil.

$^1$H NMR (400 MHz, CD$_3$OD) δ 9.91 (s, 1H), 8.04 (s, 1H), 7.95 (s, 1H), 7.63 (s, 1H), 7.28 (t, 1H), 6.86 (dd, 1H), 6.80 (dd, 1H), 4.12 (t, 2H), 3.92 (t, 2H).

Step 2

6-chloro-5-[2-fluoro-4-(2-hydroxyethoxy)phenyl]-1H-indole-3-carboxylic acid

To a solution of 6-chloro-5-[2-fluoro-4-(2-hydroxyethoxy)phenyl]-1H-indole-3-carbaldehyde (40 mg, 0.12 mmol) in water (1 mL) and t-butanol (1 mL) was added sodium chlorite (210 mg, 2.30 mmol), 2-methyl-2-butene (0.5 mL) and sodium dihydrogen phosphate (350 mg, 2.30 mmol). The reaction solution was stirred at room temperature for 10 hrs. The reaction was diluted with water (5 mL) and extracted with dichloromethane (20 mL×3). The combined organic phase was washed with water (20 mL), brine (20 mL) dried over sodium sulfate and concentrated to give a crude product. The crude was purified by reverse phase HPLC to give the title compound (14 mg, 59% yield) as an off-white solid. MS (ES−) 348.1 (M−H)−. $^1$H NMR (400 MHz, CD$_3$OD) δ 8.04 (s, 2H), 7.63 (s, 1H), 7.28 (s, 1H), 6.91 (dd, 2H), 6.86 (dd, 2H), 4.16 (t, 2H), 3.96 (t, 2H).

Example 87

6-chloro-5-[(2R)-2-(hydroxymethyl)-2,3-dihydro-1,4-benzodioxin-6-yl]-1H-indole-3-carboxylic acid

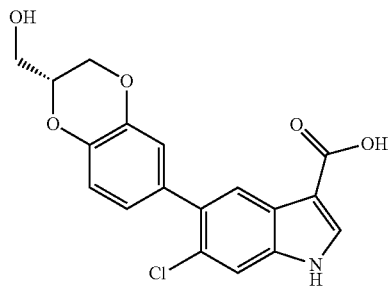 [SMILES: O=C(O)c1c[nH]c2cc(Cl)c(-c3ccc4c(c3)OC[C@@H](CO)O4)cc12]

Step 1

6-chloro-5-[(2R)-2-(hydroxymethyl)-2,3-dihydro-1,4-benzodioxin-6-yl]-1H-indole-3-carbaldehyde A mixture of [(2R)-6-bromo-2,3-dihydro-1,4-benzodioxin-2-yl]methanol (0.54 g, 2.05 mmol) (which can be prepared as in Biorg. Med. Chem. 2007, 15, 4048.), 6-chloro-5-(5,5-dimethyl-1,3,2-dioxaborinan-2-yl)-1H-indole (0.52 g, 4.06 mmol) in DMF (4 mL) and dioxane (4 mL) was stirred at room temperature for 30 min. under N$_2$. Pd(dppf)Cl$_2$ (100 mg, 0.137 mmol) and 2 N potassium carbonate (10 mL, 20 mmol) was added. The resulting mixture was stirred for 30 min. at 90° C. under N$_2$. TLC showed the reaction was complete. Water (50 mL) and methylene chloride (50 mL) was added. The aqueous layer was extracted with methylene chloride (30 mL×3). The combined organic layer was dried over sodium sulfate, filtered and evaporated to give the title compound (1 g) which was used in the next step without further purification.

Step 2

6-chloro-5-[(2R)-2-(hydroxymethyl)-2,3-dihydro-1,4-benzodioxin-6-yl]-1H-indole-3-carboxylic acid A mixture of 6-chloro-5-[(2R)-2-(hydroxymethyl)-2,3-dihydro-1,4-benzodioxin-6-yl]-1H-indole-3-carbaldehyde (1.0 g, 2.9 mmol), sodium chlorite (5.28 g, 58.3 mmol), sodium dihydrogen phosphate (9.06 g, 58.1 mmol) in 2-methyl-2-butene (10 mL), water (10 mL), t-butanol (10 mL) and acetonitrile (10 mL) was stirred overnight at room temperature. The mixture was quenched with saturated aqueous sodium bisulfite. Water (50 mL) and methylene chloride (50 mL) was added. The aqueous layer was extracted with methylene chloride (50 mL×3). The combined organic layer was dried over sodium sulfate, filtered and evaporated to give residue which was purified by reverse phase HPLC to give the title compound (105 mg, 14.3% yield).

MS (AP+) 360.1 (M+H)+. ¹H NMR (400 MHz, CD₃OD) δ 7.99 (s, 1 H), 7.98 (s, 1 H), 7.54 (s, 1 H), 6.90-6.93 (m, 3 H), 4.36 (dd, 1 H), 4.22-4.24 (m, 1 H), 4.09 (dd, 1 H), 3.79-3.81 (m, 2 H).

Example 88

5-[4-(1-carboxycyclopropyl)phenyl]-6-chloro-1H-indole-3-carboxylic acid

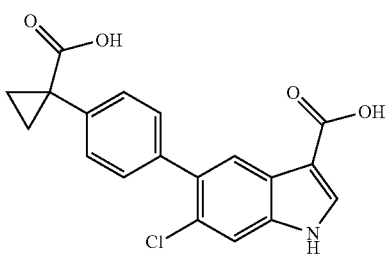 [SMILES: O=C(O)c1c[nH]c2cc(Cl)c(-c3ccc(C4(C(=O)O)CC4)cc3)cc12]

Step 1

1-[4-(6-chloro-3-formyl-1H-indol-5-yl)phenyl]cyclopropane carboxylic acid

To a solution of 6-chloro-5-(5,5-dimethyl-1,3,2-dioxaborinan-2-yl)-1H-indole (152 mg, 0.577 mmol) in anhydrous dioxane (5 mL) and DMF (1 mL) was added N,N-dimethylformiminium chloride (170 mg, 1.33 mmol). The reaction mixture was stirred at room temperature for 20 mins. A thick solution was observed after 20 mins. 2 N potassium carbonate (400 mg, 2.90 mmol), 1-(4-bromophenyl)cyclopropanecarboxylic acid (137 mg, 0.568 mmol) and Pd(dppf)Cl₂ (50 mg, 0.068 mmol) were then added. The reaction was degassed with N₂ for 2 minutes. The reaction was then heated to 90° C. for 30 minutes. The mixture was poured into water (60 mL) and the layers separated. The aqueous layer was extracted with ethyl acetate (50 mL×2). The aqueous phase was acidified to pH=5 with 1 N HCl and then extracted with ethyl acetate (50 mL×3). The combined organic phases were washed with brine (50 mL), dried and concentrated to give the title compound (253 mg, quantitative yield) as a brown oil, which was used in the next step without further purification.

Step 2

5-[4-(1-carboxycyclopropyl)phenyl]-6-chloro-1H-indole-3-carboxylic acid

1-[4-(6-chloro-3-formyl-1H-indol-5-yl)phenyl]cyclopropanecarboxylic acid (253 mg, 0.577 mmol) was dissolved in MeCN (6 mL) and warm t-butanol (6 mL). 2-methyl-2-butene (4 mL) was added and the mixture was cooled to 0° C. Sodium chlorite (780 mg, 11.6 mmol) and sodium dihydrogen phosphate dihydrate (1800 mg, 11.54 mmol) were dissolved in water (4 mL). The aqueous solution was added to the organic solution dropwise via addition funnel and the ice bath was removed and the mixture was allowed to warm to room temperature overnight. The reaction was concentrated to remove the organics and extracted with ethyl acetate (20 mL×3). The combined organics were washed with brine (20 mL), dried and concentrated and then purified by reverse phase HPLC to give the title compound (62.4 mg, 30.5% yield) as a white solid. MS (AP+) 377.9 (M+Na)+. ¹H NMR (400 MHz, CD₃OD) δ 8.02 (s, 1H), 8.00 (s, 1H), 7.57 (s, 1H), 7.40 (m, 4H), 1.61 (m, 2H), 1.27 (m, 2H).

Example 89

6-chloro-5-[4-(oxetan-3-ylmethoxy)phenyl]-1H-indole-3-carboxylic acid

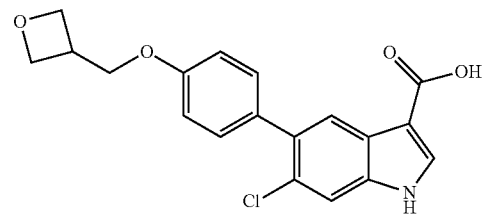 [SMILES: O=C(O)c1c[nH]c2cc(Cl)c(-c3ccc(OCC4COC4)cc3)cc12]

Step 1

3-[(4-bromophenoxy)methyl]oxetane

To a solution of oxetan-3-ylmethanol (1.00 g, 11.3 mmol) in DMF (10 mL) was added NaH (300 mg, 13.6 mmol) at 0° C. The mixture was then stirred at 0° C. for 10 min. 1-Bromo-4-fluorobenzene (2.30 g, 13.6 mmol) was added to the solution. The mixture was stirred at 90° C. for 2 h. The mixture was partitioned between water and EtOAc (30 mL×3). The combined organics was dried and concentrated to give the title compound (420 mg, 15% yield) as a yellow oil.

Step 2

6-chloro-5-[4-(oxetan-3-ylmethoxy)phenyl]-1H-indole-3-carbaldehyde

To a sealed tube was added 6-chloro-5-(5,5-dimethyl-1,3,2-dioxaborinan-2-yl)-1H-indole (100 mg, 0.38 mmol) and N,N-dimethylformiminium chloride (97.7 mg, 0.76 mmol) in dioxane/DMF=5/1 (6 mL). The sealed vial was stirred at room temperature for 10 min. to give a white slurry. To the slurry was added 2 M potassium carbonate (1.0 mL, 1.9 mmol), 3-[(4-bromophenoxy)methyl]oxetane (92.3 mg, 0.38 mmol) and Pd(dppf)Cl₂ (30 mg, 0.05 mmol). The sealed vial was heated to 90° C. for 30 min. TLC (petroleum ether/ethyl acetate=1:1) showed the reaction was complete. The reaction was quenched with water (20 mL), then washed with EtOAc (20 mL×3). The combined organics was dried over sodium sulfate, filtered, concentrated, and purified by combi-flash to give the title compound (70 mg, 53% yield) as a yellow solid. ¹H NMR (400 MHz, CD₃OD) δ 9.90 (s, 1 H), 8.17 (s, 1 H), 8.11 (s, 1H), 7.62 (s, 1 H), 7.38 (d, 2 H) 7.03 (d, 2H), 4.92 (m, 2 H), 4.65 (t, 1 H), 4.61 (s, 1 H), 4.28-4.27 (m, 2 H), 3.50 (m, 1 H).

Step 3

6-chloro-5-[4-(oxetan-3-ylmethoxy)phenyl]-1H-indole-3-carboxylic acid

To a mixture of 6-chloro-5-[4-(oxetan-3-ylmethoxy)phenyl]-1H-indole-3-carbaldehyde (70 mg, 0.2 mmol) in acetonitrile/t-butanol=1/1 (5 mL) was added 2-methyl-2-butene (0.5 mL). The reaction was cooled to 0° C. and an aqueous solution of sodium chlorite (180 mg, 2.00 mmol) and sodium dihydrogen phosphate (270 mg, 6.00 mmol) in water (0.5 mL) were added dropwise via additional funnel. Then ice bath was removed, the reaction was stirred at room temperature for 12 h. The reaction was quenched with sodium sulfite. The mixture was partitioned between EtOAc (20 mL×3) and water. The combined organics was concentrated to give a residue, which was purified by reverse phase HPLC to give the title compound (25 mg, 35% yield) as an off-white solid. MS (AP+) 358.1 (M+H)+. 1H NMR (400 MHz, DMSO-d6) δ 8.04 (s, 1H), 7.95 (s, 1H), 7.61 (s, 1H), 7.35 (d, 2H), 7.04 (d, 2H), 4.74 (t, 2H), 4.46 (t, 2H), 4.26 (t, 2H), 3.44-3.42 (m, 1H).

Example 90

5-[4-(2-carboxyethoxy)phenyl]-6-chloro-1H-indole-3-carboxylic acid

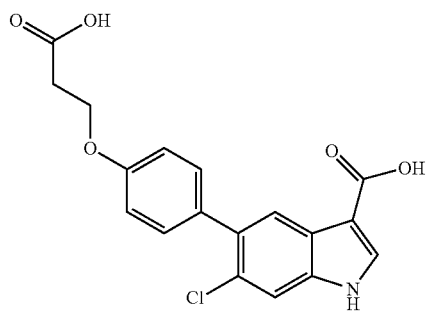 [SMILES: O=C(O)CCOc1ccc(-c2cc3c(C(=O)O)c[nH]c3cc2Cl)cc1]

Step 1

3-[4-(6-chloro-3-formyl-1H-indol-5-yl)phenoxy]propanoic acid

To a solution of 6-chloro-5-(5,5-dimethyl-1,3,2-dioxaborinan-2-yl)-1H-indole (150 mg, 0.57 mmol) in dioxane (5 mL) and DMF (1 mL) was added N,N-dimethylformiminium chloride (155 mg, 1.21 mmol). The reaction mixture was stirred at room temperature for 20 min. 2 N potassium carbonate (314 mg, 2.28 mmol), 3-(4-bromophenoxy)propanoic acid (139 mg, 0.57 mmol) and Pd(dppf)Cl2 (21 mg, 0.028 mmol) were then added. The reaction was degassed with N2 and heated to 90° C. for 30 min. The reaction was extracted with ethyl acetate (10 mL×2). The organic layers were washed with brine (10 mL), dried over sodium sulfate, and concentrated to give the title compound (170 mg, 87% yield) as a brown oil.

Step 2

5-[4-(2-carboxyethoxy)phenyl]-6-chloro-1H-indole-3-carboxylic acid

To a solution of 3-[4-(6-chloro-3-formyl-1H-indol-5-yl)phenyl]propanoic acid (170 mg, 0.496 mmol) in acetonitrile (7.7 mL), t-butanol (7.7 mL) and 2-methyl-2-butene (7.0 mL) was added a solution of sodium chlorite (668 mg, 9.91 mmol) and sodium dihydrogen phosphate (1.37 g, 9.91 mmol) in water (7.7 mL) at 0° C. The reaction mixture was stirred at room temperature for 18 h. The reaction was quenched with a solution of sodium sulfite (1.37 mg, 10.9 mmol) in water (5.0 mL), and extracted with ethyl acetate (30 mL×2). The organic layers were washed with brine (30 mL) and dried over sodium sulfate, filtered and concentrated to give a crude product, which was purified by reverse phase HPLC to give the title compound (34 mg, 19% yield) as a white solid. MS (AP−) 358.1 (M−1)−. 1H NMR (400 MHz, CD3OD) δ 8.01 (s, 1 H), 7.99 (s, 1 H), 7.55 (s, 1 H), 7.36 (d, 2 H), 6.99 (d, 2 H), 4.30 (t, 2 H), 2.79 (t, 2 H).

Example 91

5-[4-(azetidin-3-yl)phenyl]-6-chloro-1H-indole-3-carboxylic acid

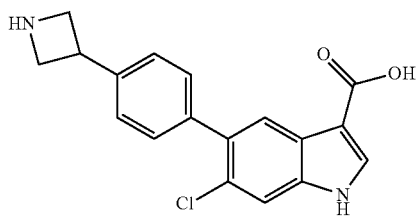 [SMILES: O=C(O)c1c[nH]c2cc(Cl)c(-c3ccc(C4CNC4)cc3)cc12]

Step 1

5-[4-(azetidin-3-yl)phenyl]-6-chloro-1H-indole-3-carbaldehyde

To a solution of 6-chloro-5-(5,5-dimethyl-1,3,2-dioxaborinan-2-yl)-1H-indole (80 mg, 0.30 mmol) in dioxane (2 mL) was added Vilsmeier salt (150 mg, mmol) and DMF (0.1 mL). The resulting mixture was stirred at room temperature for 20 min. The reaction was quenched with 2 N K2CO3 (1.5 mL, 3.0 mmol). 3-(4-Bromophenyl)azetidine (64 mg, 0.30 mmol) and Pd(dppf)Cl2 (20 mg, 0.030 mmol) were next added, and then heated to 90° C. for 30 min. The reaction mixture was extracted with ethyl acetate (3 mL×3). The combined organic layers were concentrated in vacuo to afford the title compound (94 mg, quantitative yield), which was used directly for the next step without further purification.

Step 2

5-[4-(azetidin-3-yl)phenyl]-6-chloro-1H-indole-3-carboxylic acid

To 5-[4-(azetidin-3-yl)phenyl]-6-chloro-1H-indole-3-carbaldehyde (94 mg, 0.30 mmol) in 2-methyl-2-butene/t-BuOH/H2O (v/v/v=1/1/1, 4 mL) was added sodium dihydrogen phosphate (364 mg, 3.04 mmol) and sodium chlorite (274 mg, 3.04 mmol) at room temperature. The resulting mixture was stirred at room temperature for 24 hours. To the reaction mixture was added sodium sulfite (383 mg, 3.04 mmol), then concentrated in vacuo and purified via reverse phase HPLC to give the title compound (10 mg, 10% yield). 1H NMR (400 MHz, CD3OD) δ 8.03-80.4 (d, 2 H), 7.62 (s, 1 H), 7.48-7.52 (m, 4 H), 4.44-4.48 (m, 2 H), 4.32-4.34 (m, 3 H).

Example 92

6-chloro-5-(5-phenylpyrazin-2-yl)-1H-indole-3-carboxylic acid

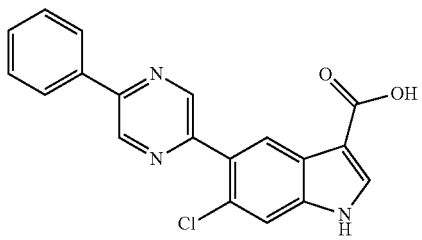 [SMILES: O=C(O)c1c[nH]c2cc(Cl)c(-c3cnc(-c4ccccc4)cn3)cc12]

Step 1

6-chloro-5-(5-phenylpyrazin-2-yl)-1H-indole-3-carbaldehyde

To a 0.4 M solution of chloromethylene dimethylammonium chloride in DMF (7.5 mL, 3.8 mmol) was added 6-chloro-5-(5,5-dimethyl-1,3,2-dioxaborinan-2-yl)-1H-indole (493 mg, 1.88 mmol). The mixture was stirred at 30° C. for 2 hrs. 0.50 mL of this solution (0.15 mmol) was placed in a vial with a 0.3 M solution of 2-chloro-5-phenylpyrazine in DMF (0.50 mL, 0.15 mmol). 2 M potassium carbonate (0.30 mL, 0.60 mmol) was then added and the mixture purged with nitrogen. PddppfCl$_2$ (9 mg, 0.01 mmol) was then added and the vial capped and heated to 90° C. for 3 hours. The reaction mixture was concentrated by Speedvac and purified via preparative TLC to give the title compound that was taken forward without further purification.

Step 2

6-chloro-5-(5-phenylpyrazin-2-yl)-1H-indole-3-carboxylic acid

A solution of 2.5 M/2.65 M of sodium chlorite/sodium dihydrogen phosphate in water was prepared and 1.0 mL (2.5 mmol sodium chlorite and 2.6 mmol sodium dihydrogen phosphate) was added to a vial containing 6-chloro-5-(5-phenylpyrazin-2-yl)-1H-indole-3-carbaldehyde, 1.0 mL THF, 0.5 mL t-butanol, 0.5 mL 2-methyl-2-butene, and sealed then heated to 30° C. for 3 hours. Sodium sulfite (315 mg, 2.50 mmol) was then added and the mixture stirred for 15 min. Ethyl acetate was then added to extract (3×1 mL). The organic layer was separated and solvents removed by speedvac. The residue was purified by reverse phase HPLC to give the title compound. MS(AP−) 348 (M−H)⁻. RT=2.093 Column Xbridge C18 2.1×50 mm 5 μm, Temperature 50° C. Mobile Phase A=0.05% NH4OH in water. Mobile Phase B=100% acetonitrile. Gradient: Initial 5% B Time 0.00 mins, 5% B Time 0.50 mins, 5% B Time 3.40 mins, 100% B Time 4.20 mins, 100% B Time 4.21 mins, 5% B Time 4.70 mins, 5% B Flow rate, 0.8 mL/min Injection volume 2 μL. Agilent 1200 HPLC/1956 MSD/SEDEX 75 ELSD Ionization Mode API-ES Polarity Negative.

Example 93

6-chloro-5-[4-(2-hydroxyethyl)-3-methoxyphenyl]-1H-indole-3-carboxylic acid

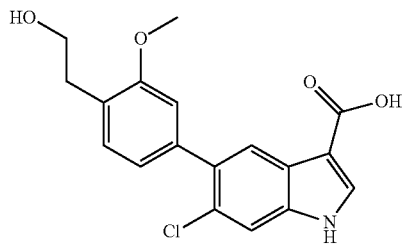 [SMILES: COc1cc(-c2cc3c(C(=O)O)c[nH]c3cc2Cl)ccc1CCO]

Step 1

6-chloro-5-[4-(2-hydroxyethyl)-3-methoxyphenyl]-1H-indole-3-carbaldehyde

To a 0.4 M solution of chloromethylene dimethylammonium chloride in DMF (7.5 mL, 3.8 mmol) was added 6-chloro-5-(5,5-dimethyl-1,3,2-dioxaborinan-2-yl)-1H-indole (493 mg, 1.88 mmol). The mixture was stirred at 30° C. for 2 hrs. 0.50 mL of this solution (0.15 mmol) was placed in a vial with a 0.3 M solution of 2-(4-bromo-2-methoxyphenyl)ethanol in DMF (0.50 mL, 0.15 mmol). 2 M potassium carbonate (0.30 mL, 0.60 mmol) was then added and the mixture was purged with nitrogen. PddppfCl$_2$ (9 mg, 0.01 mmol) was then added and the vial capped and heated to 90° C. for 3 hours. The reaction mixture was concentrated by Speedvac and purified via preparative TLC to give the title compound that was taken forward without further purification.

Step 2

6-chloro-5-[4-(2-hydroxyethyl)-3-methoxyphenyl]-1H-indole-3-carboxylic acid

A solution of 2.5 M/2.65 M of sodium chlorite/sodium dihydrogen phosphate in water was prepared and 1.0 mL (2.5 mmol sodium chlorite and 2.6 mmol sodium dihydrogen phosphate) was added to a vial containing 6-chloro-5-[4-(2-hydroxyethyl)-3-methoxyphenyl]-1H-indole-3-carbaldehyde, 1.0 mL THF, 0.5 mL t-butanol, 0.5 mL 2-methyl-2-butene, and sealed then heated to 30° C. for 3 hours. Sodium sulfite (315 mg, 2.50 mmol) was then added and the mixture stirred for 15 min. Ethyl acetate was then added to extract (3×1 mL). The organic layer was separated and solvents removed by speedvac. The residue was purified by reverse phase HPLC to give the title compound. MS(AP−) 344 (M−H)⁻. Retention time=1.892 Column Xbridge C18 2.1×50 mm 5 μm, Temperature 50° C. Mobile Phase A=0.05% NH4OH in water. Mobile Phase B=100% acetonitrile. Gradient: Initial 5% B Time 0.00 mins, 5% B Time 0.50 mins, 5% B Time 3.40 mins, 100% B Time 4.20 mins, 100% B Time 4.21 mins, 5% B Time 4.70 mins, 5% B Flow rate, 0.8 mL/min Injection volume 2 μL. Agilent 1200 HPLC/1956 MSD/SEDEX 75 ELSD Ionization Mode API-ES Polarity Negative

Example 94

6-chloro-5-[4-(pyridin-3-ylmethoxy)phenyl]-1H-indole-3-carboxylic acid

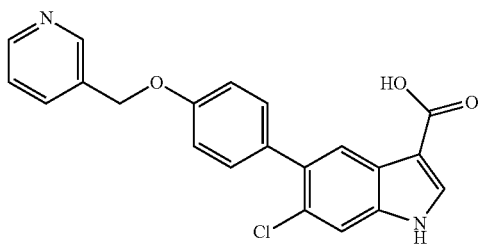 [SMILES: O=C(O)c1c[nH]c2cc(Cl)c(-c3ccc(OCc4cccnc4)cc3)cc12]

Step 1

1-tert-butyl 3-methyl 5-bromo-6-chloro-1H-indole-1,3-dicarboxylate

A solution of methyl 5-bromo-6-chloro-1H-indole-3-carboxylate (756 mg, 2.62 mmol) in anhydrous tetrahydrofuran (13 mL) was treated with di-tert-butyl dicarbonate (686 mg, 3.14 mmol) and DMAP (30 mg, 0.26 mmol). The reaction was stirred at room temperature for two hours, and was then partitioned between ethyl acetate and water. The organic layer was separated, washed with brine, and dried over sodium sulfate. The mixture was filtered and concentrated in vacuo to give a pink, oily solid. This material was triturated with a mixture of ethyl acetate and heptane (1:3), and the resulting solids were collected by filtration. The solids were then washed with heptane and dried in vacuo to give a light pink solid (320 mg). The filtrate was concentrated in vacuo, and the resulting material triturated as above to get a second batch of product (380 mg). The two batches were combined to give the title compound (700 mg, 68% yield). $^1$H NMR (500 MHz, DMSO-$d_6$) δ 8.30 (s, 1H), 8.27 (m, 2H), 3.88 (s, 3H), 1.65 (s, 9H).

Step 2

1-tert-butyl 3-methyl 6-chloro-5-(4-hydroxyphenyl)-1H-indole-1,3-dicarboxylate A mixture of 1-tert-butyl 3-methyl 5-bromo-6-chloro-1H-indole-1,3-dicarboxylate (300 mg, 0.78 mmol), 4-(4,4,5,5-tetramethyl-1,3,2-dioxaborolan-2-yl)phenol (255 mg, 1.16 mmol), 1,4-dioxane (4.2 mL) and aqueous potassium phosphate tribasic (4.6 mL, 0.5 M, 2.3 mmol) was treated with [1,1'-bis(diphenylphosphino)ferrocene]dichloropalladium (II) (57 mg, 0.78 mmol). The pink mixture was evacuated and refilled with nitrogen three times. The sealed reaction was heated at 85° C. for 10 minutes. The cooled reaction mixture was filtered through Celite, and the filter pad was washed with water followed by three washes with ethyl acetate. The filtrate layers were separated, and the aqueous layer was extracted again with ethyl acetate. The organic extracts were combined, washed with brine and then dried over sodium sulfate. The mixture was filtered and concentrated in vacuo to give an oily solid which was purified by flash chromatography eluting with heptanes/ethyl acetate (90:10 to 40:60) to give the title compound (279 mg, 89% yield) as a white solid. MS (ES+) 302 (M-Boc+1)$^+$. $^1$H NMR (500 MHz, DMSO-$d_6$) δ 9.62 (s, 1H), 8.26 (s, 1H), 8.21 (s, 1H), 7.95 (s, 1H), 7.26 (d, J=8.29 Hz, 2H), 6.86 (d, J=8.54 Hz, 2H), 3.32 (s, 3H), 1.66 (s, 9H).

Step 3

1-tert-butyl 3-methyl 6-chloro-5-[4-(pyridin-3-ylmethoxy)phenyl]-1H-indole-1,3-dicarboxylate A mixture of 1-tert-butyl 3-methyl 6-chloro-5-(4-hydroxyphenyl)-1H-indole-1,3-dicarboxylate (30 mg, 0.075 mmol), polymer supported triphenylphosphine (50 mg, 0.15 mmol), anhydrous tetrahydrofuran (1.0 mL), pyridin-3-ylmethanol (0.015 mL, 0.15 mmol), and bis(2-methoxyethyl)-diazene-1,2-dicarboxylate) (35 mg, 0.15 mmol) was sealed in a vial and stirred vigorously at 70° C. for 18 hours. The cooled reaction mixture was filtered through a pad of Celite, and the filter pad was washed with diethyl ether twice. The filtrate was concentrated in vacuo, and the residue partitioned between diethyl ether and water. The organic layer was separated and washed sequentially with water and then brine. The ether layer was concentrated in vacuo and to give the title compound, which was used directly in the next step. MS (ES+) 493 (M+1)$^+$.

Step 4

6-chloro-5-[4-(pyridin-3-ylmethoxy)phenyl]-1H-indole-3-carboxylic acid

A mixture of crude 1-tert-butyl 3-methyl 6-chloro-5-[4-(pyridin-3-ylmethoxy)phenyl]-1H-indole-1,3-dicarboxylate (37 mg, 0.075 mmol), methanol (0.8 mL) and 1M aqueous sodium hydroxide (0.45 mL, 0.45 mmol) was sealed in a vial and heated at 75° C. for 17 hours, causing a solution to form. After cooling to room temperature, the reaction mixture was concentrated via a stream of nitrogen, and diluted with ethyl acetate and saturated aqueous citric acid slowly. The layers were separated, and the aqueous layer was extracted two times with ethyl acetate. The organic layers were combined, concentrated in vacuo, and the resulting clear oil was dissolved in DMSO (0.9 mL) and purified via reverse phase prep-HPLC to give the title compound (6.4 mg, 23% over two steps). MS (ES+) 379.1 (M+H)$^+$. Retention time: 2.28 min. Column: Waters Atlantis dC18 4.6×50 mm, 5 μm. Modifier: TFA 0.05%. Gradient: 95% $H_2O$/5% MeCN linear to 5% $H_2O$/95% MeCN over 4.0 min, HOLD at 5% $H_2O$/95% MeCN to 5.0 min. Flow: 2.0 mL/min.

Example 95

6-cyano-5-[4-(2-hydroxyethoxy)phenyl]-1H-indole-3-carboxylic acid

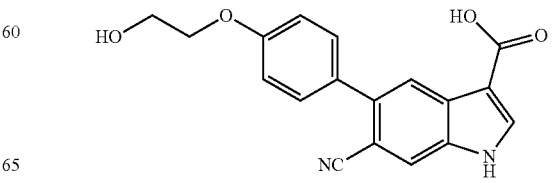

3-formyl-5-[4-(2-hydroxyethoxy)phenyl]-1H-indole-6-carbonitrile

A mixture of 5-bromo-3-formyl-1H-indole-6-carbonitrile (100 mg, 0.401 mmol), 5,5,5',5'-tetramethyl-2,2'-bi-1,3,2-dioxaborinane (150 mg, 0.439 mmol), and oven-dried potassium acetate (177 mg, 1.80 mmol) in 1,4-dioxane (2 mL) was degassed with nitrogen for 10 minutes, then treated with [1,1'-bis(diphenylphosphino)ferrocene]dichloropalladium(II) (29.3 mg, 0.040 mmol) and heated to 110° C. in an oil bath for 3.5 hours. The cooled reaction mixture was filtered through a plug of celite eluting with ethyl acetate (45 mL). The filtrate was evaporated in vacuo to give a black solid (160 mg), and the crude product was partially dissolved in toluene (1.5 mL). A microwave vial was charged with the stock solution in toluene prepared above (0.75 mL, assume 0.2 mmol), 2-(4-bromophenoxy)ethanol (54 mg, 0.25 mmol), ethanol (0.37 mL), and 2M aqueous potassium carbonate (0.4 mL, 0.8 mmol). The mixture was degassed with nitrogen for 10 minutes, then treated with [1,1'-bis(diphenylphosphino)ferrocene]dichloropalladium(II) (13.9 mg, 0.019 mmol). The reaction mixture was heated at 90° C. for two hours. The cooled reaction mixture was poured into saturated aqueous ammonium chloride (15 mL). The product was extracted with ethyl acetate (4×10 mL) and the combined organic layers were dried over sodium sulfate, filtered and evaporated in vacuo to give the title compound as an amber oil (110 mg). MS (ES−) 305.2 (M−H)⁻.

Step 2

6-cyano-5-[4-(2-hydroxyethoxy)phenyl]-1H-indole-3-carboxylic acid

To a solution of crude 3-formyl-5-[4-(2-hydroxyethoxy)phenyl]-1H-indole-6-carbonitrile (110 mg, assume 0.2 mmol) in a mixture of THF (1.5 mL) and tert-butanol (1.5 mL) was added 2-methyl-2-butene (0.638 mL, 6.0 mmol) followed by a solution of sodium chlorite (169 mg, 2.0 mmol) and sodium phosphate monobasic monohydrate (284 mg, 2.06 mmol) in water (1.1 mL) via glass pipet at room temperature. The mixture was stirred at room temperature for 15.5 hours. The reaction mixture was poured into saturated aqueous ammonium chloride solution (10 mL) and extracted with ethyl acetate (3×8 mL). The combined organic layers were dried over sodium sulfate and concentrated in vacuo. The residue was dissolved in DMSO (1.8 mL) and half of this solution was purified by reverse phase prep-HPLC to give the title compound (5 mg). MS (ES−) 321.1 (M−H)⁻. Retention time: 0.90 min Waters Xbridge dC18 5 um 4.6×50 mm, 95% H2O/5% MeCN linear to 5% H2O/95% MeCN over 4.0 min, HOLD at 5% H2O/95% MeCN to 5.0 min. (0.03% NH₄OH). Flow: 2.0 mL/min.

Example 96

6-chloro-5-{4-[3-(hydroxymethyl)oxetan-3-yl]phenyl}-1H-indole-3-carboxylic acid

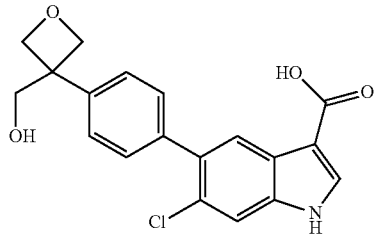 [SMILES: O=C(O)c1c[nH]c2cc(Cl)c(-c3ccc(C4(CO)COC4)cc3)cc12]

Step 1

2-benzyloxymethyl-2-(4-bromo-phenyl)-malonic acid diethyl ester

To a room temperature suspension of sodium hydride (210 mg, 5.26 mmol) in N,N-dimethylacetamide (5 mL) was added diethyl 4-bromophenylmalonate (2.03 g, 6.13 mmol) dropwise. Once bubbling had ceased, benzyl chloromethyl ether (700 mg, 4.4 mmol) was added. The reaction mixture was heated to 100° C. for 5 hours, then diluted with ethyl acetate (200 mL), washed with water and saturated brine (1×50 mL each), dried over magnesium sulfate, filtered and concentrated in vacuo to afford 2.45 g yellow oil. The crude material was purified by flash chromatography (80 g silica, 0-20% ethyl acetate/heptane, 8 column volumes). Product fractions were combined and concentrated in vacuo to afford the title compound as a colorless oil (1.7 g, 89% yield). MS (ES+) 457/459 (M+H+Na)⁺; ¹H NMR (500 MHz, CDCl₃) δ ppm 7.45-7.53 (m, 2 H), 7.25-7.37 (m, 7 H), 4.57 (s, 2 H), 4.21-4.28 (m, 4 H), 4.19 (s, 2 H), 1.20-1.31 (m, 6 H).

Step 2

2-benzyloxymethyl-2-(4-bromo-phenyl)-propane-1,3-diol

To a 0° C. suspension of LAH (444 mg, 11.1 mmol) in diethyl ether (10 mL) was added a solution of 2-Benzyloxymethyl-2-(4-bromo-phenyl)-malonic acid diethyl ester (1.67 g, 3.84 mmol) in diethyl ether (10 mL) dropwise via addition funnel. The reaction mixture was warmed to room temperature and stirred for 22 hours. The reaction was quenched with water (1.5 mL), 15% NaOH (1.5 mL), and water (3 mL) added sequentially. The white slurry was stirred for 30 minutes, diluted with ethyl acetate and filtered to remove the aluminum salts. The filtrate was concentrated in vacuo to afford a green semisolid, which was purified by flash chromatography (40 g silica, 30-82% ethyl acetate/heptane, 10 column volumes). Product fractions were combined and concentrated in vacuo to afford the title compound as a colorless oil (482 mg, 36% yield). ¹H NMR (500 MHz, CD₃OD) δ ppm 7.45 (d, J=8.54 Hz, 2 H), 7.35 (d, J=8.78 Hz, 2 H), 7.22-7.33 (m, 5 H), 4.51 (s, 2 H), 3.92 (s, 4 H), 3.82 (s, 2 H).

Step 3

3-benzyloxymethyl-3-(4-bromo-phenyl)-oxetane

To a solution of 2-Benzyloxymethyl-2-(4-bromo-phenyl)-propane-1,3-diol (475 mg, 1.35 mmol) in THF (5 mL) at 0° C. was added nBuLi (0.54 mL, 2.5M in hexanes, 1.35 mmol). The reaction mixture was stirred for 30 minutes at 0° C., at which point a solution of p-toluenesulfonyl chloride (258 mg, 1.35 mmol) in THF (5 mL) was added via syringe. The reaction mixture was stirred for 1 hour at 0° C. and nBuLi (0.54 mL, 2.5M in hexanes, 1.35 mmol) was added. The reaction mixture was stirred at 60° C. for 16 hours. The reaction mixture was cooled to room temperature, diluted with ethyl ether (100 mL) and washed with water (50 mL). The aqueous layer was extracted with ethyl ether (2×50 mL). The combined organics were dried over magnesium sulfate, filtered and concentrated in vacuo to afford 477 mg cloudy beige oil. The crude oil was purified by flash chromatography (12 g silica, 0-50% ethyl acetate/heptane, 26 column volumes). Product fractions were combined and concentrated in vacuo to afford the title compound as a colorless oil (258 mg, 57% yield).

Step 4 methyl 5-[4-(3-benzyloxymethyl-oxetan-3-yl)-phenyl]-6-chloro-1H-indole-3-carboxylate A mixture of methyl 6-Chloro-5-(5,5-dimethyl-[1,3,2]dioxaborinan-2-yl)-1H-indole-3-carboxylate (241 mg, 0.75 mmol), 3-Benzyloxymethyl-3-(4-bromo-phenyl)-oxetane (250 mg, 0.75 mmol), 2M aqueous potassium carbonate (1.51 mL, 3 mmol), toluene (9 mL), and ethanol (3 mL) was sparged with N2 for 10 minutes, then treated with [1,1'bis(diphenylphosphino)ferrocene]dichloropalladium(II) dichloromethane adduct (29 mg, 0.035 mmol). The reaction mixture was heated to 100 degrees and stirred. After 2 hours the reaction was cooled to room temperature, diluted with ethyl acetate, washed with water and saturated brine, dried over magnesium sulfate, filtered and concentrated in vacuo to afford a brown oil, which was purified by flash chromatography (40 g silica, 10-60% ethyl acetate/heptane, 17 column volumes). Product fractions were combined and concentrated in vacuo to afford the title compound as a colorless solid (215 mg, 62% yield). MS (ES+) 462 (M+H)$^+$; $^1$H NMR (500 MHz, CD$_3$OD) δ ppm 8.04 (s, 1 H), 8.02 (s, 1 H), 7.99 (s, 1 H), 7.43-7.57 (m, 4 H), 7.23-7.34 (m, 5 H), 4.90-5.01 (m, 4 H), 4.58 (s, 2 H), 3.90 (s, 3 H), 3.88 (s, 2 H).

Step 5 methyl 6-chloro-5-[4-(3-hydroxymethyl-oxetan-3-yl)-phenyl]-1H-indole-3-carboxylate To a 0° C. slurry of methyl 5-[4-(3-Benzyloxymethyl-oxetan-3-yl)-phenyl]-6-chloro-1H-indole-3-carboxylate (200 mg, 0.433 mmol) in DCM (5 mL) was added boron trichloride (1.73 mL, 1.0 M in DCM, 1.73 mmol) via syringe, and the mixture was allowed to warm to room temperature over five hours. The reaction mixture was concentrated to dryness, diluted with ethyl acetate (200 mL), washed with water (10 mL) and saturated brine (10 mL), dried over magnesium sulfate, filtered and concentrated in vacuo to afford an orange film, which was purified by flash chromatography (12 g silica, 20-100% ethyl acetate/heptane, 38 column volumes). Product fractions were combined and concentrated in vacuo to afford the title compound as a colorless oil (40 mg, 25% yield). MS (ES+) 372 (M+H)$^+$; $^1$H NMR (500 MHz, CD$_3$OD) δ ppm 8.00-8.04 (m, 2 H), 7.60 (s, 1 H), 7.44-7.55 (m, 4 H), 4.10 (s, 2 H), 3.95-4.07 (m, 4 H), 3.88 (s, 3 H).

Step 6

6-chloro-5-[4-(3-hydroxymethyl-oxetan-3-yl)-phenyl]-1H-indole-3-carboxylic acid

Methyl 6-Chloro-5-[4-(3-hydroxymethyl-oxetan-3-yl)-phenyl]-1H-indole-3-carboxylate (40 mg, 0.11 mmol) was dissolved in methanol (3 mL) and 1N aqueous sodium hydroxide (1 mL, 1 mmol), and the mixture was stirred at 70° C. for 24 hours. The mixture was cooled to room temperature and treated with saturated ammonium chloride (0.5 mL) and concentrated in vacuo to afford 39 mg colorless solid, which was purified by reversed-phase HPLC to afford the title compound (5 mg, 12% yield). MS (ES−) 356.1183 (M−H)$^-$. retention time=1.10 min; Column: Waters Atlantis dC18 4.6× 50 mm, 5 um; Modifier: TFA 0.05%; Gradient: 95% H2O/5% MeCN linear to 5% H2O/95% MeCN over 4.0 min, HOLD at 5% H2O/95% MeCN to 5.0 min; Flow: 2.0 mL/min.

Example 97

6-Chloro-5-(4-methoxyphenyl)-1H-indazole-3-carboxylic acid

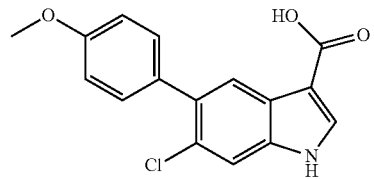 [SMILES: COc1ccc(-c2cc3c(C(=O)O)c[nH]c3cc2Cl)cc1]

To a solution of 5-bromo-6-chloro-1H-indazole-3-carboxylic acid (2.0 g, 7.3 mmol), 4-methoxyphenyl boronic acid (1.13 g, 7.40 mmol) in EtOH (50 mL) and toluene (50 mL) was added 2 N aqueous potassium carbonate solution (21.8 mL, 43.6 mmol). The reaction mixture was degassed with N$_2$ for 5 minutes, treated with [1,1'-bis(diphenylphosphino)ferrocene]dichloropalladium(II) (296 mg, 0.36 mmol) and degassed with N$_2$ for an additional 5 minutes. The reaction mixture was sealed in a pressure tube and heated to 130° C. for 3 hours. As the reaction progressed, the suspension became clear and turned to orange then dark brown. The reaction mixture was cooled to room temperature, and filtered through Celite®. The filtrate was concentrated in vacuo and the residue was partitioned between EtOAc (150 mL) and water (150 mL). The aqueous layer was acidified to pH 2, and extracted with EtOAc. Silicycle-thiol resin was added to the organic layer and the suspension was stirred for 10 minutes. The suspension was filtered and activated charcoal was added to the filtrate. The suspension was stirred at room temperature for another 20 minutes and filtered. The resulting light yellow solution was concentrated in vacuo and the residue was triturated with CH$_2$Cl$_2$ and MeCN. The solid was filtered to provide the title compound (280 mg, 13% yield) as a light yellow solid. The filtrate was concentrated, diluted with EtOAc (20 mL) and filtered to give another batch of desired product (80 mg). MS (ES+) 303.2 (M+H)$^+$. $^1$H NMR (500 MHz, DMSO-d$_6$) δ 7.98 (s, 1H), 7.86 (s, 1H), 7.38 (d, J=8.29 Hz, 2H), 7.03 (d, J=8.78 Hz, 2H), 3.82 (s, 3H).

Example 98

5-(2-Fluoro-4-methoxyphenyl)-6-methyl-1H-indazole-3-carboxylic acid

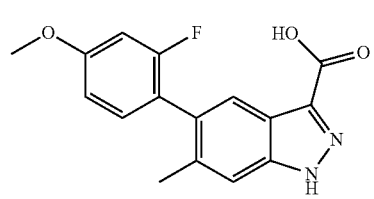 [SMILES: COc1ccc(-c2cc3c(C(=O)O)n[nH]c3cc2C)c(F)c1]

Step 1

5-Bromo-6-methyl-2-((2-(trimethylsilyl)ethoxy)methyl)-2H-indazole

To a solution of 5-bromo-6-methyl-indazole (500 mg, 2.37 mmol) in THF (6 mL) was added dicyclohexylmethylamine (0.63 mL, 3.0 mmol), followed by SEM-chloride (0.50 mL, 2.8 mmol) via syringe. The reaction mixture was stirred at room temperature for 3 hours. EtOAc (20 mL) was added followed by 0.5 N aqueous NaOH (15 mL). The layers were separated and the aqueous layer was extracted with EtOAc (3×20 mL). The combined organic layers were washed consecutively with water and brine. The organic layer was dried over $Na_2SO_4$ and concentrated in vacuo. The crude material was purified by flash chromatography (0-33% EtOAc/heptane) to provide the title compound (639 mg, 79% yield). MS (ES+) 343.1 (M+H)+. $^1$H NMR (500 MHz, $CDCl_3$) δ 8.03 (s, 1H), 7.93 (s, 1H), 7.60 (s, 1H), 5.70 (s, 2H), 3.62 (t, J=8.10 Hz, 2H), 2.52 (s, 3H), 0.95 (t, J=8.30 Hz, 2H), 0.00 (s, 9H).

Step 2

5-(2-Fluoro-4-methoxyphenyl)-6-methyl-2-((2-(trimethylsilyl)ethoxy)methyl)-2H-indazole A mixture of 5-bromo-6-methyl-2-((2-(trimethylsilyl)ethoxy)methyl)-2H-indazole (600 mg, 1.75 mmol), 2-fluoro-4-methoxyphenylboronic acid (320 mg, 1.88 mmol) and 2 N aqueous potassium carbonate solution (1.8 mL, 3.6 mmol) in 1,4-dioxane (7.2 mL) was purged with $N_2$ three times, treated with [1,1'-bis(diphenylphosphino)ferrocene]dichloropalladium(II) (66.0 mg, 0.090 mmol) and subjected to microwave irradiation at 90° C. for 40 minutes. The reaction mixture was filtered through Celite®, rinsed with EtOAc and concentrated in vacuo. The residue was purified by flash chromatography (0-33% EtOAc/heptane) to provide the title compound (657 mg, 92% yield) as a yellow solid. MS (ES+) 387.3 (M+H)+. $^1$H NMR (500 MHz, $CDCl_3$) δ 8.09 (s, 1H), 7.62 (s, 1H), 7.52 (s, 1H), 7.19 (t, J=8.54 Hz, 1H), 6.78 (dd, J=8.42, 2.56 Hz, 1H), 6.73 (dd, J=11.47, 2.44 Hz, 1H), 5.75 (s, 2H), 3.87 (s, 3H), 3.64-3.70 (m, 2H), 2.28 (s, 3H), 0.93-1.00 (m, 2H), 0.00 (s, 9H).

Step 3

Ethyl 5-(2-fluoro-4-methoxyphenyl)-6-methyl-2-((2-(trimethylsilyl)ethoxy)methyl)-2H-indazole-3-carboxylate To a solution of 5-(2-fluoro-4-methoxyphenyl)-6-methyl-2-((2-(trimethylsilyl)ethoxy)methyl)-2H-indazole (650 mg, 1.68 mmol) in THF (10 mL) at −78° C. was added n-BuLi (2.5 M in hexanes, 0.74 mL, 1.85 mmol) dropwise via syringe. The reaction was stirred at −78° C. for 10 minutes, warmed to room temperature for 5 minutes, and cooled back to −78° C. A solution of ethyl cyanocarbonate (188 mg, 1.90 mmol) in THF (1 mL) was added via syringe. The cooling bath was removed and the reaction mixture was stirred at room temperature for 30 minutes. The reaction was quenched with aqueous $NH_4Cl$ solution and diluted with EtOAc. The organic layer was washed with water and brine, dried over $MgSO_4$ and concentrated in vacuo. The residue was purified by flash chromatography (0-20% EtOAc/heptane) to provide the title compound (448 mg, 58% yield). MS (ES+) 459.3 (M+H)+. $^1$H NMR (500 MHz, $CDCl_3$) δ 7.87 (s, 1H), 7.69 (s, 1H), 7.22 (t, J=8.54 Hz, 1H), 6.81 (dd, J=8.42, 2.32 Hz, 1H), 6.75 (dd, J=11.34, 2.32 Hz, 1H), 6.20 (s, 2H), 4.49 (q, J=7.07 Hz, 2H), 3.89 (s, 3H), 3.66-3.72 (m, 2H), 2.29 (s, 3H), 1.44 (t, J=7.07 Hz, 3H), 0.93-1.00 (m, 2H), 0.00 (s, 9H).

Step 4

Ethyl 5-(2-fluoro-4-methoxyphenyl)-6-methyl-1H-indazole-3-carboxylate

To a solution of 5-(2-fluoro-4-methoxyphenyl)-6-methyl-2-((2-(trimethylsilyl)ethoxy)methyl)-2H-indazole-3-carboxylic acid ethyl ester (440 mg, 0.96 mmol) in EtOH (6 mL) was added 3 N HCl solution (1.5 mL, 4.5 mmol). The reaction mixture was heated to 90° C. for 1 hour, cooled to room temperature and concentrated in vacuo. The residue was partitioned between water and EtOAc. The organic layer was dried over $Na_2SO_4$ and concentrated in vacuo to give the title compound (292 mg, 93% yield) as an amber color solid. MS (ES+) 329.3 (M+H)+. $^1$H NMR (500 MHz, $CDCl_3$) δ 8.06 (s, 1H), 7.48 (s, 1H), 7.22 (t, J=8.54 Hz, 1H), 6.81 (dd, J=8.54, 1.95 Hz, 1H), 6.75 (d, J=11.47 Hz, 1H), 4.52 (q, J=7.16 Hz, 2H), 3.89 (s, 3H), 2.34 (s, 3H), 1.47 (t, J=7.07 Hz, 3H).

Step 5

5-(2-Fluoro-4-methoxyphenyl)-6-methyl-1H-indazole-3-carboxylic acid

To a solution of 5-(2-fluoro-4-methoxyphenyl)-6-methyl-1H-indazole-3-carboxylic acid ethyl ester (292 mg, 0.89 mmol) in THF (4 mL) was added a solution of LiOH (298.0 mg, 12.25 mmol) in water (2 mL). The reaction mixture was heated to reflux for 9 hours, and stirred at room temperature for an additional 48 hours. 1 N HCl solution was added to acidify the solution to pH 2. White solid formed, which was collected with filtration and dried in a vacuum oven at 50° C. for 4 hours to give the title compound (240 mg, 90% yield) as a solid. MS (ES+) 301.2 (M+H)+. $^1$H NMR (500 MHz, $CD_3OD$) δ 7.92 (s, 1H), 7.51 (s, 1H), 7.22 (dd, J=8.70, 8.70 Hz, 1H), 6.87 (dd, J=8.42, 2.56 Hz, 1H), 6.81 (dd, J=11.59, 2.56 Hz, 1H), 3.88 (s, 3H), 2.30 (s, 3H).

Example 99

6-Chloro-5-(4-ethoxyphenyl)-1H-indazole-3-carboxylic acid

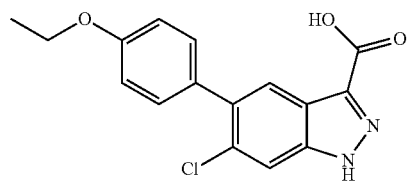 [SMILES: CCOc1ccc(-c2cc3c(C(=O)O)n[nH]c3cc2Cl)cc1]

A mixture of 5-bromo-6-chloro-1H-indazole-3-carboxylic acid (100 mg, 0.36 mmol), 4-ethoxyphenylboronic acid (63.2 mg, 0.38 mmol), and 2 N aqueous potassium carbonate solution (1.10 mL, 2.18 mmol) in toluene (1.6 mL) and EtOH (2.4 mL) was degassed with $N_2$ and treated with [1,1'-bis(diphenylphosphino)ferrocene]dichloropalladium(II) dichloromethane adduct (29.4 mg, 0.036 mmol) under $N_2$. The reaction mixture was sealed in a pressure tube and heated to 110° C. for 1 hour. The cooled reaction mixture was acidified to pH 5 and concentrated in vacuo. The resulting solid was purified by reverse phase HPLC (Column: Waters Sunfire C18 19×100, 5 μm; Mobile phase A: 0.05% TFA in water (v/v); Mobile phase B: 0.05% TFA in MeCN (v/v); 80.0% H$_2$O/20.0% MeCN linear to 40.0% H$_2$O/60.0% MeCN in 10.5 min, 40.0% H$_2$O/60.0% MeCN linear to 0% H$_2$O/100% MeCN in 0.5 min HOLD at 0% H$_2$O/100% MeCN from 11.0 to 12.0 min. Flow: 25 mL/min) to give the title compound (5.3 mg, 5% yield). MS (ES+) 317.1 (M+H)$^+$. Retention time=2.91 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 100

6-Chloro-5-(4-isopropoxyphenyl)-1H-indazole-3-carboxylic acid

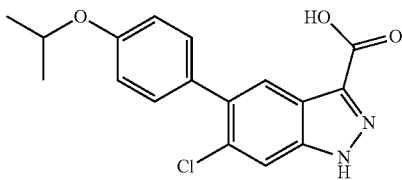 [SMILES: CC(C)Oc1ccc(-c2cc3c(C(=O)O)n[nH]c3cc2Cl)cc1]

A mixture of 5-bromo-6-chloro-1H-indazole-3-carboxylic acid (100 mg, 0.36 mmol), 4-isopropoxyphenylboronic acid (68.6 mg, 0.38 mmol), and 2 N aqueous potassium carbonate solution (1.1 mL, 2.2 mmol) in toluene (1.6 mL) and EtOH (2.4 mL) was degassed with N$_2$ and treated with [1,1'-bis(diphenylphosphino)ferrocene]dichloropalladium(II) dichloromethane adduct (29.4 mg, 0.036 mmol) under N$_2$. The reaction mixture was sealed in a pressure tube and heated to 110° C. for 1 hour. The cooled reaction mixture was acidified to pH 5 and concentrated in vacuo. The resulting solid was purified by reverse phase HPLC (Column: Waters XBridge C18 19×100 mm, 5 μm; Mobile phase A: 0.03% NH$_4$OH in water (v/v); Mobile phase B: 0.03% NH$_4$OH in MeCN (v/v); 95.0% H$_2$O/5.0% MeCN linear to 50.0% H$_2$O/50.0% MeCN in 10.5 min, 50.0% H$_2$O/50.0% MeCN linear to 0% H$_2$O/100% MeCN in 0.5 min HOLD at 0% H$_2$O/100% MeCN from 11.0 to 12.0 min. Flow: 25 mL/min) to give the title compound (13.0 mg, 11% yield). MS (ES+) 331.1 (M+H)$^+$. Retention time=3.05 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 101

6-Chloro-5-(2'-hydroxy-[1,1'-biphenyl]-4-yl)-1H-indazole-3-carboxylic acid

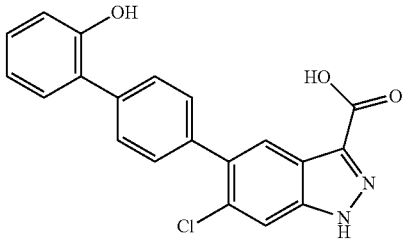 [SMILES: O=C(O)c1n[nH]c2cc(Cl)c(-c3ccc(-c4ccccc4O)cc3)cc12]

Step 1

4'-(5,5-Dimethyl-1,3,2-dioxaborinan-2-yl)[1,1'-biphenyl]-2-ol

A mixture of 2,2-dimethylpropane-1,3-diol (4.0 g, 38 mmol) and 4'-(4,4,5,5-tetramethyl-[1,3,2]dioxaborolan-2-yl)biphenyl-2-ol (1.0 g, 3.4 mmol) in 1,4-dioxane (2 mL) was subjected to microwave irradiation at 210° C. for 1 hour. The cooled reaction mixture was partitioned between water (50 mL) and 1:1 EtOAc/heptane (25 mL:25 mL). The organic layer was washed with water (30 mL) and brine (30 mL), dried over Na$_2$SO$_4$ and concentrated in vacuo to give the title compound (0.95 g, 99% yield). GC/MS, M=282 at 5.31 min. $^1$H NMR (500 MHz, CDCl$_3$) δ 7.94 (d, J=7.81 Hz, 2H), 7.48 (d, J=7.81 Hz, 2H), 7.31-7.26 (m, 2H), 7.03-6.98 (m, 2H), 3.82 (s, 4H), 1.08-1.04 (m, 6H).

Step 2

6-Chloro-5-(2'-hydroxy-[1,1'-biphenyl]-4-yl)-1H-indazole-3-carboxylic acid

A mixture of 5-bromo-6-chloro-1H-indazole-3-carboxylic acid (900 mg, 3.27 mmol) and [1,1'-bis(diphenylphosphino)ferrocene]dichloropalladium(II) (360 mg, 0.49 mmol) was purged with N$_2$. To this mixture was added 4'-(5,5-dimethyl-1,3,2-dioxaborinan-2-yl)-[1,1'-biphenyl]-2-ol (922 mg, 3.27 mmol) in toluene (5.0 mL) and EtOH (15.0 mL), followed by 2 N aqueous potassium carbonate solution (6.0 mL, 12 mmol). The reaction mixture was heated to 100° C. for 48 hours, cooled to room temperature and poured into 1 N aqueous citric acid (15 mL). The aqueous layer was extracted with EtOAc (3×25 mL). The combined organic layers were dried over Na$_2$SO$_4$ and concentrated in vacuo. The crude material was purified by reverse phase chromatography (C-18 column, 10-40% MeCN/water) to give the title compound (258 mg, 22% yield) as a solid. MS (ES$^+$) 365.0 (M+H)$^+$. $^1$H NMR (500 MHz, CD$_3$OD) δ 8.18 (s, 1H), 7.82 (s, 1H), 7.68 (d, 2H), 7.50 (d, 2H), 7.36 (d, 1H), 7.19 (dt, 1H), 6.97-6.92 (m, 2H).

Example 102

6-Chloro-5-(4-(2-hydroxypropan-2-yl)phenyl)-1H-indazole-3-carboxylic acid

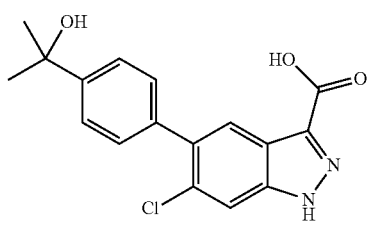 [SMILES: CC(C)(O)c1ccc(-c2cc3c(C(=O)O)n[nH]c3cc2Cl)cc1]

To a mixture of 5-bromo-6-chloro-1H-indazole-3-carboxylic acid (100 mg, 0.36 mmol) and 2-[4-(4,4,5,5-tetramethyl-[1,3,2]dioxaborolan-2-yl)-phenyl]-propan-2-ol (114 mg, 0.44 mmol) in toluene (1.5 mL) and EtOH (1.5 mL) was added 2 N aqueous potassium carbonate solution (0.7 mL, 1.4 mmol). The reaction mixture was degassed with N$_2$ for 10 minutes, treated with [1,1'-bis(diphenylphosphino)ferrocene]dichloropalladium(II) (15.0 mg, 0.018 mmol), and heated to reflux for 16 hours. After cooling to room temperature, the reaction was quenched with 1 N NaOH (1 mL). The mixture was stirred for 30 minutes, acidified with 1 N HCl to pH 5 and extracted with EtOAc. The organic layer was washed with brine, dried over Na₂SO₄ and concentrated in vacuo. The crude material was purified by reverse phase chromatography (Biotage C18 column, 0-40% MeCN/water) to give the title compound (42 mg, 35% yield) as a solid. MS (ES−) 329.1 (M−H)⁺. ¹H NMR (400 MHz, CD₃OD) δ 8.06 (s, 1H), 7.74 (s, 1H), 7.55 (d, J=8.20 Hz, 2H), 7.37 (d, J=8.20 Hz, 2H), 1.57 (s, 6H).

Example 103

6-Chloro-5-(4-(1-hydroxycyclobutyl)phenyl)-1H-indazole-3-carboxylic acid

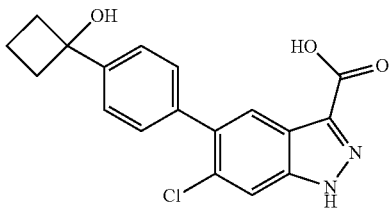 [SMILES: O=C(O)c1n[nH]c2cc(Cl)c(-c3ccc(C4(O)CCC4)cc3)cc12]

A mixture of 5,5,5',5'-tetramethyl-2,2'-bi-1,3,2-dioxaborinane (800 mg, 2.34 mmol), 1-(4-bromophenyl)cyclobutanol (500 mg, 2.20 mmol), potassium acetate (1.0 g, 10 mmol) and [1,1'-bis(diphenylphosphino)ferrocene]dichloropalladium(II) dichloromethane adduct (136 mg, 0.17 mmol) in 1,4-dioxane (12 mL) was degassed with N₂ for 5 minutes, and subjected to microwave irradiation at 115° C. for 1 hour. The cooled reaction mixture was filtered through a cotton plug and concentrated in vacuo. The resulting dark solid was dissolved in 1:1 toluene/EtOH (10 mL) and to this solution was added 5-bromo-6-chloro-1H-indazole-3-carboxylic acid (551 mg, 2.00 mmol) followed by 2 N aqueous potassium carbonate solution (4.0 mL, 8.0 mmol). The reaction mixture was degassed with N₂, treated with [1,1'-bis(diphenylphosphino)ferrocene]dichloropalladium(II) dichloromethane adduct (98.0 mg, 0.12 mmol) under N₂, and heated in a sealed pressure tube to 110° C. for 3 hours. The cooled reaction mixture was concentrated in vacuo and the residue was partitioned between EtOAc (20 mL) and 2 N citric acid solution (20 mL). The layers were separated and the aqueous layer was extracted with EtOAc. The combined organic layers were dried over Na₂SO₄ and concentrated in vacuo. The crude material was purified by reverse phase chromatography (Biotage C18 column, 20-60% MeCN/water) to give the title compound (78 mg, 10% yield) as a solid. MS (ES−) 341.5 (M−H)⁺. ¹H NMR (500 MHz, DMSO-d₆) δ 8.01 (s, 1H), 7.88 (s, 1H), 7.59 (d, J=8.05 Hz, 2H), 7.42 (d, J=8.05 Hz, 2H), 5.55 (br. s, 1H), 2.39-2.46 (m, 2H), 2.23-2.35 (m, 2H), 1.89-2.01 (m, 1H), 1.64-1.76 (m, 1H).

Example 104

6-Chloro-5-(4-(tetrahydro-2H-pyran-4-yl)phenyl)-1H-indazole-3-carboxylic acid

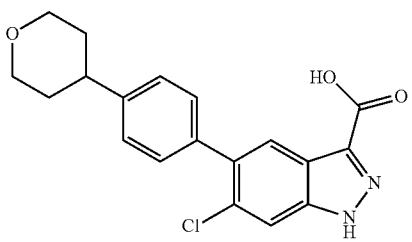 [SMILES: O=C(O)c1n[nH]c2cc(Cl)c(-c3ccc(C4CCOCC4)cc3)cc12]

A mixture of 4-(4-bromophenyl)tetrahydrofuran (300 mg, 1.24 mmol), 5,5,5',5'-tetramethyl-2,2'-bi-1,3,2-dioxaborinane (309 mg, 1.37 mmol), potassium acetate (582 mg, 5.93 mmol) and [1,1'-bis(diphenylphosphino)ferrocene]dichloropalladium(II) (45.4 mg, 0.062 mmol) in 1,4-dioxane (10 mL) was sealed in a pressure tube and stirred at 110° C. for 12 hours. The resulting suspension was cooled, filtered through Celite®, rinsed with EtOAc and concentrated in vacuo. To the residue was added 5-bromo-6-chloro-1H-indazole-3-carboxylic acid (410 mg, 1.49 mmol), [1,1'-bis(diphenylphosphino)ferrocene]dichloropalladium(II) (51 mg, 0.062 mmol), 2 N aqueous potassium carbonate solution (2.5 mL, 5.0 mmol), EtOH (5 mL) and toluene (5 mL). The reaction mixture was sealed in a pressure tube, degassed with N₂ for 10 minutes and stirred at 110° C. for 16 hours. After cooling to room temperature, the reaction was quenched with 1 N NaOH (1 mL). The mixture was stirred for 30 minutes, acidified with 1 N HCl to pH 5 and extracted with EtOAc three times. The combined organic layers were concentrated in vacuo and the crude material was purified by reverse phase chromatography (Biotage C18 column, 0-40% MeCN/water) to give a solid (62.0 mg). The solid was suspended in MeCN (2 mL) and water (0.2 mL), heated to 100° C. and slowly cooled to room temperature over 12 hours. The resulting precipitate was filtered and washed with MeCN to provide the title compound (37 mg, 8% yield) as a crystalline solid. MS (ES+) 357.0 (M+H)⁺. ¹H NMR (500 MHz, DMSO-d₆) δ 7.99 (s, 1H), 7.87 (s, 1H), 7.40 (d, J=8.29 Hz, 2H), 7.36 (d, J=8.29 Hz, 2H), 3.98 (dd, J=10.98, 2.93 Hz, 2H), 3.47 (td, J=11.22, 2.68 Hz, 2H), 2.85 (ddd, J=16.34, 11.47, 5.12 Hz, 1H), 1.67-1.80 (m, 4H).

Example 105

5-(4-Acetylphenyl)-6-chloro-1H-indazole-3-carboxylic acid

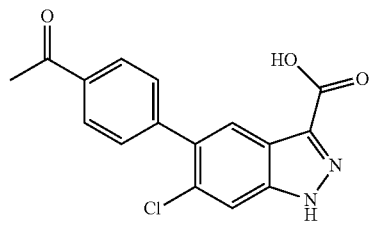 [SMILES: CC(=O)c1ccc(-c2cc3c(C(=O)O)n[nH]c3cc2Cl)cc1]

To a mixture of 5-bromo-6-chloro-1H-indazole-3-carboxylic acid (200 mg, 0.73 mmol) and 4-acetylphenylboronic acid (131 mg, 0.80 mmol) in toluene (2 mL) and EtOH (1 mL) was added 2 N aqueous potassium carbonate solution (1.45 mL, 2.90 mmol). The resulting mixture was degassed with $N_2$ for 10 minutes, treated with [1,1'-bis(diphenylphosphino)ferrocene]dichloropalladium(II) (29 mg, 0.036 mmol), and heated to reflux for 16 hours. The cooled reaction was quenched with saturated $NH_4Cl$ and the mixture was filtered. The filtrate was acidified with 1 N HCl to pH 5 and extracted with EtOAc. The organic layer was dried over $Na_2SO_4$ and concentrated in vacuo. The resulting crude material was purified by reverse phase chromatography (Biotage C18 column, 0-40% MeCN/water) to give the title compound (82 mg, 40% yield) as a solid. MS (ES+) 315.0 (M+H)+. 1H NMR (400 MHz, DMSO-$d_6$) δ 8.14 (s, 1H), 8.01 (d, J=8.39 Hz, 2H), 7.82 (s, 1H), 7.57 (d, J=8.20 Hz, 2H), 2.60 (s, 3H).

Example 106

6-Chloro-5-(4-(4-methylpiperazin-1-yl)phenyl)-1H-indazole-3-carboxylic acid

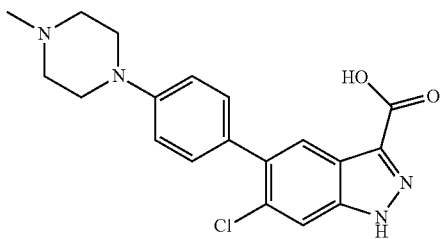 [SMILES: CN1CCN(c2ccc(-c3cc4c(C(=O)O)n[nH]c4cc3Cl)cc2)CC1]

To 5-bromo-6-chloro-1H-indazole-3-carboxylic acid (75.0 mg, 0.27 mmol) in a 5 mL microwave vial was sequentially added 1-methyl-4-[4-(4,4,5,5-tetramethyl-[1,3,2]dioxaborolan-2-yl)-phenyl]piperazine (82.2 mg, 0.27 mmol), [1,1'-bis(diphenylphosphino)ferrocene]dichloropalladium (II) (22.0 mg, 0.027 mmol), 1,4-dioxane (2 mL) and 2 N aqueous potassium carbonate solution (0.4 mL, 0.81 mmol). The reaction mixture was degassed with argon and subjected to microwave irradiation at 110° C. for 50 minutes. The cooled reaction mixture was acidified to pH 5 with 1 N HCl and diluted with EtOAc (10 mL). The organic layer was washed with brine (6 mL), dried over $MgSO_4$, and concentrated in vacuo. The resulting solid was purified by reversed phase HPLC (Column: Waters Sunfire C18 19×100, 5 μm; Mobile phase A: 0.05% TFA in water (v/v); Mobile phase B: 0.05% TFA in MeCN (v/v); Gradient: HOLD at 90.0% $H_2O$/ 10.0% MeCN for 1.0 min. 90.0% $H_2O$/10.0% MeCN linear to 60.0% $H_2O$/40.0% MeCN in 6.75 min, linear to 0% $H_2O$/ 100% MeCN to 7.0 min. HOLD at 0% $H_2O$/100% MeCN from 7.0 to 8.0 min. Flow: 30 mL/min.) to afford the title compound (4.3 mg, 4% yield). MS (ES+) 371.0 (M+H)+. Retention time=1.83 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 107

5-(4-(4-Acetylpiperazin-1-yl)phenyl)-6-chloro-1H-indazole-3-carboxylic acid

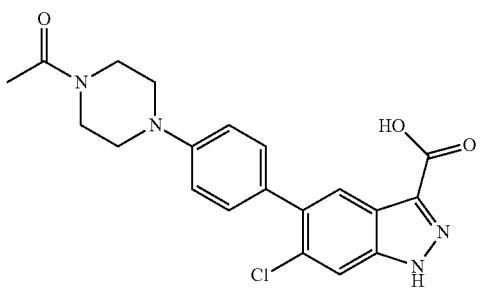 [SMILES: CC(=O)N1CCN(c2ccc(-c3cc4c(C(=O)O)n[nH]c4cc3Cl)cc2)CC1]

To 5-bromo-6-chloro-1H-indazole-3-carboxylic acid (75.0 mg, 0.27 mmol) in a 5 mL microwave vial was sequentially added 1-{4-[4-(4,4,5,5-tetramethyl[1,3,2]dioxaborolan-2-yl)phenyl]piperazin-1-yl}ethanone (89.8 mg, 0.27 mmol), [1,1'-bis(diphenylphosphino)ferrocene]dichloropalladium(II) (22.0 mg, 0.027 mmol), 1,4-dioxane (2 mL) and 2 N aqueous potassium carbonate solution (0.4 mL, 0.81 mmol). The reaction mixture was degassed with argon and subjected to microwave irradiation at 110° C. for 50 minutes. The cooled reaction mixture was acidified to pH 5 with 1 N HCl and diluted with EtOAc (10 mL). The organic layer was washed with brine (6 mL), dried over $MgSO_4$ and concentrated in vacuo. The resulting solid was purified by reversed phase HPLC (Column: Waters Sunfire C18 19×100, 5 μm; Mobile phase A: 0.05% TFA in water (v/v); Mobile phase B: 0.05% TFA in MeCN (v/v); Gradient: HOLD at 80.0% $H_2O$/ 20.0% MeCN for 1.0 min. 80.0% $H_2O$/20.0% MeCN linear to 60.0% $H_2O$/40.0% MeCN in 6.75 min, linear to 0% $H_2O$/ 100% MeCN to 7.0 min. HOLD at 0% $H_2O$/100% MeCN from 7.0 to 8.0 min. Flow: 30 mL/min.) to afford the title compound (7.6 mg, 7% yield). MS (ES+) 399.1 (M+H)+. Retention time=2.25 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 ml/min).

Example 108

6-Chloro-5-(4-(1,1,1-trifluoro-2-hydroxypropan-2-yl)phenyl)-1H-indazole-3-carboxylic acid

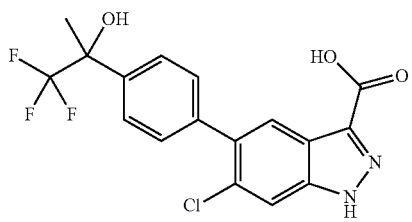 [SMILES: CC(O)(c1ccc(-c2cc3c(C(=O)O)n[nH]c3cc2Cl)cc1)C(F)(F)F]

Step 1

2-(4-(5,5-dimethyl-1,3,2-dioxaborinan-2-yl)phenyl)-1,1,1-trifluoropropan-2-ol

A mixture of 2-(4-bromophenyl)-1,1,1-trifluoropropan-2-ol (300 mg, 1.12 mmol), 5,5,5',5'-tetramethyl-2,2'-bi-1,3,2-dioxaborinane (420 mg, 1.23 mmol), potassium acetate (500 mg, 5.10 mmol) and [1,1'-bis(diphenylphosphino)ferrocene]dichloropalladium(II) (90 mg, 0.11 mmol) was purged with $N_2$, suspended in degassed 1,4-dioxane (2.0 mL) and subjected to microwave irradiation at 110° C. for 60 minutes. The cooled reaction mixture was diluted with water (15 mL) and extracted with EtOAc (2×20 mL). The combined organic layers were washed with water and brine, dried over $MgSO_4$ and concentrated in vacuo. The resulting black oil was purified by flash chromatography (0-67% EtOAc/heptane) to afford the title compound (249 mg, 74% yield) as a pale yellow oil. GC/MS, M=302 at 3.58 min. $^1$H NMR (400 MHz, $CDCl_3$) δ 7.81 (d, J=8.39 Hz, 2H), 7.54 (d, J=8.00 Hz, 2H), 3.76 (s, 4H), 1.77 (s, 3H), 1.01 (s, 6H).

Step 2

6-Chloro-5-(4-(1,1,1-trifluoro-2-hydroxypropan-2-yl)phenyl)-1H-indazole-3-carboxylic acid A mixture of 5-bromo-6-chloro-1H-indazole-3-carboxylic acid (30.0 mg, 0.11 mmol) and [1,1'-bis(diphenylphosphino)ferrocene]dichloropalladium(II) (7.3 mg, 0.010 mmol) was purged with $N_2$. To this mixture was added 2-[4-(5,5-dimethyl-1,3,2-dioxaborinan-2-yl)-phenyl]-1,1,1-trifluoropropan-2-ol (35.0 mg, 0.12 mmol) in toluene (1.0 mL) and EtOH (0.5 mL), followed by 2 N aqueous potassium carbonate solution (0.22 mL, 0.44 mmol). The reaction mixture was heated to 110° C. for 18 hours, cooled to room temperature and concentrated in vacuo. The resulting solid was partitioned between water and EtOAc, and acidified to pH 5 with aqueous 1 N citric acid. The organic layer was dried over $Na_2SO_4$ and concentrated in vacuo. The crude material was purified by reverse phase HPLC (Column: Waters Sunfire C18 19×100 mm, 5 µm; Mobile phase A: 0.05% TFA in water (v/v); Mobile phase B: 0.05% TFA in MeCN (v/v); HOLD at 100.0% $H_2O$/0.0% MeCN for 1.0 min. 100.0% $H_2O$/0.0% MeCN linear to 5.0% $H_2O$/95.0% MeCN in 6.75 min, linear to 0% $H_2O$/100% MeCN to 7.0 min. HOLD at 0% $H_2O$/100% MeCN from 7.0 to 8.0 min. Flow: 30 mL/min) to give the title compound (6.5 mg, 15% yield).

MS (ES$^+$) 384.9 (M+H)$^+$. Retention time=2.62 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 109

6-Chloro-5-(4-(2-hydroxyethyl)phenyl)-1H-indazole-3-carboxylic acid

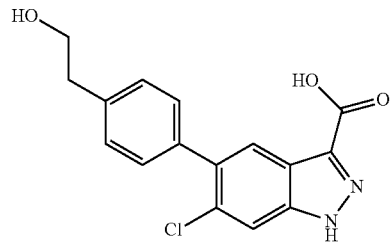 [SMILES: O=C(O)c1n[nH]c2cc(Cl)c(-c3ccc(CCO)cc3)cc12]

To a solution of 5-bromo-6-chloro-1H-indazole-3-carboxylic acid (75 mg, 0.27 mmol), 2-(4-(4,4,5,5-tetramethyl-1,3,2-dioxaborolan-2-yl)phenyl)ethanol (75 mg, 0.30 mmol) in EtOH (0.5 mL) and toluene (0.5 mL) was added 2 N aqueous potassium carbonate solution (0.5 mL, 1.0 mmol). The reaction mixture was degassed with $N_2$ for 5 minutes, treated with [1,1'-bis(diphenylphosphino)ferrocene]dichloropalladium(II) (11.4 mg, 0.014 mmol) and degassed with $N_2$ for another 5 minutes. The suspension was sealed in a pressure tube and heated to 130° C. for 1 hour. As the reaction progressed, the suspension became clear, turned to orange and then dark brown. The reaction mixture was diluted with EtOAc (5 mL) and water (5 mL), and filtered through a syringe filter. The aqueous layer was acidified to pH 5 by 1 N HCl solution, and extracted with EtOAc. The organic layer was dried over $Na_2SO_4$ and concentrated in vacuo. The crude material was purified by reverse phase HPLC (Column: Waters Sunfire C18 19×100 mm, 5 µm; Mobile phase A: 0.05% Formic acid in water (v/v); Mobile phase B: 0.05% Formic acid in MeCN (v/v); HOLD at 80.0% $H_2O$/20.0% MeCN for 1.0 min. 80.0% $H_2O$/20.0% MeCN linear to 60.0% $H_2O$/40.0% MeCN in 6.75 min, linear to 0% $H_2O$/100% MeCN to 7.0 min. HOLD at 0% $H_2O$/100% MeCN from 7.0 to 8.0 min. Flow: 30 mL/min) to provide the title compound (11.5 mg, 13% yield). MS (ES+) 317.1 (M+H)$^+$. Retention time=2.27 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 110

6-Chloro-5-(4-cyclohexylphenyl)-1H-indazole-3-carboxylic acid

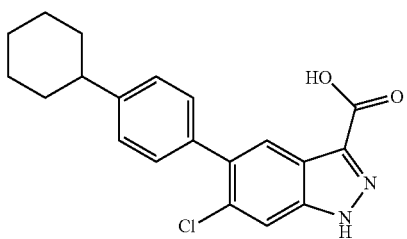 [SMILES: O=C(O)c1n[nH]c2cc(Cl)c(-c3ccc(C4CCCCC4)cc3)cc12]

A mixture of 5,5,5',5'-tetramethyl-2,2'-bi-1,3,2-dioxaborinane (75.0 mg, 0.22 mmol), oven dried potassium acetate (94.1 mg, 0.95 mmol), [1,1'-bis(diphenylphosphino)ferrocene]dichloropalladium(II) (19.0 mg, 0.023 mmol), and 1-bromo-4-cyclohexylbenzene (49.5 mg, 0.21 mmol) in 1,4-dioxane (2 mL) was degassed with N₂ for 10 minutes, and subjected to microwave irradiation at 115° C. for one hour. The black reaction mixture was cooled, filtered through cotton, and concentrated in vacuo to give a dark solid. To the dark solid was added 5-bromo-6-chloro-1H-indazole-3-carboxylic acid (55.6 mg, 0.20 mmol), 2 N aqueous potassium carbonate solution (0.40 mL, 0.81 mmol) and [1,1'-bis(diphenylphosphino)ferrocene]dichloropalladium(II) dichloromethane adduct (16.3 mg, 0.020 mmol). The reaction mixture was diluted with degassed toluene (1 mL) and EtOH (1 mL), and heated at 110° C. for 18 hours in a sealed reaction vessel. The cooled reaction mixture was concentrated in vacuo and partitioned between 2 N citric acid (15 mL) and EtOAc (15 mL). The layers were separated, and the aqueous phase was extracted with EtOAc (15 mL). The combined organic layers were dried over Na₂SO₄ and concentrated in vacuo to give a dark oil, which was purified by reverse phase HPLC (Column: Waters XBridge C18 19×100 mm, 5 μm; Mobile phase A: 0.03% NH₄OH in water (v/v); Mobile phase B: 0.03% NH₄OH in MeCN (v/v); 80.0% H₂O/20.0% MeCN linear to 40% H₂O/60% MeCN in 8.5 min, 40% H₂O/60% MeCN linear to 0% H₂O/100% MeCN in 0.5 min, HOLD at 0% H₂O/100% MeCN to 10.0 min. Flow: 25 mL/min) to give the title compound (6.2 mg, 9% yield). MS (ES+) 355.1 (M+H)⁺. Retention time=3.65 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 111

6-Chloro-5-(4-(hydroxymethyl)phenyl)-1H-indazole-3-carboxylic acid

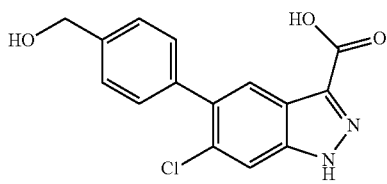

A mixture of 5-bromo-6-chloro-1H-indazole-3-carboxylic acid (200.0 mg, 0.73 mmol), 4-(hydroxymethyl)phenylboronic acid (90.0 mg, 0.59 mmol), 2 N aqueous potassium carbonate (1.1 mL, 2.2 mmol) and [1,1'-bis(diphenylphosphino)ferrocene]dichloropalladium(II) (60.0 mg, 0.073 mmol) in toluene (1.5 mL) and EtOH (2.3 mL) was degassed with N₂ for 3 minutes and heated to 110° C. for 5 hours. The reaction mixture was cooled to room temperature and concentrated in vacuo. The residue was acidified to pH 5 and concentrated in vacuo. The crude material was purified by reverse phase HPLC (Column: Phenomenex Synergi C18 150×30 mm, 4 μm; 28% MeCN in water (0.225% TFA) to 28% MeCN in water (0.225% TFA) for 12 min; Flow Rate: 30 mL/min) to afford the title compound (27 mg, 11% yield) as a white solid. MS (ES+) 302.9 (M+H)⁺. ¹H NMR (400 MHz, CD₃OD) δ 8.11 (s, 1H), 7.76 (s, 1H), 7.45 (m, 4H), 4.69 (s, 2H).

Example 112

6-Chloro-5-(3-hydroxyphenyl)-1H-indazole-3-carboxylic acid

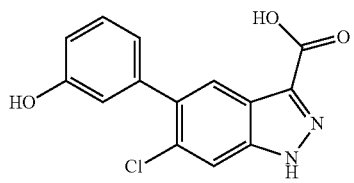 [SMILES: O=C(O)c1n[nH]c2cc(Cl)c(-c3cccc(O)c3)cc12]

A mixture of 5-bromo-6-chloro-1H-indazole-3-carboxylic acid (100 mg, 0.36 mmol), 3-hydroxyphenylboronic acid (51.0 mg, 0.36 mmol), potassium carbonate (301 mg, 2.18 mmol) and [1,1'-bis(diphenylphosphino)ferrocene]dichloropalladium(II) (30.0 mg, 0.036 mmol) in toluene (1.5 mL) and water (1.1 mL) was degassed with N₂ for 3 minutes and heated to 110° C. for 16 hours. The reaction mixture was cooled to room temperature and concentrated in vacuo. The brown residue was acidified to pH 4 with 1 N HCl and extracted with n-butanol (3×20 mL). The combined organic layers were washed with brine (2×20 mL), dried over Na₂SO₄ and concentrated in vacuo. The crude material was purified by reverse phase HPLC (Column: Phenomenex Synergi C18 150×30 mm, 4 μm; 25% MeCN in water (0.225% TFA) to 45% MeCN in water (0.225% TFA) to afford the title compound (4 mg, 4% yield) as a white solid.
MS (ES+) 289.1 (M+H)⁺. ¹H NMR (400 MHz, DMSO-d₆) δ 9.57 (s, 1H), 8.04 (s, 1H), 7.83 (s, 1H), 7.28 (t, J=8.20 Hz, 1H), 6.82 (m, 3H).

Example 113

6-Chloro-5-(2,3-dihydrobenzofuran-5-yl)-1H-indazole-3-carboxylic acid

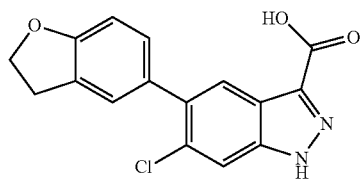 [SMILES: O=C(O)c1n[nH]c2cc(Cl)c(-c3ccc4c(c3)CCO4)cc12]

To a solution of 5-bromo-6-chloro-1H-indazole-3-carboxylic acid (100 mg, 0.36 mmol), 2,3-dihydrobenzofuran-5-boronic acid (65.0 mg, 0.39 mmol) in EtOH (0.5 mL) and toluene (0.5 mL) was added 2 N aqueous potassium carbonate solution (0.5 mL, 1.0 mmol). The reaction mixture was degassed with N₂ for 5 minutes, treated with [1,1'-bis(diphenylphosphino)ferrocene]dichloropalladium(II) (14.7 mg, 0.018 mmol) and degassed with N₂ for another 5 minutes. The suspension was sealed in a pressure tube and heated to 130° C. for 1 hour. As the reaction progressed, the suspension became clear, turned to orange and then dark brown. The reaction mixture was diluted with EtOAc (5 mL) and water (5 mL), and filtered through a syringe filter. The aqueous layer was acidified to pH 5 by 1 N HCl solution, and extracted with EtOAc. The organic layer was dried over $Na_2SO_4$ and concentrated in vacuo. The crude material was purified by reverse phase HPLC (Column: Waters XBridge C18 19×100 mm, 5 μm; Mobile phase A: 0.03% $NH_4OH$ in water (v/v); Mobile phase B: 0.03% $NH_4OH$ in MeCN (v/v); 95.0% $H_2O$/5.0% MeCN linear to 50.0% $H_2O$/50.0% MeCN in 8.5 min, 50.0% $H_2O$/50.0% MeCN linear to 0% $H_2O$/100% MeCN in 0.5 min HOLD at 0% $H_2O$/100% MeCN from 9.0 to 10.0 min. Flow: 25 mL/min) to provide the title compound (24.8 mg, 22% yield). MS (ES+) 315.1 $(M+H)^+$. Retention time=2.68 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 114

6-Chloro-5-(4-(1-methylpiperidin-4-yl)phenyl)-1H-indazole-3-carboxylic acid

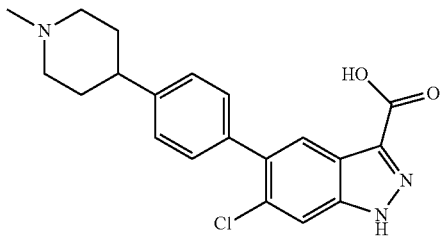 [SMILES: CN1CCC(c2ccc(-c3cc4c(C(=O)O)n[nH]c4cc3Cl)cc2)CC1]

A mixture of 5,5,5',5'-tetramethyl-2,2'-bi-1,3,2-dioxaborinane (92.0 mg, 0.27 mmol), oven dried potassium acetate (116 mg, 1.18 mmol), [1,1'-bis(diphenylphosphino)ferrocene]dichloropalladium(II) dichloromethane adduct (22 mg, 0.027 mmol) and 4-(4-bromophenyl)-1-methylpiperidine (65 mg, 0.26 mmol) in 1,4-dioxane (2.6 mL) was degassed with $N_2$ for 10 minutes, sealed in a pressure tube, and heated to 100° C. for 2 hours. The cooled reaction mixture was filtered through cotton and concentrated in vacuo to give a dark solid. To the dark solid was added 5-bromo-6-chloro-1H-indazole-3-carboxylic acid (59.8 mg, 0.22 mmol), 2 N aqueous potassium carbonate solution (0.4 mL, 0.87 mmol) and [1,1'-bis(diphenylphosphino)ferrocene]dichloropalladium(II) dichloromethane adduct (18 mg, 0.022 mmol). The reaction mixture was diluted with degassed toluene (0.8 mL) and EtOH (0.8 mL), sealed in a pressure tube and heated at 100° C. for 1.5 hours then 75° C. for an additional 16 hours. The cooled reaction mixture was concentrated in vacuo. The resulting dark solid was purified by reverse phase HPLC (Column: Waters XBridge C18 19×100 mm, 5 μm; Mobile phase A: 0.03% $NH_4OH$ in water (v/v); Mobile phase B: 0.03% $NH_4OH$ in MeCN (v/v); 95.0% $H_2O$/5.0% MeCN linear to 0% $H_2O$/100% MeCN in 8.5 min, HOLD at 0% $H_2O$/100% MeCN to 10.0 min. Flow: 25 mL/min) to give the title compound (8.2 mg, 9% yield). MS (ES+) 370.2 $(M+H)^+$. Retention time=2.00 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 115

6-Chloro-5-(4-(1-hydroxy-2-methylpropan-2-yl)phenyl)-1H-indazole-3-carboxylic acid

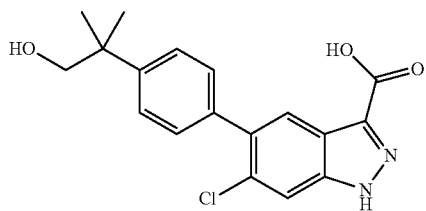 [SMILES: CC(C)(CO)c1ccc(-c2cc3c(C(=O)O)n[nH]c3cc2Cl)cc1]

A suspension of 2-(4-bromophenyl)-2-methylpropan-1-ol (168 mg, 0.73 mmol), 5,5,5',5'-tetramethyl-2,2'-bi-1,3,2-dioxaborinane (275 mg, 0.81 mmol), [1,1'-bis(diphenylphosphino)ferrocene]dichloropalladium(II) (30 mg, 0.037 mmol) and potassium acetate (216 mg, 2.20 mmol) in 1,4-dioxane (2 mL) was sealed in a pressure tube and heated to 130° C. for 1 hour. To the mixture was added 5-bromo-6-chloro-1H-indazole-3-carboxylic acid (100 mg, 0.36 mmol), [1,1'-bis(diphenylphosphino)ferrocene]dichloropalladium(II) (14.7 mg, 0.018 mmol), 2 N aqueous potassium carbonate solution (0.5 mL, 1.0 mmol) and EtOH (2 mL). The reaction mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters XBridge C18 19×100 mm, 5 μm; Mobile phase A: 0.03% $NH_4OH$ in water (v/v); Mobile phase B: 0.03% $NH_4OH$ in MeCN (v/v); 90.0% $H_2O$/10.0% MeCN linear to 70.0% $H_2O$/30.0% MeCN in 8.5 min, 70.0% $H_2O$/30.0% MeCN linear to 0% $H_2O$/100% MeCN in 0.5 min HOLD at 0% $H_2O$/100% MeCN from 9.0 to 10.0 min. Flow: 25 mL/min) to afford the title compound (25.1 mg, 20% yield). MS (ES+) 345.1 $(M+H)^+$. Retention time=1.59 minutes (Column: Waters XBridge dC18 4.6×50 mm, 5 μm; Mobile phase A: 0.03% $NH_4OH$ in water (v/v); Mobile phase B: 0.03% $NH_4OH$ in MeCN (v/v); Gradient: 95:5 A:B linear to 5:95 A:B in 4.0 min, hold at 5:95 A:B to 5.0 min. Flow: 2 ml/min).

Example 116

6-Chloro-5-(2,3-dihydro-1H-inden-5-yl)-1H-indazole-3-carboxylic acid

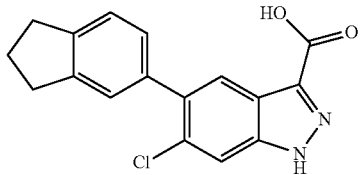 [SMILES: O=C(O)c1n[nH]c2cc(Cl)c(-c3ccc4c(c3)CCC4)cc12]

A suspension of 5-bromoindane (100.0 mg, 0.51 mmol), 5,5,5',5'-tetramethyl-2,2'-bi-1,3,2-dioxaborinane (191 mg, 0.56 mmol), [1,1'-bis(diphenylphosphino)ferrocene]dichloropalladium(II) (42.0 mg, 0.025 mmol) and potassium acetate (150 mg, 1.50 mmol) in 1,4-dioxane (1 mL) was sealed in a pressure tube and heated to 130° C. for 1 hour. To this mixture was added 5-bromo-6-chloro-1H-indazole-3-carboxylic acid (100 mg, 0.36 mmol), [1,1'-bis(diphenylphosphino)ferrocene]dichloropalladium(II) (14.7 mg, 0.018 mmol), 2 N aqueous potassium carbonate solution (0.5 mL, 1.0 mmol) and EtOH (2 mL). The reaction mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters XBridge C18 19×100 mm, 5 μm; Mobile phase A: 0.03% $NH_4OH$ in water (v/v); Mobile phase B: 0.03% $NH_4OH$ in MeCN (v/v); 80.0% $H_2O$/20.0% MeCN linear to 70.0% $H_2O$/30.0% MeCN in 8.5 min, 70.0% $H_2O$/30.0% MeCN linear to 0% $H_2O$/100% MeCN in 0.5 min HOLD at 0% $H_2O$/100% MeCN from 9.0 to 10.0 min. Flow: 25 mL/min) to afford the title compound (6.2 mg, 6% yield). MS (ES+) 313.1 $(M+H)^+$. Retention time=3.11 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 117

5-(4-(1-Acetylpiperidin-4-yl)phenyl)-6-chloro-1H-indazole-3-carboxylic acid

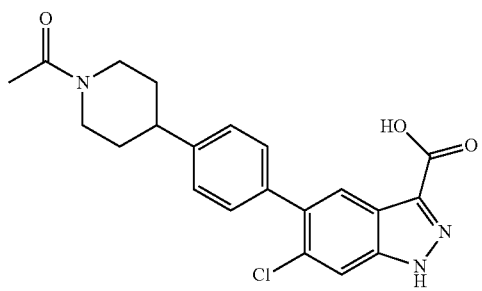 [SMILES: CC(=O)N1CCC(c2ccc(-c3cc4c(C(=O)O)n[nH]c4cc3Cl)cc2)CC1]

A mixture of 5,5,5',5'-tetramethyl-2,2'-bi-1,3,2-dioxaborinane (110 mg, 0.32 mmol), oven dried potassium acetate (139 mg, 1.41 mmol), [1,1'-bis(diphenylphosphino)ferrocene]dichloropalladium(II) dichloromethane adduct (26 mg, 0.032 mmol), and 1-(4-(4-bromophenyl)piperidin-1-yl)ethanone (86 mg, 0.30 mmol) in 1,4-dioxane (3.1 mL) was degassed with $N_2$ for 10 minutes, and subjected to microwave irradiation at 115° C. for 1 hour. The cooled reaction mixture was filtered through cotton and concentrated in vacuo to give a dark solid. To the dark solid was added 5-bromo-6-chloro-1H-indazole-3-carboxylic acid (68.9 mg, 0.25 mmol), 2 N aqueous potassium carbonate solution (0.5 mL, 1.0 mmol) and [1,1'-bis(diphenylphosphino)ferrocene]dichloropalladium(II) dichloromethane adduct (20.4 mg, 0.025 mmol). The reaction mixture was diluted with degassed toluene (0.8 mL) and EtOH (0.8 mL), sealed in a pressure tube and heated at 100° C. for 1 hour then 75° C. for an additional 16 hours. The cooled reaction mixture was concentrate in vacuo, and the residue was partitioned between 0.5 N HCl (14 mL) and EtOAc (15 mL). The layers were separated and the aqueous layer was extracted with EtOAc (3×8 mL). The combined organic layers were dried over $Na_2SO_4$ and concentrated in vacuo. The resulting reddish solid was purified by reverse phase HPLC Column: Waters XBridge C18 19×100 mm, 5 μm; Mobile phase A: 0.03% $NH_4OH$ in water (v/v); Mobile phase B: 0.03% $NH_4OH$ in MeCN (v/v); 85.0% $H_2O$/15.0% MeCN linear to 65.0% $H_2O$/35.0% MeCN in 10.5 min, 65.0% $H_2O$/35.0% MeCN linear to 0% $H_2O$/100% MeCN in 0.5 min HOLD at 0% $H_2O$/100% MeCN from 11.0 to 12.0 min. Flow: 25 mL/min) to give the title compound (14.4 mg, 15% yield). MS (ES+) 398.2 $(M+H)^+$. Retention time=2.55 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 118

6-Chloro-5-(4-methoxyphenyl)-N-(phenylsulfonyl)-1H-indazole-3-carboxamide

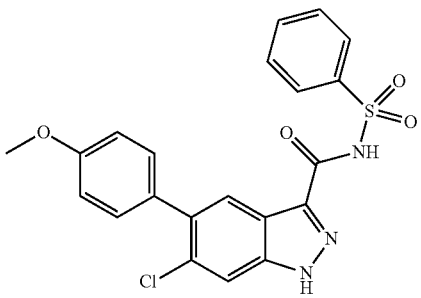 [SMILES: COc1ccc(-c2cc3c(C(=O)NS(=O)(=O)c4ccccc4)n[nH]c3cc2Cl)cc1]

Step 1

6-Chloro-5-(4-methoxyphenyl)-1H-indazole-3-carboxylic acid p-tolyl ester

A mixture of 6-chloro-5-(4-methoxyphenyl)-1H-indazole-3-carboxylic acid (547 mg, 1.81 mmol) in thionyl chloride (10 mL) was heated to 60° C. for 4 hours, cooled to room temperature and concentrated in vacuo. The residue was dissolved in $CH_2Cl_2$ (20 mL) and treated with p-cresol (399 mg, 3.61 mmol) followed by triethylamine (369 mg, 3.61 mmol). The reaction mixture was stirred for 16 hours and quenched with water (20 mL). The layers were separated and the organic phase was concentrated in vacuo. The residue was purified by flash chromatography (25-50% EtOAc/heptane) to give the title compound (192 mg, 27% yield).
MS $(ES^+)$ 393.2 $(M+1)^+$.

Step 2

6-Chloro-5-(4-methoxyphenyl)-N-(phenylsulfonyl)-1H-indazole-3-carboxamide

A mixture of benzenesulfonamide (25.6 mg, 0.163 mmol) and potassium tert-butoxide (22.0 mg, 0.196 mmol) in THF (10 mL) was stirred for 10 minutes, and treated with 6-chloro-5-(4-methoxyphenyl)-1H-indazole-3-carboxylic acid p-tolyl ester (64 mg, 0.16 mmol). The reaction mixture was heated to 65° C. for 16 hours, cooled to room temperature and concentrated in vacuo. The residue was partitioned between water (5 mL) and EtOAc (5 mL), and the layers were separated. The organic layer was concentrated in vacuo and the crude material was purified by reverse phase HPLC (Column: Waters Sunfire C18 19×100 mm, 5 µm; Mobile phase A: 0.05% TFA in water (v/v); Mobile phase B: 0.05% TFA in MeCN (v/v); Gradient: 60:40 A:B linear to 30:70 A:B in 8.5 min to 100% B to 9.0 min, hold at 100% B from 9.0 to 10.0 min. Flow: 25 mL/min) to give the title compound (2.2 mg, 3% yield). MS (ES+) 442.0 (M+1)+. Retention time=3.29 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 119

6-Chloro-5-(4-(2-hydroxyethoxy)phenyl)-1H-indazole-3-carboxylic acid

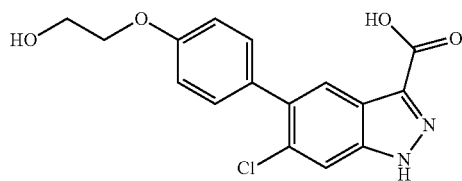 [SMILES: O=C(O)c1n[nH]c2cc(Cl)c(-c3ccc(OCCO)cc3)cc12]

A suspension of 2-(4-bromophenoxy)ethanol (100 mg, 0.46 mmol), 5,5,5',5'-tetramethyl-2,2'-bi-1,3,2-dioxaborinane (173 mg, 0.50 mmol), [1,1'-bis(diphenylphosphino)ferrocene]dichloropalladium(II) (38.0 mg, 0.025 mmol) and potassium acetate (135 mg, 1.38 mmol) in 1,4-dioxane (1 mL) was sealed in a pressure tube and heated to 130° C. for 1 hour. To the mixture was added 5-bromo-6-chloro-1H-indazole-3-carboxylic acid (100 mg, 0.36 mmol), [1,1'-bis(diphenylphosphino)ferrocene]dichloropalladium(II) (14.7 mg, 0.018 mmol), 2 N aqueous potassium carbonate solution (0.5 mL, 1.0 mmol) and EtOH (2 mL). The mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters Sunfire C18 19×100 mm, 5 µm; Mobile phase A: 0.05% Formic acid in water (v/v); Mobile phase B: 0.05% Formic acid in MeCN (v/v); HOLD at 75.0% $H_2O$/25.0% MeCN for 1.0 min. 75.0% $H_2O$/25.0% MeCN linear to 45.0% $H_2O$/55.0% MeCN in 6.75 min, linear to 0% $H_2O$/100% MeCN to 7.0 min. HOLD at 0% $H_2O$/100% MeCN from 7.0 to 8.0 min. Flow: 30 ml/min) to afford the title compound (23.1 mg, 15% yield). MS (ES+) 333.0 (M+H)+. Retention time=2.19 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 120

6-Chloro-5-(4-((1S,3S)-3-hydroxycyclobutyl)phenyl)-1H-indazole-3-carboxylic acid

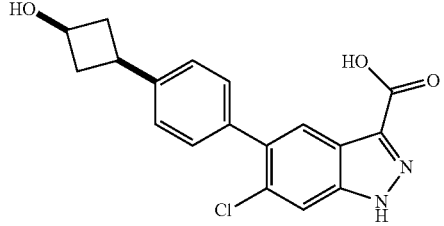

A suspension of 3-(4-bromophenyl)cyclobutanol (90.6 mg, 0.37 mmol), 5,5,5',5'-tetramethyl-2,2'-bi-1,3,2-dioxaborinane (136 mg, 0.37 mmol), [1,1'-bis(diphenylphosphino)ferrocene]dichloropalladium(II) (15.0 mg, 0.018 mmol) and potassium acetate (107 mg, 1.09 mmol) in 1,4-dioxane (1 mL) was sealed in a pressure tube and heated to 130° C. for 1 hour. To the mixture was added 5-bromo-6-chloro-1H-indazole-3-carboxylic acid (100 mg, 0.36 mmol), [1,1'-bis(diphenylphosphino)ferrocene]dichloropalladium (II) (14.7 mg, 0.018 mmol), 2 N aqueous potassium carbonate solution (0.5 mL, 1.0 mmol) and EtOH (2 mL). The mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters Sunfire C18 19×100 mm, 5 µm; Mobile phase A: 0.05% TFA in water (v/v); Mobile phase B: 0.05% TFA in MeCN (v/v); 95.0% $H_2O$/5.0% MeCN linear to 0% $H_2O$/100% MeCN in 10.5 min, HOLD at 0% $H_2O$/100% MeCN to 12.0 min. Flow: 25 mL/min) to afford the title compound (17.4 mg, 14% yield). MS (ES+) 343.1 (M+H)+. Retention time=2.45 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 121

6-Chloro-5-(2,3-dihydrobenzo[b][1,4]dioxin-6-yl)-1H-indazole-3-carboxylic acid

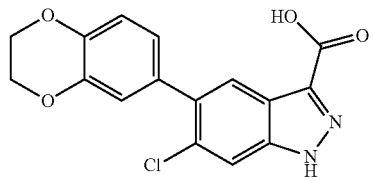 [SMILES: O=C(O)c1n[nH]c2cc(Cl)c(-c3ccc4c(c3)OCCO4)cc12]

A mixture of 5-bromo-6-chloro-1H-indazole-3-carboxylic acid (40.0 mg, 0.14 mmol), (2,3-dihydrobenzo[b][1,4]dioxin-6-yl)boronic acid (27.4 mg, 0.152 mmol) and 2 N aqueous potassium carbonate solution (0.2 mL, 0.4 mmol) in toluene (0.3 mL) and EtOH (0.7 mL) was purged with $N_2$, and treated with [1,1'-bis(diphenylphosphino)ferrocene]dichloropalladium(II) under $N_2$. The reaction mixture was heated to 100° C. for 48 hours, cooled to room temperature and concentrated in vacuo. The crude material was purified by reverse phase HPLC (Column: Waters XBridge C18 19×100 mm, 5 μm; Mobile phase A: 0.03% $NH_4OH$ in water (v/v); Mobile phase B: 0.03% $NH_4OH$ in MeCN (v/v); 95.0% $H_2O$/5.0% MeCN linear to 50.0% $H_2O$/50.0% MeCN in 10.5 min, 50.0% $H_2O$/50.0% MeCN linear to 0% $H_2O$/100% MeCN in 0.5 min HOLD at 0% $H_2O$/100% MeCN from 11.0 to 12.0 min. Flow: 25 mL/min) to afford the title compound (4.7 mg, 10% yield). MS (ES+) 331.1 $(M+H)^+$. Retention time=2.62 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 122

5-(4-(1-Carbamoylcyclobutyl)phenyl)-6-chloro-1H-indazole-3-carboxylic acid

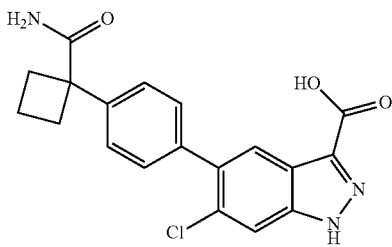 [SMILES: NC(=O)C1(c2ccc(-c3cc4c(C(=O)O)n[nH]c4cc3Cl)cc2)CCC1]

A suspension of 1-(4-bromophenyl)cyclobutanecarboxylic acid amide (101 mg, 0.37 mmol), 5,5,5',5'-tetramethyl-2,2'-bi-1,3,2-dioxaborinane (136 mg, 0.37 mmol), [1,1'-bis(diphenylphosphino)ferrocene]dichloropalladium(II) (15.0 mg, 0.018 mmol) and potassium acetate (107 mg, 1.09 mmol) in 1,4-dioxane (1 mL) was sealed in a pressure tube and heated to 130° C. for 1 hour. To the mixture was added 5-bromo-6-chloro-1H-indazole-3-carboxylic acid (100 mg, 0.36 mmol), [1,1'-bis(diphenylphosphino)ferrocene]dichloropalladium(II) (14.7 mg, 0.018 mmol), 2 N aqueous potassium carbonate solution (0.5 mL, 1.0 mmol) and EtOH (2 mL). The mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters Sunfire C18 19×100 mm, 5 μm; Mobile phase A: 0.05% TFA in water (v/v); Mobile phase B: 0.05% TFA in MeCN (v/v); 95.0% $H_2O$/5.0% MeCN linear to 0% $H_2O$/100% MeCN in 10.5 min, HOLD at 0% $H_2O$/100% MeCN to 12.0 min. Flow: 25 mL/min) to afford the title compound (4.3 mg, 3% yield). MS (ES+) 343.1 $(M+H)^+$. Retention time=2.45 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 123

5-(4-(2-Amino-2-oxoethyl)phenyl)-6-chloro-1H-indazole-3-carboxylic acid

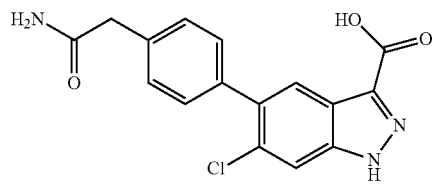 [SMILES: NC(=O)Cc1ccc(-c2cc3c(C(=O)O)n[nH]c3cc2Cl)cc1]

A suspension of 2-(4-bromophenyl)acetamide (85.0 mg, 0.37 mmol), 5,5,5',5'-tetramethyl-2,2'-bi-1,3,2-dioxaborinane (136 mg, 0.37 mmol), [1,1'-bis(diphenylphosphino)ferrocene]dichloropalladium(II) (15.0 mg, 0.018 mmol) and potassium acetate (107 mg, 1.09 mmol) in 1,4-dioxane (1 mL) was sealed in a pressure tube and heated to 130° C. for 1 hour. To the mixture was added 5-bromo-6-chloro-1H-indazole-3-carboxylic acid (100 mg, 0.36 mmol), [1,1'-bis(diphenylphosphino)ferrocene]dichloropalladium(II) (14.7 mg, 0.018 mmol), 2 N aqueous potassium carbonate solution (0.5 mL, 1 mmol) and EtOH (2 mL). The mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters Sunfire C18 19×100 mm, 5 μm; Mobile phase A: 0.05% TFA in water (v/v); Mobile phase B: 0.05% TFA in MeCN (v/v); 95.0% $H_2O$/5.0% MeCN linear to 0% $H_2O$/100% MeCN in 10.5 min, HOLD at 0% $H_2O$/100% MeCN to 12.0 min. Flow: 25 mL/min) to afford the title compound (3.3 mg, 3% yield). MS (ES+) 330.1 $(M+H)^+$. Retention time=2.04 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 124

(±)-6-Chloro-5-(4-(tetrahydrofuran-3-yl)phenyl)-1H-indazole-3-carboxylic acid

Step 1

(±)-3-(4-Bromophenyl)tetrahydrofuran

A mixture of 4-bromophenylboronic acid (1.7 g, 8.1 mmol), nickel iodide (102 mg, 0.32 mmol), solid sodium hexamethyldisilazide (1.6 g, 8.1 mmol) and trans-2-aminocyclohexanol (49.0 mg, 0.32 mmol) was sealed in a microwave vial, diluted with dry i-PrOH (7 mL), and evacuated/backfilled with $N_2$ three times. The reaction mixture was stirred at room temperature for 5 minutes, treated with a solution of 3-iodotetrahydrofuran (800 mg, 4.04 mmol) in i-PrOH (1 mL) and evacuated/backfilled with $N_2$. The reaction mixture was subjected to microwave irradiation at 80° C. for 20 minutes. The cooled reaction mixture was poured into 0.3 N HCl (30 mL) and extracted with heptane/EtOAc (2:1, 3×20 mL). The combined organic layers were dried over $Na_2SO_4$ and concentrated in vacuo to give a yellow solid. The crude material was purified by flash chromatography (0-5% EtOAc/Heptane) to give the title compound (471 mg, 51% yield) as a clear oil. $^1$H NMR (400 MHz, $CDCl_3$) δ 7.41 (d, J=8.39 Hz, 2H), 7.11 (d, J=8.39 Hz, 2H), 4.09 (t, J=8.00 Hz, 1H), 4.04 (td, J=8.39, 4.69 Hz, 1H), 3.89 (q, J=8.00 Hz, 1H), 3.65-3.70 (m, 1H), 3.34 (quin, J=7.66 Hz, 1H), 2.35 (dtd, J=12.37, 7.77, 7.77, 4.68 Hz, 1H), 1.94 (dq, J=12.37, 8.04 Hz, 1H).

Step 2

(±)-6-Chloro-5-(4-(tetrahydrofuran-3-yl)phenyl)-1H-indazole-3-carboxylic acid

A mixture of 5,5,5',5'-tetramethyl-2,2'-bi-1,3,2-dioxaborinane (110 mg, 0.32 mmol), oven dried potassium acetate (140 mg, 1.42 mmol), [1,1'-bis(diphenylphosphino)ferrocene]dichloropalladium(II) dichloromethane adduct (27.0 mg, 0.033 mmol), and (±)-3-(4-bromophenyl)tetrahydrofuran (70.0 mg, 0.31 mmol) in 1,4-dioxane (3.1 mL) was degassed with $N_2$ for 10 minutes, and subjected to microwave irradiation at 115° C. for 1 hour. The cooled reaction mixture was filtered through cotton and concentrated in vacuo to give a dark solid. To the dark solid was added 5-bromo-6-chloro-1H-indazole-3-carboxylic acid (75.0 mg, 0.270 mmol), 2 N aqueous potassium carbonate solution (0.543 mL, 1.09 mmol) and [1,1'-bis(diphenylphosphino)ferrocene]dichloropalladium(II) dichloromethane adduct (22.0 mg, 0.027 mmol). The reaction mixture was diluted with degassed toluene (0.8 mL) and EtOH (0.8 mL), and heated at 100° C. for 1.5 hours in a sealed tube. The cooled reaction mixture was concentrated in vacuo, and the residue was partitioned between 0.5 N HCl (15 mL) and EtOAc (10 mL). The layers were separated and the aqueous layer was extracted with EtOAc (3×10 mL). The combined organic layers were dried over $Na_2SO_4$ and concentrated in vacuo. The resulting brown solid was purified by reverse phase HPLC (Column: Waters XBridge C18 19×100 mm, 5 µm; Mobile phase A: 0.03% $NH_4OH$ in water (v/v); Mobile phase B: 0.03% $NH_4OH$ in MeCN (v/v); 95.0% $H_2O$/5.0% MeCN linear to 50.0% $H_2O$/50.0% MeCN in 10.5 min, 50.0% $H_2O$/50.0% MeCN linear to 0% $H_2O$/100% MeCN in 0.5 min HOLD at 0% $H_2O$/100% MeCN from 11.0 to 12.0 min. Flow: 25 mL/min) to give the title compound (9.6 mg, 10% yield). MS (ES+) 343.1 (M+H)$^+$. Retention time=2.63 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 125

6-Chloro-5-(4-(1-methoxyethyl)phenyl)-1H-indazole-3-carboxylic acid

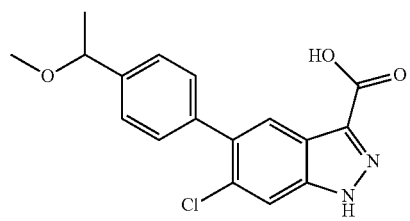 [SMILES: COC(C)c1ccc(-c2cc3c(C(=O)O)n[nH]c3cc2Cl)cc1]

A mixture of 5-bromo-6-chloro-1H-indazole-3-carboxylic acid (40.0 mg, 0.14 mmol), 4-(1-methoxyethyl)phenylboronic acid (27.4 mg, 0.152 mmol) and 2 N aqueous potassium carbonate solution (0.2 mL, 0.4 mmol) in toluene (0.3 mL) and EtOH (0.7 mL) was purged with $N_2$, and treated with [1,1'-bis(diphenylphosphino)ferrocene]dichloropalladium (II) under $N_2$. The reaction mixture was heated to 100° C. for 48 hours, cooled to room temperature and concentrated in vacuo. The crude material was purified by reverse phase HPLC (Column: Waters Sunfire C18 19×100 mm, 5 µm; Mobile phase A: 0.05% TFA in water (v/v); Mobile phase B: 0.05% TFA in MeCN (v/v); 95.0% $H_2O$/5.0% MeCN linear to 0% $H_2O$/100% MeCN in 7.0 min, HOLD at 0% $H_2O$/100% MeCN to 8.5 min. Flow: 25 mL/min) to afford the title compound (4.9 mg, 11% yield). MS (ES+) 331.1 (M+H)$^+$. Retention time=2.71 minutes (Column: Waters Atlantis dC18 4.6×50 mm, 5 µm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 126

6-Chloro-5-(4-((1R,3R)-3-hydroxycyclobutyl)phenyl)-1H-indazole-3-carboxylic acid

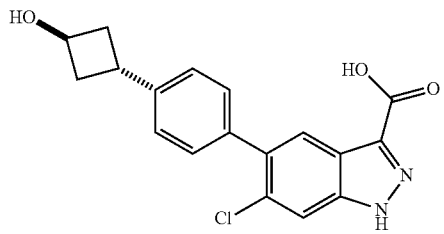

A suspension of 3-(4-bromophenyl)cyclobutanol (90.6 mg, 0.37 mmol), 5,5,5',5'-tetramethyl-2,2'-bi-1,3,2-dioxaborinane (136 mg, 0.37 mmol), [1,1'-bis(diphenylphosphino)ferrocene]dichloropalladium(II) (15.0 mg, 0.018 mmol) and potassium acetate (107 mg, 1.09 mmol) in 1,4-dioxane (1 mL) was sealed in a pressure tube and heated to 130° C. for 1 hour. To the mixture was added 5-bromo-6-chloro-1H-indazole-3-carboxylic acid (100.0 mg, 0.36 mmol), [1,1'-bis(diphenylphosphino)ferrocene]dichloropalladium(II) (14.7 mg, 0.018 mmol), 2 N aqueous potassium carbonate solution (0.5 mL, 1.0 mmol) and EtOH (2 mL). The mixture was sealed and heated to 130° C. for 1 hour. Water (3 mL) was added to the reaction mixture, followed by 1 N HCl solution to adjust the pH to 2. The layers were separated and the aqueous layer was extracted with EtOAc (3×5 mL). The combined organic layers were dried over $Na_2SO_4$ and concentrated in vacuo. The crude material was purified by reverse phase HPLC (Column: Waters Sunfire C18 19×100 mm, 5 μm; Mobile phase A: 0.05% Formic acid in water (v/v); Mobile phase B: 0.05% Formic acid in MeCN (v/v); HOLD at 75.0% $H_2O$/25.0% MeCN for 1.0 min. 75.0% $H_2O$/25.0% MeCN linear to 55.0% $H_2O$/45.0% MeCN in 6.75 min, linear to 0% $H_2O$/100% MeCN to 7.0 min. HOLD at 0% $H_2O$/100% MeCN from 7.0 to 8.0 min. Flow: 30 ml/min) to afford the title compound (2.4 mg, 2% yield). MS (ES+) 343.1 (M+H)$^+$. Retention time=2.42 minutes (Column: Waters Atlantis dC18 4.6×50 mm, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 127

6-Chloro-5-(4-(1-(hydroxymethyl)cyclopentyl)phenyl)-1H-indazole-3-carboxylic acid

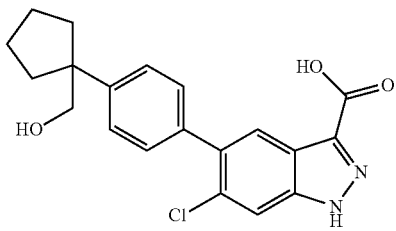 [SMILES: O=C(O)c1n[nH]c2cc(Cl)c(-c3ccc(C4(CO)CCCC4)cc3)cc12]

Step 1

[1-(4-Bromophenyl)cyclopentyl]methanol

Lithium aluminum hydride (827 mg, 20.7 mmol) was stirred in ethyl ether (15 mL) at 0° C. A slurry of 1-(4-bromophenyl)cyclopentanecarboxylic acid (1.86 g, 8.28 mmol) in ethyl ether (30 mL) was added to the solution of lithium aluminum hydride and the mixture was allowed to warm to room temperature slowly overnight. After 22 hours, the reaction was quenched with 15% sodium hydroxide until the slurry turned from gray to white and stopped bubbling. The mixture was stirred vigorously for 30 minutes and filtered through Celite®, the filter pad was washed with ethyl ether, and the filtrate was concentrated to afford 3 g of a colorless oil, which was purified by flash chromatography (0:1 to 1:1 ethyl acetate/heptane, 15 column volumes). The product fractions were concentrated in vacuo to afford the title compound as a colorless solid (700 mg, 74% yield). GCMS 254/256 (M)$^+$. $^1$H NMR (500 MHz, $CDCl_3$) δ 7.45 (d, J=8.29 Hz, 2H), 7.20 (d, J=8.29 Hz, 2H), 3.49 (s, 2H), 1.96-2.04 (m, 2H), 1.79-1.88 (m, 2H), 1.69-1.78 (m, 4H).

Step 2

6-Chloro-5-{4-[1-(hydroxymethyl)cyclopentyl]phenyl}-1H-indazole-3-carboxylic acid A mixture of [1-(4-bromophenyl)cyclopentyl]methanol (700 mg, 2.74 mmol), 5,5,5',5'-tetramethyl-2,2'-bi-1,3,2-dioxaborinane (1030 mg, 3.02 mmol) and potassium acetate (808 mg, 8.23 mmol) was stirred in 1,4-dioxane (6 mL) and degassed under high vacuum. The mixture was treated with [1,1'-bis(diphenylphosphino)ferrocene]dichloropalladium (II) dichloromethane adduct (112 mg, 0.137 mmol) and stirred at 100° C. for 1.5 hours. To this mixture was added 5-bromo-6-chloro-1H-indazole-3-carboxylic acid (686 mg, 2.49 mmol), ethanol (4 mL), 2 N aqueous potassium carbonate (6 mL) and [1,1'-bis(diphenylphosphino)ferrocene] dichloropalladium(II) dichloromethane adduct (108 mg, 0.132 mmol) and stirring was continued at 100° C. for 4 hours. The mixture was cooled to room temperature, treated with water, adjusted to pH 2 with 1 M HCl, and extracted with ethyl acetate (twice). The combined organics were dried over magnesium sulfate, filtered and concentrated in vacuo to afford 1.6 g viscous brown oil, which was purified by reversed-phase HPLC (Column: Phenomenex Gemini C18 150×21.2 mm 5 μm; Mobile phase A: 0.1% $NH_4OH$ in water (v/v); Mobile phase B: 0.1% $NH_4OH$ in acetonitrile (v/v); Gradient: 95.0% $H_2O$/5.0% MeCN linear to 95.0% MeCN/5.0% $H_2O$ in 11 min, Flow: 28 mL/min eluting at 9.2 min) to afford the title compound (300 mg, 33% yield). MS (ES+) 371.2 (M+H)$^+$. $^1$H NMR (500 MHz, $CD_3OD$) δ 8.09 (s, 1H), 7.77 (s, 1H), 7.42 (m, 4H), 3.62 (s, 2H), 1.88-2.13 (m, 4H), 1.77 (m, 4H).

Example 128

6-Chloro-5-(4-morpholinophenyl)-1H-indazole-3-carboxylic acid

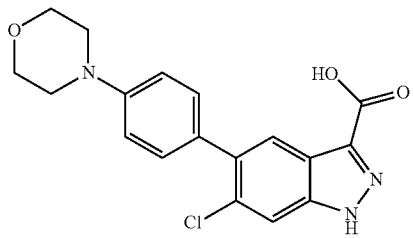 [SMILES: O=C(O)c1n[nH]c2cc(Cl)c(-c3ccc(N4CCOCC4)cc3)cc12]

Step 1

6-Chloro-5-[4-(morpholin-4-yl)phenyl]-1H-indazole

A mixture of 6-bromo-5-chloro-1H-indazole (72.2 mg, 0.312 mmol), 4-(morpholin-4-yl)phenylboronic acid (71 mg, 0.34 mmol), cesium carbonate (304 mg, 0.935 mmol) and [1,1'-bis(diphenylphosphino)ferrocene]dichloropalladium (II) dichloromethane adduct (35.9 mg, 0.031 mmol) was sealed in a microwave vial and purged with nitrogen. The reaction mixture was diluted with tetrahydrofuran (2.5 mL) and water (1 mL) and purged with nitrogen for five minutes. The reaction mixture was heated to 110° C. for four hours. The reaction mixture was concentrated in vacuo, poured into water and extracted three times with dichloromethane. The combined organic layers were concentrated in vacuo and purified using flash chromatography (heptanes/ethyl acetate 0:100 to 70:30) to give the title compound (71.9 mg). $^1$H NMR (500 MHz, $CDCl_3$) δ 8.07 (br. s., 1H), 7.70 (s, 1H), 7.65 (s, 1H), 7.41 (d, J=8.5 Hz, 2H), 7.06 (m, 2H), 4.00-3.88 (m, 4 H), 3.28 (m, 4H).

Step 2

6-Chloro-3-iodo-5-[4-(morpholin-4-yl)phenyl]-1H-indazole

A solution of 6-chloro-5-[4-(morpholin-4-yl)phenyl]-1H-indazole (72 mg, 0.23 mmol) and N,N-dimethylformamide (3 mL) was treated with iodine (91 mg, 0.36 mmol) and freshly ground potassium hydroxide (16 mg, 0.26 mmol). The reaction mixture was stirred at room temperature for three hours, then treated with additional iodine (50 mg) and potassium hydroxide (20 mg) and heated to 40° C. for 20 minutes. The reaction mixture was poured into ethyl acetate and saturated aqueous ammonium chloride. The layers were separated and the organic phase was washed with 2 N sodium thiosulfate. The organic layer was dried over sodium sulfate, filtered and concentrated in vacuo. The crude product was purified by flash chromatography utilizing heptanes/ethyl acetate (100:0 to 0:70) to give the title compound (86.7 mg). MS (ES−): 438.0 (M−H)−.

Step 3

Ethyl 6-chloro-5-[4-(morpholin-4-yl)phenyl]-1H-indazole-3-carboxylate

A Parr shaker bottle was charged with 6-chloro-3-iodo-5-[4-(morpholin-4-yl)phenyl]-1H-indazole (86.6 mg, 0.197 mmol), sodium acetate (68 mg, 0.83 mmol), [1,1'-bis(diphenylphosphino)ferrocene]dichloropalladium(II) (30.0 mg, 0.039 mmol), and ethanol (20 mL) and shaken under an atmosphere of carbon monoxide (40 psi) at 70° C. for 72 hours. The reaction was cooled and the pressure released. The resultant orange liquid was filtered and washed with ethanol. The filtrate was concentrated in vacuo to give the crude product, which was purified by flash chromatography utilizing heptanes/ethyl acetate (0:100 to 60:40) to give the title compound (72 mg). MS (ES−) 384.1 (M−H)−. $^1$H NMR (500 MHz, CD$_3$OD) δ 8.07 (s, 1H), 7.78 (s, 1H), 7.36 (d, J=8.78 Hz, 2H), 7.07 (d, J=8.54 Hz, 2H), 4.48 (q, J=7.07 Hz, 2H), 3.80-3.94 (m, 4H), 3.12-3.27 (m, 4H), 1.44 (t, J=7.07 Hz, 3H).

Step 4

6-Chloro-5-[4-(morpholin-4-yl)phenyl]-1H-indazole-3-carboxylic acid

To a solution of ethyl 6-chloro-5-[4-(morpholin-4-yl)phenyl]-1H-indazole-3-carboxylate (72 mg, 0.19 mmol) in ethanol (2 mL) was added 6 N aqueous sodium hydroxide (0.5 mL, 3.0 mmol). The mixture was stirred for three hours at 70° C. The cooled reaction mixture was neutralized with Dowex acid resin concentrated in vacuo. The crude product was purified by reverse phase column (water/acetonitrile, 0-40%, 20CV) to give the title compound (21 mg).

MS (ES+) 358.1 (M+H). $^1$H NMR (400 MHz, DMSO-d$_6$) δ 7.94 (s, 1H), 7.80 (s, 1H) 7.29 (d, J=8.59 Hz, 2H) 7.00 (d, J=8.78 Hz, 2H) 3.58-3.82 (m, 4H) 3.08-3.20 (m, 4H).

Example 129

6-Chloro-5-(4-(phenylethynyl)phenyl)-1H-indazole-3-carboxylic acid

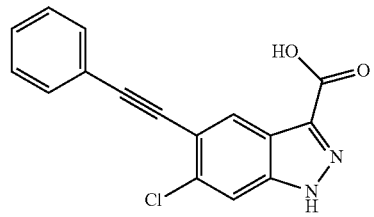 [SMILES: O=C(O)c1n[nH]c2cc(Cl)c(C#Cc3ccccc3)cc12]

Step 1

Methyl 6-chloro-5-(phenylethynyl)-1H-indazole-3-carboxylate

A mixture of methyl 5-bromo-6-chloro-1H-indazole-3-carboxylate (50 mg, 0.17 mmol), triethylamine (0.05 mL, 0.4 mmol), tetrakis(triphenylphosphine)palladium(0) (10.7 mg, 0.009 mmol), copper iodide (3.0 mg, 0.017 mmol) and phenyl acetylene (20 mg, 0.20 mmol) in tetrahydrofuran (1.0 mL) was sealed and heated to 120° C. for 16 hours. The cooled reaction mixture was concentrated in vacuo and purified by flash chromatography utilizing heptanes/ethyl acetate (1:1 to 0:1) to give the title compound (20 mg) as a yellow solid. MS (ES−): 309.0 (M−H)− Step 2

6-Chloro-5-(phenylethynyl)-1H-indazole-3-carboxylic acid

A solution of methyl 6-chloro-5-(phenylethynyl)-1H-indazole-3-carboxylate (20 mg, 0.064 mmol) in methanol (1 mL) was treated with 10 N aqueous sodium hydroxide (2 drops) and stirred at room temperature for 16 hours. The reaction mixture was then treated with additional 10 N aqueous sodium hydroxide (2 drops) and heated to 70° C. for two hours. The cooled reaction mixture was evaporated in vacuo, and treated with 1 N citric acid. The resulting solids were collected by filtration, dried and purified using prep-HPLC to afford the title compound (1 mg). MS (ES+) 374.9 (M+DMSO)+. Retention time: 1.8 min; Xbridge C18 5 μm 4.6×50 mm, 95% H$_2$O/5% MeCN linear to 5% H$_2$O/95% MeCN over 4.0 min, HOLD at 5% H$_2$O/95% MeCN to 5.0 min. (0.03% NH$_4$OH). Flow: 2.0 mL/min.

Example 130

6-Fluoro-5-(4-(tetrahydro-2H-pyran-4-yl)phenyl)-1H-indazole-3-carboxylic acid

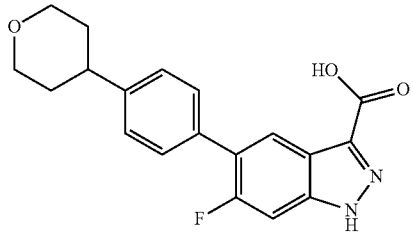 [SMILES: O=C(O)c1n[nH]c2cc(F)c(-c3ccc(C4CCOCC4)cc3)cc12]

Step 1

5,5-Dimethyl-2-[4-(tetrahydro-2H-pyran-4-yl)phenyl]-1,3,2-dioxaborinane

A suspension of 4-(4-bromophenyl)tetrahydro-2H-pyran (1.00 g, 4.15 mmol), 5,5,5',5'-tetramethyl-2,2'-bi-1,3,2-dioxaborinane (1.70 g, 4.98 mmol), potassium acetate (1.22 g, 12.4 mmol), and [1,1'-bis(diphenylphosphino)ferrocene]dichloropalladium(II) (169 mg, 0.207 mmol) in 1,4-dioxane (10 mL) and stirred for three hours at 120° C. The cooled reaction mixture was poured into water (20 mL) and extracted with ethyl acetate (3×20 mL). The combined organic layers were dried over sodium sulfate, filtered and concentrated in vacuo. The crude product was purified using silica gel chromatography (100:0 to 75:25, heptanes/ethyl acetate) to give the title compound (740 mg, % yield). GC/MS: 274 (M)$^+$. $^1$H NMR (500 MHz, CDCl$_3$) δ 7.76 (d, J=7.8 Hz, 2H), 7.23 (d, J=7.8 Hz, 2H), 4.09 (dd, J=3.8, 11.1 Hz, 2H), 3.77 (s, 4H), 3.54 (dt, J=2.1, 11.6 Hz, 2H), 2.71-2.78 (m, 1H), 1.91-1.74 (m, 4H), 1.03 (s, 6H).

Step 2

5-Bromo-6-fluoro-1H-indazole-3-carboxylic acid

A mixture of 6-fluoro-1H-indazole-3-carboxylic acid (4.95 g, 23.8 mmol) and acetic acid (50 mL) was treated with bromine (2.0 mL, 38 mmol) dropwise at room temperature. The reaction mixture was heated to 90° C. and stirred for 16 hours under an atmosphere of nitrogen. The reaction mixture was then exposed to the atmosphere and stirred at 95° C. for 72 hours. The resulting solids were collected while the reaction mixture was still hot and rinsed with diethyl ether two times. The solids were dried at 50° C. under reduced pressure to give the title compound (2.89 g). $^1$H NMR (500 MHz, DMSO-d$_6$) δ 8.31 (d, J=6.8 Hz, 1H), 7.71 (d, J=8.8 Hz, 1H).

Step 3

6-Fluoro-5-[4-(tetrahydro-2H-pyran-4-yl)phenyl]-1H-indazole-3-carboxylic acid A mixture of 5-bromo-6-fluoro-1H-indazole-3-carboxylic acid (793 mg, 3.06 mmol), 5,5-dimethyl-2-[4-(tetrahydro-2H-pyran-4-yl)phenyl]-1,3,2-dioxaborinane (839 mg, 3.06 mmol) and [1,1'-bis(diphenylphosphino)ferrocene]dichloropalladium(II) (175 mg, 0.214 mmol) were sealed in a vial and purged with nitrogen. Ethanol (4 mL), toluene (2 mL) and aqueous 2 M potassium carbonate (3.67 ml, 7.34 mmol) were added and the mixture was heated at 110° C. for 50 minutes. The cooled reaction mixture was poured into dilute HCl and extracted with ethyl acetate. The combined organic layers were dried over sodium sulfate, filtered and concentrated in vacuo to give crude material, which was purified using reverse-phase chromatography. The product was crystallized from isopropanol/hexane to give the title compound as a crystalline solid (110 mg, 11% yield). MS (ES–) 339.1 (M–H)$^−$. $^1$H NMR (500 MHz, CD$_3$OD) δ 8.34 (d, J=7.32 Hz, 1 H), 7.54 (d, 2H), 7.35 (d, 2H), 7.27 (d, J=10.25 Hz, 1H), 4.08 (d, J=10.25 Hz, 2H), 3.61 (td, J=10.98, 3.42 Hz, 2H), 2.88 (m, 1H), 1.81-1.90 (m, 4H). m.p.=295° C.

Example 131

6-Chloro-5-[4-(1-hydroxycyclobutyl)-3-methoxyphenyl]-1H-indazole-3-carboxylic acid

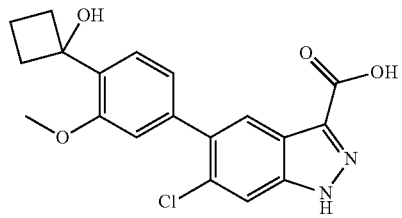 [SMILES: COc1cc(-c2cc3c(C(=O)O)n[nH]c3cc2Cl)ccc1C1(O)CCC1]

A sealed tube was charged with 1-[4-(5,5-dimethyl-1,3,2-dioxaborinan-2-yl)-2-methoxyphenyl]cyclobutanol (50 mg, 0.17 mmol), 5-bromo-6-chloro-1H-indazole-3-carboxylic acid (47.4 mg, 0.172 mmol), toluene (0.80 mL), THF (0.40 mL), EtOH (0.40 mL), and 2 M potassium carbonate (0.40 mL, 0.80 mmol). Nitrogen was then bubbled through the mixture for 5 minutes. [1,1'-bis(diphenylphosphino)ferrocene]dichloropalladium(II) (14.6 mg, 0.017 mmol) was added and the tube sealed and heated to 115° C. for 2 hours. The reaction was cooled to room temperature, opened, neutralized with 1 M NaHSO4, and diluted with ethyl acetate. The layers were separated and the aqueous layer was extracted with ethyl acetate (×2). The combined organic layers were dried over sodium sulfate, filtered, and concentrated in vacuo to provide the crude material (80 mg). 40 mg was dissolved in DMSO and subjected to reverse phase chromatography to provide 8 mg (10% yield) of title compound.

MS (ES–) 371.2 (M–H)$^−$. Retention time: 3.62 min; Waters Xbridge dC18 5 μm 4.6×50 mm, 95% H$_2$O/5% MeCN linear to 5% H$_2$O/95% MeCN over 4.0 min, HOLD at 5% H$_2$O/95% MeCN to 5.0 min. (0.03% NH$_4$OH). Flow: 2.0 mL/min.

Example 132

6-Chloro-5-(4-methoxyphenyl)-1H-indole-3-sulfonic acid

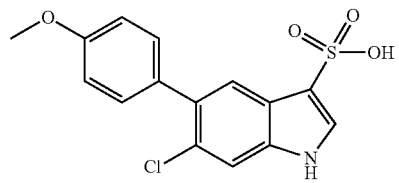 [SMILES: COc1ccc(-c2cc3c(S(=O)(=O)O)c[nH]c3cc2Cl)cc1]

Step 1

6-Chloro-5-(4-methoxyphenyl)-1H-indole

A mixture of 5-bromo-6-chloro-1H-indole (3.20 g, 13.9 mmol), sodium carbonate (3.68 g, 34.7 mmol), and 4-methoxyphenylboronic acid (2.41 g, 15.9 mmol) in EtOH (18 mL), toluene (18 mL) and water (18 mL) was degassed with N$_2$ for 15 minutes, treated with tetrakis(triphenylphosphine)palladium(0) (1.20 g, 0.99 mmol) and heated to 90° C. for 23 hours. The cooled reaction mixture was poured into half-saturated NH₄Cl solution (200 mL) and extracted with dichloromethane (3×120 mL). The combined organic layers were dried over Na₂SO₄ and concentrated in vacuo. The resulting dark solid was purified by flash chromatography (5-20% EtOAc/heptane) to give the title compound (1.40 g, 39%) as a white solid. MS (ES+) 258.5 (M+H)⁺. ¹H NMR (500 MHz, CDCl₃) δ 8.16 (br. s., 1 H), 7.56 (s, 1 H), 7.42 (d, J=8.1 Hz, 2 H), 7.24 (s, 1 H), 6.98 (d, J=8.1 Hz, 2 H), 6.55 (br. s., 1 H), 3.88 (s, 3 H).

Step 2

6-Chloro-5-(4-methoxyphenyl)-1H-indole-3-sulfonic acid

A solution of 6-chloro-5-(4-methoxyphenyl)-1H-indole (650 mg, 2.52 mmol) and sulfur trioxide pyridine complex (608 mg, 3.78 mmol) in pyridine (2.52 mL) was heated to 115° C. After 17 hours, the reaction mixture was treated with additional sulfur trioxide pyridine complex (150 mg, 0.93 mmol). After stirring an additional 8 hours at 115° C., the reaction mixture was cooled to room temperature and stirred for an additional 16 hours. The reaction mixture was diluted with water (50 mL) and washed with Et₂O (2×20 mL). The aqueous layer was diluted with MeCN (40 mL) and concentrated in vacuo. The residue was re-diluted with MeCN (50 mL) and concentrated to give an off-white semi-solid. The semi-solid was dissolved in MeOH (15 mL), treated with amberjet 1200(H) ion-exchange resin (5 g) and stirred at room temperature for 16 hours. The mixture was filtered through cotton and concentrated. The resulting oil was purified by reverse phase chromatography (C18 column, 0-40% MeCN/water) to give an oil. This material was dissolved in MeOH (4 mL) and treated with sodium methoxide (91 mg). The mixture was stirred at room temperature for 15 minutes, and then evaporated under reduced pressure to give a solid glass, which was purified by reverse phase chromatography (C18 column, 0-50% MeCN/H₂O). The fractions containing product were combined and concentrated in vacuo. The resulting residue was suspended in toluene (4 mL) and evaporated. This procedure was repeated twice to give a white solid, which was dried under high vacuum at room temperature for 16 hours, then at 80° C. for 2 hours to give the title compound (459 mg, 50%) as a white solid. MS (ES+) 359.8 (M+Na)⁺. ¹H NMR (500 MHz, DMSO-d₆) δ 11.09 (br. s, 1 H), 7.69 (s, 1 H), 7.47 (s, 1 H), 7.37 (d, J=2.44 Hz, 1 H), 7.31 (d, J=7.81 Hz, 2 H), 7.01 (d, J=8.05 Hz, 2 H), 3.81 (s, 3 H). m.p.=240° C. (dec.)

Example 133

6-Chloro-5-(2'-hydroxy-[1,1'-biphenyl]-4-yl)-1H-indole-3-sulfonic acid

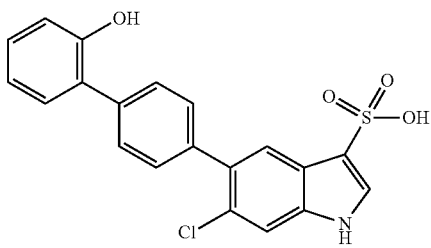 [SMILES: O=S(=O)(O)c1c[nH]c2cc(Cl)c(-c3ccc(-c4ccccc4O)cc3)cc12]

A mixture of 5-bromo-6-chloro-1H-indole (300 mg, 1.30 mmol) and sulfur trioxide pyridine complex (622 mg, 3.91 mmol) in pyridine (2 mL) was sealed in a pressure tube and heated to 100° C. for 48 hours. The reaction mixture was concentrated in vacuo to provide 5-bromo-6-chloro-1H-indole-3-sulfonic acid as a pyridinium salt, which was used directly in the next step without further purification. A mixture of 5-bromo-6-chloro-1H-indole-3-sulfonic acid (100 mg, 0.32 mmol), 4'-(4,4,5,5-tetramethyl-[1,3,2]dioxaborolan-2-yl)-biphenyl-2-ol (114 mg, 0.39 mmol), 2 N aqueous potassium carbonate solution (0.64 mL, 1.29 mmol) and [1,1'-bis(diphenylphosphino)ferrocene]dichloropalladium (II) (13.0 mg, 0.016 mmol) in EtOH (5 mL) was sealed and heated to 130° C. for 2 hours. The reaction mixture was diluted with water (10 mL) and washed with EtOAc (2×10 mL). The aqueous layer was concentrated in vacuo and purified by reversed phase HPLC (Column: Waters Sunfire C18 19×100, 5 μm; Mobile phase A: 0.05% TFA in water (v/v); Mobile phase B: 0.05% TFA in MeCN (v/v); HOLD at 100.0% H₂O/0.0% MeCN for 1.0 min. 100.0% H₂O/0.0% MeCN linear to 5.0% H₂O/95.0% MeCN in 6.75 min, linear to 0% H₂O/100% MeCN to 7.0 min. HOLD at 0% H₂O/100% MeCN from 7.0 to 8.0 min. Flow: 30 mL/min.) to provide the title compound (2.3 mg, 2%). MS (ES−) 398.0 (M−H)⁺. Retention time=2.28 minutes (Waters Atlantis dC18 4.6×50, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 134

6-Chloro-5-(4-(tetrahydro-2H-pyran-4-yl)phenyl)-1H-indole-3-sulfonic acid

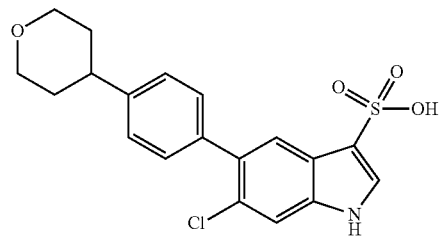 [SMILES: O=S(=O)(O)c1c[nH]c2cc(Cl)c(-c3ccc(C4CCOCC4)cc3)cc12]

A mixture of 5-bromo-6-chloro-1H-indole (300 mg, 1.30 mmol) and sulfur trioxide pyridine complex (622 mg, 3.91 mmol) in pyridine (2 mL) was sealed in a pressure tube and heated to 100° C. for 48 hours. The reaction mixture was concentrated in vacuo to provide 5-bromo-6-chloro-1H-indole-3-sulfonic acid as a pyridinium salt, which was used directly in the next step without further purification. A mixture of 4-(4-bromophenyl)tetrahydropyran (77.0 mg, 0.32 mmol), 5,5,5',5'-tetramethyl-2,2'-bi-1,3,2-dioxaborinane (121 mg, 0.35 mmol), potassium acetate (95.0 mg, 0.97 mmol), and [1,1'-bis(diphenylphosphino)ferrocene]dichloropalladium(II) (13.0 mg, 0.016 mmol) in 1,4-dioxane (1 mL) was sealed and heated to 100° C. for 1 hour. To the mixture was added the above freshly prepared 5-bromo-6-chloro-1H-indole-3-sulfonic acid (100 mg, 0.32 mmol), [1,1'-bis(diphenylphosphino)ferrocene]dichloropalladium(II) (13.0 mg, 0.016 mmol), 2 N aqueous potassium carbonate solution (0.65 mL, 1.30 mmol) and EtOH (5 mL). The reaction mixture was sealed and heated to 130° C. for 1 hour. The reaction mixture was diluted with water (10 mL), acidified to pH 2 and washed with EtOAc (10 mL). The aqueous layer was concentrated in vacuo and purified by reversed phase HPLC (Column: Waters Sunfire C18 19×100, 5 μm; Mobile phase A: 0.05% TFA in water (v/v); Mobile phase B: 0.05% TFA in MeCN (v/v); HOLD at 100.0% H$_2$O/0.0% MeCN for 1.0 min. 100.0% H$_2$O/0.0% MeCN linear to 5.0% H$_2$O/95.0% MeCN in 6.75 min, linear to 0% H$_2$O/100% MeCN to 7.0 min. HOLD at 0% H$_2$O/100% MeCN from 7.0 to 8.0 min. Flow: 30 mL/min.) to provide the title compound (4.1 mg, 3%). MS (ES−) 390.0 (M−H)$^+$. Retention time=2.12 minutes (Waters Atlantis dC18 4.6×50, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 135

6-fluoro-5-(2'-hydroxybiphenyl-4-yl)-1H-indole-3-carboxylic acid

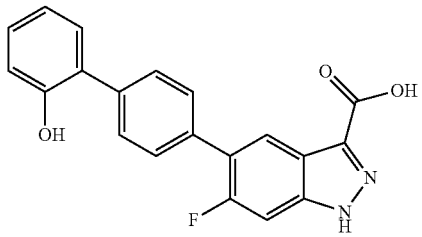 [SMILES: O=C(O)c1n[nH]c2cc(F)c(-c3ccc(-c4ccccc4O)cc3)cc12]

Step 1

6-fluoro-5-(2'-hydroxybiphenyl-4-yl)-1H-indole-3-carbaldehyde

A glass tube was charged with 4'-(4,4,5,5-tetramethyl-1,3,2-dioxaborolan-2-yl)-[1,1'-biphenyl]-2-ol (73.5 mg, 0.25 mmol), 5-bromo-6-fluoro-1H-indole-3-carbaldehyde (60 mg, 0.25 mmol), toluene (1.2 mL), THF (0.6 mL), EtOH (0.6 mL), and 2.0 M potassium carbonate solution (0.6 mL, 1.2 mmol). Nitrogen was then bubbled through the mixture for 5 minutes then [1,1'-bis(diphenylphosphino)ferrocene]dichloropalladium(II) (21.5 mg, 0.025 mmol) was added. The tube was sealed and heated to 115° C. for 2 hours. The reaction was cooled to room temperature, opened, and neutralized with 1.0 M sodium hydrogensulfate then diluted with ethyl acetate. The layers were separated and the aqueous extracted with ethyl acetate (×2). The combined organic layers were dried over sodium sulfate, filtered, and concentrated in vacuo. The residue was dissolved in methylene chloride and methanol, silica was added, and the solvent removed in vacuo. The dry-loaded silica gel was then subjected to flash column chromatography (20% to 100% ethyl acetate/heptane) to provide the title compound as a white solid (20 mg, 24%). MS (ES+) 332.3 (M+H). $^1$H NMR (500 MHz, DMSO-d$_6$) δ ppm 12.24 (br. s, 1 H) 9.96 (s, 1 H) 9.59 (s, 1 H) 8.36 (s, 1 H) 8.19 (d, 1 H) 7.67 (d, 2 H) 7.58 (d, 2 H) 7.46 (d, 1 H) 7.33 (d, 1 H) 7.18 (t, 1 H) 6.97 (d, 1 H) 6.91 (t, 1 H).

Step 2

6-fluoro-5-(2'-hydroxybiphenyl-4-yl)-1H-indole-3-carboxylic acid

A round bottomed flask was charged with 6-fluoro-5-(2'-hydroxybiphenyl-4-yl)-1H-indole-3-carbaldehyde (20 mg, 0.60 mmol), acetonitrile, (1.0 mL), t-butanol (1.0 mL) and cooled to 0° C. 2-methyl-2-butene (0.49 mL, 4.6 mmol) was then added. In a separate flask, sodium chlorite (102 mg, 1.20 mmol) and NaH$_2$PO$_4$ (170 mg, 1.23 mmol) were dissolved in water (1 mL) then added to the reaction. The reaction was sealed and reacted at room temperature for 15 h. Ethyl acetate and water were added and the layers were separated. The organic layer was dried over sodium sulfate, filtered, and concentrated in vacuo. Reverse phase HPLC was then used to provide the title compound (8.4 mg, 40%). MS (ES−) 346.1 (M−H)$^−$. Retention time: 1.86 min Waters Xbridge dC18 5 um 4.6×50 mm, 95% H2O/5% MeCN linear to 5% H2O/95% MeCN over 4.0 min, HOLD at 5% H2O/95% MeCN to 5.0 min. (0.03% NH$_4$OH). Flow: 2.0 mL/min.

Example 136

6-Chloro-5-[4-(tetrahydro-2H-pyran-4-yl)phenyl]-1H-indole-3-carboxylic acid

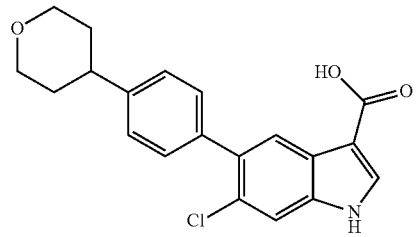 [SMILES: O=C(O)c1c[nH]c2cc(Cl)c(-c3ccc(C4CCOCC4)cc3)cc12]

Step 1

Methyl 6-chloro-5-[4-(tetrahydro-2H-pyran-4-yl)phenyl]-1H-indole-3-carboxylate

To a solution of methyl 6-chloro-5-(5,5-dimethyl-1,3,2-dioxaborinan-2-yl)-1H-indole-3-carboxylate (440 mg, 1.37 mmol) and 4-(4-bromophenyl)tetrahydro-2H-pyran (300 mg, 1.24 mmol) in toluene (6 mL), ethanol (3 mL), and tetrahydrofuran (3 mL) followed by the addition of 2M potassium carbonate aqueous (3 mL, 6 mmol). Nitrogen was bubbled through the reaction for 5 minutes then [1,1'-bis(diphenylphosphino)ferrocene]dichloro palladium-dichloromethane complex (120 mg, 0.143 mmol) was added and the reaction heated to 115° C. for 16 hours. The reaction was then cooled to room temperature and filtered through a pad of celite washing with ethyl acetate. The filtrate was concentrated under reduced pressure. The crude product was purified using the Biotage Isolera One (SNAP 50 g silica gel column) and eluting with a gradient of 0-100% ethyl acetate/heptane yielding 360 mg of the title compound as a solid.

MS (ES+) 370.2 (M+H)$^+$. $^1$H NMR (500 MHz, DMSO-d$_6$) ppm 12.06 (s, 1 H), 8.17 (s, 1 H), 7.92 (s, 1 H), 7.65 (s, 1 H), 7.27-7.45 (m, 4 H), 3.94-4.01 (m, 2 H), 3.79 (s, 3 H), 3.47 (td, 2 H), 2.75-2.94 (m, 1 H), 1.64-1.82 (m, 4 H).

Step 2

6-Chloro-5-[4-(tetrahydro-2H-pyran-4-yl)phenyl]-1H-indole-3-carboxylic acid

To a solution of methyl 6-chloro-5-[4-(tetrahydro-2H-pyran-4-yl)phenyl]-1H-indole-3-carboxylate (360 mg, 0.973 mmol) in methanol (10 mL) was added sodium hydroxide (1

M, 4.0 mL, 4 mmol) and the reaction was heated to 70° C. for 24 hours. The reaction was concentrated under reduced pressure. The crude reaction was diluted with methanol (9 mL) to which was added additional sodium hydroxide (1M, 6.0 mL, 6 mmol) and heated to 70° C. for 24 hours. The reaction was concentrated under reduced pressure and acidified using 1N aqueous hydrochloric acid and extracted three times with ethyl acetate. The combined organic layers were washed with brine, dried over sodium sulfate, filtered and concentrated under reduced pressure. The crude material was purified using the Biotage Isolera One (SNAP 50 g silica gel column) and eluting with a gradient of 0-20% methanol/dichloromethane yielding 215 mg of the title compound as a solid. To a round bottom flask containing the title compound was added methanol (10 mL) and the reaction was heated to reflux. Additional methanol (5 mL) was added and the solution was allowed to cool to room temperature and stirred overnight at room temperature. The resulting precipitate was filtered and washed with 1 mL of methanol and dried by pulling high vacuum yielding 119 mg of the title compound. MS (ES−) 354.0 (M−H)−. $^1$H NMR (500 MHz, DMSO-$d_6$) δ ppm 12.10 (s, 1 H), 11.93 (br. d, 1 H), 8.07 (d, 1 H), 7.93 (s, 1 H), 7.62 (s, 1 H), 7.21-7.46 (m, 4 H), 3.86-4.02 (m, 2H), 3.46 (td, 2 H), 2.71-2.93 (m, 1 H), 1.60-1.85 (m, 4 H).

Example 137

6-Chloro-5-{4-[1-(hydroxymethyl)cyclobutyl]-3-methoxyphenyl}-1H-indole-3-carboxylic acid

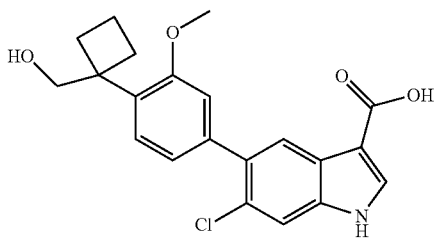 [SMILES: COc1cc(-c2cc3c(C(=O)O)c[nH]c3cc2Cl)ccc1C1(CO)CCC1]

Step 1

4-Bromo-2-methoxybenzaldehyde

The mixture of 4-bromo-2-fluorobenzaldehyde (6.1 g, 0.03 mol) and sodium methoxide (1.78 g, 0.033 mol) in dry methanol (60 mL) was stirred at reflux for 16 hours. The methanol was evaporated. The residue was partitioned between DCM and water. The organic layers were dried over sodium sulfate, concentrated in vacuo to give a yellow solid, which was purified by silica gel chromatography (Petroleum ether/EtOAc=20:1 to 10:1) to give the title compound (6.3 g, 97%) as a light yellow solid. $^1$H NMR (500 MHz, DMSO-$d_6$) δ 10.23 (s, 1H), 7.60 (d, 1H), 7.48 (s, 1H), 7.28 (d, 1H), 3.94 (s, 3H)

Step 2

(4-Bromo-2-methoxyphenyl)acetonitrile

To a solution of potassium tert-butoxide (6.5 g, 0.058 mol) in 1,2-dimethoxyethane (150 mL) was added p-toluenesulfonylmethyl isocyanide (5.6 g, 0.029 mol) portionwise at −78° C. Then a solution of 4-bromo-2-methoxybenzaldehyde (6.3 g, 0.029 mol) in 1,2-dimethoxyethane was added dropwise and the reaction mixture was warmed to room temperature. The mixture was stirred at room temperature for 1 hour and methanol (150 mL) was added, then heated to reflux and stirred for 2 hours. Solvent was evaporated, and saturated ammonium chloride (100 mL) was added and extracted with ethyl acetate (100 mL×2). The organic layers were combined, dried over sodium sulfate and concentrated in vacuo to give a residue, which was purified by combiflash (Petroleum ether/EtOAc=10:1 to 5:1) to give the title compound (5.4 g, 82%) as a light yellow solid. $^1$H NMR (400 MHz, CDCl$_3$) δ 7.25 (d, 1H), 7.12 (d, 1H), 7.03 (s, 1H), 3.87 (s, 3H), 3.63 (s, 2H)

Step 3

1-(4-Bromo-2-methoxyphenyl)cyclobutanecarbonitrile

To a stirring mixture of (4-bromo-2-methoxyphenyl)acetonitrile (904 mg, 4.00 mmol), 1,3-dibromo-propane (880 mg, 4.40 mmol) in dimethylformamide (10 mL) was added sodium hydride (352 mg, 8.80 mmol) at 0° C. After addition, the mixture was stirred at room temperature for 3 hours. The reaction mixture was quenched with water and extracted with dichloromethane (50 mL×3). The organic phases were combined, dried over sodium sulfate and concentrated in vacuo to give a brown solid. The solid was purification by combiflash chromatography (Petroleum ether/EtOAc=20:1 to 5:1) to give the title compound (370 mg, 34.8%) as a white solid. $^1$H NMR (400 MHz, CDCl$_3$) δ 7.10 (dd, 1H), 7.02 (d, 1H), 7.00 (d, 1H), 3.87 (s, 3H), 2.78 (m, 2H), 2.50 (m, 3H), 1.95 (m, 1H)

Step 4

1-(4-Bromo-2-methoxyphenyl)cyclobutanecarboxylic acid

The mixture of 1-(4-bromo-2-methoxyphenyl)cyclobutanecarbonitrile (370 mg, 1.04 mmol) in aqueous KOH (80%, 5 mL) and ethylene glycol (5 mL) was heated at 100° C. and stirred for 16 hours. The mixture was added water (20 ml) and acidified by concentrated HCl to pH=1 and extracted with dichloromethane. The combined organic layers was dried over sodium sulfate, filtered, and concentrated in vacuo to give the title compound (327 mg, 82%) as a yellow solid. $^1$H NMR (500 MHz, DMSO-$d_6$) δ 12.05 (s, 1H), 7.19 (d, 1H), 7.13 (s, 1H), 7.12 (d, 1H), 3.72 (s, 3H), 2.59 (m, 2H), 2.30 (q, 2H), 2.05 (m, 1H), 1.78 (m, 1H)

Step 5

[1-(4-Bromo-2-methoxyphenyl)cyclobutyl]methanol

To a mixture of 1-(4-bromo-2-methoxyphenyl)cyclobutanecarboxylic acid (320 mg, 1.12 mmol) in dry tetrahydrofuran (10 mL) was added borane-tetrahydrofuran (0.67 mL, 6.7 mmol) dropwise. The mixture was stirred at room temperature for 3 hours. The reaction mixture was quenched by water and extracted with dichloromethane. The organic layers were combined, dried over sodium sulfate, and concentrated to give the title compound (280 mg, 92%) as a colorless oil. $^1$H NMR (500 MHz, DMSO-$d_6$) δ 7.05 (m, 2H), 6.86 (d, 1H), 4.57 (t, 1H), 3.73 (s, 3H), 3.55 (d, 2H), 2.05-2.17 (m, 4H), 1.95 (m, 1H), 1.69 (m, 1H).

Step 6

Methyl 6-chloro-5-{4-[1-(hydroxymethyl)cyclobutyl]-3-methoxyphenyl}-1H-indole-3-carboxylate To a mixture of [1-(4-bromo-2-methoxyphenyl)cyclobutyl]methanol (180 mg, 0.660 mmol) in dioxane (10 mL) and water (4 mL) was added methyl 6-chloro-5-(5,5-dimethyl-1,3,2-dioxaborinan-2-yl)-1H-indole-3-carboxylate (213 mg, 0.660 mmol), Pd (dppf)Cl$_2$ (48 mg, 0.070 mmol) and potassium carbonate (273 mg, 2.00 mmol). The reaction mixture was purged with nitrogen for 3 minutes and stirred at 80° C. for 2 hours. The mixture was extracted with dichloromethane. The organic phases were combined, dried over sodium sulfate, filtered, and concentrated in vacuo to give the title compound (220 mg, 83%) as a brown solid. It was used for next step without further purification.

Step 7

6-Chloro-5-{4-[1-(hydroxymethyl)cyclobutyl]-3-methoxyphenyl}-1H-indole-3-carboxylic acid The mixture of methyl 6-chloro-5-{4-[1-(hydroxymethyl)cyclobutyl]-3-methoxyphenyl}-1H-indole-3-carboxylate (220 mg, 0.55 mmol) in aqueous sodium hydroxide (10%, 3 mL) and methanol (5 mL) was stirred at 80° C. for 16 hours. The mixture was acidified by concentrated HCl to pH-4 and extracted with dichloromethane. The organic phases were combined, dried over sodium sulfate, filtered, and concentrated in vacuo to give a residue, which was purified by reverse phase HPLC to give the title compound (25 mg, 12%) as a white solid. MS (AP+) 368.1 (M−H2O+H)$^+$, 408.1 (M+Na)$^+$. $^1$H NMR (500 MHz, CD$_3$OD) δ 8.03 (s, 1H), 7.98 (s, 1H), 7.57 (s, 1H), 7.08 (d, 1H), 6.98 (d, 2H), 3.86 (s, 2H), 3.80 (s, 3H), 2.36 (m, 4H), 2.11 (m, 1H), 1.86 (m, 1H)

Example 138

6-Chloro-5-[4-(trans-3-hydroxycyclobutyl)phenyl]-1H-indole-3-carboxylic acid

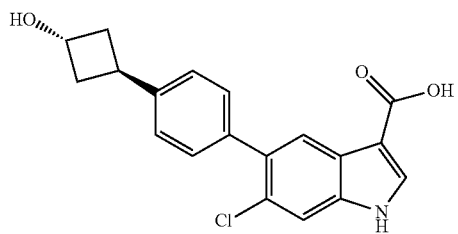 [SMILES: O=C(O)c1c[nH]c2cc(Cl)c(-c3ccc([C@H]4C[C@H](O)C4)cc3)cc12]

Step 1

Methyl 6-chloro-5-[4-(trans-3-hydroxycyclobutyl)phenyl]-1H-indole-3-carboxylate

To a solution of trans-3-(4-bromophenyl)cyclobutanol (200 mg, 0.88 mmol) in toluene/ethanol (4 mL, v/v=1/1) was added methyl 6-chloro-5-(5,5-dimethyl-1,3,2-dioxaborinan-2-yl)-1H-indole-3-carboxylate (296 mg, 0.968 mmol), potassium carbonate (360 mg, 2.64 mmol), water (1 mL) and Pd(dppf)C12 (46 mg, 0.06 mmol) under nitrogen. The mixture was stirred at 110° C. for 2 hours. The mixture was diluted with ethyl acetate and water. The layers were separated and the aqueous layer was extracted with ethyl acetate. The combined organic layers were washed with brine, dried and concentrated. The residue was purified by silica gel combiflash to give the title compound (190 mg, 61%) as a light yellow solid. $^1$H NMR (500 MHz, CD$_3$OD) δ 8.02 (s, 1 H), 8.01 (s, 1 H), 7.60 (s, 1 H), 7.40-7.35 (m, 4 H), 4.52 (m, 1 H), 3.88 (s, 3 H), 3.66 (m, 1 H), 2.57-2.44 (m, 4 H).

Step 2

6-chloro-5-[4-(trans-3-hydroxycyclobutyl)phenyl]-1H-indole-3-carboxylic acid

To a solution of methyl 6-chloro-5-[4-(trans-3-hydroxycyclobutyl)phenyl]-1H-indole-3-carboxylate (290 mg, 0.82 mmol) in methanol/water (20 mL, v/v=1/1) was added sodium hydroxide (326 mg, 8.17 mmol). The mixture was stirred at 90° C. for 5 hours. The mixture was then acidified with 1 M HCl to pH~5. The resulting suspension was extracted with dichloromethane. The combined organic layers were washed with brine, dried over sodium sulfate and concentrated. The residue was purified by reverse phase HPLC to give the title compound (150 mg, 54%) as a white solid. MS (AP+) 342.0 (M+H)$^+$: $^1$H NMR (500 MHz, CD$_3$OD) δ 8.03 (s, 1 H), 8.02 (s, 1 H), 7.59 (s, 1 H), 7.41 (d, 2 H), 7.34 (d, 2 H), 4.53-4.50 (m, 1 H), 3.67-3.65 (m, 1 H), 2.55-2.43 (m, 4 H).

Example 139

6-Chloro-5-(4-(2-hydroxyethoxy)phenyl)-1H-indole-3-carboxylic acid

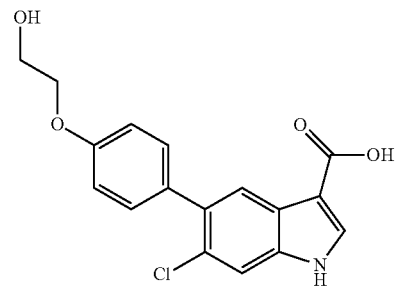 [SMILES: O=C(O)c1c[nH]c2cc(Cl)c(-c3ccc(OCCO)cc3)cc12]

Step 1

Methyl 6-chloro-5-(4-(2-hydroxyethoxy)phenyl)-1H-indole-3-carboxylate

A mixture of methyl 5-bromo-6-chloro-1H-indole-3-carboxylate (5.2 g, 18.0 mmol), 2-(4-(5,5-dimethyl-1,3,2-dioxaborinan-2-yl)phenoxy)ethanol (5.7 g, 22.8 mmol), PdCl$_2$ (dppf) (0.54 g, 0.72 mmol), 2 M aqueous solution of potassium carbonate (27 ml, 54.0 mmol), ethanol (30 ml), and toluene (90 ml) was stirred in a closed bottle at 80° C. for 2 hours and at 90° C. for 2 more hours. The reaction mixture was cooled to room temperature, ethyl acetate (50 ml) was added, and the mixture was filtered through a pad of Celite. The organic phase of the mother liquor was separated. Filter cake was washed with 10% of methanol in THF and this wash was combined with the first organic extract. The combined organic solution was dried over anhydrous magnesium sulfate and loaded on silica gel. Chromatography on a silica gel column, eluting with a gradient from 40% to 90% of ethyl acetate in heptanes to give the title compound (6.15 g, 98%). MS (ES+) 346.0 (M+1)⁺. ¹H NMR (CDCl₃): δ 8.74 (br. s, 1H), 8.13 (s, 1H), 7.95 (d, J=2.4 Hz, 1H), 7.56 (s, 1H), 7.44 (d, J=8.5 Hz, 2H), 7.02 (d, J=8.5 Hz, 2H), 4.18 (t, 2H), 4.02 (t, 2H), 3.92 (s, 3H).

Step 2

6-Chloro-5-(4-(2-hydroxyethoxy)phenyl)-1H-indole-3-carboxylic acid

A mixture of methyl 6-chloro-5-(4-(2-hydroxyethoxy) phenyl)-1H-indole-3-carboxylate (6.15 g, 17.8 mmol), 300 ml of methanol (300 ml), and 1 M aqueous sodium hydroxide (100 ml, 100 mmol) was stirred at 75° C. for 18 hours. Additional 30 ml of 1 M aq. sodium hydroxide added and the reaction was stirred at 75° C. for 5 more hours. The reaction was concentrated at 45° C. to remove most of methanol, the residue was diluted with water (100 ml) and washed with methyl t-butyl ether (2×100 ml). The aqueous phase was acidified with 37% hydrochloric acid (14 ml) and extracted with ethyl acetate (250 ml). The organic extract was washed with brine (2×100 ml), and dried over anhydrous magnesium sulfate. The obtained yellow solution was stirred with activated carbon (5 g) and silica gel (10 g) for 3 hours at room temperature. The suspension was filtered through a pad of silica gel and concentrated to obtain crude target product (3.7 g). The obtained material was dissolved in ethyl acetate (220 ml) after heating at 85° C. for 2 hours. To the stirred clear solution was added in drops heptane (40 ml) at the same temperature (the solution became cloudy at this point). The mixture was cooled under stirring to room temperature in 1.5 hours and stirred for 2.5 days. The precipitate was filtered off and dried in high vacuum at 55° C. to obtain the title compound (2.5 g, 44%).

MS (ES−) 330.1 (M−H)⁻. ¹H NMR (DMSO-d₆): δ 12.11 (br. s, 1H), 11.93 (br. s, 1H), 8.07 (s, 1H), 7.93 (s, 1H), 7.62 (s, 1H), 7.34 (d, J=8.8 Hz, 2H), 7.02 (d, J=8.8 Hz, 2H), 4.89 (br. s, 1H), 4.04 (t, J=4.9 Hz, 2H), 3.75 (t, J=4.9 Hz, 2H).

Example 140

6-chloro-5-{4-[2-(1H-1,2,4-triazol-1-yl)ethoxy]phenyl}-1H-indole-3-carboxylic acid

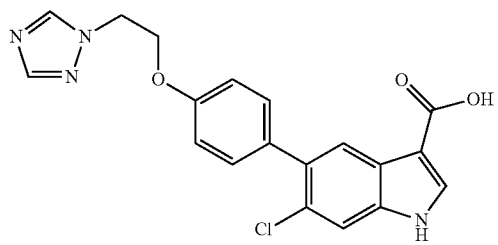 [SMILES: O=C(O)c1c[nH]c2cc(Cl)c(-c3ccc(OCCn4cncn4)cc3)cc12]

A vial was charged with 1-tert-butyl 3-methyl 6-chloro-5-(4-hydroxyphenyl)-1H-indole-1,3-dicarboxylate (30 mg, 0.075 mmol), 1-(2-chloroethyl)-1H-1,2,4-triazole (15 mg, 0.12 mmol) and tetrahydrofuran (1 mL). Cesium carbonate (64 mg, 0.18 mmol) was then added and the vial was sealed and stirred at room temperature for 3 hours then heated to 70° C. for 18 h. The reaction was filtered and the filtrate was concentrated in vacuo. Methanol (1 mL) and 1.0 M sodium hydroxide (0.3 mL, 0.3 mmol) were added and the reaction stirred for 18 h at 70° C. The reaction was then concentrated in vacuo and purified by reverse phase HPLC to provide 1 mg of the title compound. MS (ES⁺) 383.1 (M+H)⁺. Retention time=2.38 minutes (Waters Atlantis dC18 4.6×50, 5 μm; Mobile phase A: 0.05% TFA in water (v/v); Mobile phase B: 0.05% TFA in MeCN (v/v); Gradient: 95:5 A:B linear to 5:95 A:B in 4.0 min, hold at 5:95 A:B to 5.0 min. Flow: 2 mL/min).

Example 141

4,6-difluoro-5-(4-(1-(hydroxymethyl)cyclobutyl) phenyl)-1H-indole-3-carboxylic acid

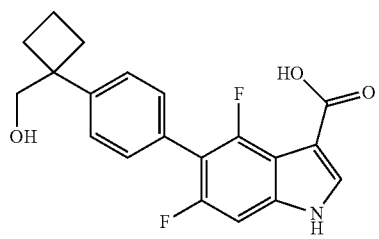 [SMILES: O=C(O)c1c[nH]c2cc(F)c(-c3ccc(C4(CO)CCC4)cc3)c(F)c12]

Step 1

4,6-difluoro-5-(4-(1-(hydroxymethyl)cyclobutyl) phenyl)-1H-indole-3-carbaldehyde

[1-(4-bromophenyl)cyclobutyl]methanol, prepared as described in Example 72 (steps 1 and 2), is treated with 5-bromo-4,6-difluoro-1H-indole-3-carbaldehyde, prepared as described in Example 6 (steps 1-4), in a manner similar as described in Example 6 step 5 to provide the title compound.

Step 2

4,6-difluoro-5-(4-(1-(hydroxymethyl)cyclobutyl) phenyl)-1H-indole-3-carboxylic acid The title compound is prepared by treating 4,6-difluoro-5-(4-(1-(hydroxymethyl)cyclobutyl)phenyl)-1H-indole-3-carbaldehyde in a similar manner as described in Example 6 (step 6) to provide the title compound.

Example 142

6-chloro-5-{3-fluoro-4-[1-(hydroxymethyl)cyclobutyl]phenyl}-1H-indole-3-carboxylic acid

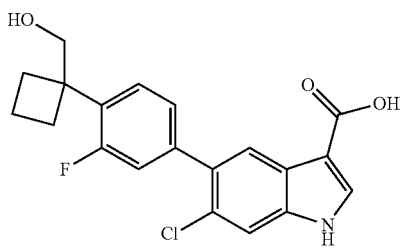 [SMILES: O=C(O)c1c[nH]c2cc(Cl)c(-c3ccc(C4(CO)CCC4)c(F)c3)cc12]

This was prepared by the method of example 137, steps 3-7, but starting with commercially available (4-bromo-2-fluorophenyl)acetonitrile to give the title compound. MS (ES−) 372.4 (M−H)⁻. 1H NMR (400 MHz, DMSO-d6) δ ppm 12.16 (s, 1 H) 11.97 (br. s., 1 H) 8.10 (d, 1 H) 7.96 (s, 1 H) 7.65 (s, 1 H) 7.17 (m, 3 H) 4.85 (t, 1 H) 3.66 (d, 2 H) 2.33 (m, 4 H) 2.06 (m, 1 H) 1.83 (m, 1 H).

Example 143

6-fluoro-5-{4-[1-(hydroxymethyl)cyclobutyl]phenyl}-1H-indole-3-carboxylic acid

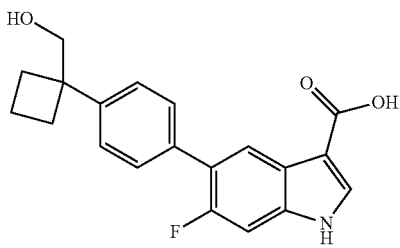 [SMILES: O=C(O)c1c[nH]c2cc(F)c(-c3ccc(C4(CO)CCC4)cc3)cc12]

This was prepared by the method of example 37, steps 1-4, but starting with [1-(4-bromophenyl)cyclobutyl]methanol and 5-bromo-6-fluoro-1H-indole to give the title compound. MS (ES+) 340.1 (M+H)⁺. 1H NMR (400 MHz, DMSO-d6) δ 12.06 (s, 1H), 11.88 (d, 1H), 7.98-8.05 (m, 2H), 7.45 (dd, 2H), 7.35 (d, 1H), 7.18-7.25 (m, 2H), 4.77 (t, 1H), 3.54 (d, 2H), 2.13-2.32 (m, 4H), 1.93-2.08 (m, 1H), 1.70-1.86 (m, 1H).

Example 144

6-chloro-5-[(2S)-2-(hydroxymethyl)-2,3-dihydro-1,4-benzodioxin-6-yl]-1H-indole-3-carboxylic acid

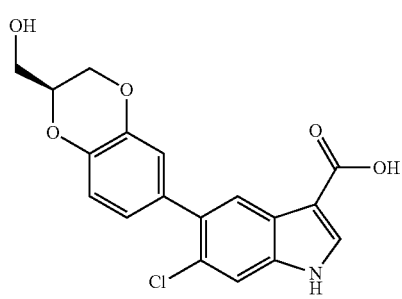 [SMILES: O=C(O)c1c[nH]c2cc(Cl)c(-c3ccc4c(c3)OC[C@H](CO)O4)cc12]

This was prepared by the method of Example 37, Steps 3-4, using [(2S)-6-bromo-2,3-dihydro-1,4-benzodioxin-2-yl]methanol (0.54 g, 2.05 mmol) (which can be prepared as in Biorg. Med. Chem. 2007, 15, 4048.) to give the title compound. MS (ES+) 360.1 (M+H)⁺. 1H NMR (400 MHz, CD₃OD) δ 7.97 (s, 2H), 7.54 (s, 1H), 6.90 (m, 3H), 4.35 (dd, 1H), 4.22 (m, 1H), 4.09 (dd, 1H), 3.80 (m, 2H).

Example 145

6-chloro-5-[(2S)-2-(hydroxymethyl)-2,3-dihydro-1,4-benzodioxin-6-yl]-1H-indole-3-carboxylic acid

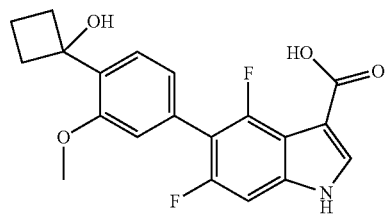 [SMILES: COc1cc(-c2c(F)cc3[nH]cc(C(=O)O)c3c2F)ccc1C1(O)CCC1]

Was prepared in a manner similarly described in Example 6, Steps 5-6 with 1-[4-(5,5-dimethyl-1,3,2-dioxaborinan-2-yl)-2-methoxyphenyl]cyclobutanol and 5-bromo-4,6-difluoro-1H-indole-3-carbaldehyde to give the title compound. MS (ES+) 396.0 (M+Na)+ ¹HNMR (400 MHz, DMSO-d6) δ ppm 8.08 (s, 1 H) 7.36 (d, 1 H) 7.26 (d, 1 H) 7.01 (s, 1 H) 6.96 (d, 1 H) 5.07 (s, 1 H) 3.08 (s, 3 H) 2.59 (m, 2 H) 2.21 (m, 2 H) 2.01 (m, 1 H) 1.66 (m, 1 H).

Example 146

6-chloro-5-[4-(trans-3-hydroxycyclobutyl)-3-methoxyphenyl]-1H-indole-3-carboxylic acid

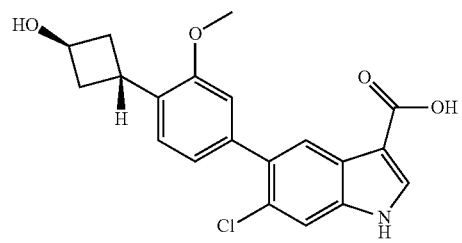 [SMILES: COc1cc(-c2cc3c(C(=O)O)c[nH]c3cc2Cl)ccc1[C@H]1C[C@H](O)C1]

Step 1

4-bromo-2-methoxybenzaldehyde

A mixture of 4-bromo-2-fluorobenzaldehyde (25.0 g, 0.123 mol) and sodium methoxide (13.99 g, 0.2600 mol) in dry methanol (250 mL) was stirred at reflux temperature for 16 hours. The mixture was concentrated and the residue was partitioned between dichloromethane (500 mL) and water (250 mL). The organic layers were combined and dried over sodium sulfate then concentrated in vacuo to provide the title compound as yellow solid (25 g, 94.5%).

Step 2

4-bromo-1-ethenyl-2-methoxybenzene

To a suspension of Methyltriphenylphosphonium bromide (5.7 g, 15.6 mmol) in anhydrous toluene (7 mL) was added Lithium bis(trimethylsilyl)amide (14.28 mL, 1M tetrahydrofuran) at 0° C. After addition, the mixture was stirred at room temperature for 1 h, then cooled to 0° C. and a solution of 4-bromo-2-fluorobenzaldehyde (2.0 g, 9.3 mmol) in anhydrous toluene (33 mL) was added dropwise. The mixture was stirred at room temperature overnight. The mixture was cooled to 0° C. and aqueous ammonium chloride (12 mL) was added. The mixture was extracted with ethyl acetate (300 mL) and the organic layers were washed with brine (300 mL), dried over sodium sulfate and filtered, the filtrate was concentrated in vacuum to give crude product (4 g), which was purified via silica gel chromatography to give the title compound (1.4 g, 42%) as an oil.

Step 3

3-(4-bromo-2-methoxyphenyl)-2,2-dichlorocyclobutanone

To a suspension of activated Zn—Cu complex (1.4 g, 19 mmol) and 4-bromo-1-ethenyl-2-methoxybenzene (2.700 g, 12.67 mmol) in dry tetrahydrofuran (30 mL) was added dropwise through addition funnel a solution of thrichloroacetic chloride (2.11 g, 19.0 mmol) and phosphoryl chloride (11.7 ml, 12.7 mmol) in tetrahydrofuran (20 mL) during 2 hr at refluxing temperature. Then the mixture was stirred overnight under refluxing temperature. The mixture was cooled to room temperature and filtered. The filtrate was combined with ethyl acetate (100 mL), the combined solution was concentrated to give the title compound (1.45 g, 35%) which was used into next step without further purification.

Step 4

3-(4-bromo-2-methoxyphenyl)cyclobutanone

In a 50 mL round-bottom flask equipped with a reflux condenser is placed 3-(4-bromo-2-methoxyphenyl)-2,2-dichlorocyclobutanone (300 mg, 1.08 mmol) and activated zinc (280 mg, 4.30 mmol), in a saturated methanolic ammonium chloride solution (2 ml), the suspension is refluxed for 6 hr, then cooled to 23° C. and filtered through celite and rinsed with petroleum ether (10 mL), and organics are rinsed with water (10 mL), sat sodium bicarbonate (10 mL) and brine (10 ml), dried over sodium sulfate and concentrated under reduced pressure, the crude material was purified by silica gel chromatography to give the title compound (200 mg, 85%).

Step 5 cis-3-(4-bromo-2-methoxyphenyl)cyclobutanol

Sodium borohydride (0.25 g, 6.75 mmol) was added to a solution of 3-(4-bromo-2-methoxyphenyl)cyclobutanone (1.87 g, 7.3 mmol) in tetrahydrofuran (70 mL) at 0° C., the reaction was stirred room temperature 1 hr, extracted with 1:1 solution of ethyl acetate in heptane, the organic layers was washed with brine (50 mL), dried over sodium sulfate, and concentrated to give the title compound (1.34 g, 77.18%).

Step 6 trans-3-(4-bromo-2-methoxyphenyl)cyclobutanol

To a solution of triphenylphosphine (142.7 mg, 0.546 mmol) in tetrahydrofuran (2 mL) was added diisopropyl azodicarboxylate (11 mg, 0.54 mmol), and the resulting mixture was stirred at room temperature for 30 min. The mixture was cooled to −50° C. and cis-3-(4-bromo-2-methoxyphenyl) cyclobutanol (100 mg, 0.389 mmol) in tetrahydrofuran (0.5 mL) was added. The reaction was stirred for 20 min, followed by addition of solid 4-nitrobenzoic acid (90.97 mg, 0.546 mmol), the resulting mixture was warmed to room temperature and allowed to stir at room temperature for 15 hr. The reaction was then cooled to 0° C., to which was added sodium hydroxide (5 mL, 0.5 M in methanol). After 40 min the reaction was quenched with sat. ammonium chloride (5 mL), and diluted with ethyl acetate (15 mL). The organic layer was separated, dried over sodium sulfate, filtered and evaporated to dryness to give the title compound (78 mg, 54%) as an oil.

Step 7

6-chloro-5-[4-(trans-3-hydroxycyclobutyl)-3-methoxyphenyl]-1H-indole-3-carboxylic acid This was prepared in a manner similar to Example 37, Steps 3-4 with trans-3-(4-bromo-2-methoxyphenyl)cyclobutanol to give the title compound. MS (ES+) 396.0 (M+Na)+ 1H NMR (400 MHz, DMSO-d6) δ 8.08 (s, 1 H) 7.36 (d, 1 H) 7.26 (d, 1 H) 7.01 (s, 1 H) 6.96 (d, 1 H) 5.07 (s, 1 H) 3.08 (s, 3 H) 2.59 (m, 2 H) 2.21 (m, 2 H) 2.01 (m, 1 H) 1.66 (m, 1 H).

Example 147

6-chloro-5-[4-(1-hydroxycyclobutyl)phenyl]-N-(methylsulfonyl)-1H-indole-3-carboxamide

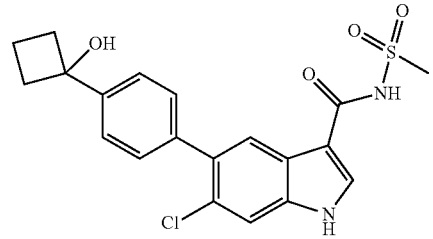 [SMILES: CS(=O)(=O)NC(=O)c1c[nH]c2cc(Cl)c(-c3ccc(C4(O)CCC4)cc3)cc12]

To a mixture of 6-chloro-5-[4-(1-hydroxycyclobutyl)phenyl]-1H-indole-3-carbaldehyde (40 mg, 0.123 mmol), Bis (tert-butylcarbonyloxy)iodobenzene (104 mg, 0.256 mmol) in isopropyl acetate (2 mL) was added methanesulfonamide (12 mg, 0.126 mmol). After stirring 5 minutes, Bis[rhodium (α,α,α',α'-tetramethyl-1,3-benzenedipropionic acid)] (5 mg, 0.007 mmol) was added and heated to 80° C. overnight. The mixture was concentrated to give a crude residue, which was purified by preparative HPLC to afford the title compound (6.6 mg, 13%) as a yellow solid.

MS (ES+) 419.2 (M+H)+. 1H NMR (400 MHz, CD3OD) δ 8.18 (s, 2H), 8.17 (s, 2H), 7.63 (s, 1H), 7.60 (d, 2H), 7.47 (d, 2H), 3.39 (s, 3H), 2.62 (m, 2H), 2.42 (m, 2H), 2.06 (m, 1H), 1.78 (m, 1H).

Example 148

6-chloro-5-[3-hydroxy-4-(1-hydroxy-2-methylpropan-2-yl)phenyl]-1H-indole-3-carboxylic acid

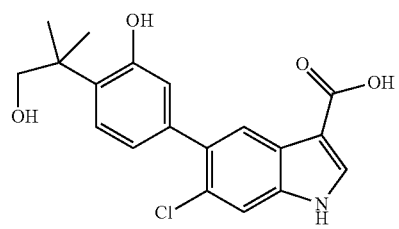 [SMILES: CC(C)(CO)c1ccc(-c2cc3c(C(=O)O)c[nH]c3cc2Cl)cc1O]

Step 1

5-bromo-2-(1-hydroxy-2-methylpropan-2-yl)phenol

To a solution of 2-(4-bromo-2-methoxyphenyl)-2-methylpropan-1-ol (300 mg, 1.16 mmol) in dichloromethane (5 mL) was added dropwise boron tribromide (580 mg, 2.32 mmol) at −78° C. under nitrogen. The reaction mixture was warmed to room temperature and stirred for 30 minutes. The reaction was quenched with water (10 mL) and extracted with dichloromethane (20 mL). The organic layer was washed with aq. sodium bicaronate (20 mL), brine (20 mL), dried over sodium sulfate, filtered and concentrated to give a crude residue, which was purified by flash chromatography to give the title compound (90 mg, 32%) as a white solid.

Step 2

6-chloro-5-[3-hydroxy-4-(1-hydroxy-2-methylpropan-2-yl)phenyl]-1H-indole-3-carboxylic acid This was prepared in a manner similar to Example 37, Steps 3-4 with 5-bromo-2-(1-hydroxy-2-methylpropan-2-yl)phenol to give the title compound. MS (ES+) 360.1 (M+H)+. 1H NMR (400 MHz, CD3OD) δ 7.99 (s, 1H), 7.96 (s, 1H), 7.54 (s, 1H), 7.25 (d, 1H), 6.86 (d, 2H), 3.85 (s, 2H), 1.41 (s, 6H).

Example 149 chloro-5-[5-(3-hydroxypyrrolidin-1-yl)-6-methoxypyridin-2-yl]-1H-indole-3-carboxylic acid

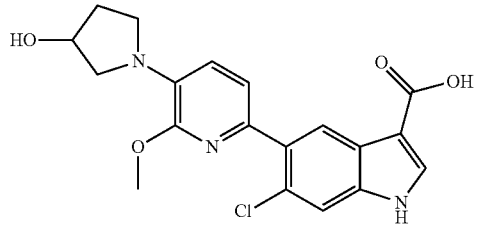 [SMILES: COc1nc(-c2cc3c(C(=O)O)c[nH]c3cc2Cl)ccc1N1CCC(O)C1]

Step 1

3-bromo-6-chloro-2-methoxypyridine

To a solution of 3-bromo-2,6-dichloropyridine (3.00 g, 13.2 mmol) in acetonitrile (20 mL) was added sodium methoxide (methanol solution, 4.83 mol/L, 3.0 mL) dropwise at 0° C. The mixture was stirred at room temperature over night. To the mixture was added 30 mL of water, and the organic was evaporated. The resulting suspension was filtered, and the pad was washed with water for several times. The pad was dried under reduce pressure to give title compound (2.74 g, 93.2%) as white solid.

Step 2

1-(6-chloro-2-methoxypyridin-3-yl)pyrrolidin-3-ol

A vial was charged 3-bromo-6-chloro-2-methoxypyridine (0.50 g, 2.2 mmol), pyrrolidin-3-ol (0.39 g, 4.5 mmol), tris(dibenzylideneacetone)dipalladium(0) (0.10 g, 0.10 mmol), Xantphos (0.13 g, 0.20 mmol), sodium tertbutoxide (0.32 g, 3.4 mmol) and toluene (5 mL). The mixture was purged with nitrogen then sealed. The mixture was heated to 100° C. overnight. The mixture was cooled to room temperature, filtered and diluted with 15 mL of water. The solution was extracted with ethyl acetate (10 mL×3). The organic layers were combined, dried over sodium sulfate, filtered and concentrated. The resulting residue was purified by silica gel chromatography to give the title compound (29.5 mg, 5.7%) as light brown solid.

Step 3

6-chloro-5-[5-(3-hydroxypyrrolidin-1-yl)-6-methoxypyridin-2-yl]-1H-indole-3-carboxylic acid This was prepared in a manner similar to Example 37, Steps 3-4 with 1-(6-chloro-2-methoxypyridin-3-yl)pyrrolidin-3-ol to give the title compound. MS (ES+) 388.1 (M+H)+. 1H NMR (400 MHz, CD3OD) δ 8.43 (s, 1H), 8.25 (s, 1H), 7.98 (s, 1 H), 7.11 (d, 1H) 6.98 (d, 1 H), 4.48 (m, 1H), 3.99 (s, 3 H), 3.70 (m, 1H), 3.60 (m, 1H), 3.38 (m, 2H), 2.15 (m, 1 H), 1.96 (m, 1 H).

Examples 150 and 151

6-fluoro-5-[4-(tetrahydrofuran-2-yl)phenyl]-1H-indole-3-carboxylic acid

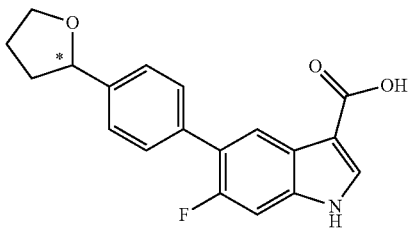 [SMILES: O=C(O)c1c[nH]c2cc(F)c(-c3ccc(C4CCCO4)cc3)cc12]

Step 1

1-(4-bromophenyl)-4-chlorobutan-1-ol

To a solution of 1-(4-bromophenyl)-4-chlorobutan-1-one (1.00 g, 3.83 mmol) in methanol (20 mL) was added sodium borohydride (260 mg, 7.66 mmol) at 0° C. The mixture was stirred at 0° C. for 1 hour. 1 M HCl was added and the mixture was stirred for 15 minutes. Solvents were removed and the residue was extracted with ethyl acetate (10 mL×2). The combined organic layer were washed with brine, dried and concentrated to give target compound (1 g, 99%) as a light yellow oil.

Step 2

2-(4-bromophenyl)tetrahydrofuran

To a solution of 1-(4-bromophenyl)-4-chlorobutan-1-ol (1.0 g, 3.8 mmol) in tetrahydrofuran (20 mL) was added sodium hydroxide (110 mg, 4.56 mmol) at 0° C. After being stirred for 2 hours, the reaction mixture was quenched with water, brought to pH=6 with 1 M HCl aqueous, and extracted with ethyl acetate. The organic was washed with brine, dried over sodium sulfate, filtered and concentrated to give the target compound (910 mg, 100%) as a yellow solid.

Step 3

Racemic-6-fluoro-5-[4-(tetrahydrofuran-2-yl)phenyl]-1H-indole-3-carboxylic acid

This was prepared in a similar manner to example 4, steps 1-3 with 2-(4-bromophenyl)tetrahydrofuran to provide the title compound.

Step 4

6-fluoro-5-[4-(tetrahydrofuran-2-yl)phenyl]-1H-indole-3-carboxylic acid—Isomer 1

6-fluoro-5-[4-(tetrahydrofuran-2-yl)phenyl]-1H-indole-3-carboxylic acid—Isomer 2

Racemic 6-fluoro-5-[4-(tetrahydrofuran-2-yl)phenyl]-1H-indole-3-carboxylic acid was subjected to preparative SFC (Column: AD(250×30 mm, 5 um); Mobile phase: 35% MEOH 50 ML/MIN; Wavelength: 220 nm). Peak 1 was isolated as Isomer 1 (Example 150), Retention time=2.22 min; Column: Chiralpak AD-3 150×4.6 mm I.D., 3 um Mobile phase: methanol (0.05% DEA) in CO2 from 5% to 40% Flow rate: 2.5 mL/min Wavelength: 220 nm; MS (ES+) 326.0 (M+H)+. 1H NMR (400 MHz, Methanol-d4) δ ppm 8.12 (d, 1 H) 7.97 (s, 1 H) 7.54 (d, 2 H) 7.42 (d, 2 H) 7.25 (d, 1 H) 4.94 (t, 1 H) 4.13 (q, 1 H) 3.95 (q, 1 H) 2.39 (m, 1 H) 2.08 (m, 2 H) 1.86 (m, 1 H). Peak 2 was isolated as Isomer 2 (Example 151), Retention time=2.55 min; Column: Chiralpak AD-3 150×4.6 mm I.D., 3 um Mobile phase: methanol (0.05% DEA) in CO2 from 5% to 40% Flow rate: 2.5 mL/min Wavelength: 220 nm; MS (ES+) 326.1 (M+H)+. 1H NMR (400 MHz, METHANOL-d4) δ ppm 8.12 (d, 1 H) 7.97 (s, 1 H) 7.54 (d, 2 H) 7.42 (d, 2 H) 7.25 (d, 1 H) 4.94 (t, 1 H) 4.13 (q, 1 H) 3.95 (q, 1 H) 2.39 (m, 1 H) 2.07 (m, 2 H) 1.86 (m, 1 H).

Examples 152 and 153

4,6-difluoro-5-[4-(tetrahydrofuran-2-yl)phenyl]-1H-indole-3-carboxylic acid

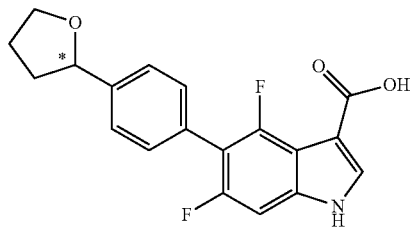 [SMILES: O=C(O)c1c[nH]c2cc(F)c(-c3ccc(C4CCCO4)cc3)c(F)c12]

Step 1

Racemic-4,6-difluoro-5-[4-(tetrahydrofuran-2-yl)phenyl]-1H-indole-3-carboxylic acid This was prepared in a manner similarly described in Example 6, Steps 5-6 with 2-(4-bromophenyl)tetrahydrofuran and 5-bromo-4,6-difluoro-1H-indole-3-carbaldehyde to give the title compound.

Step 2

4,6-difluoro-5-[4-(tetrahydrofuran-2-yl)phenyl]-1H-indole-3-carboxylic acid Isomer 1

4,6-difluoro-5-[4-(tetrahydrofuran-2-yl)phenyl]-1H-indole-3-carboxylic acid Isomer 2

Racemic-4,6-difluoro-5-[4-(tetrahydrofuran-2-yl)phenyl]-1H-indole-3-carboxylic acid was subjected to separation by preparative SFC (Column: OJ (250 MM*30 MM, 5 UM); Mobile phase: 30% MEOH NH3H2O 60 ML/MIN 3; Wavelength: 220 nm) Peak 1 was isolated and arbitrarily called 4,6-difluoro-5-{4-[(2S)-tetrahydrofuran-2-yl]phenyl}-1H-indole-3-carboxylic acid. Peak 1 was isolated as Isomer 1 (Example 152) Retention time=8.43 min; Column: Chiralcel OJ-H 250×4.6 mm I.D., 5 um Mobile phase: methanol (0.05% DEA) in CO2 from 5% to 40% Flow rate: 2.5 mL/min Wavelength: 220 nm. MS (ES+) 343.8 (M+H)+. 1H NMR (400 MHz, DMSO-d6) δ 8.06 (s, 1 H) 7.42 (m, 5 H) 7.25 (d, 1 H) 4.88 (t, 1 H) 4.03 (q, 1 H) 3.85 (q, 1 H) 2.35 (m, 1 H) 1.99 (m, 2 H) 1.75 (m, 1 H). Peak 2 was isolated as Isomer 2 (Example 153), Retention time=8.86 min; Column: Chiralcel OJ-H 250×4.6 mm I.D., 5 um Mobile phase: methanol (0.05% DEA) in CO2 from 5% to 40% Flow rate: 2.5 mL/min Wavelength: 220 nm.

MS (ES+) 343.9 (M+H)+. 1H NMR (400 MHz, DMSO-d6) δ 8.06 (s, 1 H) 7.41 (m, 4 H) 7.24 (d, 1 H) 4.87 (t, 1 H) 4.02 (q, 1 H) 3.84 (q, 1 H) 2.35 (dq, 1 H) 1.97 (m, 2 H) 1.73 (m, 1 H).

Examples 154 and 155

6-chloro-5-[4-(tetrahydrofuran-2-yl)phenyl]-1H-indole-3-carboxylic acid Isomer 1

6-chloro-5-[4-(tetrahydrofuran-2-yl)phenyl]-1H-indole-3-carboxylic acid Isomer 2

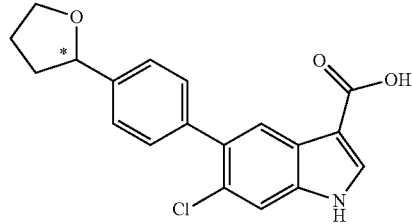 [SMILES: O=C(O)c1c[nH]c2cc(Cl)c(-c3ccc(C4CCCO4)cc3)cc12]

This was prepared in a manner similar to example 37, steps 3-4 with 2-(4-bromophenyl)tetrahydrofuran and subjected to preparative chiral SFC. Column: Chiral Tech IC-H 250 mm×21.2 mm 5u. Isocratic 70% CO2 30% Methanol. Detection 210 nM. Flow: 80.0 mL/min, backpressure 120 Bar. Peak 1 was isolated as Isomer 1 (Example 154); Retention time=6.994; Chiral Tech IC-H 250 mm×4.6 mm 5u. Gradient Mobile Phase A: CO2 B: Methanol Time: 0 min: 95% A 5% B. 1 min: 95% A 5% B 9 min: 40% A 60% B. 9.5 min: 40% A, 60% B 10.0 min: 95% A 5% B. Detection: 210 nm. Backpressure 120 Bar. MS (ES−): 340.2 (M−H)[−1]H NMR (500 MHz, DMSO-d$_6$) ppm 11.98-12.17 (br. s, 1 H) 11.94 (br. s, 1 H) 8.07 (s, 1 H) 7.94 (s, 1 H) 7.62 (s, 1 H) 7.39 (s, 4 H) 4.86 (t, 1 H) 3.97-4.04 (m, 1 H) 3.83 (dt, 1 H) 2.33 (ddt, 1 H) 1.89-2.02 (m, 2 H) 1.73 (dq, 1 H). Peak 2 was isolated as Isomer 2 (Example 155), Retention time=7.530; Chiral Tech IC-H 250 mm×4.6 mm 5u. Gradient Mobile Phase A: CO2 B: Methanol Time: 0 min: 95% A 5% B. 1 min: 95% A 5% B 9 min: 40% A 60% B. 9.5 min: 40% A, 60% B 10.0 min: 95% A 5% B. Detection: 210 nm. Backpressure 120 Bar. MS (ES−): 340.2 (M−H)⁻. $^1$H NMR (500 MHz, DMSO-$d_6$) ppm 11.47-12.13 (m, 1 H) 8.06 (s, 1 H) 7.94 (s, 1 H) 7.62 (s, 1 H) 7.39 (s, 4 H) 4.86 (t, 1 H) 4.01 (m, 1 H) 3.83 (dt, 1 H) 2.29-2.37 (m, 1 H) 1.93-2.00 (m, 2 H) 1.73 (dq, 1 H)

Example 156

6-chloro-5-(4-(2-(oxetan-3-yl)ethoxy)phenyl)-1H-indole-3-carboxylic acid

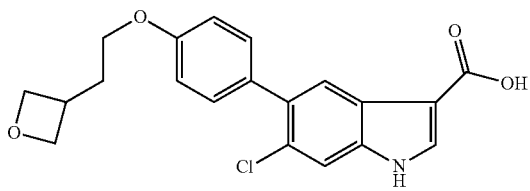 [SMILES: O=C(O)c1c[nH]c2cc(Cl)c(-c3ccc(OCCC4COC4)cc3)cc12]

Step 1

1-bromo-4-(2-bromoethoxy)benzene

To a suspension of 4-bromophenol (2.00 g, 11.6 mmol) in water (20 mL) was added 1,2-dibromoethane (5.40 g, 28.8 mmol) and sodium hydroxide (0.700 g, 17.5 mmol). Then, the mixture was heated at reflux for 12 hours. Water was added, and the mixture was extracted with ethyl acetate (4×30 mL). The combined organic layers were washed with brine (3×20 mL), dried over sodium sulfate, filtered, and concentrated under reduced pressure to give the crude product. The crude product was purified by flash chromatography (0-10% ethyl acetate/petroleum ether) to afford the title compound (1.8 g, 56%) as a colorless oil.
$^1$H NMR (400 MHz, CDCl$_3$) ppm 7.40 (d, 2 H), 6.81 (d, 2 H), 4.27 (t, 2 H), 3.64 (t, 2 H).

Step 2 diethyl 2-(2-(4-bromophenoxy)ethyl)malonate

To a solution of NaH (0.160 g, 6.68 mmol) in anhydrous tetrahydrofuran (20 mL) was added diethyl malonate (1.07 g, 6.68 mmol) dropwise at 0° C. The resulting colorless solution was stirred at 0° C. for 15 minutes, then at room temperature for 30 minutes before cooling again to 0° C. A solution of 1-bromo-4-(2-bromoethoxy)benzene (1.70 g, 6.07 mmol) in anhydrous tetrahydrofuran (10 mL) was added over 5 minutes. The resulting mixture was heated at reflux until complete as judged by TLC. The mixture was cooled to room temperature and carefully quenched with water and then extracted with ethyl acetate (4×50 mL). The combined organic phases were dried over sodium sulfate filtered and concentrated under reduced pressure to give the title compound (2.5 g) as a colorless oil which was used in the next step without purification. $^1$H NMR (400 MHz, CDCl$_3$) ppm 7.43-7.32 (m, 2H), 6.84-6.68 (m, 2H), 4.32-4.14 (m, 4H), 4.01 (m, 2H), 3.64 (m, 1H), 2.43-2.32 (m, 2H), 1.33-1.18 (m, 6H).

Step 3

2-(2-(4-bromophenoxy)ethyl)propane-1,3-diol

To a solution of diethyl 2-(2-(4-bromophenoxy)ethyl)malonate (2.50 g, 6.96 mmol) in anhydrous MeOH (15 mL) was added sodium borohydride (1.32 g, 34.8 mmol) in portions at 0° C. The reaction mixture was stirred for 30 minutes at this temperature. The reaction mixture was then carefully quenched with water and extracted with ethyl acetate (4×50 mL). The combined organic layers were dried over sodium sulfate, filtered, and concentrated under reduced pressure to give the crude product. The crude product was purified by flash chromatography (ethyl acetate:petroleum ether) to deliver the title compound (1.0 g, 52%) as a white solid.
$^1$H NMR (400 MHz, CDCl$_3$) ppm 7.38 (d, 2 H), 6.78 (d, 2 H), 4.04 (t, 2 H), 3.91-3.82 (m, 2 H), 3.81-3.72 (m, 2 H), 2.19-2.12 (m, 2 H), 2.06-1.97 (m, 1 H), 1.89-1.84 (m, 2 H).

Step 4

4-(4-bromophenoxy)-2-(hydroxymethyl)butyl 4-methyl benzenesulfonate

To a suspension of NaH (0.11 g, 4.58 mmol) in anhydrous tetrahydrofuran (10 mL) was added a solution of 2-(2-(4-bromophenoxy)ethyl)propane-1,3-diol (0.63 g, 2.29 mmol) in anhydrous tetrahydrofuran (10 mL) dropwise. The reaction mixture was stirred at room temperature for 30 minutes. Then, tosyl chloride (0.44 g, 2.3 mmol) was added in portions. The reaction mixture was then stirred at room temperature for 2 hours. The reaction mixture was carefully quenched with water and extracted with ethyl acetate (4×30 mL). The combined organic layers were dried over anhydrous sodium sulfate, filtered, and concentrated under reduced pressure to give the crude product, which was purified by flash chromatography (0-35% ethyl acetate/petroleum ether) to afford the title compound (0.45 g, 46%) as white solid. $^1$H NMR (400 MHz, CDCl$_3$) ppm 7.80 (d, 2 H), 7.40-7.30 (m, 4 H), 6.71 (d, 2 H), 4.21-4.09 (m, 2 H), 4.00-3.90 (m, 2 H), 3.74-3.62 (m, 2 H), 2.45 (s, 3H), 2.14 (m, 1 H), 1.89-1.74 (m, 3H).

Step 5

3-(2-(4-bromophenoxy)ethyl)oxetane

To a solution of 4-(4-bromophenoxy)-2-(hydroxymethyl) butyl 4-methylbenzenesulfonate (0.450 g, 1.04 mmol) in anhydrous tetrahydrofuran (10 mL) was added n-butyl lithium (0.42 mL, 2.5 M, 1.04 mmol) dropwise at 0° C. After complete addition of the n-butyl lithium solution, the resulting mixture was heated at reflux overnight. The reaction was carefully quenched with water and extracted with ethyl acetate (5×20 mL). The combined organic layers were dried over sodium sulfate, filtered and concentrated under reduced pressure to give the crude product. The crude product was purified by flash chromatography (0-20% ethyl acetate/petroleum ether) to afford the title compound (0.10 g, 37%) as a white solid. $^1$H NMR (400 MHz, CDCl$_3$) ppm 7.37 (d, 2 H), 6.74 (d, 2 H), 4.89-4.78 (m, 2 H), 4.56-4.45 (m, 2 H), 3.94-3.87 (m, 2 H), 3.30-3.17 (m, 1 H), 2.23-2.12 (m, 2 H)

Step 6

6-chloro-5-(4-(2-(oxetan-3-yl)ethoxy)phenyl)-1H-indole-3-carboxylic acid 3-(2-(4-bromophenoxy)ethyl)oxetane This was prepared in a manner similar to Example 37, Steps 3-4 with 3-(2-(4-bromophenoxy)ethyl)oxetane to give the title compound. MS (ES+) 372.2 (M+H)+. ¹H NMR (400 MHz, DMSO-d₆) ppm 11.91 (br. s., 1 H), 8.06 (s, 1 H), 7.92 (s, 1 H), 7.62 (s, 1 H), 7.33 (d, 2 H), 6.97 (d, 2 H), 4.73-4.63 (m, 2 H), 4.43-4.33 (m, 2 H), 4.05-3.95 (m, 2 H), 3.20-3.09 (m, 1 H), 2.15-2.03 (m, 2 H).

Example 157

6-chloro-5-(4-(3-(oxetan-3-yl)propoxy)phenyl)-1H-indole-3-carboxylic acid

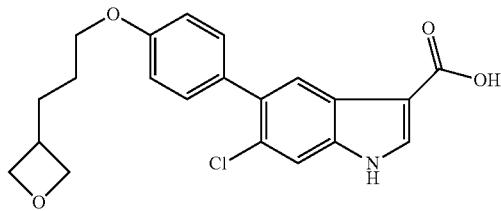 [SMILES: O=C(O)c1c[nH]c2cc(Cl)c(-c3ccc(OCCCC4COC4)cc3)cc12]

Step 1

1-bromo-4-(3-bromopropoxy)benzene

To a suspension of 4-bromophenol (2.00 g, 11.56 mmol) and potassium carbonate (4.79 g, 34.68 mmol) in DMF (12 mL) was added 1,3-dibromopropane (7.00 g, 37.3 mmol). The mixture was stirred at room temperature overnight. Water was added, and the mixture was extracted with ethyl acetate (4×30 mL). The combined organic layers were washed with brine (3×20 mL), dried over sodium sulfate, filtered, and concentrated under reduced pressure to give the crude product. The crude product was purified by flash chromatography (0-5% ethyl acetate/petroleum ether to afford the title compound (2.35 g, 69%) as a colorless oil. ¹H NMR (400 MHz, CDCl₃) ppm 7.39 (d, 2 H), 6.80 (d, 2 H), 4.16-4.01 (m, 2 H), 3.55-3.53 (m, 2 H), 2.41-2.26 (m, 2 H).

Step 2

6-chloro-5-(4-(3-(oxetan-3-yl)propoxy)phenyl)-1H-indole-3-carboxylic acid

This was prepared in a similar manner to example 156, steps 2-6 with 1-bromo-4-(3-bromopropoxy)benzene to provide the title compound. MS (ES+) 386.2 (M+1)⁺. ¹H NMR (400 MHz, DMSO-d₆) ppm 11.91 (br. s., 1 H), 8.06 (s, 1 H), 7.94 (s, 1 H), 7.62 (s, 1 H), 7.34 (d, 2 H), 7.02 (d, 2 H), 4.71-4.64 (m, 2 H), 4.32-4.24 (m, 2 H), 4.04-3.97 (m, 2 H), 3.07-2.96 (m, 1 H), 1.85-1.75 (m, 2 H), 1.74-1.61 (m, 2 H).

Example 158

6-chloro-5-(4-{[(2R)-1-methoxypropan-2-yl]oxy}phenyl)-1H-indole-3-carboxylic acid

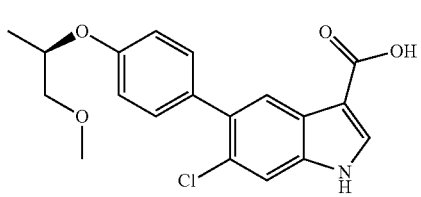 [SMILES: COC[C@@H](C)Oc1ccc(-c2cc3c(C(=O)O)c[nH]c3cc2Cl)cc1]

This was synthesized in a manner similar to Example 94, Steps 2-4 with (S)-1-methoxypropan-2-ol to give the title compound, 15 mg. MS (ES+) 382.0 (M+Na)⁺. ¹H NMR (400 MHz, DMSO-d₆) ppm 12.10 (br. s., 1 H), 11.94 (br s), 8.08 (d, 1 H), 7.93 (s, 1 H), 7.62 (s, 1 H), 7.33 (d, 2 H), 7.01 (d, 2 H), 4.67 (m, 1 H), 3.51 (dddd, 2 H), 3.32 (s, 3H), 1.27 (d, 3H).

Example 159

6-chloro-5-(4-{[(2S)-1-methoxypropan-2-yl]oxy}phenyl)-1H-indole-3-carboxylic acid

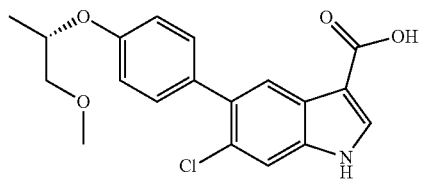 [SMILES: COC[C@H](C)Oc1ccc(-c2cc3c(C(=O)O)c[nH]c3cc2Cl)cc1]

This was synthesized in a manner similar to Example 94, Steps 2-4 with (R)-1-methoxypropan-2-ol to give the title compound, 20 mg. MS (ES+) 360.0 (M+H)⁺. ¹H NMR (400 MHz, DMSO-d₆) ppm 12.10 (br. s., 1 H), 11.94 (br s), 8.08 (d, 1 H), 7.93 (s, 1 H), 7.62 (s, 1 H), 7.33 (d, 2 H), 7.01 (d, 2 H), 4.67 (m, 1 H), 3.51 (dddd, 2 H), 3.32 (s, 3H), 1.27 (d, 3H).

Example 160

6-chloro-5-[4-(pyrimidin-2-ylmethoxy)phenyl]-1H-indole-3-carboxylic acid

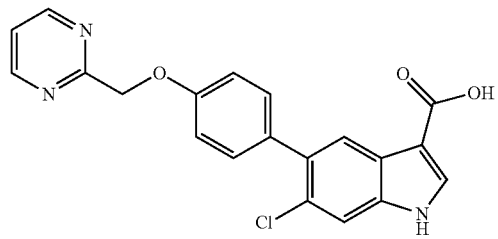 [SMILES: O=C(O)c1c[nH]c2cc(Cl)c(-c3ccc(OCc4ncccn4)cc3)cc12]

This was synthesized in a manner similar to Example 94, Steps 2-4 with pyrimidin-2-ylmethanol to give the title compound, 24.0 mg. MS (ES+) 380.0 (M+H)⁺. ¹H NMR (400 MHz, DMSO-d₆) ppm 12.10 (br. s., 1 H), 11.94 (br s), 8.87 (d, 2H), 8.05 (s, 1 H), 7.92 (s, 1 H), 7.61 (s, 1 H), 7.49 (t, 1H), 7.33 (d, 2 H), 7.05 (d, 2 H), 5.33 (s, 2H).

Example 161

6-chloro-5-[6-(3-hydroxypyrrolidin-1-yl)-2-methoxypyridin-3-yl]-1H-indole-3-carboxylic acid

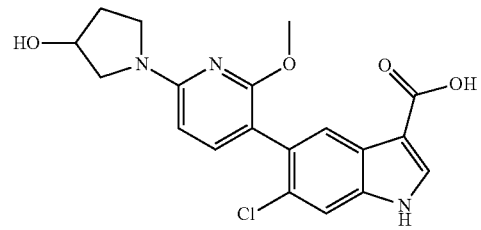 [SMILES: COc1nc(N2CCC(O)C2)ccc1-c1cc2c(C(=O)O)c[nH]c2cc1Cl]

291

Step 1

1-(5-bromo-6-methoxypyridin-2-yl)pyrrolidin-3-ol

A vial was charged with 3-bromo-6-chloro-2-methoxypyridine (1.00 g, 4.5 mmol), rac-pyrrolidin-3-ol (0.59 g, 6.7 mmol), triethylamine (0.91 g, 8.9 mmol) and dimethylsulfoxide (4 mL). The mixture was heated to 150° C. for 5 hrs. The mixture was cooled to room temperature and diluted with 20 mL of water. The solution was extracted with ethyl acetate (10 mL×3). The extracts were combined, dried (sodium sulfate) and concentrated. The resulting residue was purified through flash column chromatography (petroleum ether/ethyl acetate=5:1~2:1) to give the title compound (0.26 g, 25.3%) as light brown gum.

Step 2

Methyl 6-chloro-5-[6-(3-hydroxypyrrolidin-1-yl)-2-methoxypyridin-3-yl]-1H-indole-3-carboxylate A vial was charged with 1-(5-bromo-6-methoxypyridin-2-yl)pyrrolidin-3-ol (100.0 mg, 0.37 mmol), methyl 6-chloro-5-(5,5-dimethyl-1,3,2-dioxaborinan-2-yl)-1H-indole-3-carboxylate (176.4 mg, 0.55 mmol), Pd(dppf)C12 (26.8 mg, 0.04 mmol), potassium carbonate (152 mg, 1.10 mmol, 2M/L aqueous) and toluene/ethanol (1.5 mL/0.5 mL). The mixture was purged with nitrogen for 5 minutes and then sealed. The reaction was heated to 80° C. overnight. The mixture was cooled to room temperature and filtered. The filtrate was diluted with water (5 mL) and extracted with ethyl acetate (5 mL×3). The organic layer was dried (sodium sulfate) and concentrated. The resulting residue was purified through prep. TLC (petroleum ether: ethyl acetate, 2:1) to give the title compound (52.5 mg, 35.7%) as an off-white solid. $^1$H NMR (400 MHz, CDCl3) ppm: 8.62 (br. s), 8.05 (s, 1H), 7.89 (d, 1H), 7.50 (s, 1H), 7.35 (d, 1H), 6.00 (d, 1H), 4.61 (m, 1H), 3.89 (s, 3H), 3.87 (s, 3H), 3.73-3.57 (m, 4H), 2.24-2.05 (m, 2H).

Step 3

6-chloro-5-[6-(3-hydroxypyrrolidin-1-yl)-2-methoxypyridin-3-yl]-1H-indole-3-carboxylic acid A vial was charged with methyl 6-chloro-5-[6-(3-hydroxypyrrolidin-1-yl)-2-methoxypyridin-3-yl]-1H-indole-3-carboxylate (52.5 mg, 0.130 mmol), NaOH aqueous (2 mL, 2M) and methanol (2 mL). The mixture was heated at 80° C. for 3 hrs. The mixture was cooled to room temperature and neutralized with conc. HCl aqueous to pH=6. The mixture was evaporated to dryness, and the resulting residue was purified through prep. HPLC to give the title compound (18.9 mg, 37.3%) as off-white solid.

MS (ES+) 388.1 (M+H)$^+$. $^1$H NMR (400 MHz, methanol-d$_4$) ppm: 7.96 (s, 1H), 7.92 (s, 1H), 7.51 (s, 1H), 7.29 (d, 1H), 6.02 (d, 1H), 4.60-4.50 (m, 1H), 3.83 (s, 3H), 3.68-3.58 (m, 3H), 3.56-3.50 (m, 1H), 2.18 (m, 1H), 2.04 (m, 1H).

292

Example 162

6-chloro-5-[4-(propan-2-yl)phenyl]-1H-indole-3-carboxylic acid

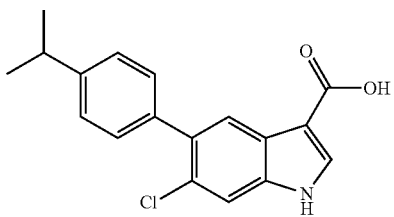 [SMILES: CC(C)c1ccc(-c2cc3c(C(=O)O)c[nH]c3cc2Cl)cc1]

Step 1

6-chloro-5-[4-(propan-2-yl)phenyl]-1H-indole-3-carbaldehyde

A vial was charged with 1 mL of a 0.1M solution of 5-bromo-6-chloro-1H-indole-3-carbaldehyde (100 uM) in dioxane, 150 umol of (4-isopropylphenyl)boronic acid solution in dioxane, 200 uL of a 1.0M cesium carbonate solution in water, and 1,1'-bis(di-tert-butylphosphino) ferrocene palladium dichloride), (2 umol, 0.02 eq). The vial was purged with nitrogen, sealed and heat to 100° C. for 16 h. The solvent was evaporated and the vial diluted with ethyl acetate. The organic layer was collected, washed with brine, dried over magnesium sulfate, filtered, and concentrated in vacuo to give the title compound.

Step 2

6-chloro-5-[4-(propan-2-yl)phenyl]-1H-indole-3-carboxylic acid

A vial was charged with 6-chloro-5-[4-(propan-2-yl)phenyl]-1H-indole-3-carbaldehyde, 1 mL acetonitrile, and 500 uL of a 1.0M solution of potassium permanganate in water. The vial was sealed and heated to 30° C. for 16 hrs. Sodium bisulfite (72 mg, 1.0 mmol) was then added and the reaction heated to 30° C. for 1 hr. The reaction was then filtered, and the solvent removed in vacuo. The residue was then purified by reverse phase prep HPLC to give the title compound. MS(AP−) 312 (M−H)$^−$. RT=2.378 Column Xbridge C18 2.1× 50 mm 5 μm, Temperature 50° C. Mobile Phase A=0.05% NH4OH in water. Mobile Phase B=100% acetonitrile. Gradient: Initial 5% B Time 0.00 mins, 5% B Time 0.50 mins, 5% B Time 3.40 mins, 100% B Time 4.20 mins, 100% B Time 4.21 mins, 5% B Time 4.70 mins, 5% B Flow rate, 0.8 mL/min Injection volume 2 μL. Agilent 1200 HPLC/1956 MSD/SEDEX 75 ELSD Ionization Mode API-ES Polarity Negative.

Example 163

6-chloro-5-[3-fluoro-4-(1-hydroxy-2-methylpropan-2-yl)phenyl]-1H-indole-3-carboxylic acid

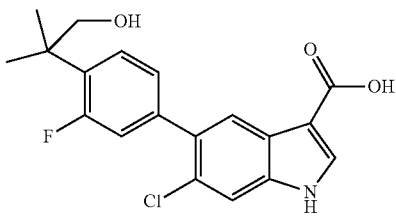 [SMILES: CC(C)(CO)c1ccc(-c2cc3c(C(=O)O)c[nH]c3cc2Cl)cc1F]

This was prepared in a manner similar to Example 142 but substituting methyl iodide instead of 1,3-dibromopropane.
MS (ES−): 360.2 (M−H)⁻ ¹H NMR (400 MHz, DMSO-$d_6$) ppm 12.15 (br. s., 1 H) 11.98 (br. s., 1 H) 8.10 (d, 1 H) 7.96 (s, 1H) 7.65 (s, 1H) 7.44 (t, 1H) 7.12-7.24 (m, 2H) 4.79 (t, 1H) 3.61 (d, 2H) 1.34 (s, 6H).

Example 164

6-chloro-5-{2-fluoro-4-[1-(hydroxymethyl)cyclobutyl]phenyl}-1H-indole-3-carboxylic acid

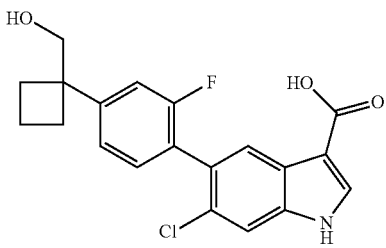

Step 1

(1-(4-bromo-3-fluorophenyl)cyclobutyl)methanol

This was prepared in a manner similar to Example 137, steps 2-5 but starting from (4-bromo-3-fluorophenyl)acetonitrile to prepare the title compound.

Step 2

6-chloro-5-{2-fluoro-4-[1-(hydroxymethyl)cyclobutyl]phenyl}-1H-indole-3-carboxylic acid This was prepared in a manner similar to Example 137, steps 6-7, but starting from (1-(4-bromo-3-fluorophenyl)cyclobutyl)methanol to prepare the title compound (49 mg). MS (ES−): 372.4 (M−H)− ¹H NMR (500 MHz, DMSO-$d_6$) ppm 12.13 (s, 1 H), 11.98 (d, 1 H), 8.09 (s, 1 H), 7.91 (s, 1 H), 7.64 (s, 1 H), 7.29 (d, 1 H), 7.03 (dd, 1 H), 6.99 (dd, 1 H), 4.83 (t, 1 H), 3.57 (d, 2 H), 2.13-2.33 (m, 4 H), 1.90-2.10 (m, 1 H), 1.57-1.90 (m, 1 H).

Example 165

6-fluoro-5-{2-fluoro-4-[1-(hydroxymethyl)cyclobutyl]phenyl}-1H-indole-3-carboxylic acid

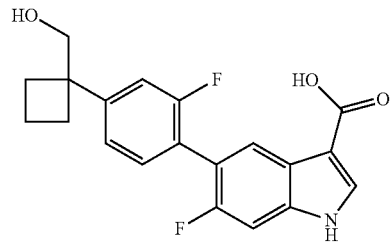 [SMILES: O=C(O)c1c[nH]c2cc(F)c(-c3ccc(C4(CO)CCC4)cc3F)cc12]

This was prepared in a manner similar to Example 143 using (1-(4-bromo-3-fluorophenyl)cyclobutyl)methanol obtained from Example 164, step 1 to provide the title compound (61 mg). MS (ES−): 356.4 (M−H)⁻ ¹H NMR (500 MHz, DMSO-$d_6$) ppm 12.08 (s, 1 H), 11.93 (d, 1 H), 8.04 (d, 1 H), 7.94 (d, 1 H), 7.38 (t, 1 H), 7.35 (s, 1 H), 7.05 (dd, 1 H), 7.00 (dd, 1H), 4.82 (t, 1 H), 3.57 (d, 2 H), 2.16-2.29 (m, 4 H), 1.94-2.05 (m, 1 H), 1.74-1.85 (m, 1 H).

Example 166

4,6-difluoro-5-[4-(tetrahydro-2H-pyran-4-yl)phenyl]-1H-indole-3-carboxylic acid

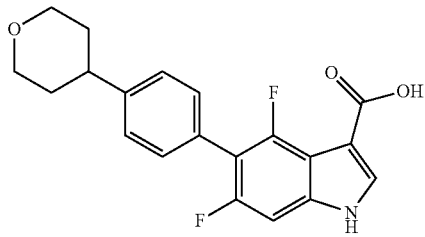 [SMILES: O=C(O)c1c[nH]c2cc(F)c(-c3ccc(C4CCOCC4)cc3)c(F)c12]

This was prepared in a manner similarly described in Example 6, Steps 5-6 with 4-(4-bromophenyl)tetrahydro-2H-pyran and 5-bromo-4,6-difluoro-1H-indole-3-carbaldehyde to give the title compound (5.9 mg). MS (ES+): 358.1 (M+H)⁺. retention time=2.73 min; Column: Waters Atlantis dC18 4.6×50 mm, 5 m; Modifier: TFA 0.05%; Gradient: 95% H₂O/5% MeCN linear to 5% H₂O/95% MeCN over 4.0 min, HOLD at 5% H₂O/95% MeCN to 5.0 min; Flow: 2.0 mL/min.

Example 167

4,6-difluoro-5-{4-[1-(hydroxymethyl)cyclobutyl]phenyl)-1H-indole-3-carboxylic acid

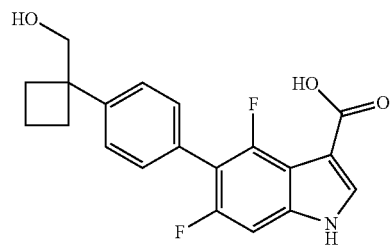 [SMILES: O=C(O)c1c[nH]c2cc(F)c(-c3ccc(C4(CO)CCC4)cc3)c(F)c12]

Step 1

{1-[4-(4,4,5,5-tetramethyl-1,3,2-dioxaborolan-2-yl)phenyl]cyclobutyl}methanol

To a mixture of [1-(4-bromophenyl)cyclobutyl]methanol (241 mg, 1.00 mmol) in dioxane (5 mL) and aq.potassium carbonate (1.5 mL, 2.0 M) was added 5,5,5',5'-tetramethyl-2,2'-bi(1,3,2-dioxaborinane) (381 mg, 1.50 mmol), PdCl2dppf (73.1 mg, 0.100 mmol). The reaction mixture was purged with nitrogen for 3 minutes and stirred at 80° C. for 4 hours. TLC (petroleum ether/ethyl acetate=1:1) showed the reaction was complete. The mixture was extracted with ethyl acetate (20 mL×3). The organic phases were combined, dried over sodium sulfate, filtered, and concentrated in vacuo to give a residue, which was purified by silica gel chromatography to give the title compound (106 mg, 36%) as a pale solid. $^1$H NMR (400 MHz, CD3OD) δ ppm 7.79 (d, 2 H) 7.16 (d, 2 H) 3.75 (s, 2H) 2.33 (m, 2H) 2.25 (m, 2H) 2.07 (m, 1H) 1.89 (m, 1H) 1.34 (s, 12H)

Step 2

4,6-difluoro-5-{4-[1-(hydroxymethyl)cyclobutyl]phenyl}-1H-indole-3-carbaldehyde

To a mixture of {1-[4-(4,4,5,5-tetramethyl-1,3,2-dioxaborolan-2-yl)phenyl]cyclobutyl}methanol (106 mg, 0.37 mmol) in toluene/ethanol 3:1 (3 mL) and aq.potassium carbonate (0.55 mL, 2.0 M) was added 5-bromo-4,6-difluoro-1H-indole-3-carbaldehyde (96 mg, 0.37 mmol), PdCl2dppf (27 mg, 0.037 mmol). The reaction mixture was purged with nitrogen for 3 minutes and stirred at 130 degree centigrade under microwave irradiation for 30 minutes. TLC (petroleum ether/ethyl acetate=1:1) showed the reaction was complete. The mixture was extracted with ethyl acetate (20 mL×3). The organic phases were combined, dried over sodium sulfate, filtered, and concentrated in vacuo to give a residue, which was purified by combi flash to give compound 15 (34 mg, 27%) as a white solid. $^1$H NMR (400 MHz, CD3OD) δ ppm 10.03 (s, 1 H) 8.14 (s, 1 H) 7.41 (d, 2 H) 7.28 (d, 2 H) 7.19 (d, 1 H) 3.75 (s, 2H) 2.37 (m, 4H) 2.11 (m, 1H) 1.91 (m, 1H)

Step 3

4,6-difluoro-5-{4-[1-(hydroxymethyl)cyclobutyl]phenyl}-1H-indole-3-carboxylic acid To a solution of 4,6-difluoro-5-{4-[1-(hydroxymethyl)cyclobutyl]phenyl}-1H-indole-3-carbaldehyde (34 mg, 0.10 mmol) in acetonitrile (5 mL) and tert butanol (5 mL) was added 2-methyl-2-butene (700 g, 10.0 mmol). The mixture was cooled to 0° C. with ice bath. The sodium chlorite (273 mg, 3.00 mmol) and sodium dihydrogenphosphate (360 mg, 3.00 mmol) were dissolved in water (5 mL). The aqueous was added to the organic solution and the mixture was allowed to warm to room temperature. The reaction mixture was stirred at room temperature for 48 hours. TLC (petroleum ether/ethyl acetate=1:1) showed the reaction was complete. A solution of sodium sulfite was added slowly to the stirring mixture. The reaction mixture was allowed to stir 1 hour. Then the organics were removed under reduced pressure. The aqueous layer was extracted with ethyl acetate (20 mL×3). The combined organic layers were dried over sodium sulfate, filtered, and concentrated in vacuo to give a brown residue. The residue was purified by preparative reverse phase HPLC to give the title compound (15 mg, 42%) as a white solid. MS (ES+) 380.0 (M+Na)+. 1H NMR (400 MHz, CD3OD) δ 8.01 (s, 1H), 7.41 (d, 1H), 7.28 (d, 2H), 7.14 (d, 2H), 3.76 (s, 2H), 2.36 (m, 4H), 2.13 (m, 1H), 1.93 (m, 1H).

Example 168

6-chloro-5-[4-(tetrahydro-2H-pyran-3-yl)phenyl]-1H-indole-3-carboxylic acid

Step 1

5-bromo-3,4-dihydro-2H-pyran

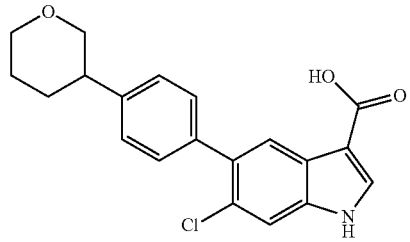 [SMILES: O=C(O)c1c[nH]c2cc(Cl)c(-c3ccc(C4CCCOC4)cc3)cc12]

To a solution of 3,4-dihydro-2H-pyran (20.0 g, 0.238 mol) in dichloromethane (200 mL) was added bromine (37.8 g, 0.238 mol, 12.2 mL) in dichloromethane (100 mL) at −78° C. dropwise. The mixture was stirred at −78° C. for 2 hours, then at room temperature (30° C.) for 15 hours. Triethylamine (48.0 g, 0.476 mol, 66.0 mL) in dichloromethane (100 mL) was added dropwise at room temperature (30° C.) and then stirred for 5 hours. Dichloromethane was removed, and petroleum ether was added, and the solid was removed by filtration. The filtrate was evaporated, and the residue was purified by vacuum distillation (80° C., 0.02 mmHg) to give the title compound (6.2 g, 16%) as colorless oil. $^1$H NMR (400 MHz, CD3OD) δ ppm 6.60 (s, 1 H), 4.00 (t, 2 H), 2.40 (t, 2 H), 2.00 (m, 2 H)

Step 2

5-(4-chlorophenyl)-3,4-dihydro-2H-pyran

A mixture of 5-bromo-3,4-dihydro-2H-pyran (1.0 g, 6.13 mmol), (4-chlorophenyl)boronic acid (1.05 g, 6.74 mmol), potassium carbonate (2.5 g, 18.4 mmol), Pd(dppf)C12 (449 mg, 0.613 mmol), and ethanol/water (2/2 mL) in toluene (10 mL) was stirred at 100° C. for 12 hours. The mixture was filtered, and the filtrate was evaporated and purified by silica gel chromatography to give the title compound (700 mg, 58.8%) as orange solid. $^1$H NMR (400 MHz, CD3OD) δ ppm 7.25 (d, 2 H), 7.20 (d, 2 H) 6.90 (s, 1 H), 4.03 (t, 2 H), 2.37 (t, 2 H), 2.02 (m, 2 H)

Step 3

3-(4-chlorophenyl)tetrahydro-2H-pyran

To a solution of 5-(4-chlorophenyl)-3,4-dihydro-2H-pyran (350 mg, 1.80 mmol) in ethyl acetate (8 mL) was added platinum oxide (41 mg, 0.18 mmol) and the reaction was charged with a hydrogen balloon and stirred at room temperature for 6 hours. The reaction was filtered, and the filtrate was evaporated to give crude title compound (340 mg, 96.3%) as white solid.

Step 4

6-chloro-5-[4-(tetrahydro-2H-pyran-3-yl)phenyl]-1H-indole-3-carboxylic acid

This was prepared in a manner similar to Example 37, Steps 3-4 with 3-(4-chlorophenyl)tetrahydro-2H-pyran to give the title compound. MS (ES−) 354.1 (M−1)−. $^1$H NMR (400 MHz, CD3OD) δ ppm 8.03 (s, 1 H), 8.00 (s, 1 H), 7.59 (s, 1 H), 7.41 (d, 2 H), 7.33 (d, 2 H), 4.00 (d, 2 H), 3.52 (t, 2 H), 2.92 (m, 1 H), 2.2 (m, 1 H), 1.84 (m, 3 H).

Examples 169 and 170

4,6-difluoro-5-[4-(tetrahydro-2H-pyran-2-yl)phenyl]-1H-indole-3-carboxylic acid

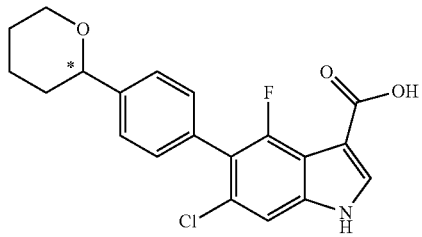 [SMILES: O=C(O)c1c[nH]c2cc(Cl)c(-c3ccc(C4CCCCO4)cc3)c(F)c12]

Step 1

4-bromo-2-(4-bromophenyl)tetrahydro-2H-pyran

To a solution of 4-bromobenzaldehyde (1.00 g, 5.41 mmol) and 3-buten-1-ol (800 mg, 10.8 mmol) in dichloromethane (20 mL) at room temperature was added zinc (II) bromide (25 mg, 0.11 mmol) followed by 33% hydrobromic acid (2.4 g) in acetic acid (4.9 g, 81 mmol) and stirred at room temperature for 5 hours. Reaction was quenched by aqueous sodium bicarbonate, then extracted with ethyl acetate, washed with brine, dried over sodium sulfate, filtered and concentrated. The residue was purified by silica gel chromatography to give the title compound (1.00 g) which contained some of 4-bromobenzaldehyde $^1$H NMR (400 MHz, CDCl3) δ ppm 7.49 (d, 2H) 7.24 (d, 2H) 5.19 (dd, 1H) 4.25 (m, 1H) 4.12 (m, 1H) 3.60 (m, 1H) 2.75 (m, 1H) 2.68 (m, 1H) 2.11 (m, 2H).

Step 2

2-(4-bromophenyl)-3,6-dihydro-2H-pyran

To a solution of 4-bromo-2-(4-bromophenyl)tetrahydro-2H-pyran (320 mg, 1.00 mmol) in toluene (5 mL) was added 1,8-Diazabicyclo[5.4.0]undec-7-ene (304 mg, 2.00 mmol). The mixture was stirred at 100° C. for 16 hours. The mixture was then diluted with ethyl acetate and water. The organic layer was washed with brine, dried over sodium sulfate, filtered and concentrated. The residue was purified by silica gel chromatography to give the title compound (150 mg) which contained some impurity of 4-bromobenzaldehyde. $^1$H NMR (400 MHz, CDCl3) δ ppm 7.48 (d, 2H) 7.30 (d, 2H) 5.92 (m, 1H) 5.82 (m, 1H) 4.52 (dd, 1H) 4.36 (m, 2H) 2.27 (m, 2H).

Step 3

2-(4-bromophenyl)tetrahydrofuran

A solution of 2-(4-bromophenyl)-3,6-dihydro-2H-pyran (140 mg, 0.586 mmol) in toluene/ethanol (10 mL, v/v=1/1) was charged into a hydrogenation Parr bottle followed by tris(triphenylphosphine)rhodium(I) chloride (55 mg, 0.0586 mmol). The mixture was set up for 45 psi of hydrogen at 80° C. overnight. The mixture was filtered through celite and the filtrate was concentrated. The residue was purified by silica gel chromatography to give the title compound (50 mg, 35%) as a colorless oil. $^1$H NMR (400 MHz, CDCl3) δ ppm 7.46 (d, 2H) 7.23 (d, 2H) 4.29 (d, 1H) 4.13 (m, 1H) 3.60 (t, 1H) 1.95 (m, 1H) 1.81 (d, 1H) 1.60 (m, 3H) 1.27 (m, 1H).

Step 4

6-difluoro-5-[4-(tetrahydro-2H-pyran-2-yl)phenyl]-1H-indole-3-carbaldehyde

A mixture of 5,5-dimethyl-2-[4-(tetrahydro-2H-pyran-2-yl)phenyl]-1,3,2-dioxaborinane (444 mg, 1.62 mmol), 5-bromo-4,6-difluoro-1H-indole-3-carbaldehyde (400 mg, 1.54 mmol), potassium carbonate (638 mg, 4.62 mmol) and Pd(dppf)Cl2 (44 mg, 0.06 mmol) in dioxane (4.6 mL) and water (2.3 mL) were stirred at 100° C. for 3 hours. To the reaction was added water (20 mL) and extracted with ethyl acetate (20 mL*3). The combined organic layer was washed with brine (20 mL), dried over sodium sulfate, filtered and concentrated to give a crude residue, which was triturated with (petroleum ether/MTPE=1:1) then filtered to give the title compound (400 mg, 76.2%) as a red solid and taken on without purification.

Step 5

Racemic-4,6-difluoro-5-[4-(tetrahydro-2H-pyran-2-yl)phenyl]-1H-indole-3-carboxylic acid To a solution of 6-difluoro-5-[4-(tetrahydro-2H-pyran-2-yl)phenyl]-1H-indole-3-carbaldehyde (400 mg, 1.17 mmol) in acetonitrile (24 mL), tert-butanol (24 mL) and 2-methyl-2-butene (15.6 mL) was added a solution of sodium chlorite (1.58 g, 23.4 mmol) and sodium dihydrogen phosphate (3.20 g, 23.4 mmol) in water (24 mL) at ice-bath. The reaction mixture was stirred at room temperature for 2 days. A solution of sodium sulfite (4.40 g, 35.1 mmol) in water (10 mL) was added to the mixture and stirred for 30 minutes. The reaction was extracted with ethyl acetate (50 mL×2). The combined organic layer was washed with brine (50 mL), dried over sodium sulfate, filtered and concentrated to give a crude residue, which was purified by reverse phase prep-HPLC to give the title compound (80 mg, 19%) as an off-white solid. MS (ES+) 357.9 (M+H)+. 1H NMR (400 MHz, DMSO-d6) δ ppm 12.15 (br. s, 2H), 8.06 (s, 1H) 7.41 (m, 4H) 7.24 (d, 1H) 4.38 (d, 1H) 4.05 (d, 1H) 3.55 (m, 1H) 1.86 (m, 2H) 1.56 (m, 4H).

Step 6

4,6-difluoro-5-[4-(tetrahydro-2H-pyran-2-yl)phenyl]-1H-indole-3-carboxylic acid Isomer 1

4,6-difluoro-5-[4-(tetrahydro-2H-pyran-2-yl)phenyl]-1H-indole-3-carboxylic acid Isomer 2

Racemic 4,6-difluoro-5-[4-(tetrahydro-2H-pyran-2-yl)phenyl]-1H-indole-3-carboxylic acid was subjected to preparative SFC. (Column: OJ (250 MM*30 MM, 5 UM); Mobile phase: 30% MEOH NH3H2O 60 ML/MIN 3; Wavelength: 220 nm). Peak 1 was isolated as Isomer 1 (Example 169). Retention time=7.491. Column: Chiralcel OJ-H 250× 4.6 mm I.D., 5 um Mobile phase: methanol (0.05% DEA) in CO2 from 5% to 40% Flow rate: 2.35 mL/min Wavelength: 220 nm. MS (ES+) 357.9 (M+H)+. 1H NMR (400 MHz, DMSO-d6) δ 12.15 (br. s, 2H), 8.06 (s, 1 H) 7.41 (m, 4 H) 7.24 (d, 1 H) 4.38 (d, 1 H) 4.05 (d, 1 H) 3.55 (m, 1 H) 1.86 (m, 2 H) 1.56 (m, 4 H) Peak 2 was isolated as Isomer 2 (Example 170). Retention time=8.054. Column: Chiralcel OJ-H 250×4.6 mm I.D., 5 um Mobile phase: methanol (0.05% DEA) in CO2 from 5% to 40% Flow rate: 2.35 mL/min Wavelength: 220 nm. MS (ES+) 379.9 (M+Na)+. 1H NMR (400 MHz, DMSO-d6) δ 12.15 (br. s, 2H), 8.06 (s, 1 H) 7.41 (m, 4 H) 7.24 (d, 1 H) 4.38 (d, 1 H) 4.05 (d, 1 H) 3.56 (m, 1 H) 1.86 (m, 2 H) 1.53 (m, 4 H).

Examples 171 and 172

6-fluoro-5-[4-(tetrahydro-2H-pyran-2-yl)phenyl]-1H-indole-3-carboxylic acid

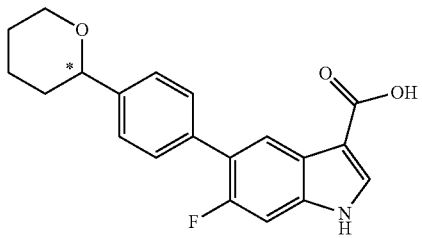 [SMILES: O=C(O)c1c[nH]c2cc(F)c(-c3ccc(C4CCCCO4)cc3)cc12]

Step 1

Rac-6-fluoro-5-[4-(tetrahydro-2H-pyran-2-yl)phenyl]-1H-indole-3-carboxylic acid

This was prepared in a manner similarly described in Example 6, Steps 5-6 with 2-(4-bromophenyl)tetrahydrofuran and 5-bromo-6-fluoro-1H-indole-3-carbaldehyde to give the title compound.

Step 2

6-fluoro-5-[4-(tetrahydro-2H-pyran-2-yl)phenyl]-1H-indole-3-carboxylic acid Isomer 1

6-fluoro-5-[4-(tetrahydro-2H-pyran-2-yl)phenyl]-1H-indole-3-carboxylic acid Isomer 2

Racemic-6-fluoro-5-[4-(tetrahydro-2H-pyran-2-yl)phenyl]-1H-indole-3-carboxylic acid was subjected to separation by preparative SFC (Column: OJ (250 MM*30 MM, 5 UM); Mobile phase: 35% MEOH NH3H2O 55 ML/MIN 2; Wavelength: 220 nm) Peak 1 was isolated as Isomer 1 (Example 171), Retention Time: 9.44 min; Column: Chiralcel OJ-H 250×4.6 mm I.D., 5 um; Mobile phase: methanol (0.05% DEA) in CO2 from 5% to 40%; Flow rate: 2.5 mL/min Wavelength: 220 nm. MS (ES+) 340.0 (M+Na)+. 1H NMR (400 MHz, DMSO-d6) δ ppm 8.04 (s, 1H) 8.03 (d, 1H) 7.50 (m, 2H) 7.43 (m, 2H) 7.37 (d, 1H) 4.38 (d, 1H) 4.05 (d, 1H) 3.57 (m, 1H) 1.87 (m, 2H) 1.55 (m, 4H).

Peak 2 was isolated as Isomer 2 (Example 172), Retention Time: 9.66 min; Column: Chiralcel OJ-H 250×4.6 mm I.D., 5 um; Mobile phase: methanol (0.05% DEA) in CO2 from 5% to 40%; Flow rate: 2.5 mL/min Wavelength: 220 nm. MS (ES+) 340.0 (M+Na)+. 1H NMR (400 MHz, DMSO-d6) δ ppm 8.04 (s, 1H) 8.03 (d, 1H) 7.50 (m, 2H) 7.43 (m, 2H) 7.37 (d, 1H) 4.38 (d, 1H) 4.05 (d, 1H) 3.57 (m, 1H) 1.87 (m, 2H) 1.55 (m, 4H).

Example 173

6-chloro-5-[6-(dimethylamino)-2-methoxypyridin-3-yl]-1H-indole-3-carboxylic acid

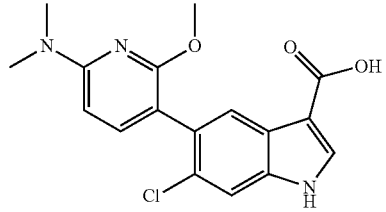 [SMILES: COc1nc(N(C)C)ccc1-c1cc2c(C(=O)O)c[nH]c2cc1Cl]

Step 1

5-bromo-6-methoxy-N, N-dimethylpyridin-2-amine

This was prepared in a manner similar to Example 161, step 1 with dimethylamine to give the title compound.

Step 2

6-chloro-5-[6-(dimethylamino)-2-methoxypyridin-3-yl]-1H-indole-3-carboxylic acid This was prepared in a manner similar to Example 161, steps 2-3 with 5-bromo-6-methoxy-N,N-dimethylpyridin-2-amine to give the title compound. MS (ES+) 346.1 (M+H)+. 1H NMR (400 MHz, CD3OD) δ 7.94 (d, 1H), 7.92 (s, 1H), 7.49 (s, 1H), 7.30 (d, 1H), 6.18 (d, 1H), 3.18 (s, 3 H), 3.11 (s, 6H).

Alternative Preparation of Example 173

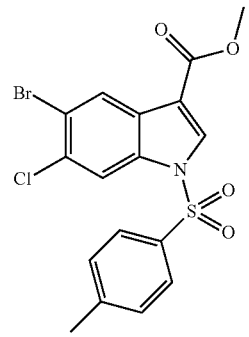 [SMILES: COC(=O)c1cn(S(=O)(=O)c2ccc(C)cc2)c2cc(Cl)c(Br)cc12]

5-bromo-6-chloro-1-(toluene-4-sulfonyl)-1H-indole-3-carboxylic acid methyl ester To a solution of 5-bromo-6-chloro-1H-indole-3-carboxylic acid methyl ester (80.0 g, 277 mmol) in N,N-dimethylformamide (600 mL) at 0° C. was added sodium hydride (60% dispersion in oil, 16.6 g, 416 mmol) portion-wise over 20 minutes. The reaction was stirred at 0° C. for 60 minutes followed by the addition of 4-methylbenzenesulphonyl chloride (63.4 g, 333 mmol), which was added portion-wise to the stirring solution. The reaction was allowed to stir for 2 hours at 0° C. and the ice bath was removed and the reaction was allowed to warm to room temperature and stirred overnight. The reaction was poured into water (1200 mL) and stirred for 12 hours. The suspension was filtered and the filter cake was washed with a further portion of water (700 mL) then heptane (2×300 mL), 160 g of crude material was recovered. The material was placed in a 3 L round bottom flask and placed on rotorary evaporated with a 40° C. bath under vacuum overnight to remove residual water. This afforded 116 g of pink solid which was suspended in acetone (600 mL) and heated to reflux for 1 hour, then removed from the heat, cooled to room temperature, and stirred for a further hour. The suspension was filtered and the filter cake was washed with acetone (~500 mL) until the filtrate was colorless. The filter cake was dried to afford desired product (108.7 g, 89% yield). $^1$H NMR (CDCl$_3$, 400 MHz) 5=8.39 (s, 1 H) 8.24 (s, 1 H) 8.11 (s, 1 H) 7.82 (d, J=8.59 Hz, 2 H) 7.32 (d, J=8.20 Hz, 2 H) 3.93 (s, 3 H) 2.40 (s, 3 H); MS (ES+) 441.9 (M+H)$^+$.

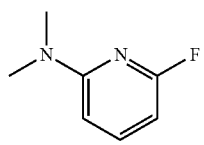

(6-fluoro-pyridin-2-yl)-dimethyl-amine

Dimethylamine hydrochloride (19.0 g, 91.2 mmol) was added to a suspension of 2,6-difluoropyridine (10.0 g, 86.9 mmol) and potassium carbonate (24.4 g, 177 mmol) in acetonitrile (100 mL). The suspension was stirred at reflux for 2 h before cooling to room temperature and filtering through a pad of celite, washing the filter cake with acetonitrile (500 mL). The filtrate was concentrated in vacuo to product desired product (11.3 g, 93% yield) as an orange oil. $^1$H NMR (CDCl$_3$, 600 MHz) 5=7.33-7.66 (m, 1 H) 6.28 (dd, J=8.22, 2.35 Hz, 1 H) 6.09 (dd, J=7.63, 2.35 Hz, 1 H) 3.07 (s, 6 H); MS (FID)=140.0 (M)$^+$.

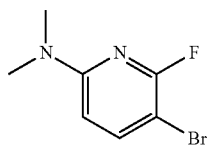

(5-bromo-6-fluoro-pyridin-2-yl)-dimethyl-amine

To a solution of Intermediate (6-fluoro-pyridin-2-yl)-dimethyl-amine (12.4 g, 88.4 mmol) in acetonitrile (400 mL) at 0° C. was added a solution of N-bromosuccinimide (7.87 g, 44.2 mmol) in acetonitrile (95 mL) dropwise over 15 min. The resulting solution was stirred at 0° C. for 1 hour. Another portion of N-bromosuccinimide (7.87 g, 44.2 mmol) in acetonitrile (95 mL) was subsequently added at 0° C. dropwise over 15 min. The solution was slowly warmed to room temperature and stirred overnight. The solution was concentrated in vacuo and diluted with dichloromethane (500 mL). This was washed with water (300 mL) and the aqueous layer back extracted with dichloromethane (3×200 mL), before drying over MgSO$_4$, filtering, and concentrating in vacuo. The material was passed through a silica pad, eluting with 0-10% ethyl acetate in heptanes. The organics were concentrated in vacuo to afford desired material (18.4 g, 95% yield) that solidified upon standing. $^1$H NMR (CDCl$_3$, 400 MHz) 5=7.48-7.67 (m, 1 H) 6.21 (dd, J=8.59, 1.56 Hz, 1 H) 3.05 (s, 6 H); MS (FID)=218.0 (M)$^+$.

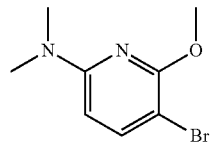

(5-bromo-6-methoxy-pyridin-2-yl)-dimethyl-amine

To a solution of potassium methoxide (25% in methanol, 74.2 mL, 251 mmol) was added Intermediate (5-bromo-6-fluoro-pyridin-2-yl)-dimethyl-amine (18.36 g, 83.8 mmol). The reaction was stirred at reflux for 3 h before cooling to room temperature. The contents were poured into a solution of saturated ammonium chloride (500 mL) and this was extracted with ethyl acetate (3×300 mL). The combined organics were washed with brine (250 mL), dried over MgSO$_4$, filtered, and concentrated in vacuo to afford desired product as an oil that solidified upon standing to give an off white/yellow solid (18.3 g, 95% yield). $^1$H NMR (CDCl$_3$, 400 MHz) 5=7.49 (d, J=8.59 Hz, 1 H) 5.95 (d, J=8.59 Hz, 1 H) 3.96 (s, 3 H) 3.05 (s, 6 H); MS (FID)=230.1 (M)$^+$.

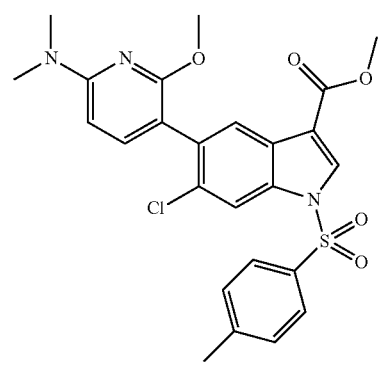

6-chloro-5-(6-dimethylamino-2-methoxy-pyridin-3-yl)-1-(toluene-4-sulfonyl)-1H-indole-3-carboxylic acid methyl ester To a solution of Intermediate (5-bromo-6-methoxy-pyridin-2-yl)dimethyl-amine (78.8 g, 341 mmol) in THF (400 mL) at −70° C. was added a solution of n-butyllithium (2.5 M in hexanes, 127 mL, 317 mmol) dropwise, keeping the internal temperature below −60° C. The purple solution was stirred between −65° C. and −70° C. for 20 min. A solution of ZnCl$_2$ in 2-methyltetrahydrofuran (1.9 M, 167 mL, 317 mmol) was added dropwise to the aryl lithium solution, keeping the internal temperature below −60° C. The resulting mixture was stirred between −65° C. and −70° C. for 20 min and then warmed to room temperature and stirred for 2 h, resulting in a clear pale yellow solution. The aryl zinc solution was then cannulated into a flask containing Intermediate 5-bromo-6-chloro-1-(toluene-4-sulfonyl)-1H-indole-3-carboxylic acid methyl ester (107.8 g, 244 mmol) and dichloro[bis(2-(diphenylphosphino)phenyl)ether]palladium(II) (8.72 g, 12.2 mmol) in THF (200 mL). The resulting mixture was stirred at room temperature for 2.5 h before quenching with sat. aq. NH₄Cl (800 mL) and extracting with ethyl acetate (1500 mL). The aqueous layer was back extracted with ethyl acetate (750 mL) and the combined organics washed with brine (1000 mL), dried over MgSO₄, filtered, and concentrated in vacuo. The residue was triturated with methanol (~600 mL) and stirred overnight. The suspension was filtered to give a tan solid. This was dissolved in hot acetone (2 L) which was partially concentrated to ~500 mL, then slowly cooled and stirred overnight. The resulting solid was filtered to yield one crop of desired product (109.1 g). The filtrate was also concentrated to a dark solid which was slurried in acetone, filtered, and the solid dissolved in hot acetone, which was then cooled to yield a second crop (3.3 g) of desired product as an off white solid. (90% total yield). ¹H NMR (DMSO-d₆, 400 MHz) δ=8.51 (s, 1H), 8.11 (d, J=8.6 Hz, 2H), 8.00 (s, 1H), 7.88 (s, 1H), 7.49 (d, J=8.2 Hz, 2H), 7.31 (d, J=8.2 Hz, 1H), 6.22 (d, J=8.2 Hz, 1H), 3.84 (s, 3H), 3.74 (s, 3H), 3.06 (s, 6H), 2.37 (s, 3H); MS (ES+) 514.2 (M+H)⁺.

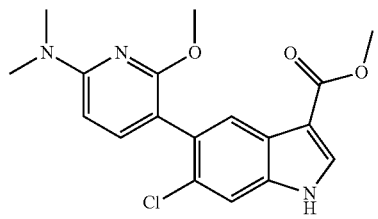

6-chloro-5-(6-dimethylamino-2-methoxy-pyridin-3-yl)-1H-indole-3-carboxylic acid methyl ester To a solution of Intermediate 6-chloro-5-(6-dimethylamino-2-methoxy-pyridin-3-yl)-1-(toluene-4-sulfonyl)-1H-indole-3-carboxylic acid methyl ester (109 g, 212 mmol) in THF (1000 mL) at room temperature was added tetrabutylammonium fluoride (1.0 M in THF, 400 mL, 400 mmol). The reaction was stirred at reflux for 3 h before cooling to room temperature and diluting with ethyl acetate (2000 mL). This was washed with sat. aq. NaHCO₃ (2×750 mL), sat. aq. NH₄Cl (2×750 mL), water (750 mL), and brine (750 mL), and then dried over MgSO₄, filtered, and concentrated in vacuo. The residue was triturated with methanol (~500 mL) and filtered. The solids were washed with methanol (300 mL) and suction dried overnight to afford desired product (71.8 g, 94%) as a white solid. ¹H NMR (DMSO-d₆, 400 MHz) δ=11.99 (s, 1 H) 8.13 (s, 1 H) 7.82 (s, 1 H) 7.57 (s, 1 H) 7.32 (d, J=8.20 Hz, 1 H) 6.22 (d, J=8.20 Hz, 1 H) 3.78 (s, 3 H) 3.76 (s, 3 H) 3.07 (s, 6 H); MS (ES+) 360.1 (M+H)⁺.

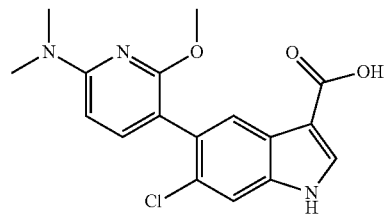 [SMILES: COc1nc(N(C)C)ccc1-c1cc2c(C(=O)O)c[nH]c2cc1Cl]

6-chloro-5-[6-(dimethylamino)-2-methoxypyridin-3-yl]-1H-indole-3-carboxylic acid To a solution of Intermediate 6-chloro-5-(6-dimethylamino-2-methoxy-pyridin-3-yl)-1H-indole-3-carboxylic acid methyl ester (45.0 g, 130 mmol) in 1:1 tetrahydrofuran:methanol (1250 mL) at 50° C. was added 2 N NaOH (1250 mL). After 60 h, the reaction was cooled to <5° C. and with stirring, 6 N HCl (417 mL) was added dropwise until pH 6-7. The solution was divided in half and each was diluted with ethyl acetate (1.5 L) and the layers separated. The aqueous layers were back extracted with ethyl acetate (2×600 mL). All organics were combined and washed with sat. aq. NH₄Cl (1 L) and brine (1 L), and dried over MgSO₄, filtered and concentrated in vacuo to give crude material. Several batches of crude material were combined (117 g) and acetone (3.5 L) was added. This was refluxed to dissolve all solids and then partially concentrated to ~1.5 L and slowly cooled to lead to solids crashing out. These solids were suspended in heptanes (~500 mL) and stirred at 80° C. for 48 h. Solids were collected by filtration and suction dried for 15 h to afford desired product (80.0 g) as a solid. ¹H NMR (DMSO-d₆, 400 MHz) δ=12.03 (br. s., 1 H) 11.86 (br. s., 1 H) 8.04 (d, J=2.73 Hz, 1 H) 7.83 (s, 1 H) 7.55 (s, 1 H) 7.32 (d, J=8.20 Hz, 1 H) 6.21 (d, J=8.20 Hz, 1 H) 3.76 (s, 3 H) 3.07 (s, 6 H); MS (ES+) 346.1 (M+H)⁺.

Example 174

6-chloro-5-[2-methoxy-6-(morpholin-4-yl)pyridin-3-yl]-1H-indole-3-carboxylic acid

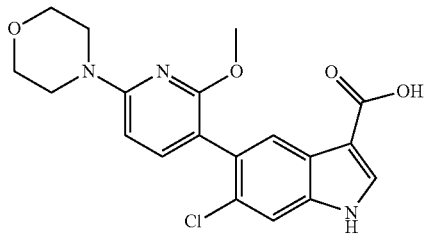 [SMILES: COc1nc(N2CCOCC2)ccc1-c1cc2c(C(=O)O)c[nH]c2cc1Cl]

Step 1

4-(5-bromo-6-methoxypyridin-2-yl)morpholine

This was prepared in a manner similar to Example 161, step 1 with morpholine to give the title compound.

Step 2

6-chloro-5-[2-methoxy-6-(morpholin-4-yl)pyridin-3-yl]-1H-indole-3-carboxylic acid This was prepared in a manner similar to Example 161, steps 2-3 with 4-(5-bromo-6-methoxypyridin-2-yl)morpholine to give the title compound. MS (ES+) 388.1 (M+H)+. 1H NMR (400 MHz, DMSO-d6) δ 11.93 (s, 1H), 8.05 (d, 1H), 7.84 (s, 1H), 7.57 (s, 1H), 7.39 (d, 1H), 6.41 (d, 1H), 3.75 (s, 3H), 3.74 (m, 4H), 3.48 (m, 4H).

Example 175

6-chloro-5-{2-methoxy-6-[(3R)-3-methoxypyrrolidin-1-yl]pyridin-3-yl}-1H-indole-3-carboxylic acid

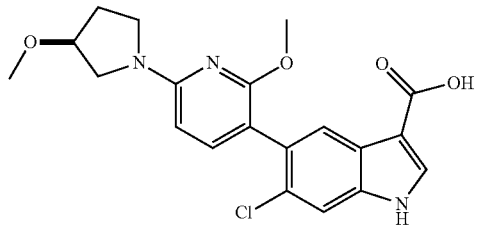 [SMILES: COc1nc(N2CC[C@H](OC)C2)ccc1-c1cc2c(C(=O)O)c[nH]c2cc1Cl]

Step 1

3-bromo-2-methoxy-6-[(3R)-3-methoxypyrrolidin-1-yl]pyridine

This was prepared in a manner similar to Example 161, step 1 with (S)-3-methoxypyrrolidine to give the title compound.

Step 2

6-chloro-5-{2-methoxy-6-[(3R)-3-methoxypyrrolidin-1-yl]pyridin-3-yl}-1H-indole-3-carboxylic acid This was prepared in a manner similar to Example 161, steps 2-3 with 3-bromo-2-methoxy-6-[(3R)-3-methoxypyrrolidin-1-yl]pyridine to give the title compound. MS (ES+) 401.8 (M+H)+. 1H NMR (400 MHz, DMSO-d6) δ 11.90 (br. s, 1H), 8.03 (s, 1 H), 7.83 (s, 1 H), 7.55 (s, 1 H), 7.30 (d, 1 H), 6.04 (d, 1 H), 4.08 (m, 1 H), 3.75 (s, 3H), 3.53 (m, 2H), 3.41 (m, 2H), 3.28 (s, 3H), 2.08 (m, 2H).

Example 176

6-chloro-5-{2-methoxy-6-[(3S)-3-methoxypyrrolidin-1-yl]pyridin-3-yl}-1H-indole-3-carboxylic acid

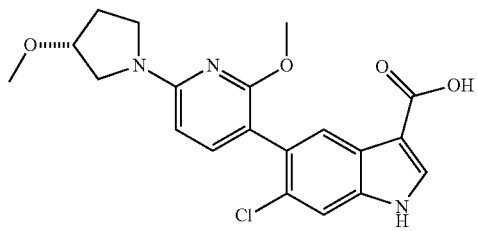 [SMILES: COc1nc(N2CC[C@@H](OC)C2)ccc1-c1cc2c(C(=O)O)c[nH]c2cc1Cl]

Step 1

3-bromo-2-methoxy-6-[(3S)-3-methoxypyrrolidin-1-yl]pyridine

This was prepared in a manner similar to Example 161, steps 1 with (R)-3-methoxypyrrolidine to give the title compound.

Step 2

6-chloro-5-{2-methoxy-6-[(3S)-3-methoxypyrrolidin-1-yl]pyridin-3-yl}-1H-indole-3-carboxylic acid This was prepared in a manner similar to Example 161, steps 2-3 with 3-bromo-2-methoxy-6-[(3S)-3-methoxypyrrolidin-1-yl]pyridine to give the title compound. MS (ES+) 401.8 (M+H)+. 1H NMR (400 MHz, DMSO-d6) δ 11.88 (s, 1H), 8.03 (s, 1 H), 7.83 (s, 1 H), 7.55 (s, 1 H), 7.30 (d, 1 H), 6.04 (d, 1 H), 4.09 (m, 1 H), 3.75 (s, 3H), 3.53 (m, 2H), 3.41 (m, 2H), 3.28 (s, 3H), 2.07 (m, 2H).

Example 177

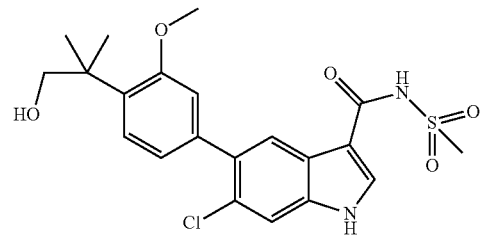 [SMILES: COc1cc(-c2cc3c(C(=O)NS(C)(=O)=O)c[nH]c3cc2Cl)ccc1C(C)(C)CO]

6-chloro-5-[4-(1-hydroxy-2-methylpropan-2-yl)-3-methoxyphenyl]-N-(methylsulfonyl)-1H-indole-3-carboxamide Step 1

5-bromo-6-chloro-N-(methylsulfonyl)-1H-indole-3-carboxamide

To a mixture of 5-bromo-6-chloro-1H-indole-3-carbaldehyde (445 mg, 1.72 mmol), Bis(tert-butylcarbonyloxy)iodobenzene (961 mg, 2.30 mmol) in isopropyl acetate (2 mL) was added methanesulfonamide (111 mg, 1.15 mmol). After stirring 5 minutes, Bis[rhodium(α,α,α',α'-tetramethyl-1,3-benzenedipropionic acid)] (18.3 mg, 0.0230 mmol) was added and heated to 50° C. for 2 h. The reaction was filtered and the collected solid (245 mg) was identified as a mixture of the title compound and 5-bromo-6-chloro-1H-indole-3-carbaldehyde. The mixture was taken forward without any further purification.

Step 2

A round bottomed flask was charged with a 1:1 mixture of 5-bromo-6-chloro-1H-indole-3-carbaldehyde and 5-bromo-6-chloro-N-(methylsulfonyl)-1H-indole-3-carboxamide (96 mg, 0.27 mmol) as prepared in step 1, 2-[4-(5,5-dimethyl-1,3,2-dioxaborinan-2-yl)-2-methoxyphenyl]-2-methylpropan-1-ol (40 mg, 0.14 mmol) (prepared from 2-(4-Bromo-2-methoxyphenyl)-2-methylpropan-1-ol in a manner similar to Example 8, Step 4), potassium carbonate solution (2.0M, 0.27 mL), toluene (0.75 mL), ethanol (0.28 mL), and THF (0.28 mL) then degassed with nitrogen for 5 minutes. PddppfCl2 was then added and the reaction heated to 110° C. for 3 hours. The reaction was then cooled to rt, diluted with water and ethyl acetate. The layers were separated and the aqueous extracted with ethyl acetate×3. The combined organic layers were dried over sodium sulfate, filtered, and concentrated in vacuo. The crude residue was then dissolved in DMSO and purified by reverse phase HPLC to provide the title compound as an ammonium salt (8.0 mg). MS (ES−): 449.1 (M−H)− HPLC retention time: 1.86 min, Waters XBridge C18, 5 μm, 4.6×50 mm, 0.03% NH$_4$OH, 5-95% acetonitrile in water gradient over 4.0 min, hold at 95% acetonitrile in water to 5.0 min, flow 2.0 mL/min.

Examples 178 and 179

6-chloro-5-{4-[(2R)-tetrahydro-2H-pyran-2-yl]phenyl}-1H-indole-3-carboxylic acid

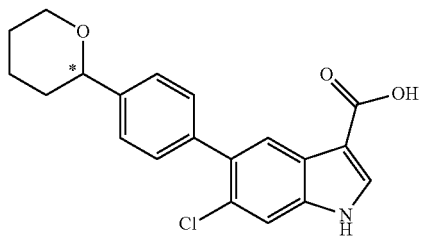 [SMILES: O=C(O)c1c[nH]c2cc(Cl)c(-c3ccc(C4CCCCO4)cc3)cc12]

6-chloro-5-[4-(tetrahydro-2H-pyran-2-yl)phenyl]-1H-indole-3-carboxylic acid

Step 1

Racemic-methyl 6-chloro-5-[4-(tetrahydro-2H-pyran-2-yl)phenyl]-1H-indole-3-carboxylate This was prepared by the method of Example 37, Steps 3, using 2-(4-bromophenyl)tetrahydro-2H-pyran $^1$H NMR (400 MHz, CDCl$_3$) δ ppm 8.01 (s, 1H), 7.98 (s, 1H), 7.58 (s, 1H) 7.41 (s, 4H) 4.40 (d, 1 H), 4.12 (d, 1 H), 3.86 (s, 3 H) 3.68 (t, 1 H), 1.92 (m, 2H) 1.71 (m, 4H)

Step 2

Methyl 6-chloro-5-[4-(tetrahydro-2H-pyran-2-yl)phenyl]-1H-indole-3-carboxylate

Racemic methyl 6-chloro-5-[4-(tetrahydro-2H-pyran-2-yl)phenyl]-1H-indole-3-carboxylate was subjected to preparative chiral SFC. Column: Chiralpak AD-H 250×4.6 mm I.D., 5 um Mobile phase: methanol (0.05% DEA) in CO2 from 5% to 40% Flow rate: 2.35 mL/min Wavelength: 220 nm. Peak 1 was isolated as Isomer 1. Retention time=8.928 minutes; Column: Chiralpak AD-H 250×4.6 mm I.D., 5 um Mobile phase: methanol (0.05% DEA) in CO2 from 5% to 40% Flow rate: 2.35 mL/min Wavelength: 220 nm, $^1$H NMR (400 MHz, CDCl$_3$) δ ppm 8.11 (s, 1H), 7.95 (d, 1H), 7.54 (s, 1H) 7.47 (d, 2H) 7.43 (d, 2H) 4.40 (d, 1 H), 4.18 (d, 1 H), 3.90 (s, 3 H) 3.66 (t, 1 H), 1.92 (m, 2H) 1.71 (m, 4H). Peak 2 was isolated as Isomer 2. Retention time=9.311 minutes; Column: Chiralpak AD-H 250×4.6 mm I.D., 5 um Mobile phase: methanol (0.05% DEA) in CO2 from 5% to 40% Flow rate: 2.35 mL/min Wavelength: 220 nm
$^1$H NMR (400 MHz, CDCl$_3$)) δ ppm 8.11 (s, 1H), 7.95 (d, 1H), 7.54 (s, 1H) 7.47 (d, 2H) 7.43 (d, 2H) 4.40 (d, 1 H), 4.18 (d, 1 H), 3.90 (s, 3 H) 3.66 (t, 1 H), 1.92 (m, 2H) 1.71(m, 4H)

Step 3

6-chloro-5-[4-(tetrahydro-2H-pyran-2-yl)phenyl]-1H-indole-3-carboxylic acid Isomer 1

This was prepared by the method of Example 37, Steps 4, using methyl 6-chloro-5-[4-(tetrahydro-2H-pyran-2-yl)phenyl]-1H-indole-3-carboxylate Isomer 1 from step 2 to give the title compound Example 178. Retention time=7.119 Column: IC 250*4.6 mm I.D., 5 um. Mobile phase: ethanol (0.05% DEA) in CO2 from 5% to 40%. Flow rate: 2.35 mL/min Wavelength: 220 nm. MS (ES+) 337.9 (M−H$_2$O)$^{+1}$ $^1$H NMR (400 MHz, CD3OD) δ ppm 8.05 (s, 1H), 7.96 (s, 1H), 7.56 (s, 1H) 7.41 (s, 4H) 4.43 (d, 1 H), 4.12 (d, 1 H), 3.68 (m, 1 H) 1.94 (m, 2 H), 1.70 (m, 4H).

6-chloro-5-[4-(tetrahydro-2H-pyran-2-yl)phenyl]-1H-indole-3-carboxylic acid Isomer 2

This was prepared by the method of Example 37, Steps 4, using methyl 6-chloro-5-[4-(tetrahydro-2H-pyran-2-yl)phenyl]-1H-indole-3-carboxylate Isomer 2 from step 2 to give the title compound Example 179. Retention time=7.343 Column: IC 250*4.6 mm I.D., 5 um. Mobile phase: ethanol (0.05% DEA) in CO2 from 5% to 40%. Flow rate: 2.35 mL/min Wavelength: 220 nm. MS (ES+) 337.9 (M−H$_2$O)$^{+1}$ $^1$H NMR (400 MHz, CD3OD)) δ ppm 8.03 (s, 1H), 7.97 (s, 1H), 7.57 (s, 1H) 7.41 (s, 4H) 4.43 (d, 1 H), 4.12 (d, 1 H), 3.68 (m, 1 H) 1.94 (m, 2 H), 1.70 (m, 4H).

Example 180

6-chloro-5-{4-[2-(1H-pyrazol-1-yl)ethoxy]phenyl}-1H-indole-3-carboxylic acid

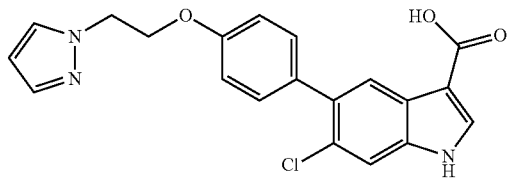 [SMILES: O=C(O)c1c[nH]c2cc(Cl)c(-c3ccc(OCCn4cccn4)cc3)cc12]

Step 1

1-[2-(4-bromophenoxy)ethyl]-1H-pyrazole

The mixture of 1-bromo-4-(2-bromoethoxy)benzene (1.00 g, 3.57 mmol), pyrazole (0.360 g, 5.36 mmol) and cesium carbonate (1.75 g, 5.36 mmol) in acetonitrile (10 mL) was heated at 80° C. and stirred for 2 hours. The reaction mixture was filtered. The filtrate was concentrated in vacuo to give a white solid, which was purified by silica gel chromatography to give the title compound (1.0 g, 100%) as a white solid. 1H NMR (400 MHz, CDCl3) δ ppm 7.56 (d, 1H) 7.54 (d, 1H) 7.35 (d, 2H), 6.74 (d, 2H), 6.26 (m, 1H), 4.53 (t, 2H), 4.30 (t, 2H).

Step 2

6-chloro-5-{4-[2-(1H-pyrazol-1-yl)ethoxy]phenyl}-1H-indole-3-carboxylic acid This was performed in a manner similar to Example 37, Steps 3-4 using 1-[2-(4-bromophenoxy)ethyl]-1H-pyrazole to give 52 mg of the title compound. MS (ES+): 382.1 (M+H). 1H NMR (400 MHz, DMSO-d6) δ ppm 12.13 (s, 1 H) 11.95 (br. s, 1 H) 8.08 (s, 1 H) 7.93 (s, 1 H) 7.83 (m, 1H), 7.62 (s, 1 H) 7.49 (m, 1H) 7.35 (d, 2H), 7.01 (d, 2H), 6.27 (m, 1H), 4.53 (t, 2H), 4.40 (t, 2H).

Example 181

6-chloro-5-[4-(2-methoxyethoxy)phenyl]-1H-indole-3-carboxylic acid

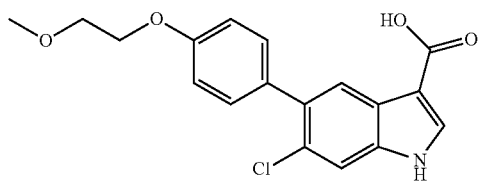 [SMILES: COCCOc1ccc(-c2cc3c(C(=O)O)c[nH]c3cc2Cl)cc1]

Step 1

1-bromo-4-(2-methoxyethoxy)benzene

Potassium carbonate (2.4 g, 17.3 mmol) was suspended in N,N-dimethyl formamide (15 mL). 4-bromophenol (1.00 g, 5.78 mmol) and 1-bromo-2-methoxyethane (0.964 g, 6.94 mmol) were added into the reaction sequentially and the resulting mixture was stirred at 60° C. for 17 hours. The reaction mixture was diluted with water and extracted with ethyl acetate (3×50 mL). The combined organic layers were washed with brine (50 mL) dried over sodium sulfate and evaporated to give the title compound (1.3 g, 99%) as a yellow oil.

Step 2

6-chloro-5-[4-(2-methoxyethoxy)phenyl]-1H-indole-3-carboxylic acid

This was performed in a manner similar to Example 37, Steps 3-4 using 1-bromo-4-(2-methoxyethoxy)benzene to give 108 mg of the title compound. MS (ES+): 345.9 (M+H). 1H NMR (400 MHz, METHANOL-d4) ppm 8.03 (s, 1 H) 8.01 (s, 1 H) 7.58 (s, 1 H) 7.38 (d, 2 H) 7.02 (d, 2 H) 4.19 (m, 2 H) 3.73-3.85 (m, 2 H) 3.47 (s, 3 H).

Example 182

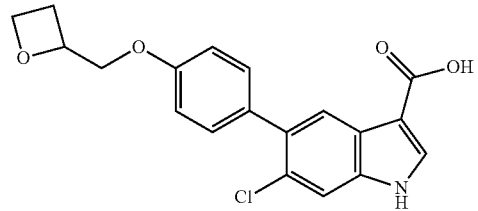 [SMILES: O=C(O)c1c[nH]c2cc(Cl)c(-c3ccc(OCC4CCO4)cc3)cc12]

6-chloro-5-[4-(oxetan-2-ylmethoxy)phenyl]-1H-indole-3-carboxylic acid

Step 1

4,4,5,5-tetramethyl-2-{4-[(3-methyloxetan-3-yl)methoxy]phenyl}-1,3,2-dioxaborolane A vial was charged with 4-(4,4,5,5-tetramethyl-1,3,2-dioxaborolan-2-yl)phenol (220 mg, 1.00 mmol), (3-methyloxetan-3-yl)methanol (122 mg, 1.20 mmol), triphenylphosphine (353 mg, 1.50 mmol) and tetrahydrofuran (2 mL). The mixture was stirred at 30° C. for 15 min under nitrogen atmosphere. To the mixture was added Diisopropyl azodicarboxylate (300 mg, 1.50 mmol). The mixture was purged with nitrogen and heated to 50° C. for 17 hrs. The mixture was diluted with ethyl acetate and washed with brine. The organic layer was dried (sodium sulfate) and concentrated to give crude product (900 mg) as yellow gum, which was purified through flash column chromatography to give the title compound (263 mg, 87%) as white solid.

Step 2

6-chloro-5-[4-(oxetan-2-ylmethoxy)phenyl]-1H-indole-3-carboxylic acid

This was prepared in a manner similar to Example 43, Step 1-2 with 4,4,5,5-tetramethyl-2-{4-[(3-methyloxetan-3-yl)methoxy]phenyl}-1,3,2-dioxaborolane to give 8.5 mg of the title compound. MS (ES+): 380.1 (M+Na)¹H NMR (400 MHz, DMSO-d6) ppm 11.95 (br. s, 1 H), 8.08 (d, 1 H), 7.93 (s, 1 H), 7.64 (s, 1 H), 7.36 (d, 2 H), 7.06 (d, 2 H), 5.05 (m, 1 H), 4.47-4.60 (m, 2 H), 4.11-4.26 (m, 2 H) 2.67-2.78 (m, 1 H) 2.53-2.62 (m, 1 H).

Example 183

6-chloro-5-{4-[(1-hydroxypropan-2-yl)oxy]phenyl}-1H-indole-3-carboxylic acid

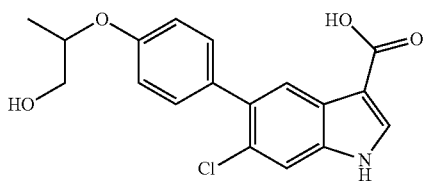 [SMILES: CC(CO)Oc1ccc(-c2cc3c(C(=O)O)c[nH]c3cc2Cl)cc1]

Step 1

1-(trityloxy)propan-2-yl methanesulfonate

To a solution of propane-1,2-diol (4.00 g, 52.0 mmol) in dry dichloromethane (50 mL) at 0° C. was added trityl chloride (15 g, 0.052 mol), N,N-dimethylaminopyridine (0.82 g, 6.8 mmol) and triethylamine (13.13 g, 1.33 mmol). The resulting mixture was stirred at room temperature for 14 hours. Methanesulfonyl chloride (6.36 g, 56.0 mmol) slowly at 0° C. Then the reaction was stirred at room temperature for 2 hours. The reaction mixture was diluted with water (100 mL) and extracted with dichloromethane (100 mL*3). The organic layer was washed with water (100 mL), and 1 N hydrochloric acid (100 mL*2). The combined organic layers were dried over sodium sulfate and concentrated to give a crude product, which was purified on silica gel column (petroleum ether: ethyl acetate=8:1 to 10:1) to give the title compound (15 g) as a viscous oil, which was used in the next step without further purification.

Step 2

1-iodo-4-{[1-(trityloxy)propan-2-yl]oxy}benzene

To a solution of potassium carbonate (0.63 g, 4.5 mmol) in dimethylformaide (10 mL) was purged with nitrogen for 10 min at 75° C. 4-iodophenol (0.55 g, 2.5 mmol) was added to the mixture and the solution was purged with nitrogen for additional 10 min. To the reaction mixture 1-(trityloxy)propan-2-yl methanesulfonate (1.00 g, 2.53 mmol) was added and stirred for 24 hours at the same temperature. The reaction mixture was diluted with water (20 mL) and extracted with ethyl acetate (20 mL*3). The combined organic layer was dried over sodium sulfate and concentrated. The crude product was purified by combiflash silica gel chromatography (petroleum ether:ethyl acetate=10:1) to give the title compound (600 mg, 46%) as colorless oil.

Step 3

2-(4-iodophenoxy)propan-1-ol

To a solution of 1-iodo-4-{[1-(trityloxy)propan-2-yl]oxy}benzene (350 mg, 0.67 mmol) in dichloromethane (5 mL) was added trifluoroacetic acid (5 mL). The mixture was stirred at room temperature for 4 hours. The reaction mixture was concentrated and purified by combiflash (petroleum ether:ethyl acetate=10:1 to 4:1) to give the title compound (100 mg, 55%) as a white solid, which was used into next step directly. $^1$H NMR (400 MHz, CDCl3) ppm 7.55 (d, 2H), 6.72 (d, 2H), 4.45 (m, 1H), 3.70 (m, 2H), 1.96 (t, 1H), 1.25 (d, 3H).

Step 4

6-chloro-5-{4-[(1-hydroxypropan-2-yl)oxy]phenyl}-1H-indole-3-carboxylic acid This was performed in a manner similar to Example 37, Steps 3-4 using 2-(4-iodophenoxy)propan-1-ol to give 24 mg of the title compound. MS (ES+): 368.1 (M+Na).

$^1$H NMR (400 MHz, DMSO-d$_6$) ppm 11.54 (br. s, 1 H) 8.18 (br. s., 1 H) 7.87 (s, 1 H) 7.53 (s, 1 H) 7.31 (d, 2 H) 6.99 (d, 2 H) 4.92 (br. s., 1 H) 4.41-4.52 (m, 1 H) 3.45-3.65 (m, 2 H) 1.25 (d, 3H).

Example 184

6-chloro-5-{6-[(3S)-3-hydroxypyrrolidin-1-yl]-2-methoxypyridin-3-yl}-1H-indole-3-carboxylic acid

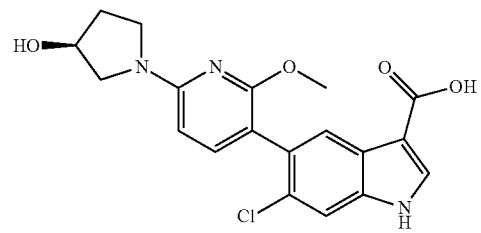 [SMILES: COc1nc(N2CC[C@H](O)C2)ccc1-c1cc2c(C(=O)O)c[nH]c2cc1Cl]

Step 1

(3S)-1-(6-methoxypyridin-2-yl)pyrrolidin-3-ol

To a solution of 2-chloro-6-methoxypyridine (1.966 g, 3.750 mmol) and commercially available (3S)-pyrrolidin-3-ol (1.437 g, 16.50 mmol) in tetrahydrofuran/methanol (137 mL/6.7 mL), was added Pd$_2$(dba)$_3$ (62.2 mg, 0.0688 mmol), BippyPhos (139.2 mg, 0.2750 mmol) and potassium hydroxide (1.16 g, 20.6 mmol, 88% pellets). The reaction was then was purged with nitrogen for 2 minutes and stirred at 70° C. for 18 hours. The reaction was filtered, quenched with saturated ammonium chloride solution, adjusted to pH=7~8 with 1N hydrochloric acid and extracted with dichloromethane (100 mL*2) and ethyl acetate (100 mL*3). The combined organic phase was washed with saturated brine, dried over sodium sulfate and evaporated in vacuo. The residue was then purified by silica gel chromatography with ethyl acetate/petroleum ether, 0-25% to give the title compound (1.65 g, 62%) as a yellow gum that was used without further purification.

Step 2

(3S)-1-(5-bromo-6-methoxypyridin-2-yl)pyrrolidin-3-ol

To a solution of (3S)-1-(6-methoxypyridin-2-yl)pyrrolidin-3-ol (1.6 g, 8.24 mmol) in chloroform (90 mL), was added N-bromosuccinimide (1.47 g, 8.24 mmol) at 0° C. with an ice bath. The reaction was allowed to stir at room temperature (8° C.) for 5 hour. TLC (petroleum ether/ethyl acetate) showed that the reaction was complete. The reaction mixture was evaporated to remove chloroform, dissolved in DCM (20 mL) and diluted with water (15 mL). The resulting mixture was separated and the aqueous phase was extracted with dichloromethane (25 mL*3). The combined organic phase was washed with brine, dried over sodium sulfate and evaporated in vacuo. The residue was purified by silica gel chromatography with ethyl acetate/petroleum ether, 0-25% to give the title compound (187 mg, 8.5%) as a yellow gum. $^1$H NMR (400 MHz, CDCl3) ppm 7.46 (d, 1 H) 5.77 (d, 1 H) 4.44-4.59 (m, 1 H) 3.92 (s, 3 H) 3.37-3.61 (m, 4 H) 1.96-2.24 (m, 3 H).

Step 3

6-chloro-5-{6-[(3S)-3-hydroxypyrrolidin-1-yl]-2-methoxypyridin-3-yl}-1H-indole-3-carboxylic acid This was prepared in a manner similar to Example 161, steps 2-3 with (3S)-1-(5-bromo-6-methoxypyridin-2-yl)pyrrolidin-3-ol to give 30.3 mg of the title compound. MS (ES+) 387.9 (M+H)+. 1H NMR (400 MHz, CD3OD) ppm 11.44 (br. s, 1 H) 7.98 (s, 1 H) 7.94 (s, 1 H) 7.54 (s, 1 H) 7.30 (d, 1 H) 6.06 (d, 1 H) 4.51-4.59 (m, 1 H) 3.85 (s, 3 H) 3.50-3.72 (m, 4 H) 2.13-2.25 (m, 1 H) 2.00-2.12 (m, 1 H). Retention Time: 1.829 Column: Chiralpak AD-3 50*4.6 mm I.D., 3 um in; Mobile phase: iso-propanol (0.05% DEA) in CO2 from 5% to 40%; Flow rate: 4 mL/min Wavelength: 220 nm.

Example 185

6-chloro-5-{6-[(3R)-3-hydroxypyrrolidin-1-yl]-2-methoxypyridin-3-yl}-1H-indole-3-carboxylic acid

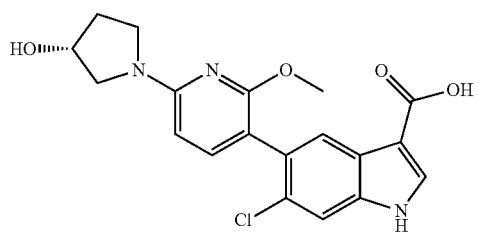 [SMILES: COc1nc(N2CC[C@@H](O)C2)ccc1-c1cc2c(C(=O)O)c[nH]c2cc1Cl]

This was prepared in a manner similar to Example 184, using (3R)-pyrrolidin-3-ol as the starting material to provide 39.2 mg of the title compound. MS (ES+) 387.9 (M+H)+. 1H NMR (400 MHz, CD3OD) ppm 11.43 (br. s, 1 H) 7.98 (s, 1 H) 7.94 (s, 1 H) 7.53 (s, 1 H) 7.31 (d, 1 H) 6.05 (d, 1 H) 4.52-4.58 (m, 1 H) 3.86 (s, 3 H) 3.50-3.71 (m, 4 H) 2.12-2.24 (m, 1 H) 2.00-2.11 (m, 1 H). Retention Time: 1.999 Column: Chiralpak AD-3 50*4.6 mm I.D., 3 um in; Mobile phase: iso-propanol (0.05% DEA) in CO2 from 5% to 40%; Flow rate: 4 mL/min Wavelength: 220 nm.

Example 186

6-chloro-5-{6-[(2-hydroxyethyl)(methyl)amino]-2-methoxypyridin-3-yl}-1H-indole-3-carboxylic acid

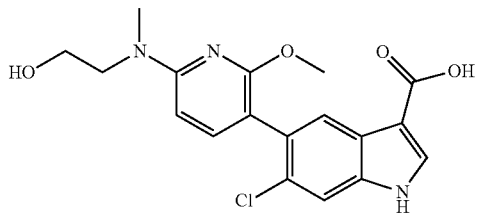 [SMILES: COc1nc(N(C)CCO)ccc1-c1cc2c(C(=O)O)c[nH]c2cc1Cl]

This was prepared by the method of Example 161, Steps 1-3, using 2-(methylamino)ethanol to give the title compound. MS: (ES+): 375.9 (M+H)+. 1H NMR (400 MHz, DMSO-d6) ppm 11.86 (br s, 1H), 8.03 (s, 1H), 7.83 (s, 1H), 7.55 (s, 1H), 7.30 (d, 1H), 6.19 (d, 1H), 4.69 (br s, 1H), 3.74 (s, 3H), 3.61 (br s, 4H), 3.08 (s, 3H).

Example 187

6-chloro-5-{4-[3-(4-methoxypiperidin-1-yl)propoxy]phenyl}-1H-indole-3-carboxylic acid

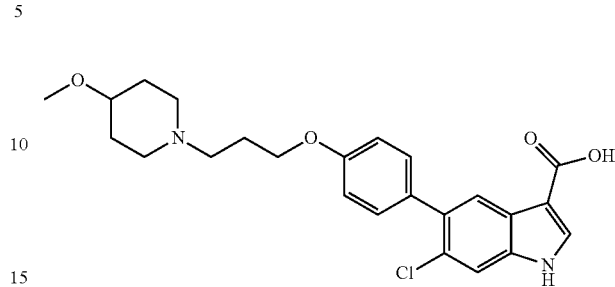

This was prepared by the method of Example 180, Steps 1-2, using 4-methoxypiperidine and 1-bromo-4-(3-bromopropoxy)benzene to give the title compound. MS (ES+): 443.2 (M+H)+1H NMR (400 MHz, DMSO-d6) ppm 11.94 (br s, 1H), 8.20 (br s, 1H), 8.06 (s, 1H), 7.92 (s, 1H), 7.61 (s, 1H), 7.33 (d, 2H), 7.00 (d, 2H), 4.04 (t, 2H), 3.22 (s, 3H), 3.17 (m, 1H), 2.70 (m, 2H), 2.45 (m, 2H), 2.10 (m, 2H), 1.89 (m, 2H), 1.84 (m, 2H), 1.42 (m, 2H).

Example 188

6-chloro-5-{4-[3-(4-methyl-3-oxopiperazin-1-yl)propoxy]phenyl}-1H-indole-3-carboxylic acid

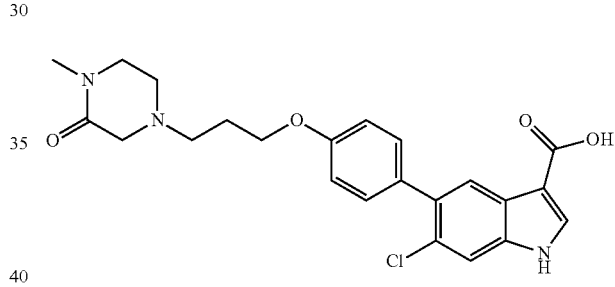

This was prepared by the method of Example 180, Steps 1-2, using 1-methylpiperazin-2-one and 1-bromo-4-(3-bromopropoxy)benzene to give the title compound. MS (ES+): 441.9 (M+H)+. 1H NMR (400 mHz, DMSO-d6) ppm 11.90 (br s, 1H), 8.04 (s, 1H), 7.93 (s, 1H), 7.60 (s, 1H), 7.33 (d, 2H), 7.00 (d, 2H), 4.05 (t, 2H), 3.27 (m, 4H), 3.00 (s, 2H), 2.81 (s, 3H), 2.66 (m, 2H), 1.92 (quint, 2H).

Example 189

6-chloro-5-(4-{3-[(3R)-3-fluoropyrrolidin-1-yl]propoxy}phenyl)-1H-indole-3-carboxylic acid

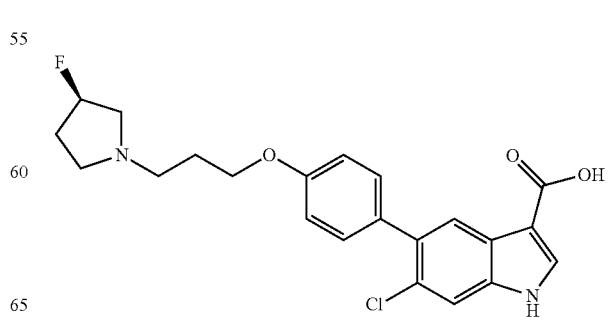

This was prepared by the method of Example 180, Steps 1-2, using (R)-3-fluoropyrrolidine and 1-bromo-4-(3-bromopropoxy)benzene to give the title compound. MS (ES+): 416.9 (M+H)+. 1H NMR (400 mHz, DMSO-d6) ppm 11.91 (br s, 1H), 8.05 (s, 1H), 7.93 (s, 1H), 7.61 (s, 1H), 7.34 (d, 2H), 7.00 (d, 2H), 5.19 (m, 1H), 4.06 (t, 2H), 2.82 (m, 2H), 2.65 (m, 1H), 2.58 (m, 2H), 2.31 (m, 1H), 2.13 (m, 1H), 1.91 (m, 2H), 1.83 (m, 1H).

Example 190

4,6-difluoro-5-{4-[2-(tetrahydrofuran-3-yl)ethoxy]phenyl}-1H-indole-3-carboxylic acid

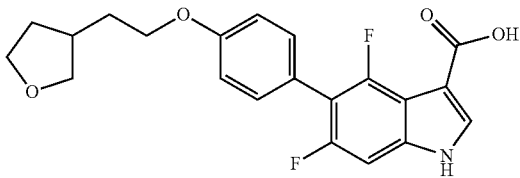 [SMILES: O=C(O)c1c[nH]c2cc(F)c(-c3ccc(OCCC4CCOC4)cc3)c(F)c12]

Step 1

4,4,5,5-tetramethyl-2-(4-(2-(tetrahydrofuran-3-yl)ethoxy)phenyl)-1,3,2-dioxaborolane This was prepared by the method of Example 182, Step 1 using 2-(tetrahydrofuran-3-yl)ethanol to give the title compound.

Step 2

4,6-difluoro-5-{4-[2-(tetrahydrofuran-3-yl)ethoxy]phenyl}-1H-indole-3-carboxylic acid This was prepared by the method of Example 167, Steps 2-3 using 4,4,5,5-tetramethyl-2-(4-(2-(tetrahydrofuran-3-yl)ethoxy)phenyl)-1,3,2-dioxaborolane to give the title compound. MS(APCI+): 388.1 (M+H)+. 1H NMR (300 mHz, DMSO-d6) ppm 12.12 (br s, 1H), 11.98 (br s, 1H), 8.06 (s, 1H), 7.35 (d, 2H), 7.23 (d, 1H), 7.04 (d, 2H), 4.06 (m, 2H), 3.85 (m, 1H), 3.75 (m, 1H), 3.64 (m, 1H), 3.33 (m, 1H, obscured by water peak), 2.33 (m, 1H), 2.05 (m, 1H), 1.83 (m, 2H), 1.56 (m, 1H)

Example 191

4,6-difluoro-5-{4-[2-(tetrahydrofuran-2-yl)ethoxy]phenyl}-1H-indole-3-carboxylic acid

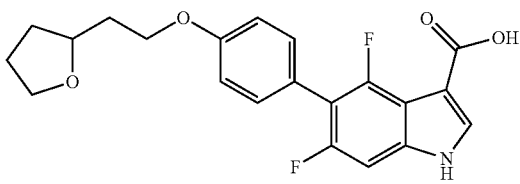 [SMILES: O=C(O)c1c[nH]c2cc(F)c(-c3ccc(OCCC4CCCO4)cc3)c(F)c12]

Step 1

4,4,5,5-tetramethyl-2-(4-(2-(tetrahydrofuran-2-yl)ethoxy)phenyl)-1,3,2-dioxaborolane This was prepared by the method of Example 182 Step 1 using 2-(tetrahydrofuran-2-yl)ethanol to give the title compound.

Step 2

4,6-difluoro-5-{4-[2-(tetrahydrofuran-2-yl)ethoxy]phenyl}-1H-indole-3-carboxylic acid This was prepared in a similar method to Example 167, Steps 2-3 using 4,4,5,5-tetramethyl-2-(4-(2-(tetrahydrofuran-2-yl)ethoxy)phenyl)-1,3,2-dioxaborolane to give the title compound. MS(APCI+): 388.1 (M+H)+. 1H NMR (300 mHz, DMSO-d6) ppm 12.12 (br s, 1H), 11.98 (br s, 1H), 8.05 (s, 1H), 7.35 (d, 2H), 7.23 (d, 1H), 7.04 (d, 2H), 4.10 (t, 2H), 3.94 (m, 1H), 3.78 (m, 1H), 3.61 (m, 1H), 2.08-1.81 (m, 5H), 1.50 (m, 1H)

AMPK In Vitro Biochemical Assay

Expression and Purification of AMPK

We designed a tricistronic AMPK expression construct that included open reading frames encoding the full-length $\gamma_1$, $\beta_1$ and $\alpha_1$ subunits of human AMPK with a ribosome-binding site (RBS) ahead of each coding region and subcloned this into pET-14b expression vector (Novagen, Madison, Wis.) using standard molecular biology techniques. AMPK tricistronic construct was transformed into E. coli BL21-Codon-Plus™ (DE3)-RIPL strain (Stratagene) and transformants were selected on LB (Luria-Bertani) agar plates containing ampicillin (100 µg/ml). Ten liters of LB medium (MP Biomedical LB broth #11-3002-032) containing 100 ug/ml carbenicillin was inoculated with 100 ml E. coli shake flask culture (BL-21, pET-14b, AMPK 111) in a BF4 10 L working volume bioreactor (New Brunswick Scientific Co.) at 37° C., 600 rpm, 6 L/minute aeration. Optical density sample measurements were made on an UltroSpec 2000 spectrophotometer (Pharmacia Biotech) at 600 nm. When the cell density reached ~0.9 OD, the temperature was reduced to 18° C. and the culture was induced at 18° C. with 0.1 mM Isopropylthiogalactoside (IPTG). The cell paste was collected at ~18 hours post induction by refrigerated continuous flow centrifugation (Heraeus, rotor #8575) at 15,000 rpm at 4° C. The cell pellets were aliquoted into four portions, flash frozen in liquid nitrogen and were stored at −80° C. until purification. For purification, frozen cell paste was thawed and resuspended in 50 ml lysis buffer (50 mM Tris, pH 8.0, 150 mM NaCl, 10% glycerol, 2 mM Tris-2-carboxyethyl phosphine (TCEP), 20 mM imidazole and 0.001% Triton X-100). After sonication, insoluble material was removed by centrifugation at 15,000 rpm in a Sorvall® RC5 plus centrifuge for 30 min at 4° C. and the supernatant was loaded onto a 5 ml HisTrap™ HP column (GE Healthcare, Piscataway, N.J.) and washed with five column volumes of lysis buffer. Bound proteins were eluted using an elution buffer containing 300 mM imidazole. Fractions containing AMPK subunits were pooled based on SDS-10% PAGE analysis and dialyzed overnight in dialysis buffer (50 mM Tris, pH 8.0, 150 mM NaCl, 10% glycerol, 2 mM TCEP, and 0.001% Triton X-100). The purified AMPK was phosphorylated on its activation loop Thr 172 by incubating 1.0 µM AMPK complex in the presence of 200 nM CaMKKβ

(calmodulin-dependent protein kinase kinase β obtained from the University of Dundee) in phosphorylation buffer for 30 min at 30° C. The phosphorylated AMPK complex was re-purified on HisTrap™ HP column as before, dialyzed over night in dialysis buffer. The phosphorylated AMPK complex was further purified by gel filtration chromatography with a Superdex 200 HiLoad 16/60 column (GE Healthcare) in SEC buffer (50 mM Tris, pH 8.0, 150 mM NaCl, 10% glycerol, 2 mM TCEP, and 0.001% Triton X-100). The final samples were stored at −20° C. with 25% glycerol.

Expression and Purification of PP2A

We cloned human recombinant Protein Phosphatase 2A catalytic subunit (PP2A C; 309 aa, NM_004156.2) into pFast-Bac HT-A expression vector and expressed in insect cells (Sf9) with a N-terminal 10×-His Tag. The Sf9 cells were cultured in SF-900-III SFM medium (Invitrogen #12658-027) in a Wave cellbag disposable bioreactor (GE Healthcare #CB0050L10-02) at 27° C. under 0.3 L/min aeration. 2×1 ml aliquots of baculovirus infected insect cells (BIIC1) were removed from −80° C. preservation, rapidly thawed and used to infect 20 liters of log phase Sf-9 cells at a viable cell density ~1.5×106 vc/ml at >95% viability. The harvest time (72 hours post infection) was indicated by percent cell viability (to 85-90%) and increased cell diameter (3-4 µm). The cell paste was collected by refrigerated continuous flow centrifugation at 3500×g (Heraeus/Thermo Scientific model Contifuge 28rs and #8575 rotor), aliquoted, flash frozen in liquid nitrogen and stored at −80° C. For purification, the cell paste was resuspended in 500 mL lysis buffer (50 mM Tris pH 8.0, 150 mM NaCl, 25 mM imidazole, 10% glycerol, 2 mM MgCl2, 2 mM TCEP+protease inhibitor cocktail. After lysis, cellular debris was removed by centrifugation at 36K×g for 1 hour. The resulting supernatant was filtered at 0.2 micron before applying to a 1 mL nickel charged IMAC column (HisTrap, GE). The bound resin was washed to baseline with 50 CV of 50 mM Tris pH 8.0, 150 mM NaCl, 25 mM imidazole, 10% glycerol, 2 mM MgCl2, 2 mM TCEP before eluting over a 20 CV gradient to 100% with wash buffer containing 500 mM imidazole. Pooled fractions containing PP2A were combined and diluted 10× with 50 mM Tris pH 8.0, 10% glycerol, 1 mM TCEP and applied to a 1 mL AIEX resin (HiTrap QFF, GE). The bound resin was washed with dilution buffer and PP2A was eluted over a 20 CV gradient to 100% 50 mM Tris pH 8.0, 500 mM NaCl, 10% glycerol, 1 mM TCEP and was further diluted 1:1 with 50 mM Tris pH 8.0, 150 mM NaCl, 10% glycerol, and 1 mM TCEP buffer.

Biochemical Profiling of AMPK Activators by

The biochemical $EC_{50}$ (half-maximal concentration required for full activation) of compounds for the activation of AMPK was evaluated by $^{33}$P-based assay using SAMS peptide (commercially available) derived from ACC-1. Twenty µl of phosphorylated AMPK diluted in assay buffer, (50 mM HEPES, 1 mM EGTA, 10 mM MgCl2, 0.25 mM DTT, 0.01% Tween-20, 0.01% BSA (pH 7.5)) was added to 384 well plates containing 1 µL of test compound. Following a fifteen minute room temperature incubation, 10 µL of protein phosphatase PP2A was added to the plate to dephosphorylate pThr172 of AMPK. After incubation for 90 minutes, 10 µL of substrate mixture containing 41 nM okadaic acid, 82 µM SAMS peptide, 82 µM ATP and tracer amounts (6.8 nM) of $^{33}$P-containing ATP was added to the plate. The reaction was terminated after 60 minutes incubation at room temperature by the addition of 15 µL of 2% $H_3PO_4$. Subsequently, 45 µl of reaction mix was transferred to 384 well Millipore MZPH filter plates (MZPHNO50) pre-treated with 25 µL of 2% $H_3PO_4$ and the plates were washed three times with assay buffer. 20 µL of Ready Safe scintillation fluid was added to dried plates followed by detection on the Trilux detector. Counts from basal wells (enzyme, diluent, PP2A and substrate) were subtracted from each well. Counts were expressed as a % of positive control wells (enzyme, allosteric activator or AMP, PP2A and substrate). $EC_{50}$ values were determined from this data using a 4-parameter fit algorithm and are presented in Table 1.

TABLE 1

| Example Number | $EC_{50}$ nM | n | Maximum % |
|---|---|---|---|
| 1 | 4.2 | 3 | 83 |
| 2 | 64.7 | 1 | 88 |
| 3 | 458.6 | 3 | 82 |
| 4 | 71.0 | 3 | 62 |
| 5 | 35.7 | 2 | 78 |
| 6 | 17.3 | 1 | 61 |
| 7 | 671.3 | 3 | 78 |
| 8 | 219.7 | 1 | 94 |
| 9 | 71.2 | 3 | 81 |
| 10 | 69.9 | 3 | 91 |
| 11 | 554.1 | 3 | 73 |
| 12 | 42.5 | 1 | 82 |
| 13 | 6.9 | 1 | 73 |
| 14 | 150.5 | 1 | 100 |
| 14A | 100.7 | 1 | 101 |
| 14B | 118.2 | 1 | 91 |
| 15 | 631.9 | 3 | 92 |
| 16 | 412.3 | 3 | 114 |
| 17 | 125.8 | 1 | 107 |
| 18 | 181.5 | 2 | 92 |
| 19 | 383.3 | 2 | 96 |
| 20 | 53.6 | 1 | 62 |
| 21 | 93.5 | 3 | 86 |
| 22 | 13.7 | 2 | 122 |
| 23 | 16.0 | 1 | 88 |
| 24 | 252.3 | 3 | 91 |
| 25 | 111.1 | 2 | 78 |
| 26 | 124.5 | 3 | 74 |
| 27 | 36.9 | 2 | 107 |
| 28 | 1077 | 3 | 98 |
| 29 | 382.9 | 2 | 101 |
| 30 | 30.0 | 3 | 92 |
| 31 | 130 | 3 | 104 |
| 32 | 570.2 | 1 | 97 |
| 33 | 85.3 | 5 | 83 |
| 34 | 315.3 | 1 | 122 |
| 35 | 74.2 | 4 | 72 |
| 36 | 7.1 | 1 | 70 |
| 37 | 247.8 | 1 | 81 |
| 38 | 106.2 | 1 | 93 |
| 39 | 11.1 | 1 | 75 |
| 40 | 821 | 3 | 78 |
| 41 | 9.6 | 1 | 62 |
| 42 | 21.8 | 3 | 65 |
| 43 | 1.7 | 1 | 68 |
| 44 | 85.0 | 1 | 78 |
| 45 | 224.8 | 3 | 94 |
| 47 | 65.3 | 3 | 96 |
| 48 | 110.5 | 3 | 89 |
| 50 | 203.8 | 2 | 79 |
| 51 | 320.2 | 2 | 93 |
| 52 | 38.1 | 3 | 91 |
| 53 | 22.0 | 2 | 120 |
| 54 | 32.5 | 1 | 74 |
| 55 | 209 | 2 | 87 |
| 56 | 333.5 | 2 | 137 |
| 57 | 64.5 | 3 | 107 |
| 58 | 89.2 | 1 | 107 |
| 59 | 133 | 1 | 75 |
| 60 | 7.8 | 4 | 65 |
| 61 | 2.3 | 1 | 57 |
| 62 | 33.3 | 1 | 74 |

TABLE 1-continued

| Example Number | EC$_{50}$ nM | n | Maximum % |
|---|---|---|---|
| 63 | 432.5 | 3 | 89 |
| 64 | 169.4 | 3 | 82 |
| 65 | 134.6 | 3 | 103 |
| 66 | 26.9 | 4 | 98 |
| 67 | 2.4 | 1 | 112 |
| 68 | 4.3 | 1 | 117 |
| 69 | 263.6 | 1 | 74 |
| 70 | 77.5 | 1 | 106 |
| 71 | 14.0 | 1 | 75 |
| 72 | 4.3 | 1 | 107 |
| 73 | 790.1 | 3 | 118 |
| 74 | 44.3 | 1 | 110 |
| 75 | 0.5 | 1 | 91 |
| 76 | 271.1 | 1 | 104 |
| 77 | 207 | 3 | 89 |
| 78 | 1995 | 3 | 68 |
| 79 | 103.9 | 3 | 102 |
| 80 | 181.9 | 2 | 108 |
| 81 | 182.5 | 3 | 97 |
| 82 | 215.7 | 3 | 86 |
| 83 | 819 | 3 | 108 |
| 84 | 343.6 | 3 | 72 |
| 86 | 99.2 | 3 | 99 |
| 87 | 69.5 | 3 | 112 |
| 88 | 58.1 | 2 | 78 |
| 89 | 65.4 | 3 | 99 |
| 90 | 372.3 | 2 | 120 |
| 91 | 695.4 | 3 | 101 |
| 94 | 17.9 | 1 | 92 |
| 95 | 830.4 | 2 | 91 |
| 96 | 58.1 | 3 | 83 |
| 97 | 202 | 4 | 94 |
| 98 | 1045 | 2 | 83 |
| 99 | 38.5 | 3 | 94 |
| 100 | 189.6 | 2 | 80 |
| 101 | 1.8 | 3 | 61 |
| 102 | 33.7 | 3 | 79 |
| 103 | 8.3 | 2 | 80 |
| 104 | 36.5 | 3 | 88 |
| 105 | 122.3 | 1 | 84 |
| 106 | 73.0 | 2 | 94 |
| 107 | 43.5 | 2 | 60 |
| 108 | 94.4 | 2 | 92 |
| 109 | 82.3 | 2 | 94 |
| 110 | 205.8 | 1 | 90 |
| 111 | 174.6 | 3 | 12 |
| 112 | 1316 | 1 | 80 |
| 113 | 344.5 | 3 | 100 |
| 114 | 36.8 | 2 | 94 |
| 115 | 27.0 | 2 | 95 |
| 116 | 47.8 | 2 | 104 |
| 117 | 90.2 | 2 | 107 |
| 118 | 169.1 | 1 | 125 |
| 119 | 44.8 | 2 | 97 |
| 120 | 52.4 | 2 | 88 |
| 121 | 369.2 | 3 | 102 |
| 122 | 160.3 | 2 | 75 |
| 123 | 100.4 | 1 | 57 |
| 124 | 93.8 | 2 | 93 |
| 125 | 132.5 | 2 | 90 |
| 126 | 26.8 | 2 | 110 |
| 127 | 17.2 | 1 | 81 |
| 128 | 19.8 | 3 | 70 |
| 130 | 304.8 | 3 | 100 |
| 131 | 17.9 | 2 | 95 |
| 132 | 482.7 | 1 | 46 |
| 133 | >50000 | 2 | |
| 134 | 82.8 | 1 | 16 |
| 135 | 6.5 | 4 | 82 |
| 136 | 39.3 | 2 | 100 |
| 138 | 40.4 | 1 | 117 |
| 139 | 72.8 | 3 | 84 |
| 141 | 9.3 | 2 | 119 |
| 142 | 21.5 | 3 | 92.9 |
| 143 | 17.67 | 2 | 193.8 |
| 144 | 236.3 | 1 | 118.7 |
| 145 | 57.91 | 2 | 65.15 |
| 146 | 35.26 | 1 | 119 |
| 147 | 10.14 | 1 | 131.5 |
| 148 | 6.56 | 1 | 119.1 |
| 149 | 76.92 | 2 | 88.86 |
| 150 | 165 | 1 | 111.7 |
| 151 | 37.82 | 1 | 103.8 |
| 152 | 16.75 | 1 | 111.6 |
| 153 | 136.9 | 1 | 112.3 |
| 154 | 28.31 | 1 | 104.8 |
| 155 | 47.79 | 1 | 126.9 |
| 156 | 31.9 | 3 | 98.88 |
| 157 | 50.12 | 3 | 96.1 |
| 158 | 125 | 1 | 146.1 |
| 159 | 47.83 | 1 | 98.63 |
| 160 | 17.3 | 1 | 118.3 |
| 161 | 8.328 | 2 | 92.94 |
| 162 | 192 | 1 | 123 |
| 163 | 12.9 | 2 | 110 |
| 163 | 10.31 | 1 | 112.4 |
| 164 | 17.51 | 1 | 141.6 |
| 165 | 31.9 | 1 | 159.2 |
| 166 | 129.4 | 2 | 107.1 |
| 167 | 9.33 | 2 | 143.1 |
| 168 | 170.7 | 4 | 108.6 |
| 169 | 7.063 | 1 | 116 |
| 170 | 33.95 | 1 | 100.2 |
| 171 | 32.9 | 2 | 69.2 |
| 172 | 10.96 | 1 | 101.1 |
| 173 | 11.7 | 5 | 115 |
| 174 | 15.3 | 3 | 49.4 |
| 175 | 22.6 | 3 | 78.2 |
| 176 | 5.6 | 2 | 62.4 |
| 177 | 62.3 | 2 | 110.9 |
| 178 | 2.602 | 1 | 74.92 |
| 179 | 14.21 | 1 | 90.21 |
| 180 | 11.6 | 3 | 76.2 |
| 181 | 16.9 | 2 | 81.4 |
| 182 | 19 | 1 | 80 |
| 183 | 28.1 | 2 | 87.3 |
| 184 | 6.2 | 1 | 84 |
| 185 | 2.9 | 1 | 106 |
| 186 | 84.5 | 4 | 114 |
| 187 | 61.4 | 4 | 105 |
| 188 | 52.7 | 4 | 129 |
| 189 | 57.7 | 4 | 112 |
| 190 | 109.1 | 4 | 108 |
| 191 | 120.6 | 3 | 140 |

Human Podocyte Assay

Conditionally immortalized human podocytes were seeded at a density of 10$^4$ cells/well onto a collagen I coated 24 well plate and allowed to differentiate at 37° C. for 7-10 days in glucose free RPMI with 10% FBS and the medium was replaced with fresh medium every other day. Upon differentiation, the cells were treated with the test compounds (1 mM AICAR and Ex 1) in serum free RPMI with 30 mM glucose. The medium in the negative control wells was replaced with glucose free RPMI containing 0.2% serum and the medium in positive control wells was replaced with serum free RPMI containing 30 mM glucose and DMSO. After 48 hours, apoptotic cell death was assessed using Cell Death ELISA (Roche, Inc) according to the manufacturer's instructions. Briefly, podocytes were lysed in lysis buffer provided in the kit, followed by centrifugation for 10 min at 200×G. 20 μl of the supernatant were added to streptavidin-coated microtiter plates followed by incubation with Anti-histone biotin and anti-DNA peroxidase-labeled antibodies for 2 hrs. After incubation and washing, color was developed using the provided substrate to the wells. Absorbance was measured at 405 nm. Parallel cells were lysed with Cell Lysis Buffer (Cell Signaling Technology), separated on 4-12% gradient SDS-PAGE gels (Invitrogen), transferred to nitrocellulose membrane, and probed using antibodies specific to phospho-T172 AMPK alpha, total AMPK alpha, phospho-79 Acetyl-CoA-Carboxylase, and total Acetyl-CoA-Carboxylase.

We claim:

1. A compound of structure

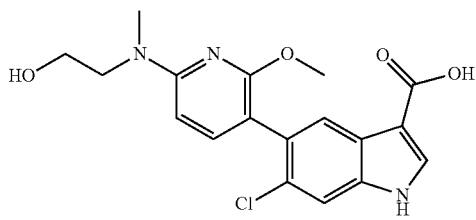 [SMILES: COc1nc(N(C)CCO)ccc1-c1cc2c(C(=O)O)c[nH]c2cc1Cl]

or a pharmaceutically acceptable salt thereof.

2. A compound of structure

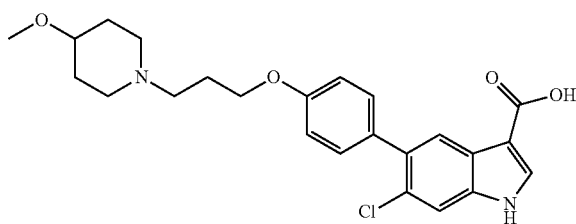 [SMILES: COC1CCN(CCCOc2ccc(-c3cc4c(C(=O)O)c[nH]c4cc3Cl)cc2)CC1]

or a pharmaceutically acceptable salt thereof.

3. A compound of structure

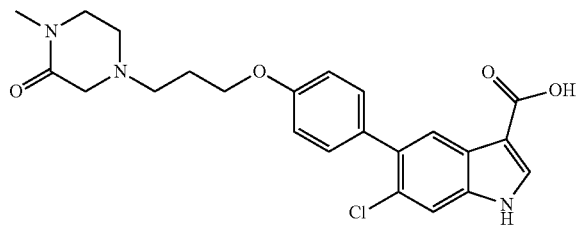 [SMILES: CN1CCN(CCCOc2ccc(-c3cc4c(C(=O)O)c[nH]c4cc3Cl)cc2)CC1=O]

or a pharmaceutically acceptable salt thereof.

4. A compound of structure

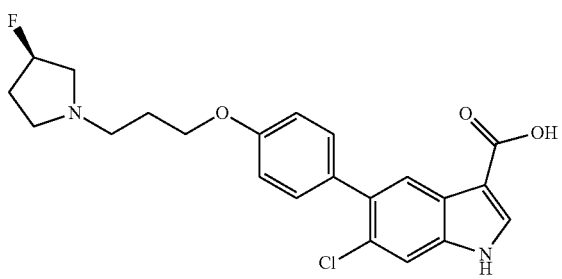 [SMILES: O=C(O)c1c[nH]c2cc(Cl)c(-c3ccc(OCCCN4CC[C@@H](F)C4)cc3)cc12]

or a pharmaceutically acceptable salt thereof.

5. A compound of structure

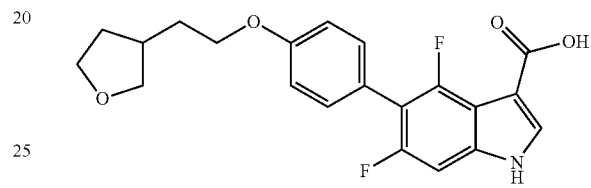

or a pharmaceutically acceptable salt thereof.

6. A compound of structure

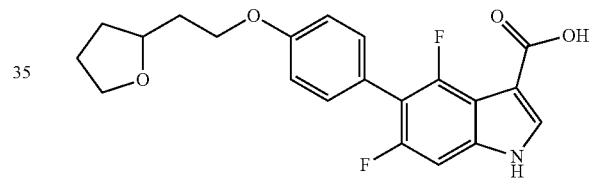

or a pharmaceutically acceptable salt thereof.

* * * * *